(12) United States Patent  (10) Patent No.: US 7,514,441 B2
Yasuma et al.  (45) Date of Patent: Apr. 7, 2009

(54) SUBSTITUTED PYRAZOLO [1,5-A]PYRIMIDINES AS CALCIUM RECEPTOR MODULATING AGENTS

(75) Inventors: Tsuneo Yasuma, Ibaraki (JP); Akira Mori, Kyoto (JP); Masahiro Kawase, Hyogo (JP); Hiroyuki Kimura, Sakai (JP); Masato Yoshida, Sanda (JP); Albert Charles Gyorkos, Westminster, CO (US); Scott Alan Pratt, Broomfield, CO (US); Christopher Peter Corrette, Arvada, CO (US)

(73) Assignee: Takeda Pharmaceutical Company Limited, Osaka (JP)

( * ) Notice: Subject to any disclaimer, the term of this patent is extended or adjusted under 35 U.S.C. 154(b) by 583 days.

(21) Appl. No.: 10/525,158

(22) PCT Filed: Aug. 21, 2003

(86) PCT No.: PCT/US03/26317

§ 371 (c)(1), (2), (4) Date: Feb. 22, 2005

(87) PCT Pub. No.: WO2004/017908

PCT Pub. Date: Mar. 4, 2004

(65) Prior Publication Data

US 2006/0079536 A1  Apr. 13, 2006

Related U.S. Application Data

(60) Provisional application No. 60/406,012, filed on Aug. 26, 2002.

(51) Int. Cl.
- *C07D 487/04* (2006.01)
- *A61K 31/519* (2006.01)
- *A61P 19/08* (2006.01)
- *A61P 19/10* (2006.01)

(52) U.S. Cl. ............... 514/259.3; 544/281; 544/263
(58) Field of Classification Search ............ 544/244, 544/281; 514/259.31, 80
See application file for complete search history.

(56) References Cited

U.S. PATENT DOCUMENTS 4,746,656 A * 5/1988 Atwal ............ 514/217.06
4,918,074 A * 4/1990 Tsuda et al. ........ 514/252.16

FOREIGN PATENT DOCUMENTS

WO  WO 01/53266 A1  7/2001
WO  WO 02/072585 A2  9/2002

OTHER PUBLICATIONS

Bellec et. al. (J. Het. Chem., 1995, 32(6), 1793-1800).*
Reddy et. al. (Ind. J. Chem., 1993, 32B(5), 586-589).*
See the CAS printout, accession No. 1991:81873, downloaded Jan. 29, 2008.*
Reddy, K.H. et al., "Synthesis of alkyl/aryl substituted pyrazolo[1,5-a]pyrimidines", *Indian Journal of Chemistry*, (1993), vol. 32B, pp. 586-589.
Branowaka et al., *Tandem vicarious nucleophilic substitution of hydrogen/intramolecular Diels-Alder reaction of 1,2,4-triazines into functionalized cycloalkenopyridines*, Chem Pharm Bull, Apr. 2002, vol. 50, No. 4, pp. 463-466, see compound 15i.

* cited by examiner

*Primary Examiner*—Brenda Coleman
*Assistant Examiner*—Susanna Moore
(74) *Attorney, Agent, or Firm*—Edwards Angell Palmer & Dodge LLP; David G. Conlin; Mark D. Russett

(57) ABSTRACT

There is provided a calcium receptor modulator comprising a compound of the formula (I):

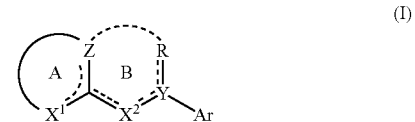

(I)

wherein ring A is an optionally substituted 5- to 7-membered ring; ring B is an optionally substituted 5- to 7-membered heterocyclic ring; $X^1$ is $CR^1$, $CR^1R^2$, N or $NR^{13}$; $X^2$ is N or $NR^3$; Y is C, $CR^4$ or N, Z is $CR^5$, $CR^5R^6$, N or $NR^7$; Ar is an optionally substituted cyclic group; R is H, an optionally substituted hydrocarbon group, etc.; and --- is a single bond or a double bond; $R^1$, $R^2$, $R^3$, $R^4$, $R^5$, $R^6$, $R^7$ and $R^{13}$ are independently H, an optionally substituted hydrocarbon group; or a salt thereof or a prodrug thereof. Compounds of the formula (II) and (III):

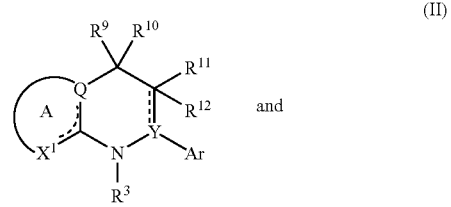

(II)

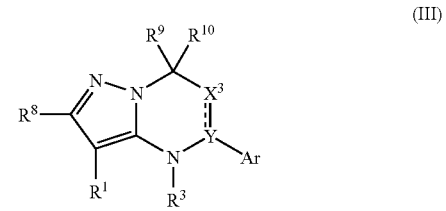

(III)

wherein ring A is an optionally substituted 5- to 7-membered ring; Q is C, $CR^5$ or N; $R^8$, $R^9$, $R^{10}$, $R^{11}$ and $R^{12}$ are independently, H, an optionally substituted hydrocarbon group, etc., or a salt thereof are also provided. Also specify $X^1$, $R^3$, $R^1$, Y and $X^3$ in formula (II) and (III) as before.

31 Claims, No Drawings

SUBSTITUTED PYRAZOLO [1,5-A]PYRIMIDINES AS CALCIUM RECEPTOR MODULATING AGENTS

This application is the National Phase filing of International Patent Application No. PCT/US03/26317, filed Aug. 21, 2003, which claims priority to U.S. 60/406/012, filed Aug. 26, 2002.

BACKGROUND OF THE INVENTION

1. Field of the Invention

The present invention relates to heterocyclic compounds having calcium-sensing receptor (CaSR, hereinafter simply referred to as Ca receptor) modulating (agonistic or antagonistic) activity, pharmaceutical compositions containing them and intermediate compounds useful for synthesizing them.

2. Background Art

Calcium ion (hereinafter simply referred to as Ca) plays an essential role to maintain and modulate functions of various cells such as endocrine and exocrine cells, etc., in addition to nerve and muscle. For this reason, the blood Ca level is strictly maintained in a narrow range. Parathyroid hormone (PTH) plays a central role in maintaining this blood Ca level. Therefore, secretion of PTH from parathyroid gland responds sharply to change in the blood Ca level and is must be modulated according to this. In fact, when the blood Ca level is changed, the blood PTH level is rapidly changed in response to this. The possibility of a mechanism by which the extracellular Ca concentration is sensed by parathyroid gland cells and the information transmitted into cells has been pointed out early by Brown et al. In 1993, they succeeded in the cloning and characterization of a Ca-sensing receptor (CaSR; hereinafter, simply referred to as Ca receptor) from bovine parathyroid (Nature, 366, 575-580(1993)).

The Ca receptor is composed of a large terminal extracellular region spanning 600 amino acids at the N-terminal, having seven transmembrane spanning domains like other G protein coupled receptors, and an intracellular region consisting of 200 or less amino acids at the caboxyl C-terminal.

It is considered that, when the extracellular Ca concentration is increased, phospholipase (PL)-C is activated, leading to increase in the intracellular Ca concentration and inhibition of PTH secretion due to increase in inositol triphosphate ($IP_3$). Since when a high value of the extracellular Ca concentration is maintained, the intracellular Ca concentration is thereafter increased continuously, it is considered that influx of Ca from the outside of a cell is also promoted. $PL-A_2$ and D are activated due to increase in extracellular Ca, but there is a possibility that these are via protein kinase (PK)-C and the like which are activated at the same time via Ca receptor. The Ca receptor also inhibits adenylyl cyclase via Gi protein or via arachidonic acid production due to activation of $PL-A_2$ and decreases intracellular cyclic AMP (Bone, 20, 303-309 (1997)).

Ca receptor mRNA is expressed in many tissues, and the expression amount is high, in parathyroid gland, thyroid gland C cell, medulla and cortex thick ascending limb (MTAL and CTAL) of kidney uriniferous tubule, intramedullary collecting tubule (IMCD) and encephalic subfornical organ (SFO) and hippocampus (Bone, 20, 303-309 (1997)). In addition, expression is recognized in many tissues such as encephalic hypothalamus, cerebellum and olfactory nucleus, regions other than TAL of renal uriniferous tubule, lung, stomach, pancreas, intestine and skin. Since the Ca receptor is present in various tissues, its physiological function has yet to be fully understood. However, it is expected that the Ca receptor modulating (agonistic or antagonistic) drug would provide for a novel treatment of various disease states which include the following:

1. Drugs for Treating Bone Diseases

Since the anabolic activity is manifested by intermittent administration of PTH, Ca receptor modulating drugs which are considered to be able to regulate secretion of PTH are promising as a drug for treating osteoporosis. In addition, Ca receptor modulating drugs which are selectable for thyroid gland C cell may be also effective for treating osteoporosis by stimulation of calcitonin secretion. Whether the same Ca receptor as that of parathyroid gland is present in osteoblast, osteoclast and bone cell or not is disputable. However, some Ca-sensing mechanism is assuredly present therein and, therefore, drugs which directly act on them can be expected as a drug for treating bone diseases.

2. Kidney-Acting Drugs

Handling of water and mineral in kidney is not only based on the results of function as a target organ for hormones, such as PTH, vitamin D etc., but also the Ca receptor in kidney is presumed to function in a response to the Ca concentration and the magnesium ion concentration in the extracellular fluid (Kidney Int, 50, 2129-2139 (1996)). Further, it is also considered that Ca receptor modulating drugs may modulate the blood amount in kidney, the amount of glomerulus filtration, renin secretion and activation of vitamin D in addition to control of influx and efflux of water and mineral.

3. Central Nervous System and Endocrine-Acting Drugs

Ca receptor is present in almost all areas in the central nervous system, and is remarkably expressed, in particular, in the hippocampus, cerebellum and subfornical organ (Brain Res, 744. 47-56 (1997)). Although the details of the function are still unclear, the term of Ca receptor expression after birth in the hippocampus is consistent with the term of acquisition of LTP (Long Tightening Phenomenon) (Develop Brain Res, 100, 13-21 (1997)) and, therefore, the relationship with memory and learning can be presumed. Therefore, Ca receptor modulating drugs which are high in brain-blood barrier permeability and selective for the central nerve system may be utilized for treating Alzheimer's disease. In addition, since dry mouth occurs in hypercalcemic patient, Ca receptor modulating drugs may control them. The presence of Ca receptor in mouse pituitary gland cells which secreteACTH has been reported (Mol Endocrinol, 10, 555-565 (1996)). It is also considered that Ca receptor modulating drugs can be applied to Sheehann's syndrome and hypopituitarism or hyperpituitarism.

4. Digestive System-Acting Drugs

It is considered that a Ca receptor is present in the Auerbach nerve plexus of the digestive tract and controls intestinal tract motion. Constipation is known in hypercalcemic patients and stimulation of digestive tract motion is known in hypocalcemic patients in clinical tests. The existence of a Ca receptor in the gastrin secreting cell (G cell) of the stomach has been reported (J. Clin Invest, 99, 2328-2333 (1997)), and intestinal tract absorption, constipation, diarrhea, defecation and secretion of acid in the stomach may be controlled by drugs which act on a Ca receptor in the digestive tract. Further, it has been found that a Ca receptor is present in human colon cancer cell strains and it controls c-myc expression and proliferation (Biochem Biophys Res Commum, 232, 80-83 (1997)), this is better consistent with the fact that the Ca uptake and sideration of colon and rectum cancers exhibit the negative correlation and, therefore, Ca receptor regulating drugs can be expected also as a drug for preventing and treating such cancers.

Various heterocyclic compounds have been disclosed in the prior art. For example, WO 01/53266 discloses a compound of the formula:

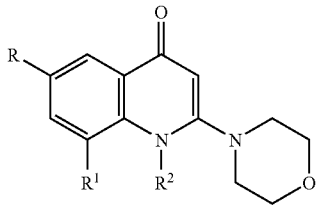

where in R, $R^1$ and $R^2$ are independently H, hydroxyl, etc. This compound has a phosphoinositide 3-kinase inhibitory activity and is useful for treating coronary obstruction, etc. Indian J. Chem., Sect. B (1993), 32B(5), 586-9 discloses the synthesis of a compound of the formula:

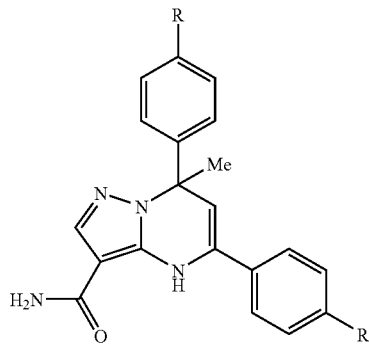

wherein R is hydrogen, chlorine, methyl or methoxy. However, no utility is disclosed. U.S. Pat. No. 4,746,656 (JP 63-33380 A) discloses a compound of the formula:

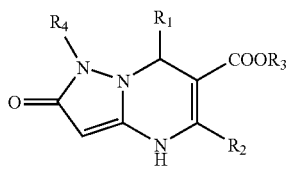

wherein $R_1$ is aryl or heterocyclic group, $R_2$ is aryl, etc., $R_3$ and $R_4$ are independently H, alkyl, etc. This compound is a Ca channel blocker.

EP 217142 discloses a compound of the formula:

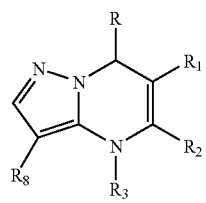

wherein R is hydrogen, alkyl, etc., $R_1$ is hydrogen, nitro, cyano, etc., $R_2$ is phenyl, cycloalkyl, etc., $R_3$ is hydrogen, acyl etc., and $R_8$ is carboxyl, carbamoyl, etc. This compound is also a Ca channel blocker.

However, a heterocyclic compound having Ca receptor modulating activity is not found in the prior art.

OBJECTS OF THE INVENTION

One object of the present invention is to provide compounds having Ca receptor modulating activity including novel compounds.

Another object of the present invention is to provide pharmaceutical compositions containing the compounds of the present invention.

These objects as well as other objects and advantages of the present invention will become apparent to those skilled in the art from the following description.

SUMMARY OF THE INVENTION

The present inventors have intensively investigated compounds having Ca receptor modulating activity. As a result, it has been found that compounds represented by formula (I) as shown hereinafter have Ca receptor modulating activity useful for medicine and, among them, compounds represented by the formulas (II), (III) and (IIIa) as shown hereinafter are novel compounds.

According to the present invention, there is provided:

1. A compound of the formula (II):

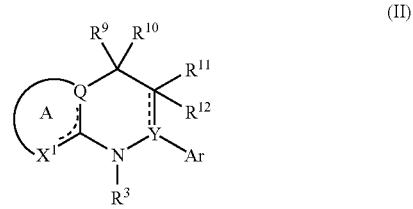

(II)

wherein ring A is an optionally substituted 5- to 7-membered ring;

Q is C, $CR^5$ (wherein $R^5$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1-$ is —CO—, —CS—, —SO— or —SO$_2$—, and $Z^2$ is an optionally substituted hydrocarbon group, an optionally substituted heterocyclic group, an optionally substituted hydroxyl group, or an optionally substituted amino group)), or N;

$X^1$ is $CR^1$ (wherein $R^1$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1-$ and $Z^2$ are as defined above)), $CR^1R^2$ (wherein $R^1$ is as defined above, and $R^2$ is H, or an optionally substituted hydrocarbon group), N, or $NR^{13}$ (wherein $R^{13}$ is H, an optionally substituted hydrocarbon group, an optionally substituted hydroxyl group, an optionally substituted amino group, an optionally substituted heterocyclic group, or a group of the formula: $-Z^1-Z^2$ (wherein $-Z^1-$ and $Z^2$ are as defined above));

$R^3$ is H, an optionally substituted hydrocarbon group, an optionally substituted hydroxyl group, an optionally substituted amino group, an optionally substituted heterocyclic group, or a group of the formula: $-Z^1-Z^2$ (wherein $-Z^1$- and $Z^2$ are as defined above);

Y is C, $CR^4$ (wherein $R^4$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above)), or N;

Ar is an optionally substituted cyclic group;

$R^9$ and $R^{10}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above); and $R^{11}$ and $R^{12}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^{1'}-Z^2$ (wherein $-Z^{1'}$- is —CS—, —SO— or —SO$_2$—, and $Z^2$ is as defined above); or $R^9$ and $R^{10}$, or $R^{11}$ and $R^{12}$ may be combined to form an oxo group, methylene group or a ring; or $R^{10}$ and $R^{11}$ may be combined to form a ring; and --- is a single bond or a double bond; provided that (1) when ring A is a 6-membered ring and Q is C or $CR^5$, $X^1$ is $C-Z^1-Z^2$, $C(-Z^1-Z^2)R^2$ or $N-Z^1-Z^2$, and both $R^9$ and $R^{10}$ are not H, or $R^9$ and $R^{10}$ are not combined to form an oxo group, or $R^{10}$ and $R^{11}$ are not combined to form a 5-membered ring, (2) when ring A is a 6-membered ring and Q is N, $X^1$ is $C-Z^1-Z^2$, $C(-Z^1-Z^2)R^2$ or $N-Z^1-Z^2$, and $R^9$ and $R^{10}$ are not combined to form an oxo group, (3) when ring A is a 5-membered ring and Q is C or $CR^5$, $X^1$ is $C-Z^1-Z^2$, $C(-Z^1-Z^2)R^2$ or $N-Z^1-Z^2$, and $Z^2$ is an optionally substituted amino group, and (4) when ring A is a 5-membered ring and Q is N, at least one of $R^9$ and $R^{10}$ is $CHR^{15}R^{16}$ (wherein at least one of $R^{15}$ and $R^{16}$ are the same or different and are H, an optionally substituted hydrocarbon group, an optionally substituted hydroxyl group, an optionally substituted amino group, an optionally substituted thiol group, a halogen atom, an optionally substituted heterocyclic group, or a group of the formula: $-Z^1-Z^2$ (wherein $-Z^1$- and $Z^2$ are as defined above)) and the other is other than an optionally substituted phenyl group; or a salt thereof;

2. A compound of the formula (III):

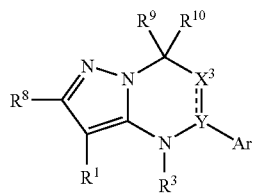

(III)

wherein $R^1$ is H, an optionally substituted hydrocarbon group, an optionally substituted hydroxyl group, an optionally substituted thiol group, an optionally substituted amino group, cyano group, a halogen atom, an optionally substituted heterocyclic group, or a group of the formula: $-Z^1-Z^2$ (wherein $-Z^1$- is —CO—, —CS—, —SO— or —SO$_2$—, and Z is an optionally substituted hydrocarbon group, an optionally substituted heterocyclic group, an optionally substituted hydroxyl group, or an optionally substituted amino group);

$R^3$ is H, an optionally substituted hydrocarbon group, an optionally substituted hydroxyl group, an optionally substituted amino group, an optionally substituted heterocyclic group, or a group of the formula: $-Z^1-Z^2$ (wherein $-Z^1$- and $Z^2$ are as defined above);

Y is C, $CR^4$ (wherein $R^4$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above)) or N;

$R^8$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above);

Ar is an optionally substituted cyclic group;

$R^9$ and $R^{10}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above), or $R^9$ and $R^{10}$ may be combined to form an oxo group, methylene group or a ring;

$X^3$ is a bond, oxygen atom, an optionally oxidized sulfur atom, N, $NR^{7'}$ (wherein $R^{7'}$ is H, an optionally substituted hydrocarbon group, an optionally substituted hydroxyl group, an optionally substituted amino group, an optionally substituted heterocyclic group, or a group of the formula $-Z^{1'}-Z^2$ (wherein $-Z^{1'}$- is —CS—, —SO— or —SO$_2$—, and $Z^2$ is as defined above)), or an optionally substituted bivalent $C_{1-2}$ hydrocarbon group; and --- is a single bond or a double bond;

provided that at least one of $R^9$ and $R^{10}$ is $CHR^{15}R^{16}$ (wherein $R^{15}$ and $R^{16}$ are the same or different and are H, an optionally substituted hydrocarbon group, an optionally substituted hydroxyl group, an optionally substituted amino group, an optionally substituted thiol group, a halogen atom, an optionally substituted heterocyclic group, or a group of the formula: $-Z^1-Z^2$ (wherein $-Z^1$- and $Z^2$ are as defined above)) and the other is other than an optionally substituted phenyl group; or a salt thereof;

3. The compound according to the above 1 or 2, wherein $R^1$ is (1) an optionally substituted heterocyclic group, or (2) a group of the formula: $-Z^1-Z^2$ (wherein $-Z^1$- is —CO—, —CS—, —SO— or —SO$_2$—, and $Z^2$ is an optionally substituted hydrocarbon group, an optionally substituted heterocyclic group, an optionally substituted hydroxyl group, or an optionally substituted amino group);

4. The compound according to the above 3, wherein $Z^1$ is —CO— and $Z^2$ is an optionally substituted hydroxyl group or an optionally substituted amino group;

5. The compound according to the above 2, wherein $R^3$ is H, a $C_{1-6}$ alkyl group or a $C_{7-14}$ aralkyl group;

6. The compound according to the above 2, wherein Re is H, a $C_{1-6}$ alkyl group, a $C_{1-6}$ alkylthio group or a $C_{1-6}$ alkoxy group which may be substituted with hydroxyl group;

7. The compound according to the above 1 or 2, wherein $R^9$ and $R^{10}$ are the same or different and are a $C_{1-6}$ alkyl group or $R^9$ and $R^{10}$ are combined each other to form a ring;

8. The compound according to the above 2, wherein $R^1$ is a group of the formula: $-Z^1-Z^2$ (wherein $-Z^1$- is —CO—, CS—, —SO— or —SO$_2$—, and $Z^2$ is an optionally substituted hydrocarbon group, an optionally substituted heterocyclic group, an optionally substituted hydroxyl group, or an optionally substituted amino group); $R^3$ is H; Ar is an optionally substituted aromatic ring group; $X^3$ is $CR^{11}R^{12}$ (wherein $R^{11}$ and $R^{12}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z$ are as defined above), or $R^{11}$ and $R^{12}$ may be combined to form an oxo group, methylene group or a ring); and $R^9$ and $R^{10}$ are the same or different and a $C_{1-6}$ alkyl group, or $R^9$ and $R^{10}$ may be combined to form a ring;

9. The compound according to the above 8, wherein $R^1$ is an optionally substituted carbamoyl group;

10. The compound according to the above 9, wherein $R^1$ is a group of the formula: —CONR$^{20}$(CR$^{21}$R$^{22}$R$^{23}$) (wherein $R^{20}$ is H or an optionally substituted hydrocarbon group, and $R^{21}$, $R^{22}$, and $R^{23}$ are the same or different and are an optionally substituted hydrocarbon group or an optionally substituted heterocyclic group, or $R^{20}$ and $R^{21}$ may be combined to form a ring);

11. A compound of the formula (IIIa):

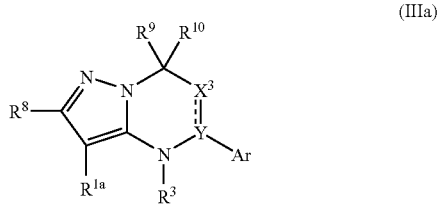

wherein $R^{1a}$ is (1) an optionally substituted heterocyclic group, or (2) a group of the formula: $-Z^{1a}-Z^{2a}$ (wherein $-Z^{1a}$- is —CO—, —CS—, —SO— or —SO$_2$—, and $Z^{2a}$ is (i) an optionally substituted heterocyclic group, (ii) —NR$^{20a}$(CR$^{21a}$R$^{22a}$R$^{23a}$) (wherein (a) $R^{20a}$ is H or an optionally substituted hydrocarbon group; and $R^{21a}$ is an optionally substituted heterocyclic group which may be fused with an optionally substituted benzene ring, or an optionally substituted phenyl group which may be fused with an optionally substituted aromatic heterocyclic ring and $R^{22a}$ and $R^{23a}$ are the same or different and are an optionally substituted hydrocarbon group or an optionally substituted heterocyclic group or $R^{22a}$ and $R^{23a}$ may be combined to form a ring, or (b) $R^{20a}$ is H or an optionally substituted hydrocarbon group; and $R^{21a}$, $R^{22a}$ and $R^{23a}$ are the same or different and are an optionally substituted $C_{1-8}$ aliphatic hydrocarbon group, provided that the sum total of the number of carbon atoms is 7 or more), (iii) —NR$^{20a}$R$^{25a}$ (wherein $R^{20a}$ is as defined above and $R^{25a}$ is an optionally substituted $C_{6-10}$ aryl-$C_{2-4}$ alkyl, $C_{6-10}$ aryloxy-$C_{2-4}$ alkyl, $C_{6-10}$ arylamino-$C_{2-4}$ alkyl, $C_{7-14}$ aralkylamino-$C_{2-4}$ alkyl, heterocyclic ring-$C_{2-4}$ alkyl or heterocyclic group), (iv) a substituted 5- to 7-membered cyclic amino group, or (v) —OR$^{24a}$ (wherein R$^{24}$ is (a) an optionally substituted $C_{7-14}$ aralkyl group, (b) an optionally substituted $C_{3-7}$ alicyclic hydrocarbon group, (c) an optionally substituted $C_{7-24}$ aliphatic hydrocarbon group, or (d) an optionally substituted heterocyclic group); $R^3$ is H, an optionally substituted hydrocarbon group, an optionally substituted hydroxyl group, an optionally substituted amino group, an optionally substituted heterocyclic group, or a group of the formula: $-Z^1-Z^2$ (wherein $-Z^1$- is —CO—, —CS—, —SO— or —SO$_2$—, and $Z^2$ is an optionally substituted hydrocarbon group, an optionally substituted heterocyclic group, an optionally substituted hydroxyl group, or an optionally substituted amino group);

Y is C, CR$^4$ (wherein R$^4$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above)) or N;

$R^8$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above);

Ar is an optionally substituted cyclic group;

$R^9$ and $R^{10}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1$- and $Z^2$ are as defined above), or $R^9$ and $R^{10}$ may be combined to form an oxo group, methylene group or a ring;

$X^3$ is a bond, oxygen atom, an optionally oxidized sulfur atom, N, NR$^{7'}$ (wherein R$^{7'}$ is H, an optionally substituted hydrocarbon group, an optionally substituted hydroxyl group, an optionally substituted amino group, an optionally substituted heterocyclic group, or a group of the formula $-Z^{1'}-Z^2$ (wherein $-Z^{1'}$- is —CS—, —SO— or —SO$_2$—, and $Z^2$ is as defined above)), or an optionally substituted bivalent $C_{1-2}$ hydrocarbon group; and --- is a single bond or a double bond;

provided that at least one of $R^9$ and $R^{10}$ is CHR$^{15}$R$^{16}$ (wherein $R^{15}$ and $R^{16}$ are the same or different and are H, an optionally substituted hydrocarbon group, an optionally substituted hydroxyl group, an optionally substituted amino group, an optionally substituted thiol group, a halogen atom, an optionally substituted heterocyclic group, or a group of the formula: $-Z^1-Z^2$ (wherein $-Z^1$- and $Z^2$ are as defined above)) and the other is other than an optionally substituted phenyl group; or a salt thereof;

12. The compound according to the above 11, wherein $R^{1a}$ is a group of the formula: —CONR$^{20a}$(CR$^{21b}$R$^{22b}$R$^{23b}$) (wherein R$^{20a}$ is as defined above and at least one of R$^{21b}$, R$^{22b}$, and R$^{23b}$ is an optionally substituted heterocyclic group which may be fused with an optionally substituted benzene ring, or an optionally substituted phenyl group which may be fused with an optionally substituted aromatic heterocyclic ring);

13. The compound according to the above 11, wherein $R^{1a}$ is (1) an optionally substituted 5- to 7-membered aromatic or non-aromatic heterocyclic group having 1-4 hetero atoms selected from nitrogen atom, oxygen atom and sulfur atom, or (2) a group of the formula: —CO-Z$^{2c}$ (wherein Z$^{2c}$ is (i) an optionally substituted 5- to 7-membered aromatic or non-aromatic heterocyclic group having 1-4 hetero atoms selected from nitrogen atom, oxygen atom and sulfur atom, (ii) —NR$^{20c}$(CR$^{21c}$R$^{22c}$R$^{23c}$) (wherein (a) R$^{20c}$ is H or an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group; and $R^{21c}$ is 1) an optionally substituted 5- to 7-membered aromatic or non-aromatic heterocyclic group having 1-4 hetero atoms selected from nitrogen atom, oxygen atom and sulfur atom, which may be fused with an optionally substituted benzene ring, or 2) an optionally substituted $C_{6-10}$ aryl group which may be fused with an optionally substituted 5- to 7-membered aromatic heterocyclic ring having 1-4 hetero atoms selected from nitrogen atom, oxygen atom and sulfur atom; and $R^{22c}$ and $R^{23c}$ are the same or different and are an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group or an optionally substituted 5- to 7-membered aromatic or non-aromatic heterocyclic group having 1-4 hetero atoms selected from nitrogen atom, oxygen atom and sulfur atom, or $R^{22c}$ and $R^{23c}$ may be combined to form a $C_{3-7}$ carbon ring, or (b) $R^{20c}$ is H or an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group; and $R^{21c}$, $R^{22c}$ and $R^{23c}$ are the same or different and are an optionally substituted $C_{1-8}$ aliphatic hydrocarbon group, provided that the sum total of the number of carbon atoms is 7 or more), (iii) —$NR^{20c}R^{25c}$ (wherein $R^{20c}$ is as defined above and $R^{25c}$ is an optionally substituted $C_{6-10}$ aryl-$C_{2-4}$ alkyl, $C_{6-10}$ aryloxy-$C_{2-4}$ alkyl, $C_{6-10}$ arylamino-$C_{2-4}$ alkyl, $C_{7-14}$ aralkylamino-$C_{2-4}$ alkyl, 5- to 7-membered heterocyclic ring (having 1-4 hetero atoms selected from nitrogen atom, oxygen atom and sulfur atom)-$C_{2-4}$ alkyl or 5- to 7-membered heterocyclic group having 1-4 hetero atoms selected from nitrogen atom, oxygen atom and sulfur atom), (iv) a substituted 5- to 7-membered cyclic amino group, or (v) —$OR^{24c}$ (wherein $R^{24c}$ is (a) an optionally substituted $C_{7-14}$ aralkyl group, (b) an optionally substituted $C_{3-7}$ alicyclic hydrocarbon group, (c) an optionally substituted $C_{7-24}$ aliphatic hydrocarbon group, or (d) an optionally substituted 5- to 7-membered aromatic or non-aromatic heterocyclic group having 1-4 hetero atoms selected from nitrogen atom, oxygen atom and sulfur atom;

wherein said substituents for $R^{1a}$, $Z^{2c}$, $R^{20c}$, $R^{21c}$, $R^{22c}$, $R^{23c}$, $R^{24c}$ and $R^{25c}$ are 1 to 3 substituents selected from the group consisting of 1) $C_{1-6}$ alkyl,
2) $C_{2-6}$ alkenyl,
3) $C_{2-6}$ alkynyl,
4) $C_{3-7}$ cycloalkyl,
5) $C_{6-10}$ aryl which may be substituted with 1 to 3 substituents selected from the group consisting of $C_{1-6}$ alkyl, amino, N—($C_{1-6}$ alkyl)amino, N,N-di-($C_{1-6}$ alkyl)amino, amidino, carbamoyl, N—($C_{1-6}$ alkyl)carbamoyl, N,N-di-($C_{1-6}$ alkyl)carbamoyl, sulfamoyl, N—($C_{1-6}$ alkyl)sulfamoyl, N,N-di-($C_{1-6}$ alkyl)sulfamoyl, carboxyl, $C_{2-7}$ alkoxycarbonyl, hydroxyl, $C_{1-6}$ alkoxy, mercapto, $C_{1-6}$ alkylthio, sulfo, cyano, azido, halogen, nitro, nitroso, phosphono, $C_{1-6}$ alkoxyphosphoryl, di-($C_{1-6}$ alkoxy)phosphoryl and $C_{1-6}$ alkyl substituted with phosphono, $C_{1-6}$ alkoxyphosphoryl and di-($C_{1-6}$ alkoxy)phosphoryl (hereinafter the group of 5) is referred to as group "C"),
6) aromatic heterocyclic group selected from (a) aromatic 5- or 6-membered heterocyclic group having 1-4 hetero atoms selected from nitrogen atom, oxygen atom and sulfur atom, (b) fused bicyclic heterocyclic group formed by condensation of an aromatic 5- or 6-membered heterocyclic group having 1 to 3 hetero atoms selected from nitrogen atom, oxygen atom and sulfur atom with benzene ring or an aromatic 5- or 6-membered heterocyclic group having 1 to 3 hetero atoms selected from nitrogen atom, oxygen atom and sulfur atom and (c) fused tricyclic heterocyclic group formed by condensation of [1] an aromatic 5- or 6-membered heterocyclic group having 1-3 hetero atoms selected from nitrogen atom, oxygen atom and sulfur atom, [2] benzene ring, and [3] an aromatic 5- or 6-membered heterocyclic group having 1-3 hetero atoms selected from nitrogen atom, oxygen atom and sulfur atom or benzene ring,
7) heterocyclic-oxy group formed by combining each of the above aromatic heterocyclic groups (a), (b) and (c) with oxy group,
8) non-aromatic 4- or 7-membered heterocyclic group having 1 to 3 hetero atoms selected from nitrogen atom, oxygen atom and sulfur atom,
9) $C_{7-14}$ aralkyl which may be substituted with 1 to 3 substituents selected from the group "C",
10) amino group,
11) N-mono-substituted amino selected from N—($C_{1-6}$ alkyl) amino, N—($C_{2-6}$ alkenyl)amino, N—($C_{3-7}$ cycloalkyl) amino group and N—($C_{6-10}$ aryl)amino which may be substituted with 1 to 3 substituents selected from the group "C",
12) amino substituted with two substituents selected from $C_{1-6}$ alkyl, $C_{2-6}$ alkenyl, $C_{3-7}$ cycloalkenyl and $C_{6-10}$ aryl which may be substituted with 1 to 3 substituents selected from the group "C",
13) amidino,
14) acyl selected from $C_{2-8}$ alkanoyl, $C_{3-8}$ alkenoyl, $C_{3-7}$ cycloalkyl-carbonyl, $C_{3-7}$ cycloalkenyl-carbonyl, $C_{6-10}$ aryl-carbonyl which may be substituted with 1 to 3 substituents selected from the group "C", and heterocyclic-carbonyl formed by binding of an aromatic or non-aromatic 5- or 6-membered heterocyclic group having 1-3 hetero atoms selected from nitrogen atom, oxygen atom and sulfur atom with carbonyl,
15) carbamoyl,
16) mono-substituted carbamoyl group selected from N—($C_{1-6}$ alkyl)carbamoyl, N—($C_{2-6}$ alkenyl) carbamoyl, N—($C_{3-7}$ cycloalkyl)carbamoyl and N—($C_{6-10}$ aryl)carbamoyl which may be substituted with 1 to 3 substituents selected from the group "C",
17) carbamoyl substituted with two substituents selected from $C_{1-6}$ alkyl, $C_{2-6}$ alkenyl, $C_{3-7}$ cycloalkyl and $C_{6-10}$ aryl which may be substituted with 1 to 3 substituents selected from the group "C",
18) sulfamoyl,
19) N-mono-substituted sulfamoyl selected from N—($C_{1-6}$ alkyl)sulfamoyl, N—($C_{2-6}$ alkenyl)sulfamoyl, N—($C_{3-7}$ cycloalkyl)sulfamoyl and N—($C_{6-10}$ aryl)sulfamoyl which may be substituted with 1 to 3 substituents selected from the group "C",
20) sulfamoyl substituted with two substituents selected from $C_{1-6}$ alkyl, $C_{2-6}$ alkenyl, $C_{3-7}$ cycloalkyl and $C_{6-10}$ aryl which may be substituted with 1 to 3 substituents selected from the group "C",
21) carboxyl,
22) $C_{1-6}$ alkoxy-carbonyl,
23) hydroxyl,
24) $C_{1-6}$ alkoxy,
25) $C_{2-10}$ alkenyloxy,
26) $C_{3-7}$ cycloalkyloxy,
27) $C_{6-10}$ aryloxy which may be substituted with 1 to 3 substituents selected from the group "C",
28) $C_{7-14}$ aralkyloxy which may be substituted with 1 to 3 substituents selected from the group "C",
29) mercapto,
30) $C_{1-6}$ alkylthio,
31) $C_{7-14}$ aralkylthio which may be substituted with 1 to 3 substituents selected from the group "C",
32) $C_{6-10}$ arylthio which may be substituted with 1 to 3 substituents selected from the group "C",
33) $C_{1-6}$ alkylsulfinyl,
34) $C_{7-14}$ aralkylsulfinyl which may be substituted with 1 to 3 substituents selected from the group "C",
35) $C_{6-10}$ arylsulfinyl which may be substituted with 1 to 3 substituents selected from the group "C",
36) $C_{1-6}$ alkylsulfonyl,
38) $C_{7-14}$ aralkylsulfonyl which may be substituted with 1 to 3 substituents selected from the group "C",
39) $C_{6-10}$ arylsulfonyl which may be substituted with 1 to 3 substituents selected from the group "C",
40) sulfo,
41) cyano,
42) azido,
43) halogen,
44) nitro,
45) nitroso,
46) phosphono,
47) $C_{1-6}$ alkoxy-phosphoryl
48) di-$C_{1-6}$ alkoxy-phosphoryl,
49) $C_{1-6}$ alkyl substituted with phosphono, $C_{1-6}$ alkoxyphosphoryl or di-($C_{1-6}$ alkoxy)phosphoryl
50) $C_{1-6}$ alkyl substituted with 1 to 4 halogen atoms
51) $C_{1-6}$ alkoxy substituted with 1 to 4 halogen atoms and
52) $C_{1-6}$ alkylenedioxy (hereinafter the group of above 1) to 52) is referred to as group "B");
$R^3$ is H, a $C_{2-6}$ alkyl group or a $C_{7-14}$ aralkyl group;
Y is CH;
$R^8$ is H, a $C_{1-6}$ alkyl group, a $C_{1-6}$ alkylthio group or a $C_{1-6}$ alkoxy group which may be substituted with hydroxyl group; Ar is (1) a $C_{6-10}$ aryl group, (2) a 5- to 7-membered aromatic or non-aromatic heterocyclic group having 1-4 hetero atoms selected from nitrogen atom, oxygen atom and sulfur atom, or (3) a $C_{3-7}$ saturated or unsaturated alicyclic hydrocarbon group, each of which may be substituted with 1 to 3 substituents selected from the group "B";

one of $R^9$ and $R^{10}$ is a hydrogen atom or $C_{1-6}$ alkyl group which may be substituted with 1 to 3 substituents selected from the group "B" and the other is (1) a hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group, each of which may be substituted with 1 to 3 substituents selected from the group "B" or (2) a 5- to 7-membered aromatic or non-aromatic heterocyclic group having 1-4 hetero atoms selected from nitrogen atom, oxygen atom and sulfur atom, which may be substituted with 1 to 3 substituents selected from the group "B", or
$R^9$ and $R^{10}$ may be combined to form a $C_{5-7}$ carbon ring; and $X^3$ is $CH_2$;

14. The compound according to the above 8, wherein $R^1$ is a group of the formula: —$CONR^{20}$ ($CR^{21}R^{22}R^{23}$) (wherein $R^{20}$ is H, and $R^{21}$, $R^{22}$, and $R^{23}$ are the same or different and are an optionally substituted hydrocarbon group or an optionally substituted heterocyclic group); $R^3$ is H; Ar is an optionally substituted aromatic ring group; $X^3$ is $CH_2$; Y is CH; $R^8$ is H or an optionally substituted hydrocarbon group, an optionally substituted alkoxy group, an optionally substituted sulfanyl group, an optionally substituted sulfinyl group, or an optionally substituted sulfonyl group, $C_{1-6}$ alkoxy-carbonyl; and $R^9$ and $R^{10}$ are the same or different and are an optionally substituted hydrocarbon group;

15. The compound according to the above 14, wherein at least one of $R^{21}$, $R^{22}$, and $R^{23}$ is an optionally substituted heterocyclic group or an optionally substituted phenyl group;

16. The compound according to the above 14, wherein $R^{20}$ and $R^{21}$ are combined to form an optionally substituted 5- to 7-membered ring, and $R^{22}$ and $R^{23}$ are the same or different and are an optionally substituted hydrocarbon group, an optionally substituted heterocyclic group, or an optionally substituted phenyl group;

17. The compound according to the above 14, wherein $R^{21}$ and $R^{22}$ are the same or different and are a $C_{1-8}$ hydrocarbon group, and $R^{23}$ is an optionally substituted 5-membered heterocyclic group which may be fused with an optionally substituted benzene ring, or an optionally substituted phenyl group;

18. The compound according to the above 16, wherein $R^{20}$ and $R^{21}$ are combined to form a 5- or 6-membered ring which may be fused with benzene ring and/or substituted with 1 to 3 substituents selected from the group consisting of (1) halogen, (2) hydrogen, (3) a phenoxy which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl,
(4) $C_{1-6}$ alkoxy which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl, N,N-di-$C_{1-6}$ alkyl-carbamoyl and phenyl which may be substituted with 1 to 3 substituents selected from halogen, hydroxyl, $C_{1-6}$ alkyl, $C_{1-6}$ alkoxy, $C_{1-6}$ acyl, cyano, halogeno $C_{1-6}$ alkyl, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl, and (5) a $C_{1-8}$ hydrocarbon group which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl, N,N-di-$C_{1-6}$ alkyl-carbamoyl and phenyl which may be substituted with 1 to 3 substituents selected from halogen, hydroxyl, $C_{1-6}$ alkyl, $C_{1-6}$ alkoxy, $C_{1-6}$ acyl, cyano, halogeno $C_{1-6}$ alkyl, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl, and $R^{22}$ and $R^{23}$ are the same or different and $C_{1-8}$ hydrocarbon group which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl, N,N-di-$C_{1-6}$ alkyl-carbamoyl and phenyl which may be substituted with 1 to 3 substituents selected from halogen, hydroxyl, $C_{1-6}$ alkyl, $C_{1-6}$ alkoxy, $C_{1-6}$ acyl, cyano, halogeno $C_{1-6}$ alkyl, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl;

19. N-(1-ethyl-1-(4-methylphenyl)propyl)-7,7-dimethyl-5-phenyl-4,5,6,7-tetrahydropyrazolo[1,5-a]pyrimidine-3-carboxamide or a salt thereof, N-(1-ethyl-1-(4-methylphenyl)propyl)-5-(2-fluorophenyl)-7,7-dimethyl-4,5,6,7-tetrahydropyrazolo[1,5-a]pyrimidine-3-carboxamide or a salt thereof, N-(1-ethyl-1-(4-methylphenyl)propyl)-2,7,7-trimethyl-5-phenyl-4,5,6,7-tetrahydropyrazolo[1,5-a]pyrimidine-3-carboxamide or a salt thereof, N-(1-ethyl-1-(4-ethylphenyl)propyl)-2,7,7-trimethyl-5-phenyl-4,5,6,7-tetrahydropyrazolo[1,5-a]pyrimidine-3-carboxamide or a salt thereof, N-(1-ethyl-1-(4-methylphenyl)propyl)-5-(2-fluorophenyl)-2,7,7-trimethyl-4,5,6,7-tetrahydropyrazolo[1, 5-a]pyrimidine-3-carboxamide or a salt thereof, N-(1-ethyl-1-(4-ethylphenyl)propyl)-5-(2-fluorophenyl)-2,7,7-trimethyl-4,5,6,7-tetrahydropyrazolo[1,5-a]pyrimidine-3-carboxamide or a salt thereof, 5-(2-chlorophenyl)-N-(1-ethyl-1-(4-methylphenyl)propyl)-2,7,7-trimethyl-4,5,6,7-tetrahydropyrazolo[1,5-a]pyrimidine-3-carboxamide or a salt thereof, N-(1-(4-(dimethylamino)phenyl)-1-ethylpropyl)-5-(2-fluorophenyl)-2,7,7-trimethyl-4,5,6,7-tetrahydropyrazolo[1,5-a]pyrimidine-3-carboxamide or a salt thereof, N-(1,1-diethylbutyl)-5-(2-fluorophenyl)-2,7,7-trimethyl-4,5,6,7-tetrahydropyrazolo[1,5-a]pyrimidine-3-carboxamide or a salt thereof, N-(1-ethyl-1-phenylpropyl)-5-(2-fluorophenyl)-2,7,7-trimethyl-4,5,6,7-tetrahydropyrazolo[1,5-a]pyrimidine-3-carboxamide or a salt thereof, 3-(5-(1-ethyl-1-(4-methylphenyl)propyl)-1,3,4-oxadiazol-2-yl)-2,7,7-trimethyl-5-phenyl-4,5,6,7-tetrahydropyrazolo[1,5-a]pyrimidine or a salt thereof, 3-(5-(1-ethyl-1-(4-methylphenyl)propyl)-1,3,4-thiadiazol-2-yl)-2,7,7-trimethyl-5-phenyl-4,5,6,7-tetrahydropyrazolo[1,5-a]pyrimidine or a salt thereof, 3-((4-(benzyloxy)-2,2-diethyl-1-pyrrolidinyl)carbonyl)-7,7-dimethyl-5-phenyl-4,5,6,7-tetrahydropyrazolo[1,5-a]pyrimidine or a salt thereof, 3-((2,2-diethyl-4-methoxy-1-pyrrolidinyl)carbonyl)-7,7-dimethyl-5-phenyl-4,5,6,7-tetrahydropyrazolo[1,5-a]pyrimidine or a salt thereof, or 3-((2,2-diethyl-4-fluoro-1-pyrrolidinyl)carbonyl)-7,7-dimethyl-5-phenyl-4,5,6,7-tetrahydropyrazolo[1,5-a]pyrimidine or a salt thereof;

20. The compound according to the above 19, which is an optically active compound;
21. A prodrug of the compound according to the above 1, 2 or 13;
22. A pharmaceutical composition which comprises the compound according to the above 1, 2 or 13 or a prodrug thereof;
23. A composition for modulating calcium receptor which comprises a compound of the formula (I):

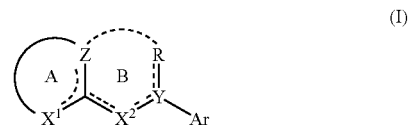

wherein ring A is an optionally substituted 5- to 7-membered ring;

ring B is an optionally substituted 5- to 7-membered heterocyclic ring;

$X^1$ is $CR^1$ (wherein $R^1$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- is —CO—, —CS—, —SO— or —$SO_2$—, and $Z^2$ is an optionally substituted hydrocarbon group, an optionally substituted heterocyclic group, an optionally substituted hydroxyl group, or an optionally substituted amino group)), $CR^1R^2$ (wherein $R^1$ is as defined above, $R^2$ is H or an optionally substituted hydrocarbon group), N or $NR^{13}$ (wherein $R^{13}$ is H, an optionally substituted hydrocarbon group, an optionally substituted hydroxyl group, an optionally substituted amino group, cyano group, a halogen atom, an optionally substituted heterocyclic group, or a group of the formula: -$Z^1$-$Z^2$ (wherein -$Z^1$- and $Z^2$ are as defined above));

$X^2$ is N or $NR^3$ (wherein $R^3$ is H, an optionally substituted hydrocarbon group, an optionally substituted hydroxyl group, an optionally substituted amino group, cyano group, a halogen atom, an optionally substituted heterocyclic group, or a group of the formula: -$Z^1$-$Z^2$ (wherein -$Z^1$- and $Z^2$ are as defined above);

Y is C, $CR^4$ (wherein $R^4$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above)) or N;

Z is $CR^5$ (wherein $R^5$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above)), $CR^5R^6$ (wherein $R^5$ and $R^6$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above)), N or $NR^7$ (wherein $R^7$ is H, an optionally substituted hydrocarbon group, an optionally substituted hydroxyl group, an optionally substituted amino group, cyano group, a halogen atom, an optionally substituted heterocyclic group, or a group of the formula: -$Z^1$-$Z^2$ (wherein -$Z^1$- and $Z^2$ are as defined above));

Ar is an optionally substituted cyclic group;

R is H, an optionally substituted hydrocarbon group, an optionally substituted hydroxyl group, an optionally substituted amino group, an optionally substituted thiol group, an optionally substituted sulfonyl group or an optionally substituted sulfinyl group, or R and Z may be combined to form a ring B; and --- is a single bond or a double bond;

or a salt thereof or a prodrug thereof;

24. The composition according to the above 23, which is a calcium receptor antagonist;

25. The composition according to the above 23, which is an agent for preventing or treating diseases caused by abnormality of calcium concentration in a living body or a calcium receptor;

26. The composition according to the above 23, which is an agent for preventing or treating bone diseases;

27. The composition according to the above 23, which is an agent for preventing or treating osteoporosis or fracture;

28. A method for modulating a calcium receptor which comprises administering to a mammal an effective amount of a compound of the formula (I) or a salt thereof or a prodrug thereof according to the above 23;

29. A method for preventing or treating bone diseases, which comprises administering to a mammal an effective amount of a compound of the formula (I) or a salt thereof or a prodrug thereof according to the above 23;

30. Use of the compound of the formula (I) or a salt thereof or a prodrug thereof according to the above 23 for producing a calcium receptor modulator; and 31. Use of the compound of the formula (I) or a salt thereof or a prodrug thereof according to the above 23 for producing a composition for preventing or treating bone diseases.

DETAILED DESCRIPTION OF THE PREFERRED EMBODIMENTS

The above formula (I) includes a monocyclic heterocyclic compound containing ring A and a condensed heterocyclic compound containing rings A and B.

In the above formulas, ring A of the formulas (I) and (II) is an optionally substituted 5- to 7-membered ring.

Examples of the "5- to 7-membered ring" of "an optionally substituted 5- to 7-membered ring" includes an aromatic or non-aromatic 5- to 7-membered hydrocarbon ring or 5- to 7-membered heterocyclic ring which may contain 1 to 3 heteroatoms selected from nitrogen, oxygen and sulfur atoms as the ring constituting atoms in addition to carbon atoms. Specific examples thereof include a hydrocarbon ring such as benzene, tropilidene, cyclopentane, cyclohexane, cycloheptane, 1-cyclopentene, 2-cyclopentene, 3-cyclopentene, 1-cyclohexene, 2-cyclohexene, 3-cyclohexene, 1-cycloheptene, 2-cycloheptene, 3-cycloheptene, 2,4-cycloheptadiene, etc.; a heterocyclic ring such as pyridine, pyrazine, pyrimidine, imidazole, furan, thiophene, dihydropyridine, diazepine, oxazepine, pyrrolidine, piperidine, hexamethylenimine, heptamethylenimine, tetrahydrofuran, piperazine, homopiperazine, tetrahydrooxazepine, morpholine, thiomorpholine, pyrrole, pyrazole, 1,2,3-triazole, oxazole, oxazolidine, thiazole, thiazolidine, isoxazole, imidazoline, triazole, thiadiazole, oxadiazole, oxathiadiazole, triazine, etc.; and the like.

Examples of the substituent(s) of "an optionally substituted 5- to 7-membered ring group" include halogen, nitro, cyano, oxo, an optionally substituted hydrocarbon group, an optionally substituted heterocyclic group, an optionally substituted sulfinyl group, an optionally substituted sulfonyl group, an optionally substituted hydroxyl group, an optionally substituted thiol group, an optionally substituted amino group, an optionally substituted acyl group, an optionally esterified or amidated carboxyl group, an optionally substituted phosphoryl group, or the like.

Examples of halogen include fluorine, chlorine, bromine, iodine, and the like, preferably, fluorine and chlorine.

Examples of the hydrocarbon group in an optionally substituted hydrocarbon group as the substituent of the 5- to 7-membered ring group include an optionally substituted aliphatic hydrocarbon group, an optionally substituted alicyclic hydrocarbon group, an optionally substituted alicyclic-aliphatic hydrocarbon group, an optionally substituted aromatic hydrocarbon group, an optionally substituted aromatic-aliphatic hydrocarbon group (an aralkyl group), and the like.

Examples of said aliphatic hydrocarbon group include a saturated aliphatic hydrocarbon group having 1-8 carbon atoms (e.g., alkyl group) such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; and an unsaturated aliphatic hydrocarbon group having 2-8 carbon atoms (e.g., alkenyl group, alkynyl group, alkadienyl group, alkadiynyl group, etc.) such as vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 2,4-hexadienyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl, 1-heptynyl, 1-octynyl, etc.

Examples of said alicyclic hydrocarbon group include a saturated alicyclic hydrocarbon group having 3-7 carbon atoms (e.g., cycloalkyl group, etc.) such as cyclopropyl, cyclobutyl, cyclopentyl, cyclohexyl, cycloheptyl, and the like; an unsaturated alicyclic hydrocarbon group having 3-7 carbon atoms (e.g., cycloalkenyl group, cycloalkadienyl group, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.; a partly saturated and fused bicyclic hydrocarbon group [preferably, $C_{9-10}$ (partly saturated and fused bicyclic hydrocarbon group, etc. (including those where the benzene ring is combined to 5- or 6-membered non-aromatic cyclic hydrocarbon group)] such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc.; and the like. Said alicyclic hydrocarbon group may be cross-linked.

Examples of said alicyclic-aliphatic hydrocarbon group include those where the above-mentioned alicyclic hydrocarbon group and the above-mentioned aliphatic hydrocarbon group are combined, for example, those having 4-14 carbon atoms such as cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphtyl)ethyl, 2-(1,2,3,4-tetrahydro-2-naphtyl)ethyl, 2-(3,4-dihydro-2-naphtyl)ethenyl, etc. (e.g., $C_{3-7}$ cycloalkyl-$C_{1-4}$ alkyl group, $C_{3-7}$ cycloalkenyl-$C_{1-4}$ alkyl group, $C_{3-7}$ cycloalkyl-$C_{2-4}$ alkenyl group, $C_{3-7}$ cycloalkenyl-$C_{2-4}$ alkenyl group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl groups, etc.).

Examples of said aromatic hydrocarbon group include an aryl group having 6-10 carbon atoms (including that where a 5- to 6-membered non-aromatic hydrocarbon ring is fused with phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of said aromatic-aliphatic hydrocarbon group include an aralkyl group having 7-14 carbon atoms ($C_{6-10}$ aryl-$C_{1-4}$ alkyl group) such as phenyl-$C_{1-4}$ alkyl group, e.g., benzyl, phenethyl, 1-phenylethyl, 1-phenylpropyl, 2-phenylpropyl, 3-phenylpropyl, etc.; naphthyl-$C_{1-4}$ alkyl group such as α-naphthylmethyl, α-naphthylethyl, β-naphthylmethyl, β-naphthylethyl, etc.; $C_{6-10}$ aryl-$C_{2-4}$ alkenyl group such as phenyl-$C_{2-4}$ alkenyl group, e.g., styryl, cinnamyl, etc.; and the like.

Examples of the heterocyclic group in an optionally substituted heterocyclic group as the substituent of the 5- to 7-membered ring include (i) a 5- to 7-membered heterocyclic group containing one sulfur atom, one nitrogen atom, or one oxygen atom, (ii) a 5- to 6-membered heterocyclic group containing 2-4 nitrogen atoms, (iii) a 5- to 6-membered heterocyclic group containing 1-2 nitrogen atoms and one sulfur or oxygen atom, or the like; and (iv) these heterocyclic groups may be fused with a 5- to 6-membered ring containing 2 or less nitrogen atoms, benzene ring, or a 5-membered ring containing one sulfur atom. In addition, each of the heterocyclic groups exemplified in (i) to (iv) may be a saturated or unsaturated heterocyclic group and the unsaturated heterocyclic group may be either aromatic or non-aromatic.

Examples of the heterocyclic group in an optionally substituted heterocyclic group as the substituent of the 5- to 7-membered ring include an aromatic monocyclic heterocyclic group, an aromatic fused heterocyclic group, and a non-aromatic heterocyclic group.

Specific examples of the heterocyclic group in an optionally substituted heterocyclic group as the substituent of the 5- to 7-membered ring include (i) an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,2,3-triazolyl, 1,2,4-triazolyl, tetrazolyl, pyridyl, pyrimidinyl, pyridazinyl, pyrazinyl, triazinyl, etc.); (ii) an aromatic fused heterocyclic group (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benztriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); and (iii) a non-aromatic, heterocyclic group (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.).

Examples of sulfinyl group in an optionally substituted sulfinyl group as the substituent of the 5- to 7-membered ring include that where —SO— is combined with "the hydrocarbon group" or "the heterocyclic group" in "an optionally substituted hydrocarbon group" or "an optionally substituted heterocyclic group" of the substituent of the 5- to 7-membered ring.

Preferred examples include a $C_{1-8}$ alkylsulfinyl group where sulfinyl group is combined with a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; a $C_{6-10}$ arylsulfinyl group where sulfinyl group is combined with a $C_{6-10}$ aryl group such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; a group where sulfinyl group is combined with an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.); and a group where sulfinyl group is combined with an aromatic fused heterocyclic group (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benztriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.).

More preferred examples include a $C_{1-8}$ alkylsulfinyl group where sulfinyl group is combined with a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.

Examples of sulfonyl group in an optionally substituted sulfonyl group as the substituent of the 5- to 7-membered ring include a group where —$SO_2$— is combined with "the hydrocarbon group" or "the heterocyclic group" in "an optionally substituted hydrocarbon group" or "an optionally substituted heterocyclic group" of the substituent of the 5- to 7-membered ring.

Preferred examples include a $C_{1-8}$ alkylsulfonyl group where sulfonyl group is combined with a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; a $C_{6-10}$ arylsulfonyl group where sulfonyl group is combined with a $C_{6-10}$ aryl group such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; a group where sulfonyl group is combined with an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, or the like); and a group where the sulfonyl group is combined with an aromatic, fused heterocyclic group (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benztriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.).

More preferred examples include a $C_{1-8}$ alkylsulfonyl group where sulfonyl group is combined with a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.

Examples of an optionally substituted hydroxyl group as the substituent of the 5- to 7-membered ring include hydroxyl group and that having an appropriate substituent, for example, "an optionally substituted hydrocarbon group" or "an optionally substituted heterocyclic group" of the above substituent of the 5- to 7-membered ring.

Preferred examples include a $C_{1-8}$ alkyloxy group whose substituent is a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; a $C_{6-10}$ aryloxy group whose substituent is a $C_{6-10}$ aryl group such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; a hydroxyl group substituted with an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.); a hydroxyl group substituted with an aromatic fused heterocyclic group (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benztriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.).

More preferred examples include a $C_{6-10}$ aryloxy group (in particular, phenyloxy) or a hydroxyl group substituted with an aromatic monocyclic heterocyclic group (in particular, pyridyl) or an aromatic fused heterocyclic group (in particular, quinolyl).

"The hydrocarbon group" or "the heterocyclic group" as the substituent of the substituted hydroxyl group exemplified above may have the same substituent as that of "the hydrocarbon group" or "the heterocyclic group" in "an optionally substituted hydrocarbon group or an optionally substituted heterocyclic group" of the substituent of the 5- to 7-membered ring.

Examples of an optionally substituted thiol group as the substituent of the 5- to 7-membered ring include thiol group and that substituted with an appropriate group such as "an optionally substituted hydrocarbon group" or "an optionally substituted heterocyclic group" of the substituent of the 5- to 7-membered ring.

Preferred examples include a $C_{1-8}$ alkylthio group, whose substituent is a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; a $C_{6-10}$ arylthio group, whose substituent is a $C_{6-10}$ aryl group such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; a thiol group substituted with an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.); and a thiol group substituted with an aromatic fused heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.).

"The hydrocarbon group" or "the heterocyclic group" as the substituent of the substituted thiol group exemplified above may have the same substituent as that of "the hydrocarbon group" or "the heterocyclic group" in "an optionally substituted hydrocarbon group" or "an optionally substituted heterocyclic group" of the substituent of the 5- to 7-membered ring.

More preferred examples include a $C_{1-8}$ alkylthio group substituted with a $C_{1-8}$ alkyl such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, or the like.

Examples of an optionally substituted amino group as the substituent of the 5- to 7-membered ring include amino group, an N-mono-substituted amino group, and an N,N-di-substituted amino group. Examples of said substituted amino groups include that having one or two substituents of an optionally substituted hydrocarbon group (e.g., the same group as an optionally substituted hydrocarbon group of the substituent of the 5- to 7-membered ring, more specifically, a $C_{1-8}$ alkyl group, a $C_{3-7}$ cycloalkyl group, a $C_{2-8}$ alkenyl group, a $C_{2-8}$ alkynyl group, a $C_{3-7}$ cycloalkenyl group, a $C_{6-10}$ aryl group that may have a $C_{1-4}$ alkyl group, etc.), an optionally substituted heterocyclic group (e.g., the same group as an optionally substituted heterocyclic group of the substituent of the 5- to 7-membered ring), or the formula:

—COR' (wherein R' represents hydrogen atom or an optionally substituted hydrocarbon group or an optionally substituted heterocyclic group. As for "the hydrocarbon group" or "the heterocyclic group" in "an optionally substituted hydrocarbon group" or "an optionally substituted heterocyclic group" of R' may have the same substituent as that of "the hydrocarbon group" or "the heterocyclic group" in "an optionally substituted hydrocarbon group" or "an optionally substituted heterocyclic group" of the substituent of the 5- to 7-membered ring), preferably a $C_{1-10}$ acyl group (e.g., a $C_{2-7}$ alkanoyl, benzoyl, nicotinoyl, etc.). Specific examples thereof include methylamino, dimethylamino, ethylamino, diethylamino, dipropylamino, dibutylamino, diallylamino, cyclohexylamino, phenylamino, N-methyl-N-phenylamino, acetylamino, propionylamino, benzoylamino, nicotinoylamino, and the like.

In addition, the two groups in said substituted amino groups may be combined to form a nitrogen-containing 5- to 7-membered ring (e.g., piperidino, piperadino, morpholino, thiomorpholino, etc.).

Examples of the optionally substituted acyl group as the substituent of the 5- to 7-membered ring include (i) formyl or (ii) a group where the carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group, or an aromatic group (e.g., phenyl group, pyridyl group, etc.) (e.g., acetyl, propionyl, butyryl, isobytyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.) and the like.

Examples of the optionally esterified carboxyl group as the substituent of the 5- to 7-membered ring include, in addition to carboxyl group, an alkyloxycarbonyl group, an alkenyloxycarbonyl, an alkynyloxycarbonyl, an aralkyloxycarbonyl group, an acyoxycarbonyl group, an aryloxycarbonyl group, and the like.

Examples of the alkyl group in said alkyloxycarbonyl group include a $C_{1-6}$ alkyl group (e.g., methyl, ethyl, propyl, isopropyl, butyl, isobutyl, sec-butyl, tert-butyl, etc.).

Examples of the alkenyl group in said alkenyloxycarbonyl group include a $C_{2-6}$ alkenyl group (e.g., vinyl, allyl, isopropenyl, 1-propenyl, 1-butenyl, 2-butenyl, 3-methylallyl, etc.).

Examples of the alkynyl group in said alkynyloxycarbonyl group include a $C_{2-6}$ alkynyl group (e.g., ethynyl, 2-propynyl, etc.).

The aralkyl group in said aralkyloxycarbonyl group means an aryl-alkyl group (e.g., $C_{6-10}$ aryl-$C_{1-6}$ alkyl, etc.). The aryl group in said aryl-alkyl group means a monocyclic or condensed polycyclic aromatic hydrocarbon group, and preferred examples include phenyl, naphthyl, anthryl, phenanthryl, acenaphthenyl, and the like. They may have a substituent such as a $C_{1-10}$ alkyl group, a $C_{2-10}$ alkenyl group, a $C_{2-10}$ alkynyl group, a $C_{3-8}$ cycloalkyl group, a $C_{3-8}$ cycloalkenyl group, a $C_{4-8}$ cycloalkadienyl group, an aryl group (e.g., $C_{6-14}$ aryl, etc.), an aromatic heterocyclic group (e.g., the same aromatic heterocyclic group as that of the substituent of the hydrocarbon group, the acyl group, the sulfonyl group, the sulfinyl group and the heterocyclic group of the above substituent of the 5- to 7-membered ring, etc.), a non-aromatic heterocyclic group (e.g., the same non-aromatic heterocyclic group as that of the substituent of the hydrocarbon group, the acyl group, the sulfonyl group, the sulfinyl group and the heterocyclic group of the above substituent of the 5- to 7-membered ring, etc.), an aralkyl group (e.g., a $C_{6-14}$ aryl-$C_{1-6}$ alkyl group, etc.), amino group, an N-mono-substituted amino group (e.g., the same N-mono-substituted amino group as that of the substituent of the hydrocarbon group, the acyl group, the sulfonyl group, the sulfinyl group and the heterocyclic group of the above substituent of the 5- to 7-membered ring, preferably a N-mono-$C_{1-4}$ alkylamino group, etc.), a N,N-disubstituted amino group (e.g., the same N,N-disubstituted amino group as that of the substituent in the hydrocarbon group, the acyl group, the sulfonyl group, the sulfinyl group and the heterocyclic group of the above substituent of the 5- to 7-membered ring, preferably a N,N-di-$C_{1-4}$ alkylamino group, etc.), amidino group, an acyl group (e.g., the same acyl group as that of the substituent of the hydrocarbon group, the acyl group, the sulfonyl group, the sulfinyl group and the heterocyclic group of the above substituent of the 5- to 7-membered ring, etc.), carbamoyl group, a N-mono-substituted carbamoyl group (e.g., a N-mono-$C_{1-4}$ alkyl-carbamoyl group such as methylcarbamoyl, ethylcarbamoyl, etc.; phenylcarbamoyl; etc.), a N,N-disubstituted carbamoyl group (a N,N-di-$C_{1-4}$ alkyl-carbamoyl group such as N,N-dimethylcarbamoyl, N,N-diethylcarbamoyl, etc.; piperidinocarbamoyl; morpholinocarbamoyl; etc.), sulfamoyl group, a N-mono-substituted sulfamoyl group (e.g., a N-mono-$C_{1-4}$ alkylsulfamoyl group such as methylsulfamoyl, ethylsulfamoyl, etc.; phenylsulfamoyl; p-toluenesulfamoyl; etc.), a N,N-disubstituted sulfamoyl group (e.g., a N,N-disubstituted $C_{1-4}$ alkylsulfamoyl group such as N,N-dimethylsulfamoyl, etc.; a N—$C_{1-4}$ alkyl-N-phenylsulfamoyl group such as N-methyl-N-phenylsulfamoyl, etc.; piperidinosulfamoyl; morpholinosulfamoyl; etc.), carboxyl group, a $C_{1-10}$ alkoxy-carbonyl group (e.g., methoxycarbonyl, ethoxycarbonyl, isopropoxycarbonyl, sec-butoxycarbonyl, isobutoxycarbonyl, tert-butoxycarbonyl, etc.), hydroxyl group, a $C_{1-10}$ alkoxy group, a $C_{2-10}$ alkenyloxy group, a $C_{3-7}$ cycloalkyloxy group, an aralkyloxy group (e.g., $C_{6-14}$ aryl-$C_{1-6}$ alkyloxy, etc.), an aryloxy group (e.g., $C_{6-14}$ aryloxy, etc.), mercapto group, a $C_{1-10}$ alkylthio group, an aralkylthio group (e.g., $C_{6-14}$ aryl-$C_{1-6}$ alkylthio, etc.), an arylthio group (e.g., $C_{6-14}$ arythio, etc.), sulfo group, cyano group, azido group, nitro group, nitroso group, a halogen atom, or the like. As for an alkyl group in said aryl-alkyl group, a $C_{1-6}$ alkyl group (e.g., methyl, ethyl, propyl, butyl, etc.) is preferred. Preferred examples of said aralkyl group, i.e., an aryl-alkyl group include benzyl, phenethyl, 3-phenylpropyl, (1-naphthyl)methyl, (2-naphthyl)methyl, and the like. Among them, benzyl, phenethyl, and the like are preferred.

As the acyl group in said acyloxycarbonyl group, for example, there are formyl, a $C_{2-4}$ alkanoyl group, a $C_{3-4}$ alkenoyl group, a $C_{3-4}$ alkynoyl group, and the like.

As the aryl group in said aryloxycarbonyl group, for example, there are phenyl, naphthyl, and the like.

Examples of the amidated carboxyl group as the substituent of the hydrocarbon group, the acyl group, the sulfonyl group, the sulfinyl group and the heterocyclic group of the substituent of the 5- to 7-membered ring include the carboxyl group amidated with an optionally substituted amino group as the substituent of the hydrocarbon group, the acyl group, the sulfonyl group, and the heterocyclic group of the above substituent of the 5- to 7-membered ring, each of which may be substituted.

Example of an optionally substituted phosphoryl group of the substituent of the 5- to 7-membered ring include phosphoryl group, a ($C_{1-6}$ alkoxy)phosphoryl group such as ethoxyphosphoryl, a di-($C_{1-6}$ alkoxy)phosphoryl group such as diethoxyphosphoryl, etc.; a lower ($C_{1-6}$) alkyl group substituted with an optionally esterified phosphono group such as a phosphono-$C_{1-6}$ alkyl group, a $C_{1-6}$ alkoxyphosphoryl-$C_{1-6}$ alkyl group, a di-($C_{1-6}$ alkoxy)phosphoryl-$C_{1-6}$ alkyl group such as diethoxyphosphorylmethyl, etc.; and the like.

"The hydrocarbon group", "the heterocyclic group", "the sulfinyl group", or "the sulfonyl group" in "an optionally substituted hydrocarbon group", "an optionally substituted heterocyclic group", "an optionally substituted sulfinyl group", or "an optionally substituted sulfonyl group" of the substituent of the 5- to 7-membered ring may be further substituted with 1 to 3 substituents. Examples of said substituents include a lower ($C_{1-6}$) alkyl group (e.g., methyl, ethyl, propyl, isopropyl, butyl, isobutyl, sec-butyl, tert-butyl, pentyl, isopentyl, neopentyl, hexyl, etc.); a lower ($C_{2-6}$) alkenyl group (e.g., vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 4-hexenyl, 5-hexenyl, etc.); a lower ($C_{2-6}$) alkynyl group (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.); a $C_{3-7}$ cycloalkyl group (e.g., cyclopropyl, cyclobutyl, cyclopentyl, cyclohexyl, cycloheptyl, etc.); a $C_{6-10}$ aryl group (e.g., phenyl, α-naphthyl, β-naphthyl, etc.); an aromatic heterocyclic group [e.g., (i) an aromatic 5- or 6-membered heterocyclic group having 1-4 heteroatoms selected from nitrogen atom, oxygen atom, and sulfur atom; (ii) a fused bicyclic heterocyclic group formed by condensation of an aromatic 5- or 6-membered heterocyclic group having 1 to 3 heteroatoms selected from nitrogen atom, oxygen atom, and sulfur atom with benzene ring or an aromatic 5- or 6-membered heterocyclic group having 1 to 3 heteroatoms selected from nitrogen atom, oxygen atom, and sulfur atom; (iii) a fused tricyclic heterocyclic group formed by condensation of [1] an aromatic, 5- or 6-membered heterocyclic group having 1-3 heteroatoms selected from nitrogen atom, oxygen atom and sulfur atom, [2] benzene ring, and [3] an aromatic 5- or 6-membered heterocyclic group having 1-3 heteroatoms selected from nitrogen atom, oxygen atom and sulfur atom or benzene ring, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzisothiazolyl, 1H-benztriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.]; a heterocyclic-oxy group formed by combining each of the above heterocyclic groups (i), (ii) and (iii) with oxy group; a non-aromatic heterocyclic group (e.g., a non-aromatic, 4- or 7-membered heterocyclic group having 1 to 3 heteroatoms selected from nitrogen atom, oxygen atom and sulfur atom, such as oxiranyl, azetidinyl, oxetanyl, thietanyl, pyrrolidinyl, tetrahydrofuryl, thiolanyl, piperidinyl, tetrahydropyranyl, morpholinyl, thiomorpholinyl, piperazinyl, etc.); a $C_{7-14}$ aralkyl group (e.g., a $C_{6-10}$ aryl-$C_{1-4}$ alkyl group such as benzyl, phenethyl, 1-phenylethyl, 1-phenylpropyl, 2-phenylpropyl, 3-phenylpropyl, α-naphthylmethyl, α-naphthylethyl, β-naphthylmethyl, β-naphthylethyl, etc.); amino group; a N-mono-substituted amino group [e.g., a N—($C_{1-6}$ alkyl) amino group such as methylamino, ethylamino, allylamino, cyclohexylamino, phenylamino, a N—($C_{2-6}$ alkenyl)amino group, a N—($C_{3-7}$ cycloalkyl)amino group, a N—($C_{6-10}$ aryl) amino group, etc.]; a N,N-disubstituted amino group [e.g., an amino group substituted with two substituents selected from a $C_{1-6}$ alkyl group, a $C_{2-6}$ alkenyl group, a $C_{3-7}$ cycloalkenyl group, and a $C_{6-10}$ aryl group, such as dimethylamino, diethylamino, dibutylamino, diallylamino, N-methyl-N-phenylamino, etc.]; amidino group; an acyl group (e.g., formyl, a $C_{2-8}$ alkanoyl group such as acetyl, propionyl, butyryl, isobytyryl, valeryl, isovaleryl, pivaloyl, hexanoyl, heptanoyl, octanoyl, cyclopropanecarbonyl, cyclobutanecarbonyl, cyclopentanecarbonyl, cyclohexanecarbonyl, crotonyl, 2-cyclohexenecarbonyl, benzoyl, nicotinoyl, etc.; a $C_{3-8}$ alkenoyl group; a $C_{3-7}$ cycloalkyl-carbonyl group; a $C_{3-7}$ cycloalkenyl-carbonyl group; a $C_{6-10}$ aryl-carbonyl group; a heterocyclic-carbonyl group formed by binding of an aromatic or non-aromatic 5- or 6-membered heterocyclic group having 1-3 heteroatoms selected from nitrogen atom, oxygen atom and sulfur atom with carbonyl group, etc.); carbamoyl group; a mono-substituted carbamoyl group [e.g., a N—($C_{1-6}$ alkyl) carbamoyl group such as methylcarbamoyl, ethylcarbamoyl, cyclohexylcarbamoyl, phenylcarbamoyl, etc.]; a N—($C_{2-6}$ alkenyl)carbamoyl group; a N—($C_{3-7}$ cycloalkyl)carbamoyl group; a N—($C_{6-10}$ aryl)carbamoyl group; etc.]; a N,N-disubstituted carbamoyl group [e.g., a carbamoyl group substituted with two substituents selected from a $C_{1-6}$ alkyl group, a $C_{2-6}$ alkenyl group, a $C_{3-7}$ cycloalkyl group, and a $C_{6-10}$ aryl group, such as dimethylcarbamoyl, diethylcarbamoyl, dibutylcarbamoyl, diallylcarbamoyl, N-methyl-N-phenylcarbamoyl, etc.]; sulfamoyl group, a N-mono-substituted sulfamoyl group [e.g., a N—($C_{1-6}$ alkyl)sulfamoyl group such as methylsulfamoyl, ethylsulfamoyl, cyclohexylsulfamoyl, phenylsulfamoyl, etc.; a N—($C_{2-6}$ alkenyl)sulfamoyl group; a N—($C_{3-7}$ cycloalkyl)sulfamoyl group; a N—($C_{6-10}$ aryl)sulfamoyl group; etc.], a N,N-disubstituted sulfamoyl group [e.g., sulfamoyl group substituted with two substituents selected from a $C_{1-6}$ alkyl group, a $C_{2-6}$ alkenyl group, a $C_{3-7}$ cycloalkyl group, and a $C_{6-10}$ aryl group, such as dimethylsulfamoyl, diethylsulfamoyl, dibutylsulfamoyl, diallylsulfamoyl, N-methyl-N-phenylsulfamoyl, etc.]; carboxyl group; a lower ($C_{1-6}$) alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.); hydroxyl group; a lower ($C_{1-6}$) alkoxy group (e.g., methoxy, ethoxy, propoxy, isopropoxy, butoxy, isobutoxy, sec-butoxy, tert-butoxy, pentyloxy, hexyloxy, etc.); a lower ($C_{2-10}$) alkenyloxy group (e.g., allyloxy, 2-butenyloxy, 2-pentenyloxy, 3-hexenyloxy, etc.); a $C_{3-7}$ cycloalkyloxy group (e.g., cyclopropyloxy, cyclobutyloxy, cyclopentyloxy, cyclohexyloxy, cycloheptyloxy, etc.); a $C_{6-10}$ aryloxy group (e.g., phenoxy, naphthyloxy, etc.); a $C_{7-14}$ aralkyloxy group (e.g., a $C_{6-10}$ aryl-$C_{1-4}$ alkyloxy group such as phenyl-$C_{1-4}$ alkyloxy, naphthyl-$C_{1-4}$ alkyloxy, etc.); mercapto group; a lower ($C_{1-6}$) alkylthio group (e.g., methylthio, ethylthio, propylthio, isopropylthio, butylthio, isobutylthio, sec-butylthio, tert-butylthio, pentylthio, isopentylthio, neopentylthio, hexylthio, etc.), a $C_{7-14}$ aralkylthio group (e.g., a $C_{6-0}$ aryl-$C_{1-4}$ alkylthio group such as phenyl-$C_{1-4}$ alkylthio, naphthyl-$C_{1-4}$ alkylthio, etc.); a $C_{6-10}$ arylthio group (e.g., phenylthio, naphtylthio, etc.), a lower ($C_{1-6}$) alkylsulfinyl group (e.g., methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, hexylsulfinyl, etc.); a $C_{7-14}$ aralkylsulfinyl group (e.g., a $C_{6-10}$ aryl-$C_{1-4}$ alkylsulfinyl group such as phenyl-$C_{1-4}$ alkylsulfinyl, naphthyl-$C_{1-4}$ alkylsulfinyl, etc.); a $C_{6-10}$ arylsulfinyl group (e.g., phenylsulfinyl, naphtylsulfinyl, etc.); a lower ($C_{1-6}$) alkylsulfonyl group (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, hexylsulfonyl, etc.), a $C_{7-14}$ aralkylsulfonyl group (e.g., a $C_{6-10}$ aryl-$C_{1-4}$ alkylsulfonyl group such as phenyl-$C_{1-4}$ alkylsulfonyl, naphthyl-$C_{1-4}$ alkylsulfonyl, etc.), a $C_{6-1}$ arylsulfonyl group (e.g., phenylsulfonyl, naphtylsulfonyl, etc.); sulfo group; cyano group; azido group; a halogen atom (e.g., fluorine, chlorine, bromine, iodine, etc.); nitro group; nitroso group; an optionally esterified phosphono group [e.g., phosphono group, a ($C_{1-6}$ alkoxy) phosphoryl group such as ethoxyphosphoryl, a di-($C_{1-6}$ alkoxy)phosphoryl group such as diethoxyphosphoryl, etc.]; a lower ($C_{1-6}$) alkyl group substituted with an optionally esterified phosphono group (e.g., a phosphono-$C_{1-6}$ alkyl group, a $C_{1-6}$ alkoxyphosphoryl-$C_{1-6}$ alkyl group, a di-($C_{1-6}$ alkoxy)phosphoryl-$C_{1-6}$ alkyl group such as diethoxyphosphorylmethyl, etc.); a $C_{1-6}$ haloalkyl group (e.g., a $C_{1-6}$ alkyl group substituted with 1 to 4 halogen such as trifluoromethyl, etc.); a $C_{1-6}$ haloalkoxy group (e.g., a $C_{1-6}$ alkoxy group substituted with 1 to 4 halogen such as trifluoromethoxy, etc.); and the like.

Among the above substituents, when hydroxyl group is located adjacent to a lower ($C_{1-6}$) alkoxy group, they may form $C_{1-6}$ alkylenedioxy groups such as methylenedioxy, ethylenedioxy, or the like.

The above $C_{6-10}$ aryl group, the $C_{6-10}$ aryl group as a substituent of the aromatic heterocyclic group and the N-mono-substituted amino group, the $C_{6-10}$ aryl group as a substituent of the N,N-di-substituted amino group, the $C_{6-10}$ aryl group as a substituent of the N-mono-substituted carbamoyl group, the $C_{6-10}$ aryl group as a substituent of the N,N-di-substituted carbamoyl group, the $C_{6-10}$ aryl as a substituent of the N-mono-substituted sulfamoyl group, the $C_{6-10}$ aryl group as a substituent of the N,N-disubstituted sulfamoyl group, the $C_{6-10}$ aryl group as a substituent of the $C_{6-10}$ aryloxy group, the $C_{6-10}$ aryl group of the $C_{7-14}$ aralkyloxy group, the $C_{6-10}$ aryl group of the $C_{7-14}$ aralkylthio groups, the $C_{6-10}$ aryl group of the $C_{6-10}$ arylthio groups, the $C_{6-10}$ aryl group of the $C_{7-14}$ aralkylsulfinyl groups, the $C_{6-10}$ aryl group of the $C_{6-10}$ arylsulfinyl group, the $C_{6-10}$ aryl group of the $C_{7-14}$ aralkylsulfonyl groups, and the $C_{6-10}$ aryl group in the $C_{6-10}$ arylsulfonyl group may be substituted further with 1 to 3 substituents. Examples of said substituent include a lower ($C_{1-6}$) alkyl group, amino group, a N—($C_{1-6}$ alkyl)amino group, a N,N-di-($C_{1-6}$ alkyl)amino group, amidino group, carbamoyl group, a N—($C_{1-6}$ alkyl)carbamoyl group, a N,N-di-($C_{1-6}$ alkyl)carbamoyl group, sulfamoyl group, a N—($C_{1-6}$ alkyl) sulfamoyl group, a N,N-di-($C_{1-6}$ alkyl)sulfamoyl group, carboxyl group, a lower ($C_{2-7}$) alkoxycarbonyl group, hydroxyl group, a lower ($C_{1-6}$) alkoxy group, mercapto group, a lower ($C_{1-6}$)alkylthio group, sulfo group, cyano group, azido group, a halogen atom, nitro group, nitroso group, an optionally substituted phosphono group [e.g., phosphono group, a $C_{1-6}$ alkoxyphosphoryl group, a di-($C_{1-6}$ alkoxy)phosphoryl group, etc.], a lower ($C_{0-6}$) alkyl group substituted with an optionally esterified phosphono group [e.g., a phosphono-$C_{1-6}$ alkyl group, a $C_{1-6}$ alkoxyphosphoryl-$C_{1-6}$ alkyl group, a di-($C_{1-6}$ alkoxy)phosphoryl-$C_{1-6}$ alkyl group such as diethoxyphosphorylmethyl, etc.], and the like.

Among the above substituent, when hydroxyl group is located adjacent to a lower ($C_{1-6}$) alkoxyl group, they may form a $C_{1-6}$ alkylenedioxy group such as methylenedioxy, ethylenedioxy, or the like.

The number of the substituents of the 5- to 7-membered ring is 1 to 3, preferably 1 to 2 and the substituents may be the same or different and present at any possible positions of the ring.

Q of the formula (II) is C, $CR^5$, or N.

$R^5$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- is —CO—, —CS—, —SO— or —$SO_2$—, and $Z^2$ is an optionally substituted hydrocarbon group, an optionally substituted heterocyclic group, an optionally substituted hydroxyl group, or an optionally substituted amino group).

Examples of an optionally substituted hydrocarbon group, an optionally substituted hydroxyl group, an optionally substituted amino group and an optionally substituted heterocyclic group of $R^5$ or $Z^2$ include the same groups as those exemplified with respect to the above substituents of the 5- to 7-membered ring of ring A.

Examples of halogen and an optionally substituted thiol group of $R^5$ include the same groups as those exemplified with respect to the above substituent of the 5- to 7-membered ring of ring A.

$X^1$ in the formulas (I) and (II) is $CR^1$, $CR^1R^2$, N or $NR^{13}$.

$R^1$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above).

Examples of an optionally substituted hydrocarbon group, an optionally substituted hydroxyl group, an optionally substituted amino group, an optionally substituted thiol group, halogen and an optionally substituted heterocyclic group of $R^1$ include the same groups as those exemplified with respect to the substituents of the 5- to 7-membered ring of ring A.

$R^2$ is H, or an optionally substituted hydrocarbon group, and examples of an optionally substituted hydrocarbon group of $R^2$ include the same group as that exemplified with respect to the substituent of the 5- to 7-membered ring of ring A.

$R^{13}$ is H, an optionally substituted hydrocarbon group, an optionally substituted hydroxyl group, an optionally substituted amino group, an optionally substituted heterocyclic group, or a group of the formula: -$Z^1$-$Z^2$ (wherein -$Z^1$- and $Z^2$ are as defined above).

Examples of an optionally substituted hydrocarbon group, an optionally substituted hydroxyl group, an optionally substituted amino group and an optionally substituted heterocyclic group of $R^{13}$ include the same groups as those exemplified with respect to the substituents of the 5- to 7-membered ring of ring A.

$R^1$ of the formula (III) is H, an optionally substituted hydrocarbon group, an optionally substituted hydroxyl group, an optionally substituted thiol group, an optionally substituted amino group, cyano group, a halogen atom, an optionally substituted heterocyclic group, or a group of the formula: -$Z^1$-$Z^2$ (wherein -$Z^1$- is —CO—, —CS—, —SO— or —$SO_2$—, and $Z^2$ is an optionally substituted hydrocarbon group, an optionally substituted heterocyclic group, an optionally substituted hydroxyl group, or an optionally substituted amino group).

In $R^1$ of the formula (III), preferred example of the group of the formula: $-Z^1-Z^2$ is a group of the formula: $-CONR^{20}(CR^{21}R^{22}R^{23})$, wherein $R^{20}$ is H or an optionally substituted hydrocarbon group, and $R^{21}$, $R^{22}$, and $R^{23}$ are the same or different and are an optionally substituted hydrocarbon group, an optionally substituted heterocyclic group, or $R^{20}$ and $R^{21}$ may be combined to form a ring.

Examples of an optionally substituted hydrocarbon group of $R^1$, $R^{20}$, $R^{21}$, $R^{22}$ and $R^{23}$, an optionally substituted heterocyclic group of $R^1$, $R^{21}$, $R^{22}$ and $R^{23}$, and an optionally substituted hydroxyl group, an optionally substituted amino group, an optionally substituted thiol group and halogen of $R^1$ include the same groups as those exemplified with respect to the substituents of the 5- to 7-membered ring of ring A of the formulas (I) and (II).

Preferably, at least one of $R^{21}$, $R^{22}$ and $R^{23}$ is an optionally substituted heterocyclic group which may be fused with an optionally substituted benzene ring, or an optionally substituted phenyl group which may be fused with an optionally substituted aromatic heterocyclic ring.

Examples of the "fused heterocyclic group" of the "optionally substituted heterocyclic group which may be fused with an optionally substituted benzene ring" and the "fused phenyl group" of the "optionally substituted phenyl group which may be fused with an optionally substituted aromatic heterocyclic ring" of $R^{21}$, $R^{22}$ and $R^{23}$ include the same groups as those exemplified with respect to the aromatic fused heterocyclic group as the substituents of the 5- to 7-membered ring of ring A.

Examples of these substituents include the same groups as those exemplified with respect to the substituents of the 5- to 7-membered ring of ring A of the formulas (I) and (II).

The ring formed in combination with $R^{20}$ and $R^{21}$ is preferably an optionally substituted 5- to 7-membered ring, more preferably an optionally substituted 5- or 6-membered ring, and may be fused with an optionally substituted benzene ring. Such rings include the same rings as those exemplified with respect to the "5- to 7-membered ring" of "an optionally substituted 5- to 7-membered ring" in the ring A of the formulas (I) and (II).

These rings may have 1 to 3 substituents selected from the group consisting of (1) halogen, (2) hydrogen, (3) a phenoxy which may be substituted with 1 to 3 substituents selected from halogen, hydroxyl, $C_{1-6}$ alkyl, $C_{1-6}$ alkoxy, $C_{1-6}$ acyl (e.g., formyl, $C_{2-6}$ alkanoyl, etc.), cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl, (4) $C_{1-6}$ alkoxy which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl, N,N-di-$C_{1-6}$ alkyl-carbamoyl and phenyl which may be substituted with 1 to 3 substituents selected from halogen, hydroxyl, $C_{1-6}$ alkyl, $C_{0-6}$ alkoxy, $C_{1-6}$ acyl, cyano, halogeno $C_{1-6}$ alkyl (e.g., trifluoromethyl, etc.), amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl, and (5) a $C_{1-8}$ hydrocarbon group (e.g., $C_{1-8}$ alkyl, $C_{3-7}$ cycloalkyl, $C_{2-8}$ alkenyl, $C_{2-8}$ alkynyl, $C_{3-7}$ cycloalkenyl, etc.) which may be substituted with 1 to 3 substituents selected from halogen, hydroxyl, $C_{1-6}$ alkyl, $C_{1-6}$ alkoxy, $C_{1-6}$ acyl, cyano, amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl, N,N-di-$C_{1-6}$ alkyl-carbamoyl and phenyl which may be substituted with 1 to 3 sunstituents selected from halogen, hydroxyl, $C_{1-6}$ alkyl, $C_{1-6}$ alkoxy, $C_{1-6}$ acyl, cyano, halogeno $C_{1-6}$ alkyl (e.g., trifluoromethyl, etc.), amino, mono-$C_{1-6}$ alkyl-amino, di-$C_{1-6}$ alkyl-amino, $C_{1-6}$ alkyl-sulfanyl, $C_{1-6}$ alkyl-sulfinyl, $C_{1-6}$ alkyl-sulfonyl, $C_{1-6}$ alkoxy-carbonyl, carbamoyl, N—$C_{1-6}$ alkyl-carbamoyl and N,N-di-$C_{1-6}$ alkyl-carbamoyl.

Specific examples of these substituents include the same groups as those exemplified with respect to the substituents of the 5- to 7-membered ring of ring A of the formulas (I) and (II).

$R^{1a}$ of the formula (IIIa) is (1) an optionally substituted heterocyclic group or (2) a group of the formula: $-Z^{1a}-Z^{2a}$ (wherein $-Z^{1a}-$ is $-CO-$, $-CS-$, $-SO-$ or $-SO_2-$, and $Z^{2a}$ is (i) an optionally substituted heterocyclic group, (ii)-$NR^{20a}(CR^{21a}R^{22a}R^{23a})$ (wherein (a) $R^{20a}$ is H or an optionally substituted hydrocarbon group; and $R^{21a}$ is an optionally substituted heterocyclic group which may be fused with an optionally substituted benzene ring, or an optionally substituted $C_{6-10}$ aryl group which may be fused with an optionally substituted aromatic heterocyclic ring and $R^{22a}$ and $R^{23a}$ are the same or different and are an optionally substituted hydrocarbon group or an optionally substituted heterocyclic group or $R^{22a}$ and $R^{23a}$ may be combined to form a ring, or (b) $R^{20a}$ is H or an optionally substituted hydrocarbon group; and $R^{21a}$, $R^{22a}$ and $R^{23a}$ are the same or different and are an optionally substituted $C_{1-8}$ aliphatic hydrocarbon group, provided that the sum total of the number of carbon atoms is 7 or more), (iii)-$NR^{20a}R^{25a}$ wherein $R^{20a}$ is as defined above and $R^{25a}$ is an optionally substituted $C_{6-10}$ aryl-$C_{2-4}$ alkyl, $C_{6-10}$ aryloxy-$C_{2-4}$ alkyl, $C_{6-10}$ arylamino-$C_{2-4}$ alkyl, $C_{7-14}$ aralkylamino-$C_{2-4}$ alkyl, heterocyclic ring-$C_{2-4}$ alkyl or heterocyclic group), (iv) a substituted 5- to 7-membered cyclic amino group, or (v) $-OR^{24a}$ (wherein $R^{24a}$ is (a) an optionally substituted $C_{7-14}$ aralkyl group, (b) an optionally substituted $C_{3-7}$ alicyclic hydrocarbon group, (c) an optionally substituted $C_{7-24}$ aliphatic hydrocarbon group, or (d) an optionally substituted heterocyclic group)).

Examples of an optionally substituted hydrocarbon group of $R^{20a}$, $R^{22a}$ and $R^{23a}$ and an optionally substituted heterocyclic group of $R^{1a}$, $Z^{2a}$, $R^{21a}$, $R^{22a}$ and $R^{23a}$ include the same groups as those exemplified with respect to the substituents of the 5- to 7-membered ring of ring A of the formulas (I) and (II).

Examples of the "fused heterocyclic group" of the "optionally substituted heterocyclic group which may be fused with an optionally substituted benzene ring" and the "fused phenyl group" of "an optionally substituted phenyl group which may be fused with an optionally substituted aromatic heterocyclic ring" of $R^{21a}$, $R^{22a}$ and $R^{23a}$ include the same groups as those exemplified with respect to the aromatic fused heterocyclic group as the substituents of the 5- to 7-membered ring of ring A.

Examples of the ring formed in combination with $R^{20a}$ and $R^{21a}$ and the substituents thereof include the same rings and substituents as those exemplified with respect to the ring formed in combination with $R^{20}$ and $R^{21}$ and the substituents thereof.

Examples of the "optionally substituted $C_{1-8}$ aliphatic hydrocarbon group" of $R^{20a}$ include the same groups as those exemplified with respect to the aliphatic hydrocarbon group as the substituents of the 5- to 7-membered ring of ring A.

Examples of the "optionally substituted $C_{7-14}$ aralkyl group", the "optionally substituted $C_{3-7}$ alicyclic hydrocarbon group" and the "optionally substituted heterocyclic group" of $R^{24a}$ include the same groups as those exemplified with respect to the substituents of the 5- to 7-membered ring of ring A respectively.

Examples of the "$C_{7-24}$ aliphatic hydrocarbon group" of the "optionally substituted $C_{7-24}$ aliphatic hydrocarbon group" in $R^{24a}$ include, for example, $C_{7-24}$ alkyl, $C_{7-24}$ alkenyl, $C_{7-24}$ alkynyl, $C_{7-24}$ alkadienyl, $C_{7-24}$ alkadiynyl such as heptyl, octyl, 1-heptenyl, 1-octenyl, 1-heptynyl, 1-octynyl, etc.

Examples of the substituents of the "optionally substituted $C_{7-24}$ aliphatic hydrocarbon group" in $R^{24a}$ include the same substituents as those exemplified with respect to the substituents of the hydrocarbon group as the substituents of 5- to 7-membered ring of ring A.

In the formula (IIIa), $R^{1a}$ is preferably (1) an optionally substituted 5- to 7-membered aromatic or non-aromatic heterocyclic group having 1-4 hetero atoms selected from nitrogen atom, oxygen atom and sulfur atom, or (2) a group of the formula: —CO-$Z^{2c}$ (wherein $Z^{2c}$ is (i) an optionally substituted 5- to 7-membered aromatic or non-aromatic heterocyclic group having 1-4 hetero atoms selected from nitrogen atom, oxygen atom and sulfur atom, (ii) —$NR^{20c}$($CR^{21c}R^{22c}R^{23c}$) (wherein (a) $R^{20c}$ is H or an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group; and $R^{21c}$ is 1) an optionally substituted 5- to 7-membered aromatic or non-aromatic heterocyclic group having 1-4 hetero atoms selected from nitrogen atom, oxygen atom and sulfur atom, which may be fused with an optionally substituted benzene ring, or 2) an optionally substituted $C_{6-10}$ aryl group (e.g., phenyl group, etc.) which may be fused with an optionally substituted 5- to 7-membered aromatic heterocyclic ring having 1-4 hetero atoms selected from nitrogen atom, oxygen atom and sulfur atom; and $R^{22c}$ and $R^{23c}$ are the same or different and are an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $c_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group, or an optionally substituted 5- to 7-membered aromatic or non-aromatic heterocyclic group having 1-4 hetero atoms selected from nitrogen atom, oxygen atom and sulfur atom or $R^{22c}$ and $R^{23c}$ may be combined to form a $C_{3-7}$ carbon ring, or (b) $R^{20c}$ is H or an optionally substituted hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group; and $R^{21c}$, $R^{22c}$ and $R^{23c}$ are the same or different and are an optionally substituted $C_{1-8}$ aliphatic hydrocarbon group, provided that the sum total of the number of carbon atoms is 7 or more), (iii) —$NR^{20c}R^{25c}$ (wherein $R^{20c}$ is as defined above and $R^{25c}$ is an optionally substituted $C_{6-10}$ aryl-$C_{2-4}$ alkyl, $C_{6-10}$ aryloxy-$C_{2-4}$ alkyl, $C_{6-10}$ arylamino-$C_{2-4}$ alkyl, $C_{7-14}$ aralkylamino-$C_{2-4}$ alkyl, 5- to 7-membered heterocyclic ring (having 1-4 hetero atoms selected from nitrogen atom, oxygen atom and sulfur atom)-$C_{2-4}$ alkyl or 5- to 7-membered heterocyclic group having 1-4 hetero atoms selected from nitrogen atom, oxygen atom and sulfur atom), (iv) a substituted 5- to 7-membered cyclic amino group (e.g., piperidino, piperadino, morpholino, thiomorpholino, etc.), or (v) —$OR^{24c}$ (wherein $R^{24c}$ is (a) an optionally substituted $C_{7-14}$ aralkyl group, (b) an optionally substituted $C_{3-7}$ alicyclic hydrocarbon group, (c) an optionally substituted $C_{7-24}$ aliphatic hydrocarbon group, or (d) an optionally substituted 5- to 7-membered aromatic or non-aromatic heterocyclic group having 1-4 hetero atoms selected from nitrogen atom, oxygen atom and sulfur atom;

wherein said substituents for $R^{1a}$, $Z^{2c}$, $R^{20c}$, $R^{21c}$, $R^{22c}$, $R^{23c}$, $R^{24c}$ and $R^{25c}$ are 1 to 3 substituents selected from the group consisting of 1) $C_{1-6}$ alkyl,
2) $C_{2-6}$ alkenyl,
3) $C_{2-6}$ alkynyl,
4) $C_{3-7}$ cycloalkyl,
5) $C_{6-10}$ aryl which may be substituted with 1 to 3 substituents selected from the group consisting of $C_{1-6}$ alkyl, amino, N—($C_{1-6}$ alkyl)amino, N,N-di-($C_{1-6}$ alkyl)amino, amidino, carbamoyl, N—($C_{1-6}$ alkyl)carbamoyl, N,N-di-($C_{1-6}$ alkyl)carbamoyl, sulfamoyl, N—($C_{1-6}$ alkyl)sulfamoyl, N,N-di-($C_{1-6}$ alkyl)sulfamoyl, carboxyl, $C_{2-7}$ alkoxycarbonyl, hydroxyl, $C_{1-6}$ alkoxy, mercapto, $C_{1-6}$ alkylthio, sulfo, cyano, azido, halogen, nitro, nitroso, phosphono, $C_{1-6}$ alkoxyphosphoryl, di-($C_{1-6}$ alkoxy)phosphoryl and $C_{1-6}$ alkyl substituted with phosphono, $C_{1-6}$ alkoxyphosphoryl and di-($C_{1-6}$ alkoxy)phosphoryl (hereinafter the group of 5) is referred to as group "C"),
6) aromatic heterocyclic group selected from (a) aromatic 5- or 6-membered heterocyclic group having 1-4 hetero atoms selected from nitrogen atom, oxygen atom and sulfur atom, (b) fused bicyclic heterocyclic group formed by condensation of an aromatic 5- or 6-membered heterocyclic group having 1 to 3 hetero atoms selected from nitrogen atom, oxygen atom and sulfur atom with benzene ring or an aromatic 5- or 6-membered heterocyclic group having 1 to 3 hetero atoms selected from nitrogen atom, oxygen atom and sulfur atom and (c) fused tricyclic heterocyclic group formed by condensation of [1] an aromatic 5- or 6-membered heterocyclic group having 1-3 hetero atoms selected from nitrogen atom, oxygen atom and sulfur atom, [2] benzene ring, and [3] an aromatic 5- or 6-membered heterocyclic group having 1-3 hetero atoms selected from nitrogen atom, oxygen atom and sulfur atom or benzene ring,
7) heterocyclic-oxy group formed by combining each of the above aromatic heterocyclic groups (a), (b) and (c) with oxy group,
8) non-aromatic 4- or 7-membered heterocyclic group having 1 to 3 hetero atoms selected from nitrogen atom, oxygen atom and sulfur atom,
9) $C_{7-14}$ aralkyl which may be substituted with 1 to 3 substituents selected from the group "C", 10) amino group,
11) N-mono-substituted amino selected from N—($C_{1-6}$ alkyl) amino, N—($C_{2-6}$ alkenyl)amino, N—($C_{3-7}$ cycloalkyl) amino group and N—($C_{6-10}$ aryl)amino which may be substituted with 1 to 3 substituents selected from the group "C",
12) amino substituted with two substituents selected from $C_{1-6}$ alkyl, $C_{2-6}$ alkenyl, $C_{3-7}$ cycloalkenyl and $C_{6-10}$ aryl which may be substituted with 1 to 3 substituents selected from the group "C",
13) amidino,
14) acyl selected from $C_{2-8}$ alkanoyl, $C_{3-8}$ alkenoyl, $C_{3-7}$ cycloalkyl-carbonyl, $C_{3-7}$ cycloalkenyl-carbonyl, $C_{6-10}$ aryl-carbonyl which may be substituted with 1 to 3 substituents selected from the group "C", and heterocyclic-carbonyl formed by binding of an aromatic or non-aromatic 5- or 6-membered heterocyclic group having 1-3 hetero atoms selected from nitrogen atom, oxygen atom and sulfur atom with carbonyl,
15) carbamoyl,
16) mono-substituted carbamoyl group selected from N—($C_{1-6}$ alkyl)carbamoyl, N—($C_{2-6}$ alkenyl)carbamoyl, N—($C_{3-7}$ cycloalkyl)carbamoyl and N—($C_{6-10}$ aryl)carbamoyl which may be substituted with 1 to 3 substituents selected from the group "C",
17) carbamoyl substituted with two substituents selected from $C_{1-6}$ alkyl, $C_{2-6}$ alkenyl, $C_{3-7}$ cycloalkyl and $C_{6-10}$ aryl which may be substituted with 1 to 3 substituents selected from the group "C",
18) sulfamoyl,
19) N-mono-substituted sulfamoyl selected from N—($C_{1-6}$ alkyl)sulfamoyl, N—($C_{2-6}$ alkenyl)sulfamoyl, N—($C_{3-7}$ cycloalkyl)sulfamoyl and N—($C_{6-10}$ aryl)sulfamoyl which may be substituted with 1 to 3 substituents selected from the group "C",
20) sulfamoyl substituted with two substituents selected from $C_{1-6}$ alkyl, $C_{2-6}$ alkenyl, $C_{3-7}$ cycloalkyl and $C_{6-10}$ aryl which may be substituted with 1 to 3 substituents selected from the group "C",
21) carboxyl,
22) $C_{1-6}$ alkoxy-carbonyl,
23) hydroxyl,
24) $C_{1-6}$ alkoxy,
25) $C_{2-10}$ alkenyloxy,
26) $C_{3-7}$ cycloalkyloxy,
27) $C_{6-10}$ aryloxy which may be substituted with 1 to 3 substituents selected from the group "C",
28) $C_{7-14}$ aralkyloxy which may be substituted with 1 to 3 substituents selected from the group "C",
29) mercapto,
30) $C_{1-6}$ alkylthio,
31) $C_{7-14}$ aralkylthio which may be substituted with 1 to 3 substituents selected from the group "C",
32) $C_{6-10}$ arylthio which may be substituted with 1 to 3 substituents selected from the group "C",
33) $C_{1-6}$ alkylsulfinyl,
34) $C_{7-14}$ aralkylsulfinyl which may be substituted with 1 to 3 substituents selected from the group "C",
35) $C_{6-10}$ arylsulfinyl which may be substituted with 1 to 3 substituents selected from the group "C",
36) $C_{1-6}$ alkylsulfonyl,
38) $C_{7-14}$ aralkylsulfonyl which may be substituted with 1 to 3 substituents selected from the group "C",
39) $C_{6-10}$ arylsulfonyl which may be substituted with 1 to 3 substituents selected from the group "C",
40) sulfo,
41) cyano,
42) azido,
43) halogen,
44) nitro,
45) nitroso,
46) phosphono,
47) $C_{1-6}$ alkoxy-phosphoryl
48) di-$C_{1-6}$ alkoxy-phosphoryl,
49) $C_{1-6}$ alkyl substituted with phosphono, $C_{1-6}$ alkoxyphosphoryl or di-($C_{1-6}$ alkoxy)phosphoryl
50) $C_{1-6}$ alkyl substituted with 1 to 4 halogen atoms
51) $C_{1-6}$ alkoxy substituted with 1 to 4 halogen atoms and
52) $C_{1-6}$ alkylenedioxy (hereinafter the group of above 1) to 52) is referred to as group "B")

Specific examples of these substituents include the same groups as those exemplified with respect to the substituents of the 5- to 7-membered ring of ring A.

As $R^{1a}$ of the formula (IIIa), more preferred is the group represented by the formula: —$CONR^{20c}(CR^{21c}R^{22c}R^{23c})$ (wherein $R^{20c}$, $R^{21c}$, $R^{22c}$ and $R^{23c}$ are as defined above).

Further more preferably, $R^{1a}$ is (1) a 5- to 7-membered aromatic heterocyclic group having 1-4 hetero atoms selected from nitrogen atom, oxygen atom and sulfur atom (e.g., 1,3,4-oxadiazolyl, 1,3,4-thiadiazolyl, etc.) which is substituted with $C_{1-4}$ alkyl-$C_{7-14}$ aralkyl (e.g., 1-ethyl-1-(4-methylphenyl)propyl, etc.), or (2) a group represented by the formula: —CO-$Z^{2c'}$ (wherein $Z^{2c'}$ is (i) —$NR^{20c'}(CR^{21c'}R^{22c'}R^{23c'})$ (wherein (a) $R^{20c'}$ is H or $C_{1-6}$ alkyl; $R^{21c'}$ is a $C_{6-10}$ aryl group or a 5- to 7-membered aromatic heterocyclic group having 1-4 hetero atoms selected from nitrogen atom, oxygen atom and sulfur atom, each of which may be substituted with 1 to 3 substituents selected from the group consisting of halogen, $C_{1-6}$ alkyl, $C_{2-6}$ alkenyl, halogeno $C_{1-6}$ alkyl, hydroxy-$C_{1-6}$ alkyl, $C_{1-6}$ alkoxy, carboxyl, $C_{1-6}$ alkoxy-carbonyl, $C_{1-6}$ alkyl-carbonyloxy, $C_{1-6}$ alkyl-carbonyloxy-$C_{1-6}$ alkyl, carboxy-$C_{1-6}$ alkoxy, $C_{1-6}$ alkoxy-carbonyl-$C_{1-6}$ alkyl, $C_{1-6}$ alkoxy-carbonyl-$C_{1-6}$ alkoxy, $C_{1-6}$ alkoxy-carbonyl-$C_{1-6}$ alkoxy-$C_{1-6}$ alkyl, carbonyl, $C_{1-6}$ alkyl-carbonyl, amino, mono- or di-$C_{1-6}$ alkylamino, phenyl (said phenyl may be substituted with 1 to 3 substituents selected from halogen, $C_{1-6}$ alkyl and halogeno $C_{1-6}$ alkyl) and a 5- to 7-membered aromatic heterocyclic group having 1-4 hetero atoms selected from nitrogen atom, oxygen atom and sulfur atom; $R^{22c'}$ and $R^{23c'}$ are the same or different and are $C_{1-6}$ alkyl group, $C_{5-7}$ cycloalkyl group, phenyl group (said phenyl group may be substituted with 1 to 3 substituents selected from $C_{1-6}$ alkyl, halogeno $C_{1-6}$ alkyl and $C_{1-6}$ alkoxy), $C_{1-6}$ alkoxy-carbonyl-$C_{1-6}$ alkyl group or $C_{1-6}$ alkyl-carbonyl-$C_{2-6}$ alkenyl group, or $R^{22c}$ and $R^{23c}$ may be combined each other to form a $C_{3-7}$ carbon ring; or (b) $R^{20c'}$ and $R^{21c'}$ are combined each other to form a 5- to 7-membered ring and said ring may be substituted with $C_{1-6}$ alkoxy or $C_{7-14}$ aralkyl, and $R^{22c'}$ and $R^{23c'}$ are $C_{1-6}$ alkyl group), (ii) —$NR^{20c'}R^{25c'}$ (wherein $R^{20c'}$ is H or $C_{1-6}$ alkyl group; $R^{25c'}$ is $C_{6-10}$ aryl-$C_{2-4}$ alkyl group, $C_{6-10}$ aryloxy-$C_{2-4}$ alkyl group, $C_{6-10}$ arylamino-$C_{2-4}$ alkyl group, $C_{7-14}$ aralkylamino-$C_{2-4}$ alkyl group, 5- to 7-membered heterocyclic ring-$C_{2-4}$ alkyl group or 5- to 7-membered heterocyclic group, each of which may be substituted with 1 or 2 substituents selected from the group consisting of halogen, $C_{1-6}$ alkyl, $C_{6-10}$ aryl, $C_{1-6}$ alkoxy, amino, mono- or di-$C_{1-6}$ alkylamino, 5- to 7-membered cyclic amino, hydroxy, oxo, $C_{1-6}$ alkoxy-carbonyl and cyano), or (iii) a 5- to 7-membered cyclic amino group which is substituted with 1 to 3 substituents selected from the group consisting of halogen, $C_{1-6}$ alkyl, $C_{2-6}$ alkenyl, $C_{1-6}$ alkoxy- $C_{1-6}$ alkyl, $C_{5-7}$ cycloalkyl, $C_{6-10}$ aryl (said aryl may have 1 or 2 substituents selected from halogen, $C_{1-6}$ alkyl, halogeno $C_{1-6}$ alkyl and $C_{1-6}$ alkoxy), $C_{7-14}$ aralkyl (said aralkyl may have 1 or 2 substituents selected from halogen, $C_{1-6}$ alkyl, halogeno $C_{1-6}$ alkyl and $C_{1-6}$ alkoxy), hydroxy, hydroxy-$C_{1-6}$ alkyl, $C_{6-10}$ aryloxy (said aryloxy may have 1 or 2 substituents selected from halogen, $C_{1-6}$ alkyl, halogeno $C_{1-6}$ alkyl and $C_{1-6}$ alkoxy), $C_{7-14}$ aralkyloxy, $C_{6-10}$ aryl-carbonyl, carboxyl, $C_{1-6}$ alkoxy-carbonyl, carbamoyl, $C_{6-10}$ aryl-carbamoyl, amino, $C_{6-10}$ aryl-carbonylamino, $C_{1-6}$ alkyl-carbonylamino, $C_{1-6}$ alkoxy-carbonylamino, $C_{6-10}$ arylthio, $C_{6-10}$ arylsulfonyl, cyano, oxo and 5- to 7-membered heterocyclic group.).

$R^3$ of the formulas (II), (III) and (IIIa) is H, an optionally substituted hydrocarbon group, an optionally substituted hydroxyl group, an optionally substituted amino group, an optionally substituted heterocyclic group, or a group of the formula: -$Z^1$-$Z^2$ (wherein -$Z^1$- and $Z^2$ are as defined above).

Examples of an optionally substituted hydrocarbon group, an optionally substituted hydroxyl group, an optionally substituted amino group and an optionally substituted heterocyclic group of $R^3$ include the same groups as those exemplified with respect to the substituents of the 5- to 7-membered ring of ring A.

$R^3$ is preferably H, a $C_{1-6}$ alkyl group or a $C_{7-14}$ aralkyl group, and more preferably $R^3$ is H.

Y in the formulas (I), (II), (III) and (IIIa) is C, $CR^4$, or N.

$R^4$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above).

Examples of an optionally substituted hydrocarbon group, an optionally substituted hydroxyl group, an optionally substituted amino group, an optionally substituted heterocyclic group and halogen of $R^4$ include the same groups as those exemplified with respect to the substituents of the 5- to 7-membered ring of ring A.

Y is preferably CH.

$R^8$ of the formulas (III) and (IIIa) is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above).

Examples of an optionally substituted hydrocarbon group, an optionally substituted hydroxyl group, an optionally substituted amino group, an optionally substituted thiol group, halogen atom and an optionally substituted heterocyclic group of $R^8$ include the same groups as those exemplified with respect to the substituents of the 5- to 7-membered ring of ring A.

$R^8$ is preferably H, a $C_{1-6}$ alkyl group, a $C_{1-6}$ alkylthio group or a $C_{1-6}$ alkoxy group which may be substituted with hydroxyl group, and more preferably $R^8$ is H or a $C_{1-6}$ alkyl group.

Ar in the formulas (I), (II), (III) and (IIIa) is an optionally substituted cyclic group.

Examples of the optionally substituted cyclic group of Ar include an optionally substituted aromatic or non-aromatic hydrocarbon ring group or an optionally substituted aromatic or non-aromatic heterocyclic group, and the like.

Examples of the aromatic hydrocarbon ring group and the heterocyclic group of Ar include the same aromatic hydrocarbon group and heterocyclic group as exemplified with respect to the above substituents of the 5- to 7-membered ring of ring A.

Examples of the non-aromatic hydrocarbon ring group include a saturated alicyclic hydrocarbon group having 3-7 carbon atoms (e.g., cycloalkyl group, etc.) such as cyclopropyl, cyclobutyl, cyclopentyl, cyclohexyl, cycloheptyl, and the like; an unsaturated alicyclic hydrocarbon group having 3-7 carbon atoms (e.g., cycloalkenyl group, cycloalkadienyl group, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.; a partly saturated and fused bicyclic hydrocarbon group [preferably, $c_{9-10}$ partly saturated and fused bicyclic hydrocarbon group, etc. (including those where the benzene ring is combined to 5- or 6-membered non-aromatic cyclic hydrocarbon group)] such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc.; and the like.

Examples of the substituent of an optionally substituted aromatic ring group and an optionally substituted heterocyclic group of Ar include the same groups as those exemplified with respect to the above substituents of the 5- to 7-membered ring of ring A.

Ar is preferably (1) a $C_{6-10}$ aryl group, (2) a 5- to 7-membered aromatic or non-aromatic heterocyclic group having 1-4 hetero atoms selected from nitrogen atom, oxygen atom and sulfur atom, or (3) a $C_{3-7}$ saturated or unsaturated alicyclic hydrocarbon group, each of which may be substituted with 1 to 3 substituents selected from the group "B".

More preferably, Ar is a $C_{6-10}$ aryl group which may be substituted with 1 to 3 substituents selected from the group "B", a 5- to 7-membered aromatic heterocyclic group having 1-4 hetero atoms selected from nitrogen atom, oxygen atom and sulfur atom which may be substituted with 1 to 3 substituents selected from the group "B", or a $C_{3-7}$ saturated or unsaturated alicyclic hydrocarbon group.

Further more preferably, Ar is (1) a $C_{6-10}$ aryl group (e.g., phenyl, naphthyl, etc.) which may be substituted with 1 or 2 substituents selected from the group consisting of halogen atom, $C_{1-6}$ alkyl, $C_{1-6}$ alkoxy, hydroxy, $C_{7-14}$ aralkyloxy and mono- or di-$C_{1-4}$ alkylamino, (2) a 5- to 7-membered aromatic heterocyclic group having 1-4 hetero atoms selected from nitrogen atom, oxygen atom and sulfur atom (e.g., pyridyl, furyl, thiazolyl, thienyl, etc.) which may be substituted with $C_{1-4}$ alkyl or (3) a $C_{5-7}$ cycloalkyl group (e.g., cyclohexyl etc.), and most preferably, Ar is an optionally halogenated phenyl group.

$R^9$ and $R^{10}$ of the formulas (II), (III) and (IIIa) are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: -$Z^1$-$Z^2$ (wherein -$Z^1$- and $Z^2$ are as defined above), or $R^9$ and $R^{10}$ may be combined to form an oxo group, methylene group or a ring.

Examples of an optionally substituted hydrocarbon group, an optionally substituted hydroxyl group, an optionally substituted amino group, an optionally substituted thiol group, a halogen atom and an optionally substituted heterocyclic group of $R^9$ and $R^{10}$ include the same groups as those exemplified with respect to the above substituents of the 5- to 7-membered ring of ring A.

One of $R^9$ and $R^{10}$ is preferably a hydrogen atom or $C_{1-6}$ alkyl group which may be substituted with 1 to 3 substituents selected from the group "B" and the other is (1) a hydrocarbon group selected from $C_{1-8}$ saturated aliphatic hydrocarbon group, $C_{2-8}$ unsaturated aliphatic hydrocarbon group, $C_{3-7}$ saturated alicyclic hydrocarbon group, $C_{3-7}$ unsaturated alicyclic hydrocarbon group, $C_{9-10}$ partly saturated and fused bicyclic hydrocarbon group, $C_{3-7}$ saturated or unsaturated alicyclic-$C_{1-8}$ saturated or unsaturated aliphatic hydrocarbon group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl group, $C_{6-10}$ aryl group and $C_{7-14}$ aralkyl group, each of which may be substituted with 1 to 3 substituents selected from the group "B" or (2) a 5- to 7-membered aromatic or non-aromatic heterocyclic group having 1-4 hetero atoms selected from nitrogen atom, oxygen atom and sulfur atom, which may be substituted with 1 to 3 substituents selected from the group "B", or $R^9$ and $R^{10}$ may be combined to form a $C_{5-7}$ carbon ring.

More preferably, one of $R^9$ and $R^{10}$ is preferably a hydrogen atom or $C_{1-6}$ alkyl group and the other is an optionally halogenated $C_{1-6}$ alkyl group, $C_{6-10}$ aryl group, $C_{7-10}$ aralkyl group or a 5- to 7-membered aromatic heterocyclic group, or $R^9$ and $R^{10}$ are a $C_{5-7}$ carbon ring formed by combining together.

Examples of $R^{11}$ and $R^{12}$ of the formula (II) are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^{1'}-Z^2$ (wherein $-Z^{1'}-$ is —CS—, —SO— or —$SO_2$—, and $Z^2$ is as defined above).

Examples of an optionally substituted hydrocarbon group, an optionally substituted hydroxyl group, an optionally substituted amino group, an optionally substituted thiol group, a halogen atom and an optionally substituted heterocyclic group of $R^{11}$ and $R^{12}$ include the same groups as those exemplified with respect to the above substituents of the 5- to 7-membered ring of ring A.

$R^9$ and $R^{10}$, or $R^{11}$ and $R^{12}$ may be combined to form an oxo group, methylene group or a ring such as a $C_{3-6}$ saturated or unsaturated carbon ring (e.g., cyclopropyl, cyclobutyl, cyclopentyl, cyclohexyl, 1-cyclopentenyl, 2-cyclopentenyl, 3-cyclopentenyl, 1-cyclohexenyl, 2-cyclohexenyl, 3-cyclohexenyl, etc.); or $R^{10}$ and $R^{11}$ may be combined to form a ring such as a $C_{3-6}$ saturated or unsaturated carbon ring (e.g., cyclopropyl, cyclobutyl, cyclopentyl, cyclohexyl, 1-cyclopentenyl, 2-cyclopentenyl, 3-cyclopentenyl, 1-cyclohexenyl, 2-cyclohexenyl, 3-cyclohexenyl, etc.).

--- is a single bond or a double bond.

Z in the formula (I) is $CR^5$, $CR^5R^6$, N or $NR^7$, and $CR^5$ is as defined above.

$R^6$ is H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1-$ and $Z^2$ are as defined above)).

Examples of an optionally substituted hydrocarbon group, an optionally substituted hydroxyl group, an optionally substituted amino group, an optionally substituted thiol group, and an optionally substituted heterocyclic group of $R^6$ include the same groups as those exemplified with respect to the above substituents of the 5- to 7-membered ring of ring A.

$R^7$ is H, an optionally substituted hydrocarbon group, an optionally substituted hydroxyl group, an optionally substituted amino group, cyano group, a halogen atom, an optionally substituted heterocyclic group, or a group of the formula: $-Z^1-Z^2$ (wherein $-Z^1-$ and $Z^2$ are as defined above)).

Examples of an optionally substituted hydrocarbon group, an optionally substituted hydroxyl group, an optionally substituted amino group, a halogen atom and an optionally substituted heterocyclic group of $R^7$ include the same groups as those exemplified with respect to the above substituents of the 5- to 7-membered ring of ring A.

$R^5$, $R^6$ and $R^7$ may be the same or different.

$R^5$ is H, an optionally substituted hydrocarbon group, an optionally substituted hydroxyl group, an optionally substituted amino group, an optionally substituted thiol group, an optionally substituted sulfonyl group or an optionally substituted sulfinyl group.

Examples of an optionally substituted hydrocarbon group, an optionally substituted hydroxyl group, an optionally substituted amino group, an optionally substituted thiol group, an optionally substituted sulfonyl group and an optionally substituted sulfinyl group of R include the same groups as those exemplified with respect to the above substituents of the 5- to 7-membered ring of ring A.

R and Z may be combined to form a ring B

Ring B in the formula (I) is an optionally substituted 5- to 7-membered heterocyclic ring and examples thereof include the same group as that exemplified with respect to the 5- to 7-membered ring of ring A.

$X^2$ of the formula (I) is N or $NR^3$ and $R^3$ are as defined above.

$X^3$ of the formula (III) and (IIIa) is a bond, oxygen atom, an optionally oxidized sulfur atom, N, $NR^{7'}$, or an optionally substituted bivalent $C_{1-2}$ hydrocarbon group.

$R^{7'}$ is H, an optionally substituted hydrocarbon group, an optionally substituted hydroxyl group, an optionally substituted amino group, an optionally substituted heterocyclic group, or a group of the formula $-Z^{1'}-Z^2$ (wherein $-Z^{1'}-$ is —CS—, —SO— or —$SO_2$—, and $Z^2$ is as defined above)).

Examples of an optionally substituted hydrocarbon group, an optionally substituted hydroxyl group, an optionally substituted amino group, and an optionally substituted heterocyclic group of $R^{7'}$ include the same groups as those exemplified with respect to the substituents of the 5- to 7-membered ring of ring A.

Examples of an optionally substituted bivalent $C_{1-2}$ hydrocarbon group include —$CH_2$—, —$(CH_2)_2$—, —CH=CH— and the like which may be substituted with one or two substituents selected from those exemplified with respect to the substituents of the 5- to 7-membered ring of ring A.

In the formula (IIIa), $X^3$ is preferably $CH_2$.

Prefered compounds of the formula (I) include not only the compounds of the formula (IIIa) but also the other compounds wherein $-Z^1-$ is —CO— and $Z^2$ is an optionally substituted hydroxyl group (e.g., hydroxy, $C_{1-6}$ alkoxy, etc.) or amino group which is substituted with an optionally substituted phenyl group or an optionally substituted condensed phenyl group (e.g., phenylamino, 3,5-dimethoxyphenylamino, 3-biphenylylamino, 2,3-dihydro-1H-inden-5-yl-amino, quinolin-6-yl-amino, etc.).

In the formula (II), (1) when ring A is a 6-membered ring and Q is C or $CR^5$, $X^1$ is $C-Z^1-Z^2$, $C(-Z^1-Z^2)R^2$ or $N-Z^1-Z^2$, and both $R^9$ and $R^{10}$ are not H, or $R^9$ and $R^{10}$ are not combined to form an oxo group, or $R^{10}$ and $R^{11}$ are not combined to form a 5-membered ring;

(2) when ring A is a 6-membered ring and Q is N, $X^1$ is $C-Z^1-Z^2$, $C(-Z^1-Z^2)R^2$ or $N-Z^1-Z^2$, and $R^9$ and $R^{10}$ are not combined to form an oxo group;

(3) when ring A is a 5-membered ring and Q is C or $CR^5$, $X^1$ is $C-Z^1-Z^2$, $C(-Z^1-Z^2)R^2$ or $N-Z^1-Z^2$, and $Z^2$ is an optionally substituted amino group; and (4) when ring A is a 5-membered ring and Q is N, at least one of $R^9$ and $R^{10}$ is $CHR^{15}R^{16}$ (wherein $R^{15}$ and $R^{16}$ are the same or different and are H, an optionally substituted hydrocarbon group, an optionally substituted hydroxyl group, an optionally substituted amino group, an optionally substituted thiol group, a halogen atom, an optionally substituted heterocyclic group, or a group of the formula: $-Z^1-Z^2$ (wherein $-Z^1-$ and $Z^2$ are as defined above).

Examples of an optionally substituted hydrocarbon group, an optionally substituted hydroxyl group, an optionally substituted amino group, an optionally substituted thiol group, a halogen atom and an optionally substituted heterocyclic group include the same groups as those exemplified with respect to the above substituents of the 5- to 7-membered ring of ring A.

In the formulas (II) and (III), preferably, $R^1$ is a group of the formula: $-Z^1-Z^2$; $Z^1$ is —CO— and $Z^2$ is an optionally substituted hydroxyl group or an optionally substituted amino group; Ar is an optionally substituted aromatic ring group; and both $R^9$ and $R^{10}$ are the same or different and are $C_{1-6}$ alkyl groups or $R^9$ and $R^{10}$ are combined to form a ring such as a saturated or unsaturated $C_{3-6}$ ring as described above.

In the formula (III), preferably, $R^3$ is H. More preferably, in the formula (III), $R^1$ is a group of the formula: $-Z^1-Z^2$ (wherein $-Z^1-$ is —CO—, —CS—, —SO— or —SO$_2$—, and $Z^2$ is an optionally substituted hydrocarbon group, an optionally substituted heterocyclic group, an optionally substituted hydroxyl group, or an optionally substituted amino group); $R^3$ is H; Ar is an optionally substituted aromatic ring group; $X^3$ is $CR^{11}R^{12}$ (wherein $R^{11}$ and $R^{12}$ are the same or different and are H, an optionally substituted hydrocarbon group, an optionally substituted hydroxyl group, an optionally substituted amino group, an optionally substituted thiol group, cyano group, a halogen atom, an optionally substituted heterocyclic group, or a group of the formula: $-Z^1-Z^2$ (wherein $-Z^1-$ and $Z^2$ are as defined above), or $R^{11}$ and $R^{12}$ may be combined to form an oxo group, methylene group or a ring such as a saturated or unsaturated $C_{3-6}$ ring as described above); and $R^9$ and $R^{10}$ are the same or different and are a $C_{1-6}$ alkyl group, or $R^9$ and $R^{10}$ may be combined to form a ring such as a saturated or unsaturated $C_{3-6}$ ring as described above.

As for a salt of the compound of formula (I), (II), (III) or (IIIa) (hereinafter sometimes referred to as Compound (I), (II), (III) or (IIIa)), a pharmaceutically acceptable salt is preferred. Examples thereof include a salt with an inorganic base, a salt with an organic base, a salt with an inorganic acid, a salt with an organic acid, a salt with a basic or acidic amino acid, or the like. Preferred examples of a salt with an inorganic base include an alkali metal salt such as sodium salt, potassium salt, or the like; an alkaline earth metal salt such as calcium salt, magnesium salt, or the like; and aluminum salt; ammonium salt; or the like. Preferred examples of a salt with an organic base include a salt with trimethylamine, triethylamine, pyridine, picoline, ethanolamine, diethanolamine, triethanolamine, dicyclohexylamine, N,N'-dibenzylethylenediamine, or the like. Preferred examples of a salt with an inorganic acid include a salt with hydrochloric acid, hydrobromic acid, nitric acid, sulfuric acid, phosphoric acid, or the like. Preferred examples of a salt with an organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, or the like. Preferred examples of a salt with a basic amino acid include a salt with arginine, lysine, ornithine or the like. Preferred examples of a salt with an acidic amino acid include a salt with aspartic acid, glutamic acid, or the like.

Compound (I), (II), (III) or (IIIa) may be in the form of a prodrug thereof. The prodrug of Compound (I), (II), (III) or (IIIa) refers to a compound that is converted into Compound (I), (II), (III) or (IIIa) by a reaction with an enzyme, gastric acid, or the like under a physiological condition in the living body, namely, (i) a compound that is converted into Compound (I), (II), (III) or (IIIa) by an enzymatic oxidation, reduction, hydrolysis, or the like, and (ii) a compound that is converted into Compound (I), (II), (III) or (IIIa) by hydrolysis with gastric acid or the like. Examples of a prodrug of Compound (I), (II), (III) or (IIIa) to be used include a compound or its salt wherein hydroxyl group in Compound (I), (II), (III) or (IIIa) is acylated, alkylated, phosphorylated, or converted into borate (e.g., a compound or its salt wherein hydroxyl group in Compound (I), (II), (III) or (IIIa) is converted into acetyloxy, palmitoyloxy, propanoyloxy, pivaloyloxy, succinyloxy, fumaryloxy, alanyloxy, dimethylaminomethylcarbonyloxy, etc.), a compound or its salt wherein carboxyl group in Compound (I), (II), (III) or (IIIa) is esterified or amidated (e.g., a compound or its salt wherein carboxyl group in Compound (I), (II), (III) or (IIIa) is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl) methyl esterification, cyclohexyloxycarbonyl esterification, or conversion into the methyl amide, etc.), or the like. These prodrugs can be produced according to a per se known method or its modified method.

Further, a prodrug of Compound (I), (II), (III) or (IIIa) may be a compound or its salt that is converted into Compound (I), (II), (III) or (IIIa) under physiological conditions as described in "Development of Drugs", Volume 7, Molecular Design, Hirokawa Shoten, 1990; pages 163-198.

Compound (I), (II), (III) or (IIIa) may be labeled with an isotope (for example, $^2$H, $^3$H, $^{14}$C, $^{35}$S, $^{125}$I, or the like) or the like.

When the compound obtained by the present invention or a salt thereof has a double bond in its molecule and a steric configuration of Z or E exists, each of the stereoisomers and a mixture thereof are included in the present invention.

When a steric configuration exists due to an asymmetric carbon in the molecule of the compound obtained by the present invention or a salt thereof, each of them and a mixture thereof are included in the present invention.

Hereinafter, production of the compound of the present invention will be illustrated.

A process for preparing Compound (II), Compound (III) and Compound (IIIa) of the present invention will be shown in the following schemes 1 to 13.

A compound wherein Q is N, and Y is C or $CR^4$ in Compound (II) can be prepared according to the schemes 1 to 3.

A compound wherein Q is C, and Y is C or $CR^4$ in Compound (II) can be prepared according to the scheme 4.

A compound wherein Q is N, and Y is N in Compound (II) can be prepared according to the scheme 5.

A compound wherein Y is C or $CR^4$ in Compound (III) and Compound (IIIa) can be prepared by the scheme 6.

A compound wherein Y is N in Compound (III) and Compound (IIIa) can be prepared by the scheme 7.

A compound wherein Q is C, and Y is N in Compound (II) can be prepared by the scheme 13.

Scheme 1

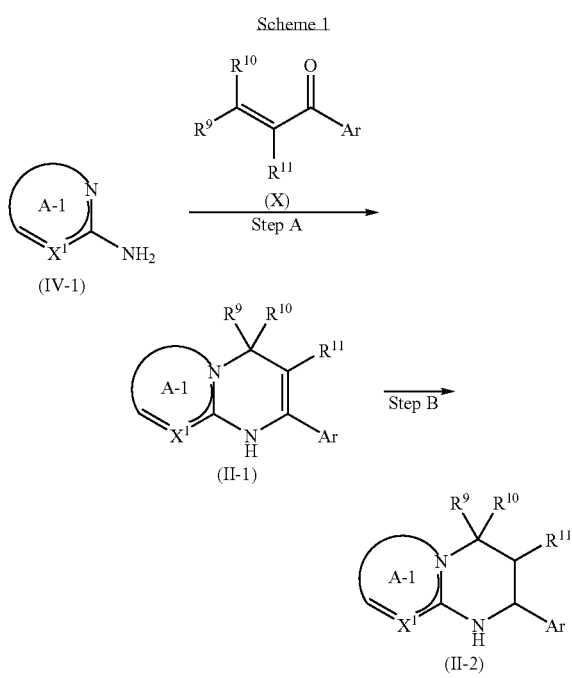

wherein A-1 is the same as A, and the other symbols are as defined above.

In step A, Compound (II-1) is prepared by cyclization reaction of Compound (IV-1) and Compound (X) with an acid or a base. Examples of the acid used in this reaction include: inorganic acids such as hydrochloric acid, hydrobromic acid, sulfuric acid and phosphoric acid; organic acids such as acetic acid, trifluoroacetic acid, methanesulfonic acid, benzenesulfonic acid and p-toluenesulfonic acid; and Lewis acids such as zinc (II) chloride, tin (IV) chloride, aluminium chloride and the like.

Examples of the base include alkali metal salts such as potassium hydroxide, sodium hydroxide, sodium bicarbonate and potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

An amount of these acids or bases to be used is preferably about 0.1 to about 5 mole equivalent relative to Compound (IV-1).

Examples of a solvent having no adverse effect on the reaction include aromatic hydrocarbons such as benzene, toluene and xylene; ethers such as tetrahydrofuran, dimethoxyethane, dioxane and diethyl ether; amides such as N,N-dimethylformamide; alcohol such as ethanol, propanol, tert-butanol and methoxyethanol; and sulfoxides such as dimethyl sulfoxide. These solvents may be used by mixing at an appropriate ratio.

A reaction temperature is usually about −50° C. to about 200° C., preferably about −10° C. to about 150° C.

A reaction time is usually about 0.5 to about 60 hours.

The thus obtained compound (II-1) can be isolated and purified by the known separating and purifying methods, for example, concentration, concentration under the reduced pressure, extraction with solvent, crystallization, recrystallization, transfer dissolution and chromatography.

Compound (IV-1) used herein can be prepared, for example, according to the method described in Bilestein, vol. 25, p. 2033. In addition, Compound (X) can be prepared, for example, according to Organometallics, vol. 11, p. 954.

In step B, Compound (II-2) is prepared by a reduction reaction for Compound (II-1).

In the present reaction, a catalytic hydrogenation method using palladium carbon, palladium hydroxide or the like, or reduction using a reducing agent is performed. As the reducing agent, sodium borohydride, aluminium lithium hydride and lithium borohydride are used. In the present reaction, if needed, any solvents can be used as long as they do not inhibit the reaction. Inter alia, alcohols (e.g. $C_{1-3}$ alcohol such as methanol, ethanol, propanol and the like) or ethers (diethyl ether, diisopropyl ether, ethylene glycol dimethyl ether, tetrahydrofuran, dioxane etc.) are preferable.

A reaction time is usually about 0.5 to about 20 hours.

The thus obtained Compound (II-2) can be isolated and purified by the known isolating and purifying methods, for example, concentration, concentration under the reduced pressure, extraction with solvent, crystallization, recrystallization, transfer dissolution and chromatography.

Scheme 2

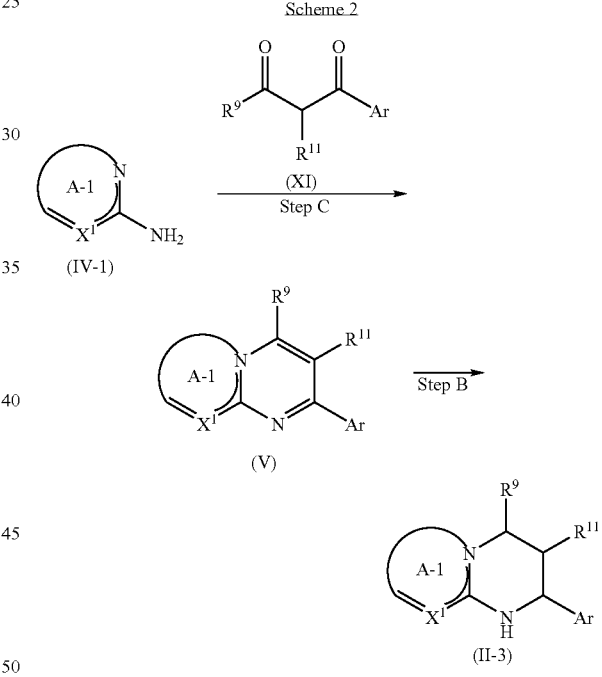

wherein A-1 is the same as A, and the other symbols are as defined above.

In step C, Compound (V) is prepared by a reaction for cyclizing Compound (IV-1) and Compound (XI). The present reaction is carried out in the presence of an acid in a solvent having no adverse effect on the reaction or without a solvent according to the conventional method.

Examples of the acid include inorganic acids such as hydrochloric acid, hydrobromic acid, sulfuric acid and phosphoric acid; organic acids such as acetic acid, trifluoroacetic acid, methanesulfonic acid, benzenesulfonic acid and p-toluenesulfonic acid; Lewis acids such as zinc (II) chloride, tin (IV) chloride, aluminium chloride and the like.

An amount of these acids is preferably about 0.1 to about 5 mole equivalent relative to Compound (IV-1).

Examples of the solvent having no adverse effect on the reaction include aromatic hydrocarbons such as benzene, toluene and xylene; ethers such as tetrahydrofuran, dioxane and diethyl ether; halogenated hydrocarbons such as chloroform and dichloromethane; amides such as N,N-dimethylformamide; and sulfoxides such as dimethyl sulfoxide. These solvents may be used by mixing at an appropriate ratio.

A reaction temperature is usually about −50° C. to 150° C., preferably about −10° C. to about 120° C.

A reaction time is usually about 0.5 to about 20 hours.

The thus obtained Compound (V) can be isolated and purified by the known isolating and purifying methods, for example, concentration, concentration under the reduced pressure, extraction with solvent, crystallization, recrystallization, transfer dissolution and chromatography.

In step B, Compound (II-3) can be prepared according to step B in the scheme 1.

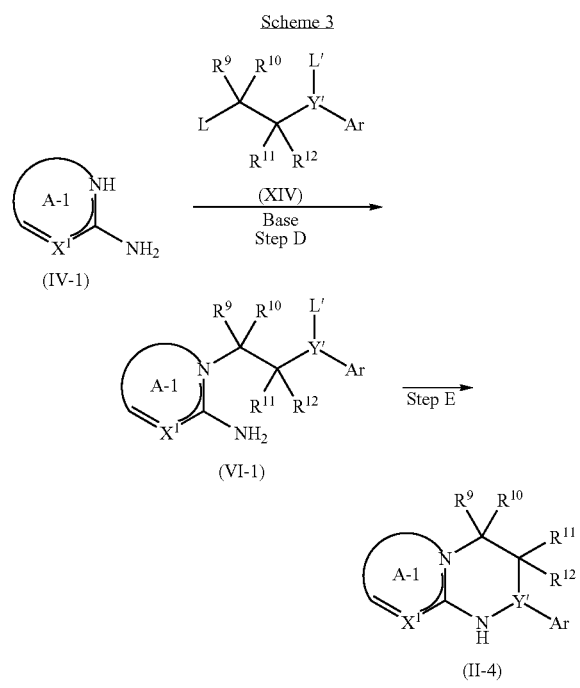

wherein Y' is C or CR$^4$, and L and L' is a leaving group, and L is more reactive than L', and the other symbols are as defined above.

In step D, Compound (VI-1) is prepared from Compound (IV-1). The present method is carried out in the presence of a base in a solvent having no adverse effect on the reaction according to the conventional method. Specific examples of leaving groups L and L' include halogen atom, sulfonyloxy group such as p-toluenesulfonyloxy group, methanesulfonyloxy group and trifluoromethanesulfonyloxy group, and acyloxy group such as acetyloxy group and benzoyloxy group.

Example of the base include alkali metal salts such as potassium hydroxide, sodium hydroxide, sodium bicarbonate and potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 5 mole equivalent relative to Compound (IV).

Examples of the solvent having no adverse effect on the reaction include: aromatic hydrocarbon such as benzene, toluene and xylene; ethers such as tetrahydrofuran, dioxane and diethyl ether; amides such as N,N-dimethylformamide; and sulfoxides such as dimethyl sulfoxide. These solvents may be used by mixing at an appropriate ratio.

A reaction temperature is usually about −50 to about 150° C., preferably about −10° C. to about 120° C.

A reaction time is usually about 0.5 about 20 hours.

The thus obtained Compound (VI-1) can be isolated and purified by the known isolating and purifying methods, for example, concentration, concentration under the reduced pressure, extraction with solvent, crystallization, recrystallization, transfer dissolution and chromatography.

In step E, Compound (II-4) is prepared by an intramolecular cyclization reaction of Compound (VI-1). The present method is carried out in the presence of an acid or a base in a solvent having no adverse effect on the reaction according to the conventional method. Specific example of a leaving group L' include halogen atom, p-toluenesulfonyloxy group, methanesulfonyloxy group and trifluoromethanesulfonyloxy group.

Examples of the acid include inorganic acids such as hydrochloric acid, hydrobromic acid, sulfuric acid and phosphoric acid; organic acids such as acetic acid, trifluoroacetic acid, methanesulfonic acid, benzenesulfonic acid and p-toluenesulfonic acid; and Lewis acids such as zinc (II) chloride, tin (IV) chloride, aluminium chloride and the like. Examples of the base include: alkali metal salts such as potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and t-butoxide.

An amount of these acids or bases to be used is preferably about 1 to about 5 mole equivalent relative to Compound (IV-1).

Examples of the solvent having no adverse effect on the reaction include aromatic hydrocarbons such as benzene, toluene and xylene; ethers such as tetrahydrofuran, dioxane and diethyl ether; haloganated hydrocarbons such as chloroform and dichloromethane; amides such as N,N-dimethylformamide; and sulfoxides such as dimethyl sulfoxide. These solvents may be used by mixing at an appropriate ratio.

A reaction temperature is usually about −50° C. to about 150° C., preferably about −10° C. to about 120° C.

A reaction time is usually about 0.5 to about 20 hours.

The thus obtained Compound (II-4) can be isolated and purified by the known isolating and purifying methods, for example, concentration, concentration under the reduced pressure, extraction with solvent, crystallization, recrystallization, transfer dissolution and chromatography.

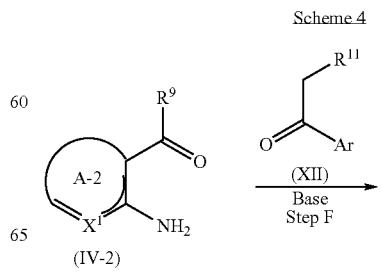

-continued

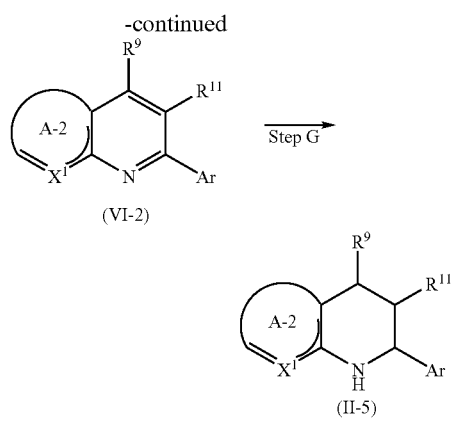

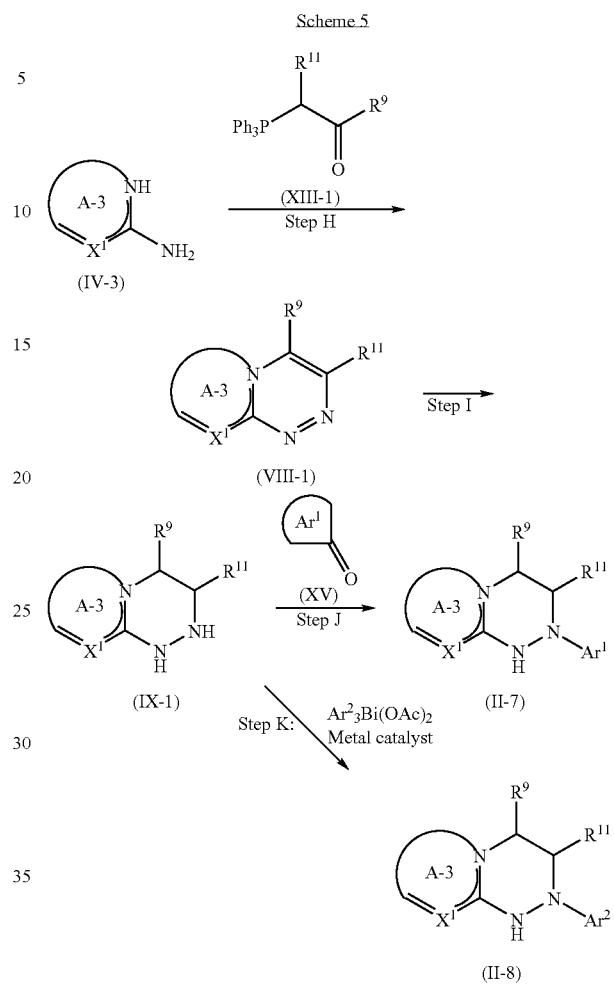

wherein A-2 is the same as A, and the other symbols are as defined above.

In step F, Compound (VI-2) is prepared from Compound (IV-2) and Compound (XII). The present method is carried out in the presence of a base in a solvent having no adverse effect on the reaction according to the conventional method.

Examples of the base include: alkali metal salts such as potassium carbonate, sodium carbonate and cesium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 5 mole equivalent relative to Compound (IV-2).

Examples of the solvent having no adverse effect on the reaction include aromatic hydrocarbons such as benzene, toluene and xylene; ethers such as tetrahydrofuran; dioxane and diethyl ether; halogenated hydrocarbons such as chloroform and dichloromethane; amides such as N,N-dimethylformamide; and sulfoxides such as dimethyl sulfoxide. These solvents may be used by mixing at an appropriate ratio.

A reaction temperature is usually about −50° C. to about 200° C., preferably about −10° C. to about 150° C.

A reaction time is usually about 0.5 to about 20 hours.

The thus obtained Compound (VI-2) can be isolated and purified by the known isolating and purifying methods, for example, concentration, concentration under the reduced pressure, extraction with solvent, crystallization, recrystallization, transfer dissolution and chromatography.

In step G, Compound (II-5) is prepared by a reaction for reducing Compound (VI-2).

In the present reaction, a catalytic hydrogenation method using palladium carbon, palladium hydroxide or Raney nickel, or reduction using a reducing agent is carried out. As the reducing agent, sodium borohydride, aluminium lithium hydride and lithium borohydride are used. In the present reaction, if needed, any solvents can be used as long as they do not inhibit the reaction. Inter alia, alcohols (e.g. $C_{1-3}$ alcohol such as methanol, ethanol, propanol and the like) or ethers (diethyl ether, diisopropyl ether, ethylene glycol dimethyl ether, tetrahydrofuran, dioxane etc.) are preferable.

A reaction time is usually about 0.5 to 20 hours.

The thus obtained Compound (II-5) can be isolated and purified by the known isolating and purifying methods, for example, concentration, concentration under the reduced pressure, extraction with solvent, crystallization, recrystallization, transfer dissolution and chromatography.

wherein $Ar^1$ is an optionally substituted non-aromatic hydrocarbon ring or an optionally substituent non-aromatic heterocyclic ring, $Ar^2$ is an optionally substituted aromatic hydrocarbon ring or an optionally substituted aromatic heterocyclic ring, and A-3 is the same as A, and the other symbols are as defined above.

In step H, an amino group of Compound (IV-3) is converted into a diazonium salt, and ylide is reacted thereon to prepare Compound (VIII-1). Diazotization in the present method is carried out in the presence of an acid in a solvent having no adverse effect on the reaction according to the conventional method. As the acid, for example, acetic acid and hydrochloric acid are used. As a diazotizing agent, sodium nitrite, alkyl nitrite or sulfated nitrosyl is used.

As the solvent, water, dioxane, tetrahydrofuran and the like are used.

A reaction temperature is usually about −50° C. to about 150° C., preferably about −10° C. to about 100° C.

A reaction time is usually about 0.5 to about 20 hours.

The thus obtained diazonium salt of Compound (IV-3) is reacted with ylide produced from Compound (XIII-1) to prepare Compound (VIII-1). The present step is carried out in the presence of a base in a solvent having no adverse effect on the reaction. Examples of the base include: alkali metal salts such as potassium carbonate; amines such as pyridine, triethylamine, N,N-dimethylaniline and 1,8-diazabicyclo [5,4,0]

undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 3 mole equivalent relative to Compound (XIII-1).

Examples of the solvent having no adverse effect on the reaction include aromatic hydrocarbons such as benzene, toluene and xylene; ethers such as tetrahyrdorufan, dioxane and diethyl ether; halogenated hydrocarbons such as chloroform and dichloromethane; amides such as N,N-dimethylformamide; and sulfoxides such as dimethyl sulfoxide. These solvents may be used by mixing at an appropriate ratio.

Since the thus obtained Compound (VIII-1) is unstable depending on a kind of the compound, it is used in the next step without isolation and purification.

In step I, a reduction reaction of Compound (VIII-1) is carried out to prepare Compound (IX-1). In the present reaction, a catalytic hydrogenation method using platinum oxide, Raney nickel, palladium carbon or palladium hydroxide, or reduction using a reducing agent is used. As the reducing agent, sodium borohydride, aluminium lithium hydride and lithium borohydride are used. In the present reaction, if needed, any solvents can be used as long as they do not inhibit the reaction. Inter alia, alcohols (e.g. $C_{1-3}$ alcohol such as methanol, ethanol, propanol etc.) or ethers (diethyl ether, diisopropyl ether, ethylene glycol dimethyl ether, tetrahydrofuran, dioxane etc.) are preferable.

A reaction time is usually about 0.5 to about 20 hours.

The thus obtained Compound (IX-1) can be isolated and purified by the known isolating and purifying methods, for example, concentration, concentration under the reduced pressure, extraction with solvent, crystallization, recrystallization, transfer dissolution and chromatography.

In step J, Compound (II-7) is prepared by a reductive amination reaction between Compound (IX-1) and ketone (XV). The present method is carried out in the presence of a reducing agent in a solvent having no adverse effect on the reaction. Examples of the reducing agent include sodium borohydride, sodium cyanoborohydride, sodium triacetoxyborohydride and lithium borohydride. Although alcohol solvents such as ethanol and methanol, dichloromethane, chloroform and carbon tetrachloride are used as a solvent, any solvents can be used as long as they do not inhibit the reaction.

The thus obtained Compound (II-7) can be isolated and purified by the known isolating and purifying methods, for example, concentration, concentration under the reduced pressure, extraction with solvent, crystallization, recrystallization, transfer dissolution and chromatography.

In step K, a bismuth regent is acted on Compound (IX-1) to prepare Compound (II-8). The present method is carried out in the presence of a metal catalyst in a solvent having no adverse effect on the reaction. As the metal catalyst, for example, copper catalysts such as copper (II) acetate and copper (II) pivalate are used. Although dichloromethane, chloroform and carbon tetrachloride are used as a solvent, any solvents can be used as long as they do not inhibit the reaction.

A reaction temperature is usually about −80° C. to about 150° C., preferably about −80° C. to about 100° C.

A reaction time is usually about 0.5 to about 20 hours.

The thus obtained Compound (II-8) can be isolated and purified by the known isolating and purifying methods, for example, concentration, concentration under the reduced pressure, extraction with solvent, crystallization, recrystallization, transfer dissolution and chromatography.

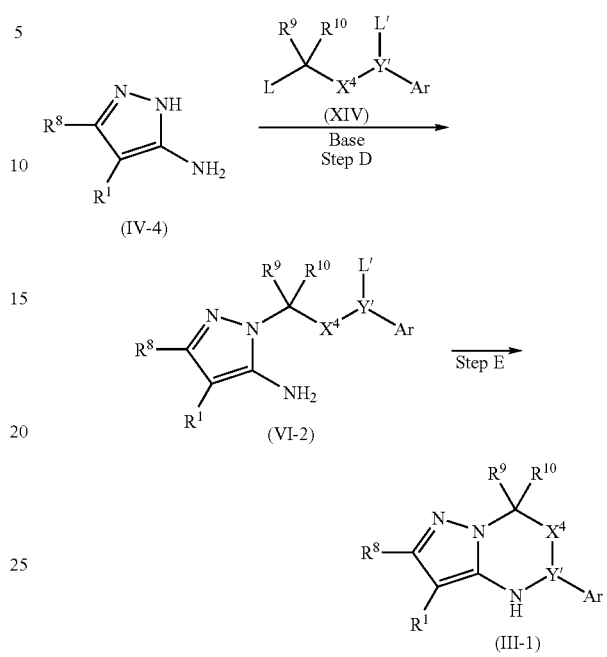

wherein $X^4$ is the same as $X^3$, and the other symbols are as defined above.

Step D and step E can be carried out according to step D and step E of the scheme 3, respectively, to prepare Compound (III-1).

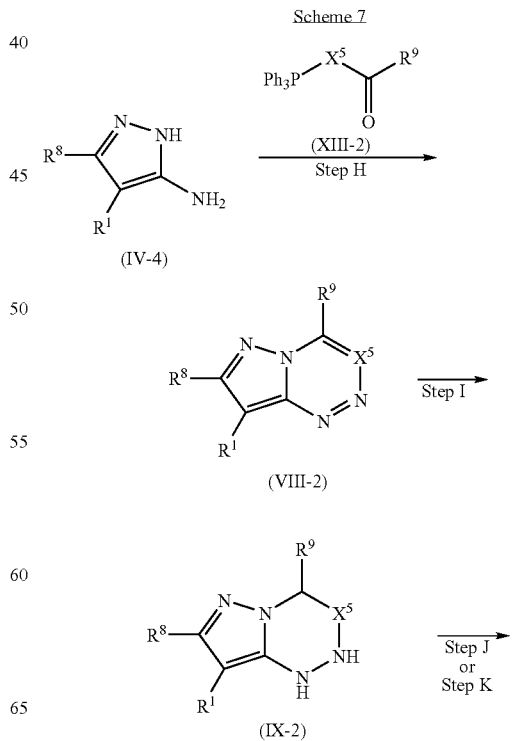

-continued

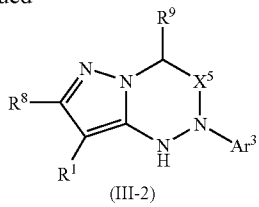

(III-2)

wherein Ar$^3$ is an optionally substituted hydrocarbon ring, an optionally substituted non-aromatic heterocyclic ring, an aromatic hydrocarbon ring or an aromatic heterocyclic ring, X$^5$ is the same as X$^3$, and other respective symbols have the same meanings as described above.)

Step H, step I, step J and step K can be carried out according to step H, step I, step J, and step K of the scheme 5, respectively, to prepare Compound (III-2).

In Compound (II), when X$^1$ is C—COOR$^{16}$, it can be converted as follows:

Scheme 8

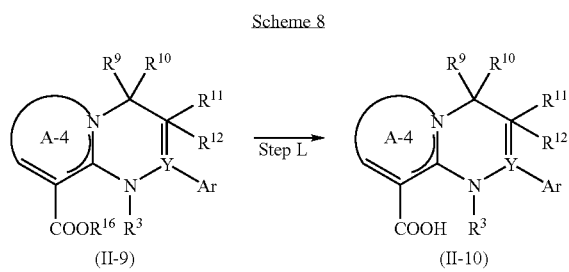

wherein A-4 denote the same meaning as that of A, R$^{16}$ denotes an optionally substituted carbon atom, and the other symbols are as defined above.

In step L, Compound (II-10) is prepared by a reaction for leaving a carboxyl-protecting group.

All conventional methods used in a reaction for leaving a carboxyl-protecting group, for example, hydrolysis, reduction and elimination using a Lewis acid can be applied to the present reaction. It is preferable that hydrolysis is carried out in the presence of a base or an acid. Examples of the suitable base include inorganic bases such as alkali metal hydroxide (e.g. sodium hydroxide and potassium hydroxide), alkaline earth metal hydroxide (e.g. magnesium hydroxide and potassium hydroxide), alkali metal carbonate (e.g. sodium carbonate and potassium carbonate), alkaline earth metal carbonate (e.g. magnesium carbonate and calcium carbonate), alkali metal bicarbonate (e.g. sodium bicarbonate and potassium bicarbonate), alkali metal acetate (e.g. sodium acetate and potassium acetate), alkaline earth metal phosphate (e.g. magnesium phosphate and calcium phosphate) and alkali metal hydrogen phosphate (e.g. disodium hydrogen phosphate and dipotassium hydrogen phosphate), and organic bases such as trialkylamine (e.g. trimethylamine and triethylamine), picoline, N-methylpyrrolidine, N-methylmorpholine, 1,5-diazabicyclo [4.3.2]non-5-ene, 1,4-diazabicyclo[2.2.2]non-5-ene and 1,8-diazabicyclo[4.3.0]-7-undecene. Hydrolysis using a base is carried out in water or a hydrophilic organic solvent or a mixed solvent in many cases. Examples of the suitable acid include formic acid, hydrobromic acid and sulfuric acid.

The present hydrolysis reaction is usually carried out in an organic solvent, water or a mixed solvent thereof. A reaction temperature is not particularly limited, but is appropriately selected depending on a kind of a carboxyl-protecting group and an elimination method. Elimination using a Lewis acid is carried out by reacting Compound (II-9) or a salt thereof with a Lewis acid, for example, trihalogenated boron (e.g. boron trichloride and boron trifluoride), tetrahalogenated titanium (e.g. titanium tetrachloride and titanium tetrabromide), and halogenated aluminium (e.g. aluminium chloride and aluminium bromide), or an organic acid (e.g. trichloroacetic acid and trifluoroacetic acid). This elimination reaction is preferably carried out in the presence of a cation scavenger (e.g. anisole and phenol) and is usually carried out in a solvent such as nitroalkane (e.g. nitromethane and nitroethane), alkylene halide (e.g., methylene chloride and ethylene chloride), diethyl ether, carbon disulfide, and a solvent having no adverse effect on the reaction. These solvents may be used as a mixture thereof.

It is preferable that elimination by reduction is applied to elimination of a protecting group such as halogenated alkyl (e.g. 2-iodoethyl and 2,2,2-trichloroethyl)ester, and aralkyl (e.g. benzyl) ester. Examples of a reduction method using in the present elimination reaction include the conventional catalytic reduction in the presence of a combination of a metal (e.g. zinc and zinc amalgam) or a salt of a chromium compound (e.g. chromate chloride and chromate acetate) and an organic or inorganic acid (e.g. acetic acid, propionic acid and hydrochloric acid); or the conventional metal catalyst (e.g. palladium carbon and Raney nickel). A reaction temperature is not particularly limited, but a reaction is carried out under cooling, at room temperature of under warming.

The thus obtained Compound (II-10) can be isolated and purified by the known isolating and purifying methods, for example, concentration, concentration under the reduced pressure, extraction with solvent, crystallization, recrystallization, transfer dissolution and chromatography.

Scheme 9

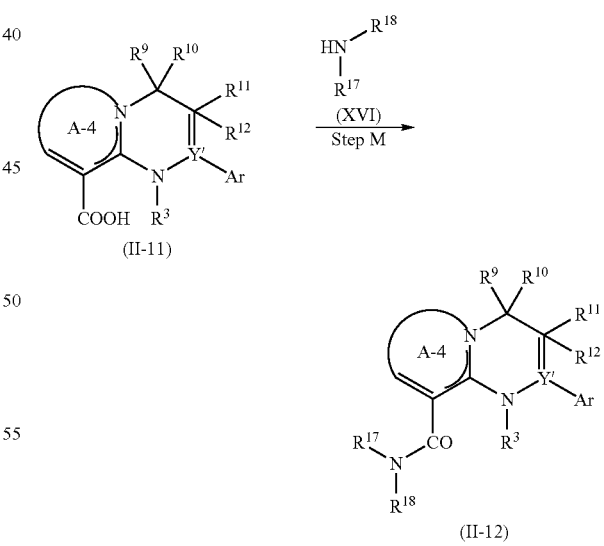

wherein R$^{17}$ and R$^{18}$ are optionally substituted alkyl group, allyl group or hydroxy group; or R$^{17}$ and R$^{18}$ may be combined each other to form a ring, Y" is the same as Y, and the other symbols are as defined above.

In the present method, Compound (II-12) is prepared by reacting Compound (II-11) or a reactive derivative at a carboxyl group thereof and a salt thereof with the above Compound (XVI) or a reactive derivative at an amino group thereof or a salt thereof. Examples of the suitable reactive derivative at an amino group of Compound (XVI) include: Schiff base type imino produced by a reaction of Compound (XVI) with a carbonyl compound such as aldehyde, ketone and the like; silyl derivative produced by a reaction of Compound (XVI) and a silyl compound such as bis(trimethylsilyl)acetamide, mono(trimethylsilyl)acetamide, bis(trimethylsilyl)urea and the like; derivative produced by a reaction of Compound (XVI) with phosphorus trichloride or phosgene.

Specific examples of the suitable reactive derivative at a carboxyl group of Compound (II-11) include acid halide, acid anhydride, activated amide, activated ester and the like. Examples of the suitable reactive derivative include: acid chloride; acid azide; mixed acid anhydride with an acid such as substituted phosphoric acid such as dialkylphosphoric acid, phenylphosphoric acid, diphenylphosphoric acid, dibenzylphosphoric acid, halogenated phosphoric acid and the like, dialkylphosphorous acid, sulfurous acid, thiosulfuric acid, sulfuric acid, sulfonic acid such as methanesulfonic acid and the like, aliphatic carboxylic acid such as acetic acid, propionic acid, butyric acid, isobutyric acid, pivalic acid, pentanoic acid, isopentanoic acid, trichloroacetic acid and the like or aromatic carboxylic acid such as benzoic acid and the like; symmetric acid anhydride; activated amide with imidazole; 4-substituted imidazole, dimethylpyrazole, triazole or tetrazole; activated ester such as cyanomethylester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxylmethyl thioester, pyranyl ester, pyridyl ester, piperidyl ester, 8-quinolyl thioester and the like, or esters with N-hydroxy compound such as N,N-dimethylhydroxyamine, 1-hydroxy-2-(1H)-pyridone, N-hydroxysuccineimide, N-hydroxyphthalimide, 1-hydroxy-1H-benzotriazole and the like. These reactive derivatives can be arbitrarily selected depending on a kind of Compound (II-11) to be used. Examples of the suitable reactive derivative of Compound (II-12) include alkali metal salts such as sodium salt, potassium salt and the like, alkaline earth metal salts such as calcium salt, magnesium salt and the like, and basic salts such as organic base salts such as ammonium salt, trimethylamine salt, triethylamine salt, pyridine salt, picoline salt, dicyclohexylamine salt, N,N-dibenzylethylenediamine salt and the like. Although the reaction is usually carried out in the conventional solvent such as water, alcohols such as methanol, ethanol and the like, acetone, dioxane, acetonitrile, chloroform, methylene chloride, ethylene chloride, tetrahydrofuran, ethyl acetate, N,N-dimethylformamide and pyridine, the reaction may be carried out in any other organic solvents as long as they have no adverse effect on the reaction. These conventional solvents may be used as a mixture with water.

When Compound (II-11) is used as the form of a free acid or a salt thereof in this reaction, it is desirable that the reaction is carried out in the presence of the normally used condensing agent such as so-called Vilsmeier regent and the like prepared by a reaction of N,N'-dicyclohexylcarbodiimide; N-cyclohexyl-N'-morpholinoethylcarbodiimide; N-cyclohexyl-N'-(4-diethylaminocyclohexyl) carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; polyethyl phosphate; polyisopropyl phosphate; phosphorus oxychloride; diphenylphosphorylazide; thionyl chloride; oxalyl chloride; lower alkyl haloformate such as ethyl chloroformate; isopropyl chloroformate and the like; triphenylphosphine; 2-ethyl-7-hydroxybenzisooxazolium salt, 2-ethyl-S-(m-sulfopheny)isooxazoliumhydroxide internal salt; N-hydroxybenzotriazole; 1-(p-chlorobenzenesulfonyloxy)-6-chloro-1H-benzotriazole; N-N'-dimethylformamide with thionyl chloride, phosgene, trichloromethyl chloroformate, phosphorus oxychloride or the like. Alternatively, the reaction may be carried out in the presence of an inorganic base or an organic base such as alkali metal bicarbonate salt, tri(lower)alkylamine, pyridine, N-(lower)alkylmorpholine, N,N-di(lower)alkylbenzylamine and the like. A reaction temperature is not particularly limited, but the reaction is carried out under cooling or under warming.

An amount of Compound (XVI) to be used is 1 to 10 mole equivalent, preferably 1 to 3 equivalent relative to Compound (II-11).

A reaction temperature is usually −30° C. to 100° C.

A reaction time is usually 0.5 to 20 hours.

In addition, when a mixed acid anhydride is used, Compound (II-11) and chlorocarbonic ester (e.g. methyl chlorocarbonate, ethyl chlorocarbonate, isobutyl chlorocarbonate etc.) are reacted in the presence of a base (e.g. triethylamine, N-methylmorpholine, N,N-dimethylaniline, sodium bicarbonate, sodium carbonate, potassium carbonate etc.) and is further reacted with Compound (XVI).

An amount of Compound (XVI) to be used is usually 1 to 10 mole equivalent, preferably 1 to 3 mole equivalent relative to Compound (II-11).

A reaction temperature is usually −30° C. to 100° C.

A reaction time is usually 0.5 to 20 hours.

The thus obtained Compound (II-12) can be isolated and purified by the known isolating and purifying methods, for example, concentration, concentration under the reduced pressure, extraction with solvent, crystallization, recrystallization, transfer dissolution and chromatography.

When $X^1$ is C—COOR$^{16}$ in Compound (III), the conversion can be carried out as follows:

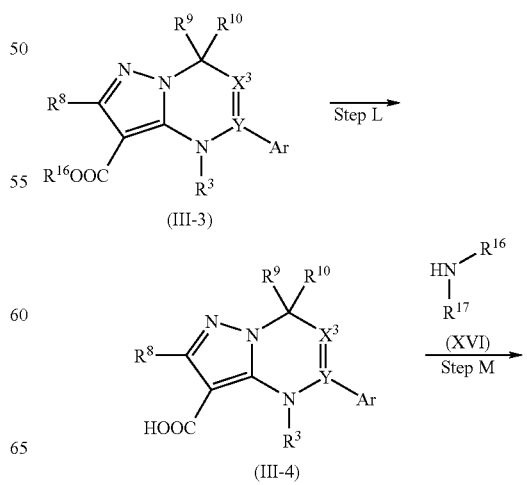

-continued

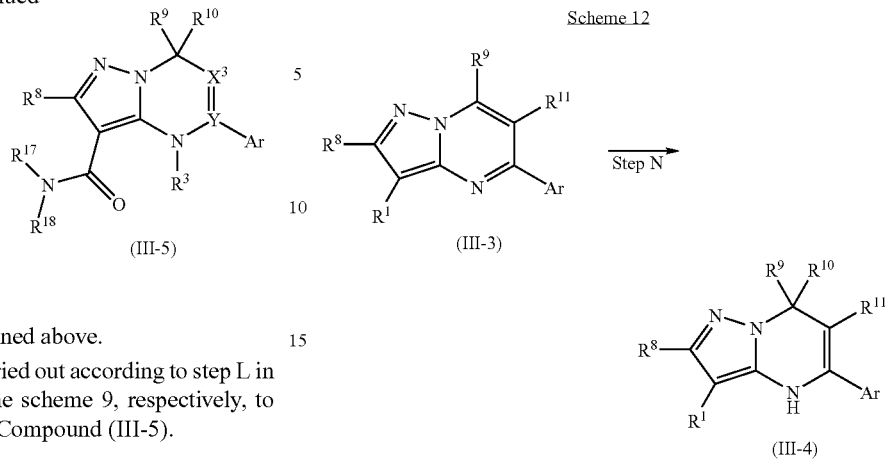

(III-5)

wherein the symbols are as defined above.

Step L and step M can be carried out according to step L in the scheme 8 and step M in the scheme 9, respectively, to prepare Compound (III-4) and Compound (III-5).

Scheme 11

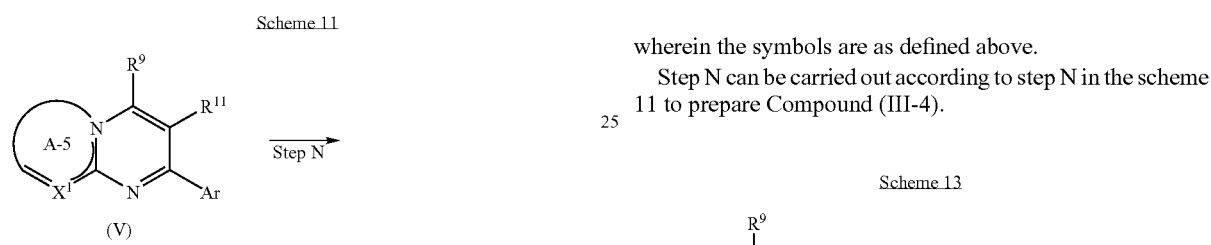

wherein $R^{19}$ is an optionally substituted alkyl group, allyl group, hydroxy group, amino group or sulfanyl group, and the other symbols are as defined above.

In the present method, Compound (II-13) is prepared by a reaction between Compound (V) and a nucleophilic regent.

Examples of the nucleophilic regent include metal phenolate, metal alcoholate, Grignard regent, alkyl metal regent, aryl metal regent and thioalcoholate.

An amount of the nucleophilic regent to be used is preferably about 1 to about 5 mole equivalent relative to Compound (V).

Examples of a solvent having no adverse effect on the reaction include: ethers such as diethyl ether, tetrahydrofuran and dioxane; aromatic hydrocarbons such as benzene, toluene and xylene; amides such as N,N-dimethylformamide and 1-methylpyrrolidone; sulfoxides such as dimethyl sulfoxide. These solvents may be used by mixing at an appropriate ratio.

A reaction temperature is usually about –50° C. to about 150° C., preferably about –10 to about 100° C.

A reaction time is usually about 0.5 to about 20 hours.

The thus obtained Compound (II-13) can be isolated and purified by the known isolating and purifying methods, for example, concentration, concentration under the reduced pressure, extraction with solvent, crystallization, recrystallization, transfer dissolution and chromatography.

Scheme 12

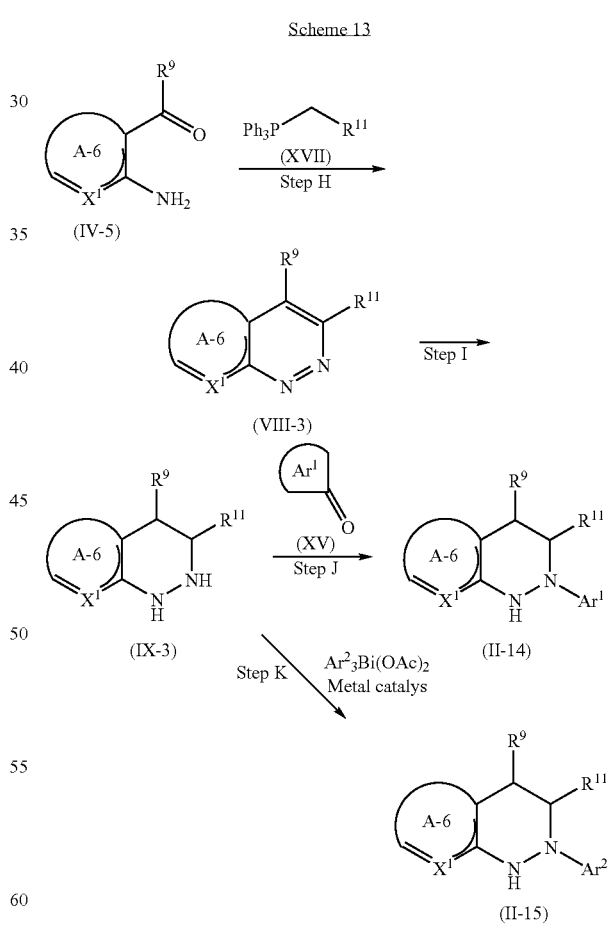

wherein the symbols are as defined above.

Step N can be carried out according to step N in the scheme 11 to prepare Compound (III-4).

wherein A-6 is the same as A, and the other symbols are as defined above.

In step H, an amino group of Compound (IV-5) is converted into a diazonium salt, and ylide is reacted thereon to prepare Compound (VIII-3). Diazotization in this method is carried out in the presence of an acid in a solvent having no adverse effect on the reaction according to the conventional method. As the acid, for example, acetic acid and hydrochloric acid are used. As the diazotizing agent, sodium nitrite, alkyl nitrite or sulfated nitrosyl is used.

As the solvent, water, dioxane, tetrahydrofuran and the like are used.

A reaction temperature is usually about −50° C. to about 150° C., preferably about −10° C. to about 100° C.

A reaction time is about 0.5 to about 20 hours.

The thus obtained diazonium salt of Compound (IV-5) is reacted with ylide produced from Compound (XVII) to prepare Compound (VIII-3). The present step is carried out in the presence of a base in a solvent having no adverse effect on the reaction. Examples of the base include: alkali metal salts such as potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 3 mole equivalent relative to Compound (XVII).

Examples of the solvent having no adverse effect on the reaction include aromatic hydrocarbons such as benzene, toluene and xylene; ethers such as tetrahydrofuran, dioxane and diethyl ether; halogenated hydrocarbons such as chloroform and dichloromethane; amides such as N,N-dimethylformamide; and sulfoxides such as dimethyl sulfoxide. These solvents may be used by mixing at an appropriate ratio.

Since the thus obtained Compound (VIII-3) is unstable depending on a kind of the compound, it is used in the next step without isolation and purification.

Step I, step J and step K can be carried out according to step I, step J and step K, respectively, to prepare Compound (II-14) and Compound (II-15).

When $R^3$ is a hydrogen atom in Compound (II) the following conversion is possible.

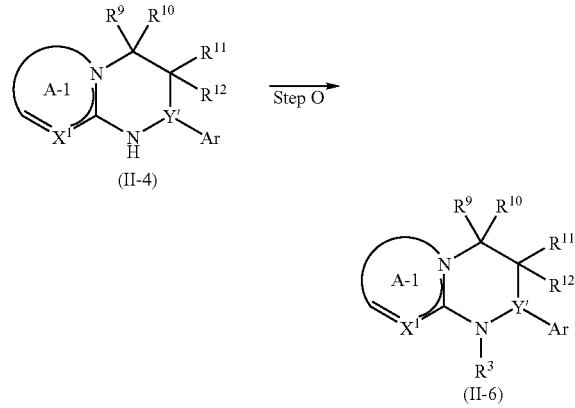

wherein the symbols are as above.

In step O, Compound (II-4) is subjected to alkylation, acylation, carbamoylation, oxycarbonization or thiocarbamoylation to prepare Compound (II-6).

The reaction is carried out according to the conventional method. In alkylation, alkyl halide is reacted, in acylation, acid halide or acid anhydride is reacted, in carbamoylation, isocyanate or carbonylimidazole is reacted and, thereafter, amine is reacted, in oxycarbonization, oxycarbonyl halide or oxycarboic acid anhydride is reacted and, in thiocarbamoylation, thioisocyanate is reacted, respectively, to prepare the compound. The present reaction is generally carried out in the presence of a base in a solvent having no adverse effect on the reaction. Examples of the base include alkali metal salts such as potassium hydroxide, sodium hydroxide, sodium bicarbonate and potassium carbonate; amines such as pyridine, triethyamine, N,N-dimethylaniline and 1,8-diazabicyclo[5,4,0]undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 5 mole equivalent relative to Compound (II-4).

Examples of the solvent having no adverse effect on the reaction include: aromatic hydrocarbons such as benzene, toluene and xylene; ethers such as tetrahydrofuran, dioxane and diethyl ether: halogenated hydrocarbons such as chloroform and dichloromethane; amides such as N,N-dimethylformamide; and sulfoxides such as dimethyl sulfoxide. These solvents may be used by mixing at an appropriate ratio.

A reaction temperature is usually about −50° C. to about 150° C., preferably about −10° C. to about 120° C.

A reaction time is usually about 0.5 to about 20 hours.

The thus obtained Compound (II-6) can be isolated and purified by the known isolating and purifying methods, for example, concentration, concentration under the reduced pressure, extraction with solvent, crystallization, recrystallization, transfer dissolution and chromatography.

When $R^3$ is a hydrogen atom in Compound (III), the following conversion is possible.

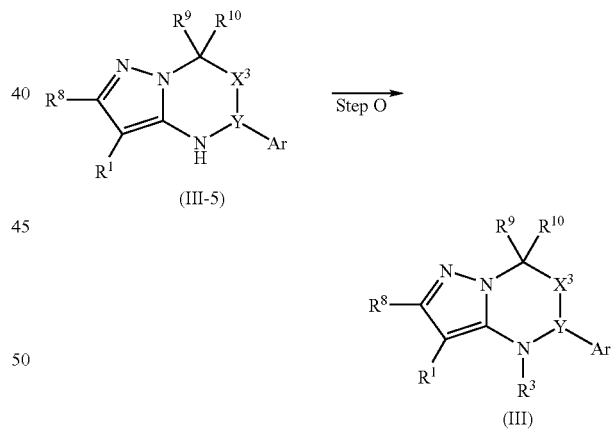

wherein the symbols are as above.

Step Or step J and step K can be carried out according to step 0 in the scheme 14, respectively, to prepare Compound (III).

All the compounds used or obtained in the present invention include corresponding salts, even if specifically stated, and they can be exchanged to one another by a per se known method or modified methods thereof.

When the compounds or salts thereof obtained by the present invention are asymmetric molecules, they can be separated into d-form isomer and 1-form isomer according to conventional optical resolution methods.

The compound or its salt obtained by the present invention may be used in a next step as its reaction mixture without sufficient purification.

Compound (I), (II), (III) or (IIIa) of the present invention has an excellent Ca receptor modulating activity and enhances the secretion of PTH, and therefore useful as drugs for treating bone diseases, kidney-acting drugs, central nervous system and endocrine-acting drugs, digestive system-acting drugs, and the like. Further, the toxicity is low. Therefore, Compound (I), (II), (III) or (IIIa) may be safely administered to mammalian animals (for example, human, rat, mouse, dog, rabbit, cat, cow, horse, pig, and the like).

Thus, a pharmaceutical composition containing compound (I), (II), (III) or (IIIa) of the present invention is expected to be useful in the treatment and prevention of diseases, in which Ca receptor modulating activity is required, such as Ca receptor modulating drugs: primary or secondary hyper parathyroidism; hypoparathyroidism; hyperthyroidism; hypothyroidism; Graves' disease; Hashimoto's toxicosis; Paget's disease; hypercalcemia associated with malignant tumor; hypercalcemia; hypocalcemia; postmenopausal osteoporosis; senile osteoporosis; secondary osteoporosis; osteomalacia; renal osteodystrophy; fracture; osteoarthritis; rheumatoid arthritis; osteosarcoma; myeloma; hypertension; diabetes; myocardial infarction; Hachington's diseases; Parkinson's diseases; Alzheimer's disease; dementia; cerebral apoplexy; brain tumor; spinal injury; diabetic renal disease; renal insufficiency; gastric ulcer; duodenal ulcer; Basedow's disease; parathyroid gland tumor; thyride gland tumor; arteriosclerosis; and the like;

Ca receptor antagonistic drugs: hyperthyroidism; hypocalcemia; postmenopausal osteoporosis; senile osteoporosis; secondary osteoporosis; osteomalacia; renal osteodystrophy; fracture; osteoarthritis; rheumatoid arthritis; osteosarcoma; myeloma; central nervous system diseases; and the like, in particular osteoporosis.

The dosage of Compound (I), (II), (III) or (IIIa) can be selected in various ways depending on the administration route and the symptom of a patient to be treated. The dosage as Compound (I), (II), (III) or (IIIa) per an adult (a body weight of 50 kg) can be usually selected in a range of about 0.1 mg to about 500 mg, preferably about 1 mg to about 100 mg in the case of oral administration and in a range of about 0.01 mg to about 100 mg, further preferably about 0.1 mg to about 10 mg in the case of parenteral administration. The dosage can be administered with being divided in 1-3 times daily.

Compound (I), (II), (III) or (IIIa) of the present invention can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The following examples, preparations and experiments describe the manner and process of making and using the present invention and are illustrative rather than limiting. It is to be understood that there may be other embodiments which fall within the spirit and scope of the present invention as defined by the claims appended hereto.

Abbreviations employed herein are defined below.
DCM=dichloromethane
DCE=dichloroethane
DMAP=dimethylaminopyridine
DMF=dimethylformamide
WSC=1-(3-Dimethylaminopropyl)-3-ethyl-carbodiimide hydrochloride
M+H=monoisotopic mass plus one proton Me=methyl
Et=ethyl
Ph=phenyl
h=hours
min=minutes
HPLC=high performance liquid chromatography
HOBt=hydroxybenzotriazole
LC/MS=liquid chromatography/mass spectrometry
MS=mass spectrometry
Rt=retention time
TEA=triethylamine
TFA=trifluoroacetic acid
IPE=diisopropylether
TLC=thin layer chromatography
THF=tetrahydrofuran
TMSCN=trimethylsilyl cyanide
HATU=O-(7-azabenzotriazol-1-yl)-N,N,N',N'-tetramethyl-uronium hexafulorophosphate
DIPEA=diisopropylethylamine

EXAMPLE 1

Ethyl 5-phenyl-7-(trifluoromethyl)-4,5,6,7-tetrahydropyrazolo[1,5-a]pyrimidine-3-carboxylate

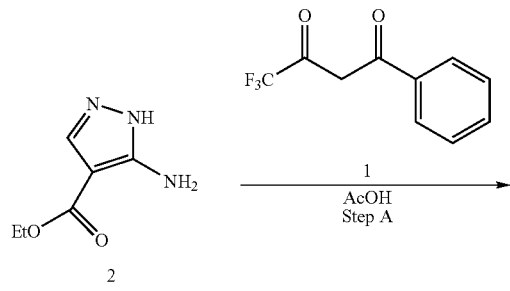

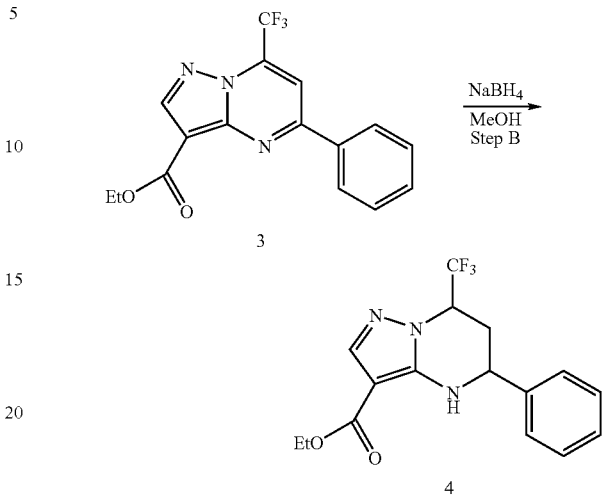

Step A: A mixture of 4,4,4-trifluoro-1-phenyl-1,3-butanedione 1 (6.97 g, 32.24 mmol) and ethyl 3-aminopyrazole-4-carboxylate 2 (5.0 g, 32.22 mmol) in AcOH (100 mL) was refluxed for 4 h. The mixture was cooled to room temperature and concentrated and precipitated crystals were collected by filtration to give 8.63 g (79%) of the title compound as yellow crystals. $^1$H NMR (CDCl$_3$, 200 MHz): 1.47 (3H, t, J=7.0 Hz), 4.47 (2H, q, J=7.0 Hz), 7.54-7.61 (3H, m), 7.80 (1H, s), 8.23-8.28 (2H, m), 8.68 (1H, s)

Step B: To a solution of 3 (3.51 g, 10.3 mmol) in MeOH was added NaBH$_4$ (1.4 g, 3.7 mmol) at room temperature. The whole was stirred at the same temperature for 5 h, quenched with saturated citric acid solution, concentrated in vacuo, and extracted with AcOEt. The extract was successively washed with aq. NaHCO$_3$, water and brine, dried over MgSO$_4$ and then concentrated to give 1.73 g (49%) of compound 4 as colorless oil. $^1$H HMR (CDCl$_3$, 200 MHz): 1.32 (3H, t, J=6.8 Hz), 2.28-2.46 (1H, m), 2.50-2.61 (1H, m), 4.25 (2H, q, J=6.8 Hz), 4.58 (1H, dd, J=11.4, 3.4 Hz), 4.85 (1H, ddd, J=3.4, 3.0, 2.6 Hz), 6.15 (1H, s)7.34-7.48 (5H, m), 7.74 (1H, s).

Compounds of Examples 2-14, shown in the Table 1, were prepared in a manner similar to that described in Example 1.

TABLE 1

| Example | Structure | Name | Physiological Data |
|---|---|---|---|
| 2 | 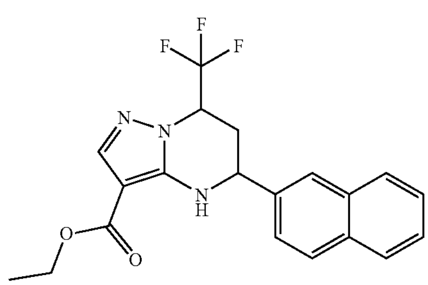 | ethyl 5-(2-naphthyl)-7-(trifluoromethyl)-4,5,6,7-tetrahydropyrazolo[1,5-a]pyrimidine-3-carboxylate | mp 120-122° C. |

TABLE 1-continued

| Example | Structure | Name | Physiological Data |
|---|---|---|---|
| 3 | 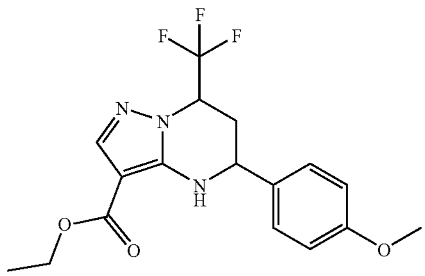 | ethyl 5-(4-methoxyphenyl)-7-(trifluoromethyl)-4,5,6,7-tetrahydropyrazolo[1,5-a]pyrimidine-3-carboxylate | mp 105-109° C. |
| 4 | 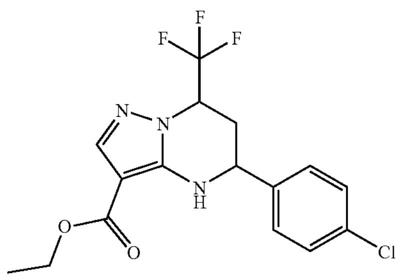 | ethyl 5-(4-chlorophenyl)-7-trifluoromethyl)-4,5,6,7-tetrahydropyrazolo[1,5-a]pyrimidine-3-carboxylate | IR(KBr) 3376, 2984, 1680, 1597, 1578, 1541 cm$^{-1}$ |
| 5 | 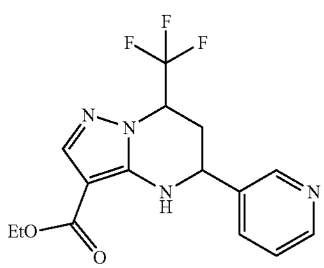 | ethyl 5-(3-pyridinyl)-7-(trifluoromethyl)-4,5,6,7-tetrahydropyrazolo[1,5-a]pyrimidine-3-carboxylate | MS(ESI, m/z) 341 (M + H)+ |
| 6 | 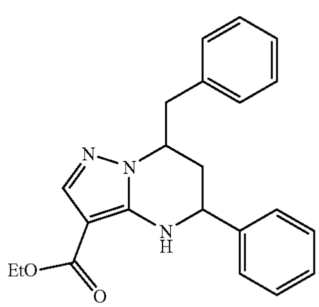 | ethyl 7-benzyl-5-phenyl-4,5,6,7-tetrahydropyrazolo[1,5-a]pyrimidine-3-carboxylate | MS(ESI, m/z) 362 (M + H)+ |
| 7 | 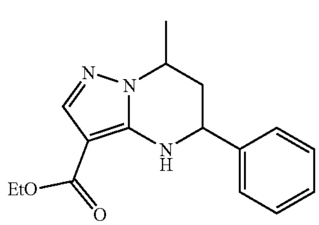 | ethyl 7-methyl-5-phenyl-4,5,6,7-tetrahydropyrazolo[1,5-a]pyrimidine-3-carboxylate | MS(ESI, m/z) 286 (M + H)+ |

TABLE 1-continued

| Example | Structure | Name | Physiological Data |
|---|---|---|---|
| 8 | 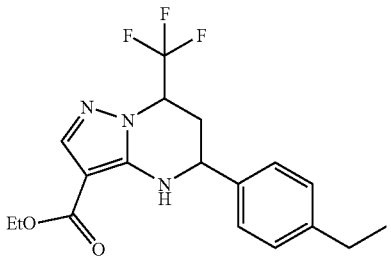 | ethyl 5-(4-ethylphenyl)-7-(trifluoromethyl)-4,5,6,7-tetrahydropyrazolo[1,5-a]pyrimidine-3-carboxylate | MS(ESI, m/z) 368 (m + H)+ |
| 9 | 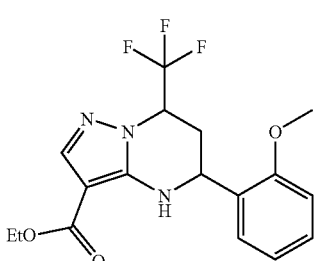 | ethyl 5-(2-methoxyphenyl)-7-(trifluoromethyl)-4,5,6,7-tetrahydropyrazolo[1,5-a]pyrimidine-3-carboxylate | $^1$H NMR (CDCl$_3$, 200 MHz): 1.33(3H, t, J=7.2 Hz), 2.16-2.34(1H, m), 2.34-2.61(1H, m)3.88(3H, s), 4.26(2H, q, J=7.2 Hz), 4.80-4.91(1H, m), 5.00(1H, dd, J=11.4, 2.6 Hz), 6.08(1H, s), 6.92-7.08(2H, m), 7.30-7.55(1H, m), 7.74(1H, s) |
| 10 | 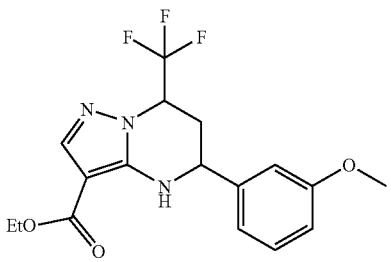 | ethyl 5-(3-methoxyphenyl)-7-(trifluoromethyl)-4,5,6,7-tetrahydropyrazolo[1,5-a]pyrimidine-3-carboxylate | $^1$H NMR (CDCl$_3$, 200 MHz): 1.32(3H, t, J=7.0 Hz), 2.27-2.45(1H, m)2.51-2.61(1H, m), 3.84(3H, s), 4.25(2H, q, J=7.0 Hz), 4.55 (1H, dd, J=11.4, 2.8 Hz), 4.76–4.93(1H, m)5.76-4.93(1H, m), 6.15(1H, s), 6.89-7.03(3H, m), 7.30-7.38(1H, m), 7.74(1H, s). |
| 11 | 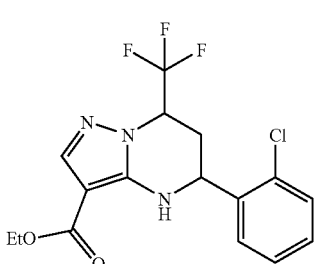 | ethyl 5-(2-chlorophenyl)-7-(trifluoromethyl)-4,5,6,7-tetrahydropyrazolo[1,5-a]pyrimidine-3-carboxylate | $^1$H NMR (CDCl$_3$, 200 MHz): 1.34(3H, t, J=7.2 Hz), 2.14-2.32(1H, m), 2.66-2.78(1H, m), 4.27(2H, q, J=7.0 Hz), 4.81-4.97(1H, m), 5.07(1H, dd, J=11.4, 3.0 Hz), 6.11(1H, s), 7.28-7.46(3H, m), 7.66-7.70(1H, m), 7.75(1H, s). |
| 12 | 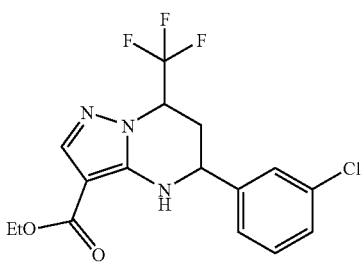 | ethyl 5-(3-chlorophenyl)-7-(trifluoromethyl)-4,5,6,7-tetrahydropyrazolo[1,5-a]pyrimidine-3-carboxylate | $^1$H NMR (CDCl$_3$, 200 MHz): 1.37(3H, t, J=7.0 Hz), 2.26-2.44(1H, m), 2.50-2.61(1H, m), 4.26(2H, q, J=7.0 Hz), 4.57(1H, dd, J=11.6, 3.0 Hz), 4.76-4.93(1H, m), 6.16(1H, s), 7.29-7.46(4H, m), 7.74(1H, s). |

TABLE 1-continued

| Example | Structure | Name | Physiological Data |
|---|---|---|---|
| 13 | 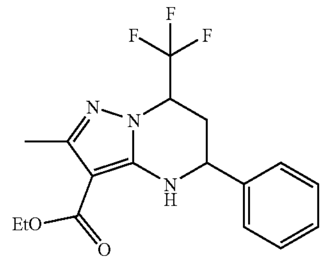 | ethyl 2-methyl-7-(trifluoromethyl)-4,5,6,7-tetrahydropyrazolo[1,5-a]pyrimidine-3-carboxylate | mp 142-143° C. |
| 14 | 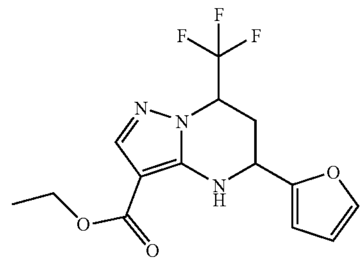 | ethyl 5-(2-furyl)-7-(trifluoromethyl)-4,5,6,7-tetrahydropyrazolo[1,5-a]pyrimidine-3-carboxylate | mp 86° C. |

EXAMPLE 15

Ethyl 7,7-dimethyl-5-(2-pyridyl)-4,5,6,7-tetrahydropyrazolo[1,5-a]pyrimidine-3-carboxylate

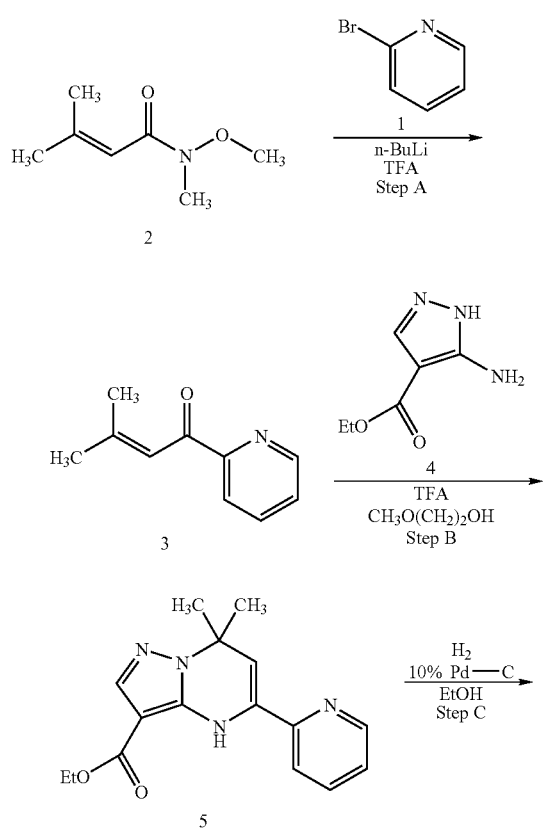

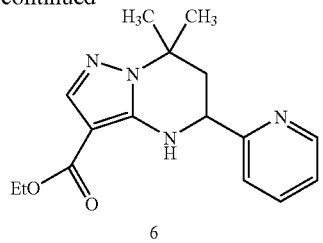

Step A: To a stirred solution of compound 1 (7.0 g, 44.3 mmol) in THF (100 mL) was added n-BuLi (1.6 M hexane solution, 28 mL, 44.8 mmol) at −78° C. After the mixture was stirred for 30 min, compound 2 (6.34 g, 44.3 mmol) was added thereto. The resulting mixture was stirred at −78—50° C. for 2 h, quenched with saturated citric acid solution and extracted with AcOEt. The extract was successively washed with water and brine, dried over $MgSO_4$ and then concentrated in vacuo. The residue was chromatographed on silica gel with AcOEt/hexane (1:9) as an eluent to give 3.16 g (44% yield) of compound 3 as colorless liquid.

Step B: To a solution of compound 3 and compound 4 in methoxyethanol (60 mL) was added TFA (4.47 g, 39.2 mmol) with ice-water cooling. The mixture was refluxed for 12 h, diluted with AcOEt, and the mixture was washed with saturated $NaHCO_3$ solution, water and brine, dried over $MgSO_4$, and then concentrated in vacuo. The residue was chromatographed on silica gel with AcOEt/hexane (1:4) as an eluent to give 2.03 g (36% yield) of compound 5 as colorless prisms.

Step C: A mixture of 5 (1.98 g, 6.96 mmol) and 10% Pd—C (1.0 g) in EtOH (100 mL) was stirred for 2 h under the $H_2$ atmosphere (balloon pressure). After the insoluble materials were filtered off, the residue was concentrated in vacuo to give the residue. Crystallization from hexane/IPE gave the title compound 6 (1.00 g, 48%) as colorless solid. $^1H$ NMR ($CDCl_3$, 200 MHz): 1.34 (3H, t, J=7.0 Hz), 4.26 (2H, q, J=7.0

Hz), 4.80 (1H, dd, J=11.4, 2.6 Hz), 6.39 (1H, s), 7.24-7.31 (1H, m), 7.51 (1H, d, J=7.6 Hz), 7.76 (1H, td, J=7.6, 1.8 Hz), 8.60-8.63 (1H, m).

Compounds of Examples 16-29, 439-447 and 924-938 shown in the Table 2, were prepared in a manner similar to that described in Example 15.

TABLE 2

| Example | Structure | Name | Physiological Data |
|---|---|---|---|
| 16 | 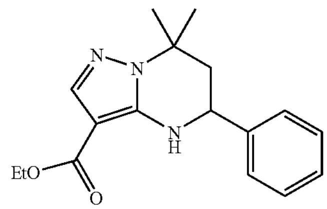 | ethyl 7,7-dimethyl-5-phenyl-4,5,6,7-tetrahydropyrazolo[1,5-a]pyrimidine-3-carboxylate | MS (ESI, m/z) 300 (M + H)+ |
| 17 | 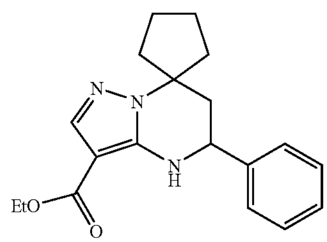 | ethyl 5'-phenyl-5',6'-dihydro-4'H-spiro[cyclopentane-1,7'-pyrazolo[1,5-a]pyrimidine]-3'-carboxylate | MS (ESI, m/z) 326 (M + H)+ |
| 18 | 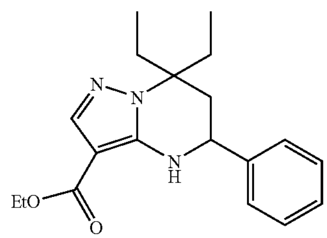 | ethyl 7,7-diethyl-5-phenyl-4,5,6,7-tetrahydropyrazolo[1,5-a]pyrimidine-3-carboxylate | MS (ESI, m/z) 300 (M + H)+ |
| 19 | 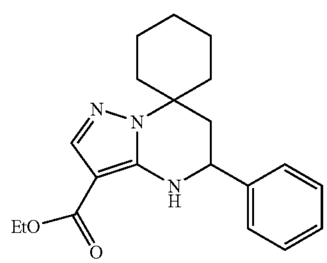 | ethyl 5'-phenyl-5',6'-dihydro-4'H-spiro[cyclohexane-1,7'-pyrazolo[1,5-a]pyrimidine]-3'-carboxylate | MS (ESI, m/z) 328 (M + H)+ |
| 20 | 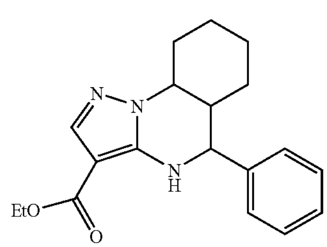 | ethyl 5-phenyl-4,5,5a,6,7,8,9,9a-octahydropyrazolo[1,5-a]quinazoline-3-carboxylate | MS (ESI, m/z) 326 (M + H)+ |
| 439 | 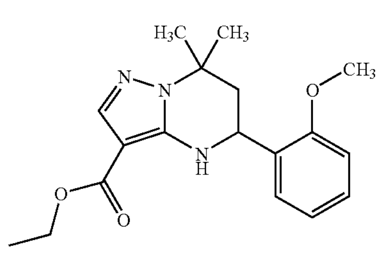 | ethyl 5-(2-methoxyphenyl)-7,7-dimethyl-4,5,6,7-tetrahydropyrazolo[1,5-a]pyrimidine-3-carboxylate | MS (ESI, m/z) 330 (M + H)+ |

TABLE 2-continued

| Example | Structure | Name | Physiological Data |
|---|---|---|---|
| 440 | 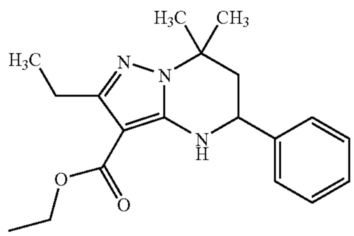 | ethyl 2-ethyl-7,7-dimethyl-5-phenyl-4,5,6,7-tetrahydropyrazolo[1,5-a]pyrimidine-3-carboxylate | MS (ESI, m/z) 328 (M + H)+ |
| 441 | 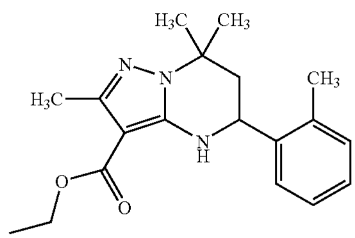 | ethyl 2,7,7-trimethyl-5-(2-methylphenyl)-4,5,6,7-tetrahydropyrazolo[1,5-a]pyrimidine-3-carboxylate | MS (ESI, m/z) 328 (M + H)+ |
| 442 | 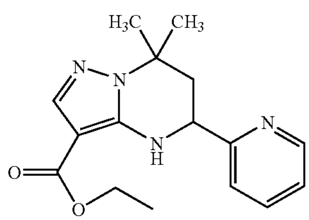 | ethyl 7,7-dimethyl-5-(2-pyridinyl)-4,5,6,7-tetrahydropyrazolo[1,5-a]pyrimidine-3-carboxylate | MS (ESI, m/z) 301 (M + H)+ |
| 443 | 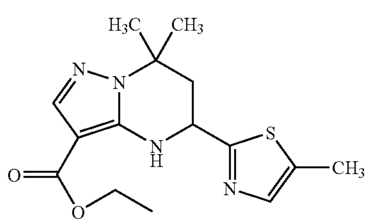 | ethyl 7,7-dimethyl-5-(5-methyl-1-3-thiazol-2-yl)-4,5,6,7-tetrahydropyrazolo[1,5-a]pyrimidine-3-carboxylate | MS (ESI, m/z) 321 (M + H)+ |
| 444 | 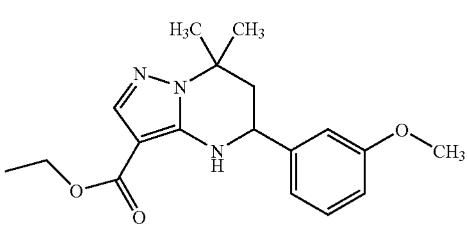 | ethyl 5-(3-methoxyphenyl)-7,7-dimethyl-4,5,6,7-tetrahydropyrazolo[1,5-a]pyrimidine-3-carboxylate | MS (ESI, m/z) 330 (M + H)+ |
| 445 | 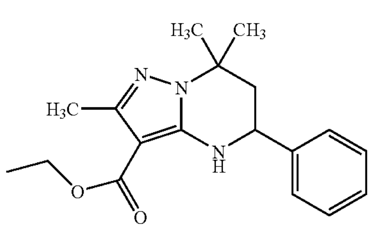 | ethyl 2,7,7-trimethyl-5-phenyl-4,5,6,7-tetrahydropyrazolo[1,5-a]pyrimidine-3-carboxylate | MS (ESI, m/z) 314 (M + H)+ |

TABLE 2-continued

| Example | Structure | Name | Physiological Data |
|---|---|---|---|
| 446 | 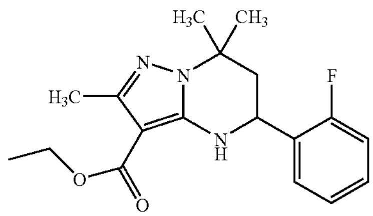 | ethyl 5-(2-fluorophenyl) 2,7,7-trimethyl-4,5,6,7-tetrahydropyrazolo[1,5-a]pyrimidine-3-carboxylate | MS (ESI, m/z) 332 (M + H)+ |
| 447 | 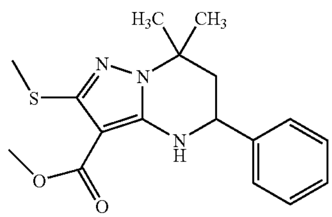 | methyl 7,7-dimethyl-2-(methylthio)-5-phenyl-4,5,6,7-tetrahydropyrazolo]1,5-a]pyrimidine-3-carboxyalate | MS (ESI, m/z) 332 (M + H)+ |
| 924 | 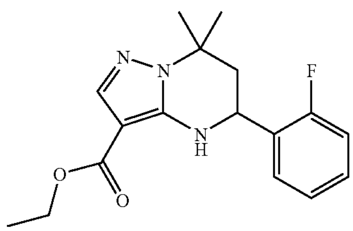 | ethyl 5-(2-fluorophenyl)-7,7-dimethyl-4,5,6,7-tetrahydropyrazolo[1,5-a]pyrimidine-3-carboxylate | MS (ESI, m/z) 318 (M + H)+ |
| 925 | 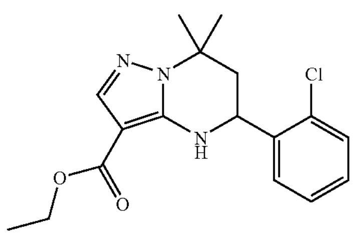 | ethyl 5-(2-chlorophenyl)-7,7-dimethyl-4,5,6,7-tetrahydropyrazolo[1,5-a]pyrimidine-3-carboxylate | MS (ESI, m/z) 334 (M + H)+ |
| 926 | 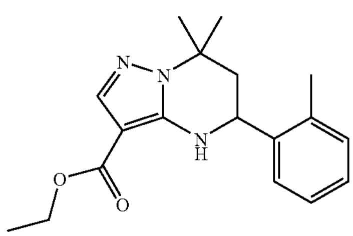 | ethyl 7,7-dimethyl-5-(2-methylphenyl)-4,5,6,7-tetrahydropyrazolo[1,5-a]pyrimidine-3-carboxylate | MS (ESI, m/z) 314 (M + H)+ |
| 927 | 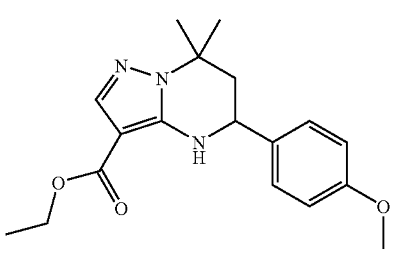 | ethyl 5-(4-methoxyphenyl)-7,7-dimethyl-4,5,6,7-tetrahydropyrazolo[1,5-a]pyrimidine-3-carboxylate | MS (ESI, m/z) 330 (M + H)+ |

TABLE 2-continued

| Example | Structure | Name | Physiological Data |
|---|---|---|---|
| 928 | 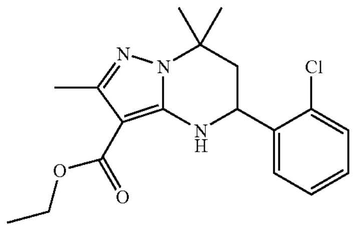 | ethyl 5-(2-chlorophenyl)-2,7,7-trimethyl-4,5,6,7-tetrahydropyrazolo[1,5-a]pyrimidine-3-carboxylate | MS (ESI, m/z) 348 (M + H)+ |
| 929 | 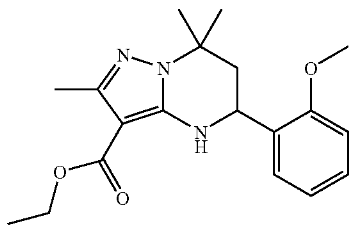 | ethy 5-(2-methoxyphenyl)-2,7,7,-trimethyl-4,5,6,7-tetrahydropyrazolo[1,5-a]-pyrimidine-3-carboxylate | MS (ESI, m/z) 344 (M + H)+ |
| 930 | 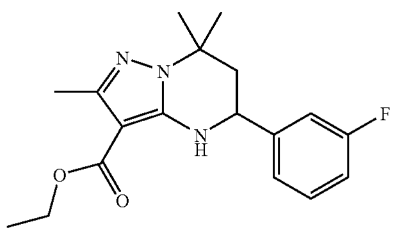 | ethyl 5-(3-fluorophenyl)-2,7,7-trimethyl-4,5,6,7-tetrahydropyrazolo[1,5-a]pyrimidine-3-carboxyalate | MS (ESI, m/z) 332 (M + H)+ |
| 931 | 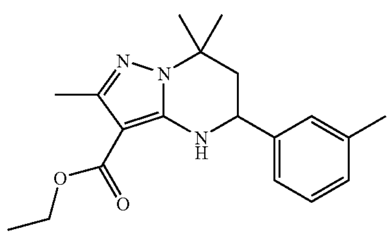 | ethyl 2,7,7-trimethyl-5-(3-methylphenyl)-4,5,6,7-tetrahydropyrazolo[1,5-a]pyrimidine-3-carboxyalate | MS (ESI, m/z) 328 (M + H)+ |
| 932 | 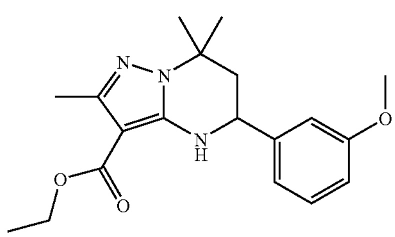 | ethyl 5-(3-methoxyphenyl)-2,7,7-trimethyl-4,5,6,7-tetrahydropyrazolo[1,5-a]pyrimidine-3-carboxylate | MS (ESI, m/z) 344 (M + H)+ |
| 933 | 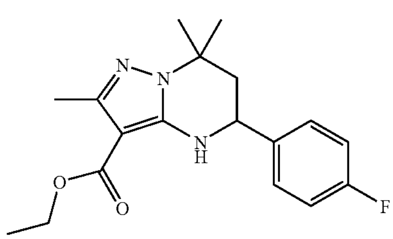 | ethyl 5-(4-fluorophenyl)-2,7,7-trimethyl-4,5,6,7-tetrahydropyrazolo[1,5-a]pyrimidine-3-carboxylate | MS (ESI, m/z) 332 (M + H)+ |

TABLE 2-continued

| Example | Structure | Name | Physiological Data |
|---|---|---|---|
| 934 | 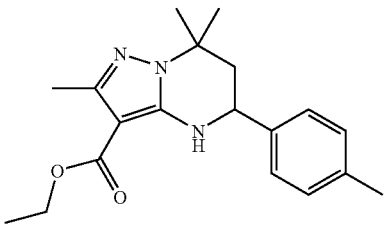 | ethyl 2,7,7-trimethyl-5-(4-methylphenyl)-4,5,6,7-tetrahydropyrazolo[1,5-a]pyrimidine-3-carboxylate | MS (ESI, m/z) 328 (M + H)+ |
| 935 | 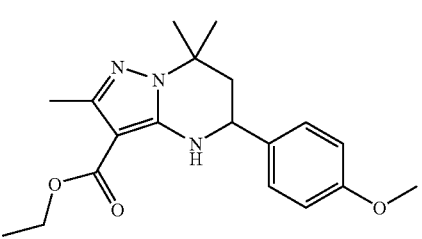 | ethyl 5-(4-methoxyphenyl)-2,7,7-trimethyl-4,5,6,7-tetrahydropyrazolo[1,5-a]pyrimidine-3-carboxylate | MS (ESI, m/z) 344 (M + H)+ |
| 936 | 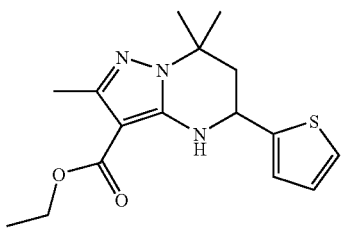 | ethyl 2,7,7-trimethyl-5-(2-thienyl)-4,5,6,7-tetrahydropyrazolo[1,5-a]pyrimidine-3-carboxylate | MS (ESI, m/z) 320 (M + H)+ |
| 937 | 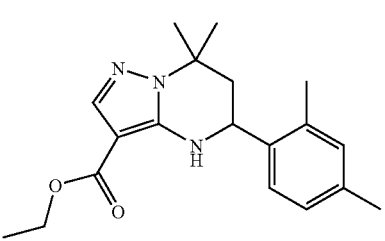 | ethyl 5-(2,4-dimethylphenyl)-7,7-dimethyl-4,5,6,7-tetrahydropyrazolo[1,5-a]pyrimidine-3-carboxylate | MS (ESI, m/z) 328 (M + H)+ |
| 938 | 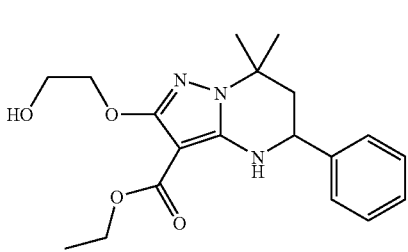 | ethyl 2-(2-hydroxyethoxyl)-7,7-dimethyl-5-phenyl-4,5,6,7-tetrahydropyrazolol[1,5-a]pyrimidine-3-carboxylate | MS (ESI, m/z) 360 (M + H)+ |

EXAMPLE 21

5-Phenyl-7-(trifluoromethyl)-4,5,6,7-tetrahydropyrazolo[1,5-a]pyrimidine-3-carboxylic acid

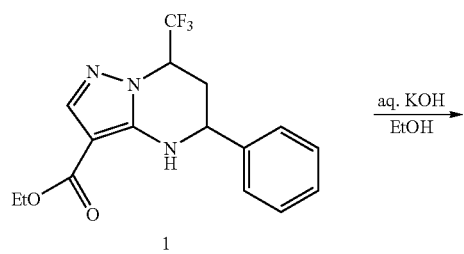

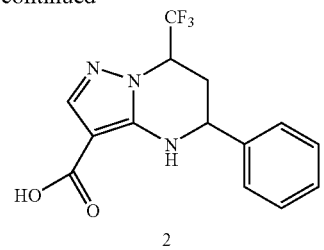

A mixture of 1, 1.5 N KOH solution (14 mL) and EtOH (20 mL) was stirred at 60° C. for 12 h, acidified with saturated citric acid solution, and the precipitated solid was collected by filtration, which was washed with water and IPE to give 1.59 g (76% yield) of the title compound as colorless prisms. mp 184.8-185.0° C., $^1$H NMR (CDCl$_3$, 300 MHz): 2.31-2.44 (1H, m), 2.50-2.59 (1H, m), 4.59 (1H, dd, J=11.4, 3.0 Hz), 4.79 (1H, m), 6.10 (1H, s), 7.20-7.26 (5H, m), 7.78 (1H, s).

Compounds of Examples 22-39, 448-458 and 939-953 shown in the Table 3, were prepared in a manner similar to that described in Example 21.

TABLE 3

| Example | Structure | Name | Physiological Data |
|---|---|---|---|
| 22 | 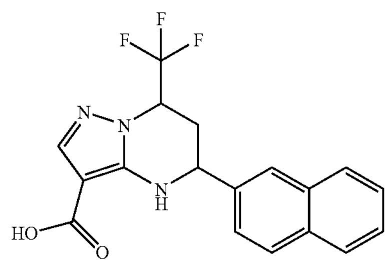 | 5-(2-naphthyl)-7-(trifluoromethyl)-4,5,6,7-tetrahydropyrazolo[1,5-a]pyrimidine-3-carboxylic acid | mp 143–145° C. |
| 23 | 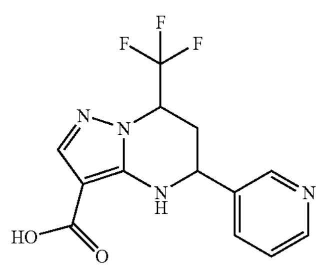 | 5-(3-pyridinyl)-7-(trifluoromethyl)-4,5,6,7-tetrahydropyrazolo[1,5-a]pyrimidine-3-carboxylic acid | MS (ESI, m/z) 315 (M + H)+ |
| 24 | 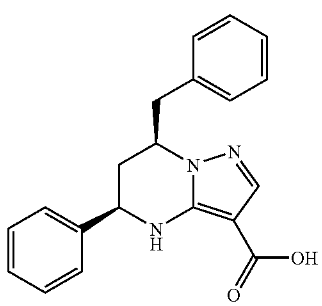 | 7-benzyl-5-phenyl-4,5,6,7-tetrahydropyrazolo[1,5-a]pyrimidine-3-carboxylic acid | MS (ESI, m/z) 336 (M + H)+ |

TABLE 3-continued

| Example | Structure | Name | Physiological Data |
|---|---|---|---|
| 25 | 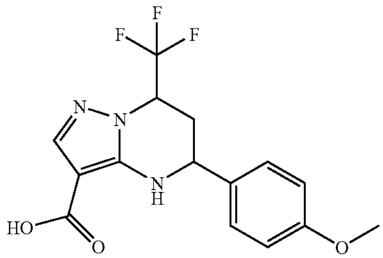 | 5-(4-methoxyphenyl)-7-(trifluoromethyl)-4,5,6,7-tetrahydropyrazolo[1,5-a]pyrimidine-3-carboxylic acid | mp 154–155° C. |
| 26 | 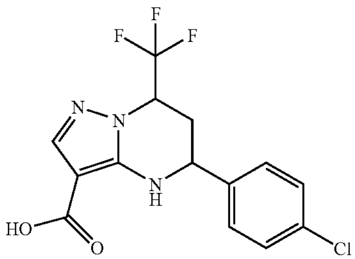 | 5-(4-chlorophenyl)-7-(trifluoromethyl)-4,5,6,7-tetrahydropyrazolo[1,5-a]pyrimidine-3-carboxylic acid | mp 186–187° C. |
| 27 | 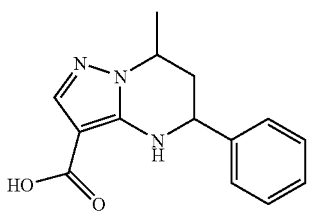 | 7-methyl-5-phenyl-4,5,6,7-tetrahydropyrazolo[1,5-a]pyrimidine-3-carboxylic acid | mp 165–167° C. |
| 28 | 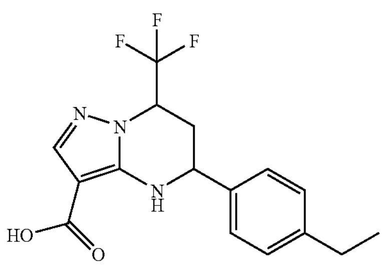 | 5-(4-ethylphenyl)-7-(trifluoromethyl)-4,5,6,7-tetrahydropyrazolo[1,5-a]pyrimidine-3-carboxylic acid | mp 165–168° C. |
| 29 | 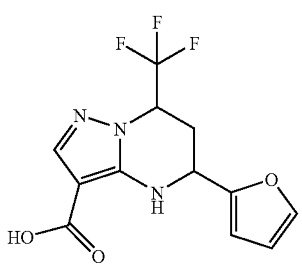 | 5-(2-furyl)-7-(trifluoromethyl)-4,5,6,7-tetrahydropyrazolo[1,5-a]pyrimidine-3-carboxylic acid | mp 156–157° C. |
| 30 | 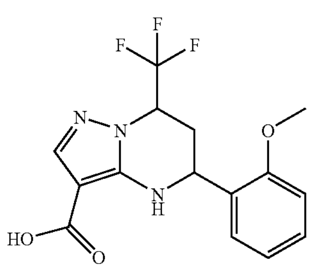 | 5-(2-methoxyphenyl)-7-(trifluoromethyl)-4,5,6,7-tetrahydropyrazolo[1,5-a]pyrimidine-3-carboxylic acid | mp 189–190° C. |

TABLE 3-continued

| Example | Structure | Name | Physiological Data |
|---|---|---|---|
| 31 | 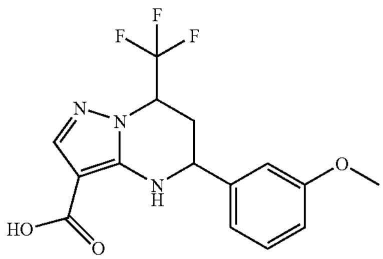 | 5-(3-methoxyphenyl)-7-(trifluoromethyl)-4,5,6,7-tetrahydropyrazolo[1,5-a]pyrimidine-3-carboxylic acid | mp 169–170° C. |
| 32 | 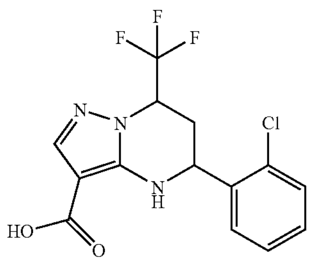 | 5-(2-chlorophenyl)-7-(trifluoromethyl)-4,5,6,7-tetrahydropyrazolo[1,5-a]pyrimidine-3-carboxylic acid | mp 177–179° C. |
| 33 | 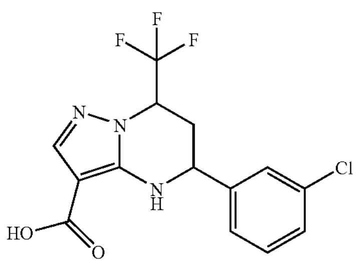 | 5-(3-chlorophenyl)-7-(trifluoromethyl)-4,5,6,7-tetrahydropyrazolo[1,5-a]pyrimidine-3-carboxylic acid | mp 194–195° C. |
| 34 | 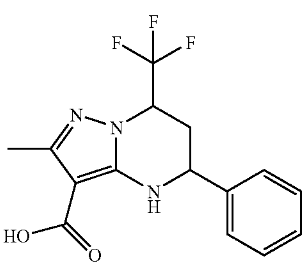 | 2-methyl-7-(trifluoromethyl)-4,5,6,7-tetrahydropyrazolo[1,5-a]pyrimidine-3-carboxylic acid | mp 165–166° C. |
| 35 | 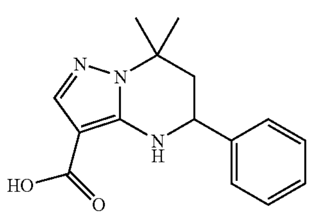 | 7,7-dimethyl-5-phenyl-4,5,6,7-tetrahydropyrazolo[1,5-a]pyrimidine-3-carboxylic acid | mp 201–202° C. |
| 36 | 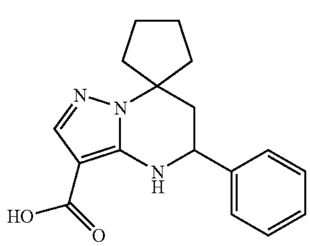 | 5'-pheny-5',6'-dihydro-4'H-spiro[cyclopentane-1,7'-pyrazolo[1,5-a]pyrimidine]-3'-carboxylic acid | MS (ESI, m/z) 298 (M + H)+ |

TABLE 3-continued

| Example | Structure | Name | Physiological Data |
|---|---|---|---|
| 37 | 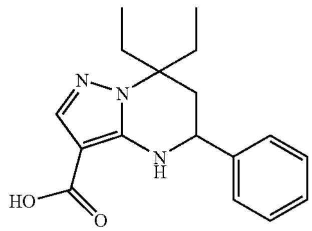 | 7,7-diethyl-5-phenyl-4,5,6,7-tetrahydropyrazolo[1,5-a]pyrimidine-3-carboxylic acid | mp 158–160° C. |
| 39 | | 5'-phenyl-5',6'-dihydro-4'H-spiro[cyclohexane-1,7'-pyrazolo[1,5-a]pyrimidine]-3'-carboxylic acid | mp 155° C. |
| 39 | | 5-phenyl-4,5,5a,6,7,8,9,9a-octahydropyrazolo[1,5-a]quinazoline-3-carboxylic acid | mp 158–160° C. |
| 448 | 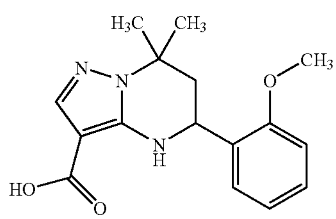 | 5-(2-methoxyphenyl)-7,7-dimethyl-4,5,6,7-tetrahydropyrazolo[1,5-a]pyrimidine-3-carboxylic acid | MS (ESI, m/z) 302 (M + H)+ |
| 449 | 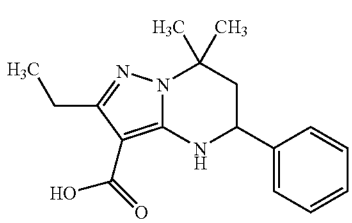 | 2-ethyl-7,7-dimethyl-5-phenyl-4,5,6,7-tetrahydropyrazolo[1,5-a]pyrimidine-3-carboxylic acid | MS (ESI, m/z) 300 (M + H)+ |
| 450 | 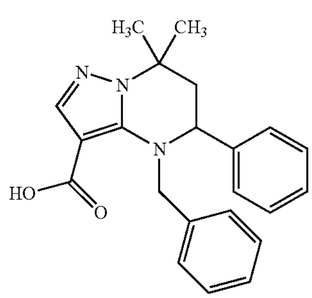 | 4-benzyl-7,7-dimethyl-5-phenyl-4,5,6,7-tetrahydropyrazolo[1,5-a]pyrimidine-3-carboxylic acid | MS (ESI, m/z) 362 (M + H)+ |

TABLE 3-continued

| Example | Structure | Name | Physiological Data |
|---|---|---|---|
| 451 | 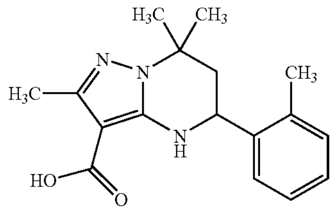 | 2,7,7-trimethyl-5-(2-methylphenyl)-4,5,6,7-tetrahydropyrazolo[1,5-a]pyrimidine-3-carboxylic acid | MS (ESI, m/z) 300 (M + H)+ |
| 452 | 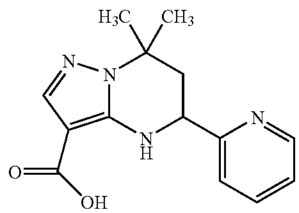 | 7,7-dimethyl-5-(2-pyridinyl)-4,5,6,7-tetrahydropyrazolo[1,5-a]pyrimidine-3-carboxylic acid | MS (ESI, m/z) 273 (M + H)+ |
| 453 | 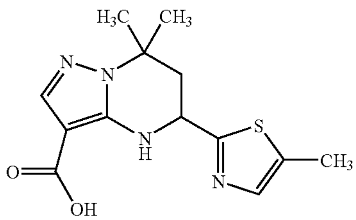 | 7,7-dimethyl-5-(5-methyl-1,3-thiazol-2-yl)-4,5,6,7-tetrahydropyrazolo[1,5-a]pyrimidine-3-carboxylic acid | MS (ESI, m/z) 293 (M + H)+ |
| 454 | 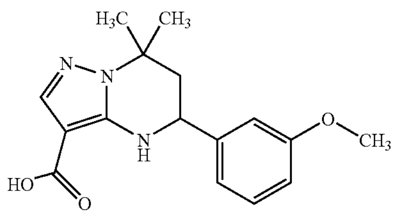 | 5-(3-methoxyphenyl)-7,7-dimethyl-4,5,6,7-tetrahydropyrazolo[1,5-a]pyrimidine-3-carboxylic acid | MS (ESI, m/z) 302 (M + H)+ |
| 455 | 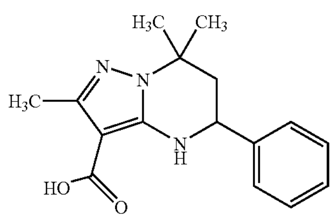 | 2,7,7-trimethyl-5-phenyl-4,5,6,7-tetrahydropyrazolo[1,5-a]pyrimidine-3-carboxylic acid | MS (ESI, m/z) 286 (M + H)+ |
| 456 | 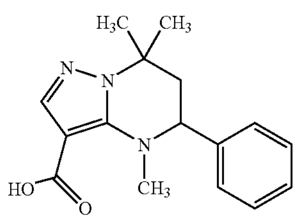 | 4,7,7-trimethyl-5-phenyl-4,5,6,7-tetrahydropyrazolo[1,5-a]pyrimidine-3-carboxylic acid | MS (ESI, m/z) 286 (M + H)+ |
| 457 | 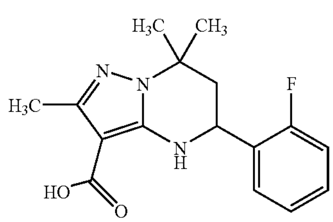 | 5-(2-fluorophenyl)-2,7,7-trimethyl-4,5,6,7-tetrahydropyrazolo[1,5-a]pyrimidine-3-carboxylic acid | MS (ESI, m/z) 304 (M + H)+ |

TABLE 3-continued

| Example | Structure | Name | Physiological Data |
| --- | --- | --- | --- |
| 458 | 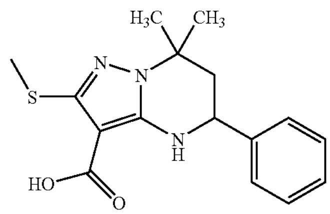 | 7,7-dimethyl-2-(methylthio)-5-phenyl-4,5,6,7-tetrahydropyrazolo[1,5-a]pyrimidine-3-carboxylic acid | MS (ESI, m/z) 318 (M + H)+ |
| 939 | 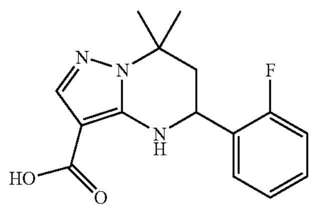 | 5-(2-fluorophenyl)-7,7-dimethyl-4,5,6,7-tetrahydropyrazolo[1,5-a]pyrimidine-3-carboxylic acid | mp 167–168° C. |
| 940 | 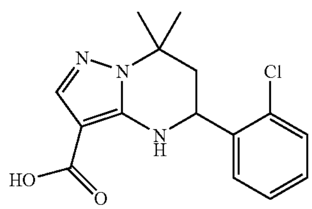 | 5-(2-chlorophenyl)-7,7-dimethyl-4,5,6,7-tetrahydropyrazolo[1,5-a]pyrimidine-3-carboxylic acid | mp 167–168° C. |
| 941 | 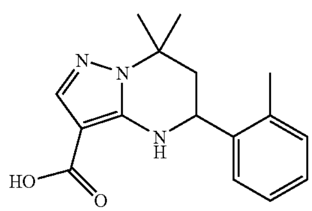 | 7,7-dimethyl-5-(2-methylphenyl)-4,5,6,7-tetrahydropyrazolo[1,5-a]pyrimidine-3-carboxylic acid | $^1$H NMR (CDCl$_3$, 300 MHz) δ 1.59 (3H, s), 1.64 (3H, s), 1.92–2.17 (2H, m), 2.38 (3H, s), 4.89 (1H, dd, J = 10.8, 3.9 Hz), 5.92 (1H, s), 7.16–7.29 (3H, m), 7.53 (1H, dd, J = 7.2, 1.8 Hz), 7.69 (1H, s). |
| 942 | 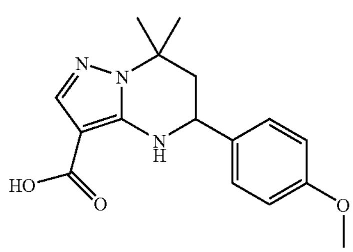 | 5-(4-methoxyphenyl)-7,7-dimethyl-4,5,6,7-tetrahydropyrazolo[1,5-a]pyrimidine-3-carboxylic acid | mp 196–197° C. |
| 943 | 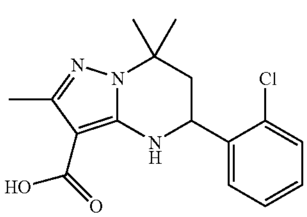 | 5-(2-chlorophenyl)-2,7,7-trimethyl-4,5,6,7-tetrahydropyrazolo[1,5-a]pyrimidine-3-carboxylic acid | mp 173–174° C. |
| 944 | 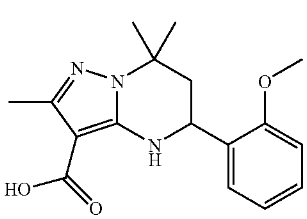 | 5-(2-methoxyphenyl)-2,7,7-trimethyl-4,5,6,7-tetrahydropyrazolo[1,5-a]pyrimidine-3-carboxylic acid | mp 198–199° C. |

TABLE 3-continued

| Example | Structure | Name | Physiological Data |
|---------|-----------|------|--------------------|
| 945 | 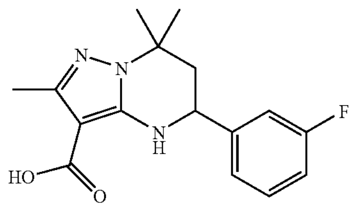 | 5-(3-fluorophenyl)-2,7,7-trimethyl-4,5,6,7-tetrahydropyrazolo[1,5-a]pyrimidine-3-carboxylic acid | mp 153–155° C. |
| 946 | 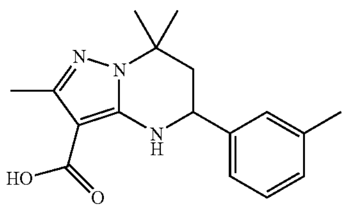 | 2,7,7-trimethyl-5-(3-methylphenyl)-4,5,6,7-tetrahydropyrazolo[1,5-a]pyrimidine-3-carboxylic acid | mp 146–148° C. |
| 947 | 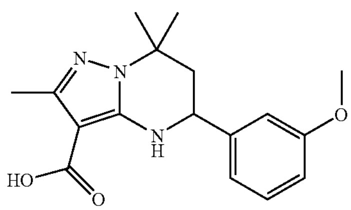 | 5-(3-methoxyphenyl)-2,7,7-trimethyl-4,5,6,7-tetrahydropyrazolo[1,5-a]pyrimidine-3-carboxylic acid | mp 151–152° C. |
| 948 | 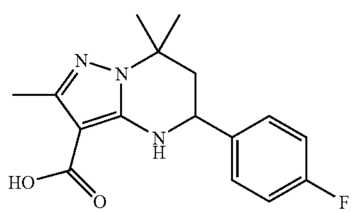 | 5-(4-fluorophenyl)-2,7,7-trimethyl-4,5,6,7-tetrahydropyrazolo[1,5-a]pyrimidine-3-carboxylic acid | mp 173–174° C. |
| 949 | 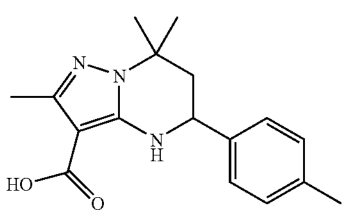 | 2,7,7-trimethyl-5-(4-methylphenyl)-4,5,6,7-tetrahydropyrazolo[1.5-a]pyrimidine-3-carboxylic acid | mp 181–182° C. |
| 950 | 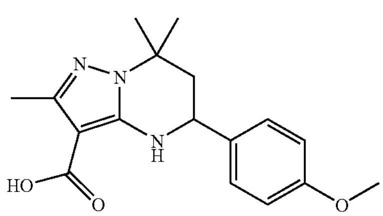 | 5-(4-methoxyphenyl)-2,7,7-trimethyl-4,5,6,7-tetrahydropyrazolo[1,5-a]pyrimidine-3-carboxylic acid | mp 178–179° C. |
| 951 | 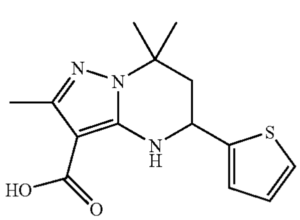 | 2,7,7-trimethyl-5-(2-thienyl)-4,5,6,7-tetrahydropyrazolo[1,5-a]pyrimidine-3-carboxylic acid | mp 186–187° C. |

TABLE 3-continued

| Example | Structure | Name | Physiological Data |
|---|---|---|---|
| 952 | 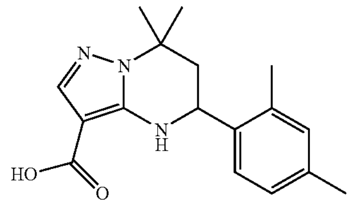 | 5-(2,4-dimethylphenyl)-7,7-dimethyl-4,5,6,7-tetrahydropyrazolo[1,5-a]pyrimidine-3-carboxylic acid | mp 155–157° C. |
| 953 | 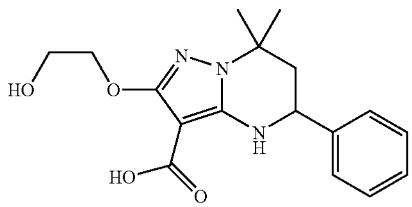 | 2-(2-hydroxyethoxy)-7,7-dimethyl-5-phenyl-4,5,6,7-tetrahydropyrazolo[1,5-a]pyrimidine-3-carboxylic acid | mp 137–139° C. |

EXAMPLE 40

N-Cyclooctyl-5-phenyl-7-(trifluoromethyl)-4,5,6,7-tetrahydropyrazolo[1,5-a]pyrimidine-3-carboxamide

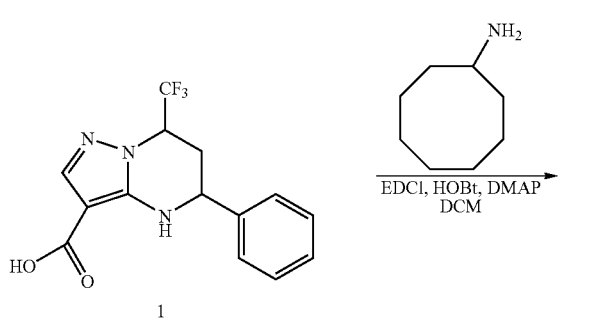

Cyclooctylamine (24 mg, 0.19 mmol) was added to a suspension of compound 1 (0.05 g, 0.16 mmol), WSC (37 mg, 0.19 mmol), HOBt (29 mg, 0.19 mmol) and DMAP (23 mg, 0.19 mmol) in DMF (1.5 mL). The reaction mixture was stirred at room temperature for 14 h, diluted with DCM (0.5 mL) and saturated NaHCO$_3$ solution (0.5 mL), and then separated using PHASE-SEP filtration syringe. The organic layer was concentrated and loaded onto preparative HPLC (Gilson 215 system). The purest fractions were combined to give 64.6 mg (96% yield) of the title compound as a white solid. Reverse Phase LC/MS: CAPCELLPAKCC18UG120, S-3 μm, 2.0×50 mm, UV detection at 220, 8 min. gradient 10-100% Solvent B/A (Solvent A: CH$_3$CN with 0.1% TFA, Solvent B: H$_2$O with 0.1% TFA), 0.5 mL/min. Rt=1.90 min, (96% pure). MS (M+H: 421).

EXAMPLE 41

N-(1-ethyl-1-(4-(trifluoromethyl)phenyl)propyl)-7,7-dimethyl-5-phenyl-4,5,6,7-tetrahydropyrazolo[1,5-a]pyrimidine-3-carboxamide

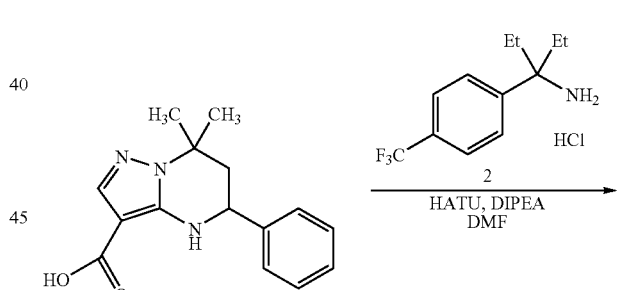

To a solution of 3 (0.5 g, 1.84 mmol) and HATU (0.84 g, 2.21 mmol) in DMF (3 mL) was added DIPEA (0.67 mL, 3.68 mmol) at room temperature. After 30 min, compound 2 (0.59 g, 2.21 mmol) was added thereto. The resulting mixture was stirred at 80° C. for 18 h, concentrated in vacuo, and the residue was chromatographed on silica gel with AcOEt/hexane (1/1) as an eluent to give 0.28 g (31% yield) of compound 4 as colorless prisms. mp 193-194° C.

Compounds of Examples 42-434, 459-867 and 954-1008 shown in the table 4, were prepared in a manner similar to that described in Example 40 or 41.

TABLE 4

| Example | Structure | Name | Physiological Data |
|---|---|---|---|
| 42 | 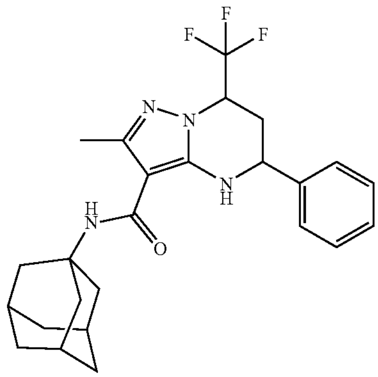 | N-(1-adamantyl)-2-methyl-7-trifluoromethyl)-4,5,6,7-tetrahydropyrazolo[1,5-a]pyrimidine-3-carboxamide | mp 162-163° C. |
| 43 | 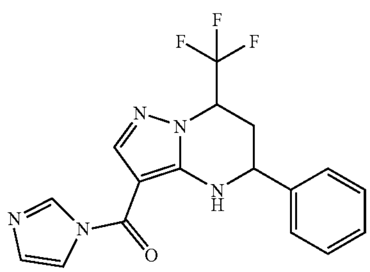 | 3-(1H-imidazol-1-ylcarbonyl)-5-phenyl-7-(trifluoromethyl)-4,5,6,7-tetrahydropyrazolo[1,5-a]pyrimidine | MS (ESI, m/z) 364 (M + H)+ |
| 44 | 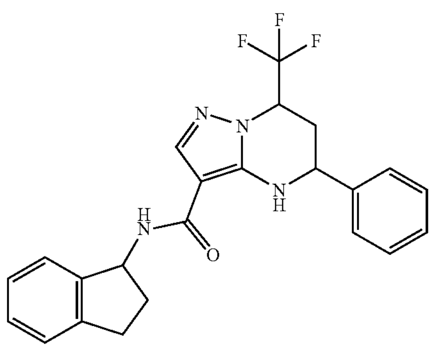 | N-(2,3-dihydro-1H-inden-1-yl)-5-phenyl-7-(trifluoromethyl)-4,5,6,7-tetrahydropyrazolo[1,5-a]pyrimidine-3-carboxamide | MS (ESI, m/z) 429 (M + H)+ |
| 45 | 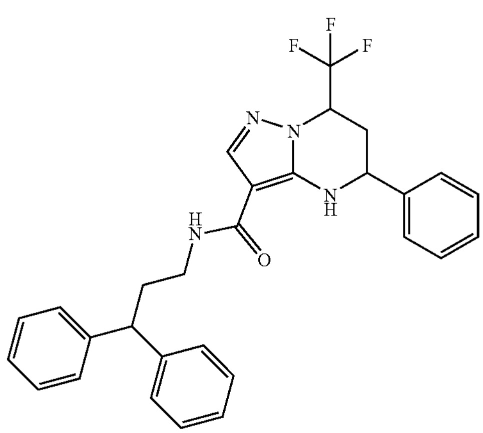 | N-(3,3-diphenylpropyl)-5-phenyl-7-(trifluoromethyl)-4,5,6,7-tetrahydropyrazolo[1,5-a]pyrimidine-3-carboxamide | MS (ESI, m/z) 508 (M + H)+ |

TABLE 4-continued

| Example | Structure | Name | Physiological Data |
|---|---|---|---|
| 46 | 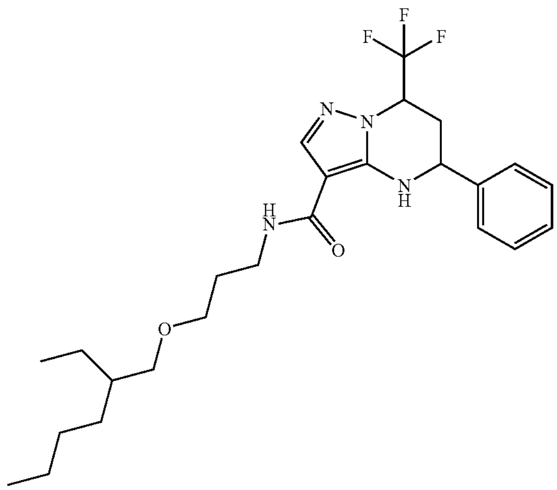 | N-(3-((2-ethylhexyl)oxy)propyl)-5-phenyl-7-(trifluoromethyl)-4,5,6,7-tetrahydropyrazolo[1,5-a]pyrimidine-3-carboxamide | MS (ESI, m/z) 484 (M + H)+ |
| 47 | 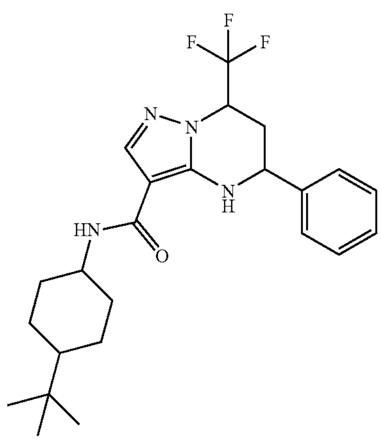 | N-(4-tert-butylcyclohexyl)-5-phenyl-7-(trifluoromethyl)-4,5,6,7-tetrahydropyrazolo[1,5-a]pyrimidine-3-carboxamide | MS (ESI, m/z) 452 (M + H)+ |
| 48 | 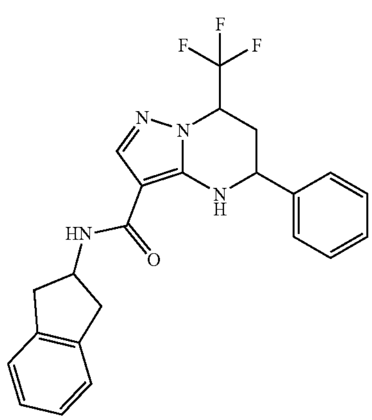 | N-(2,3-dihydro-1H-inden-2-yl)-5-phenyl-7-(trifluoromethyl)-4,5,6,7-tetrahydropyrazolo[1,5-a]pyrimidine-3-carboxamide | MS (ESI, m/z) 429 (M + H)+ |

TABLE 4-continued

| Example | Structure | Name | Physiological Data |
|---|---|---|---|
| 49 | 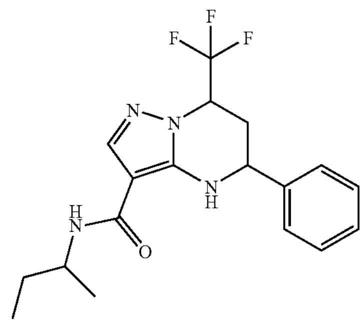 | N-(sec-butyl)-5-phenyl-7-(trifluoromethyl)-4,5,6,7-tetrahydropyrazolo[1,5-a]pyrimidine-3-carboxamide | MS (ESI, m/z) 369 (M + H)+ |
| 50 | 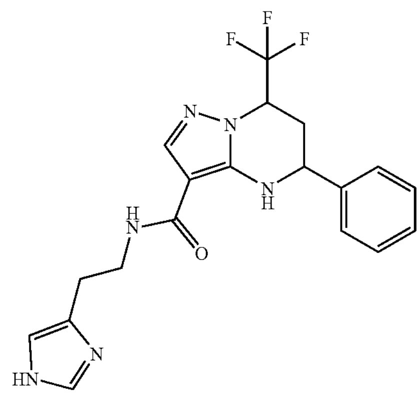 | N-(2-(1H-imidazol-4-yl)ethyl)-5-phenyl-7-(trifluoromethyl)-4,5,6,7-tetrahydropyrazolo[1,5-a]pyrimidine-3-carboxamide | MS (ESI, m/z) 407 (M + H)+ |
| 51 | 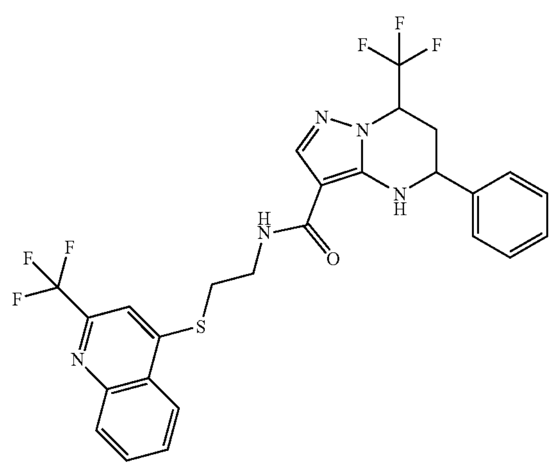 | 5-phenyl-7-(trifluoromethyl)-N-(2-((2-(tritiuoromethyl)-4-quinolinyl)thio)ethyl)-4,5,6,7-tetrahydropyrazolo[1,5-a]pyrimidine-3-carboxamide | MS (ESI, m/z) 569 (M + H)+ |
| 52 | 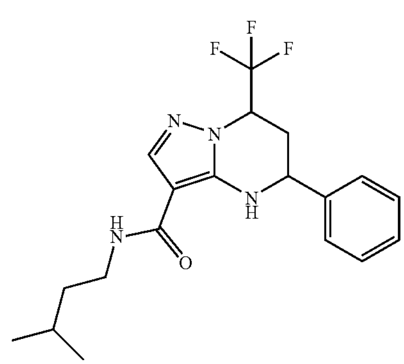 | N-(3-methylbutyl)-5-phenyl-7-trifluoromethyl)-4,5,6,7-tetrahydropyrazolo[1,5-a]pyrimidine-3-carboxamide | MS (ESI, m/z) 383 (M + H)+ |

TABLE 4-continued

| Example | Structure | Name | Physiological Data |
|---|---|---|---|
| 53 | 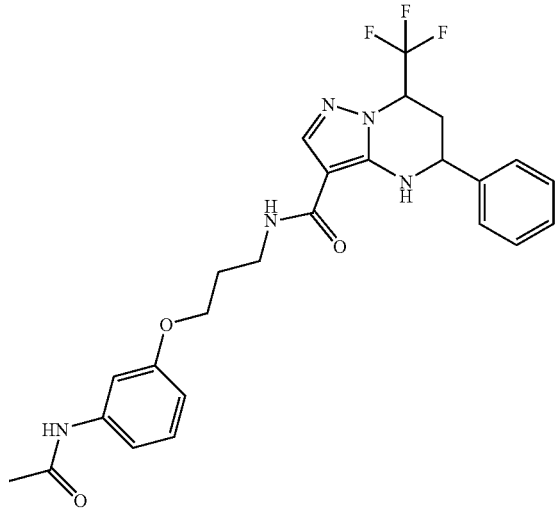 | N-(3-(3-(acetylamino)phenoxy)propyl)-5-phenyl-7-(trifluoromethyl)-4,5,6,7-tetrahydropyrazolo[1,5-a]pyrimidine-3-carboxamide | MS (ESI, m/z) 505 (M + H)+ |
| 54 | 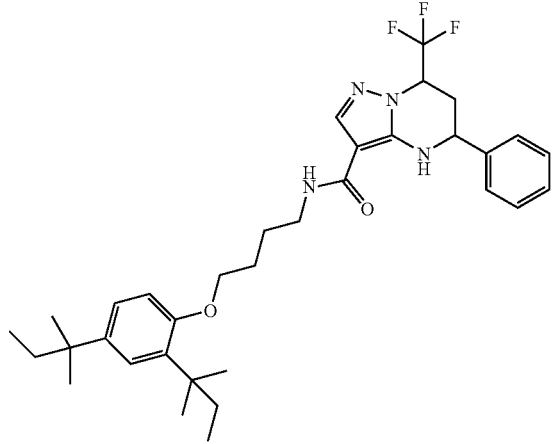 | N-(4-(2,4-bis(1,1-dimethylpropyl)phenoxy)butyl)-5-phenyl-7-(trifluoromethyl)-4,5,6,7-tetrahydropyrazolo[1,5-a]pyrimidine-3-carboxamide | MS (ESI, m/z) 602 (M + H)+ |
| 55 | 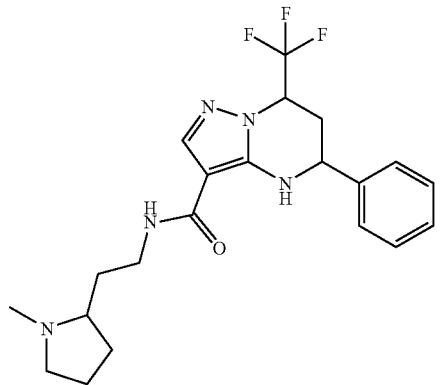 | N-(2-(1-methyl-2-pyrrolidinyl)ethyl)-5-phenyl-7-trifluoromethyl)-4,5,6,7-tetrahydropyrazolo[1,5-a]pyrimidine-3-carboxamide | MS (ESI, m/z) 424 (M + H)+ |

TABLE 4-continued

| Example | Structure | Name | Physiological Data |
|---|---|---|---|
| 56 | 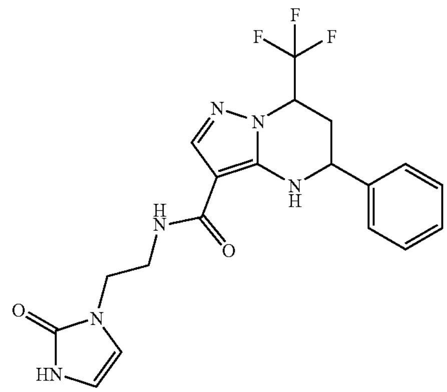 | N-(2-(2-oxo-2,3-dihydro-1H-imidazol-1-yl)ethyl)-5-phenyl-7-(trifluoromethyl)-4,5,6,7-tetrahydropyrazolo[1,5-a]pyrimidine-3-carboxamide | MS (ESI, m/z) 423 (M + H)+ |
| 57 | 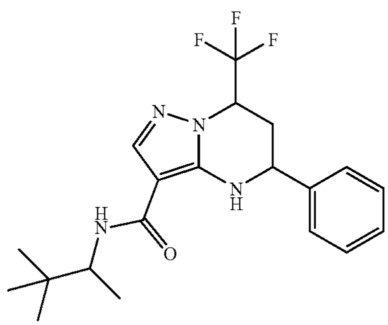 | 5-phenyl-7-(trifluoromethyl)-N-(1,2,2-trimethylpropyl)-4,5,6,7-tetrahydropyrazolo[1,5-a]pyrimidine-3-carboxamide | MS (ESI, m/z) 397 (M + H)+ |
| 58 | 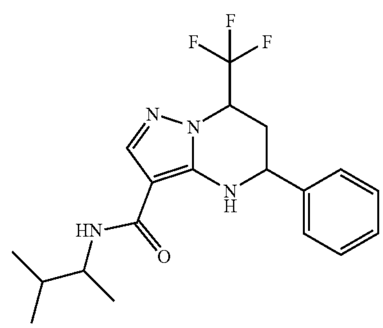 | N-(1,2-dimethylpropyl)-5-phenyl-7-(trifluoromethyl)-4,5,6,7-tetrahydropyrazolo[1,5-a]pyrimidine-3-carboxamide | MS (ESI, m/z) 383 (M + H)+ |
| 59 | 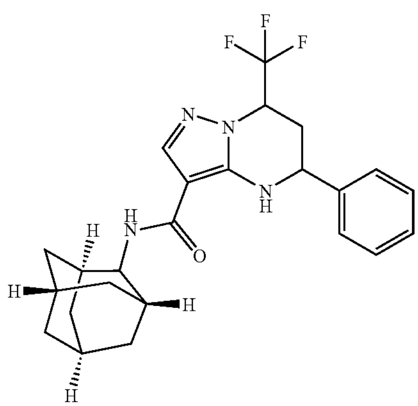 | N-(2-adamantyl)-5-phenyl-7-trifluoromethyl)-4,5,6,7-tetrahydropyrazolo[1,5-a]pyrimidine-3-carboxamide | MS (ESI, m/z) 447 (M + H)+ |

TABLE 4-continued

| Example | Structure | Name | Physiological Data |
|---|---|---|---|
| 60 | 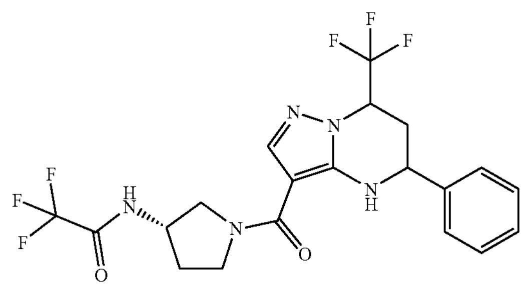 | 2,2,2-trifluoro-N-((3S)-1-((5-phenyl-7-(trifluoromethyl)-4,5,6,7-tetrahydropyrazolo[1,5-a]pyrimidin-3-yl)carbonyl)-3-pyrrolidinyl)acetamide | MS (ESI, m/z) 478 (M + H)+ |
| 61 | 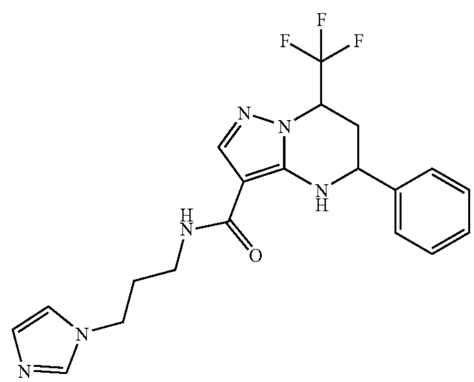 | N-(3-(1H-imidazol-1-yl)propyl)-5-phenyl-7-(trifluoromethyl)-4,5,6,7-tetrahydropyrazolo[1,5-a]pyrimidine-3-carboxamide | MS (ESI, m/z) 421 (M + H)+ |
| 62 | 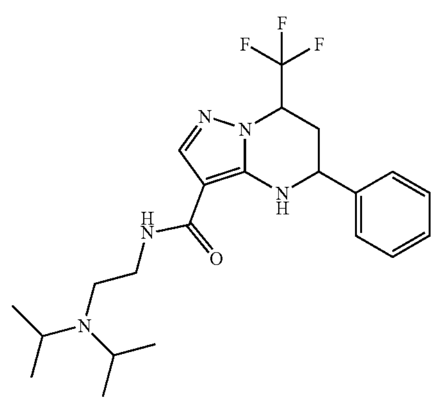 | N-(2-(diisopropylamino)ethyl)-5-phenyl-7-(trifluoromethyl)-4,5,6,7-tetrahydropyrazolo[1,5-a]pyrimidine-3-carboxamide | MS (ESI, m/z) 441 (M + H)+ |
| 63 | 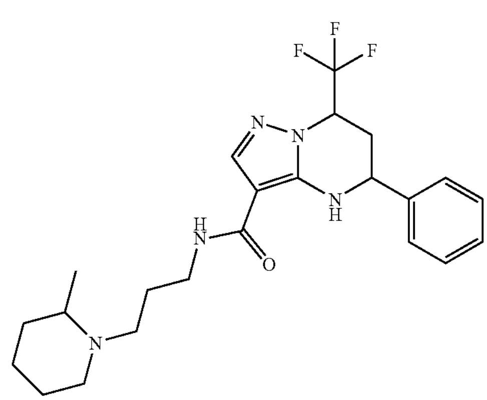 | N-(3-(2-methyl-1-piperidinyl)propyl)-5-phenyl-7-(trifluoromethyl)-4,5,6,7-tetrahydropyrazolo[1,5-a]pyrimidine-3-carboxamide | MS (ESI, m/z) 453 (M + H)+ |

TABLE 4-continued

| Example | Structure | Name | Physiological Data |
|---|---|---|---|
| 64 | 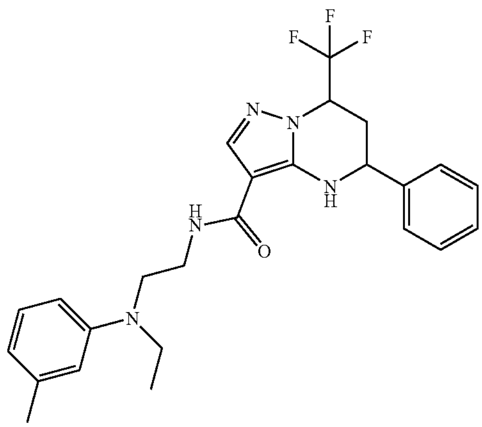 | N-(2-(ethyl(3-methylphenyl)amino)ethyl)-5-phenyl-7-(trifluoromethyl)-4,5,6,7-tetrahydropyrazolo[1,5-a]pyrimidine-3-carboxamide | MS (ESI, m/z) 475 (M + H)+ |
| 65 | 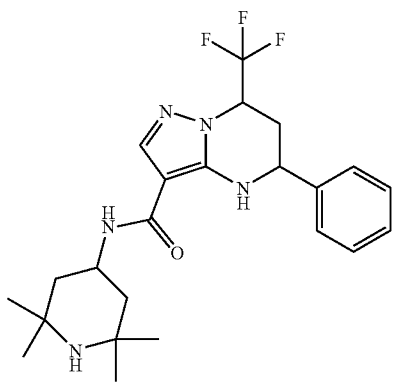 | 5-phenyl-N-(2,2,6,6-tetramethyl-4-piperidinyl)-7-(trifluoromethyl)-4,5,6,7-tetrahydropyrazolo[1,5-a]pyrimidine-3-carboxamide | MS (ESI, m/z) 453 (M + H)+ |
| 66 | 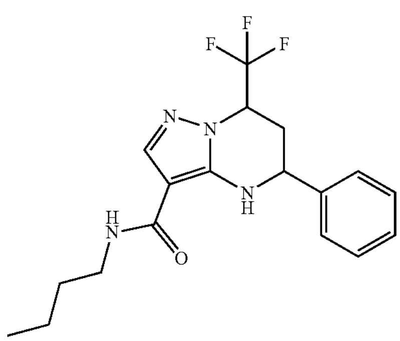 | N-butyl-5-phenyl-7-(trifluoromethyl)-4,5,6,7-tetrahydropyrazolo[1,5-a]pyrimidine-3-carboxamide | MS (ESI, m/z) 369 (M + H)+ |
| 67 | 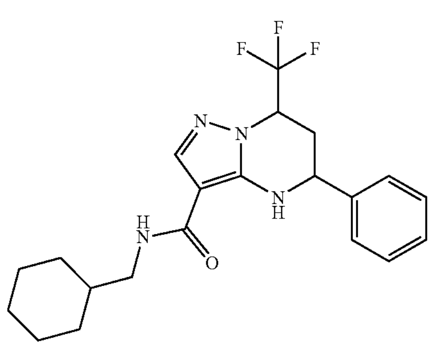 | N-(cyclohexylmethyl)-5-phenyl-7-(trifluoromethyl)-4,5,6,7-tetrahydropyrazolo[1,5-a]pyrimidine-3-carboxamide | MS (ESI, m/z) 409 (M + H)+ |

TABLE 4-continued

| Example | Structure | Name | Physiological Data |
|---|---|---|---|
| 68 | 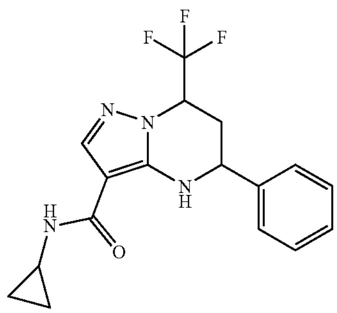 | N-cyclopropyl-5-phenyl-7-(trifluoromethyl)-4,5,6,7-tetrahydropyrazolo[1,5-a]pyrimidine-3-carboxamide | MS (ESI, m/z) 353 (M + H)+ |
| 69 | 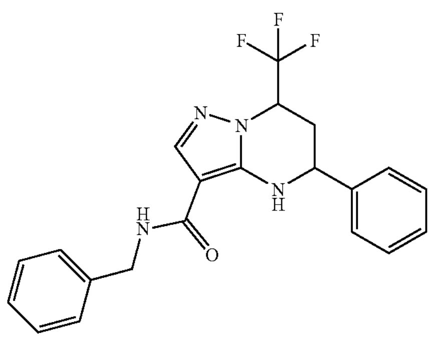 | N-benzyl-5-phenyl-7-(trifluoromethyl)-4,5,6,7-tetrahydropyrazolo[1,5-a]pyrimidine-3-carboxamide | MS (ESI, m/z) 403 (M + H)+ |
| 70 | 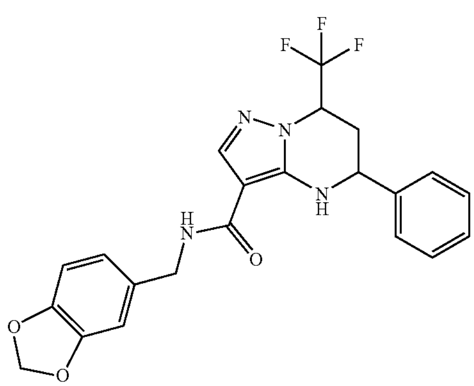 | N-(1,3-benzodioxol-5-ylmethyl)-phenyl-7-(trifluoromethyl)-4,5,6,7-tetrahydropyrazolo[1,5-a]pyrimidine-3-carboxamide | MS (ESI, m/z) 447 (M + H)+ |
| 71 | 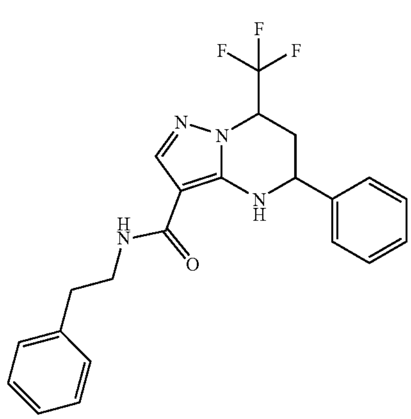 | 5-phenyl-N-(2-phenylethyl)-7-(trifluoromethyl)-4,5,6,7-tetrahydropyrazolo[1,5-a]pyrimidine-3-carboxamide | MS (ESI, m/z) 417 (M + H)+ |

TABLE 4-continued

| Example | Structure | Name | Physiological Data |
|---|---|---|---|
| 72 | 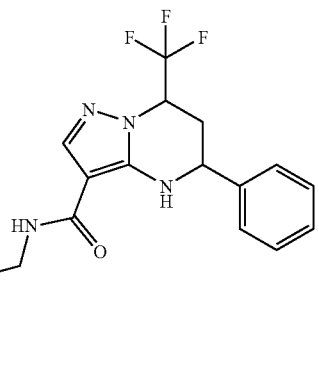 | 5-phenyl-N-(3-phenylpropyl)-7-(trifluoromethyl)-4,5,6,7-tetrahydropyrazolo[1,5-a]pyrimidine-3-carboxamide | MS (ESI, m/z) 431 (M + H)+ |
| 73 | 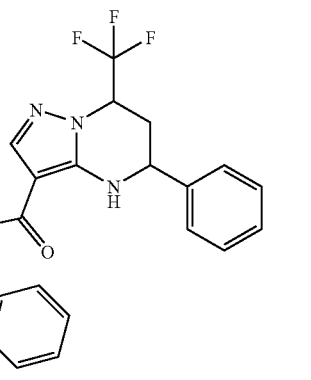 | N-benzhydryl-5-phenyl-7-(trifluoromethyl)-4,5,6,7-tetrahydropyrazolo[1,5-a]pyrimidine-3-carboxamide | MS (ESI, m/z) 480 (M + H)+ |
| 74 | 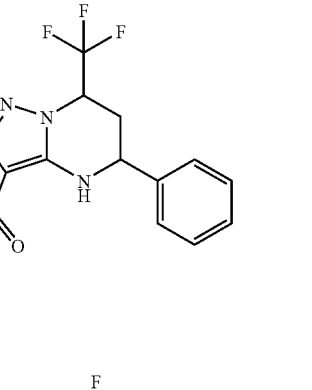 | N-(2-methoxyethyl)-5-phenyl-7-(trifluoromethyl)-4,5,6,7-tetrahydropyrazolo[1,5-a]pyrimidine-3-carboxamide | MS (ESI, m/z) 371 (M + H)+ |
| 75 | 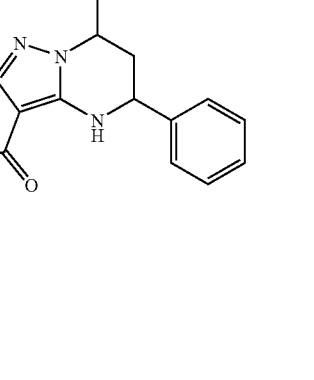 | N-(3-(methylthio)propyl)-5-phenyl-7-(trifluoromethyl)-4,5,6,7-tetrahydropyrazolo[1,5-a]pyrimidine-3-carboxamide | MS (ESI, m/z) 401 (M + H)+ |

TABLE 4-continued

| Example | Structure | Name | Physiological Data |
|---|---|---|---|
| 76 | 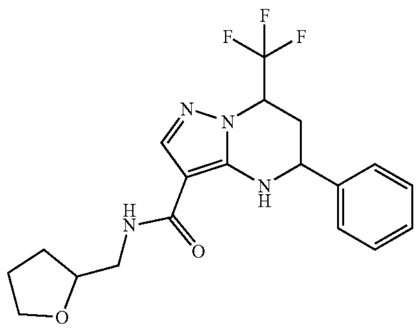 | N-phenyl-N-(tetrahydro-2-furanylmethyl)-7-(trifluoromethyl)-4,5,6,7-tetrahydropyrazolo[1,5-a]pyrimidine-3-carboxamide | MS (ESI, m/z) 397 (M + H)+ |
| 77 | 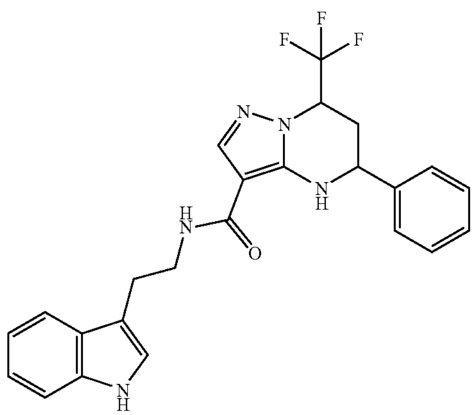 | N-(2-(1H-indol-3-yl)ethyl)-5-phenyl-7-(trifluoromethyl)-4,5,6,7-tetrahydropyrazolo[1,5-a]pyrimidine-3-carboxamide | MS (ESI, m/z) 456 (M + H)+ |
| 78 | 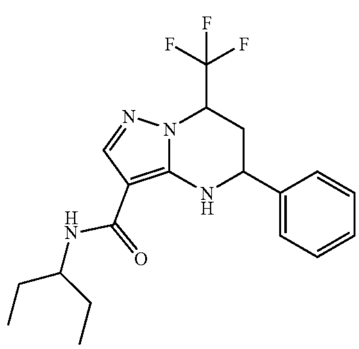 | N-(1-ethylpropyl)-5-phenyl-7-(trifluoromethy)-4,5,6,7-tetrahydropyrazolo[1,5-a]pyrimidine-3-carboxamide | MS (ESI, m/z) 383 (M + H)+ |
| 79 | 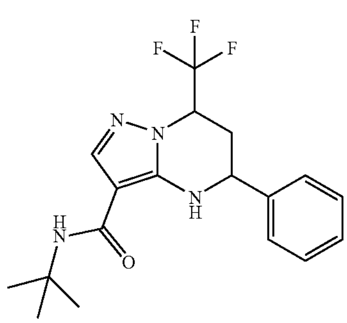 | N-(tert-butyl)-5-phenyl-7-(trifluoromethyl)-4,5,6,7-tetrahydropyrazolo[1,5-a]pyrimidine-3-carboxamide | MS (ESI, m/z) 369 (M + H)+ |

TABLE 4-continued

| Example | Structure | Name | Physiological Data |
|---|---|---|---|
| 80 | 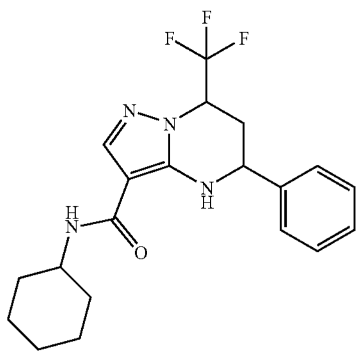 | N-cyclohexyl-5-phenyl-7-(trifluoromethyl)-4,5,6,7-tetrahydropyrazolo[1,5-a]pyrimidine-3-carboxamide | MS (ESI, m/z) 395 (M + H)+ |
| 81 | 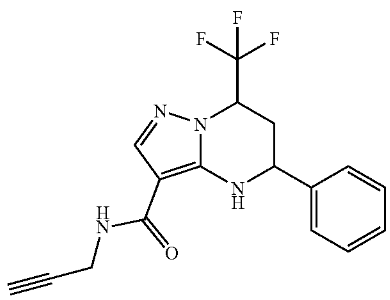 | 5-phenyl-N-2-propynyl-7-(trifluoromethyl)-4,5,6,7-tetrahydropyrazolo[1,5-a]pyrimidine-3-carboxamide | MS (ESI, m/z) 351 (M + H)+ |
| 82 | 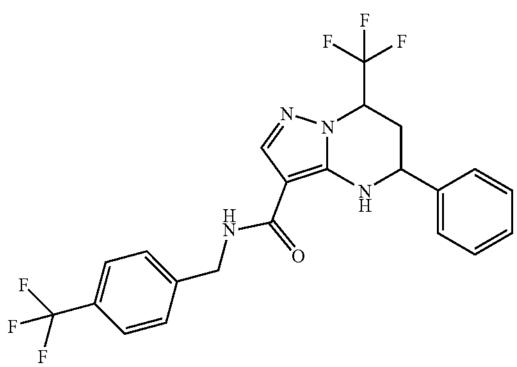 | 5-phenyl-7-(trifluoromethyl)-N-(4-(trifluoromethyl)benzyl)-4,5,6,7-tetrahydropyrazolo[1,5-a]pyrimidine-3-carboxamide | MS (ESI, m/z) 471 (M + H)+ |
| 83 | 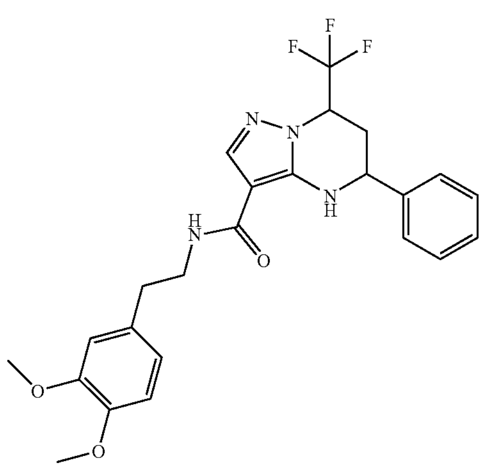 | N-(2-(3,4-dimethoxyphenyl)ethyl)-5-phenyl-7-(trifluoromethyl)-4,5,6,7-tetrahydropyrazolo[1,5-a]pyrimidine-3-carboxamide | MS (ESI, m/z) 477 (M + H)+ |

TABLE 4-continued

| Example | Structure | Name | Physiological Data |
|---------|-----------|------|--------------------|
| 84 | 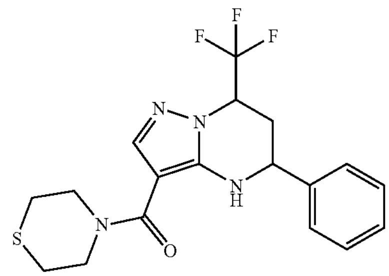 | 5-phenyl-3-(4-thiomorpholinylcarbonyl)-7-(trifluoromethyl)-4,5,6,7-tetrahydropyrazolo[1,5-a]pyrimidine | MS (ESI, m/z) 399 (M + H)+ |
| 85 | 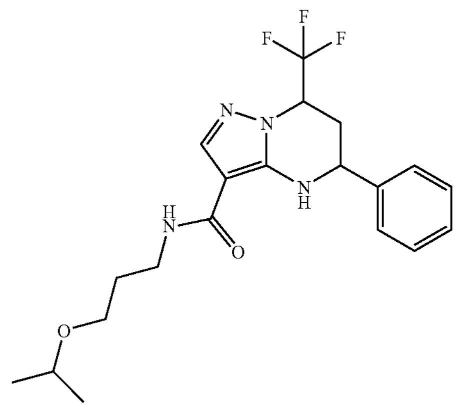 | N-(3-isopropoxypropyl)-5-phenyl-7-(trifluoromethyl)-4,5,6,7-tetrahydropyrazolo[1,5-a]pyrimidine-3-carboxamide | MS (ESI, m/z) 413 (M + H)+ |
| 86 | 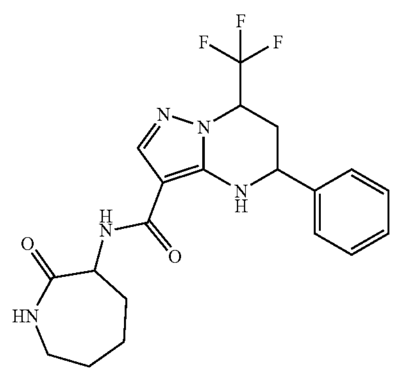 | N-(2-oxo-3-azepanyl)-5-phenyl-7-(trifluoromethyl)-4,5,6,7-tetrahydropyrazolo[1,5-a]pyrimidine-3-carboxamide | MS (ESI, m/z) 424 (M + H)+ |
| 87 | 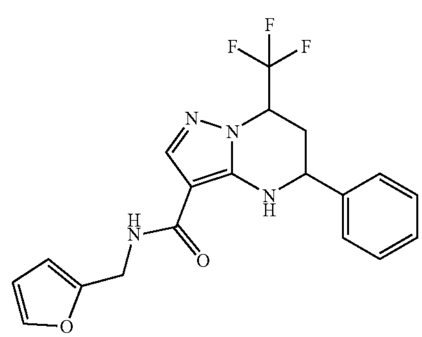 | N-(2-furylmethyl)-5-phenyl-7-(trifluoromethyl)-4,5,6,7-tetrahydropyrazolo[1,5-a]pyrimidine-3-carboxamide | MS (ESI, m/z) 393 (M + H)+ |

TABLE 4-continued

| Example | Structure | Name | Physiological Data |
|---|---|---|---|
| 88 | 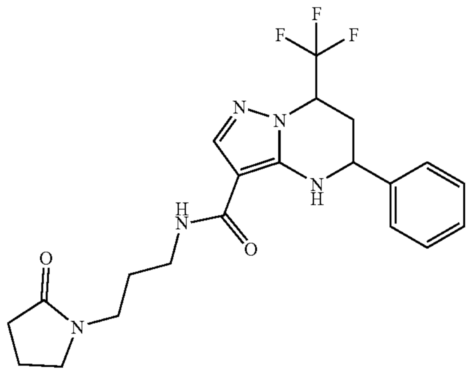 | N-(3-(2-oxo-1-pyrrolidinyl)propyl)-5-phenyl-7-(trifluoromethyl)-4,5,6,7-tetrahydropyrazolo[1,5-a]pyrimidine-3-carboxamide | MS (ESI, m/z) 438 (M + H)+ |
| 89 | 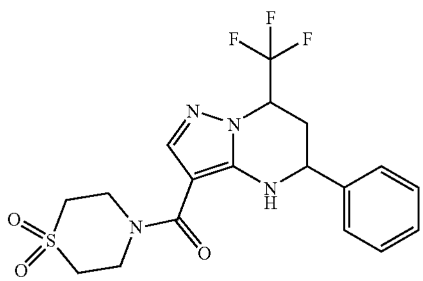 | 3-((1,1-dioxido-4-thiomorpholinyl)carbonyl)-5-phenyl-7-(trifluoromethyl)-4,5,6,7-tetrahydropyrazolo[1,5-a]pyrimidine | MS (ESI, m/z) 431 (M + H)+ |
| 90 | 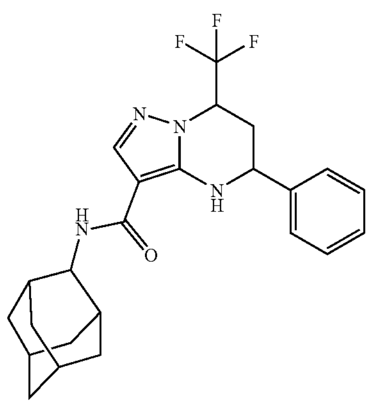 | N-(2-adamantyl)-5-(2-naphthyl)-7-(trifluoromethyl)-4,5,6,7-tetrahydropyrazolo[1,5-a]pyrimidine-3-carboxamide | Mp 280-282° C. |
| 91 | 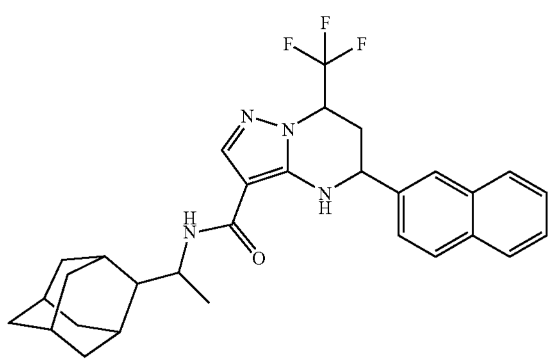 | N-(1-(2-adamantyl)ethyl)-5-(2-naphthyl)-7-(trifluoromethyl)-4,5,6,7-tetrahydropyrazolo[1,5-a]pyrimidine-3-carboxamide | Mp 94-95° C. |

TABLE 4-continued

| Example | Structure | Name | Physiological Data |
|---|---|---|---|
| 92 | 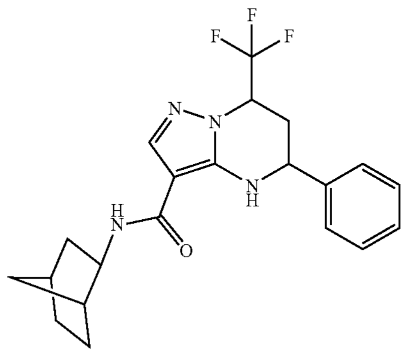 | N-(bicyclo[2.2.1]hept-2-yl)-5-phenyl-7-(trifluoromethyl)-4,5,6,7-tetrahydropyrazolo[1,5-a]pyrimidine-3-carboxamide | MS (ESI, m/z) 407 (M + H)+ |
| 93 | 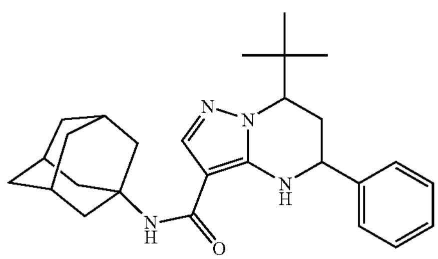 | N-(1-adamantyl)-7-tert-butyl-5-phenyl-4,5,6,7-tetrahydropyrazolo[1,5-a]pyrimidine-3-carboxamide | MS (ESI, m/z) 436 (M + H)+ |
| 94 | 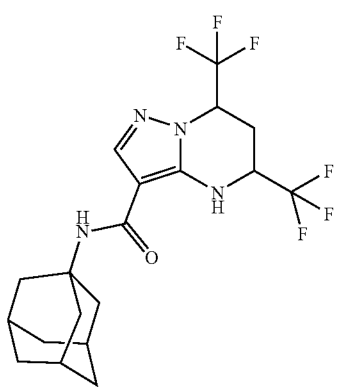 | N-(1-adamantyl)-5,7-bis(trifluoromethyl)-4,5,6,7-tetrahydropyrazolo[1,5-a]pyrimidine-3-carboxamide | MS (ESI, m/z) 439 (M + H)+ |
| 95 | 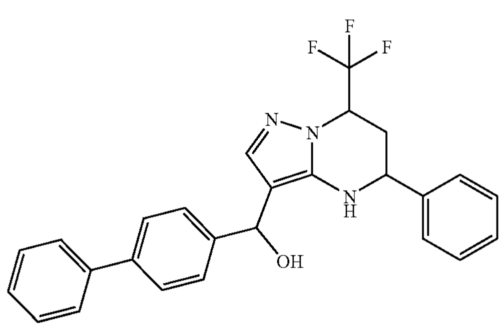 | 1,1'-biphenyl-4-yl(5-phenyl-7-(trifluoromethyl)-4,5,6,7-tetrahydropyrazolo[1,5-a]pyrimidin-3-yl)methanol | MS (ESI, m/z) 452 (M + H)+ |

TABLE 4-continued

| Example | Structure | Name | Physiological Data |
|---|---|---|---|
| 96 | 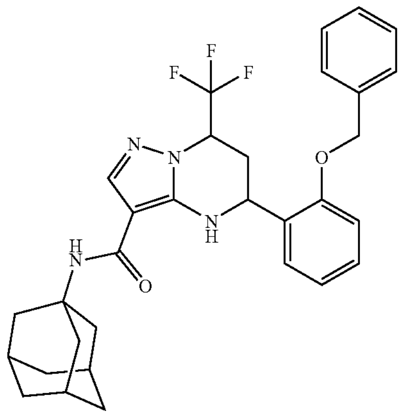 | N-(1-adamantyl)-5-(2-(benzyloxy)phenyl)-7-(trifluoromethyl)-4,5,6,7-tetrahydropyrazolo[1,5-a]pyrimidine-3-carboxamide | MS (ESI, m/z) 554 (M + H)+ |
| 97 | 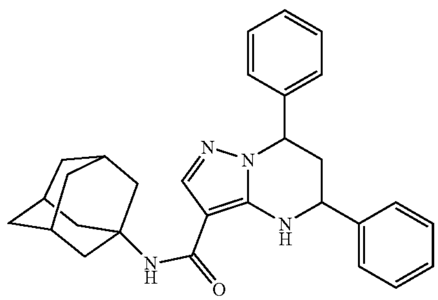 | N-(1-adamantyl)-5,7-diphenyl-4,5,6,7-tetrahydropyrazolo[1,5-a]pyrimidine-3-carboxamide | MS (ESI, m/z) 456 (M + H)+ |
| 98 | 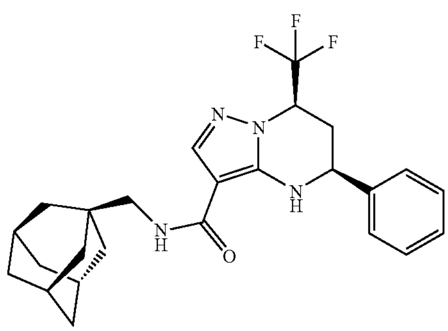 | N-(1-adamantylmethyl)-5-phenyl-7-(trifluoromethyl)-4,5,6,7-tetrahydropyrazolo[1,5-a]pyrimidine-3-carboxamide | MS (ESI, m/z) 462 (M + H)+ |
| 99 | 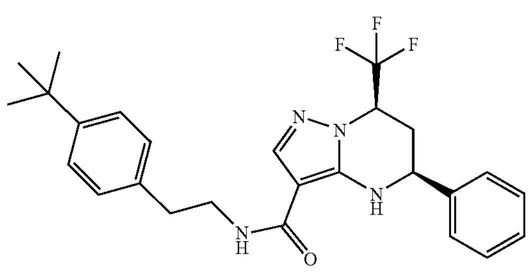 | N-(2-(4-tert-butylphenyl)ethyl)-5-phenyl-7-(trifluoromethyl)-4,5,6,7-tetrahydropyrazolo[1,5-a]pyrimidine-3-carboxamide | MS (ESI, m/z) 474 (M + H)+ |

TABLE 4-continued

| Example | Structure | Name | Physiological Data |
|---|---|---|---|
| 100 | 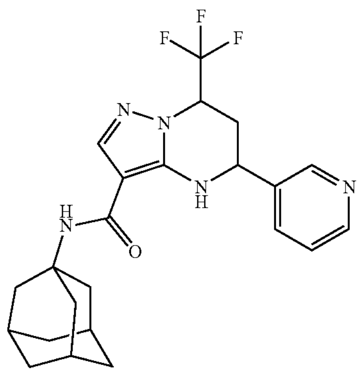 | N-(1-adamantyl)-5-(3-pyridinyl)-7-(trifluoromethyl)-4,5,6,7-tetrahydropyrazolo[1,5-a]pyrimidine-3-carboxamide | MS (ESI, m/z) 448 (M + H)+ |
| 101 | 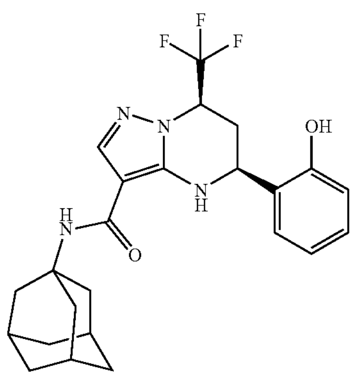 | N-(1-adamantyl)-5-(2-hydroxyphenyl)-7-(trifluoromethyl)-4,5,6,7-tetrahydropyrazolo[1,5-a]pyrimidine-3-carboxamide | MS (ESI, m/z) 463 (M + H)+ |
| 102 | 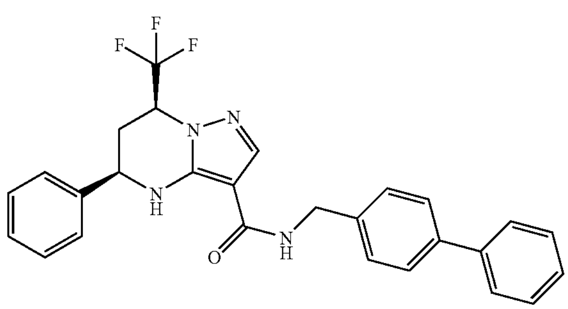 | N-(1,1'-biphenyl-4-ylmethyl)-5-phenyl-7-(trifluoromethyl)-4,5,6,7-tetrahydropyrazolo[1,5-a]pyrimidine-3-carboxamide | MS (ESI, m/z) 480 (M + H)+ |
| 103 | 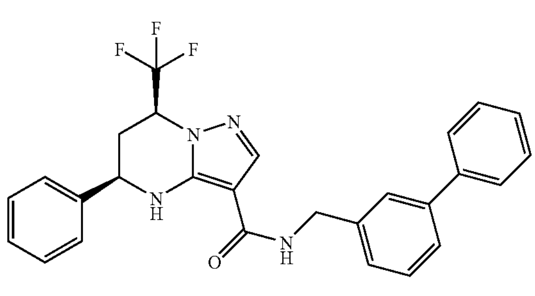 | N-(1,1'-biphenyl-3-ylmethyl)-5-phenyl-7-(trifluoromethyl)-4,5,6,7-tetrahydropyrazolo[1,5-a]pyrimidine-3-carboxamide | MS (ESI, m/z) 480 (M + H)+ |

TABLE 4-continued

| Example | Structure | Name | Physiological Data |
|---------|-----------|------|--------------------|
| 104 | 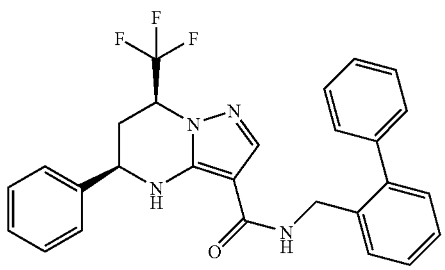 | N-(1,1'-biphenyl-2-ylmethyl)-5-phenyl-7-(trifluoromethyl)-4,5,6,7-tetrahydropyrazolo[1,5-a]pyrimidine-3-carboxamide | MS (ESI, m/z) 480 (M + H)+ |
| 105 | 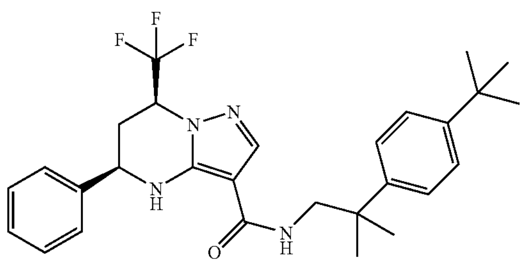 | N-(2-(4-tert-butylphenyl)-2-methylpropyl)-5-phenyl-7-(trifluoromethyl)-4,5,6,7-tetrahydropyrazolo[1,5-a]pyrimidine-3-carboxamide | MS (ESI, m/z) 502 (M + H)+ |
| 106 | 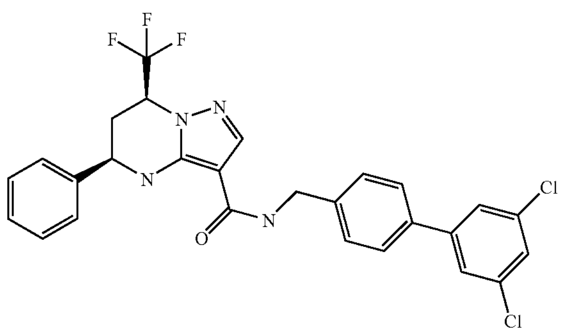 | N-((3',5'-dichloro-1,1'-biphenyl-4-yl)methyl)-5-phenyl-7-(trifluoromethyl)-4,5,6,7-tetrahydropyrazolo[1,5-a]pyrimidine-3-carboxamide | MS (ESI, m/z) 548 (M + H)+ |
| 107 | 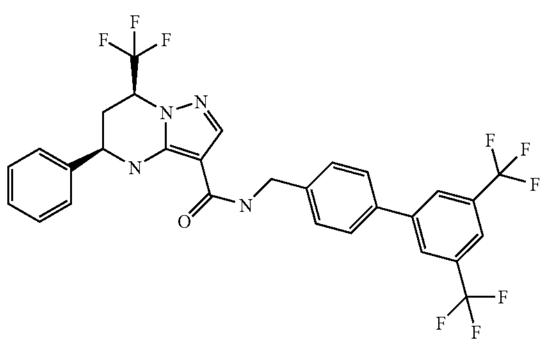 | N-((3',5'-bis(trifluoromethyl)-1,1'-biphenyl-4-yl)methyl)-5-phenyl-7-(trifluoromethyl)-4,5,6,7-tetrahydropyrazolo[1,5-a]pyrimidine-3-carboxamide | MS (ESI, m/z) 615 (M + H)+ |
| 108 | 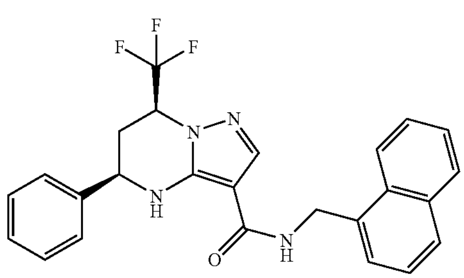 | N-(1-naphthylmethyl)-5-phenyl-7-(trifluoromethyl)-4,5,6,7-tetrahydropyrazolo[1,5-a]pyrimidine-3-carboxamide | MS (ESI, m/z) 453 (M + H)+ |

TABLE 4-continued

| Example | Structure | Name | Physiological Data |
|---|---|---|---|
| 109 | 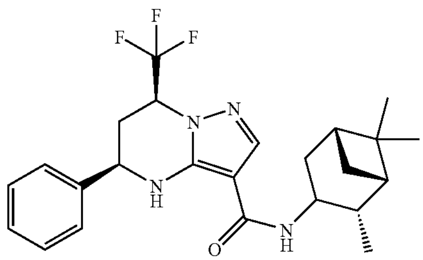 | 5-phenyl-7-(trifluoromethyl)-N-((1S,2S,5R)-2,6,6-trimethylbicyclo[3.1.1]hept-3-yl)-4,5,6,7-tetrahydropyrazolo[1,5-a]pyrimidine-3-carboxamide | MS (ESI, m/z) 450 (M + H)+ |
| 110 | 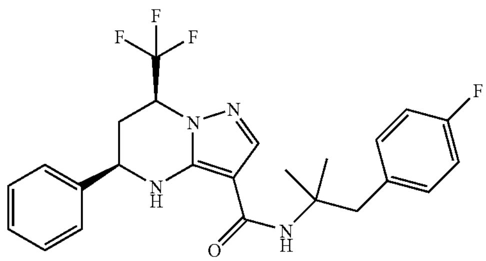 | N-(2-(4-fluorophenyl)-1,1-dimethylethyl)-5-phenyl-7-(trifluoromethyl)-4,5,6,7-tetrahydropyrazolo[1,5-a]pyrimidine-3-carboxamide | MS (ESI, m/z) 463 (M + H)+ |
| 111 | 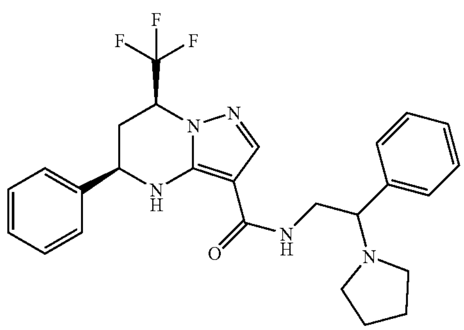 | 5-phenyl-N-(2-phenyl-2-(1-pyrrolidinyl)ethyl)-7-(trifluoromethyl)-4,5,6,7-tetrahydropyrazolo[1,5-a]pyrimidine-3-carboxamide | MS (ESI, m/z) 487 (M + H)+ |
| 112 | 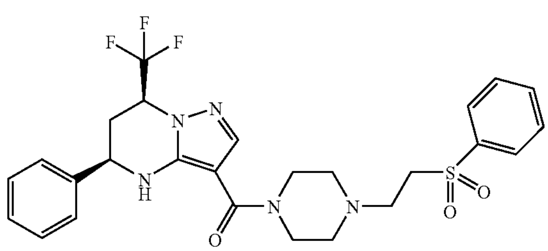 | 5-phenyl-3-((4-(2-(phenylsulfonyl)ethyl)-1-piperazinyl)carbonyl)-7-(trifluoromethyl)-4,5,6,7-tetrahydropyrazolo[1,5-a]pyrimidine | MS (ESI, m/z) 551 (M + H)+ |
| 113 | 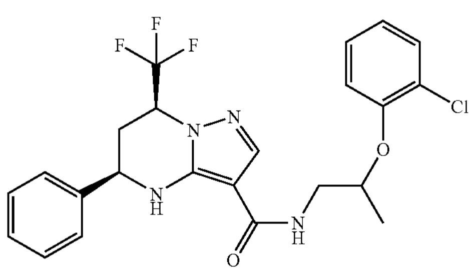 | N-(2-(2-chlorophenoxy)propyl)-5-phenyl-7-(trifluoromethyl)-4,5,6,7-tetrahydropyrazolo[1,5-a]pyrimidine-3-carboxamide | MS (ESI, m/z) 482 (M + H)+ |

TABLE 4-continued

| Example | Structure | Name | Physiological Data |
|---|---|---|---|
| 114 | 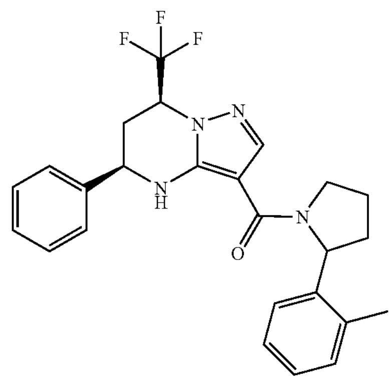 | 3-((2-(2-methylphenyl)-1-pyrrolidinyl)carbonyl)-5-phenyl-7-(trifluoromethyl)-4,5,6,7-tetrahydropyrazolo[1,5-a]pyrimidine | MS (ESI, m/z) 457 (M + H)+ |
| 115 | 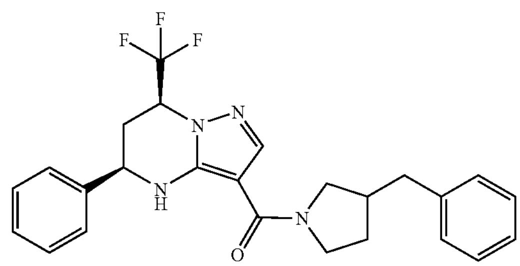 | 3-((3-benzyl-1-pyrrolidinyl)carbonyl)-5-phenyl-7-(trifluoromethyl)-4,5,6,7-tetrahydropyrazolo[1,5-a]pyrimidine | MS (ESI, m/z) 457 (M + H)+ |
| 116 | 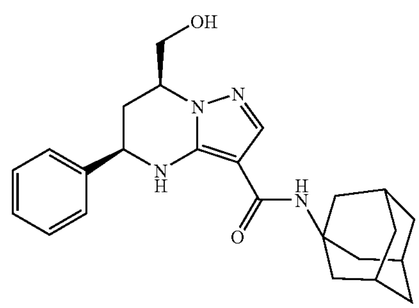 | N-(1-adamantyl)-7-(hydroxymethyl)-5-phenyl-4,5,6,7-tetrahydropyrazolo[1,5-a]pyrimidine-3-carboxamide | MS (ESI, m/z) 410 (M + H)+ |
| 117 | 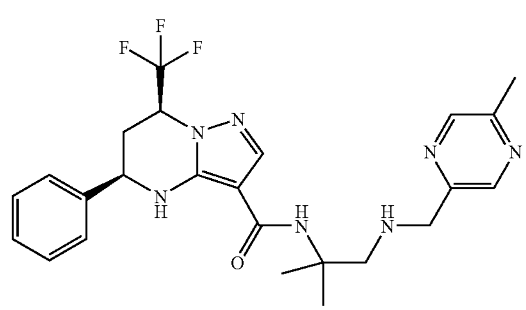 | N-(1,1-dimethyl-2-(((5-methyl-2-pyrazinyl)methyl)amino)ethyl)-5-phenyl-7-(trifluoromethyl)-4,5,6,7-tetrahydropyrazolo[1,5-a]pyrimidine-3-carboxamide | MS (ESI, m/z) 491 (M + H)+ |
| 118 | 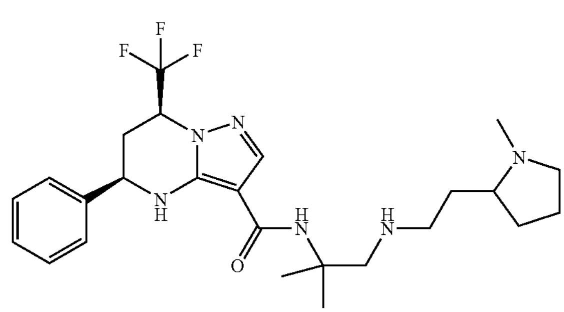 | N-(1,1-dimethyl-2-((2-(1-methyl-2-pyrrolidinyl)ethyl)amino)ethyl)-5-phenyl-7-(trifluoromethyl)-4,5,6,7-tetrahydropyrazolo[1,5-a]pyrimidine-3-carboxamide | MS (ESI, m/z) 496 (M + H)+ |

TABLE 4-continued

| Example | Structure | Name | Physiological Data |
|---|---|---|---|
| 119 | 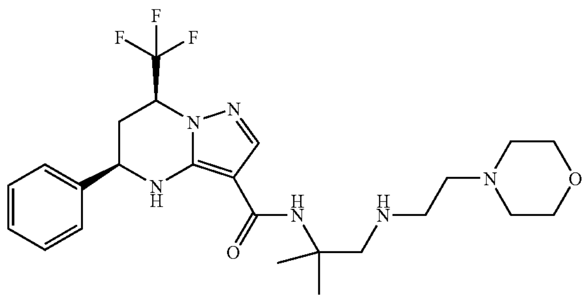 | N-(1,1-dimethyl-2-((2-(4-morpholinyl)ethyl)amino)ethyl)-5-phenyl-7-(trifluoromethyl)-4,5,6,7-tetrahydropyrazolo[1,5-a]pyrimidine-3-carboxamide | MS (ESI, m/z) 498 (M + H)+ |
| 120 | 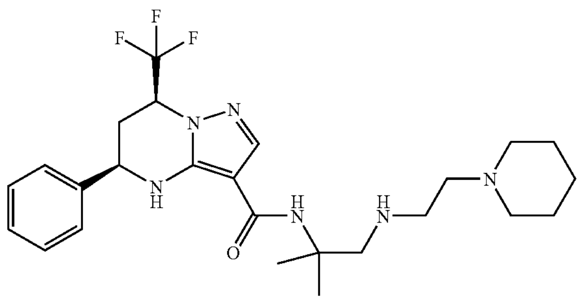 | N-(1,1-dimethyl-2-((2-(1-piperidinyl)ethyl)amino)ethyl)-5-phenyl-7-(trifluoromethyl)-4,5,6,7-tetrahydropyrazolo[1,5-a]pyrimidine-3-carboxamide | MS (ESI, m/z) 496 (M + H)+ |
| 121 | 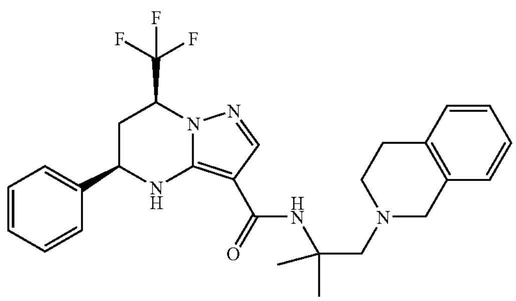 | N-(2-(3,4-dihydro-2(1H)-isoquinolinyl)-1,1-dimethylethyl)-5-phenyl-7-(trifluoromethyl)-4-5,6,7-tetrahydropyrazolo[1,5-a]pyrimidine-3-carboxamide | MS (ESI, m/z) 501 (M + H)+ |
| 122 | 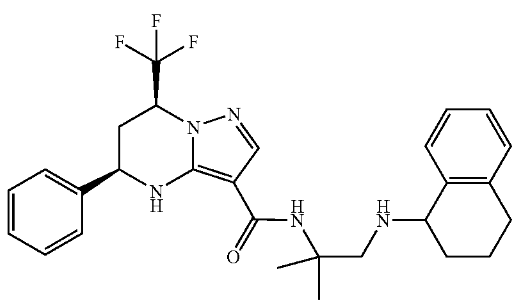 | N-(1-1-dimethyl-2-(1,2,3,4-tetrahydro-1-naphthalenylamino)ethyl)-5-phenyl-7-(trifluoromethyl)-4,5,6,7-tetrahydropyrazolo[1,5-a]pyrimidine-3-carboxamide | MS (ESI, m/z) 515 (M + H)+ |
| 123 | 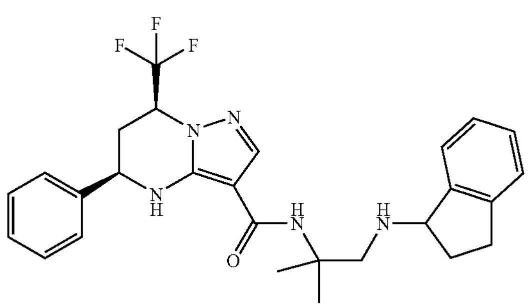 | N-(2-(2,3-dihydro-1H-inden-1-ylamino)-1,1-dimethylethyl)-5-phenyl-7-(trifluoromethyl)-4,5,6,7-tetrahydropyrazolo[1,5-a]pyrimidine-3-carboxamide | MS (ESI, m/z) 501 (M + H)+ |

TABLE 4-continued

| Example | Structure | Name | Physiological Data |
|---------|-----------|------|--------------------|
| 124 | 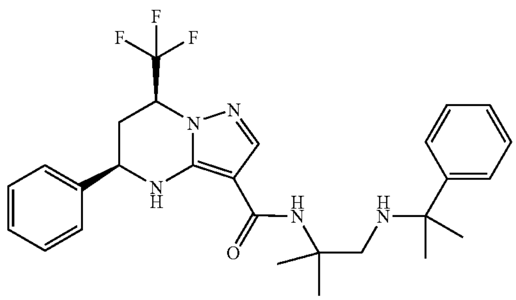 | N-(1,1-dimethyl-2-((1-methyl-1-phenylethyl)amino)ethyl)-5-phenyl-7-(trifluoromethyl)-4,5,6,7-tetrahydropyrazolo[1,5-a]pyrimidine-3-carboxamide | MS (ESI, m/z) 503 (M + H)+ |
| 125 | 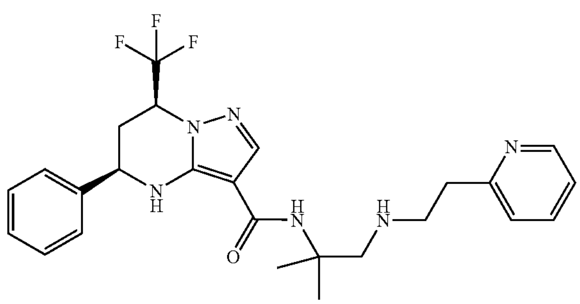 | N-(1,1-dimethyl-2-((2-(2-pyridinyl)ethyl)amino)ethyl)-5-phenyl-7-(trifluoromethyl)-4,5,6,7-tetrahydropyrazolo[1,5-a]pyrimidine-3-carboxamide | MS (ESI, m/z) 490 (M + H)+ |
| 126 | 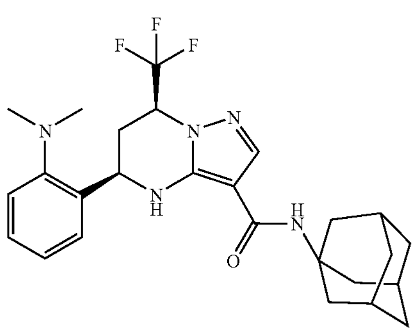 | N-(1-adamantyl)-5-(2-(dimethylamino)phenyl)-7-(trifluoromethyl)-4,5,6,7-tetrahydropyrazolo[1,5-a]pyrimidine-3-carboxamide | MS (ESI, m/z) 491 (M + H)+ |
| 127 | 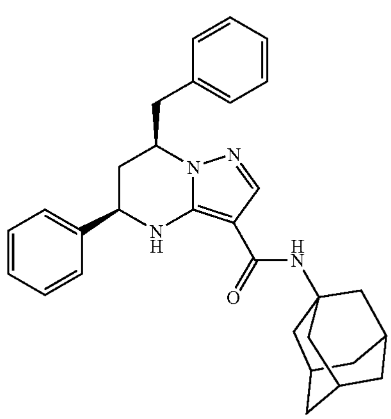 | (5R,7R)-N-(1-adamantyl)-7-benzyl-5-phenyl-4,5,6,7-tetrahydropyrazolo[1,5-a]pyrimidine-3-carboxamide | MS (ESI, m/z) 470 (M + H)+ |

TABLE 4-continued

| Example | Structure | Name | Physiological Data |
|---------|-----------|------|--------------------|
| 128 | 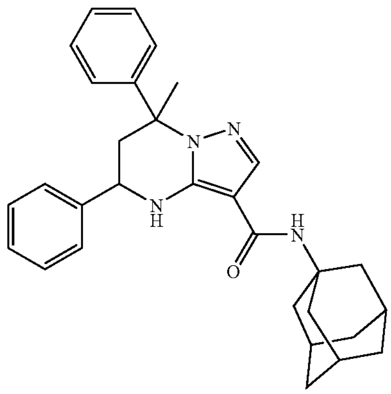 | N-(1-adamantyl)-7-methyl-5,7-diphenyl-4,5,6,7-tetrahydropyrazolo[1,5-a]pyrimidine-3-carboxamide | MS (ESI, m/z) 470 (M + H)+ |
| 129 | 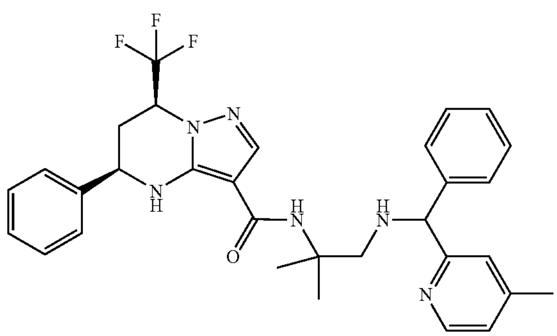 | N-(1,1-dimethyl-2-(((4-methyl-2-pyridinyl)(phenyl)methyl)amino)ethyl)-5-phenyl-7-(trifluoromethyl)-4,5,6,7-tetrahydropyrazolo[1,5-a]pyrimidine-3-carboxamide | MS (ESI, m/z) 566 (M + H)+ |
| 130 | 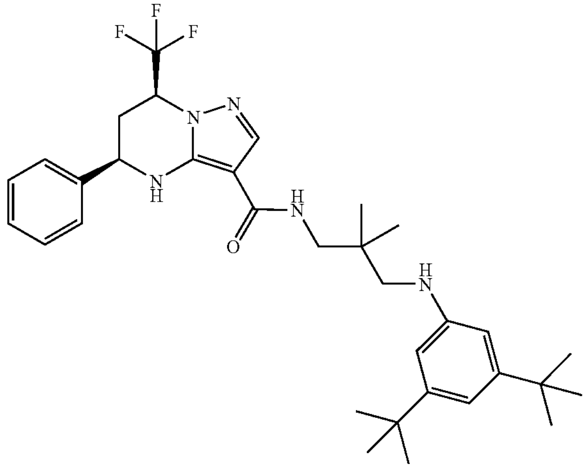 | N-(3-((3,5-di-tert-butylphenyl)amino)-2,2-dimethylpropyl)-5-phenyl-7-(trifluoromethyl)-4,5,6,7-tetrahydropyrazolo[1,5-a]pyrimidine-3-carboxamide | MS (ESI, m/z) 587 (M + H)+ |

TABLE 4-continued

| Example | Structure | Name | Physiological Data |
|---|---|---|---|
| 131 | 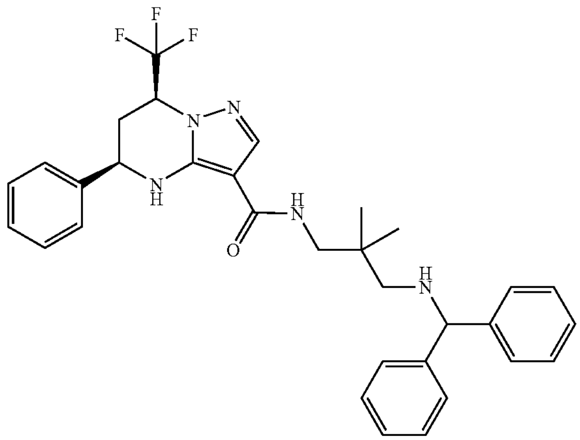 | N-(3-(benzhydrylamino)-2,2-dimethylpropyl)-5-phenyl-7-(trifluoromethyl)-4,5,6,7-tetrahydropyrazolo[1,5-a]pyrimidine-3-carboxamide | MS (ESI, m/z) 565 (M + H)+ |
| 132 | 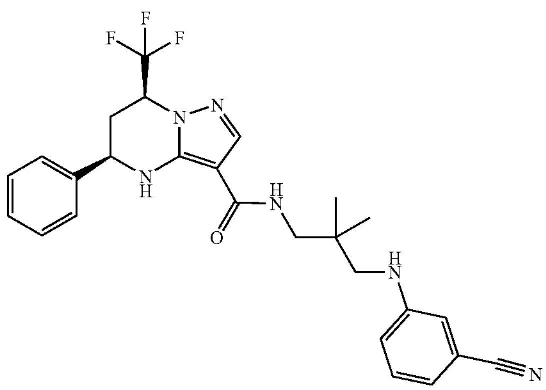 | N-(3-((3-cyanophenyl)amino)-2,2-dimethylpropyl)-5-phenyl-7-(trifluoromethyl)-4,5,6,7-tetrahydropyrazolo[1,5-a]pyrimidine-3-carboxamide | MS (ESI, m/z) 500 (M + H)+ |
| 133 | 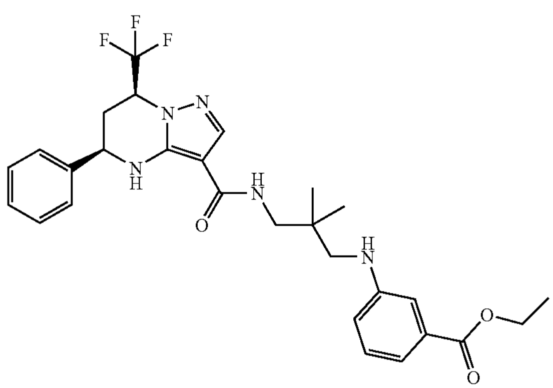 | ethyl 3-((2,2-dimethyl-3-(((5-phenyl-7-(trifluoromethyl)-4,5,6,7-tetrahydropyrazolo[1,5-a]pyrimidin-3-yl)carbonyl)amino)propyl)amino)benzoate | MS (ESI, m/z) 547 (M + H)+ |
| 134 | 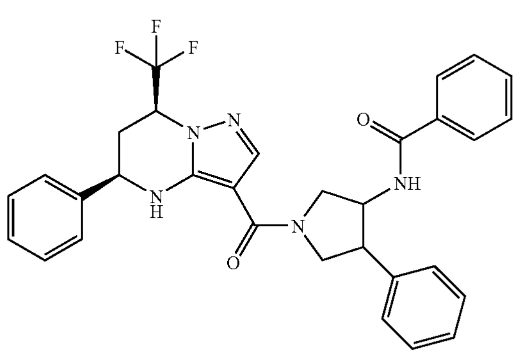 | N-(4-phenyl-1-((5-phenyl-7-(trifluoromethyl)-4,5,6,7-tetrahydropyrazalo[1,5-a]pyrimidin-3-yl)carbonyl)-3-pyrrolidinyl)benzamide | MS (ESI, m/z) 563 (M + H)+ |

TABLE 4-continued

| Example | Structure | Name | Physiological Data |
|---|---|---|---|
| 135 | 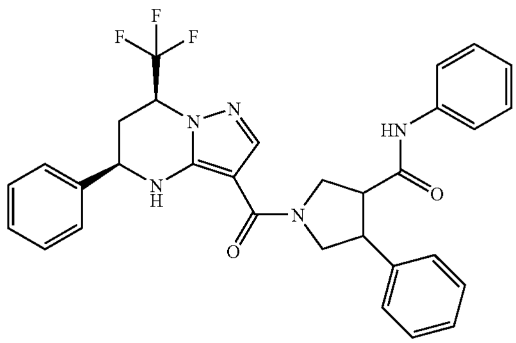 | N,4-diphenyl-1-((5-phenyl-7-(trifluoromethyl)-4,5,6,7-tetrahydropyrazolo[1,5-a]pyrimidin-3-yl)carbonyl)-3-pyrrolidinecarboxamide | MS (ESI, m/z) 563 (M + H)+ |
| 136 | 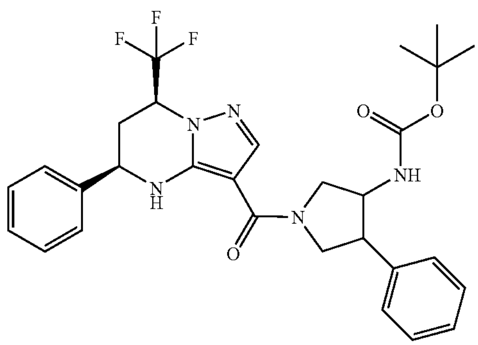 | tert-butyl 4-phenyl-1-((5-phenyl-7-(trifluoromethyl)-4,5,6,7-tetrahydropyrazolo[1,5-a]pyrimidin-3-yl)carbonyl)-3-pyrrolidinylcarbamate | MS (ESI, m/z) 559 (M + H)+ |
| 137 | 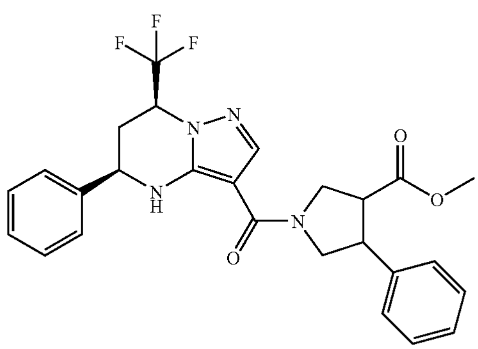 | methyl 4-phenyl-1-((5-phenyl-7-(trifluoromethyl)-4,5,6,7-tetrahydropyrazolo[1,5-a]pyrimidin-3-yl)carbonyl)-3-pyrrolidinecarboxylate | MS (ESI, m/z) 502 (M + H)+ |
| 138 | 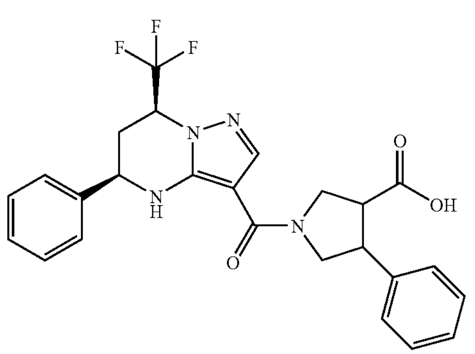 | 4-phenyl-1-((5-phenyl-7-(trifluoromethyl)-4,5,6,7-tetrahydropyrazolo[1,5-a]pyrimidin-3-yl)carbonyl)-3-pyrrolidinecarboxylic acid | MS (ESI, m/z) 487 (M + H)+ |

TABLE 4-continued

| Example | Structure | Name | Physiological Data |
|---|---|---|---|
| 139 | 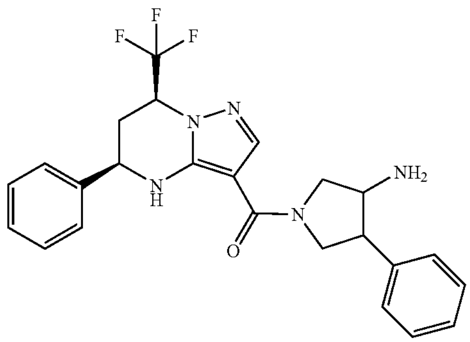 | 4-phenyl-1-((5-phenyl-7-(trifluoromethyl)-4,5,6,7-tetrahydropyrazolo[1,5-a]pyrimidin-3-yl)carbonyl)-3-pyrrolidinamine | MS (ESI, m/z) 458 (M + H)+ |
| 140 | 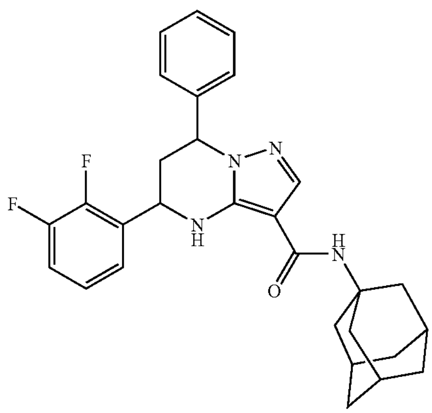 | N-(1-adamantyl)-5-(2,3-difluorophenyl)-7-phenyl-4,5,6,7-tetrahydropyrazolo[1,5-a]pyrimidine-3-carboxamide | MS (ESI, m/z) 492 (M + H)+ |
| 141 | 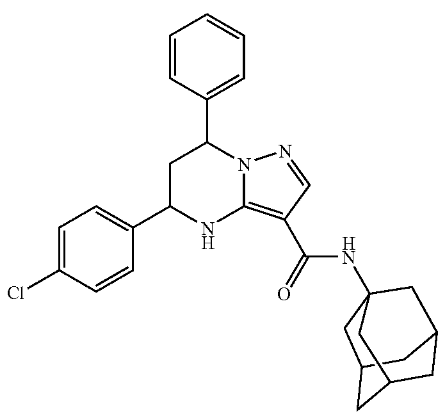 | N-(1-adamantyl)-5-(4-chlorophenyl)-7-phenyl-4,5,6,7-tetrahydropyrazolo[1,5-a]pyrimidine-3-carboxamide | MS (ESI, m/z) 490 (M + H)+ |
| 142 | 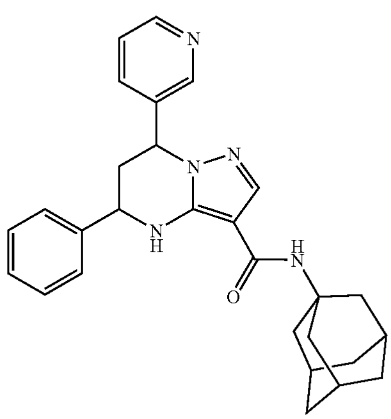 | N-(1-adamantyl)-5-phenyl-7-(3-pyridinyl)-4,5,6,7-tetrahydropyrazolo[1,5-a]pyrimidine-3-carboxamide | MS (ESI, m/z) 457 (M + H)+ |

TABLE 4-continued

| Example | Structure | Name | Physiological Data |
|---|---|---|---|
| 143 | 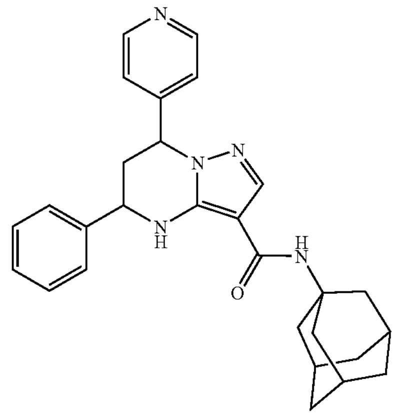 | N-(1-adamantyl)-5-phenyl-7-(4-pyridinyl)-4,5,6,7-tetrahydropyrazolo[1,5-a]pyrimidine-3-carboxamide | MS (ESI, m/z) 457 (M + H)+ |
| 144 | 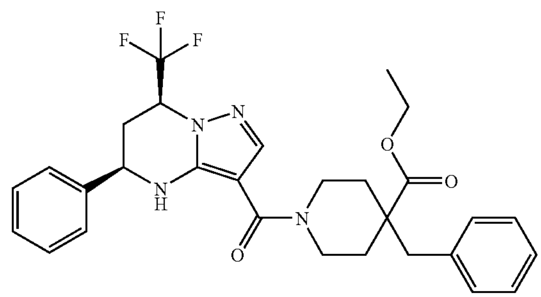 | ethyl 4-benzyl-1-((5-phenyl-7-(trifluoromethyl)-4,5,6,7-tetrahydropyrazolo[1,5-a]pyrimidin-3-yl)carbonyl)-4-piperidinecarboxylate | MS (ESI, m/z) 544 (M + H)+ |
| 145 | 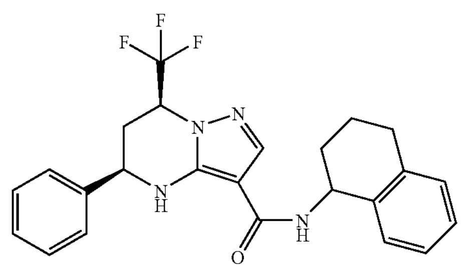 | 5-phenyl-N-(-1,2,3,4-tetrahydro-1-naphthalenyl)-7-(trifluoromethyl)-4,5,6,7-tetrahydropyrazolo[1,5-a]pyrimidine-3-carboxamide | MS (ESI, m/z) 443 (M + H)+ |
| 146 | 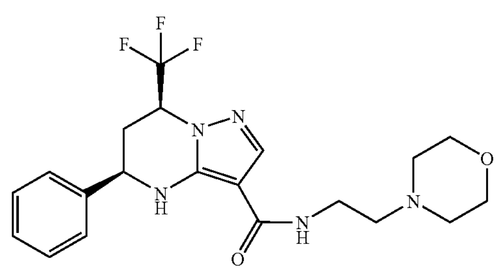 | N-(2-(4-morpholinyl)ethyl)-5-phenyl-7-(trifluoromethyl)-4,5,6,7-tetrahydropyrazolo[1,5-a]pyrimidine-3-carboxamide | MS (ESI, m/z) 426 (M + H)+ |
| 147 | 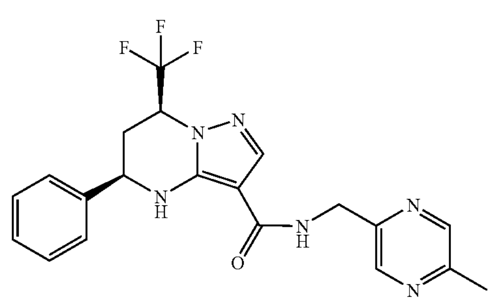 | N-((5-methyl-2-pyrazinyl)methyl)-5-phenyl-7-(trifluoromethyl)-4,5,6,7-tetrahydropyrazolo[1,5-a]pyrimidine-3-carboxamide | MS (ESI, m/z) 419 (M + H)+ |

TABLE 4-continued

| Example | Structure | Name | Physiological Data |
|---|---|---|---|
| 148 | 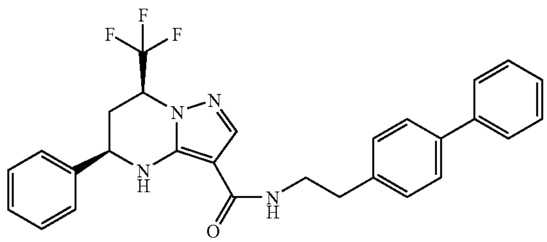 | N-(2-(1,1'-biphenyl-4-yl)ethyl)-5-phenyl-7-(trifluoromethyl)-4,5,6,7-tetrahydropyrazolo[1,5-a]pyrimidine-3-carboxamide | MS (ESI, m/z) 494 (M + H)+ |
| 149 | 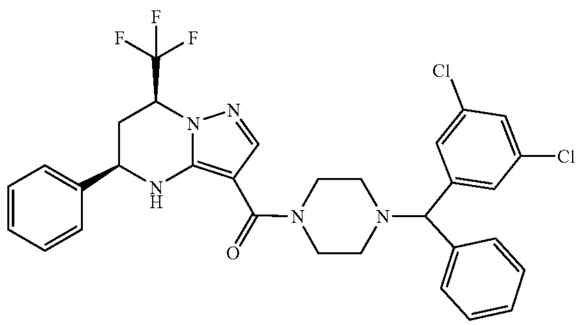 | 4-((4-((3,5-dichlorophenyl)(phenyl)methyl)-1-piperazinyl)carbonyl)-5-phenyl-7-(trifluoromethyl)-4,5,6,7-tetrahydropyrazolo[1,5-a]pyrimidine | MS (ESI, m/z) 617 (M + H)+ |
| 150 | 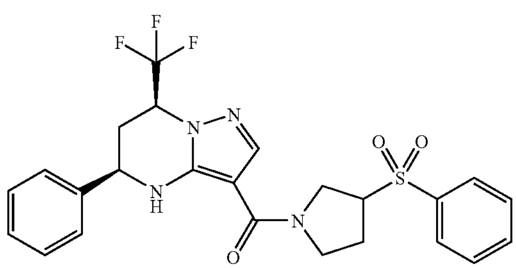 | 5-phenyl-3-((3-(phenylsulfonyl)-1-pyrrolidinyl)carbonyl)-7-(trifluoromethyl)-4,5,6,7-tetrahydropyrazolo[1,5-a]pyrimidine | MS (ESI, m/z) 508 (M + H)+ |
| 151 | 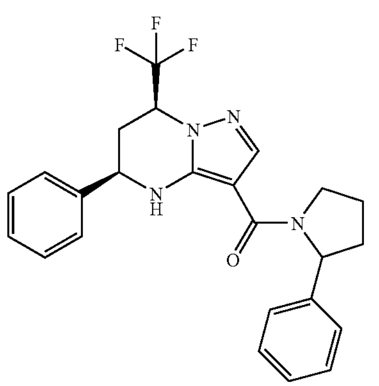 | 5-phenyl-3-((2-phenyl-1-pyrrolidinyl)carbonyl)-7-(trifluoromethyl)-4,5,6,7-tetrahydropyrazolo[1,5-a]pyrimidine | MS (ESI, m/z) 443 (M + H)+ |

TABLE 4-continued

| Example | Structure | Name | Physiological Data |
|---|---|---|---|
| 152 | 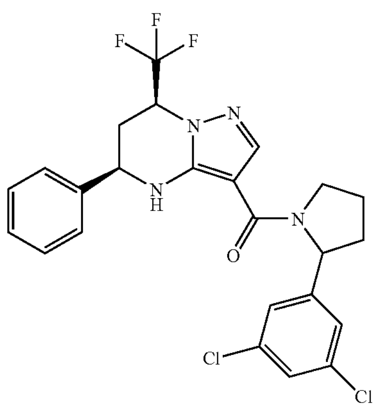 | 3-((2-(3,5-dichlorophenyl)-1-pyrrolidinyl)carbonyl)-5-phenyl-7-(trifluoromethyl)-4,5,6,7-tetrahydropyrazolo[1,5-a]pyrimidine | MS (ESI, m/z) 512 (M + H)+ |
| 153 | 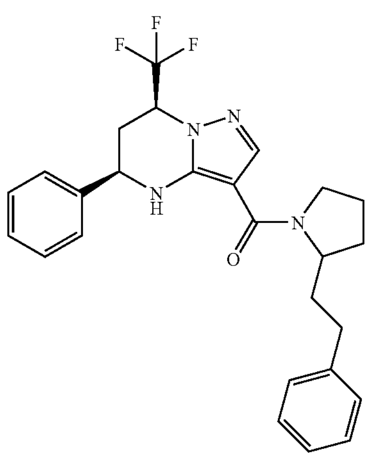 | 5-phenyl-3-((2-(2-phenylethyl)-1-pyrrolidinyl)carbonyl)-7-(trifluoromethyl)-4,5,6,7-tetrahydropyrazolo[1,5-a]pyrimidine | MS (ESI, m/z) 472 (M + H)+ |
| 154 | 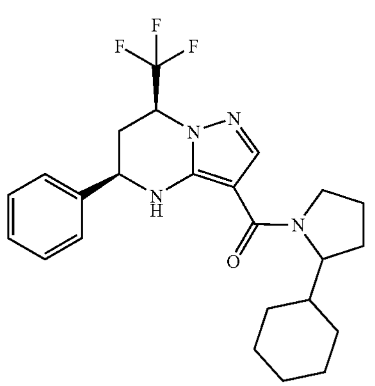 | 3-((2-cyclohexyl-1-pyrrolidinyl)carbonyl)-5-phenyl-7-(trifluoromethyl)-4,5,6,7-tetrahydropyrazolo[1,5-a]pyrimidine | MS (ESI, m/z) 450 (M + H)+ |
| 155 | 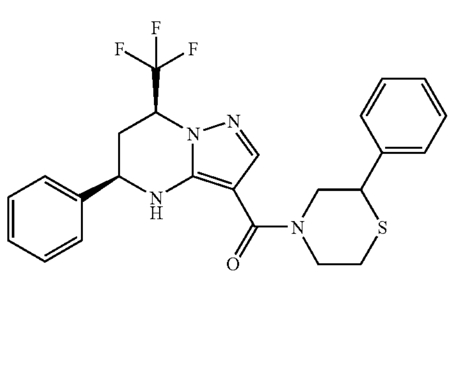 | 5-phenyl-3-((2-phenyl-4-thiomorpholinyl)carbonyl)-7-(trifluoromethyl)-4,5,6,7-tetrahydropyrazolo[1,5-a]pyrimidine | MS (ESI, m/z) 476 (M + H)+ |

TABLE 4-continued

| Example | Structure | Name | Physiological Data |
|---|---|---|---|
| 156 | 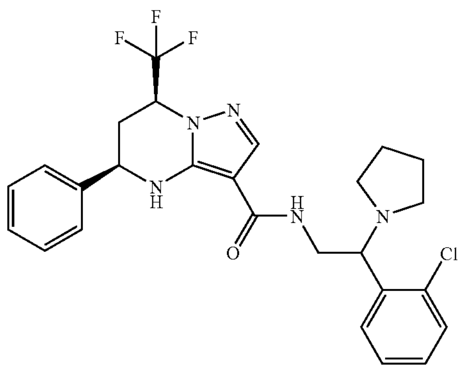 | N-(2-(2-chlorophenyl)-2-(1-pyrrolidinyl)ethyl)-5-7-(trifluoromethyl)-4,5,6,7-tetrahydropyrazolo[1,5-a]pyrimidine-3-carboxamide | MS (ESI, m/z) 521 (M + H)+ |
| 157 | 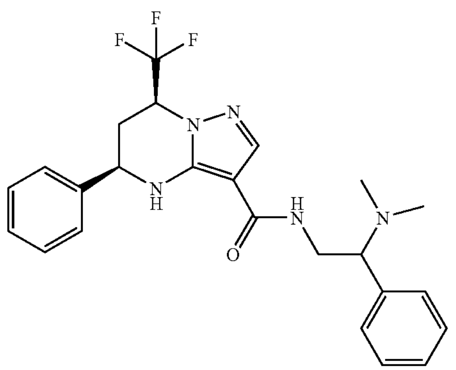 | N-(2-(dimethylamino)-2-phenylethyl)-5-phenyl-7-(trifluoromethyl)-4,5,6,7-tetrahydropyrazolo[1,5-a]pyrimidine-3-carboxamide | MS (ESI, m/z) 460 (M + H)+ |
| 158 | 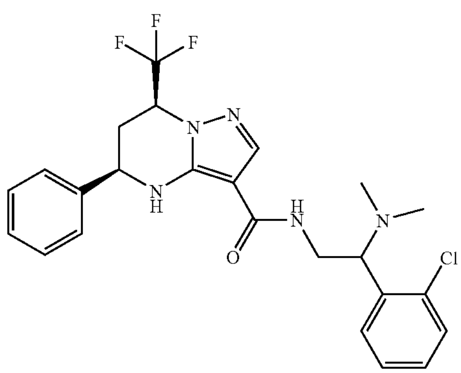 | N-(2-(2-chlorophenyl)-2-(dimethylamino)ethyl)-5-phenyl-7-(trifluoromethyl)-4,5,6,7-tetrahydropyrazolo[1,5-a]pyrimidine-3-carboxamide | MS (ESI, m/z) 495 (M + H)+ |
| 159 | 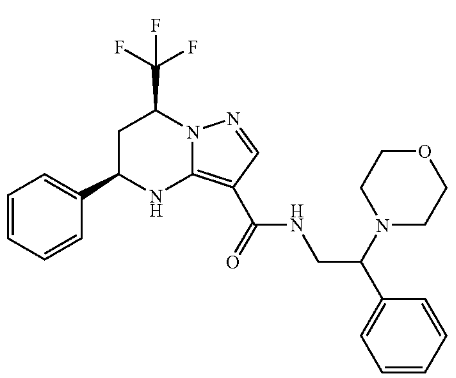 | N-(2-(4-morpholinyl)-2-phenylethyl)-5-phenyl-7-(trifluoromethyl)-4,5,6,7-tetrahydropyrazolo[1,5-a]pyrimidine-3-carboxamide | MS (ESI, m/z) 503 (M + H)+ |

TABLE 4-continued

| Example | Structure | Name | Physiological Data |
|---------|-----------|------|--------------------|
| 160 | 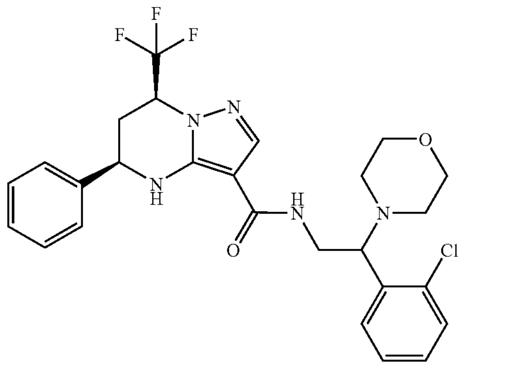 | N-(2-(2-chlorophenyl)-2-(4-morpholinyl)ethyl)-5-phenyl-7-(trifluoromethyl)-4,5,6,7-tetrahydropyrazolo[1,5-a]pyrimidine-3-carboxamide | MS (ESI, m/z) 537 (M + H)+ |
| 161 | 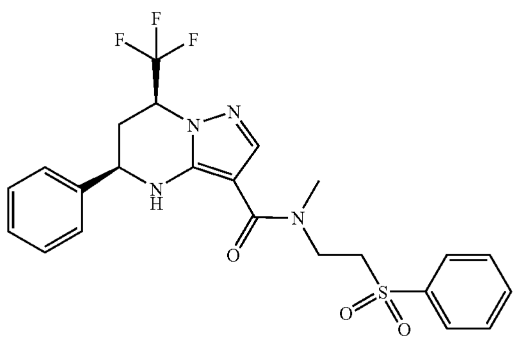 | N-methyl-5-phenyl-N-(2-(phenylsulfonyl)ethyl)-7-(trifluoromethyl)-4,5,6,7-tetrahydropyrazolo[1,5-a]pyrimidine-3-carboxamide | MS (ESI, m/z) 496 (M + H)+ |
| 162 | 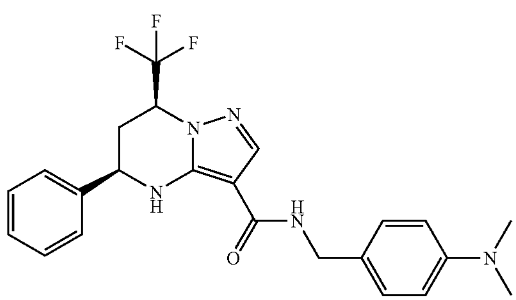 | N-(4-(dimethylamino)benzyl)-5-phenyl-7-(trifluoromethyl)-4,5,6,7-tetrahydropyrazolo[1,5-a]pyrimidine-3-carboxamide | MS (ESI, m/z) 446 (M + H)+ |
| 163 | 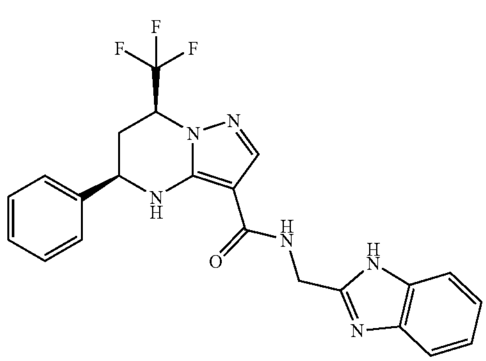 | N-(1H-benzimidazol-2-ylmethyl)-5-phenyl-7-(trifluoromethyl)-4,5,6,7-tetrahydropyrazolo[1,5-a]pyrimidine-3-carboxamide | MS (ESI, m/z) 443 (M + H)+ |

TABLE 4-continued

| Example | Structure | Name | Physiological Data |
|---|---|---|---|
| 164 | 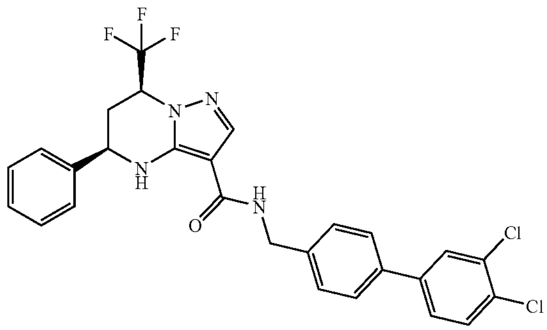 | N-((3',4'-dichloro-1,1'-biphenyl-4-yl)methyl)-5-phenyl-7-(trifluoromethyl)-4,5,6,7-tetrahydropyrazolo[1,5-a]pyrimidine-3-carboxamide | MS (ESI, m/z) 548 (M + H)+ |
| 165 | 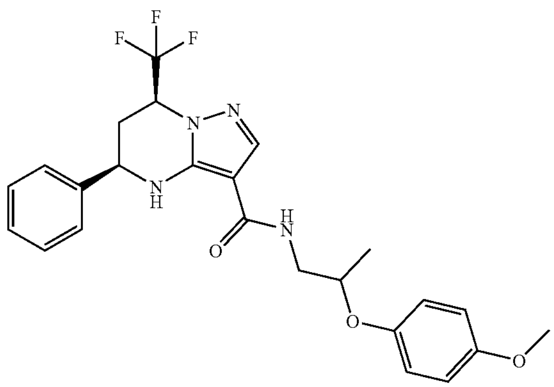 | N-(2-(4-methoxyphenoxy)propyl)-5-phenyl-7-(trifluoromethyl)-4,5,6,7-tetrahydropyrazolo[1,5-a]pyrimidine-3-carboxamide | MS (ESI, m/z) 477 (M + H)+ |
| 166 | 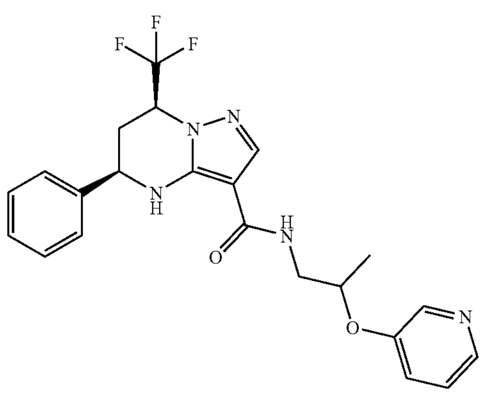 | 5-phenyl-N-(2-(3-pyridinyloxy)propyl)-7-(trifluoromethyl)-4,5,6,7-tetrahydropyrazolo[1,5-a]pyrimidine-3-carboxamide | MS (ESI, m/z) 448 (M + H)+ |
| 167 | 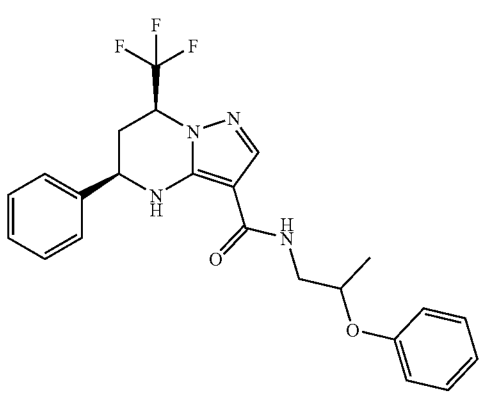 | N-(2-phenoxypropyl)-5-phenyl-7-(trifluoromethyl)-4,5,6,7-tetrahydropyrazolo[1,5-a]pyrimidine-3-carboxamide | MS (ESI, m/z) 447 (M + H)+ |

TABLE 4-continued

| Example | Structure | Name | Physiological Data |
|---|---|---|---|
| 168 | 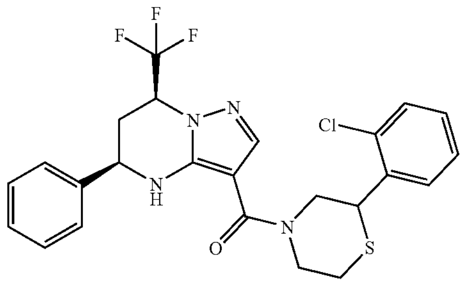 | 3-((2-(2-chlorophenyl)-4-thiomorpholinyl)carbonyl)-5-phenyl-7-(trifluoromethyl)-4,5,6,7-tetrahydropyrazolo[1,5-a]pyrimidine | MS (ESI, m/z) 510 (M + H)+ |
| 169 | 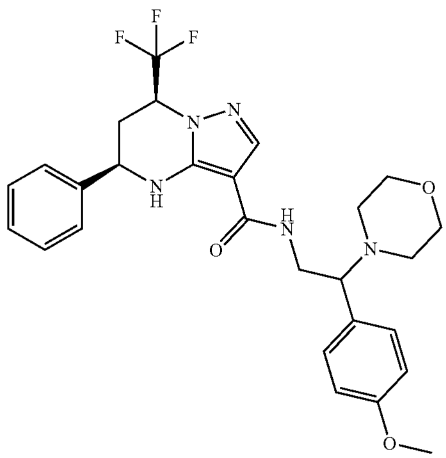 | N-(2-(4-methoxyphenyl)-2-(4-morpholinyl)ethyl)-5-phenyl-7-(trifluoromethyl)-4,5,6,7-tetrahydropyrazolo[1,5-a]pyrimidine-3-carboxamide | MS (ESI, m/z) 533 (M + H)+ |
| 170 | 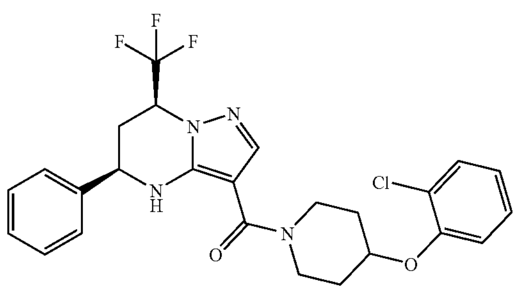 | 3-((4-(2-chlorophenoxy)-1-piperidinyl)carbonyl)-5-phenyl-7-(trifluoromethyl)-4,5,6,7-tetrahydropyrazolo[1,5-a]pyrimidine | MS (ESI, m/z) 508 (M + H)+ |
| 171 | 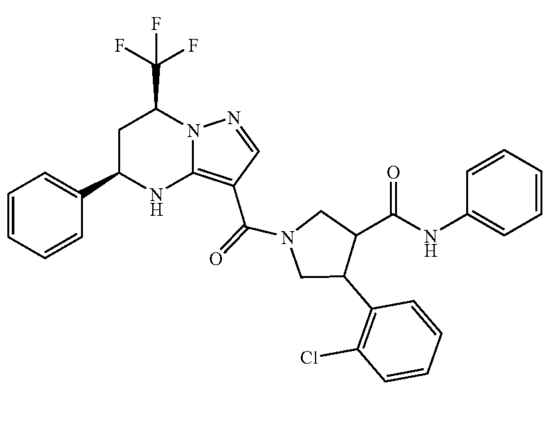 | 4-(2-chlorophenyl)-N-phenyl-1-((5-phenyl-7-(trifluoromethyl)-4,5,6,7-tetrahydropyrazolo[1,5-a]pyrimidin-3-yl)carbonyl)-3-pyrralidinecarboxamide | MS (ESI, m/z) 597 (M + H)+ |

TABLE 4-continued

| Example | Structure | Name | Physiological Data |
|---------|-----------|------|--------------------|
| 172 | 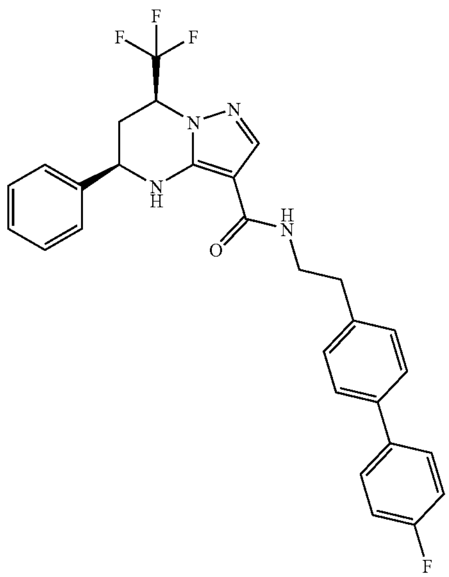 | N-(2-(4'-fluoro-1,1'-biphenyl-4-yl)ethyl)-5-phenyl-7-(trifluoromethyl)-4,5,6,7-tetrahydropyrazolo[1,5-a]pyrimidine-3-carboxamide | MS (ESI, m/z) 512 (M + H)+ |
| 173 | 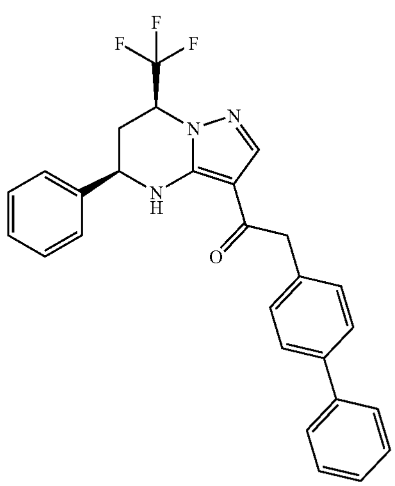 | N-(1,1'-biphenyl-4-yl)-1-(5-phenyl-7-(trifluoromethyl)-4,5,6,7-tetrahydropyrazolo[1,5-a]pyrimidin-3-yl)ethanone | MS (ESI, m/z) 464 (M + H)+ |
| 174 | 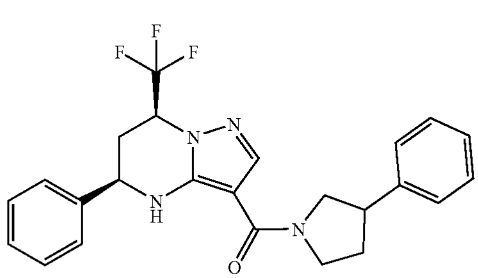 | 5-phenyl-3-((3-phenyl-1-pyrrolidinyl)carbonyl)-7-(trifluoromethyl)-4,5,6,7-tetrahydropyrazolo[1,5-a]pyrimidine | MS (ESI, m/z) 443 (M + H)+ |

TABLE 4-continued

| Example | Structure | Name | Physiological Data |
|---|---|---|---|
| 175 | 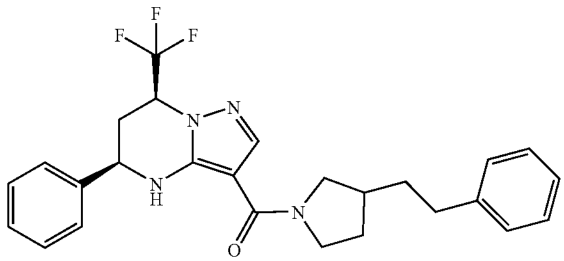 | N-phenyl-3-((3-(2-phenylethyl)-1-pyrrolidinyl)carbonyl)-7-(trifluoromethyl)-4,5,6,7-tetrahydropyrazolo[1,5-a]pyrimidine | MS (ESI, m/z) 472 (M + H)+ |
| 176 | 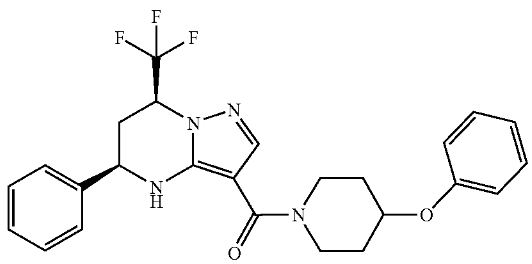 | 3-((4-phenoxy-1-piperidinyl)carbonyl)-5-phenyl-7-(trifluoromethyl)-4,5,6,7-tetrahydropyrazolo[1,5-a]pyrimidine | MS (ESI, m/z) 473 (M + H)+ |
| 177 | 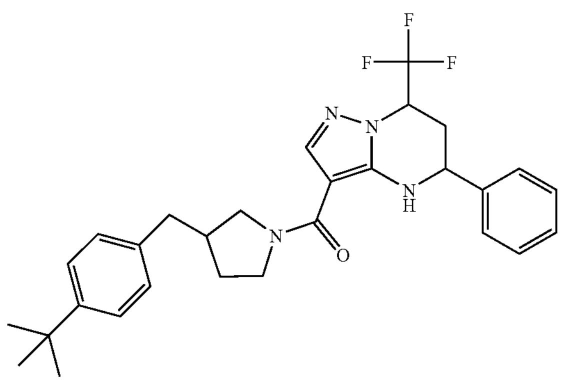 | 3-((3-(4-tert-butylbenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 514 (M + H)+ |
| 178 | 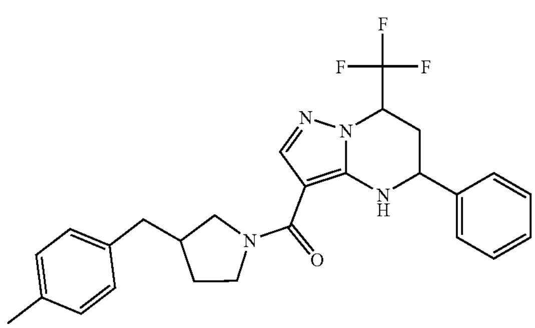 | 3-((3-(4-methylbenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 472 (M + H)+ |

TABLE 4-continued

| Example | Structure | Name | Physiological Data |
|---|---|---|---|
| 179 | 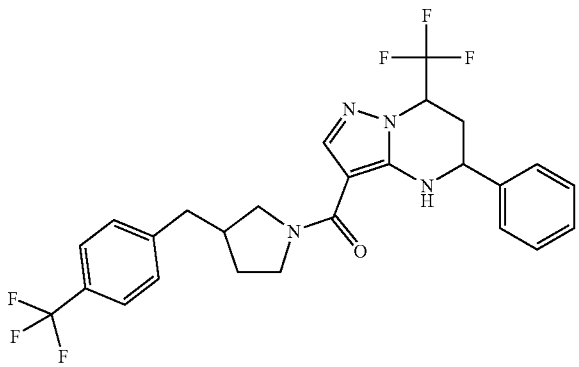 | 5-phenyl-7-(trifluoromethyl)-3-((3-(4-(trifluoromethyl)benzyl)-1-pyrrolidinyl)carbonyl)-4,5,6,7-tetrahydropyrazolo[1,5-a]pyrimidine | MS (ESI, m/z) 525 (M + H)+ |
| 180 | 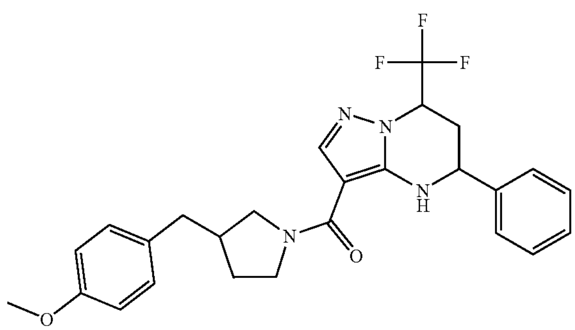 | 3-((3-(4-methoxybenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 488 (M + H)+ |
| 181 | 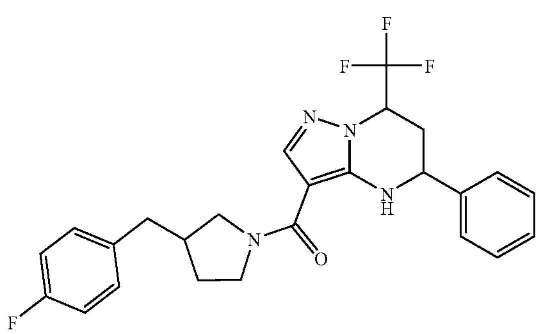 | 3-((3-(4-fluorobenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 475 (M + H)+ |
| 182 | 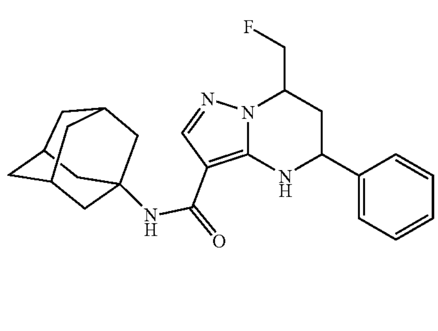 | N-(1-adamantyl)-7-ethyl-5-phenyl-4,5,6,7-tetrahydropyrazolo[1,5-a]pyrimidine-3-carboxamide | MS (ESI, m/z) 408 (M + H)+ |

TABLE 4-continued

| Example | Structure | Name | Physiological Data |
|---|---|---|---|
| 183 | 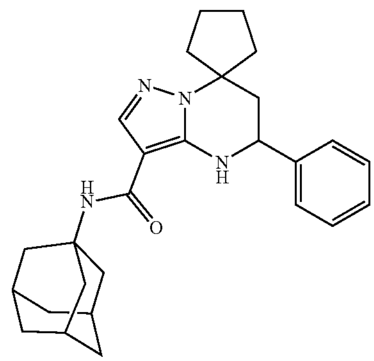 | N-(1-adamantyl)-5'-phenyl-5',6'-dihydro-4'H-spiro[cyclopentane-1,7'-pyrazolo[1,5-a]pyrimidine]-3'-carboxamide | mp 259-261° C. |
| 184 | 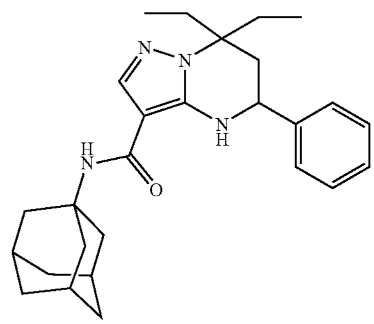 | N-(1-adamantyl)-7,7-diethyl-5-phenyl-4,5,6-7-tetrahydropyrazolo[1,5-a]pyrimidine-3-carboxamide | mp 213-214° C. |
| 185 | 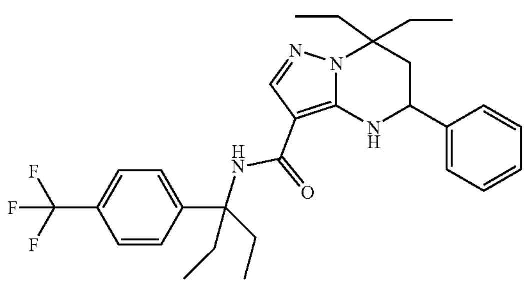 | 7,7-diethyl-N-(1-ethyl-1-(4-(trifluoromethyl)phenyl)propyl)-5-phenyl-4,5,6,7-tetrahydropyrazolo[1,5-a]pyrimidine-3-carboxamide | mp 174-175° C. |
| 186 | 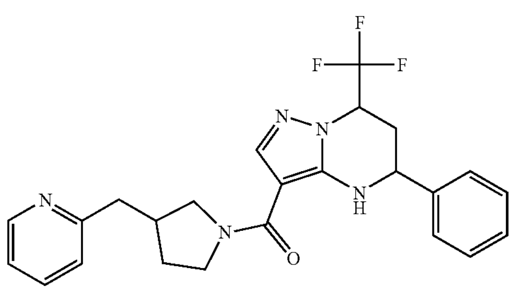 | 5-phenyl-3-((3-(2-pyridinylmethyl)-1-pyrrolidinyl)carbonyl)-7-(trifluoromethyl)-4,5,6,7-tetrahydropyrazolo[1,5-a]pyrimidine | MS (ESI, m/z) 458 (M + H)+ |

TABLE 4-continued

| Example | Structure | Name | Physiological Data |
|---|---|---|---|
| 187 | 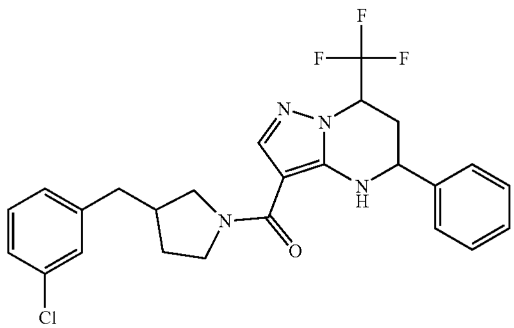 | 3-((3-(3-chlorobenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 492 (M + H)+ |
| 188 | 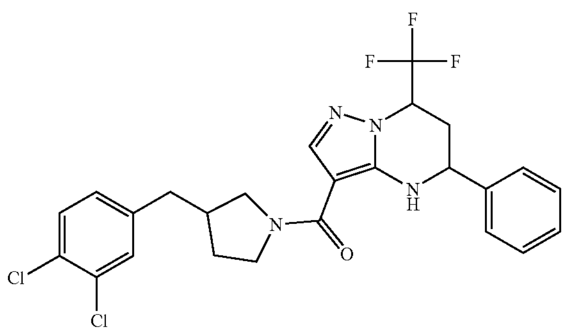 | 3-((3-(3,4-dichlorobenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 526 (M + H)+ |
| 189 | 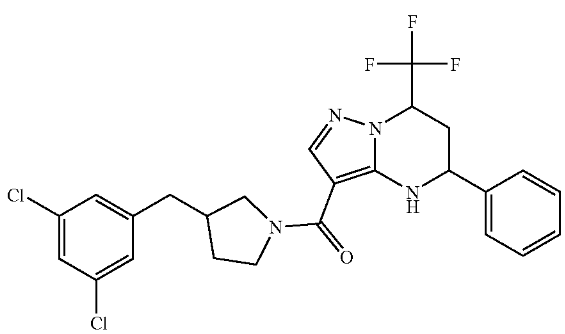 | 3-((3-(3,5-dichlorobenzyl)-1-pyrrolidinyl)carbonyl)-5-phenyl-7-(trifluoromethyl)-4,5,6,7-tetrahydropyrazolo[1,5-a]pyrimidine | MS (ESI, m/z) 526 (M + H)+ |
| 190 | 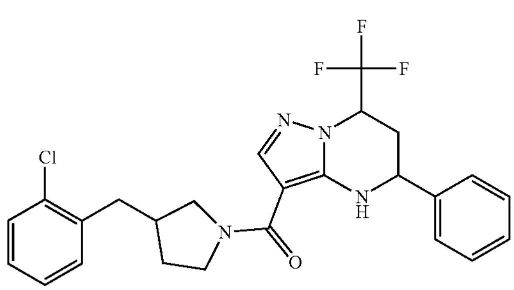 | 3-((3-(2-chlorobenzyl)-1-pyrrolidinyl)carbonyl)-5-phenyl-7-(trfluoromethyl)-4,5,6,7-tetrahydropyrazolo[1,5-a]pyrimidine | MS (ESI, m/z) 492 (M + H)+ |

TABLE 4-continued

| Example | Structure | Name | Physiological Data |
|---|---|---|---|
| 191 | 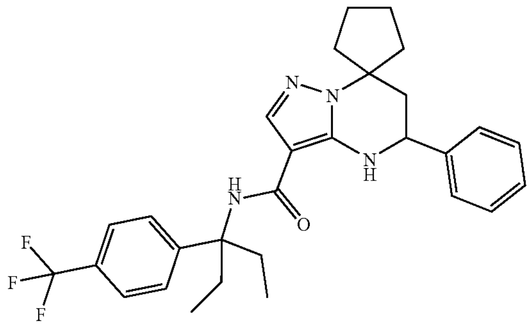 | N-(1-ethyl-1-(4-(trifluoromethyl)phenyl)propyl)-5'-phenyl-5',6'-dihydro-4'H-spiro[cyclopentane-1,7'-pyrazolo[1,5-a]pyrimidine]-3'-carboxamide | Mp 205-207° C. |
| 192 | 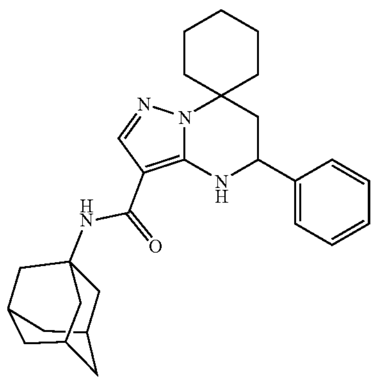 | N-(1-adamantyl)-5'-phenyl-5',6'-dihydro-4'H-spiro[cyclohexane-1,7'-pyrazolo[1,5-a]pyrimidine]-3'-carboxamide | Mp 274-275° C. |
| 193 | 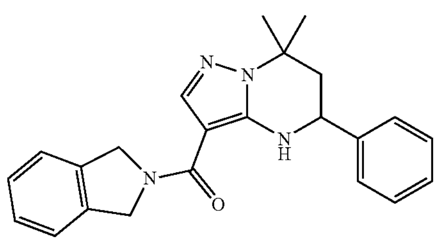 | 3-(1,3-dihydro-2H-isoindol-2-ylcarbonyl)-7,7-dimethyl-5-phenyl-4,5,6,7-tetrahydropyrazolo[1,5-a]pyrimidine | MS (ESI, m/z) 375 (M + H)+ |
| 194 | 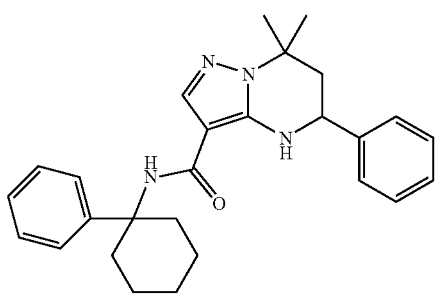 | 7,7-dimethyl-5-phenyl-N-(1-phenylcyclohexyl)-4,5,6,7-tetrahydropyrazolo[1,5-a]pyrimidine-3-carboxamide | MS (ESI, m/z) 432 (M + H)+ |
| 195 | 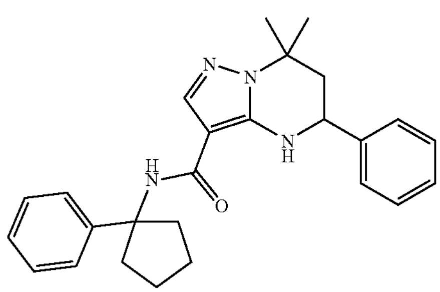 | 7,7-dimethyl-5-phenyl-N-(1-phenylcyclopentyl)-4,5,6,7-tetrahydropyrazolo[1,5-a]pyrimidine-3-carboxamide | MS (ESI, m/z) 418 (M + H)+ |

TABLE 4-continued

| Example | Structure | Name | Physiological Data |
|---|---|---|---|
| 196 | 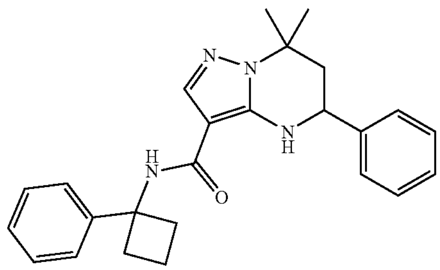 | 7,7-dimethyl-5-phenyl-N-(1-phenylcyclobutyl)-4,5,6,7-tetrahydropyrazolo[1,5-a]pyrimidine-3-carboxamide | MS (ESI, m/z) 404 (M + H)+ |
| 197 | 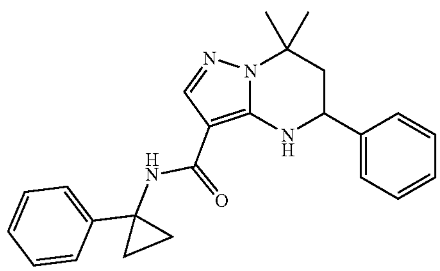 | 7,7-dimethyl-5-phenyl-N-(1-phenylcyclopropyl)-4,5,6,7-tetrahydropyrazolo[1,5-a]pyrimidine-3-carboxamide | MS (ESI, m/z) 389 (M + H)+ |
| 198 | 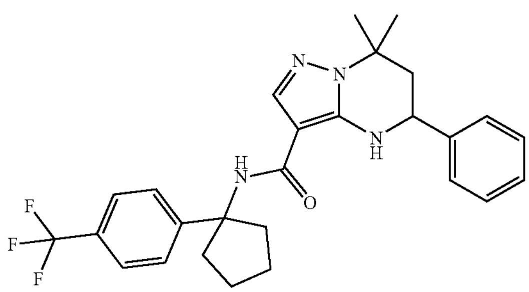 | 7,7-dimethyl-5-phenyl-N-(1-(4-(trifluoromethyl)phenyl)cyclopentyl)-4,5,6,7-tetrahydropyrazolo[1,5-a]pyrimidine-3-carboxamide | MS (ESI, m/z) 486 (M + H)+ |
| 199 | 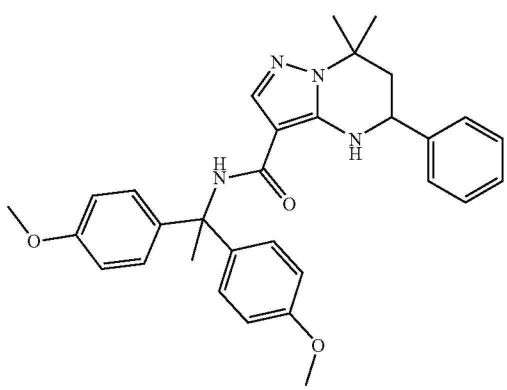 | N-(1,1-bis(4-methoxyphenyl)ethyl)-7,7-dimethyl-5-phenyl-4,5,6,7-tetrahydropyrazolo[1,5-a]pyrimidine-3-carboxamide | MS (ESI, m/z) 514 (M + H)+ |
| 200 | 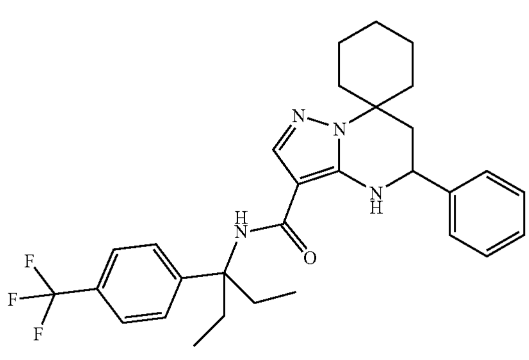 | N-(1-ethyl-1-(4-(trifluoromethyl)phenyl)propyl)-5'-phenyl-5',6'-dihydro-4'H-spiro[cyclohexane-1,7'-pyrazolo[1,5-a]pyrimidine]-3'-carboxamide | mp 274-275° C. |

TABLE 4-continued

| Example | Name | Physiological Data |
|---|---|---|
| 201 | N-(1-ethyl-1-(4-(trifluoromethyl)phenyl)propyl)-5-phenyl-4,5,5a,6,7,8,9,9a-octahydropyrazolo[1,5-a]quinazoline-3-carboxamide | mp 213-214° C. |
| 202 | N-(1-adamantyl)-5-(4-methoxyphenyl)-7-(trifluoromethyl)-4,5,6,7-tetrahydropyrazolo[1,5-a]pyrimidine-3-carboxamide | mp 241-243° C. |
| 203 | 5-(4-methoxyphenyl)-N-(2-(2-naphthyl)ethyl)-7-(trifluoromethyl)-4,5,6,7-tetrahydropyrazolo[1,5-a]pyrimidine-3-carboxamide | MS (ESI, m/z) 495 (M + H)+ |

TABLE 4-continued

| Example | Structure | Name | Physiological Data |
|---------|-----------|------|--------------------|
| 204 | 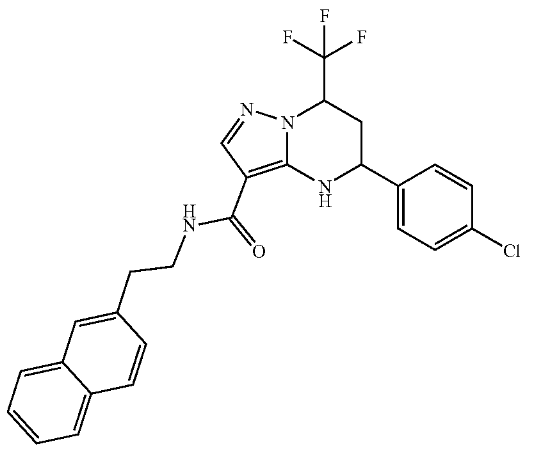 | 5-(4-chlorophenyl)-N-(2-(2-naphthyl)ethyl)-7-(trifluoromethyl)-4,5,6,7-tetrahydropyrazolo[1,5-a]pyrimidine-3-carboxamide | MS (ESI, m/z) 499 (M + H)+ |
| 205 | 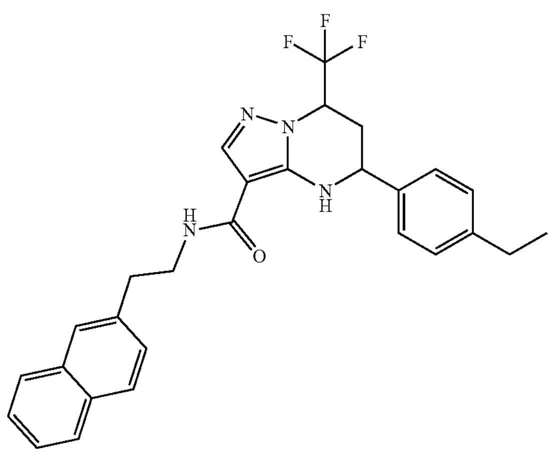 | 5-(4-ethylphenyl)-N-(2-(2-naphthyl)ethyl)-7-(trifluoromethyl)-4,5,6,7-tetrahydropyrazolo[1,5-a]pyrimidine-3-carboxamide | MS (ESI, m/z) 493 (M + H)+ |
| 206 | 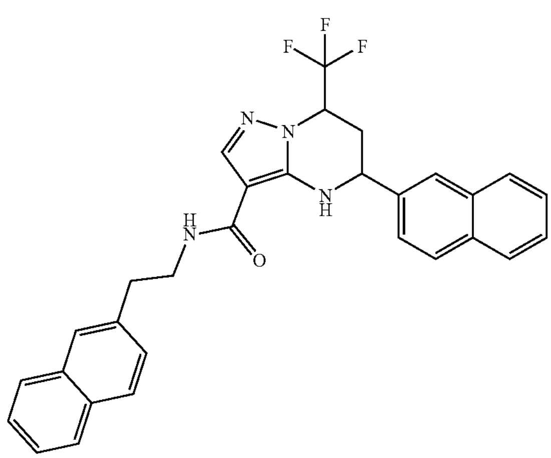 | 5-(2-naphthyl)-N-(2-(2-naphthyl)ethyl)-7-trifluoromethyl)-4,5,6,7-tetrahydropyrazolo[1,5-a]pyrimidine-3-carboxamide | MS (ESI, m/z) 515 (M + H)+ |

TABLE 4-continued

| Example | Structure | Name | Physiological Data |
|---|---|---|---|
| 207 | 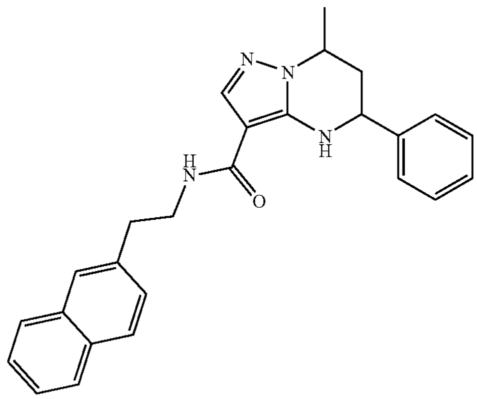 | 7-methyl-N-(2-(2-naphthyl)ethyl)-5-phenyl-4,5,6,7-tetrahydropyrazolo[1,5-a]pyrimidine-3-carboxamide | MS (ESI, m/z) 411 (M + H)+ |
| 208 | 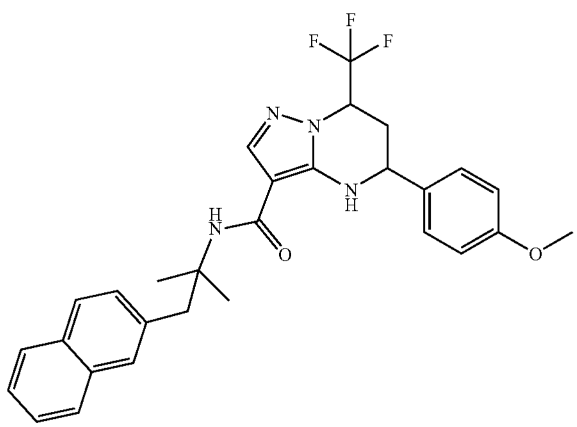 | N-(1,1-dimethyl-2-(2-naphthyl)ethyl)-5-(4-methoxyphenyl)-7-(trifluoromethyl)-4,5,6,7-tetrahydropyrazolo[1,5-a]pyrimidine-3-carboxamide | MS (ESI, m/z) 523 (M + H)+ |
| 209 | 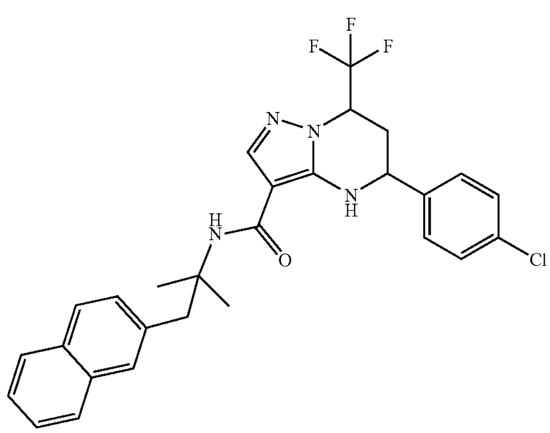 | 5-(4-chlorophenyl)-N-(1,1-dimethyl-2-(2-naphthyl)ethyl)-7-(trifluoromethyl)-4,5,6,7-tetrahydropyrazolo[1,5-a]pyrimidine-3-carboxamide | MS (ESI, m/z) 527 (M + H)+ |

TABLE 4-continued

| Example | Structure | Name | Physiological Data |
|---|---|---|---|
| 210 | 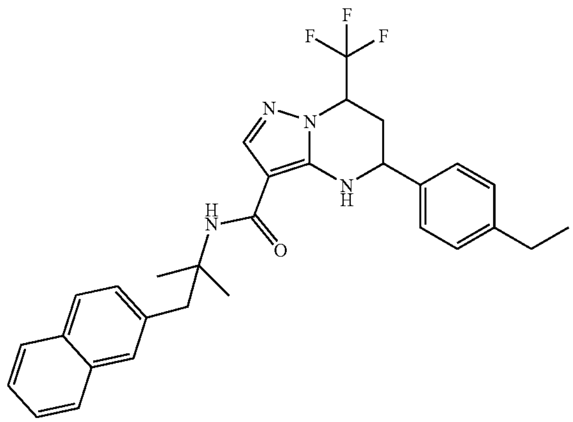 | N-(1,1-dimethyl-2-(2-naphthyl)ethyl-5-(4-ethylphenyl)-7-(trifluoromethyl)-4,5,6,7-tetrahydropyrazolo[1,5-a]pyrimidine-3-carboxamide | MS (ESI, m/z) 521 (M + H)+ |
| 211 | 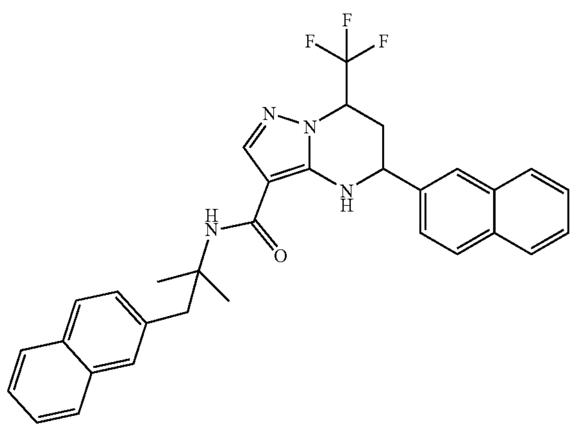 | N-(1,1-dimethyl-2-(2-naphthyl)ethyl)-5-(2-naphthyl)-7-(trifluoromethyl)-4,5,6,7-tetrahydropyrazolo[1,5-a]pyrimidine-3-carboxamide | MS (ESI, m/z) 543 (M + H)+ |
| 212 | 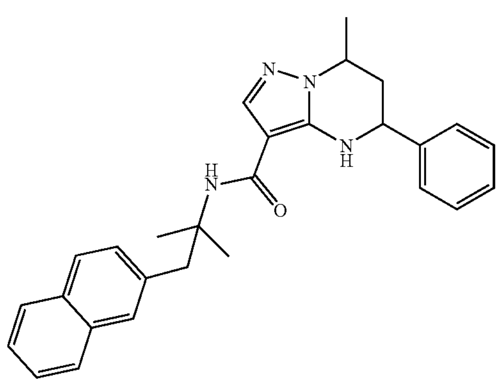 | N-(1,1-dimethyl-2-(2-naphthyl)ethyl)-7-methyl-5-phenyl-4,5,6,7-tetrahydropyrazolo[1,5-a]pyrimidine-3-carboxamide | MS (ESI, m/z) 439 (M + H)+ |

TABLE 4-continued

| Example | Structure | Name | Physiological Data |
|---|---|---|---|
| 213 | 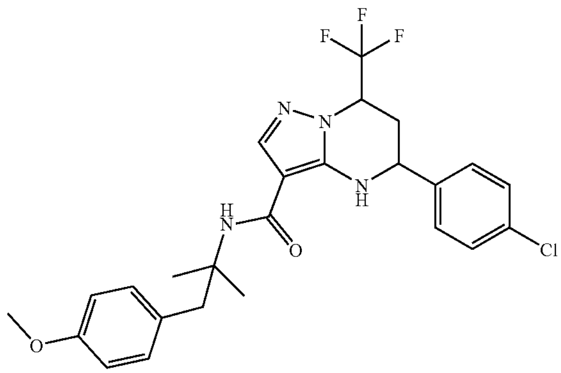 | 5-(4-chlorophenyl)-N-(2-(4-methoxyphenyl)-1,1-dimethylethyl)-7-(trifluoromethyl)-4,5,6,7-tetrahydropyrazolo[1,5-a]pyrimidine-3-carboxamide | MS (ESI, m/z) 507 (M + H)+ |
| 214 | 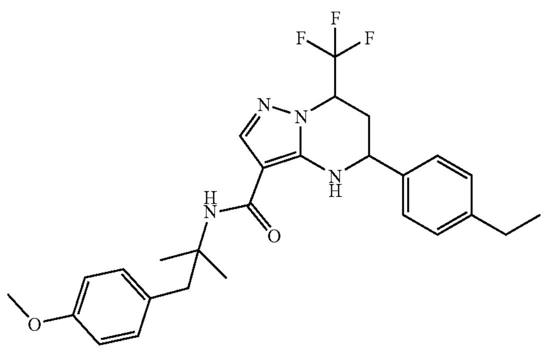 | 5-(4-ethylphenyl)-N-(2-(4-methoxyphenyl)-1,1-dimethylethyl)-7-(trifluoromethyl)-4,5,6,7-tetrahydropyrazolo[1,5-a]pyrimidine-3-carboxamide | MS (ESI, m/z) 501 (M + H)+ |
| 215 | 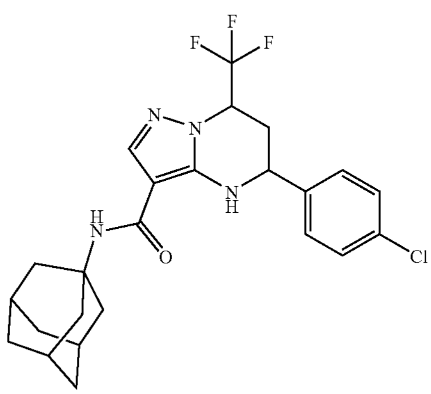 | N-(1-adamantyl)-5-(4-chlorophenyl)-7-(trifluoromethyl)-4,5,6,7-tetrahydropyrazolo[1,5-a]pyrimidine-3-carboxamide | MS (ESI, m/z) 479 (M + H)+ |
| 216 | 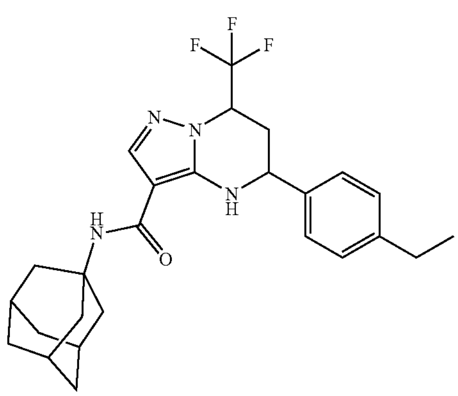 | N-(1-adamantyl)-5-(4-ethylphenyl)-7-(trifluoromethyl)-4,5,6,7-tetrahydropyrazolo[1,5-a]pyrimidine-3-carboxamide | MS (ESI, m/z) 473 (M + H)+ |

TABLE 4-continued

| Example | Structure | Name | Physiological Data |
|---------|-----------|------|--------------------|
| 217 | 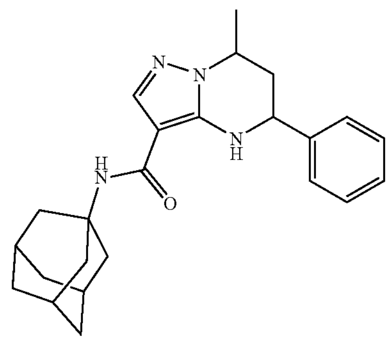 | N-(1-adamantyl)-7-methyl-5-phenyl-4,5,6,7-tetrahydropyrazolo[1,5-a]pyrimidine-3-carboxamide | MS (ESI, m/z) 391 (M + H)+ |
| 218 | 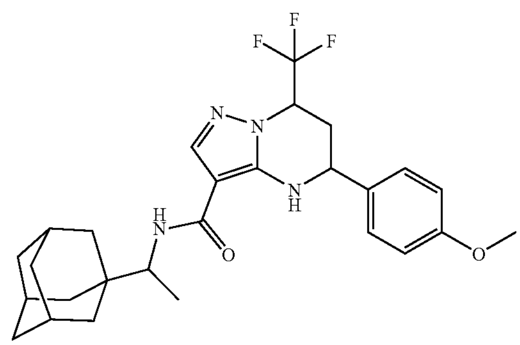 | N-(1-(1-adamantyl)ethyl)-5-(4-methoxyphenyl)-7-(trifluoromethyl)-4,5,6,7-tetrahydropyrazolo[1,5-a]pyrimidine-3-carboxamide | MS (ESI, m/z) 503 (M + H)+ |
| 219 | 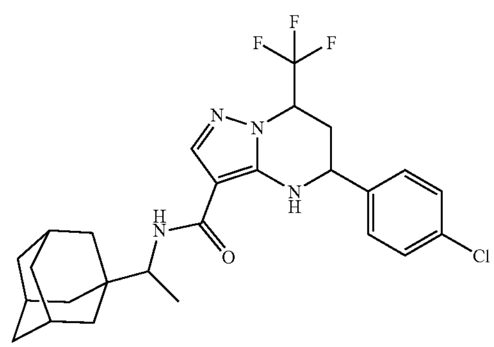 | N-(1-(1-adamantyl)ethyl)-5-(4-chlorophenyl)-7-(trifluoromethyl)-4,5,6,7-tetrahydropyrazolo[1,5-a]pyrimidine-3-carboxamide | MS (ESI, m/z) 507 (M + H)+ |
| 220 | 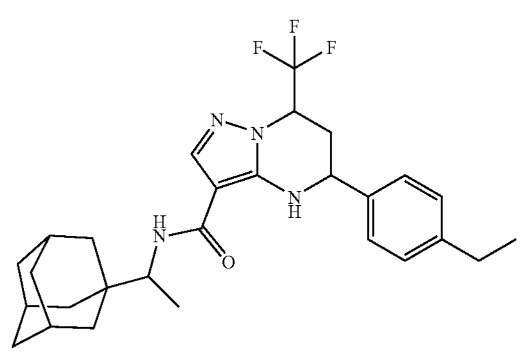 | N-(1-(1-adamantyl)ethyl)-5-(4-ethylphenyl)-7-(trifluoromethyl)-4,5,6,7-tetrahydropyrazolo[1,5-a]pyrimidine-3-carboxamide | MS (ESI, m/z) 501 (M + H)+ |

TABLE 4-continued

| Example | Structure | Name | Physiological Data |
|---|---|---|---|
| 221 | 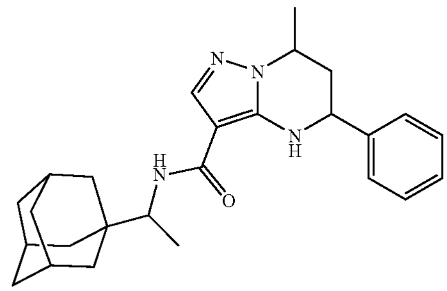 | N-(1-(1-adamantyl)ethyl)-7-methyl-5-phenyl-4,5,6,7-tetrahydropyrazolo[1,5-a]pyrimidine-3-carboxamide | MS (ESI, m/z) 419 (M + H)+ |
| 222 | 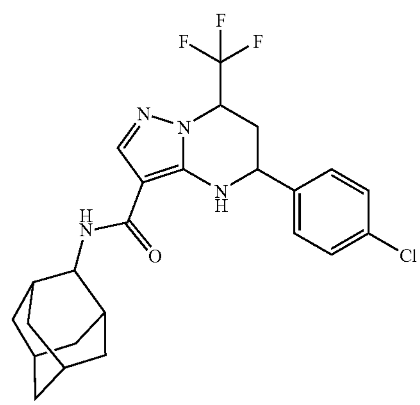 | N-(2-adamantyl)-5-(4-chlorophenyl)-7-(trifluoromethyl)-4,5,6,7-tetrahydropyrazolo[1,5-a]pyrimidine-3-carboxamide | MS (ESI, m/z) 479 (M + H)+ |
| 223 | 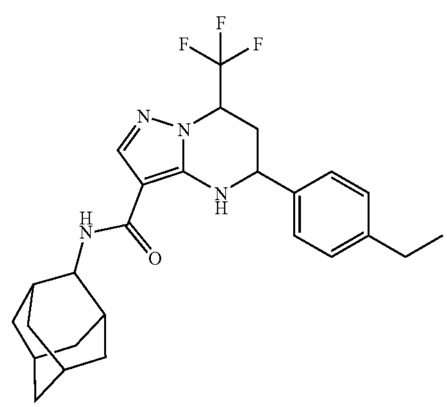 | N-(2-adamantyl)-5-(4-ethylphenyl)-7-(trifluoromethyl)-4,5,6,7-tetrahydropyrazolo[1,5-a]pyrimidine-3-carboxamide | MS (ESI, m/z) 473 (M + H)+ |
| 224 | 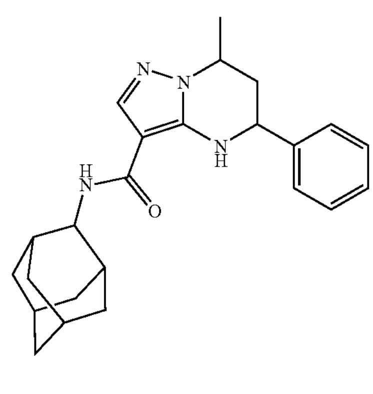 | N-(2-adamantyl)-7-methyl-5-phenyl-4,5,6,7-tetrahydropyrazolo[1,5-a]pyrimidine-3-carboxamide | MS (ESI, m/z) 391 (M + H)+ |

TABLE 4-continued

| Example | Structure | Name | Physiological Data |
|---|---|---|---|
| 225 | 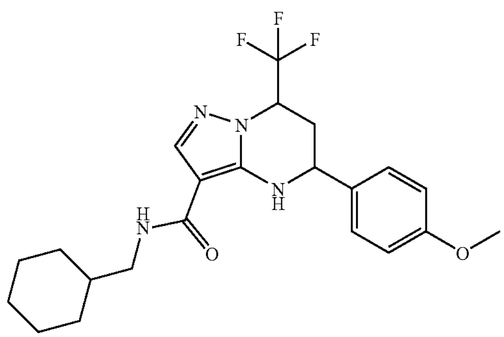 | N-(cyclohexylmethyl)-5-(4-methoxyphenyl)-7-(trifluoromethyl)-4,5,6,7-tetrahydropyrazolo[1,5-a]pyrimidine-3-carboxamide | MS (ESI, m/z) 437 (M + H)+ |
| 226 | 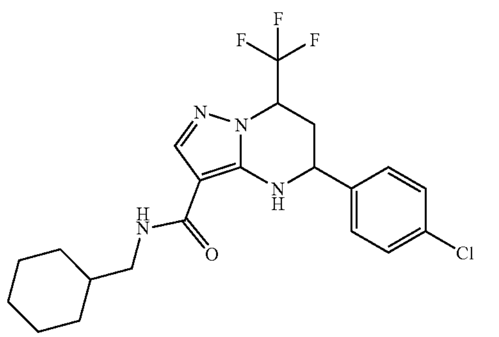 | 5-(4-chlorophenyl)-N-(cyclohexylmethyl)-7-(trifluoromethyl)-4,5,6,7-tetrahydropyrazolo[1,5-a]pyrimidine-3-carboxamide | MS (ESI, m/z) 441 (M + H)+ |
| 227 | 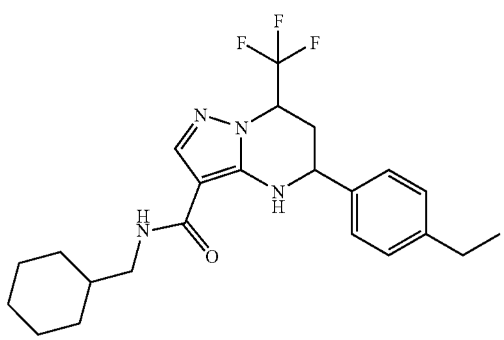 | N-(cyclohexylmethyl)-5-(4-ethylphenyl)-7-(trifluoromethyl)-4,5,6,7-tetrahydropyrazolo[1,5-a]pyrimidine-3-carboxamide | MS (ESI, m/z) 435 (M + H)+ |
| 228 | 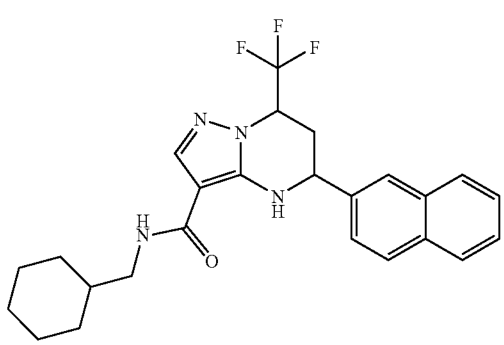 | N-(cyclohexylmethyl)-5-(2-naphthyl)-7-(trifluoromethyl)-4,5,6,7-tetrahydropyrazolo[1,5-a]pyrimidine-3-carboxamide | MS (ESI, m/z) 457 (M + H)+ |

TABLE 4-continued

| Example | Structure | Name | Physiological Data |
|---------|-----------|------|--------------------|
| 229 | 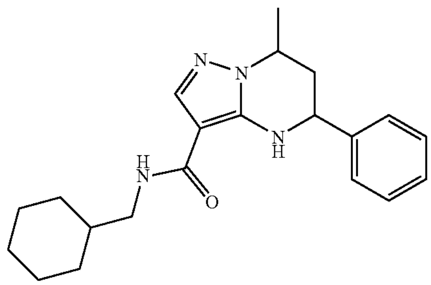 | N-(cyclohexylmethyl)-7-methyl-5-phenyl-4,5,6,7-tetrahydropyrazolo[1,5-a]pyrimidine-3-carboxamide | MS (ESI, m/z) 353 (M + H)+ |
| 230 | 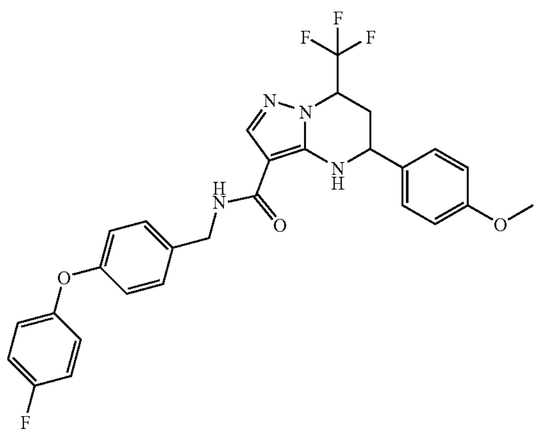 | N-(4-(4-fluorophenoxy)benzyl)-5-(4-methoxyphenyl)-7-(trifluoromethyl)-4,5,6,7-tetrahydropyrazolo[1,5-a]pyrimidine-3-carboxamide | MS (ESI, m/z) 541 (M + H)+ |
| 231 | 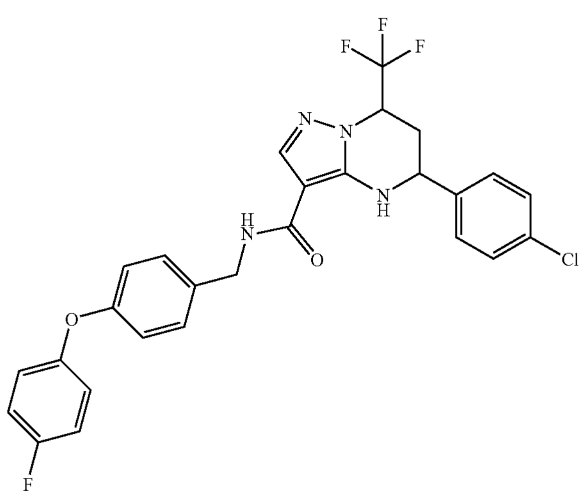 | 5-(4-chlorophenyl)-N-(4-(4-fluorophenoxy)benzyl)-7-(trifluoromethyl)-4,5,6,7-tetrahydropyrazolo[1,5-a]pyrimidine-3-carboxamide | MS (ESI, m/z) 545 (M + H)+ |

TABLE 4-continued

| Example | Structure | Name | Physiological Data |
|---|---|---|---|
| 232 | 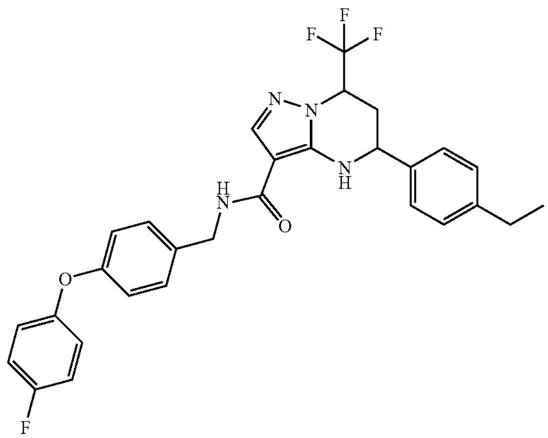 | 5-(4-ethylphenyl)-N-(4-(4-fluorophenoxy)benzyl)-7-(trifluoromethyl)-4,5,6,7-tetrahydropyrazolo[1,5-a]pyrimidine-3-carboxamide | MS (ESI, m/z) 539 (M + H)+ |
| 233 | 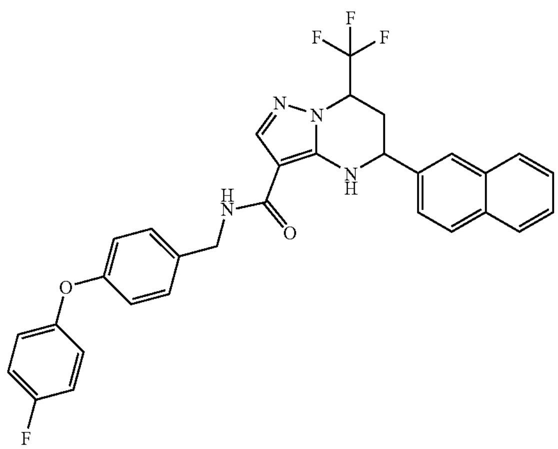 | N-(4-(4-fluorophenoxy)benzyl)-5-(2-naphthyl)-7-(trifluoromethyl)-4,5,6,7-tetrahydropyrazolo[1,5-a]pyrimidine-3-carboxamide | MS (ESI, m/z) 561 (M + H)+ |
| 234 | 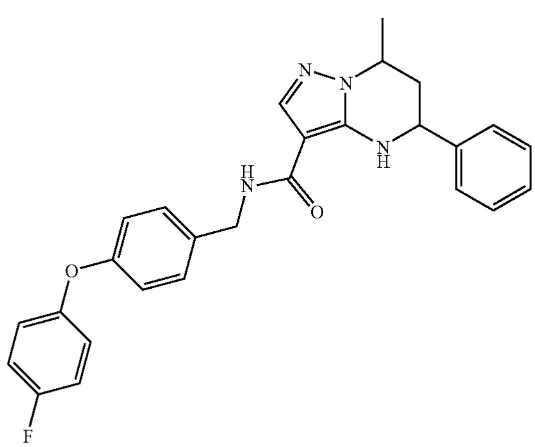 | N-(4-(4-fluorophenoxy)benzyl)-7-methyl-5-phenyl-4,5,6,7-tetrahydropyrazolo[1,5-a]pyrimidine-3-carboxamide | MS (ESI, m/z) 457 (M + H)+ |

TABLE 4-continued

| Example | Structure | Name | Physiological Data |
|---|---|---|---|
| 235 | 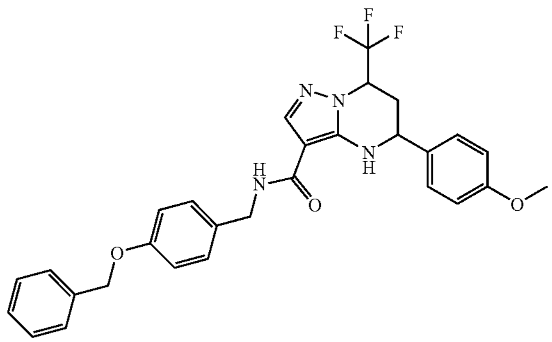 | N-(4-(benzyloxy)benzyl)-5-(4-methoxyphenyl)-7-(trifluoromethyl)-4,5,6,7-tetrahydropyrazolo[1,5-a]pyrimidine-3-carboxamide | MS (ESI, m/z) 537 (M + H)+ |
| 236 | 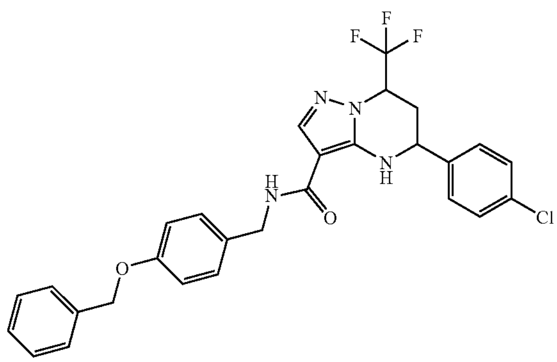 | N-(4-(benzyloxy)benzyl)-5-(4-chlorophenyl)-7-(trifluoromethyl)-4,5,6,7-tetrahydropyrazolo[1,5-a]pyrimidine-3-carboxamide | MS (ESI, m/z) 537 (M + H)+ |
| 237 | 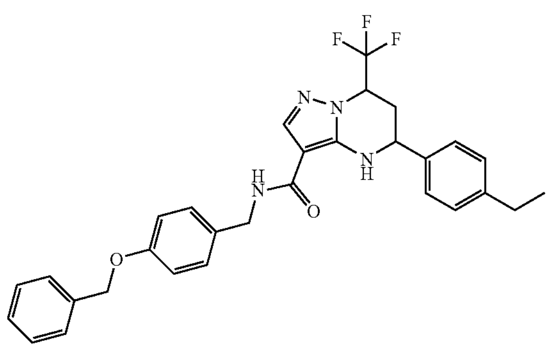 | N-(4-(benzyloxy)benzyl)-5-(4-ethylphenyl)-7-(trifluoromethyl)-4,5,6,7-tetrahydropyrazolo[1,5-a]pyrimidine-3-carboxamide | MS (ESI, m/z) 535 (M + H)+ |
| 238 | 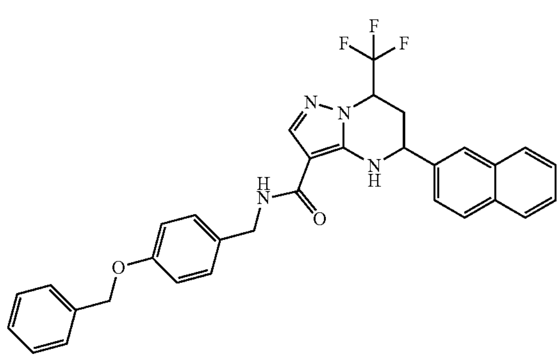 | N-(4-(benzyloxy)benzyl)-5-(2-naphthyl)-7-(trifluoromethyl)-4,5,6,7-tetrahydropyrazolo[1,5-a]pyrimidine-3-carboxamide | MS (ESI, m/z) 557 (M + H)+ |

TABLE 4-continued

| Example | Structure | Name | Physiological Data |
|---------|-----------|------|--------------------|
| 239 | 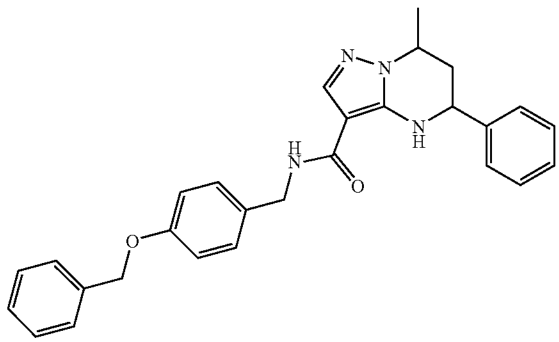 | N-(4-(benzyloxy)benzyl)-7-methyl-5-phenyl-4,5,6,7-tetrahydropyrazolo[1,5-a]pyrimidine-3-carboxamide | MS (ESI, m/z) 453 (M + H)+ |
| 240 | 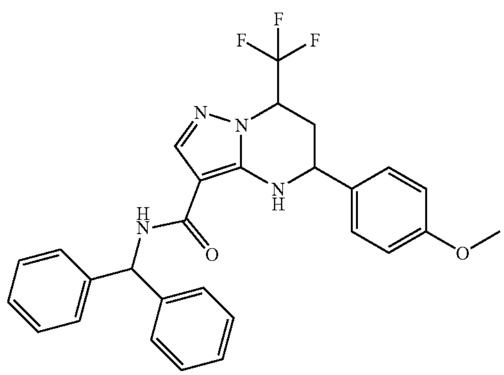 | N-benzhydryl-5-(4-methoxyphenyl)-7-(trifluoromethyl)-4,5,6,7-tetrahydropyrazolo[1,5-a]pyrimidine-3-carboxamide | MS (ESI, m/z) 507 (M + H)+ |
| 241 | 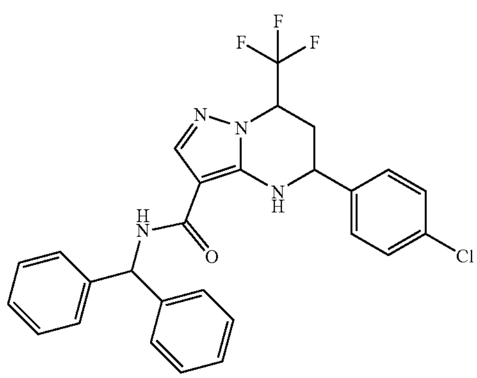 | N-benzhydryl-5-(4-chlorophenyl)-7-(trifluoromethyl)-4,5,6,7-tetrahydropyrazolo[1,5-a]pyrimidine-3-carboxamide | MS (ESI, m/z) 511 (M + H)+ |
| 242 | 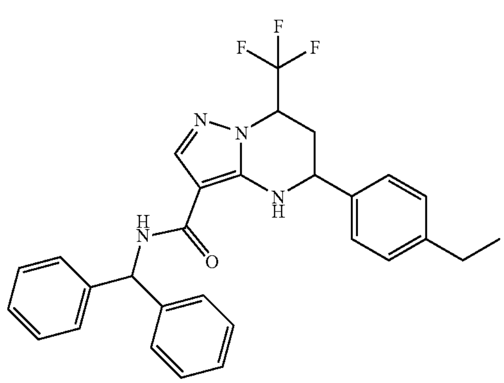 | N-benzhydryl-5-(4-ethylphenyl)-7-(trifluoromethyl)-4,5,6,7-tetrahydropyrazolo[1,5-a]pyrimidine-3-carboxamide | MS (ESI, m/z) 505 (M + H)+ |

TABLE 4-continued

| Example | Structure | Name | Physiological Data |
|---|---|---|---|
| 243 | 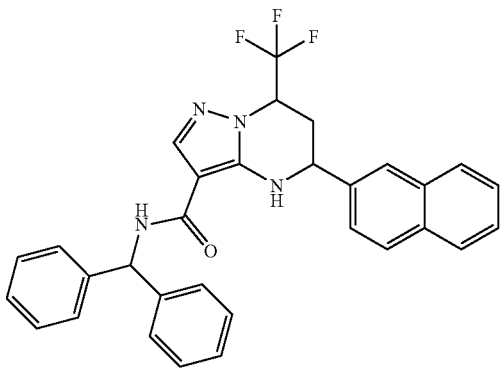 | N-benzhydryl-5-(2-naphthyl)-7-(trifluoromethyl)-4,5,6,7-tetrahydropyrazolo[1,5-a]pyrimidine-3-carboxamide | MS (ESI, m/z) 527 (M + H)+ |
| 244 | 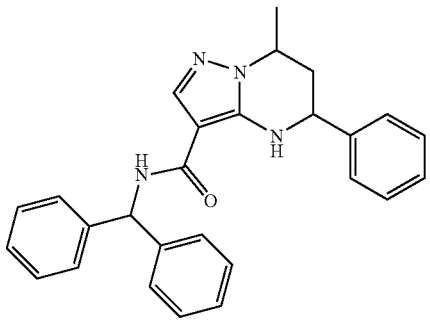 | N-benzhydryl-7-methyl-5-phenyl-4,5,6,7-tetrahydropyrazolo[1,5-a]pyrimidine-3-carboxamide | MS (ESI, m/z) 423 (M + H)+ |
| 245 | 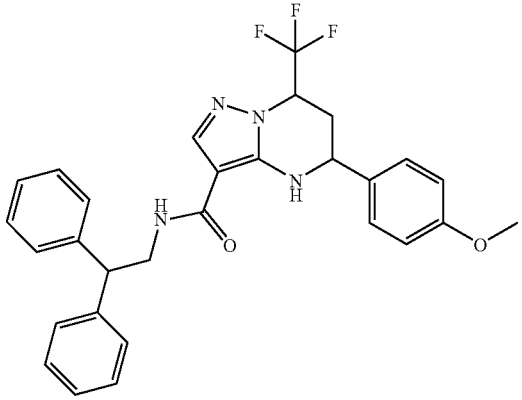 | N-(2,2-diphenylethyl)-5-(4-methoxyphenyl)-7-(trifluoromethyl)-4,5,6,7-tetrahydropyrazolo[1,5--a]pyrimidine-3-carboxamide | MS (ESI, m/z) 521 (M + H)+ |
| 246 | 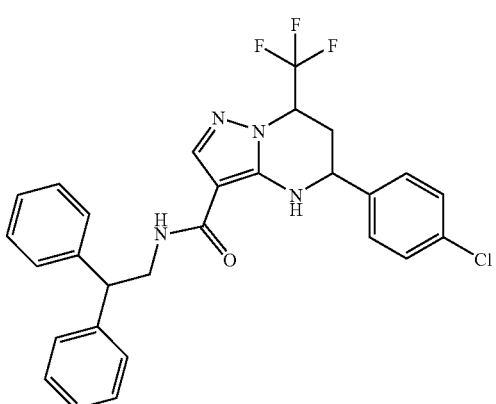 | N-(4-chlorophenyl)-N-(2,2-diphenylethyl)-7-(trifluoromethyl)-4,5,6,7-tetrahydropyrazolo[1,5-a]pyrimidine-3-carboxamide | MS (ESI, m/z) 525 (M + H)+ |

TABLE 4-continued

| Example | Structure | Name | Physiological Data |
|---|---|---|---|
| 247 | 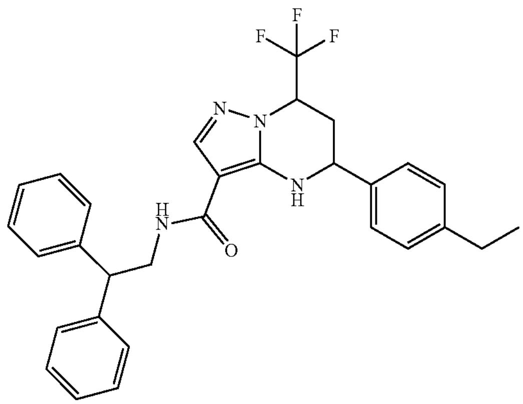 | N-(2,2-diphenylethyl)-5-(4-ethylphenyl)-7-(trifluoromethyl)-4,5,6,7-tetrahydropyrazolo[1,5-a]pyrimidine-3-carboxamide | MS (ESI, m/z) 519 (M + H)+ |
| 248 | 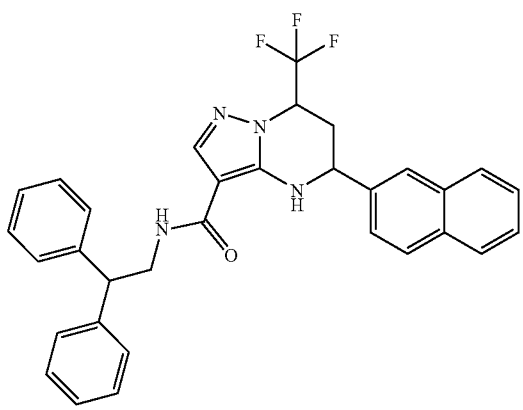 | N-(2,2-diphenylethyl)-5-(2-naphthyl)-7-(trifluoromethyl)-4,5,6,7-tetrahydropyrazolo[1,5-a]pyrimidine-3-carboxamide | MS (ESI, m/z) 541 (M + H)+ |
| 249 | 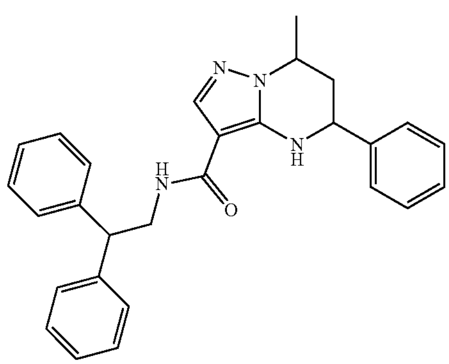 | N-(2,2-diphenylethyl)-7-methyl-5-phenyl-4,5,6,7-tetrahydropyrazolo[1,5-a]pyrimidine-3-carboxamide | MS (ESI, m/z) 437 (M + H)+ |

TABLE 4-continued

| Example | Structure | Name | Physiological Data |
|---|---|---|---|
| 250 | 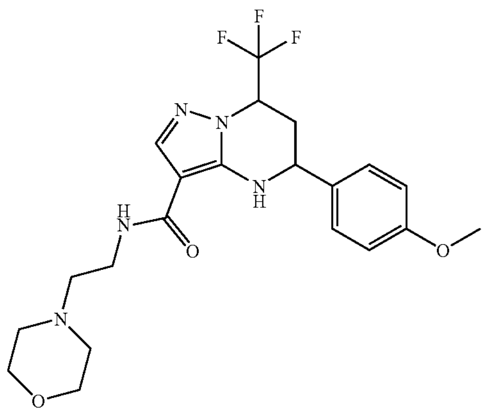 | 5-(4-methoxyphenyl)-N-(2-(4-morpholinyl)ethyl)-7-(trifluoromethyl)-4,5,6,7-tetrahydropyrazolo[1,5-a]pyrimidine-3-carboxamide | MS (ESI, m/z) 454 (M + H)+ |
| 251 | 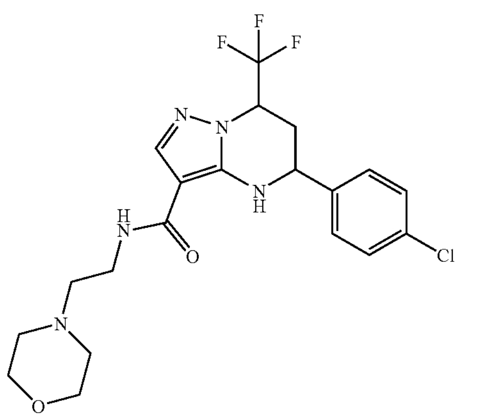 | 5-(4-chlorophenyl)-N-(2-(4-morpholinyl)ethyl)-7-(trifluoromethyl)-4,5,6,7-tetrahydropyrazolo[1,5-a]pyrimidine-3-carboxamide | MS (ESI, m/z) 458 (M + H)+ |
| 252 | 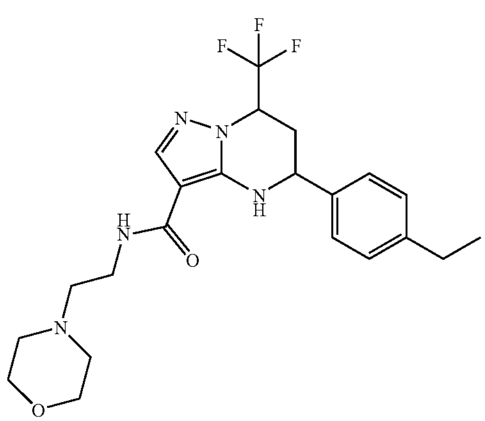 | 5-(4-ethylphenyl)-N-(2-(4-morpholinyl)ethyl)-7-(trifluoromethyl)-4,5,6,7-tetrahydropyrazolo[1,5-a]pyrimidine-3-carboxamide | MS (ESI, m/z) 452 (M + H)+ |

TABLE 4-continued

| Example | Structure | Name | Physiological Data |
|---|---|---|---|
| 253 | 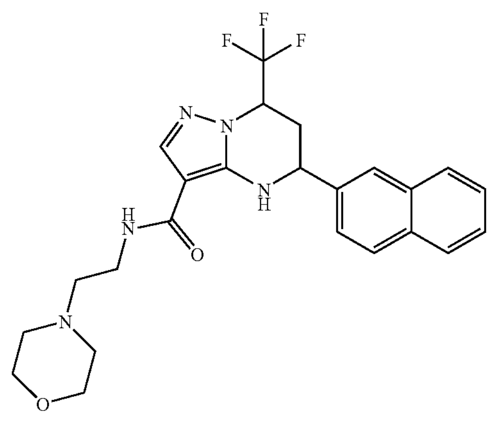 | N-(2-(4-morpholinyl)ethyl)-5-(2-naphthyl)-7-(trifluoromethyl)-4,5,6,7-tetrahydropyrazolo[1,5-a]pyrimidine-3-carboxamide | MS (ESI, m/z) 474 (M + H)+ |
| 254 | 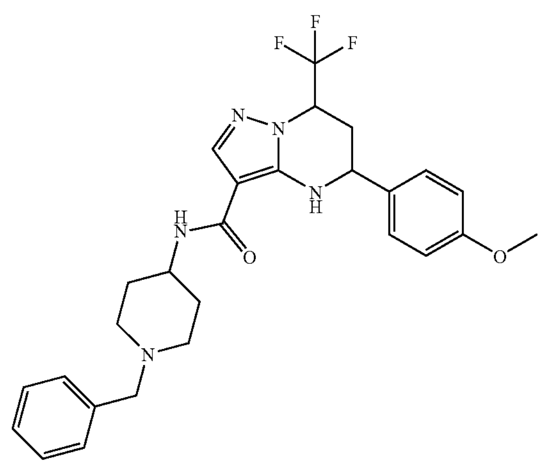 | N-(1-benzyl-4-piperidinyl)-5-(4-methoxyphenyl)-7-(trifluoromethyl)-4,5,6,7-tetrahydropyrazolo[1,5-a]pyrimidine-3-carboxamide | MS (ESI, m/z) 514 (M + H)+ |
| 255 | 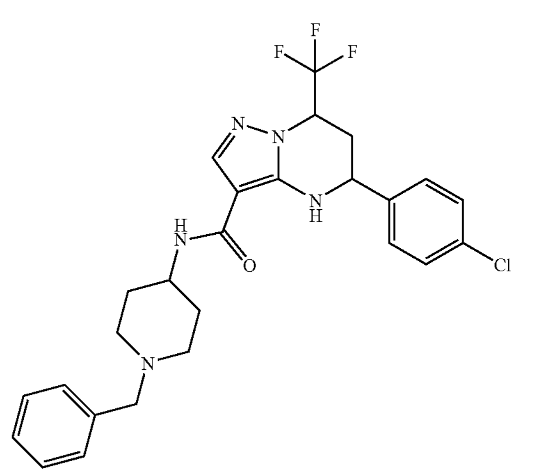 | N-(1-benzyl-4-piperidinyl)-5-(4-chlorophenyl)-7-(trifluoromethyl)-4,5,6,7-tetrahydropyrazolo[1,5-a]pyrimidine-3-carboxamide | MS (ESI, m/z) 518 (M + H)+ |

TABLE 4-continued

| Example | Structure | Name | Physiological Data |
|---|---|---|---|
| 256 | 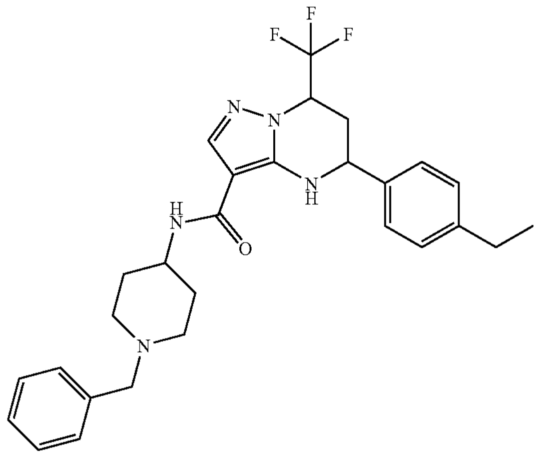 | N-(1-benzyl-4-piperidinyl)-5-(4-ethylphenyl)-7-(trifluoromethyl)-4,5,6,7-tetrahydropyrazolo[1,5-a]pyrimidine-3-carboxamide | MS (ESI, m/z) 512 (M + H)+ |
| 257 | 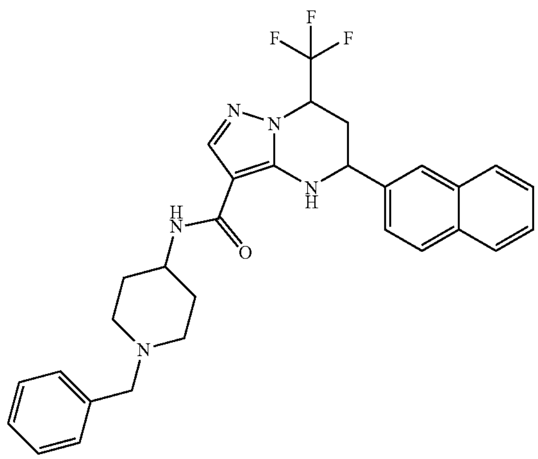 | N-(1-benzyl-4-piperidinyl)-5-(2-naphthyl)-7-(trifluoromethyl)-4,5,6,7-tetrahydropyrazolo[1,5-a]pyrimidine-3-carboxamide | MS (ESI, m/z) 534 (M + H)+ |
| 258 | 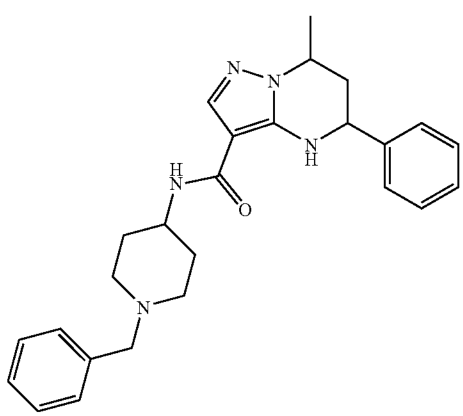 | N-(1-benzyl-4-piperidinyl)-7-methyl-5-phenyl-4,5,6,7-tetrahydropyrazolo[1,5-a]pyrimidine-3-carboxamide | MS (ESI, m/z) 430 (M + H)+ |

TABLE 4-continued

| Example | Structure | Name | Physiological Data |
|---|---|---|---|
| 259 | 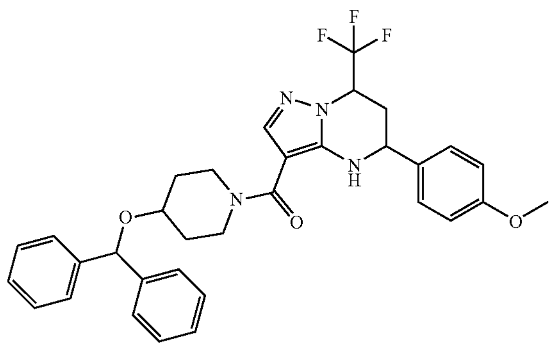 | 3-((4-(benzhydryloxy)-1-piperidinyl)carbonyl)-5-(4-methoxyphenyl)-7-(trifluoromethyl)-4,5,6,7-tetrahydropyrazolo[1,5-a]pyrimidine | MS (ESI, m/z) 592 (M + H)+ |
| 260 | 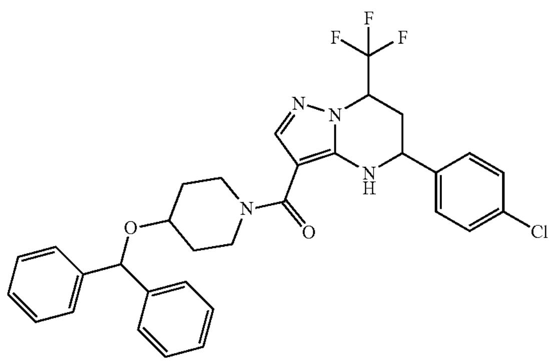 | 3-((4-(benzhydryloxy)-1-piperidinyl)carbonyl)-5-(4-chlorophenyl)-7-(trifluoromethyl)-4,5,6,7-tetrahydropyrazolo[1,5-a]pyrimidine | MS (ESI, m/z) 596 (M + H)+ |
| 261 | 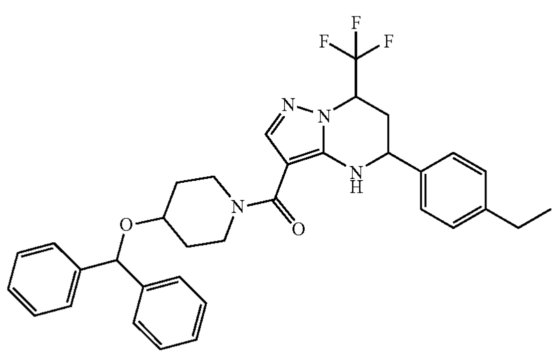 | 3-((4-(benzhydryloxy)-1-piperidinyl)carbonyl)-5-(4-ethylphenyl)-7-(trifluoromethyl)-4,5,6,7-tetrahydropyrazolo[1,5-a]pyrimidine | MS (ESI, m/z) 590 (M + H)+ |
| 262 | 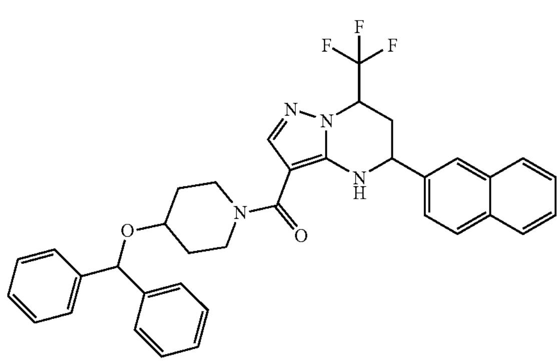 | 3-((4-(benzhydryloxy)-1-piperidinyl)carbonyl)-5-(2-naphthyl)-7-(trifluoromethyl)-4,5,6,7-tetrahydropyrazolo[1,5-a]pyrimidine | MS (ESI, m/z) 611 (M + H)+ |

TABLE 4-continued

| Example | Structure | Name | Physiological Data |
|---|---|---|---|
| 263 | 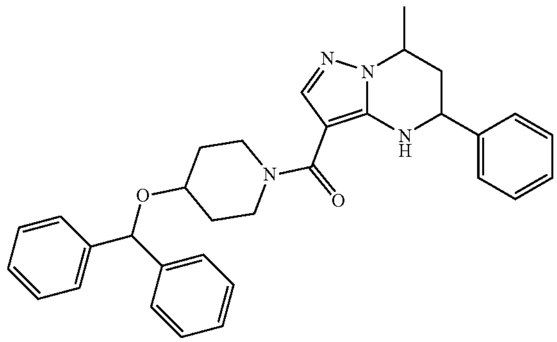 | 3-((4-(benzhydryloxy)-1-piperidinyl)carbonyl)-7-methyl-5-phenyl-4,5,6,7-tetrahydropyrazolo[1,5-a]pyrimidine | MS (ESI, m/z) 507 (M + H)+ |
| 264 | 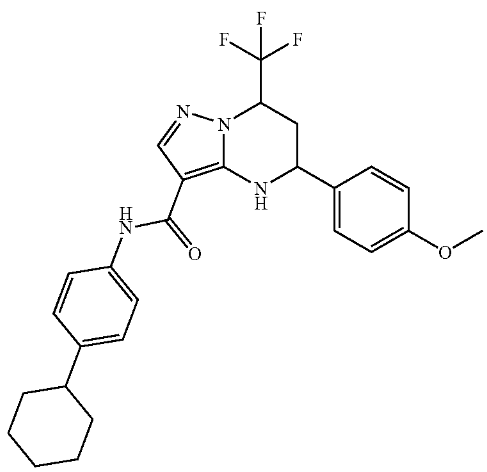 | N-(4-cyclohexylphenyl)-5-(4-methoxyphenyl)-7-(trifluoromethyl)-4,5,6,7-tetrahydropyrazolo[1,5-a]pyrimidine-3-carboxamide | MS (ESI, m/z) 499 (M + H)+ |
| 265 | 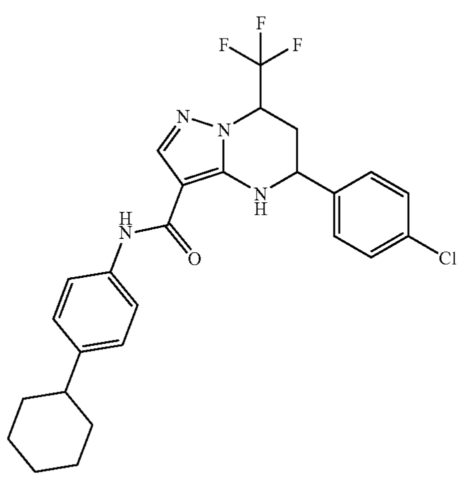 | 5-(4-chlorophenyl)-N-(4-cyclohexylphenyl)-7-(trifluoromethyl)-4,5,6,7-tetrahydropyrazolo[1,5-a]pyrimidine-3-carboxamide | MS (ESI, m/z) 503 (M + H)+ |

TABLE 4-continued

| Example | Structure | Name | Physiological Data |
|---|---|---|---|
| 266 | 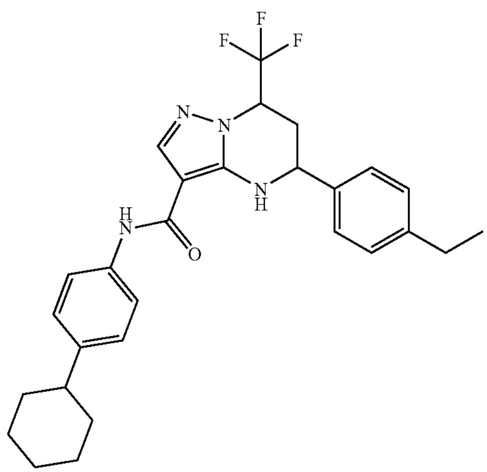 | N-(4-cyclohexylphenyl)-5-(4-ethylphenyl)-7-(trifluoromethyl)-4,5,6,7-tetrahydropyrazolo[1,5-a]pyrimidine-3-carboxamide | MS (ESI, m/z) 497 (M + H)+ |
| 267 | 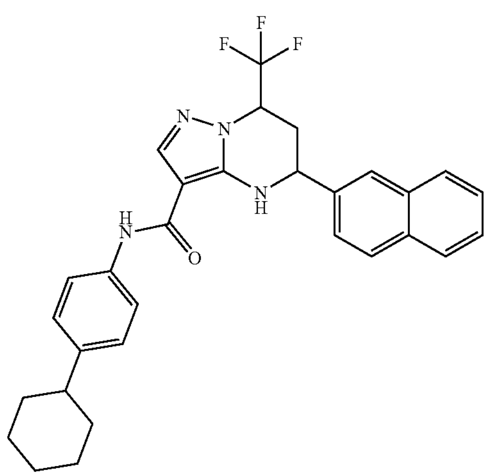 | N-(4-cyclohexylphenyl)-5-(2-naphthyl)-7-(trifluoromethyl)-4,5,6,7-tetrahydropyrazolo[1,5-a]pyrimidine-3-carboxamide | MS (ESI, m/z) 519 (M + H)+ |
| 268 | 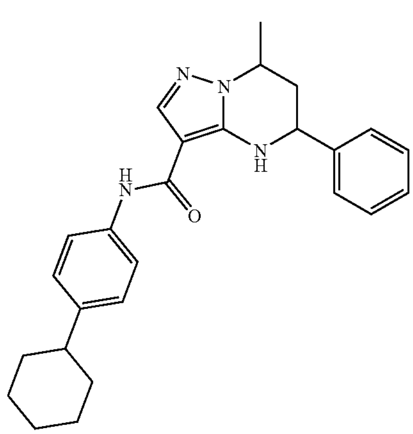 | N-(4-cyclohexylphenyl)-7-methyl-5-phenyl-4,5,6,7-tetrahydropyrazolo[1,5-a]pyrimidine-3-carboxamide | MS (ESI, m/z) 415 (M + H)+ |

TABLE 4-continued

| Example | Structure | Name | Physiological Data |
|---|---|---|---|
| 269 | 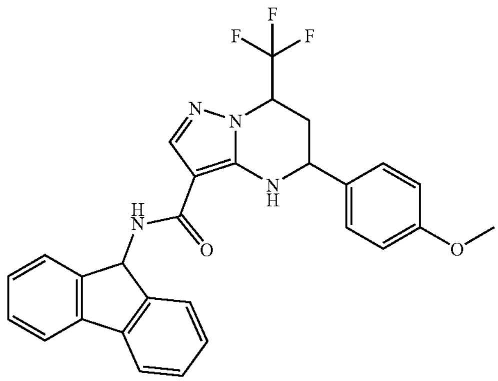 | N-(9H-fluoren-9-yl)-5-(4-methoxyphenyl)-7-(trifluoromethyl)-4,5,6,7-tetrahydropyrazolo[1,5-a]pyrimidine-3-carboxamide | IR(KBr) 3290, 3067, 2934, 2838, 1622, 1593, 1539, 15161 cm$^{-1}$ |
| 270 | 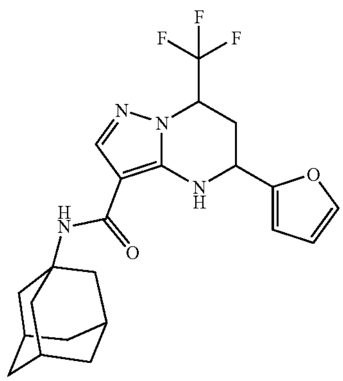 | N-(1-adamantyl)-5-(2-furyl)-7-(trifluoromethyl)-4,5,6,7-tetrahydropyrazolo[1,5-a]pyrimidine-3-carboxamide | mp 230-231° C. |
| 271 | 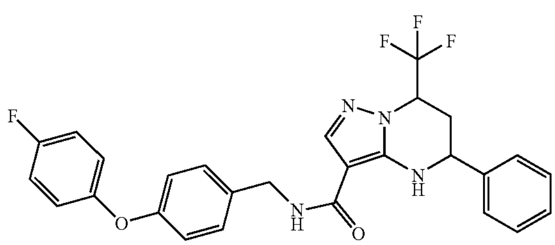 | N-(4-(4-fluorophenoxy)benzyl)-5-phenyl-7-(trifluoromethyl)-4,5,6,7-tetrahydropyrazolo[1,5-a]pyrimidine-3-carboxamide | mp 169-172° C. |
| 272 | 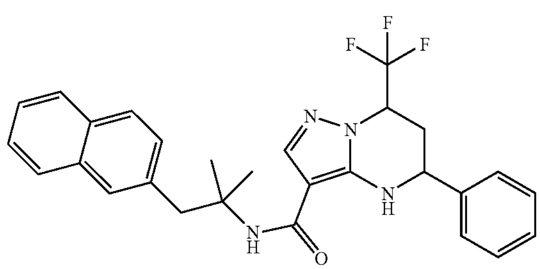 | N-(1,1-dimethyl-2-(2-naphthyl)ethyl)-5-phenyl-7-(trifluoromethyl)-4,5,6,7-tetrahydropyrazolo[1,5-a]pyrimidine-3-carboxamide | mp 187-188° C. |
| 273 | 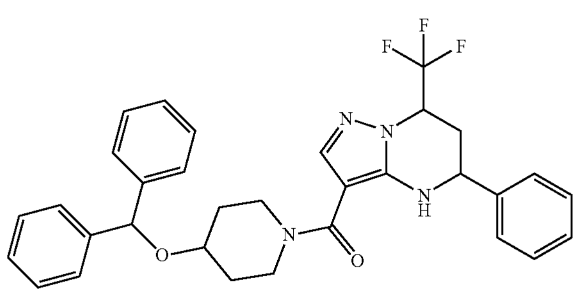 | 3-((4-(benzhydryloxy)-1-piperidinyl)carbonyl)-5-phenyl-7-(trifluoromethyl)-4,5,6,7-tetrahydropyrazolo[1,5-a]pyrimidine | IR(KBr) 2934, 2867, 1605, 1532 cm$^{-1}$ |

TABLE 4-continued

| Example | Structure | Name | Physiological Data |
|---|---|---|---|
| 274 | 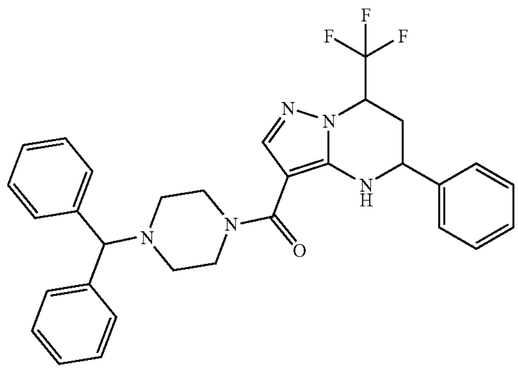 | 3-((4-benzhydryl-1-piperazinyl)carbonyl)-5-phenyl-7-(trifluoromethyl)-4,5,6,7-tetrahydropyrazolo[1,5-a]pyrimidine | mp 181-182° C. |
| 275 | 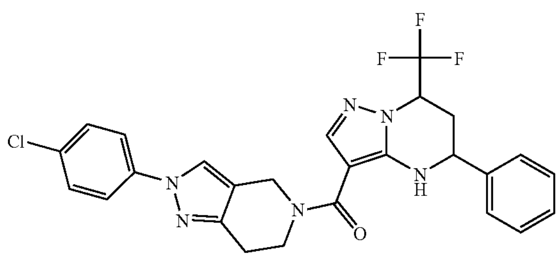 | 2-(4-chlorophenyl)-5-((5-phenyl-7-(trifluoromethyl)-4,5,6,7-tetrahydropyrazolo[1,5-a]pyrimidin-3-yl)carbonyl)-4,5,6,7-tetrahydro-2H-pyrazolo[4,3-c]pyridine | mp 183-184° C. |
| 276 | 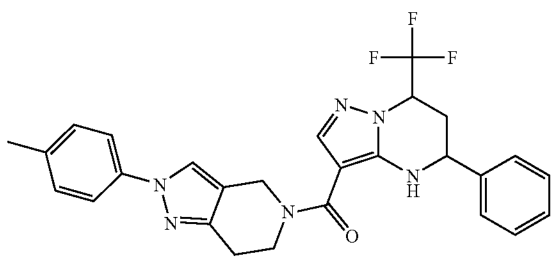 | 2-(4-methylphenyl)-5-((5-phenyl-7-(trifluoromethyl)-4,5,6,7-tetrahydropyrazolo[1,5-a]pyrimidin-3-yl)carbonyl)-4,5,6,7-tetrahydro-2H-pyrazolo[4,3-c]pyridine | mp 167-168° C. |
| 277 | 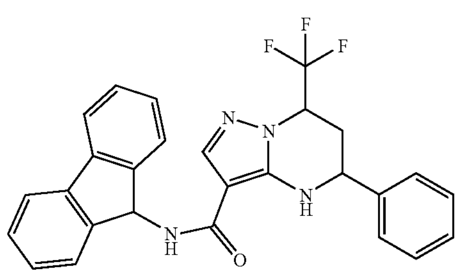 | N-(9H-fluoren-9-yl)-5-phenyl-7-(trifluoromethyl)-4,5,6,7-tetrahydropyrazolo[1,5-a]pyrimidine-3-carboxamide | IR(KBr) 3297, 3097, 3042, 1624, 1595, 1534 cm$^{-1}$ |
| 278 | 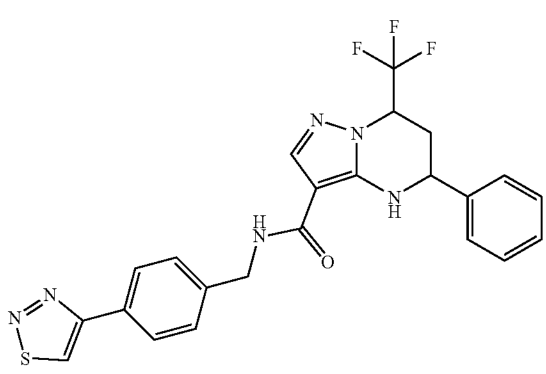 | 5-phenyl-N-(4-(1,2,3-thiadiazol-4-yl)benzyl)-7-(trifluoromethyl)-4,5,6,7-tetrahydropyrazolo[1,5-a]pyrimidine-3-carboxamide | mp 205-206° C. |

TABLE 4-continued

| Example | Structure | Name | Physiological Data |
|---|---|---|---|
| 279 | 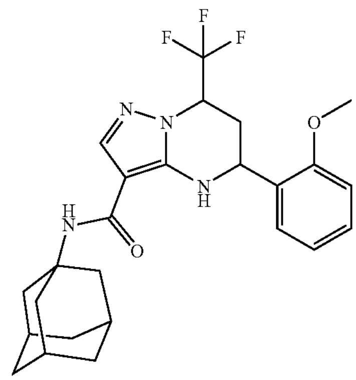 | N-(1-adamantyl)-5-(2-methoxyphenyl)-7-(trifluoromethyl)-4,5,6,7-tetrahydropyrazolo[1,5-a]pyrimidine-3-carboxamide | Mp 238-239° C. |
| 280 | 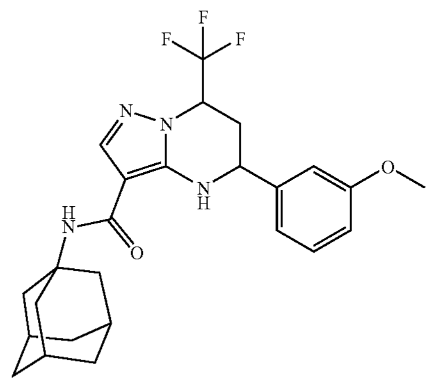 | N-(1-adamantyl)-5-(3-methoxyphenyl)-7-(trifluoromethyl)-4,5,6,7-tetrahydropyrazolo[1,5-a]pyrimidine-3-carboxamide | Mp 211-212° C. |
| 281 | 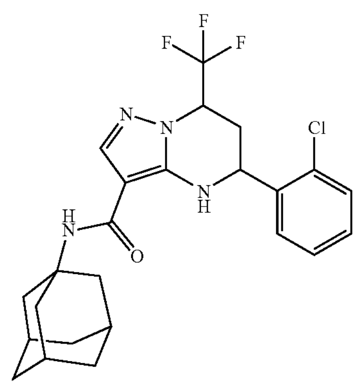 | N-(1-adamantyl)-5-(2-chlorophenyl)-7-(trifluoromethyl)-4,5,6,7-tetrahydropyrazolo[1,5-a]pyrimidine-3-carboxamide | Mp 256-257° C. |
| 282 | 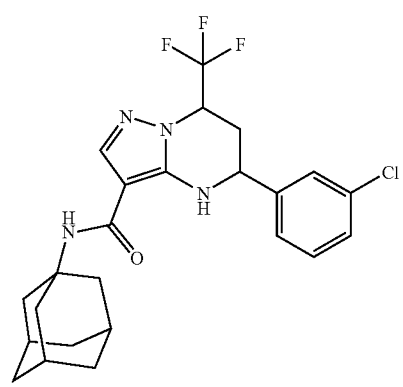 | N-(1-adamantyl)-5-(3-chlorophenyl)-7-(trifluoromethyl)-4,5,6,7-tetrahydropyrazolo[1,5-a]pyrimidine-3-carboxamide | Mp 246-247° C. |

TABLE 4-continued

| Example | Structure | Name | Physiological Data |
|---|---|---|---|
| 283 | 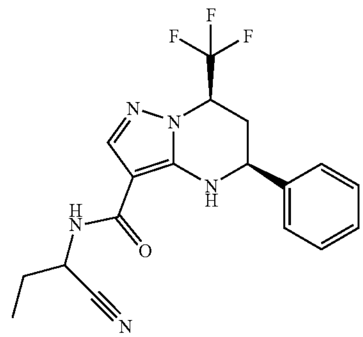 | N-(1-cyanopropyl)-5-phenyl-7-(trifluoromethyl)-4,5,6,7-tetrahydropyrazolo[1,5-a]pyrimidine-3-carboxamide | less polar mp 180-181° C. |
| 284 | 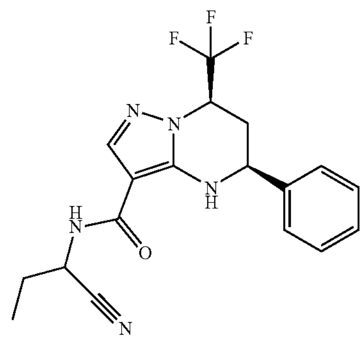 | N-(1-cyanopropyl)-5-phenyl-7-(trifluoromethyl)-4,5,6,7-tetrahydropyrazolo[1,5-a]pyrimidine-3-carboxamide | polar mp 201-202° C. |
| 285 | 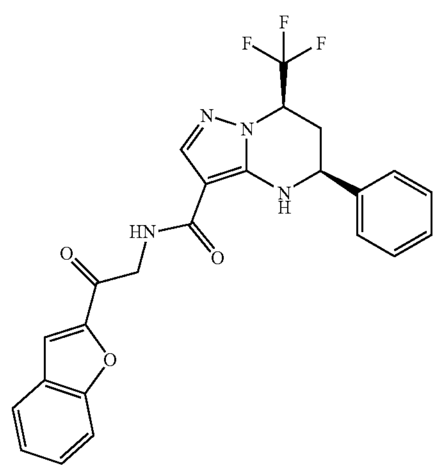 | N-(2-(1-benzofuran-2-yl)-2-oxoethyl)-5-phenyl-7-(trifluoromethyl)-4,5,6,7-tetrahydropyrazolo[1,5-a]pyrimidine-3-carboxamide | mp 244-245° C. |
| 286 | 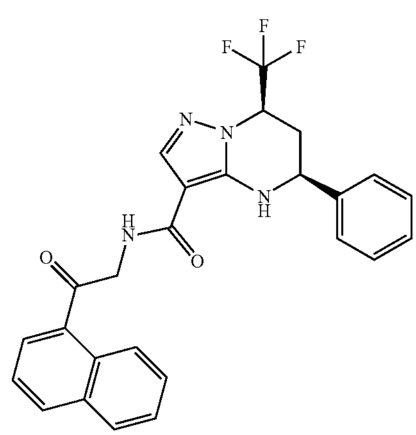 | N-(2-(1-naphthyl)-2-oxoethyl)-5-phenyl-7-(trifluoromethyl)-4,5,6,7-tetrahydropyrazolo[1,5-a]pyrimidine-3-carboxamide | mp 141-142° C. |

TABLE 4-continued

| Example | Structure | Name | Physiological Data |
|---|---|---|---|
| 287 | 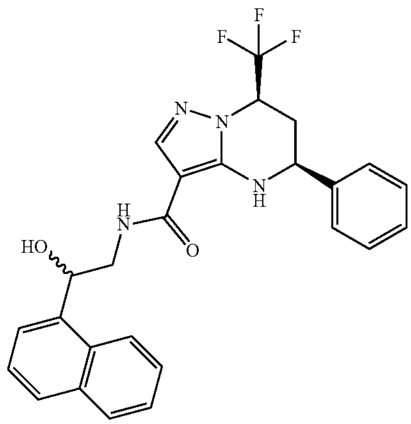 | N-(2-hydroxy-2-(1-naphthyl)ethyl)-5-phenyl-7-(trifluoromethyl)-4,5,6,7-tetrahydropyrazolo[1,5-a]pyrimidine-3-carboxamide | MS (ESI, m/z) 490 (M + H)+ |
| 288 | 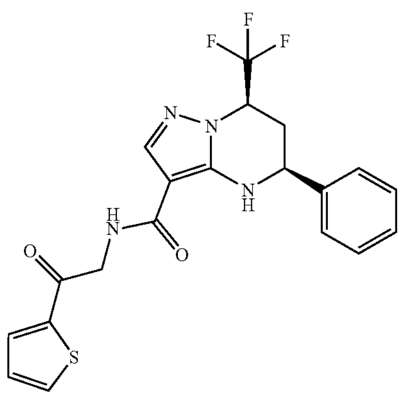 | N-(2-oxo-2-(2-thienyl)ethyl)-5-phenyl-7-(trilluoromethyl)-4,5,6,7-tetrahydropyrazolo[1,5-a]pyrimidine-3-carboxamide | mp 2191-220° C. |
| 289 | 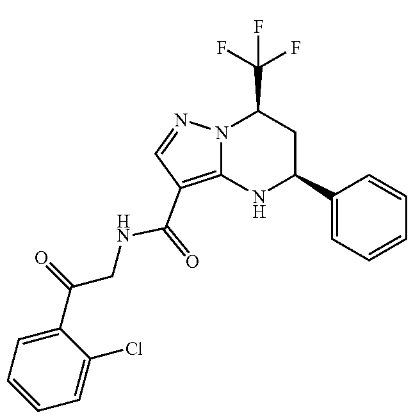 | N-(2-(2-chlorophenyl)-2-oxoethyl)-5-phenyl-7-(trifluoromethyl)-4,5,6,7-tetrahydropyrazolo[1,5-a]pyrimidine-3-carboxamide | mp 154-155° C. |

TABLE 4-continued

| Example | Structure | Name | Physiological Data |
|---|---|---|---|
| 290 | 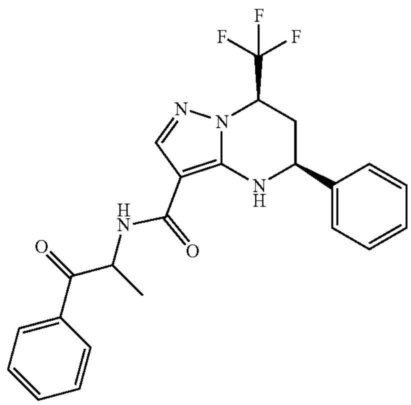 | N-(1-methyl-2-oxo-2-phenylethyl)-5-phenyl-7-(trifluoromethyl)-4,5,6,7-tetrahydropyrazolo[1,5-a]pyrimidine-3-carboxamide | mp 271-272° C. |
| 291 | 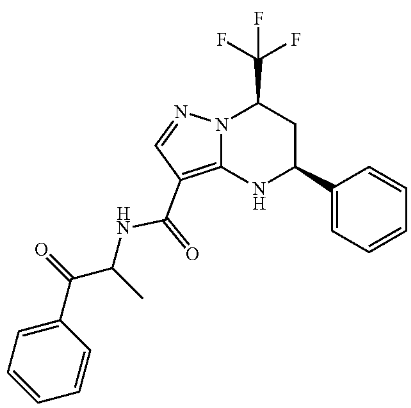 | N-(1-methyl-2-oxo-2-phenylethyl)-5-phenyl-7-(trifluoromethyl)-4,5,6,7-tetrahydropyrazolo[1,5-a]pyrimidine-3-carboxamide | mp 178-179° C. |
| 292 | 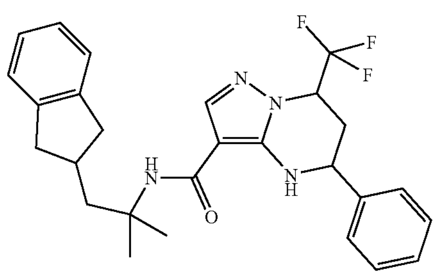 | N-(2-(2,3-dihydro-1H-inden-2-yl)-1,1-dimethylethyl-5-phenyl-7-(trifluoromethyl)-4,5,6,7-tetrahydropyrazolo[1,5-a]pyrimidine-3-carboxamide | mp 221-222° C. |
| 293 | 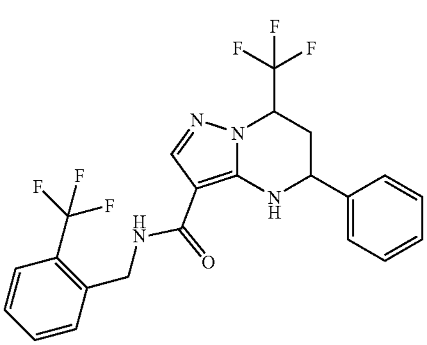 | 5-phenyl-7-(trifluoromethyl)-N-(2-(trifluoromethyl)benzyl)-4,5,6,7-tetrahydropyrazolo[1,5-a]pyrimidine-3-carboxamide | MS (ESI, m/z) 469 (M + H)+ |

TABLE 4-continued

| Example | Structure | Name | Physiological Data |
|---|---|---|---|
| 294 | 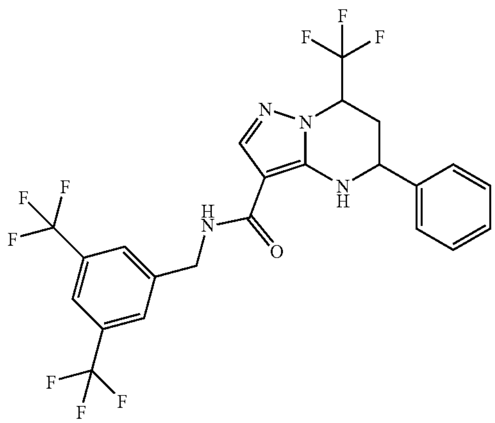 | N-(3,5-bis(trifluoromethyl)benzyl)-5-phenyl-7-(trifluoromethyl)-4,5,6,7-tetrahydropyrazolo[1,5-a]pyrimidine-3-carboxamide | MS (ESI, m/z) 537 (M + H)+ |
| 295 | 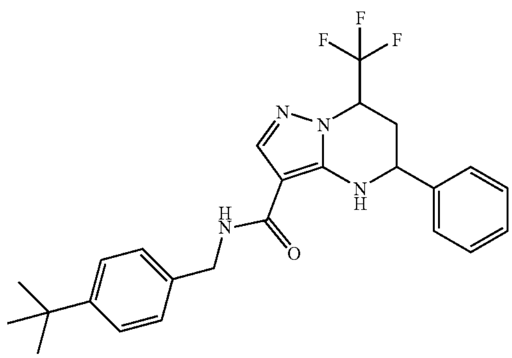 | N-(4-tert-butylbenzyl)-5-phenyl-7-(trifluoromethyl)-4,5,6,7-tetrahydropyrazolo[1,5-a]pyrimidine-3-carboxamide | MS (ESI, m/z) 457 (M + H)+ |
| 296 | 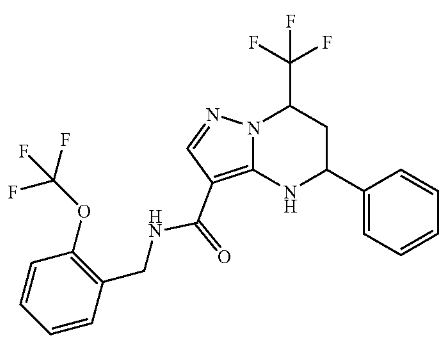 | 5-phenyl-N-(2-(trifluoromethoxy)benzyl)-7-(trifluoromethyl)-4,5,6,7-tetrahydropyrazolo[1,5-a]pyrimidine-3-carboxamide | MS (ESI, m/z) 485 (M + H)+ |
| 297 | 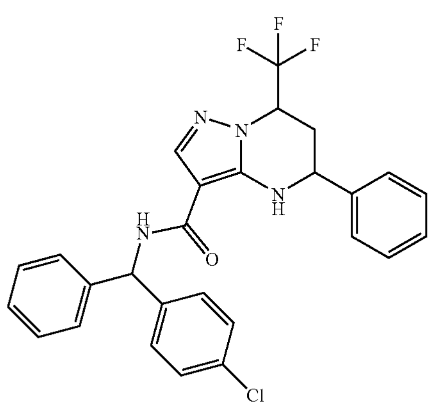 | N-((4-chlorophenyl)(phenyl)methyl)-5-phenyl-7-(trifluoromethyl)-4,5,6,7-tetrahydropyrazolo[1,5-a]pyrimidine-3-carboxamide | MS (ESI, m/z) 511 (M + H)+ |

TABLE 4-continued

| Example | Structure | Name | Physiological Data |
|---|---|---|---|
| 298 | 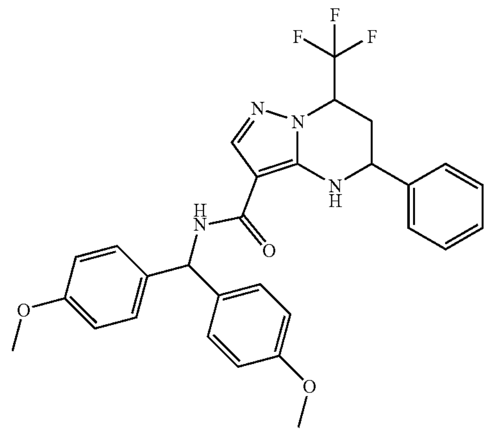 | N-(bis(4-methoxyphenyl)methyl)-5-phenyl-7-(trifluoromethyl)-4,5,6,7-tetrahydropyrazolo[1,5-a]pyrimidine-3-carboxamide | MS (ESI, m/z) 537 (M + H)+ |
| 299 | 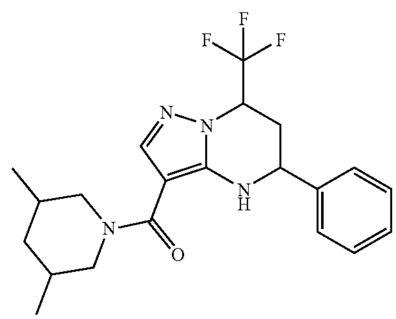 | 3-((3,5-dimethyl-1-piperidinyl)carbonyl)-5-phenyl-7-(trifluoromethyl)-4,5,6,7-tetrahydropyrazolo[1,5-a]pyrimidine | MS (ESI, m/z) 407 (M + H)+ |
| 300 | 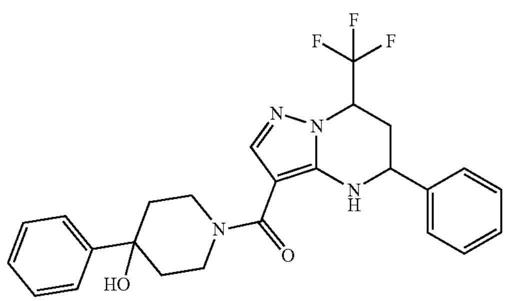 | 4-phenyl-1-((5-phenyl-7-(trifluoromethyl)-4,5,6,7-tetrahydropyrazolo[1,5-a]pyrimidin-3-yl)carbonyl)-4-piperidinol | MS (ESI, m/z) 471 (M + H)+ |
| 301 | 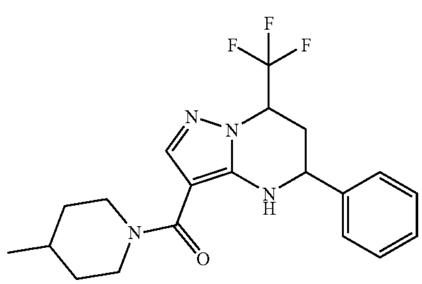 | 3-((4-methyl-1-piperidinyl)carbonyl)-5-phenyl-7-(trifluoromethyl)-4,5,6,7-tetrahydropyrazolo[1,5-a]pyrimidine | MS (ESI, m/z) 393 (M + H)+ |

TABLE 4-continued

| Example | Structure | Name | Physiological Data |
|---|---|---|---|
| 302 | 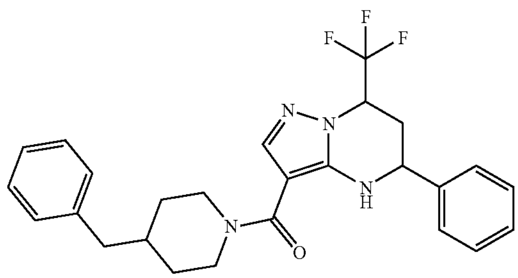 | 3-((4-benzyl-1-piperidinyl)carbonyl)-5-phenyl-7-(trifluoromethyl)-4,5,6,7-tetrahydropyrazolo[1,5-a]pyrimidine | MS (ESI, m/z) 469 (M + H)+ |
| 303 | 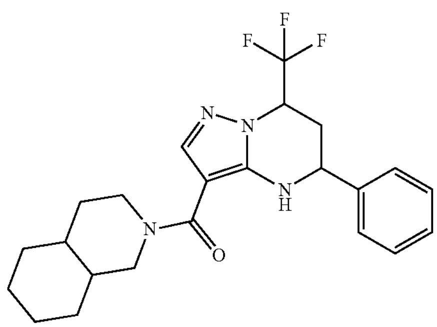 | 2-((5-phenyl-7-(trifluoromethyl)-4,5,6,7-tetrahydropyrazolo[1,5-a]pyrimidin-3-yl)carbonyl) decahydroisoquinoline | MS (ESI, m/z) 433 (M + H)+ |
| 304 | 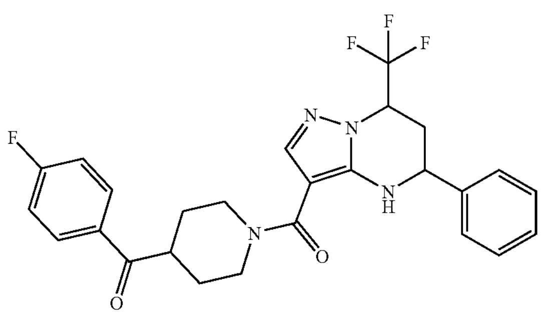 | (4-fluorophenyl)(1-((5-phenyl-7-(trifluoromethyl)-4,5,6,7-tetrahydropyrazolo[1,5-a]pyrimidin-3-yl)carbonyl)-4-piperidinyl)methanone | MS (ESI, m/z) 501 (M + H)+ |
| 305 | 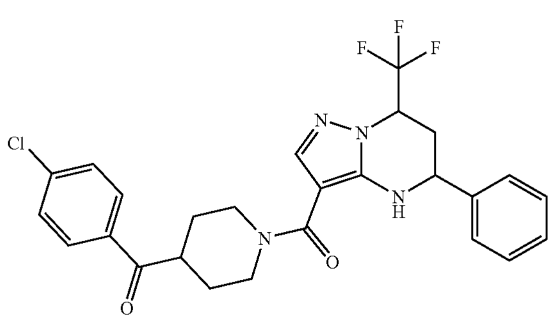 | (4-chlorophenyl)(1-((5-phenyl-7-(trifluoromethyl)-4,5,6,7-tetrahydropyrazolo[1,5-a]pyrimidin-3-yl)carbonyl)-4-piperidinyl)methanone | MS (ESI, m/z) 517 (M + H)+ |

TABLE 4-continued

| Example | Structure | Name | Physiological Data |
|---|---|---|---|
| 306 | 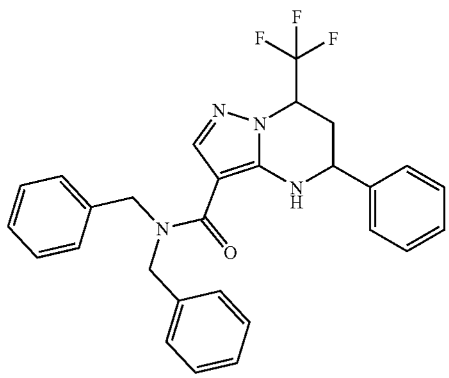 | N,N-dibenzyl-5-phenyl-7-(trifluoromethyl)-4,5,6,7-tetrahydropyrazolo[1,5-a]pyrimidine-3-carboxamide | MS (ESI, m/z) 491 (M + H)+ |
| 307 | 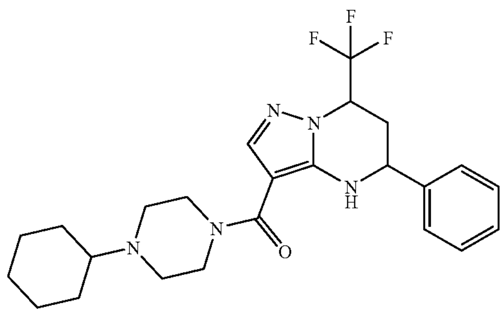 | 3-((4-cyclohexyl-1-piperazinyl)carbonyl)-5-phenyl-7-(trifluoromethyl)-4,5,6,7-tetrahydropyrazolo[1,5-a]pyrimidine | MS (ESI, m/z) 462 (M + H)+ |
| 308 | 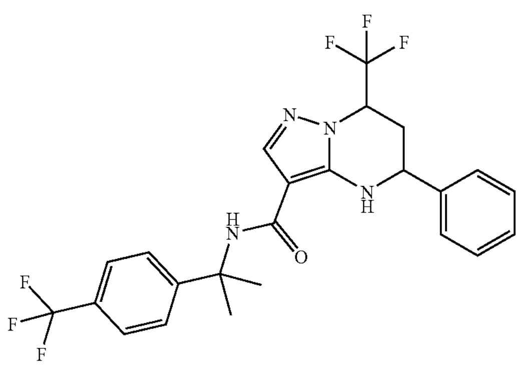 | N-(1-methyl-1-(4-(trifluoromethyl)phenyl)ethyl)-5-phenyl-7-(trifluoromethyl)-4,5,6,7-tetrahydropyrazolo[1,5-a]pyrimidine-3-carboxamide | MS (ESI, m/z) 497 (M + H)+ |
| 309 | 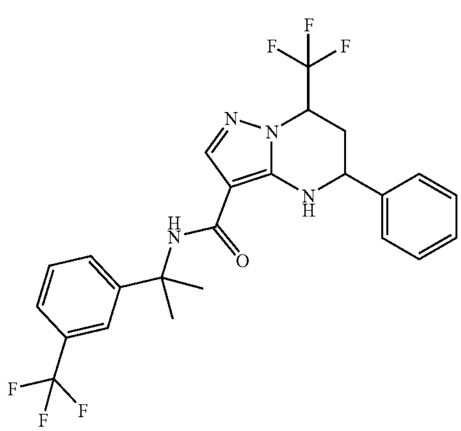 | N-(1-methyl-1-(3-(trifluoromethyl)phenyl)ethyl)-5-phenyl-7-(trifluoromethyl)-4,5,6,7-tetrahydropyrazolo[1,5-a]pyrimidine-3-carboxamide | MS (ESI, m/z) 497 (M + H)+ |

TABLE 4-continued

| Example | Structure | Name | Physiological Data |
|---|---|---|---|
| 310 | 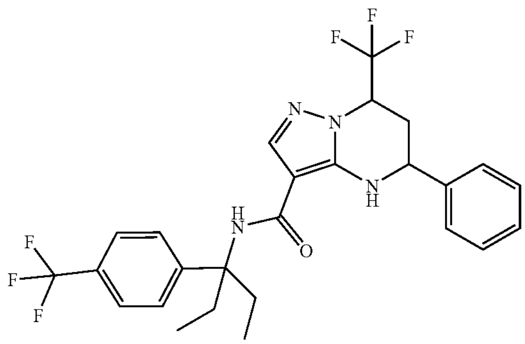 | N-(1-ethyl-1-(4-(trifluoromethyl)phenyl)propyl)-5-phenyl-7-(trifluoromethyl)-4,5,6,7-tetrahydropyrazolo[1,5-a]pyrimidine-3-carboxamide | MS (ESI, m/z) 525 (M + H)+ |
| 311 | 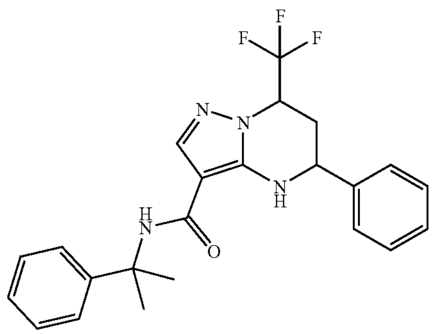 | N-(1-methyl-1-phenylethyl)-5-phenyl-7-(trifluoromethyl)-4,5,6,7-tetrahydropyrazolo[1,5-a]pyrimidine-3-carboxamide | MS (ESI, m/z) 429 (M + H)+ |
| 312 | 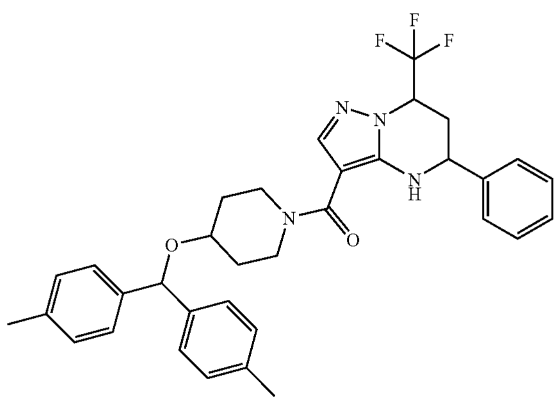 | 3-((4-(bis(4-methylphenyl)methoxy)-1-piperidinyl)carbonyl)-5-phenyl-7-(trifluoromethyl)-4,5,6,7-tetrahydropyrazolo[1,5-a]pyrimidine | MS (ESI, m/z) 589 (M + H)+ |
| 313 | 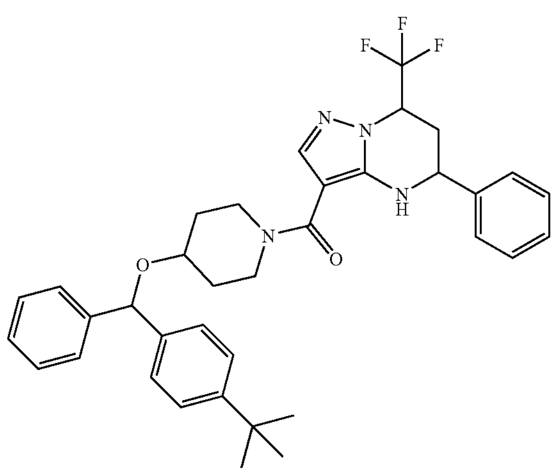 | 3-((4-((4-tert-butylphenyl)(phenyl)methoxy)-1-piperidinyl)carbonyl)-5-phenyl-7-(trifluoromethyl)-4,5,6,7-tetrahydropyrazolo[1,5-a]pyrimidine | MS (ESI, m/z) 617 (M + H)+ |

TABLE 4-continued

| Example | Structure | Name | Physiological Data |
|---------|-----------|------|--------------------|
| 314 | 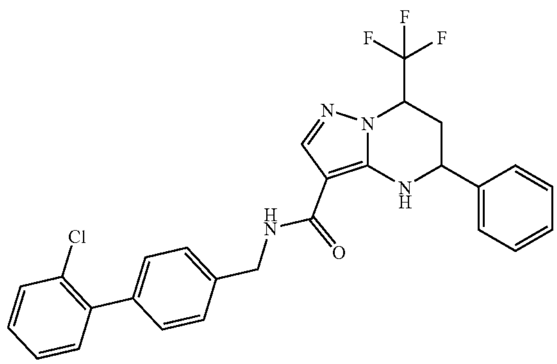 | N-((2'-chloro-1,1'-biphenyl-4-yl)methyl)-5-phenyl-7-(trifluoromethyl)-4,5,6,7-tetrahydropyrazolo[1,5-a]pyrimidine-3-carboxamide | MS (ESI, m/z) 511 (M + H)+ |
| 315 | 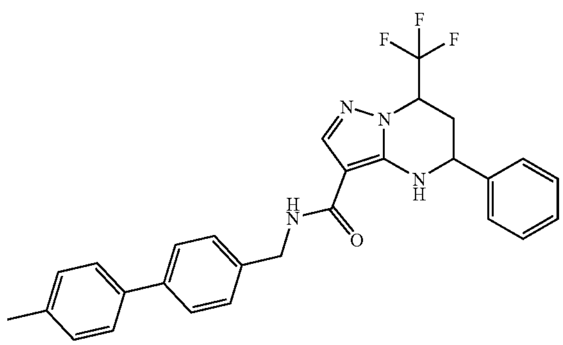 | N-((4'-methyl-1,1'-biphenyl-4-yl)methyl)-5-phenyl-7-(trifluoromethyl)-4,5,6,7-tetrahydropyrazolo[1,5-a]pyrimidine-3-carboxamide | MS (ESI, m/z) 491 (M + H)+ |
| 316 | 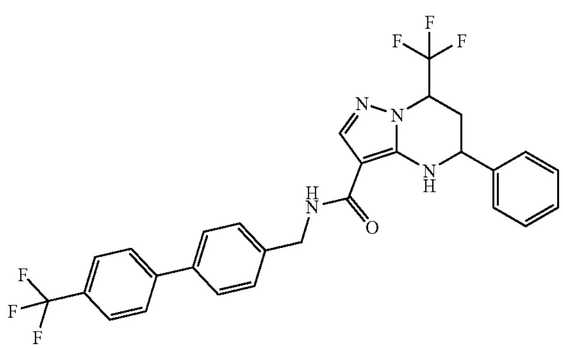 | 5-phenyl-7-(trifluoromethyl)-N-((4'-(trifluoromethyl)-1,1'-biphenyl-4-yl)methyl)-4,5,6,7-tetrahydropyrazolo[1,5-a]pyrimidine-3-carboxamide | MS (ESI, m/z) 545 (M + H)+ |
| 317 | 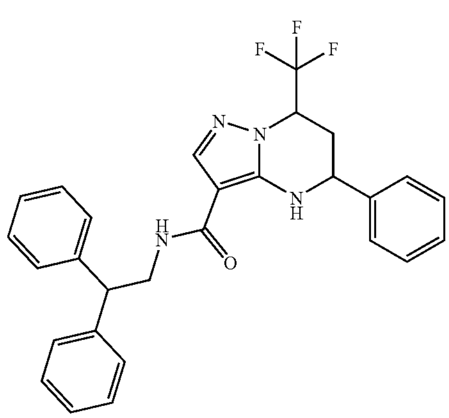 | N-(2,2-diphenylethyl)-5-phenyl-7-(trifluoromethyl)-4,5,6,7-tetrahydropyrazolo[1,5-a]pyrimidine-3-carboxamide | MS (ESI, m/z) 491 (M + H)+ |

TABLE 4-continued

| Example | Structure | Name | Physiological Data |
|---|---|---|---|
| 318 | 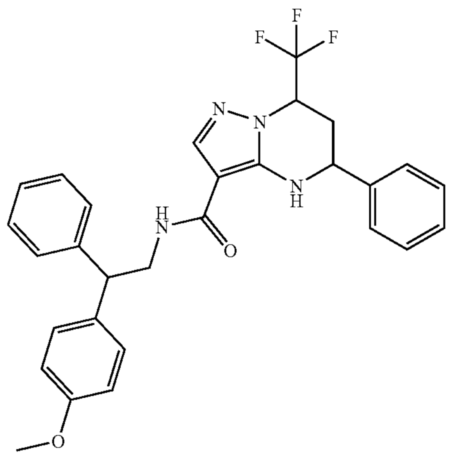 | N-(2-(4-methoxyphenyl)-2-phenylethyl)-5-phenyl-7-(trifluoromethyl)-4,5,6,7-tetrahydropyrazolo[1,5-a]pyrimidine-3-carboxamide | MS (ESI, m/z) 521 (M + H)+ |
| 319 | 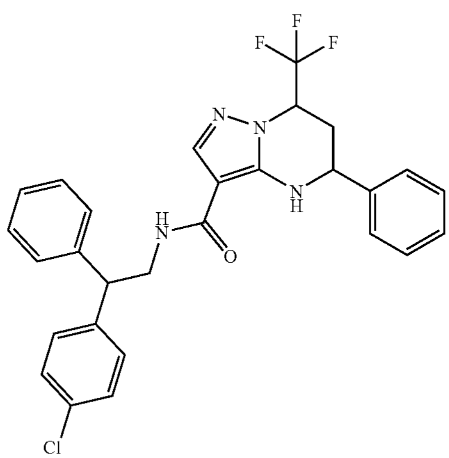 | N-(2-(4-chlorophenyl)-2-phenylethyl)-5-phenyl-7-(trifluoromethyl)-4,5,6,7-tetrahydropyrazolo[1,5-a]pyrimidine-3-carboxamide | MS (ESI, m/z) 525 (M + H)+ |
| 320 | 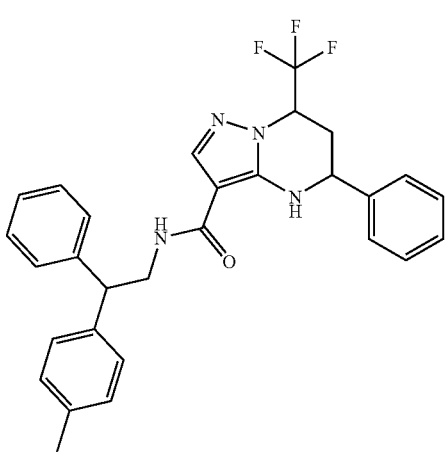 | N-(2-(4-methylphenyl)-2-phenylethyl)-5-phenyl-7-(trifluoromethyl)-4,5,6,7-tetrahydropyrazolo[1,5-a]pyrimidine-3-carboxamide | MS (ESI, m/z) 505 (M + H)+ |

TABLE 4-continued

| Example | Structure | Name | Physiological Data |
|---|---|---|---|
| 321 | 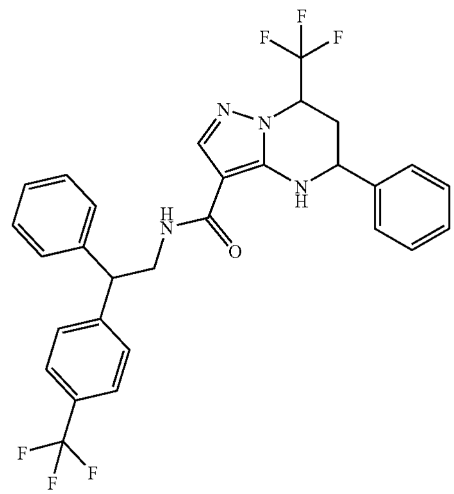 | 5-phenyl-N-(2-phenyl-2-(4-(trifluoromethyl)phenyl)ethyl)-7-(trifluoromethyl)-4,5,6,7-tetrahydropyrazolo[1,5-a]pyrimidine-3-carboxamide | MS (ESI, m/z) 559 (M + H)+ |
| 322 | 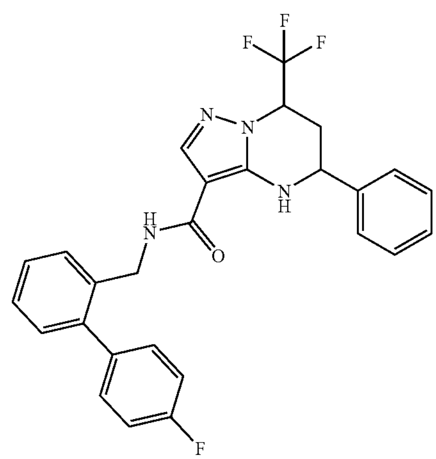 | N-((4'-fluoro-1,1'-biphenyl-2-yl)methyl)-5-phenyl-7-(trifluoromethyl)-4,5,6,7-tetrahydropyrazolo[1,5-a]pyrimidine-3-carboxamide | MS (ESI, m/z) 495 (M + H)+ |
| 323 | 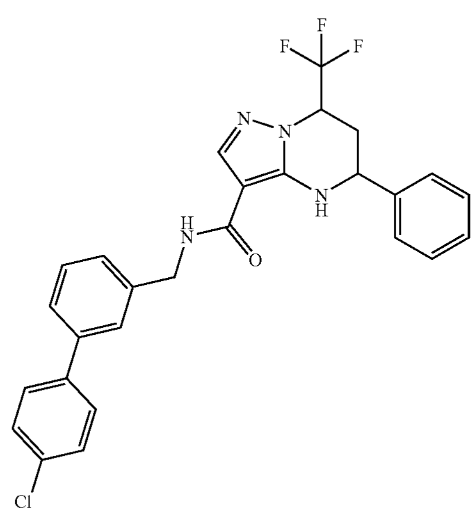 | N-((4'-chloro-1,1'-biphenyl-3-yl)methyl)-5-phenyl-7-(trifluoromethyl)-4,5,6,7-tetrahydropyrazolo[1,5-a]pyrimidine-3-carboxamide | MS (ESI, m/z) 511 (M + H)+ |

TABLE 4-continued

| Example | Structure | Name | Physiological Data |
|---|---|---|---|
| 324 | 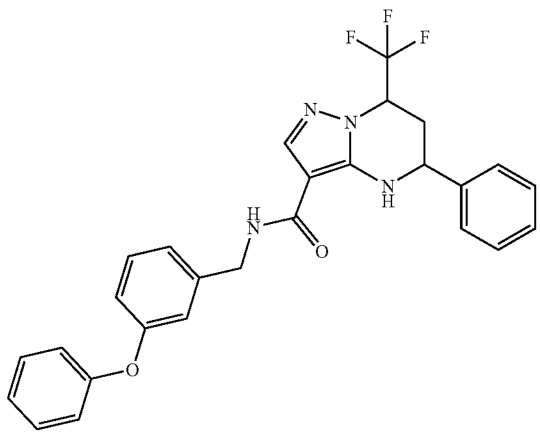 | N-(3-phenoxybenzyl)-5-phenyl-7-(trifluoromethyl)-4,5,6,7-tetrahydropyrazolo[1,5-a]pyrimidine-3-carboxamide | MS (ESI, m/z) 493 (M + H)+ |
| 325 | 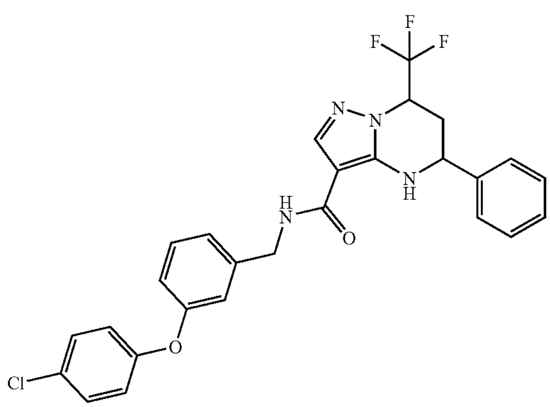 | N-(3-(4-chlorophenoxy)benzyl)-5-phenyl-7-(trifluoromethyl)-4,5,6,7-tetrahydropyrazolo[1,5-a]pyrimidine-3-carboxamide | MS (ESI, m/z) 527 (M + H)+ |
| 326 | 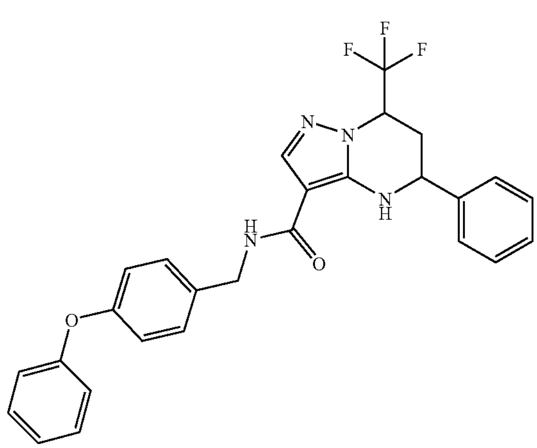 | N-(4-phenoxybenzyl)-5-phenyl-7-(trifluoromethyl)-4,5,6,7-tetrahydropyrazolo[1,5-a]pyrimidine-3-carboxamide | MS (ESI, m/z) 493 (M + H)+ |

TABLE 4-continued

| Example | Structure | Name | Physiological Data |
|---------|-----------|------|--------------------|
| 327 | 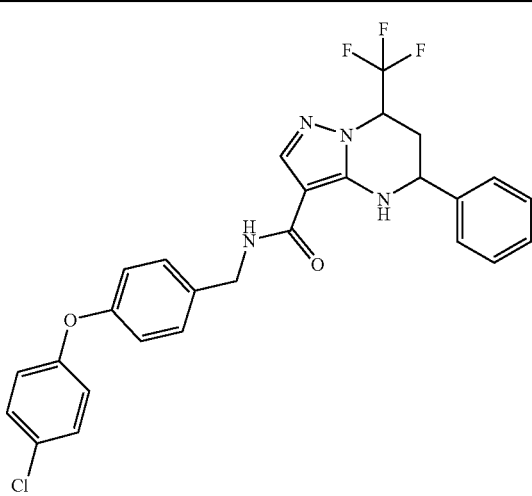 | N-(4-(4-chlorophenoxy)benzyl)-5-phenyl-7-(trifluoromethyl)-4,5,6,7-tetrahydropyrazolo[1,5-a]pyrimidine-3-carboxamide | MS (ESI, m/z) 527 (M + H)+ |
| 328 | 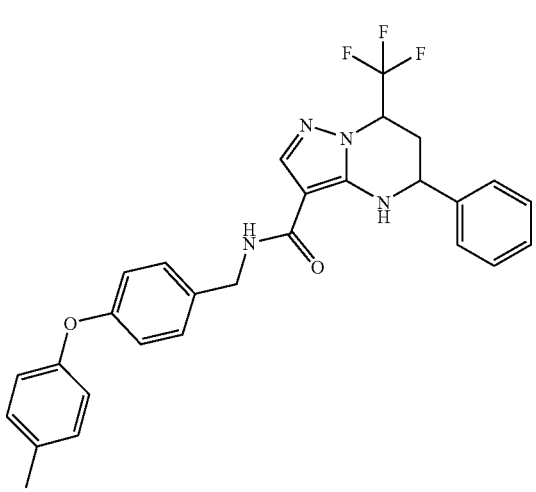 | N-(4-(4-methylphenoxy)benzyl)-5-phenyl-7-(trifluoromethyl)-4,5,6,7-tetrahydropyrazolo[1,5-a]pyrimidine-3-carboxamide | MS (ESI, m/z) 507 (M + H)+ |
| 329 | 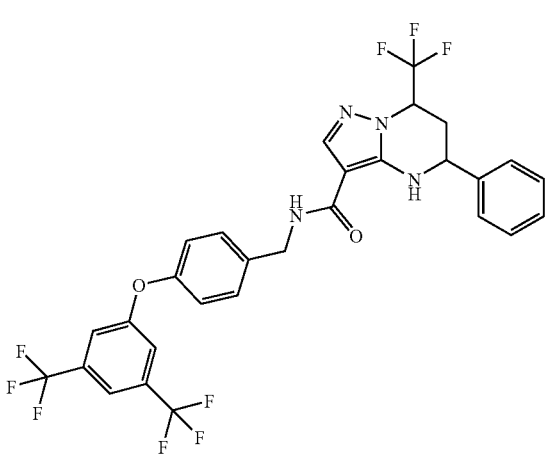 | N-(4-(3,5-bis(trifluoromethyl)phenoxy)benzyl)-5-phenyl-7-(trifluoromethyl)-4,5,6,7-tetrahydropyrazolo[1,5-a]pyrimidine-3-carboxamide | MS (ESI, m/z) 629 (M + H)+ |

TABLE 4-continued

| Example | Structure | Name | Physiological Data |
|---|---|---|---|
| 330 | 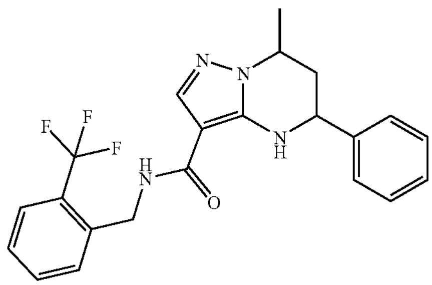 | 7-methyl-5-phenyl-N-(2-(trifluoromethyl)benzyl)-4,5,6,7-tetrahydropyrazolo[1,5-a]pyrimidine-3-carboxamide | MS (ESI, m/z) 415 (M + H)+ |
| 331 | 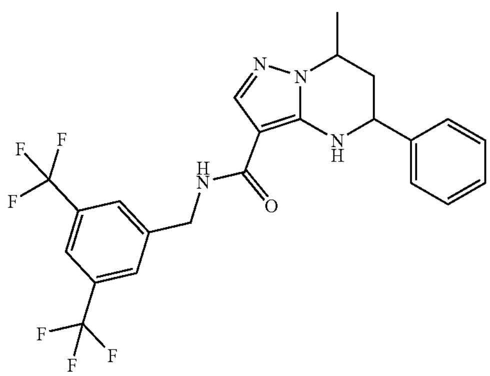 | N-(3,5-bis(trifluoromethyl)benzyl)-7-methyl-5-phenyl-4,5,6,7-tetrahydropyrazolo[1,5-a]pyrimidine-3-carboxamide | MS (ESI, m/z) 483 (M + H)+ |
| 332 | 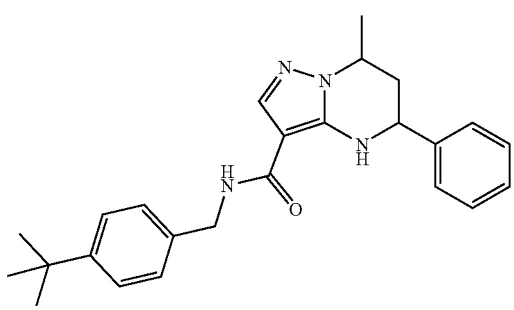 | N-(4-tert-butylbenzyl)-7-methyl-5-phenyl-4,5,6,7-tetrahydropyrazolo[1,5-a]pyrimidine-3-carboxamide | MS (ESI, m/z) 403 (M + H)+ |
| 333 | 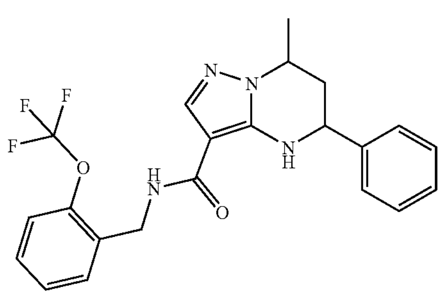 | 7-methyl-5-phenyl-N-(2-(trifluoromethoxy)benzyl)-4,5,6,7-tetrahydropyrazolo[1,5-a]pyrimidine-3-carboxamide | MS (ESI, m/z) 431 (M + H)+ |

TABLE 4-continued

| Example | Name | Physiological Data |
|---|---|---|
| 334 | N-((4-chlorophenyl)(phenyl)methyl)-7-methyl-5-phenyl-4,5,6,7-tetrahydropyrazolo[1,5-a]pyrimidine-3-carboxamide | MS (ESI, m/z) 457 (M + H)+ |
| 335 | N-(bis(4-methoxyphenyl)methyl)-7-methyl-5-phenyl-4,5,6,7-tetrahydropyrazolo[1,5-a]pyrimidine-3-carboxamide | MS (ESI, m/z) 483 (M + H)+ |
| 336 | 3-((3,5-dimethyl-1-piperidinyl)carbonyl)-7-methyl-5-phenyl-4,5,6,7-tetrahydropyrazolo[1,5-a]pyrimidine | MS (ESI, m/z) 353 (M + H)+ |
| 337 | 1-((7-methyl-5-phenyl-4,5,6,7-tetrahydropyrazolo[1,5-a]pyrimidin-3-yl)carbonyl)-4-phenyl-4-piperidinol | MS (ESI, m/z) 417 (M + H)+ |
| 338 | 7-methyl-3-((4-methyl-1-piperidinyl)carbonyl)-5-phenyl-4,5,6,7-tetrahydropyrazolo[1,5-a]pyrimidine | MS (ESI, m/z) 339 (M + H)+ |

TABLE 4-continued

| Example | Structure | Name | Physiological Data |
|---|---|---|---|
| 339 | 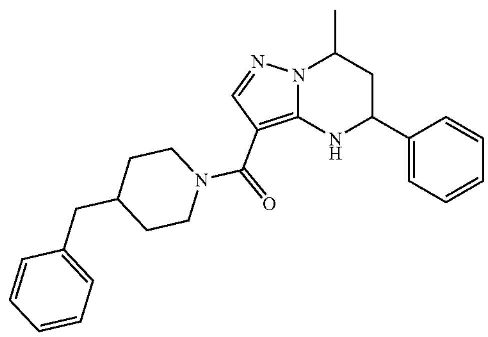 | 3-((4-benzyl-1-piperidinyl)carbonyl)-7-methyl-5-phenyl-4,5,6,7-tetrahydropyrazolo[1,5-a]pyrimidine | MS (ESI, m/z) 415 (M + H)+ |
| 340 | 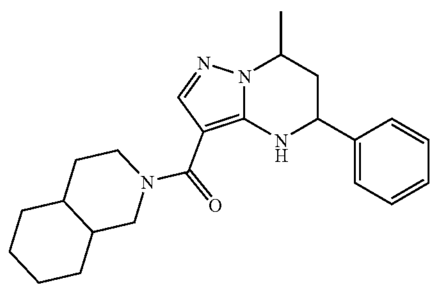 | 2-((7-methyl-5-phenyl-4,5,6,7-tetrahydropyrazolo[1,5-a[pyrimidine-3-yl)carbonyl) decahydroisoquinoline | MS (ESI, m/z) 379 (M + H)+ |
| 341 | 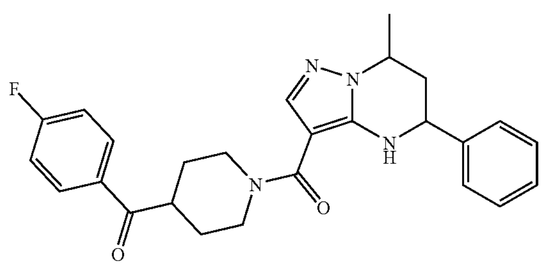 | (4-fluorophenyl)(1-((7-methyl-5-phenyl-4,5,6,7-tetrahydropyrazolo[1,5-a]pyrimidin-3-yl)carbonyl)-4-piperidinyl)methanone | MS (ESI, m/z) 447 (M + H)+ |
| 342 | 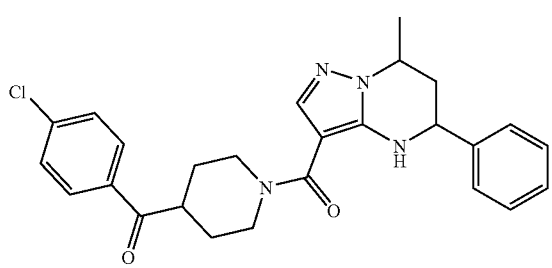 | (4-chlorophenyl)(1-((7-methyl-5-phenyl-4,5,6,7-tetrahydropyrazolo[1,5-a]pyrimidin-3-yl)carbonyl)-4-piperidinyl)methanone | MS (ESI, m/z) 463 (M + H)+ |
| 343 | 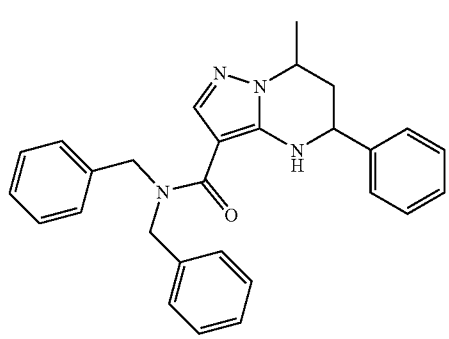 | N,N-dibenzyl-7-methyl-5-phenyl-4,5,6,7-tetrahydropyrazolo[1,5-a]pyrimidine-3-carboxamide | MS (ESI, m/z) 437 (M + H)+ |

TABLE 4-continued

| Example | Structure | Name | Physiological Data |
|---|---|---|---|
| 344 | 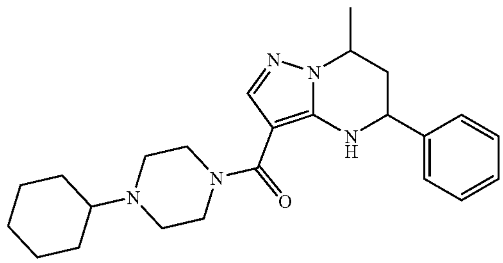 | 3-((4-cyclohexyl-1-piperazinyl)carbonyl)-7-methyl-5-phenyl-4,5,6,7-tetrahydropyrazolo[1,5-a]pyrimidine | MS (ESI, m/z) 408 (M + H)+ |
| 345 | 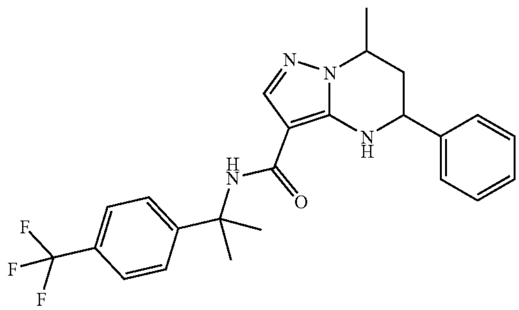 | 7-methyl-N-(1-methyl-1-(4-(trifluoromethyl)phenyl)ethyl)-5-phenyl-4,5,6,7-tetrahydropyrazolo[1,5-a]pyrimidine-3-carboxamide | MS (ESI, m/z) 443 (M + H)+ |
| 346 | 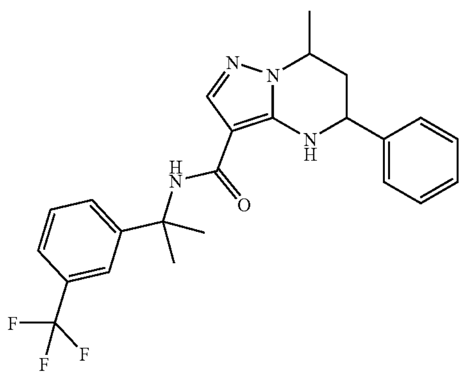 | 7-methyl-N-(1-methyl-1-(3-(trifluoromethyl)phenyl)ethyl)-5-phenyl-4,5,6,7-tetrahydropyrazolo[1,5-a]pyrimidine-3-carboxamide | MS (ESI, m/z) 443 (M + H)+ |
| 347 | 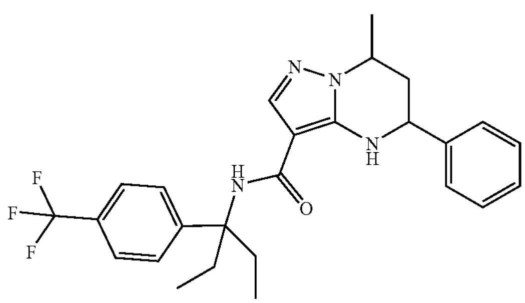 | N-(1-ethyl-1-(4-(trifluoromethyl)phenyl)propyl)-7-methyl-5-phenyl-4,5,6,7-tetrahydropyrazolo[1,5-a]pyrimidine-3-carboxamide | MS (ESI, m/z) 471 (M + H)+ |
| 348 | 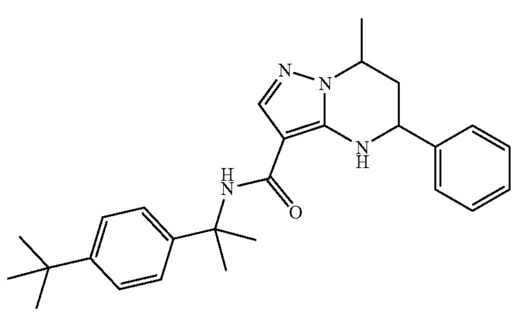 | N-(1-(4-tert-butylphenyl)-1-methylethyl)-7-methyl-5-phenyl-4,5,6,7-tetrahydropyrazolo[1,5-a]pyrimidine-3-carboxamide | MS (ESI, m/z) 431 (M + H)+ |

TABLE 4-continued

| Example | Structure | Name | Physiological Data |
|---|---|---|---|
| 349 | 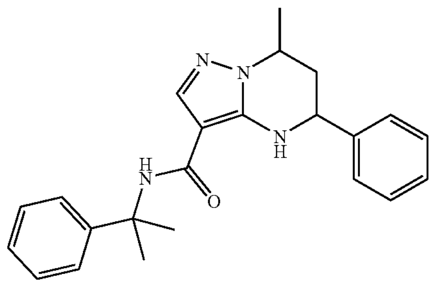 | 7-methyl-N-(1-methyl-1-phenylethyl)-5-phenyl-4,5,6,7-tetrahydropyrazolo[1,5-a]pyrimidine-3-carboxamide | MS (ESI, m/z) 375 (M + H)+ |
| 350 | 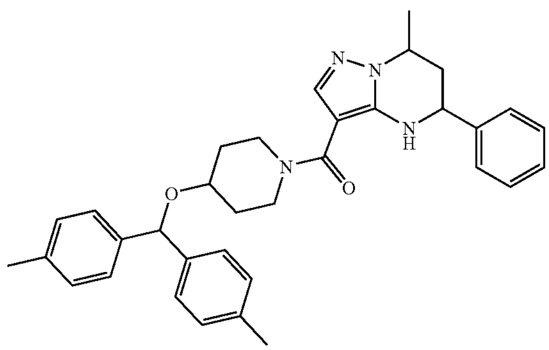 | 3-((4-(bis(4-methylphenyl)methoxy)-1-piperidinyl)carbonyl)-7-methyl-5-pheny-4,5,6,7-tetrahydropyrazolo[1,5-a]pyrimidine | MS (ESI, m/z) 535 (M + H)+ |
| 351 | 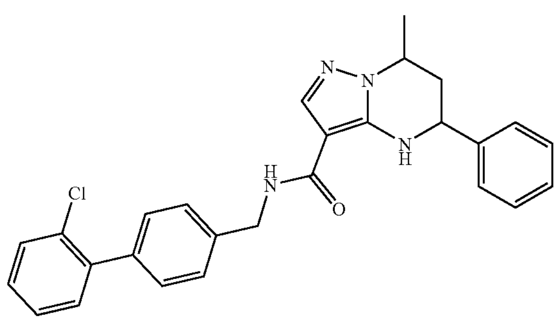 | N-((2'-chloro-1,1'-biphenyl-4-yl)methyl)-7-methyl-5-phenyl-4,5,6,7-tetrahydropyrazolo[1,5-a]pyrimidine-3-carboxamide | MS (ESI, m/z) 457 (M + H)+ |
| 352 | 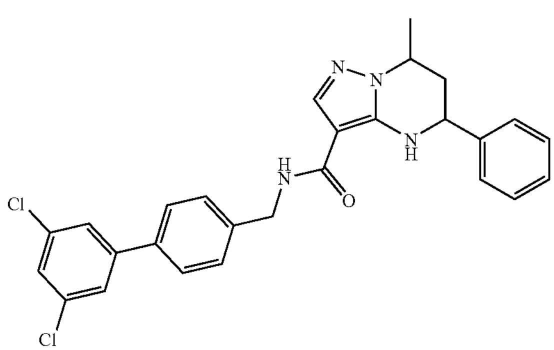 | N-((3',5'-dichloro-1,1'-biphenyl-4-yl)methyl)-7-methyl-5-phenyl-4,5,6,7-tetrahydropyrazolo[1,5-a]pyrimidine-3-carboxamide | MS (ESI, m/z) 492 (M + H)+ |

TABLE 4-continued

| Example | Name | Physiological Data |
|---|---|---|
| 353 | 7-methyl-N-((4'-methyl-1,1'-biphenyl-4-yl)methyl)-5-phenyl-4,5,6,7-tetrahydropyrazolo[1,5-a]pyrimidine-3-carboxamide | MS (ESI, m/z) 437 (M + H)+ |
| 354 | 7-methyl-5-phenyl-N-((4'-(trifluoromethyl)-1,1'-biphenyl-4-yl)methyl)-4,5,6,7-tetrahydropyrazolo[1,5-a]pyrimidine-3-carboxamide | MS (ESI, m/z) 491 (M + H)+ |
| 355 | N-(2-(4-methoxyphenyl)-2-phenylethyl)-7-methyl-5-phenyl-4,5,6,7-tetrahydropyrazolo[1,5-a]pyrimidine-3-carboxamide | MS (ESI, m/z) 467 (M + H)+ |
| 356 | N-(2-(4-chlorophenyl)-2-phenylethyl)-7-methyl-5-phenyl-4,5,6,7-tetrahydropyrazolo[1,5-a]pyrimidine-3-carboxamide | MS (ESI, m/z) 471 (M + H)+ |

TABLE 4-continued

| Example | Structure | Name | Physiological Data |
|---|---|---|---|
| 357 | 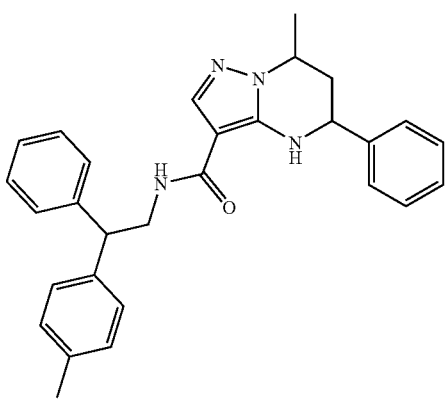 | 7-methyl-N-(2-(4-methylpheny-2-phenylethyl)-5-phenyl-4,5,6,7-tetrahydropyrazolo[1,5-a]pyrimidine-3-carboxamide | MS (ESI, m/z) 451 (M + H)+ |
| 358 | 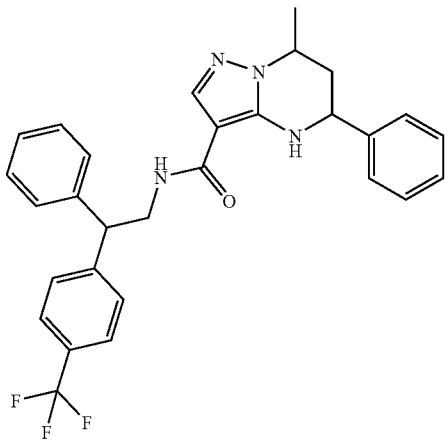 | 7-methyl-5-phenyl-N-(2-phenyl-2-(4-(trifluoromethyl)phenyl)ethyl)-4,5,6,7-tetrahydropyrazolo[1,5-a]pyrimidine-3-carboxamide | MS (ESI, m/z) 505 (M + H)+ |
| 359 | 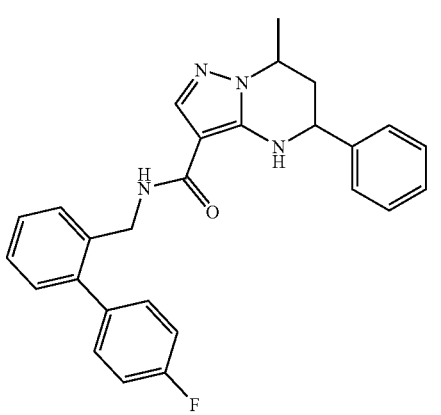 | N-((4'-fluoro-1,1-biphenyl-2-yl)methyl)-7-methyl-5-phenyl-4,5,6,7-tetrahydropyrazolo[1,5-a]pyrimidine-3-carboxamide | MS (ESI, m/z) 441 (M + H)+ |

TABLE 4-continued

| Example | Structure | Name | Physiological Data |
|---------|-----------|------|--------------------|
| 360 | 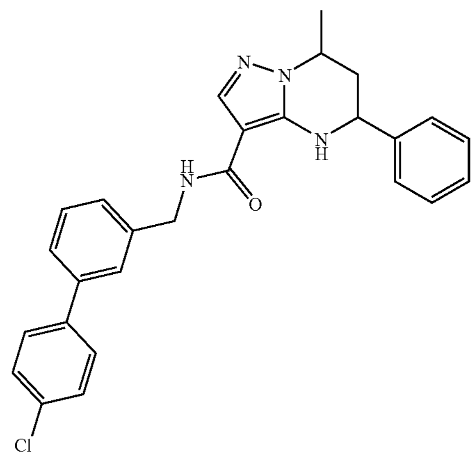 | N-((4'-chloro-1,1'-biphenyl-3-yl)methyl)-7-methyl-5-phenyl-4,5,6,7-tetrahydropyrazolo[1,5-a]pyrimidine-3-carboxamide | MS (ESI, m/z) 457 (M + H)+ |
| 361 | 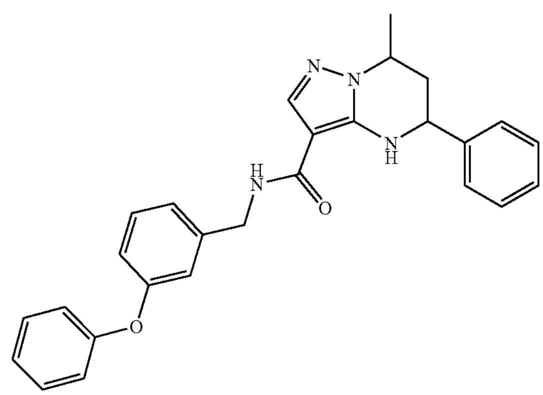 | 7-methyl-N-(3-phenoxybenzyl)-5-phenyl-4,5,6,7-tetrahydropyrazolo[1,5-a]pyrimidine-3-carboxamide | MS (ESI, m/z) 439 (M + H)+ |
| 362 | 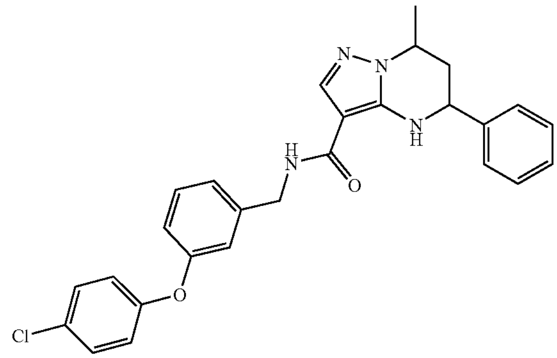 | N-(3-(4-chlorophenoxy)benzyl)-7-methyl-5-phenyl-4,5,6,7-tetrahydropyrazolo[1,5-a]pyrimidine-3-carboxamide | MS (ESI, m/z) 473 (M + H)+ |

TABLE 4-continued

| Example | Structure | Name | Physiological Data |
|---|---|---|---|
| 363 | 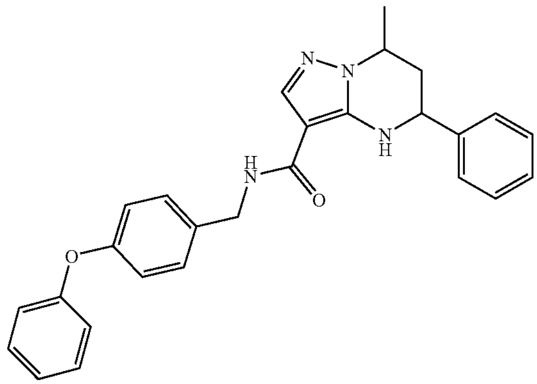 | 7-methyl-N-(4-phenoxybenzyl)-5-phenyl-4,5,6,7-tetrahydropyrazolo[1,5-a]pyrimidine-3-carboxamide | MS (ESI, m/z) 439 (M + H)+ |
| 364 | 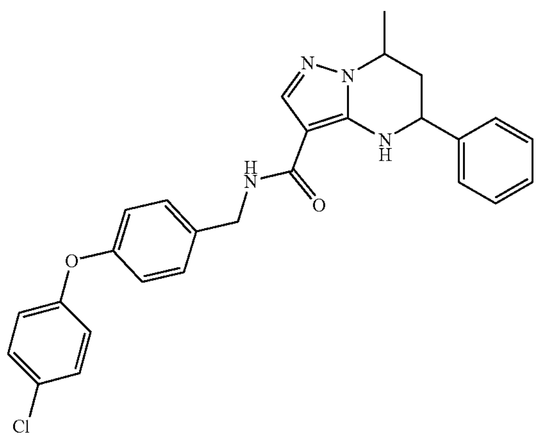 | N-(4-(4-chlorophenoxy)benzyl)-7-methyl-5-phenyl-4,5,6,7-tetrahydropyrazolo[1,5-a]pyrimidine-3-carboxamide | MS (ESI, m/z) 473 (M + H)+ |
| 365 | 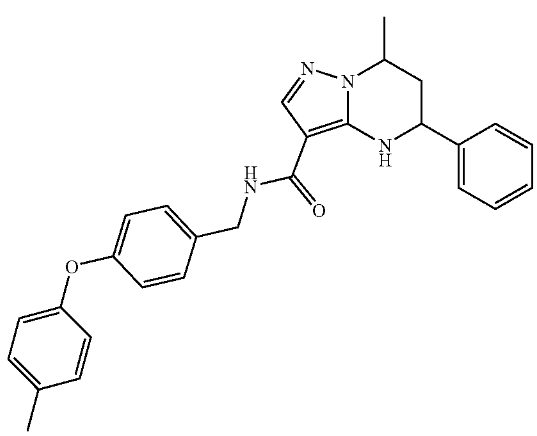 | 7-methyl-N-(4-(4-methylphenoxy)benzyl)-5-phenyl-4,5,6,7-tetrahydropyrazolo[1,5-a]pyrimidine-3-carboxamide | MS (ESI, m/z) 453 (M + H)+ |

TABLE 4-continued

| Example | Structure | Name | Physiological Data |
|---|---|---|---|
| 366 | 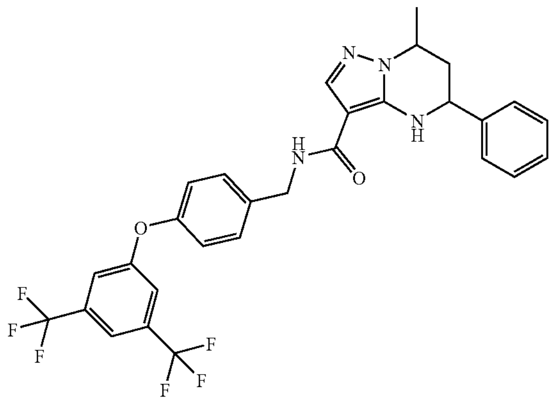 | N-(4-(3,5-bis(trifluoromethyl)phenoxy)benzyl)-7-methyl-5-phenyl-4,5,6,7-tetrahydropyrazolo[1,5-a]pyrimidine-3-carboxamide | MS (ESI, m/z) 575 (M + H)+ |
| 367 | 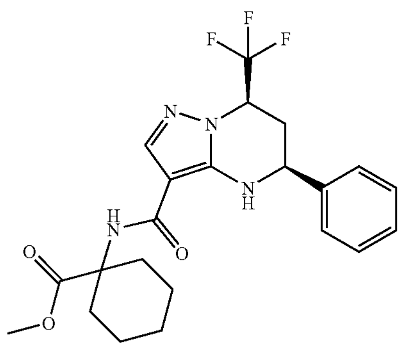 | methyl 1-(((5-phenyl-7-(trifluoromethyl)-4,5,6,7-tetrahydropyrazolo[1,5-a]pyrimidin-3-yl)carbonyl)amino)cyclohexane carboxylate | mp 213-214° C. |
| 368 | 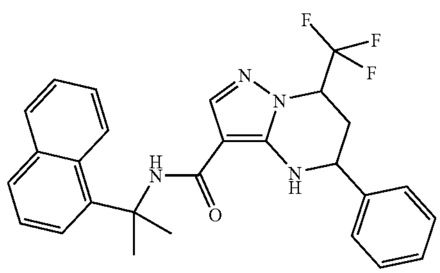 | N-(1-methyl-1-(1-naphthyl)ethyl)-5-phenyl-7-(trifluoromethyl)-4,5,6,7-tetrahydropyrazolo[1,5-a]pyrimidine-3-carboxamide | mp 221-222° C. |
| 369 | 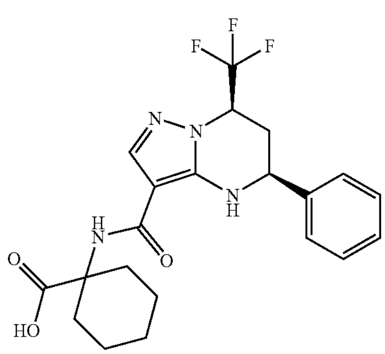 | 1-(((5-phenyl-7-(trifluoromethyl)-4,5,6,7-tetrahydropyrazolo[1,5-a]pyrimidin-3-yl)carbonyl)amino)cyclohexane carboxylic acid | mp 236-237° C. |

TABLE 4-continued

| Example | Structure | Name | Physiological Data |
|---|---|---|---|
| 370 | 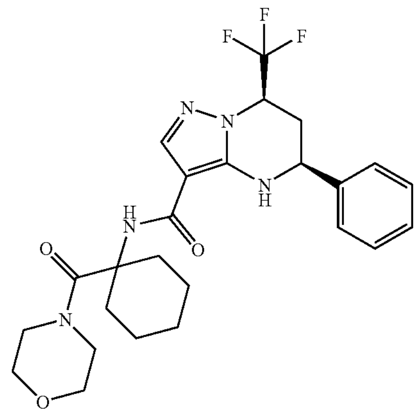 | N-(1-(4-morpholinylcarbonyl)cyclohexyl)-5-phenyl-7-(trifluoromethyl)-4,5,6,7-tetrahydropyrazolo[1,5-a]pyrimidine-3-carboxamide | mp 290-291° C. |
| 371 | 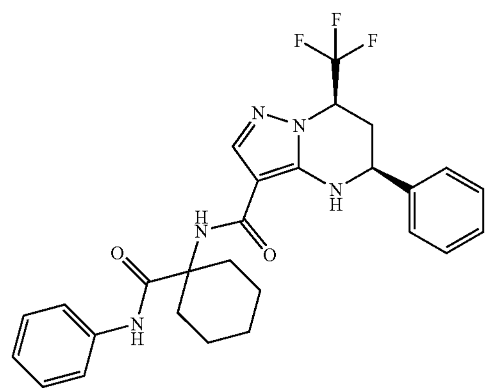 | N-(1-anilinocarbonylcyclohexyl)-5-phenyl-7-(trifluoromethyl)-4,5,6,7-tetrahydropyrazolo[1,5-a]pyrimidine-3-carboxamide | mp 262-263° C. |
| 372 | 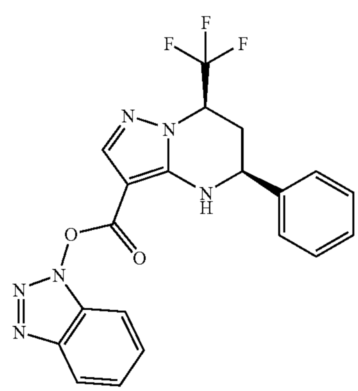 | 1-(((5-phenyl-7-(trifluoromethyl)-4,5,6,7-tetrahydropyrazolo[1,5-a]pyrimidin-3-yl)carbonyl)oxy)-1H-1,2,3-benzotriazole | mp 216-217° C. |
| 373 | 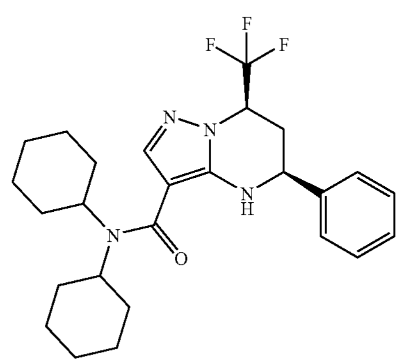 | N,N-dicyclohexyl-5-phenyl-7-(trifluoromethyl)-4,5,6,7-tetrahydropyrazolo[1,5-a]pyrimidine-3-carboxamide | mp 243-244° C. |

TABLE 4-continued

| Example | Structure | Name | Physiological Data |
|---|---|---|---|
| 374 | 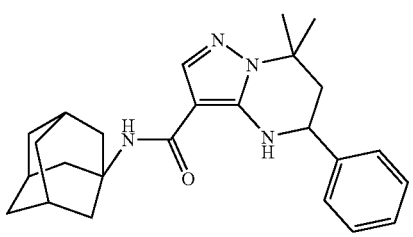 | N-(1-adamantyl)-7,7-dimethyl-5-phenyl-4,5,6,7-tetrahydropyrazolo[1,5-a]pyrimidine-3-carboxamide | mp 235-236° C. |
| 375 | 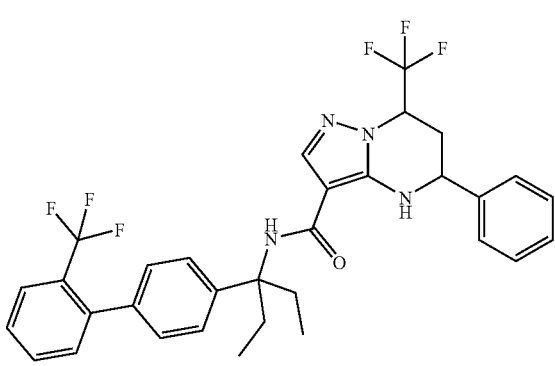 | N-(1-ethyl-1-(2'-(trifluoromethyl)-1,1'-biphenyl-4-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |
| 376 | 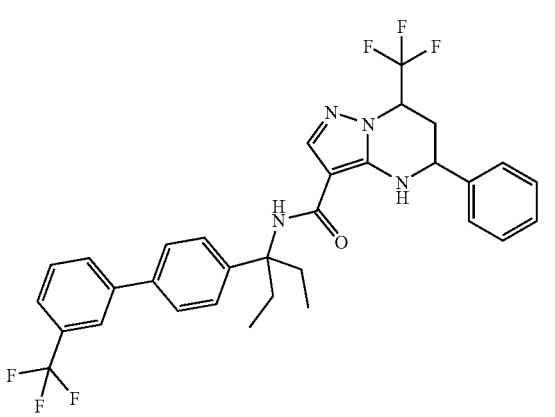 | N-(1-ethyl-1-(3'-(trifluoromethyl)-1,1'-biphenyl-4-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |
| 377 | 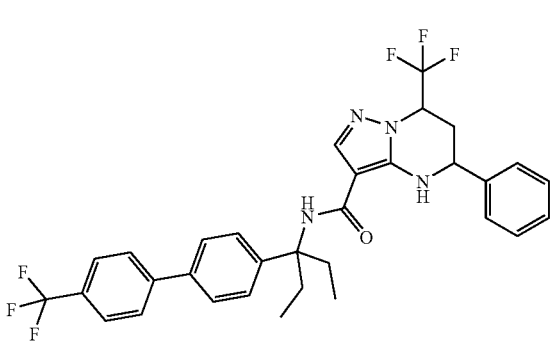 | N-(1-ethyl-1-(4'-(trifluoromethyl)-1,1'-biphenyl-4-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |

TABLE 4-continued

| Example | Structure | Name | Physiological Data |
|---|---|---|---|
| 378 | 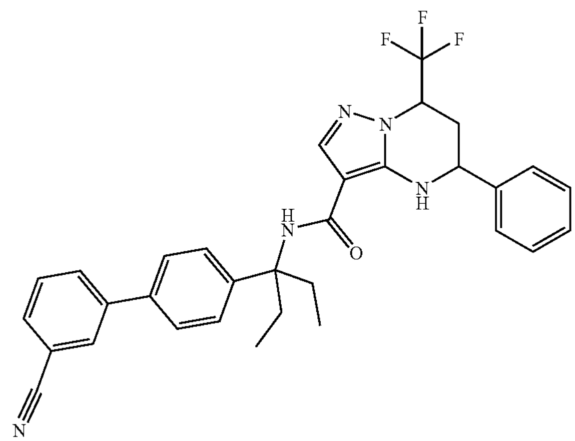 | N-(1-(3'-cyano-1,1'-biphenyl-4-yl)-1-ethylpropyl)-5-phenyl-7-(trifluoromethyl)-4,5,6,7-tetrahydropyrazolo[1,5-a]pyrimidine-3-caiboxamide | MS (ESI, m/z) 558 (M + H)+ |
| 379 | 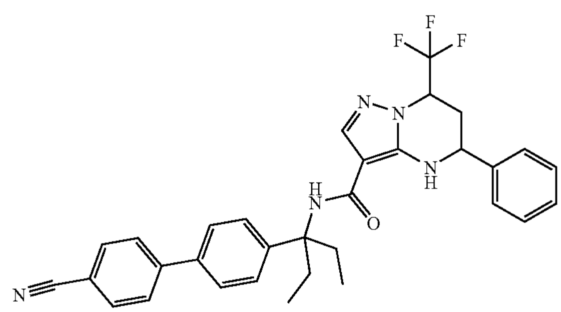 | N-(1-(4'-cyano-1,1'-biphenyl-4-yl)-1-ethylpropyl)-5-phenyl-7-(trifluoromethyl)-4,5,6,7-tetrahydropyrazolo[1,5-a]pyrimidine-3-carboxamide | MS (ESI, m/z) 558 (M + H)+ |
| 380 | 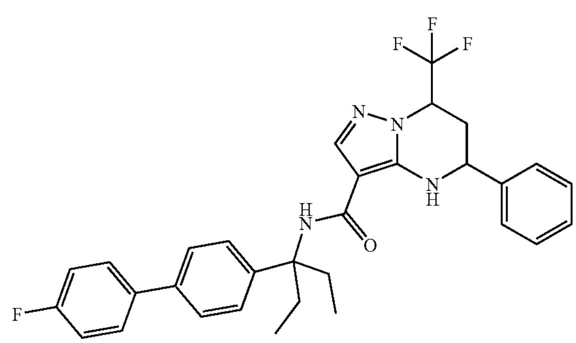 | N-(1-ethyl-1-(4'-fluoro-1,1'-biphenyl-4-yl)propyl)-5-phenyl-7-(trifluoromethyl)-4,5,6,7-tetrahydropyrazolo[1,5-a]pyrimidine-3-carboxamide | MS (ESI, m/z) 551 (M + H)+ |
| 381 | 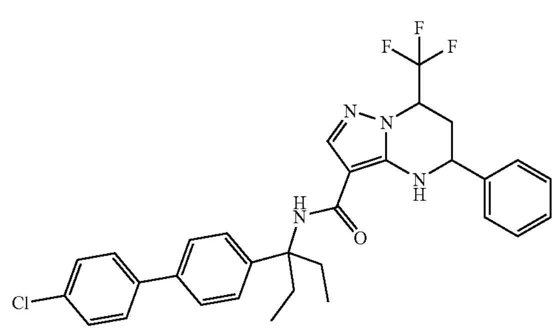 | N-(1-(4'-chloro-1,1'-biphenyl-4-yl)-1-ethylpropyl)-5-phenyl-7-(trifluoromethyl)-4,5,6,7-tetrahydropyrazolo[1,5-a]pyrimidine-3-carboxamide | MS (ESI, m/z) 567 (M + H)+ |

TABLE 4-continued

| Example | Structure | Name | Physiological Data |
|---|---|---|---|
| 382 | 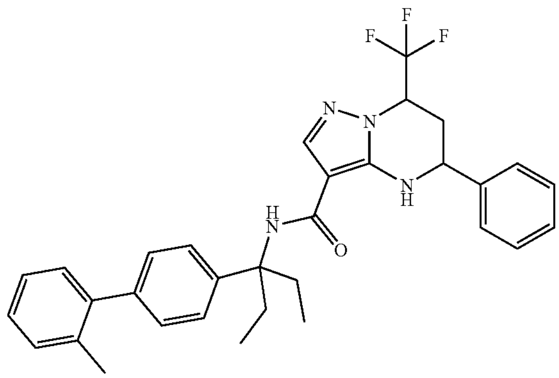 | N-(1-ethyl-1-(2'-methyl-1,1'-biphenyl-4-yl)propyl)-5-phenyl-7-(trifluoromethyl)-4,5,6,7-tetrahydropyrazolo[1,5-a]pyrimidine-3-carboxamide | MS (ESI, m/z) 547 (M + H)+ |
| 383 | 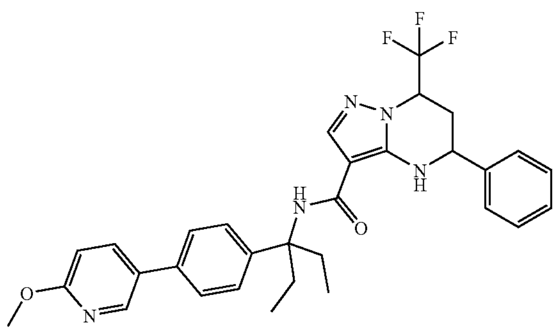 | N-(1-ethyl-1-(4-(6-methoxy-3-pyridinyl)phenyl)propyl)-5-phenyl-7-(trifluoromethyl)-4,5,6,7-tetrahydropyrazolo[1,5-a]pyrimidine-3-carboxamide | MS (ESI, m/z) 564 (M + H)+ |
| 384 | 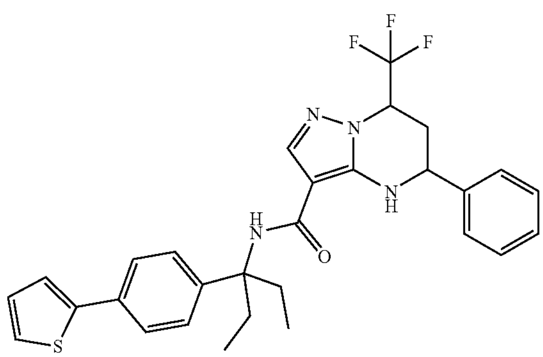 | N-(1-ethyl-1-(4-(2-thienyl)phenyl)propyl)-5-phenyl-7-(trifluoromethyl)-4,5,6,7-tetrahydropyrazolo[1,5-a]pyrimidine-3-carboxamide | MS (ESI, m/z) 539 (M + H)+ |
| 385 | 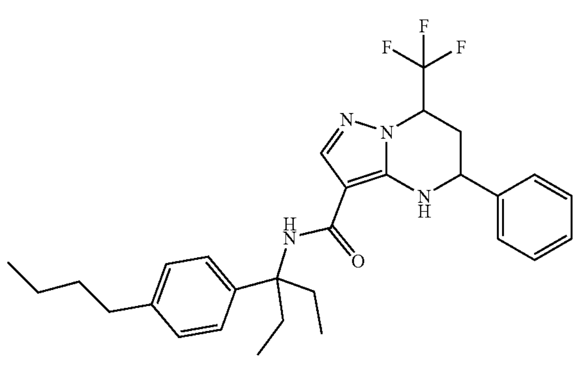 | N-(1-(4-butylphenyl)-1-ethylpropyl)-5-phenyl-7-(trifluoromethyl)-4,5,6,7-tetrahydropyrazolo[1,5-a]pyrimidine-3-carboxamide | MS (ESI, m/z) 513 (M + H)+ |

TABLE 4-continued

| Example | Structure | Name | Physiological Data |
|---------|-----------|------|--------------------|
| 386 | 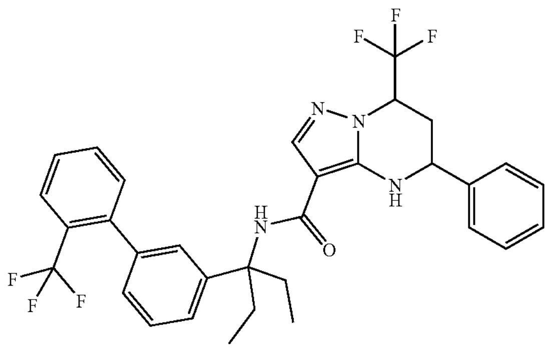 | N-(1-ethyl-1-(2'-(trifluoromethyl)-1,1'-biphenyl-3-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |
| 387 | 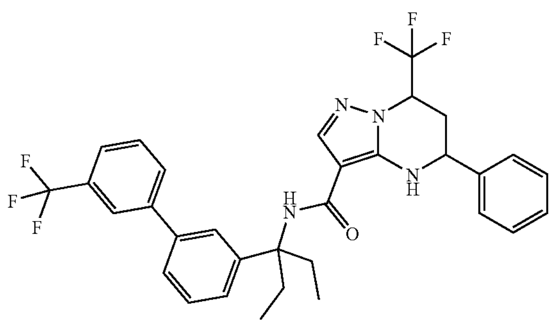 | N-(1-ethyl-1-(3'-(trifluoromethyl)-1,1'-biphenyl-3-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |
| 388 | 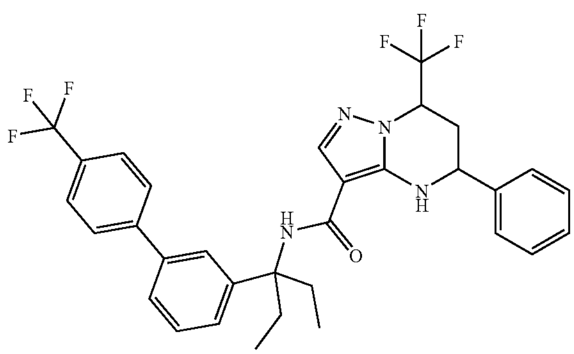 | N-(1-ethyl-1-(4'-(trifluoromethyl)-1,1'-biphenyl-3-yl)propyl)-5-phenyl-7-(trifluoromethyl)-4,5,6,7-tetrahydropyrazolo[1,5-a]pyrimidine-3-carboxamide | MS (ESI, m/z) 601 (M + H)+ |
| 389 | 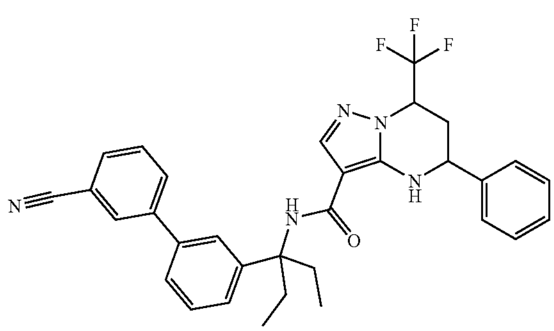 | N-(1-(3'-cyano-1,1'-biphenyl-3-yl)-1-ethylpropyl)-5-phenyl-7-(trifluoromethyl)-4,5,6,7-tetrahydropyrazolo[1,5-a]pyrimidine-3-carboxamide | MS (ESI, m/z) 558 (M + H)+ |

TABLE 4-continued

| Example | Structure | Name | Physiological Data |
|---|---|---|---|
| 390 | 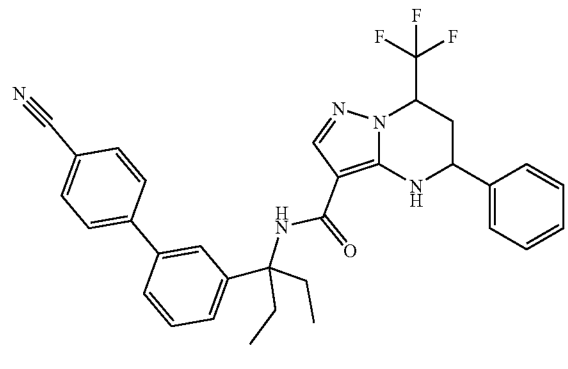 | N-(1-(4'-cyano-1,1'-biphenyl-3-yl)-1-ethylpropyl)-5-phenyl-7-(trifluoromethyl)-4,5,6,7-tetrahydropyrazolo[1,5-a]pyrimidine-3-carboxamide | MS (ESI, m/z) 558 (M + H)+ |
| 391 | 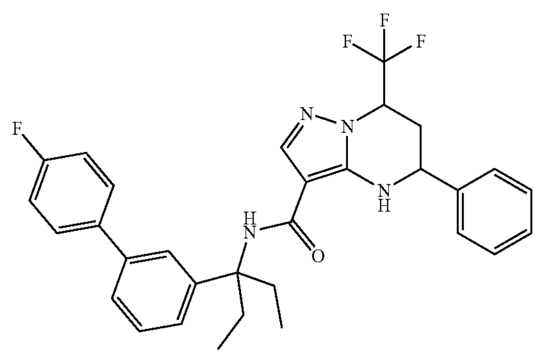 | N-(1-ethyl-1-(4'-fluoro-1,1'-biphenyl-3-yl)propyl)-5-phenyl-7-(trifluoromethyl)-4,5,6,7-tetrahydropyrazolo[1,5-a]pyrimidine-3-carboxamide | MS (ESI, m/z) 551 (M + H)+ |
| 392 | 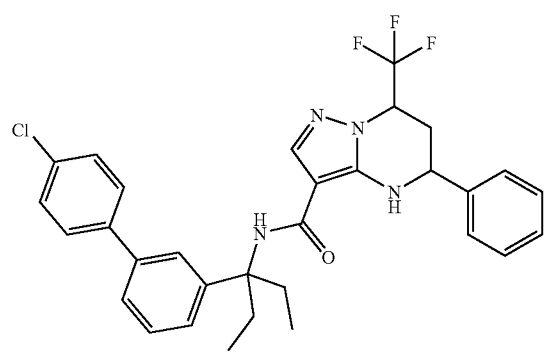 | N-(1-(4'-chloro-1,1'-biphenyl-3-yl)-1-ethylpropyl)-5-phenyl-7-(trifluoromethyl)-4,5,6,7-tetrahydropyrazolo[1,5-a]pyrimidine-3-carboxamide | MS (ESI, m/z) 567 (M + H)+ |
| 393 | 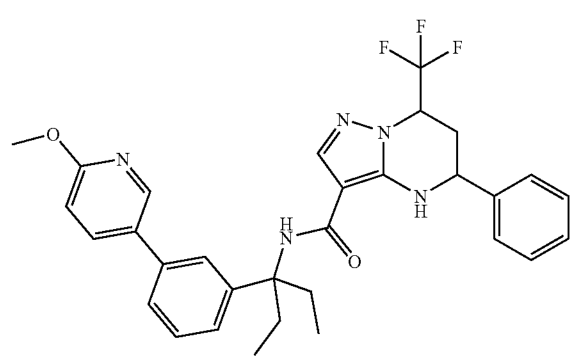 | N-(1-ethyl-1-(3-(6-methoxy-3-pyridinyl)phenyl)propyl)-5-phenyl-7-(trifluoromethyl)-4,5,6,7-tetrahydropyrazolo[1,5-a]pyrimidine-3-carboxamide | MS (ESI, m/z) 564 (M + H)+ |

TABLE 4-continued

| Example | Structure | Name | Physiological Data |
|---|---|---|---|
| 394 | 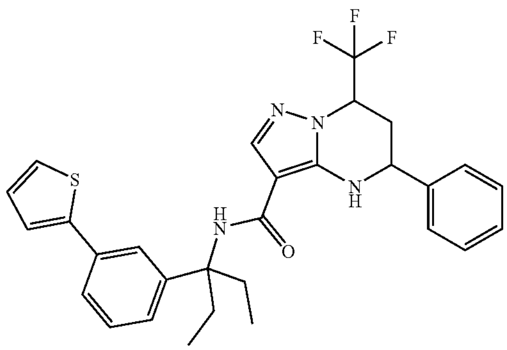 | N-(1-ethyl-1-(3-(2-thienyl)phenyl)propyl)-5-phenyl-7-(trifluoromethyl)-4,5,6,7-tetrahydropyrazolo[1,5-a]pyrimidine-3-carboxamide | MS (ESI, m/z) 539 (M + H)+ |
| 395 | 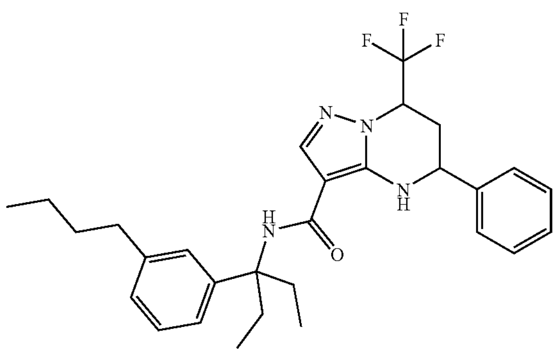 | N-(1-(3-butylphenyl)-1-ethylpropyl)-5-phenyl-7-(trifluoromethyl)-4,5,6,7-tetrahydropyrazolo[1,5-a]pyrimidine-3-carboxamide | MS (ESI, m/z) 513 (M + H)+ |
| 396 | 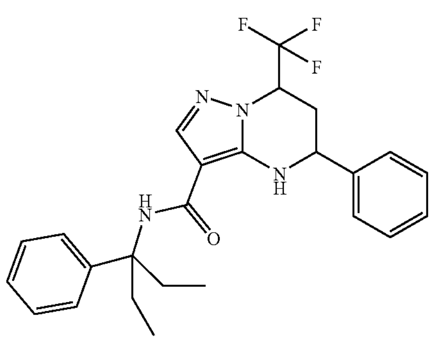 | N-(1-ethyl-1-phenylpropyl)-5-phenyl-7-(trifluoromethyl)-4,5,6,7-tetrahydropyrazolo[1,5-a]pyrimidine-3-carboxamide | mp 165-166° C. |
| 397 | 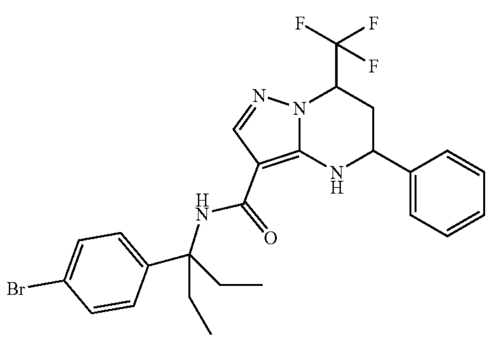 | N-(1-(4-bromophenyl)-1-ethylpropyl)-5-phenyl-7-(trifluoromethyl)-4,5,6,7-tetrahydropyrazolo[1,5-a]pyrimidine-3-carboxamide | mp 180-181° C. |

TABLE 4-continued

| Example | Structure | Name | Physiological Data |
|---|---|---|---|
| 398 | 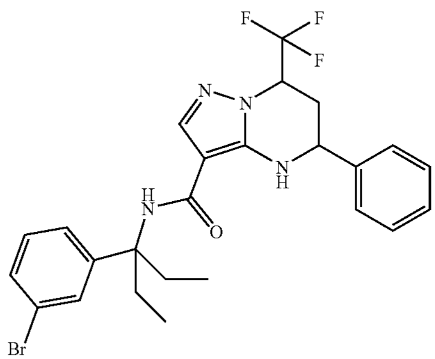 | N-(1-(3-bromophenyl)-1-ethylpropyl)-5-phenyl-7-(trifluoromethyl)-4,5,6,7-tetrahydropyrazolo[1,5-a]pyrimidine-3-carboxamide | mp 167-168° C. |
| 399 | 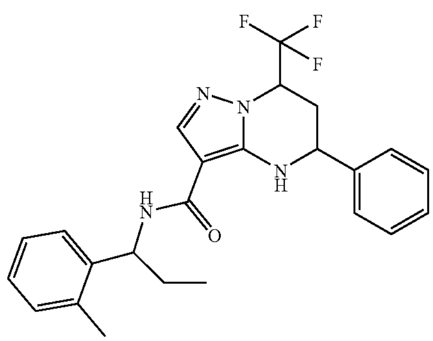 | N-(1-(2-methylphenyl)propyl)-5-phenyl-7-(trifluoromethyl)-4,5,6,7-tetrahydropyrazolo[1,5-a]pyrimidine-3-carboxamide | mp 225-226° C. |
| 400 | 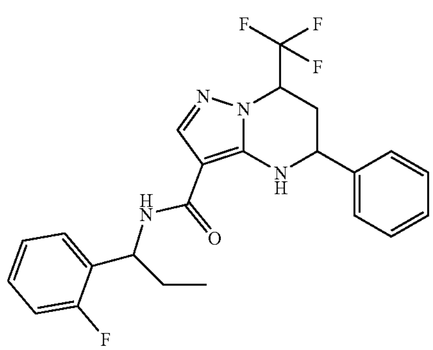 | N-(1-(2-fluorophenyl)propyl)-5-phenyl-7-(trifluoromethyl)-4,5,6,7-tetrahydropyrazolo[1,5-a]pyrimidine-3-carboxamide | mp 204-205° C. |
| 401 | 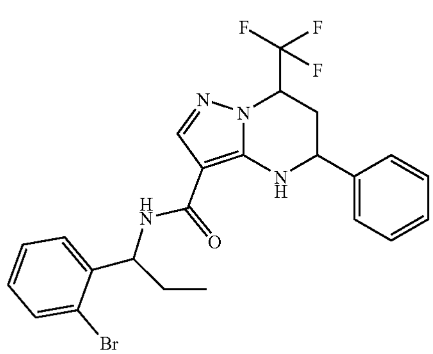 | N-(1-(2-bromophenyl)propyl)-5-phenyl-7-(trifluoromethyl)-4,5,6,7-tetrahydropyrazolo[1,5-a]pyrimidine-3-carboxamide | mp 236-237° C. |

TABLE 4-continued

| Example | Structure | Name | Physiological Data |
|---|---|---|---|
| 402 | 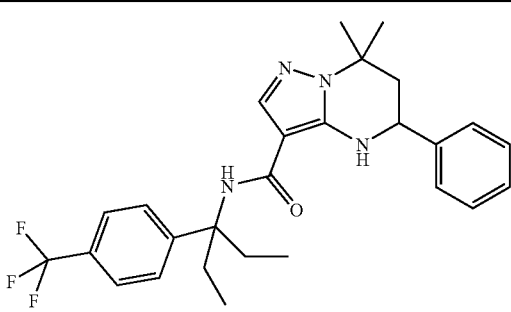 | N-(1-ethyl-1-(4-(trifluoromethyl)phenyl)propyl)-7,7-dimethyl-5-phenyl-4,5,6,7-tetrahydropyrazolo[1,5-a]pyrimidine-3-carboxamide | mp 193-194° C. |
| 403 | 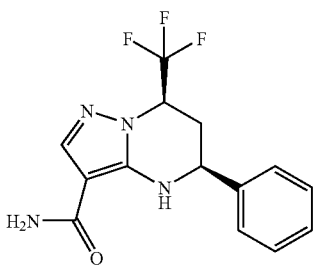 | 5-phenyl-7-(trifluoromethyl)-4,5,6,7-tetrahydropyrazolo[1,5-a]pyrimidine-3-carboxamide | mp 277-278° C. |
| 404 | 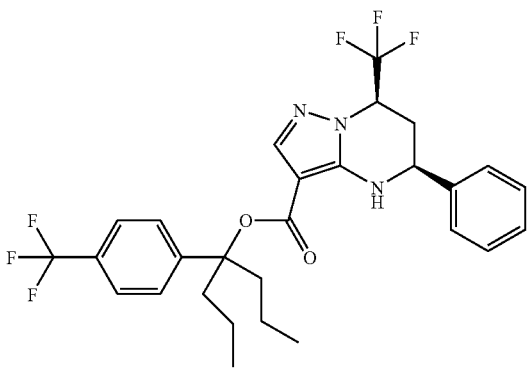 | 1-propyl-1-(4-(trifluoromethyl)phenyl)butyl 5-phenyl-7-(trifluoromethyl)-4,5,6,7-tetrahydropyrazolo[1,5-a]pyrimidine-3-carboxylate | MS (ESI, m/z) 554 (M + H)+ |
| 405 | 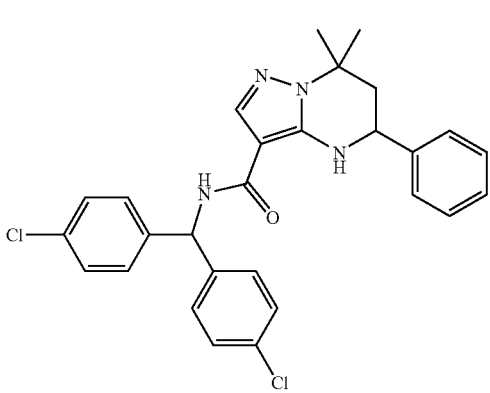 | N-(bis(4-chlorophenyl)methyl)-7,7-dimethyl-5-phenyl-4,5,6,7-tetrahydropyrazolo[1,5-a]pyrimidine-3-carboxamide | mp 180-181° C. |

TABLE 4-continued

| Example | Structure | Name | Physiological Data |
|---|---|---|---|
| 406 | 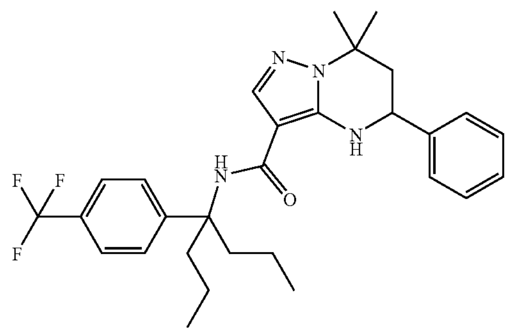 | 7,7-dimethyl-5-phenyl-N-(1-propyl-1-(4-(trifluoromethyl)phenyl)butyl)-4,5,6,7-tetrahydropyrazolo[1,5-a]pyrimidine-3-carboxamide | mp 175-1764° C. |
| 407 | 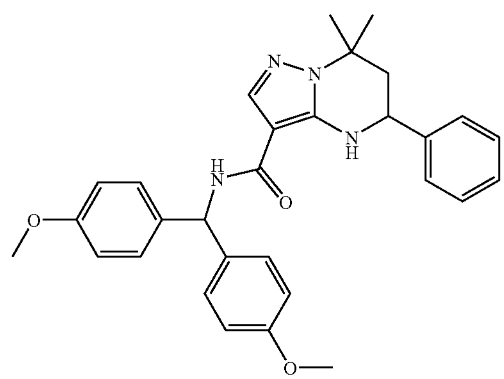 | N-(bis(4-methoxyphenyl)methyl)-7,7-dimethyl-5-phenyl-4,5,6,7-tetrahydropyrazolo[1,5-a]pyrimidine-3-carboxamide | mp 184-185° C. |
| 408 | 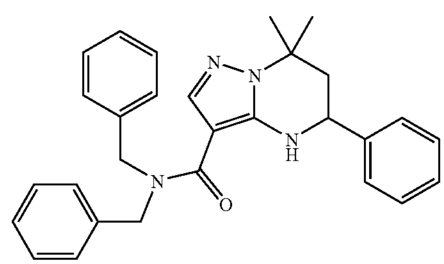 | N,N-dibenzyl-7,7-dimethyl-5-phenyl-4,5,6,7-tetrahydropyrazolo[1,5-a]pyrimidine-3-carboxamide | mp 206-207° C. |
| 409 | 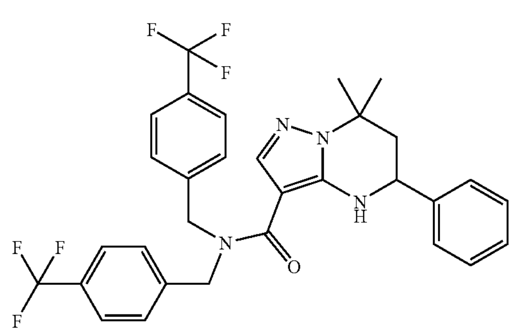 | 7,7-dimethyl-5-phenyl-N,N-bis(4-(trifluoromethyl)benzyl)-4,5,6,7-tetrahydropyrazolo[1,5-a]pyrimidine-3-carboxamide | mp 164-165° C. |

TABLE 4-continued

| Example | Structure | Name | Physiological Data |
|---|---|---|---|
| 410 | 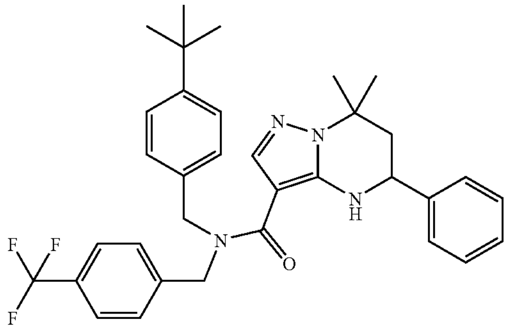 | N-(4-tert-butylbenzyl)-7,7-dimethyl-5-phenyl-N-(4-(trifluoromethyl)benzyl)-4,5,6,7-tetrahydropyrazolo[1,5-a]pyrimidine-3-carboxamide | IR(KBr) 2965, 1605, 1568, 1528, 1412, 1325, 1246, 1165, 1127 cm$^{-1}$ |
| 411 | 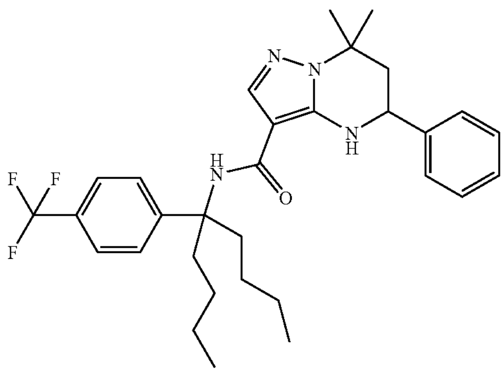 | N-(1-butyl-1-(4-(trifluoromethyl)phenyl)pentyl)-7,7-dimethyl-5-phenyl-4,5,6,7-tetrahydropyrazolo[1,5-a]pyrimidine-3-carboxamide | mp 113-114° C. |
| 412 | 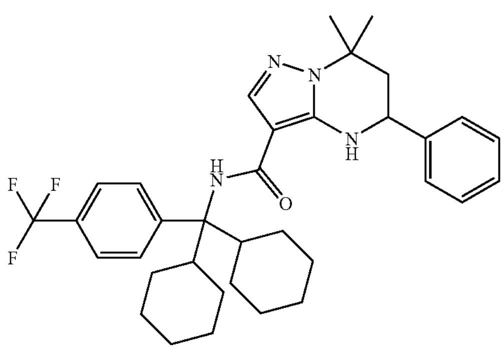 | N-(dicyclohexyl(4-(trifluoromethyl)phenyl)methyl)-7,7-dimethyl-5-phenyl-4,5,6,7-tetrahydropyrazolo[1,5-a]pyrimidine-3-carboxamide | mp 146-147° C. |
| 413 | 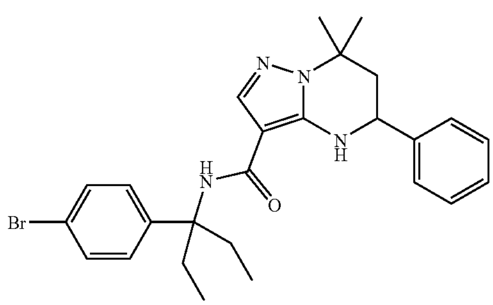 | N-(1-(4-bromophenyl)-1-ethylpropyl)-7,7-dimethyl-5-phenyl-4,5,6,7-tetrahydropyrazolo[1,5-a]pyrimidine-3-carboxamide | mp 129-130° C. |

TABLE 4-continued

| Example | Structure | Name | Physiological Data |
|---|---|---|---|
| 414 | 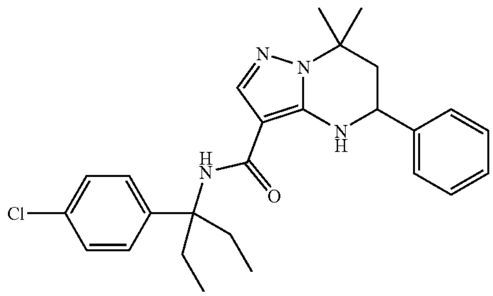 | N-(1-(4-chlorophenyl)-1-ethylpropyl)-7,7-dimethyl-5-phenyl-4,5,6,7-tetrahydropyrazolo[1,5-a]pyrimidine-3-carboxamide | mp 125-126° C. |
| 415 | 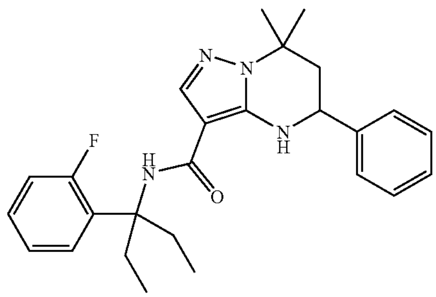 | N-(1-ethyl-1-(2-fluorophenyl)propyl)-7,7-dimethyl-5-phenyl-4,5,6,7-tetrahydropyrazolo[1,5-a]pyrimidine-3-carboxamide | MS (ESI, m/z) 435 (M + H)+ |
| 416 | 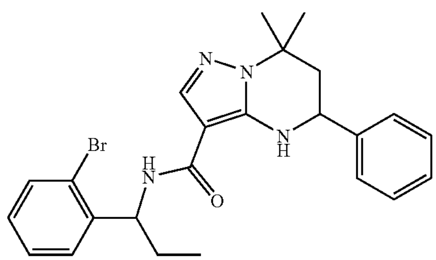 | N-(1-(2-bromophenyl)propyl)-7,7-dimethyl-5-phenyl-4,5,6,7-tetrahydropyrazolo[1,5-a]pyrimidine-3-carboxamide | mp 200-201° C. |
| 417 | 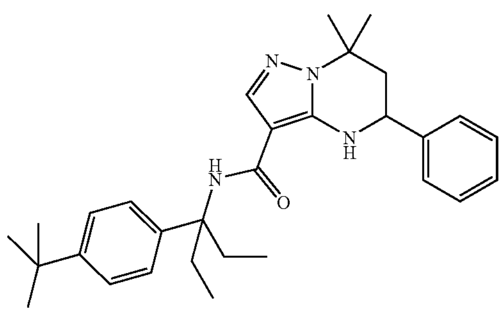 | N-(1-(4-tert-butylphenyl)-1-ethylpropyl)-7,7-dimethyl-5-phenyl-4,5,6,7-tetrahydropyrazolo[1,5-a]pyrimidine-3-carboxamide | mp 196-197° C. |
| 418 | 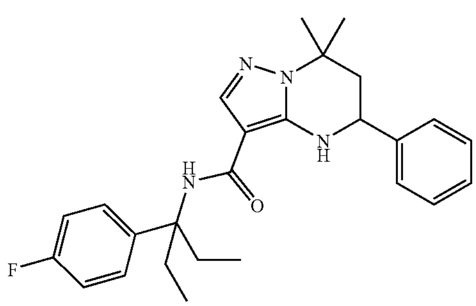 | N-(1-ethyl-1-(4-fluorophenyl)propyl)-7,7-dimethyl-5-phenyl-4,5,6,7-tetrahydropyrazolo[1,5-a]pyrimidine-3-carboxamide | mp 155-156° C. |

TABLE 4-continued

| Example | Structure | Name | Physiological Data |
|---|---|---|---|
| 419 | 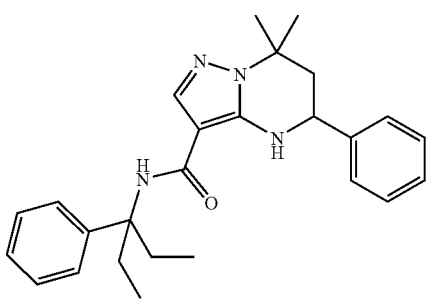 | N-(1-ethyl-1-phenylpropyl)-7,7-dimethyl-5-phenyl-4,5,6,7-tetrahydropyrazolo[1,5-a]pyrimidine-3-carboxatnide | mp 139-140° C. |
| 420 | 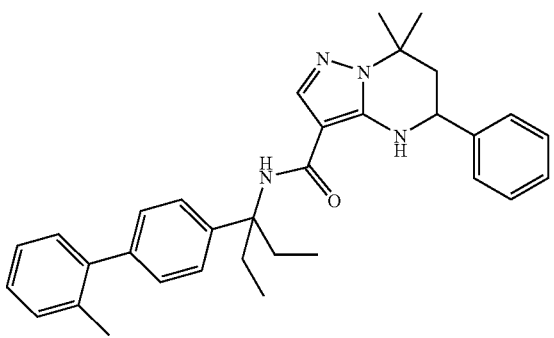 | N-(1-ethyl-1-(2'-methyl-1,1'-biphenyl-4-yl)propyl)-7,7-dimethyl-5-phenyl-4,5,6,7-tetrahydropyrazolo[1,5-a]pyrimidine-3-carboxamide | MS (ESI, m/z) 507 (M + H)+ |
| 421 | 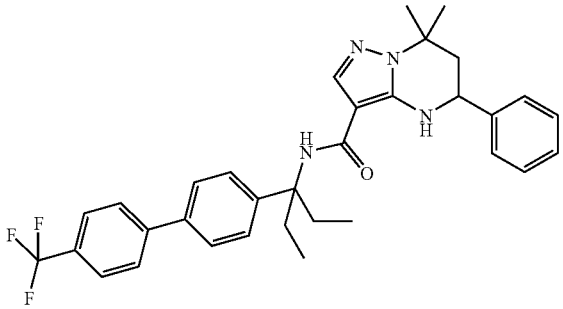 | N-(1-ethyl-1'-(4'-(trifluoromethyl)-1,1'-biphenyl-4-yl)propyl)-7,7-dimethyl-5-phenyl-4,5,6,7-tetrahydropyrazolo[1,5-a]pyrimidine-3-carboxamide | MS (ESI, m/z) 561 (M + H)+ |
| 422 | 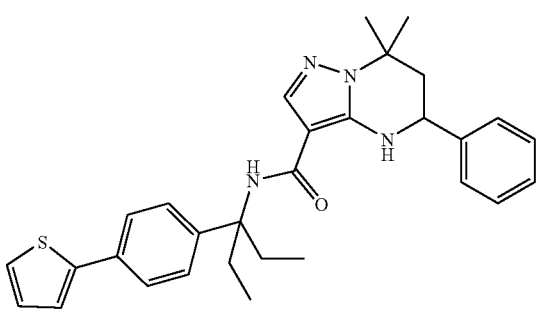 | N-(1-ethyl-1-(4-(2-thienyl)phenyl)propyl)-7,7-dimethyl-5-phenyl-4,5,6,7-tetrahydropyrazolo[1,5-a]pyrimidine-3-carboxamide | MS (ESI, m/z) 499 (M + H)+ |

TABLE 4-continued

| Example | Structure | Name | Physiological Data |
|---|---|---|---|
| 423 | 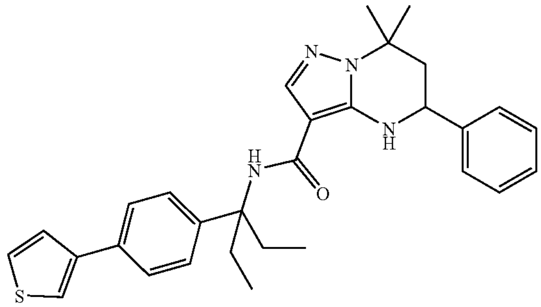 | N-(1-ethyl-1-(4-(3-thienyl)phenyl)propyl)-7,7-dimethyl-5-phenyl-4,5,6,7-tetrahydropyrazolo[1,5-a]pyrimidine-3-carboxamide | MS (ESI, m/z) 499 (M + H)+ |
| 424 | 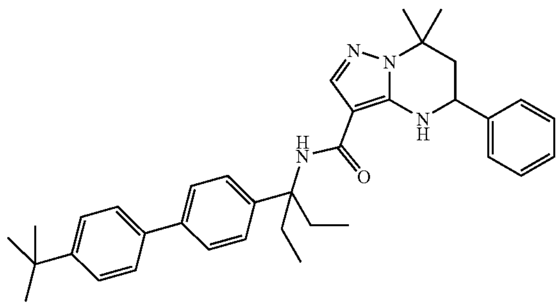 | N-(1-(4'-tert-butyl-1,1'-biphenyl-4-yl)-1-ethylpropyl)-7,7-dimethyl-5-phenyl-4,5,6,7-tetrahydropyrazolo[1,5-a]pyrimidine-3-carboxamide | MS (ESI, m/z) 550 (M + H)+ |
| 425 | 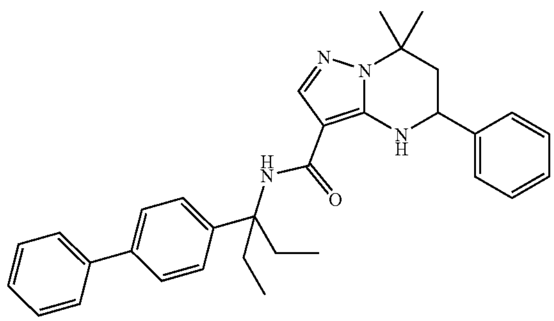 | N-(1-(1,1'-biphenyl-4-yl)-1-ethylpropyl)-7,7-dimethyl-5-phenyl-4,5,6,7-tetrahydropyrazolo[1,5-a]pyrimidine-3-carboxamide | MS (ESI, m/z) 493 (M + H)+ |
| 426 | 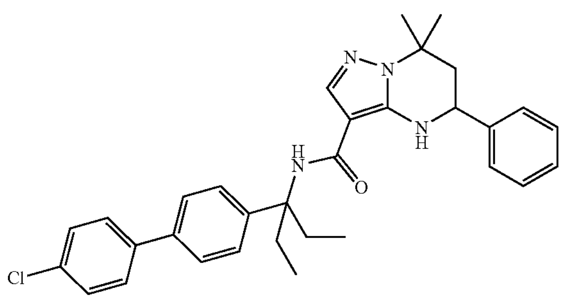 | N-(1-(4'-chloro-1,1'-biphenyl-4-yl)-1-ethylpropyl)-7,7-dimethyl-5-phenyl-4,5,6,7-tetrahydropyrazolo[1,5-a]pyrimidine-3-carboxamide | MS (ESI, m/z) 527 (M + H)+ |
| 427 | 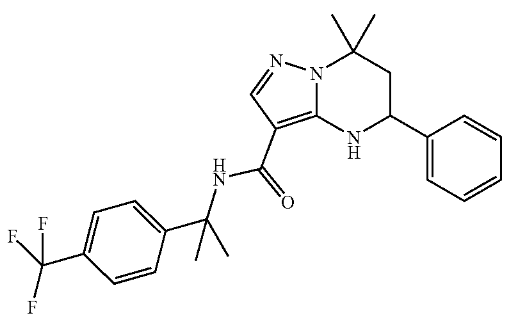 | 7,7-dimethyl-N-(1-methyl-1-(4-(trifluoromethyl)phenyl)ethyl-5-phenyl-4,5,6,7-tetrahydropyrazolo[1,5-a]pyrimidine-3-carboxamide | mp 182-183° C. |

TABLE 4-continued

| Example | Structure | Name | Physiological Data |
|---|---|---|---|
| 428 | 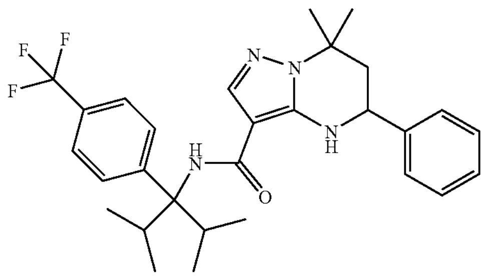 | N-(1-isopropyl-2-methyl-1-(4-(trifluoromethyl)phenyl)propyl)-7,7-dimethyl-5-phenyl-4,5,6,7-tetrahydropyrazolo[1,5-a]pyrimidine-3-carboxamide | MS (ESI, m/z) 513 (M + H)+ |
| 429 | 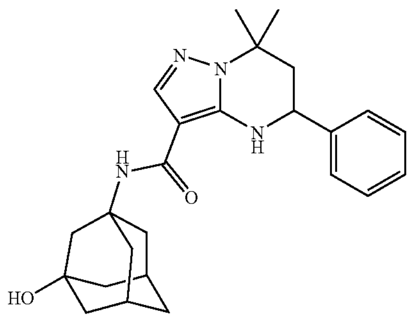 | N-(3-hydroxy-1-adamantyl)-7,7-dimethyl-5-phenyl-4,5,6,7-tetrahydropyrazolo[1,5-a]pyrimidine-3-carboxamide | MS (ESI, m/z) 421 (M + H)+ |
| 430 | 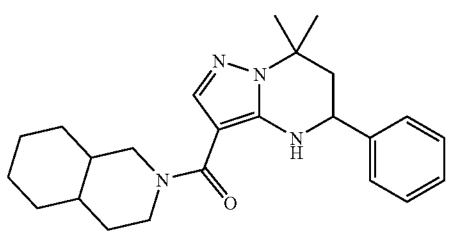 | 2-((7,7-dimethyl-5-phenyl-4,5,6,7-tetrahydropyrazolo[1,5-a]pyrimidin-3-yl)carbonyl)decahydro-isoquinoline | MS (ESI, m/z) 430 (M + H)+ |
| 431 | 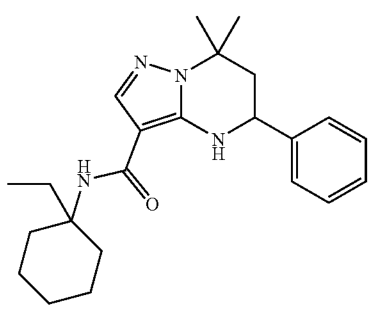 | N-(1-ethylcyclohexyl)-7,7-dimethyl-5-phenyl-4,5,6,7-tetrahydropyrazolo[1,5-a]pyrimidine-3-carboxamide | mp 166-167° C. |
| 432 | 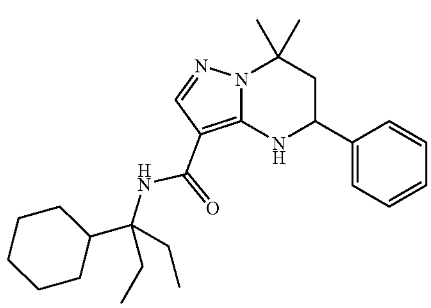 | N-(1-cyclohexyl-1-ethylpropyl)-7,7-dimethyl-5-phenyl-4,5,6,7-tetrahydropyrazolo[1,5-a]pyrimidine-3-carboxamide | mp 130-131° C. |

TABLE 4-continued

| Example | Structure | Name | Physiological Data |
|---|---|---|---|
| 433 | 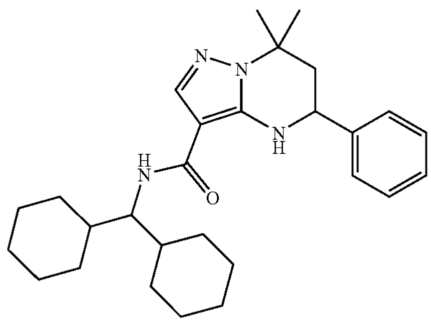 | N-(dicyclohexylmethyl)-7,7-dimethyl-5-phenyl-4,5,6,7-tetrahydropyrazolo[1,5-a]pyrimidine-3-carboxamide | mp 187-188° C. |
| 434 | 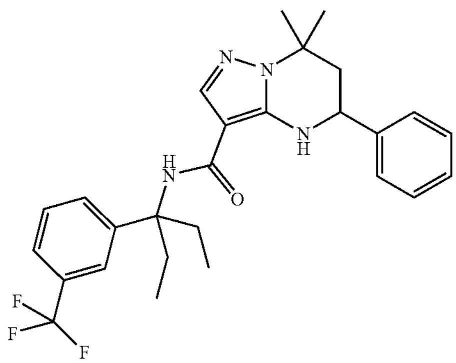 | N-(1-ethyl-1-(3-(trifluoromethyl)phenyl)propyl)-7,7-dimethyl-5-phenyl-4,5,6,7-tetrahydropyrazolo[1,5-a]pyrimidine-3-carboxamide | mp 166-167° C. |
| 459 | 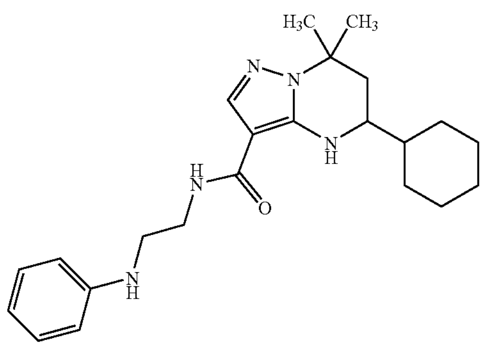 | N-(2-anilinoethyl)-5-cyclohexyl-7,7-dimethyl-4,5,6,7-tetrahydropyrazolo[1,5-a]pyrimidine-3-carboxamide | MS (ESI, m/z) 397 (M + H)+ |
| 460 | 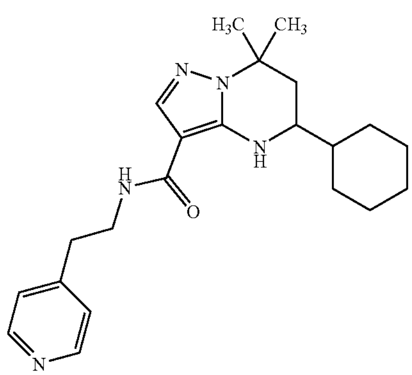 | 5-cyclohexyl-7,7-dimethyl-N-(2-(4-pyridinyl)ethyl)-4,5,6,7-tetrahydropyrazolo[1,5-a]pyrimidine-3-carboxamide | MS (ESI, m/z) 383 (M + H)+ |

TABLE 4-continued

| Example | Structure | Name | Physiological Data |
|---------|-----------|------|--------------------|
| 461 | 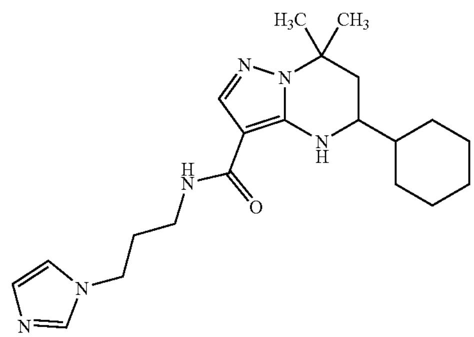 | 5-cyclohexyl-N-(3-(1H-imidazol-1-yl)propyl)-7,7-dimethyl-4,5,6,7-tetrahydropyrazolo[1,5-a]pyrimidine-3-carboxamide | MS (ESI, m/z) 385 (M + H)+ |
| 462 | 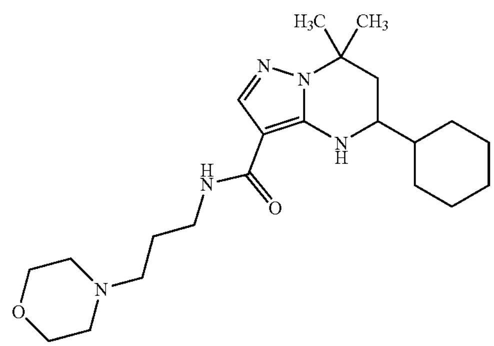 | 5-cyclohexyl-7,7-dimethyl-N-(3-(4-morpholinyl)propyl)-4,5,6,7-tetrahydropyrazolo[1,5-a]pyrimidine-3-carboxamide | MS (ESI, m/z) 404 (M + H)+ |
| 463 | 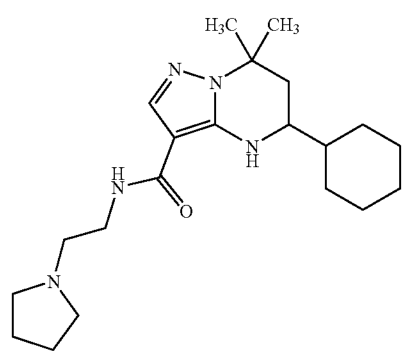 | 5-cyclohexyl-7,7-dimethyl-N-(2-(1-pyrrolidinyl)ethyl)-4,5,6,7-tetrahydropyrazolo[1,5-a]pyrimidine-3-carboxamide | MS (ESI, m/z) 374 (M + H)+ |
| 464 | 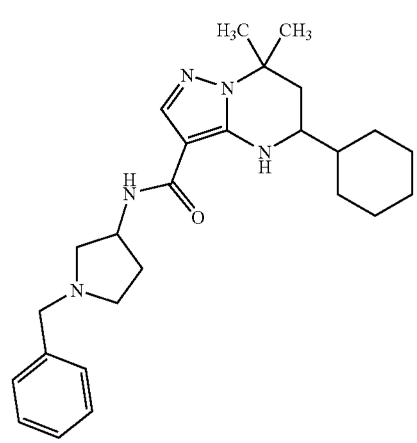 | N-(1-benzyl-3-pyrrolidinyl)-5-cyclohexyl-7,7-dimethyl-4,5,6,7-tetrahydropyrazolo[1,5-a]pyrimidine-3-carboxamide | MS (ESI, m/z) 437 (M + H)+ |

TABLE 4-continued

| Example | Structure | Name | Physiological Data |
|---|---|---|---|
| 465 | 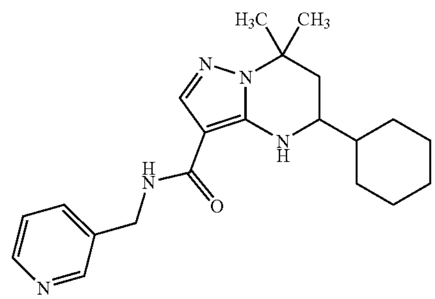 | 5-cyclohexyl-7,7-dimethyl-N-(3-pyridinylmethyl)-4,5,6,7-tetrahydropyrazolo[1,5-a]pyrimidine-3-carboxamide | MS (ESI, m/z) 368 (M + H)+ |
| 466 | 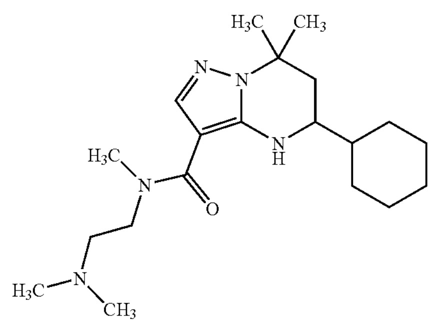 | 5-cyclohexyl-N-(2-(dimethylamino)ethyl)-N,7,7-trimethyl-4,5,6,7-tetrahydropyrazolo[1,5-a]pyrimidine-3-carboxamide | MS (ESI, m/z) 362 (M + H)+ |
| 467 | 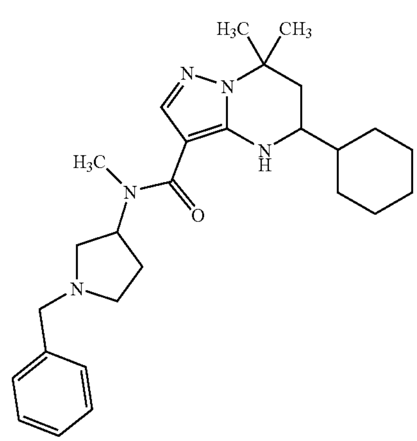 | N-(1-benzyl-3-pyrrolidinyl)-5-cyclohexyl-N,7,7-trimethyl-4,5,6,7-tetrahydropyrazolo[1,5-a]pyrimidine-3-carboxamide | MS (ESI, m/z) 451 (M + H)+ |
| 468 | 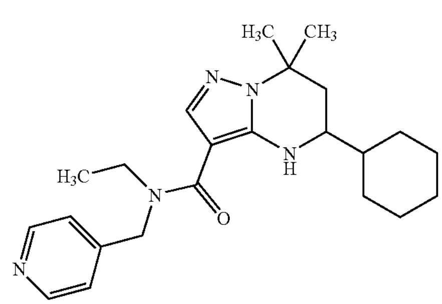 | 5-cyclohexyl-N-ethyl-7,7-dimethyl-N-(4-pyridinylmethyl)-4,5,6,7-tetrahydropyrazolo[1,5-a]pyrimidine-3-carboxamide | MS (ESI, m/z) 397 (M + H)+ |

TABLE 4-continued

| Example | Structure | Name | Physiological Data |
|---|---|---|---|
| 469 | 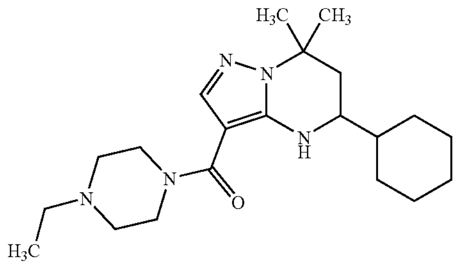 | 5-cyclohexyl-3-((4-ethyl-1-piperazinyl)carbonyl)-7,7-dimethyl-4,5,6,7-tetrahydropyrazolo[1,5-a]pyrimidine | MS (ESI, m/z) 374 (M + H)+ |
| 470 | 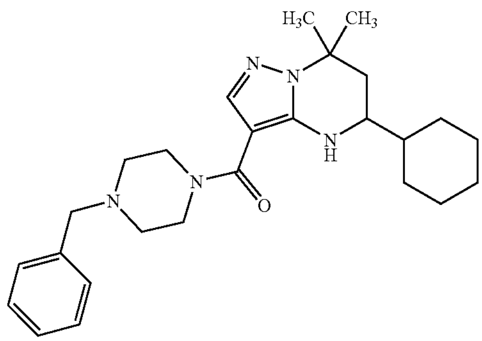 | 3-((4-benzyl-1-piperazinyl)carbonyl)-5-cyclohexyl-7,7-dimethyl-4,5,6,7-tetrahydropyrazolo[1,5-a]pyrimidine | MS (ESI, m/z) 437 (M + H)+ |
| 471 | 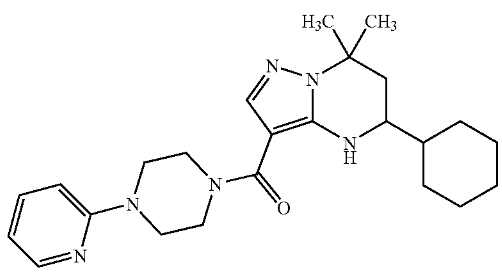 | 5-cyclohexyl-7,7-dimethyl-3-((4-(2-pyridinyl)-1-piperazinyl)carbonyl)-4,5,6,7-tetrahydropyrazolo[1,5-a]pyrimidine | MS (ESI, m/z) 424 (M + H)+ |
| 472 | 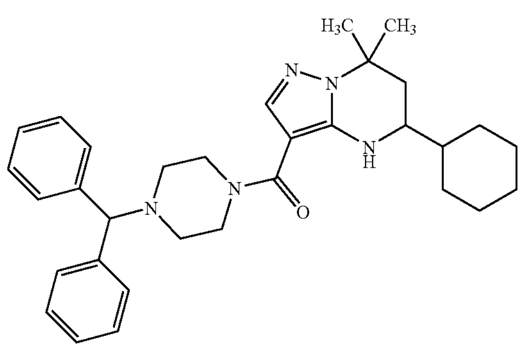 | 3-((4-benzhydryl-1-piperazinyl)carbonyl)-5-cyclohexyl-7,7-dimethyl-4,5,6,7-tetrahydropyrazolo[1,5-a]pyrimidine | MS (ESI, m/z) 513 (M + H)+ |
| 473 | 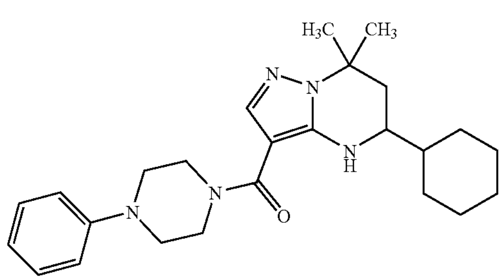 | 5-cyclohexyl-7,7-dimethyl-3-((4-phenyl-1-piperazinyl)carbonyl)-4,5,6,7-tetrahydropyrazolo[1,5-a]pyrimidine | MS (ESI, m/z) 423 (M + H)+ |

TABLE 4-continued

| Example | Name | Physiological Data |
|---------|------|--------------------|
| 474 | 1'-((5-cyclohexyl-7,7-dimethyl-4,5,6,7-tetrahydropyrazolo[1,5-a]pyrimidin-3-yl)carbonyl)-1,4'-bipiperidine | MS (ESI, m/z) 428 (M + H)+ |
| 475 | 5-cyclohexyl-N,7,7-trimethyl-N-(1-methyl-3-pyrrolidinyl)-4,5,6,7-tetrahydropyrazolo[1,5-a]pyrimidine-3-carboxamide | MS (ESI, m/z) 375 (M + H)+ |
| 476 | 5-cyclohexyl-7,7-dimethyl-3-((4-methyl-1,4-diazepan-1-yl)carbonyl)-4,5,6,7-tetrahydropyrazolo[1,5-a]pyrimidine | MS (ESI, m/z) 374 (M + H)+ |
| 477 | N-benzyl-5-cyclohexyl-N-(2-(dimethylamino)ethyl)-7,7-dimethyl-4,5,6,7-tetrahydropyrazolo[1,5-a]pyrimidine-3-carboxamide | MS (ESI, m/z) 439 (M + H)+ |
| 478 | N-(2-(dimethylamino)ethyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 363 (M + H)+ |

TABLE 4-continued

| Example | Structure | Name | Physiological Data |
|---|---|---|---|
| 479 | 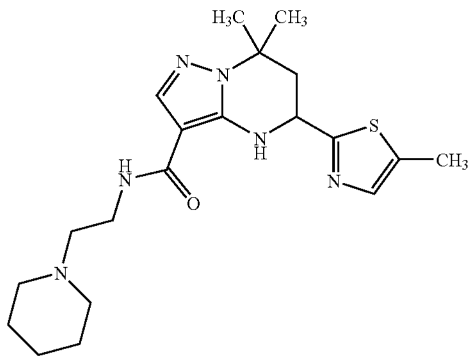 | 7,7-dimethyl-5-(5-methyl-1,3-thiazol-2-yl)-N-(2-(1-piperidinyl)ethyl)-4,5,6,7-tetrahydropyrazolo[1,5-a]pyrimidine-3-carboxamide | MS (ESI, m/z) 403 (M + H)+ |
| 480 | 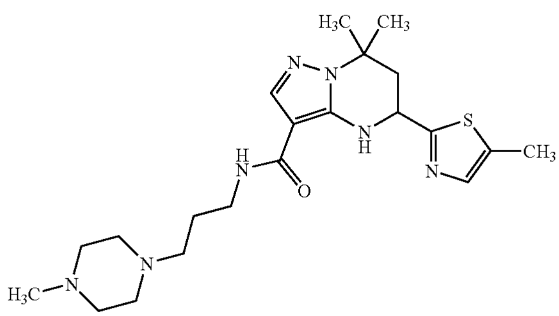 | 7,7-dimethyl-N-(3-(4-methyl-1-piperazinyl)propyl)-5-(5-methyl-1,3-thiazol-2-yl)-4,5,6,7-tetrahydropyrazolo[1,5-a]pyrimidine-3-carboxamide | MS (ESI, m/z) 432 (M + H)+ |
| 481 | 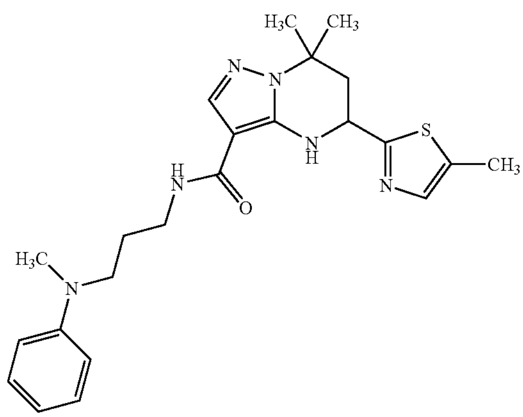 | 7,7-dimethyl-N-(3-(methyl(phenyl)amino)propyl)-5-(5-methyl-1,3-thiazol-2-yl)-4,5,6,7-tetrahydropyrazolo[1,5-a]pyrimidine-3-carboxamide | MS (ESI, m/z) 440 (M + H)+ |
| 482 | 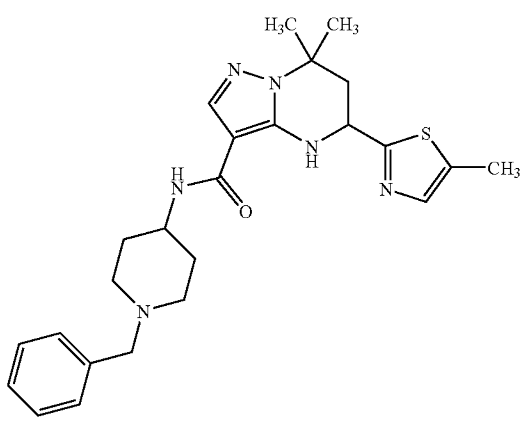 | N-(1-benzyl-4-piperidinyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 465 (M + H)+ |

TABLE 4-continued

| Example | Structure | Name | Physiological Data |
|---|---|---|---|
| 483 | 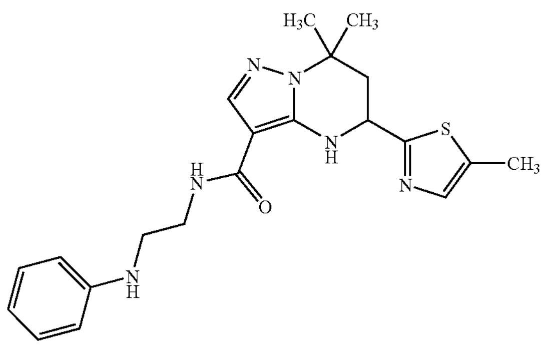 | N-(2-anilinoethyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 411 (M + H)+ |
| 484 | 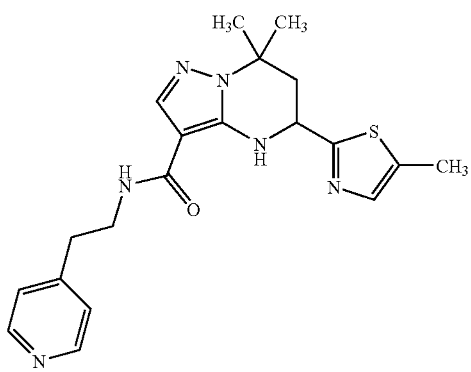 | 7,7-dimethyl-5-(5-methyl-1,3-thiazol-2-yl)-N-(2-(4-pyridinyl)ethyl)-4,5,6,7-tetrahydropyrazolo[1,5-a]pyrimidine-3-carboxamide | MS (ESI, m/z) 397 (M + H)+ |
| 485 | 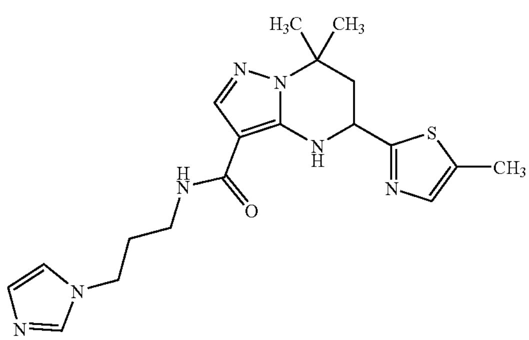 | N-(3-(1H-imidazol-1-yl)propyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 400 (M + H)+ |
| 486 | 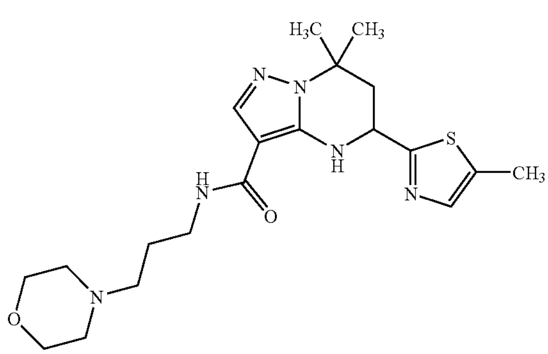 | 7,7-dimethyl-5-(5-methyl-1,3-thiazol-2-yl)-N-(3-(4-morpholinyl)propyl)-4,5,6,7-tetrahydropyrazolo[1,5-a]pyrimidine-3-carboxamide | MS (ESI, m/z) 419 (M + H)+ |

TABLE 4-continued

| Example | Name | Physiological Data |
|---|---|---|
| 487 | 7,7-dimethyl-5-(5-methyl-1,3-thiazol-2-yl)-N-(2-(1-pyrrolidinyl)ethyl)-4,5,6,7-tetrahydropyrazolo[1,5-a]pyrimidine-3-carboxamide | MS (ESI, m/z) 389 (M + H)+ |
| 488 | N-(1-benzyl-3-pyrrolidinyl)-7,7-dimethy-5-(5-methyl-1,3-thiazol-2-yl)-4,5,6,7-tetrahydropyrazolo[1,5-a]pyrimidine-3-carboxamide | MS (ESI, m/z) 451 (M + H)+ |
| 489 | 7,7-dimethyl-5-(5-methyl-1,3-thiazol-2-yl)-N-(3-pyridinylmethyl)-4,5,6,7-tetrahydropyrazolo[1,5-a]pyrimidine-3-carboxamide | MS (ESI, m/z) 383 (M + H)+ |
| 490 | N-(2-(dimethylamino)ethyl)-N,7,7-trimethyl-5-(5-methyl-1,3-thiazol-2-yl)-4,5,6,7-tetrahydropyrazolo[1,5-a]pyrimidine-3-carboxamide | MS (ESI, m/z) 377 (M + H)+ |

TABLE 4-continued

| Example | Structure | Name | Physiological Data |
|---|---|---|---|
| 491 | 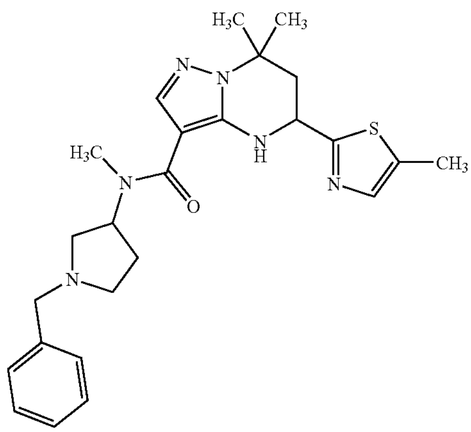 | N-(1-benzyl-3-pyrrolidinyl)-N,7,7-trimethyl-5-(5-methyl-1,3-thiazol-2-yl)-4,5,6,7-tetrahydropyrazolo[1,5-a]pyrimidine-3-carboxamide | MS (ESI, m/z) 465 (M + H)+ |
| 492 | 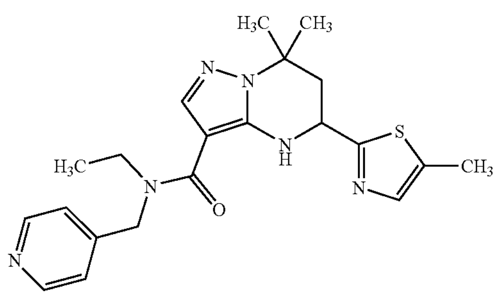 | N-ethyl-7,7-dimethyl-5-(5-methyl-1,3-thiazol-2-yl)-N-(4-pyridinylmethyl)-4,5,6,7-tetrahydropyrazolo[1,5-a]pyrimidine-3-carboxamide | MS (ESI, m/z) 411 (M + H)+ |
| 493 | 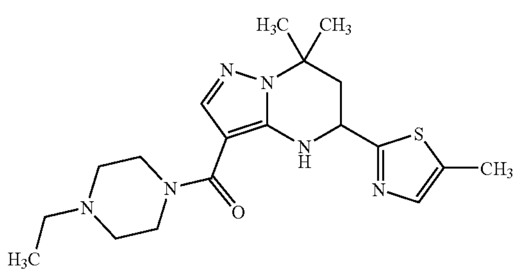 | 3-((4-ethyl-1-piperazinyl)carbonyl)-7,7-dimethyl-5-(5-methyl-1,3-thiazol-2-yl)-4,5,6,7-tetrahydropyrazolo[1,5-a]pyrimidine | MS (ESI, m/z) 389 (M + H)+ |
| 494 | 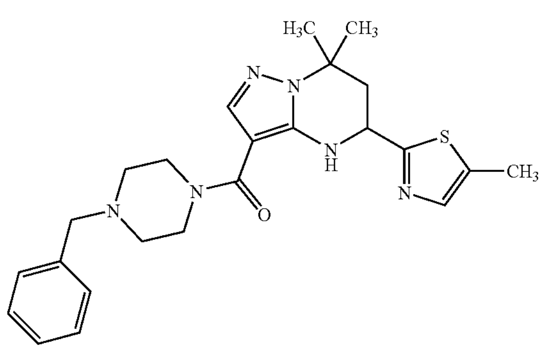 | 3-((4-benzyl-1-piperazinyl)carbonyl)-7,7-dimethyl-5-(5-methyl-1,3-thiazol-2-yl)-4,5,6,7-tetrahydropyrazolo[1,5-a]pyrimidine | MS (ESI, m/z) 451 (M + H)+ |

TABLE 4-continued

| Example | Name | Physiological Data |
|---|---|---|
| 495 | 7,7-dimethyl-5-(5-methyl-1,3-thiazol-2-yl)-3-((4-(2-pyridinyl)-1-piperazinyl)carbonyl)-4,5,6,7-tetrahydropyrazolo[1,5-a]pyrimidine | MS (ESI, m/z) 439 (M + H)+ |
| 496 | 3-((4-benzhydryl-1-piperazinyl)carbonyl)-7,7-dimethyl-5-(5-methyl-1,3-thiazol-2-yl)-4,5,6,7-tetrahydropyrazolo[1,5-a]pyrimidine | MS (ESI, m/z) 527 (M + H)+ |
| 497 | 7,7-dimethyl-5-(5-methyl-1,3-thiazol-2-yl)-3-((4-phenyl-1-piperazinyl)carbonyl)-4,5,6,7-tetrahydropyrazolo[1,5-a]pyrimidine | MS (ESI, m/z) 437 (M + H)+ |
| 498 | 1'-((7,7-dimethyl-5-(5-methyl-1,3-thiazol-2-yl)-4,5,6,7-tetrahydropyrazolo[1,5-a]pyrimidin-3-yl)carbonyl)-1,4'-bipiperidine | MS (ESI, m/z) 443 (M + H)+ |
| 499 | N,7,7-trimethyl-N-(1-methyl-3-pyrrolidinyl)-5-(5-methyl-1,3-thiazol-2-yl)-4,5,6,7-tetrahydropyrazolo[1,5-a]pyrimidine-3-carboxamide | MS (ESI, m/z) 389 (M + H)+ |

TABLE 4-continued

| Example | Structure | Name | Physiological Data |
|---------|-----------|------|--------------------|
| 500 | 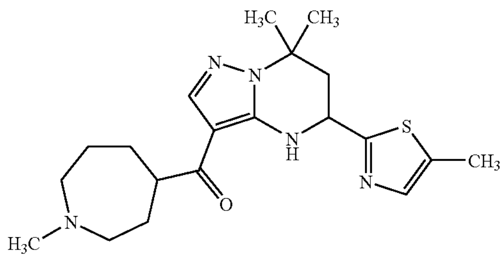 | 7,7-dimethyl-3-((4-methyl-1,4-diazepan-1-yl)carbonyl)-5-(5-methyl-1,3-thiazol-2-yl)-4,5,6,7-tetrahydropyrazolo[1,5-a-]pyrimidine | MS (ESI, m/z) 389 (M + H)+ |
| 501 | 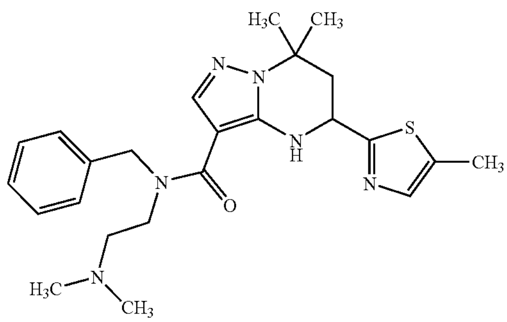 | N-benzyl-N-(2-(dimethylamino)ethyl)-7,7-dimethyl-5-(5-methyl-1,3-thiazol-2-yl)-4,5,6,7-tetrahydropyrazolo[1,5-a]pyrimidine-3-carbaxamide | MS (ESI, m/z) 453 (M + H)+ |
| 502 | 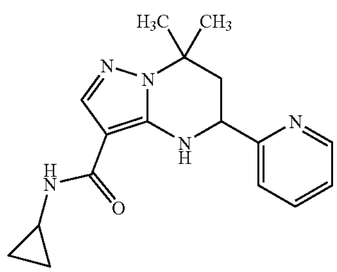 | N-cyclopropyl-7,7-dimethyl-5-(2-pyridinyl)-4,5,6,7-tetrahydropyrazolo[1,5-a]pyrimidine-3-carboxamide | MS (ESI, m/z) 312 (M + H)+ |
| 503 | 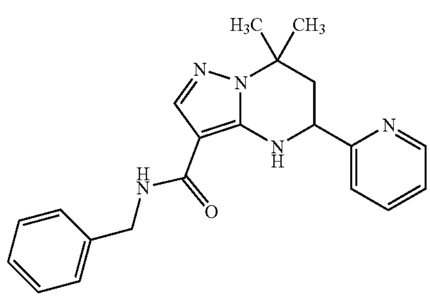 | N-benzyl-7,7-dimethyl-5-(2-pyridinyl)-4,5,6,7-tetrahydropyrazolo[1,5-a]pyrimidine-3-carboxamide | MS (ESI, m/z) 362 (M + H)+ |
| 504 | 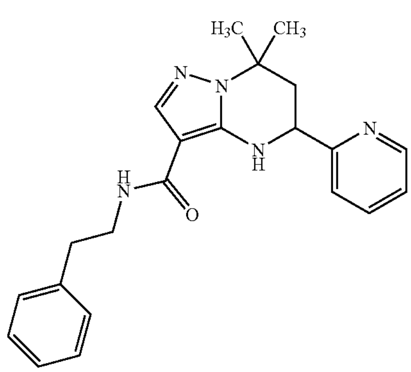 | 7,7-dimethyl-N-(2-phenylethyl)-5-(2-pyridinyl)-4,5,6,7-tetrahydropyrazolo[1,5-a]pyrimidine-3-carboxamide | MS (ESI, m/z) 376 (M + H)+ |

TABLE 4-continued

| Example | Structure | Name | Physiological Data |
|---|---|---|---|
| 505 | 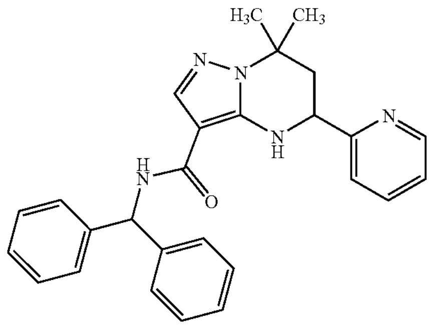 | N-benzhydryl-7,7-dimethyl-5-(2-pyridinyl)-4,5,6,7-tetrahydropyrazolo[1,5-a]pyrimidine-3-carboxamide | MS (ESI, m/z) 439 (M + H)+ |
| 506 | 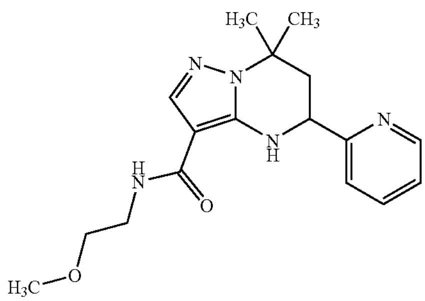 | N-(2-methoxyethyl)-7,7-dimethyl-5-(2-pyridinyl)-4,5,6,7-tetrahydropyrazolo[1,5-a]pyrimidine-3-carboxamide | MS (ESI, m/z) 330 (M + H)+ |
| 507 | 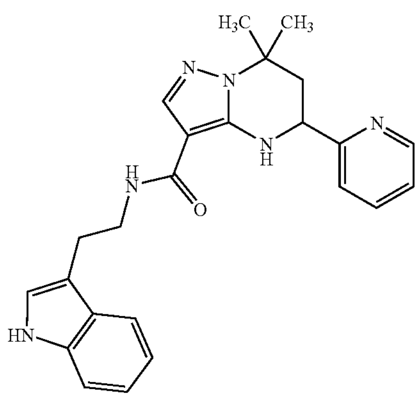 | N-(2-(1H-indol-3-yl)ethyl)-7,7-dimethyl-5-(2-pyridinyl)-4,5,6,7-tetrahydropyrazolo[1,5-a]pyrimidine-3-carboxamide | MS (ESI, m/z) 416 (M + H)+ |
| 508 | 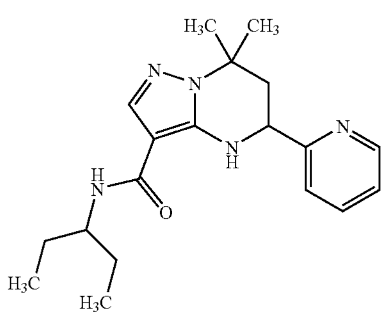 | N-(1-ethylpropyl)-7,7-dimethyl-5-(2-pyridinyl)-4,5,6,7-tetrahydropyrazolo[1,5-a]pyrimidine-3-carboxamide | MS (ESI, m/z) 342 (M + H)+ |

TABLE 4-continued

| Example | Structure | Name | Physiological Data |
|---------|-----------|------|--------------------|
| 509 | 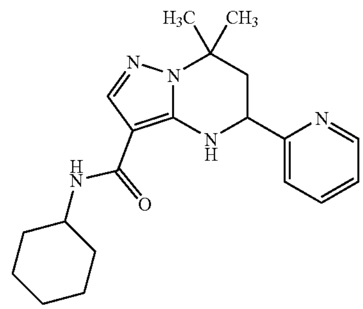 | N-cyclohexyl-7,7-dimethyl-5-(2-pyridinyl)-4,5,6,7-tetrahydropyrazolo[1,5-a]pyrimidine-3-carboxamide | MS (ESI, m/z) 354 (M + H)+ |
| 510 | 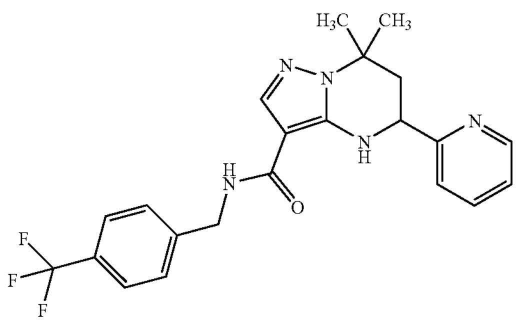 | 7,7-dimethyl-5-(2-pyridinyl)-N-(4-(trifluoromethyl)benzyl)-4,5,6,7-tetrahydropyrazolo[1,5-a]pyrimidine-3-carboxamide | MS (ESI, m/z) 430 (M + H)+ |
| 511 | 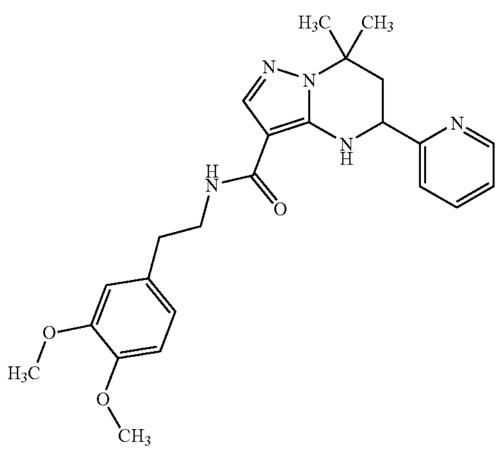 | N-(2-(3,4-dimethoxyphenyl)ethyl)-7,7-dimethyl-5-(2-pylidinyl)-4,5,6,7-tetrahydropyrazolo[1,5-a]pyrimidine-3-carboxamide | MS (ESI, m/z) 437 (M + H)+ |
| 512 | 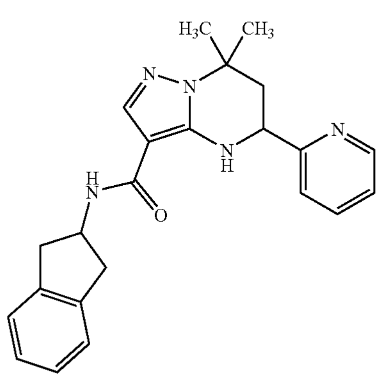 | N-2,3-dihydro-1H-inden-2-yl-7,7-dimethyl-5-(2-pyridinyl)-4,5,6,7-tetrahydropyrazolo[1,5-a]pyrimidine-3-carboxamide | MS (ESI, m/z) 388 (M + H)+ |

TABLE 4-continued

| Example | Structure | Name | Physiological Data |
|---|---|---|---|
| 513 | 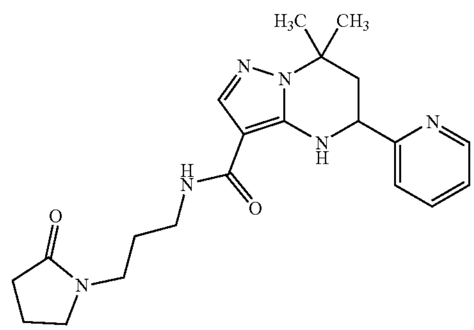 | 7,7-dimethyl-N-(3-(2-oxo-1-pyrrolidinyl)propyl)-5-(2-pyridinyl)-4,5,6,7-tetrahydropyrazolo[1,5-a]pyrimidine-3-carboxamide | MS (ESI, m/z) 397 (M + H)+ |
| 514 | 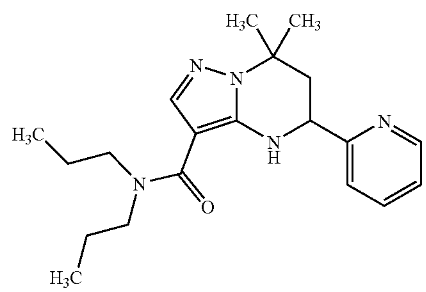 | 7,7-dimethyl-N,N-dipropyl-5-(2-pyridinyl)-4,5,6,7-tetrahydropyrazolo[1,5-a]pyrimidine-3-carboxamide | MS (ESI, m/z) 356 (M + H)+ |
| 515 | 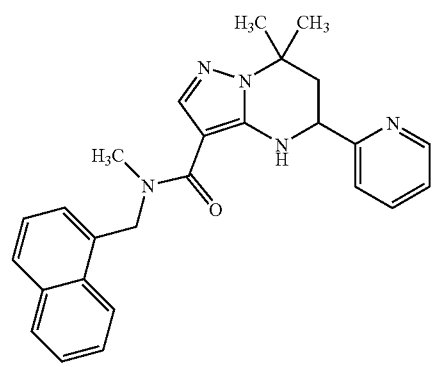 | N,7,7-trimethyl-N-(1-naphthylmethyl)-5-(2-pyridinyl)-4,5,6,7-tetrahydropyrazolo[1,5-a]pyrimidine-3-carboxamide | MS (ESI, m/z) 427 (M + H)+ |
| 516 | 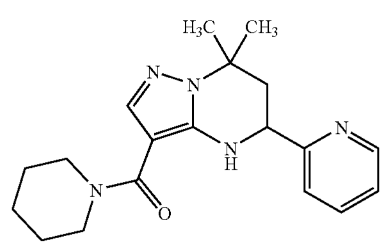 | 7,7-dimethyl-3-(1-piperidinylcarbonyl)-5-(2-pyridinyl)-4,5,6,7-tetrahydropyrazolo[1,5-a]pyrimidine | MS (ESI, m/z) 340 (M + H)+ |
| 517 | 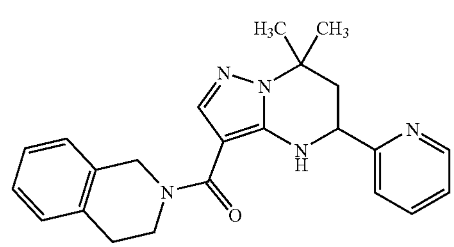 | 2-((7,7-dimethyl-5-(2-pyridinyl)-4,5,6,7-tetrahydropyrazolo[1,5-a]pyrimidin-3-yl)carbonyl)-1,2,3,4-tetrahydroisoquinoline | MS (ESI, m/z) 388 (M + H)+ |

TABLE 4-continued

| Example | Name | Physiological Data |
|---|---|---|
| 518 | 1-((7,7-dimethyl-5-(2-pyridinyl)-4,5,6,7-tetrahydropyrazolo[1,5-a]pyrimidin-3-yl)carbonyl)-4-piperidinecarboxamide | MS (ESI, m/z) 383 (M + H)+ |
| 519 | 3-((4-benzyl-1-piperidinyl)carbonyl)-7,7-dimethyl-5-(2-pyridinyl)-4,5,6,7-tetrahydropyrazolo[1,5-a]pyrimidine | MS (ESI, m/z) 431 (M + H)+ |
| 520 | N-(1-((7,7-dimethyl-5-(2-pyridinyl)-4,5,6,7-tetrahydropyrazolo[1,5-a]pyrimidin-3-yl)carbonyl)-3-pyrrolidinyl)acetamide | MS (ESI, m/z) 383 (M + H)+ |
| 521 | N-benzyl-N,7,7-trimethyl-5-(2-pyridinyl)-4,5,6,7-tetrahydropyrazolo[1,5-a]pyrimidine-3-carboxamide | MS (ESI, m/z) 376 (M + H)+ |
| 522 | 7,7-dimethyl-3-(4-morpholinylcarbonyl)-5-(2-pyridinyl)-4,5,6,7-tetrahydropyrazolo[1,5-a]pyrimidine | MS (ESI, m/z) 342 (M + H)+ |

TABLE 4-continued

| Example | Structure | Name | Physiological Data |
|---|---|---|---|
| 523 | 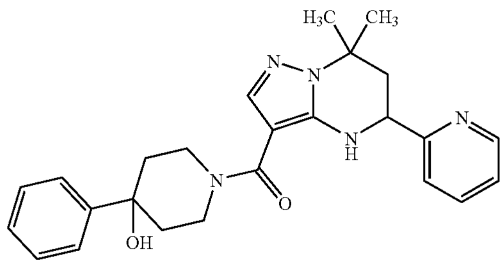 | 1-((7,7-dimethyl-5-(2-pyridinyl)-4,5,6,7-tetrahydropyrazolo[1,5-a]pyrimidin-3-yl)carbonyl)-4-phenyl-4-pipendinol | MS (ESI, m/z) 433 (M + H)+ |
| 524 | 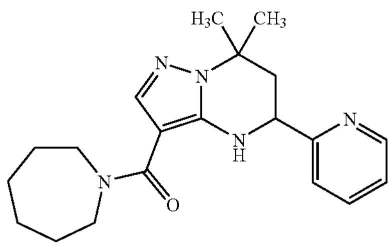 | 3-(1-azepanylcarbonyl)-7,7-dimethyl-5-(2-pyridinyl)-4,5,6,7-tetrahydropyrazolo[1,5-a]pyrimidine | MS (ESI, m/z) 354 (M + H)+ |
| 525 | 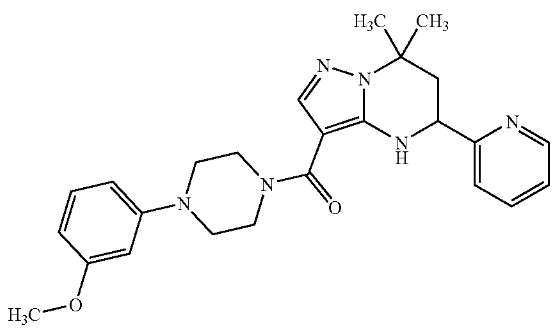 | 3-((4-(3-methoxyphenyl)-1-piperazinyl)carbonyl)-7,7-dimethyl-5-(2-pyridinyl)-4,5,6,7-tetrahydropyrazolo[1,5-a]pyrimidine | MS (ESI, m/z) 448 (M + H)+ |
| 526 | 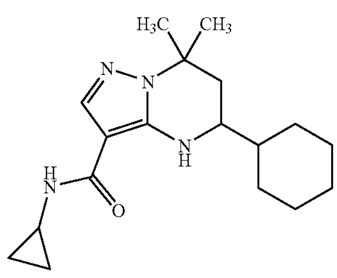 | N-cyclohexyl-N-cyclopropyl-7,7-dimethyl-4,5,6,7-tetrahydropyrazolo[1,5-a]pyrimidine-3-carboxamide | MS (ESI, m/z) 317 (M + H)+ |
| 527 | 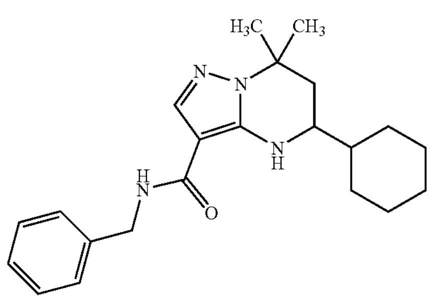 | N-benzyl-5-cyclohexyl-7,7-dimethyl-4,5,6,7-tetrahydropyrazolo[1,5-a]pyrimidine-3-carboxamide | MS (ESI, m/z) 368 (M + H)+ |

TABLE 4-continued

| Example | Structure | Name | Physiological Data |
|---|---|---|---|
| 528 | 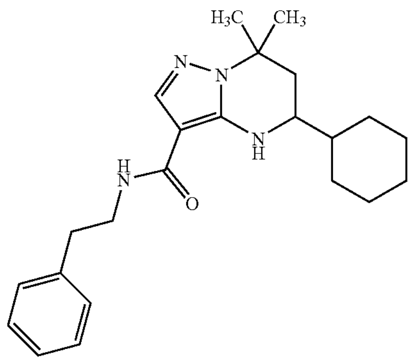 | 5-cyclohexyl-7,7-dimethyl-N-(2-phenylethyl)-4,5,6,7-tetrahydropyrazolo[1,5-a]pyrimidine-3-carboxamide | MS (ESI, m/z) 382 (M + H)+ |
| 529 | 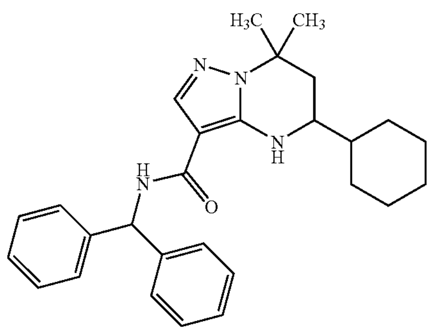 | N-benzhydryl-5-cyclohexyl-7,7-dimethyl-4,5,6,7-tetrahydropyrazolo[1,5-a]pyrimidine-3-carboxamide | MS (ESI, m/z) 444 (M + H)+ |
| 530 | 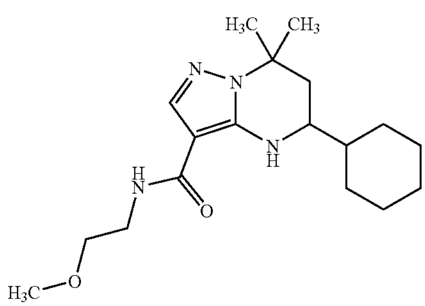 | 5-cyclohexyl-N-(2-methoxyethyl)-7,7-dimethyl-4,5,6,7-tetrahydropyrazolo[1,5-a]pyrimidine-3-carboxamide | MS (ESI, m/z) 335 (M + H)+ |
| 531 | 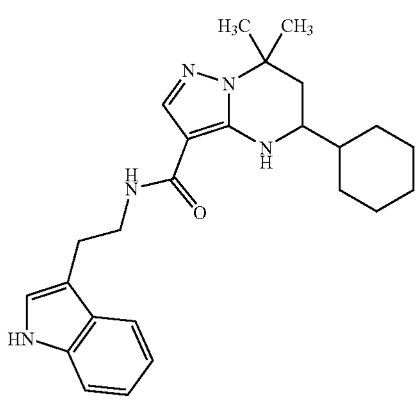 | 5-cyclohexyl-N-(2-(1H-indol-3-yl)ethyl)-7,7-dimethyl-4,5,6,7-tetrahydropyrazolo[1,5-a]pyrimidine-3-carboxamide | MS (ESI, m/z) 421 (M + H)+ |

TABLE 4-continued

| Example | Structure | Name | Physiological Data |
|---|---|---|---|
| 532 | 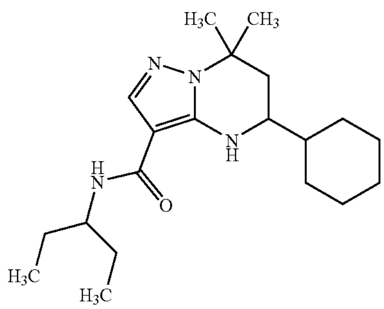 | N-cyclohexyl-N-(1-ethylpropyl)-7,7-dimethyl-4,5,6,7-tetrahydropyrazolo[1,5-a]pyrimidine-3-carboxamide | MS (ESI, m/z) 348 (M + H)+ |
| 533 | 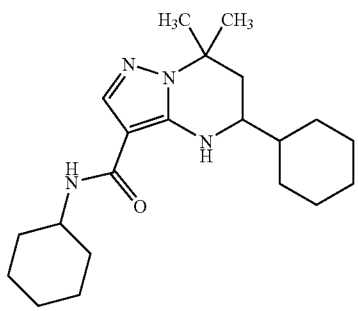 | N,5-dicyclohexyl-7,7-dimethyl-4,5,6,7-tetrahydropyrazolo[1,5-a]pyrimidine-3-carboxamide | MS (ESI, m/z) 360 (M + H)+ |
| 534 | 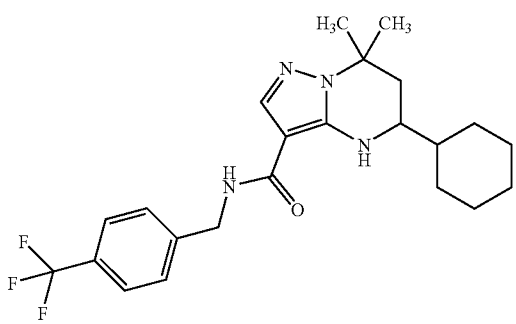 | 5-cyclohexyl-7,7-dimethyl-N-(4-(trifluoromethyl)benzyl)-4,5,6,7-tetrahydropyrazolo[1,5-a-]pyrimidine-3-carboxamide | MS (ESI, m/z) 436 (M + H)+ |
| 535 | 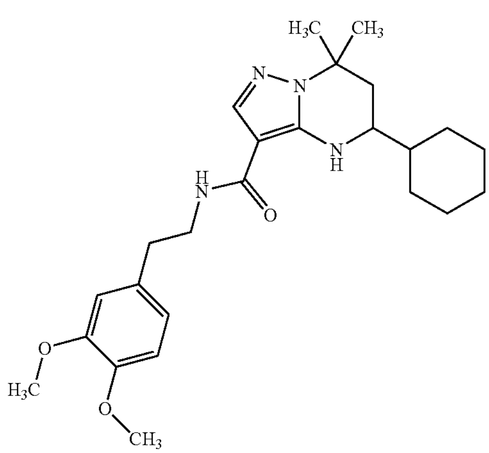 | 5-cyclohexyl-N-(2-(3,4-dimethoxyphenyl)ethyl)-7,7-dimethyl-4,5,6,7-tetrahydropyrazolo[1,5-a]pyrimidine-3-carboxamide | MS (ESI, m/z) 442 (M + H)+ |

TABLE 4-continued

| Example | Structure | Name | Physiological Data |
|---|---|---|---|
| 536 | 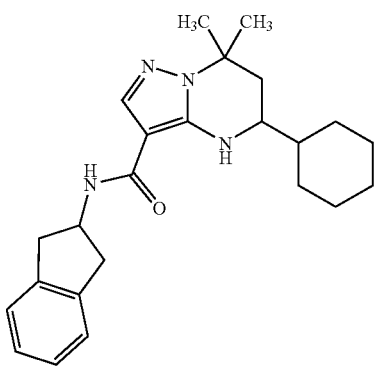 | 5-cyclohexyl-N-2,3-dihydro-1H-inden-2-yl-7,7-dimethyl-4,5,6,7-tetrahydropyrazolo[1,5-a]pyrimidine-3-carboxamide | MS (ESI, m/z) 394 (M + H)+ |
| 537 | 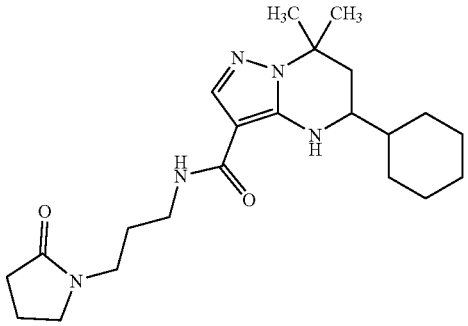 | 5-cyclohexyl-7,7-dimethyl-N-(3-(2-oxo-1-pyrrolidinyl)propyl)-4,5,6,7-tetrahydropyrazolo[1,5-a]pyrimidine-3-carboxamide | MS (ESI, m/z) 403 (M + H)+ |
| 538 | 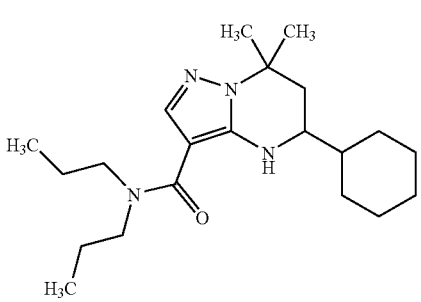 | 5-cyclohexyl-7,7-dimethyl-N,N-dipropyl-4,5,6,7-tetrahydropyrazolo[1,5-a]pyrimidine-3-carboxamide | MS (ESI, m/z) 362 (M + H)+ |
| 539 | 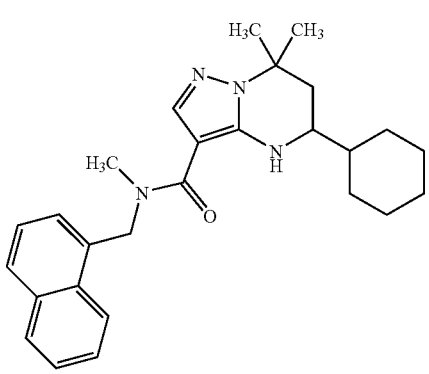 | 5-cyclohexyl-N,7,7-trimethyl-N-(1-naphthylmethyl)-4,5,6,7-tetrahydropyrazolo[1,5-a]pyrimidine-3-carboxamide | MS (ESI, m/z) 432 (M + H)+ |

TABLE 4-continued

| Example | Structure | Name | Physiological Data |
|---|---|---|---|
| 540 | 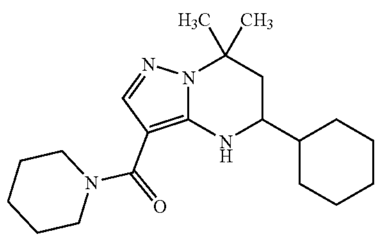 | 5-cyclohexyl-7,7-dimethyl-3-(1-piperidinylcarbonyl)-4,5,6,7-tetrahydropyrazolo[1,5-a]pyrimidine | MS (ESI, m/z) 345 (M + H)+ |
| 541 | 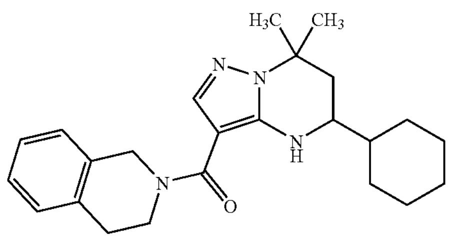 | 2-((5-cyclohexyl-7,7-dimethyl-4,5,6,7-tetrahydropyrazolo[1,5-a]pyrimidin-3-yl)carbonyl)-1,2,3,4-tetrahydroisoquinoline | MS (ESI, m/z) 394 (M + H)+ |
| 542 | 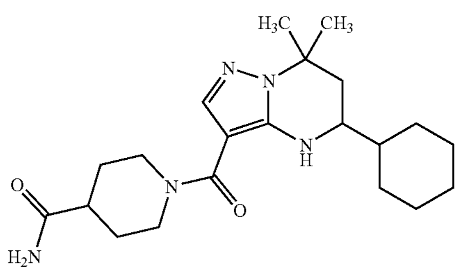 | 1-((5-cyclohexyl-7,7-dimethyl-4,5,6,7-tetrahydropyrazolo[1,5-a]pyrimidin-3-yl)carbonyl)-4-piperidinecarboxamide | MS (ESI, m/z) 389 (M + H)+ |
| 543 | 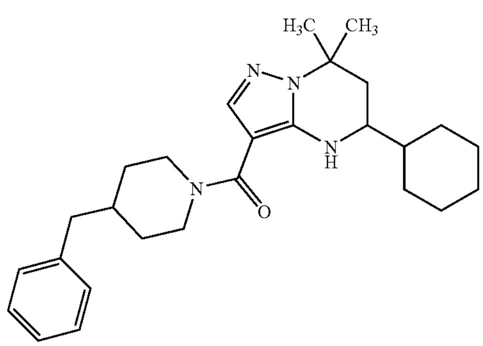 | 3-((4-benzyl-1-piperidinyl-carbonyl)-5-cyclohexyl-7,7-dimethyl-4,5,6,7-tetrahydropyrazolo[1,5-a]pyrimidine | MS (ESI, m/z) 436 (M + H)+ |
| 544 | 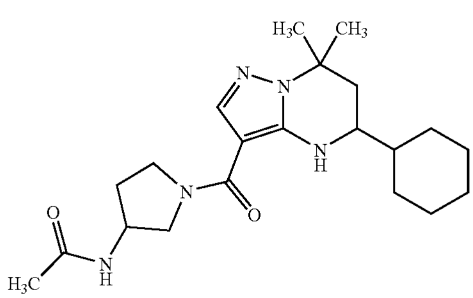 | N-(1-((5-cyclohexyl-7,7-dimethyl-4,5,6,7-tetrahydropyrazolo[1,5-a]pyrimidin-3-yl)carbonyl)-3-pyrrolidinyl)acetamide | MS (ESI, m/z) 389 (M + H)+ |

TABLE 4-continued

| Example | Structure | Name | Physiological Data |
|---|---|---|---|
| 545 | 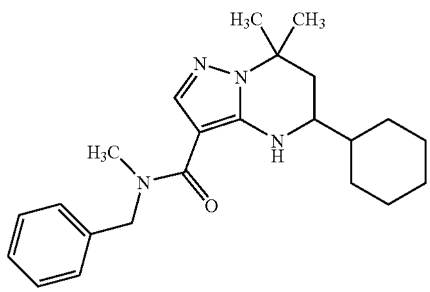 | N-benzyl-5-cyclohexyl-N,7,7-trimethyl-4,5,6,7-tetrahydropyrazolo[1,5-a]pyrimidine-3-carboxamide | MS (ESI, m/z) 382 (M + H)+ |
| 546 | 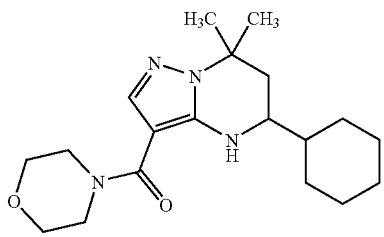 | 5-cyclohexyl-7,7-dimethyl-3-(4-morpholinylcarbonyl)-4,5,6,7-tetrahydropyrazolo[1,5-a]pyrimidine | MS (ESI, m/z) 347 (M + H)+ |
| 547 | 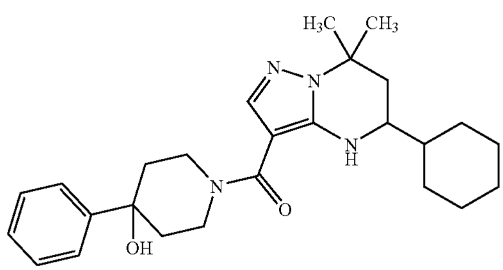 | 1-((5-cyclohexyl-7,7-dimethyl-4,5,6,7-tetrahydropyrazolo[1,5-a]pyrimidin-3-yl)carbonyl)-4-phenyl-4-pipendinol | MS (ESI, m/z) 438 (M + H)+ |
| 548 | 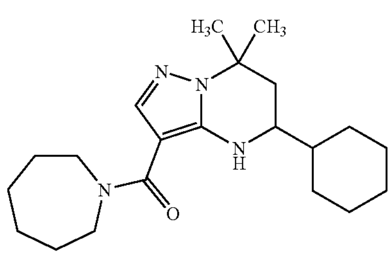 | 3-(1-azepanylcarbonyl)-5-cyclohexyl-7,7-dimethyl-4,5,6,7-tetrahydropyrazolo[1,5-a]pyrimidine | MS (ESI, m/z) 360 (M + H)+ |
| 549 | 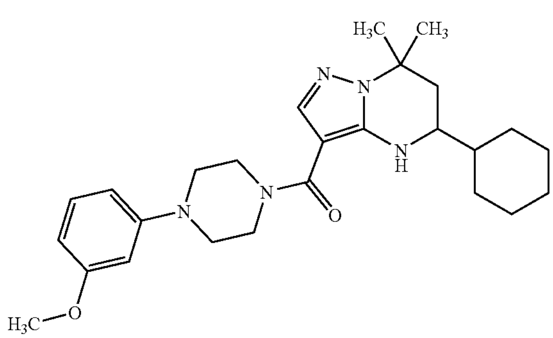 | 5-cyclohexyl-3-((4-(3-methoxyphenyl)-1-piperazinyl)carbonyl)-7,7-dimethyl-4,5,6,7-tetrahydropyrazolo[1,5-a]pyrimidine | MS (ESI, m/z) 453 (M + H)+ |

TABLE 4-continued

| Example | Structure | Name | Physiological Data |
|---|---|---|---|
| 550 | 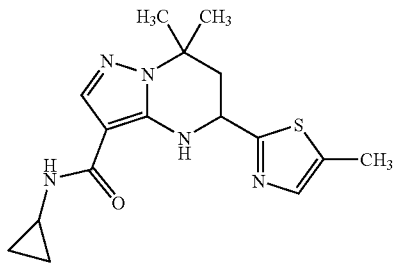 | N-cyclopropyl-7,7-dimethyl-5-(5-methyl-1,3-thiazol-2-yl)-4,5,6,7-tetrahydropyrazolo[1,5-a]pyrimidine-3-carboxamide | MS (ESI, m/z) 332 (M + H)+ |
| 551 | 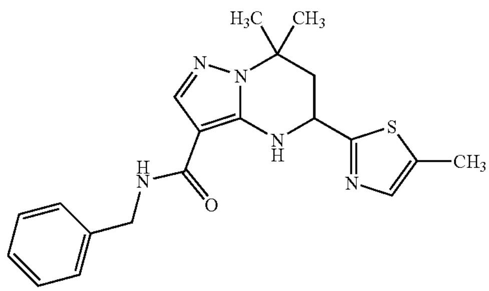 | N-benzyl-7,7-dimethyl-5-(5-methyl-1,3-thiazol-2-yl)-4,5,6,7-tetrahydropyrazolo[1,5-a]pyrimidine-3-carboxamide | MS (ESI, m/z) 382 (M + H)+ |
| 552 | 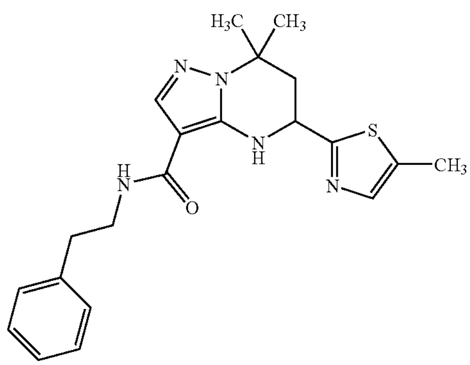 | 7,7-dimethyl-5-(5-methyl-1,3-thiazol-2-yl)-N-(2-phenylethyl)-4,5,6,7-tetrahydropyrazolo[1,5-a]pyrimidine-3-carboxamide | MS (ESI, m/z) 397 (M + H)+ |
| 553 | 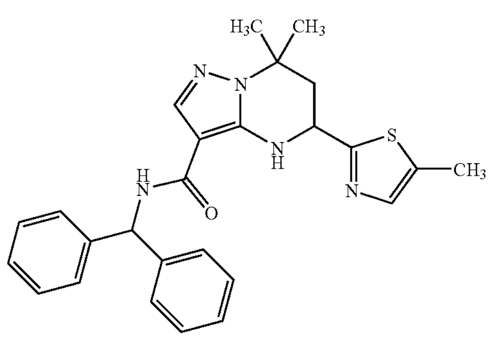 | N-benzhydryl-7,7-dimethyl-5-(5-methyl-1,3-thiazol-2-yl)-4,5,6,7-tetrahydropyrazolo[1,5-a]pyrimidine-3-carboxamide | MS (ESI, m/z) 459 (M + H)+ |
| 554 | 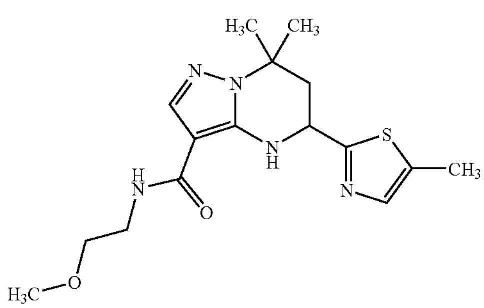 | N-(2-methoxyethyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 350 (M + H)+ |

TABLE 4-continued

| Example | Structure | Name | Physiological Data |
|---|---|---|---|
| 555 | 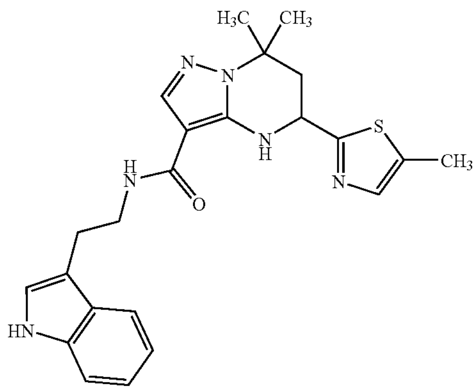 | N-(2-(1H-indol-3-yl)ethyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 436 (M + H)+ |
| 556 | 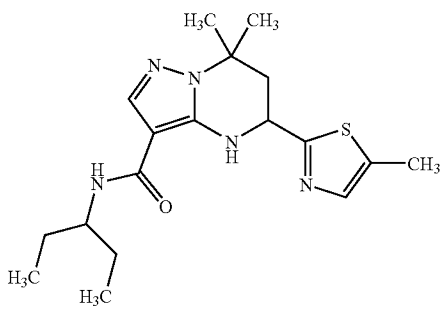 | N-(1-ethylpropyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 363 (M + H)+ |
| 557 | 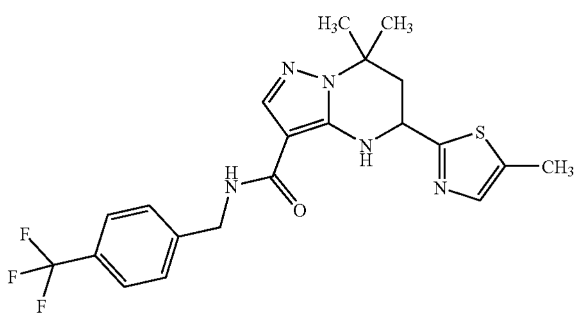 | 7,7-dimethyl-5-(5-methyl-1,3-thiazol-2-yl)-N-(4-(trifluoromethyl)benzyl)-4,5,6,7-tetrahydropyrazolo[1,5-a]pyrimidine-3-carboxamide | MS (ESI, m/z) 450 (M + H)+ |
| 558 | 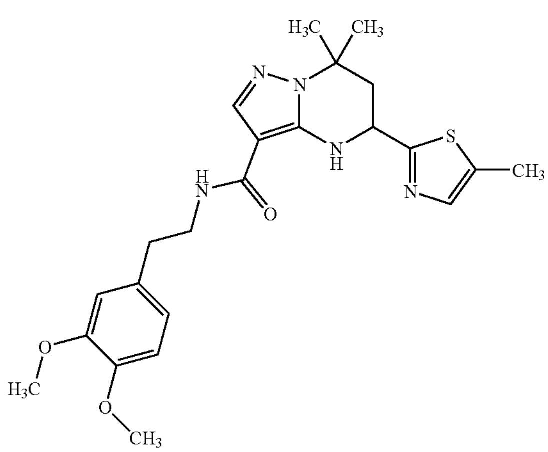 | N-(2-(3,4-dimethoxyphenyl)ethyl)-7,7-dimethyl-5-(5-methyl-1,3-thiazol-2-yl)-4,5,6,7-tetrahydropyrazolo[1,5-a]pyrimidine-3-carboxamide | MS (ESI, m/z) 457 (M + H)+ |

TABLE 4-continued

| Example | Structure | Name | Physiological Data |
|---|---|---|---|
| 559 | 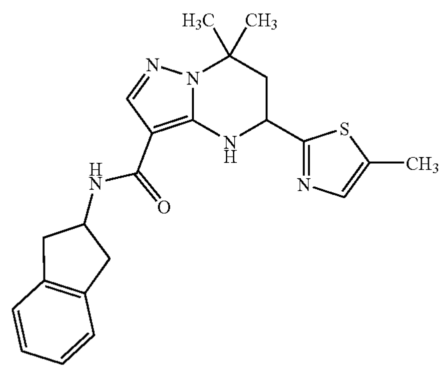 | N-2,3-dihydro-1H-inden-2-yl-7,7-dimethyl-5-(5-methyl-1,3-thiazol-2-yl)-4,5,6,7-tetrahydropyrazolo[1,5-a]pyrimidine-3-carboxamide | MS (ESI, m/z) 409 (M + H)+ |
| 560 | 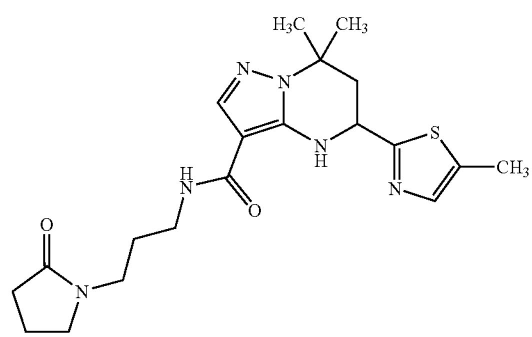 | 7,7-dimethyl-5-(5-methyl-1,3-thiazol-2-yl)-N-(3-(2-oxo-1-pyrrolidinyl)propyl)-4,5,6,7-tetrahydropyrazolo[1,5-a]pyrimidine-3-carboxamide | MS (ESI, m/z) 418 (M + H)+ |
| 561 | 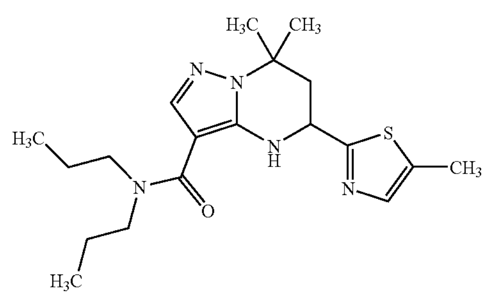 | 7,7-dimethyl-5-(5-methyl-1,3-thiazol-2-yl)-N,N-dipropyl-4,5,6,7-tetrahydropyrazolo[1,5-a]pyrimidine-3-carboxamide | MS (ESI, m/z) 377 (M + H)+ |
| 562 | 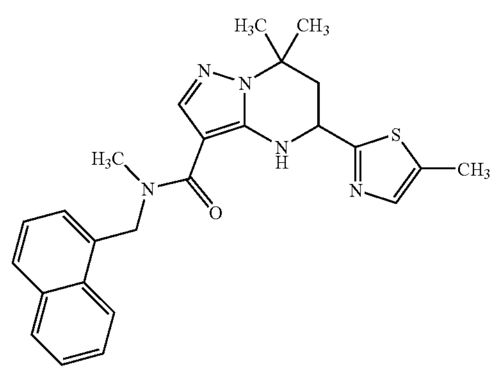 | N,7,7-trimethyl-5-(5-methyl-1,3-thiazol-2-yl)-N-(1-naphthylmethyl)-4,5,6,7-tetrahydropyrazolo[1,5-a]pyrimidine-3-carboxamide | MS (ESI, m/z) 447 (M + H)+ |

TABLE 4-continued

| Example | Structure | Name | Physiological Data |
|---|---|---|---|
| 563 | 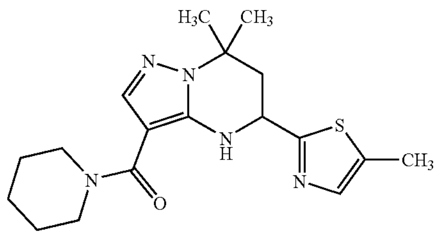 | 7,7-dimethyl-5-(5-methyl-1,3-thiazol-2-yl)-3-(1-piperidinylcarbonyl)-4,5,6,7-tetrahydropyrazolo[1,5-a]pyrimidine | MS (ESI, m/z) 360 (M + H)+ |
| 564 | 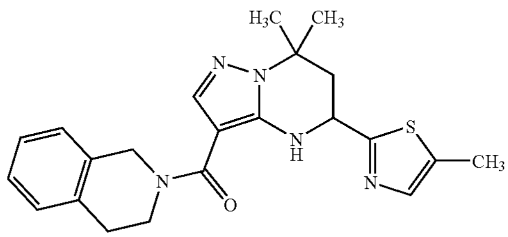 | 2-((7,7-dimethyl-5-(5-methyl-1,3-thiazol-2-yl)-4,5,6,7-tetrahydropyrazolo[1,5-a]pyrimidin-3-yl)carbonyl)-1,2,3,4-tetrahydroisoquinoline | MS (ESI, m/z) 409 (M + H)+ |
| 565 | 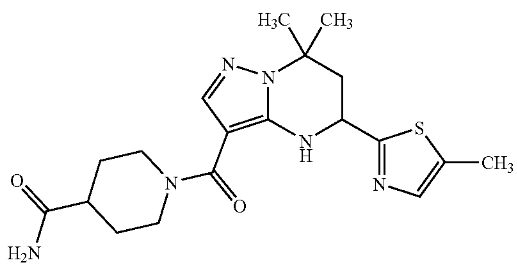 | 1-((7,7-dimethyl-5-(5-methyl-1,3-thiazol-2-yl)-4,5,6,7-tetrahydropyrazolo[1,5-a]pyrimidin-3-yl)carbonyl)-4-piperidinecarboxamide | MS (ESI, m/z) 404 (M + H)+ |
| 566 | 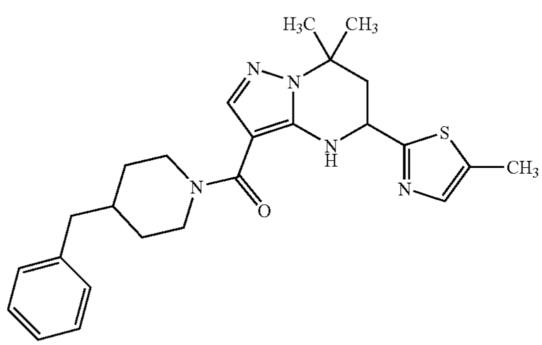 | 3-((4-benzyl-1-piperidinyl)carbonyl)-7,7-dimethyl-5-(5-methyl-1,3-thiazol-2-yl)-4,5,6,7-tetrahydropyrazolo[1,5-a]pyrimidine | MS (ESI, m/z) 451 (M + H)+ |
| 567 | 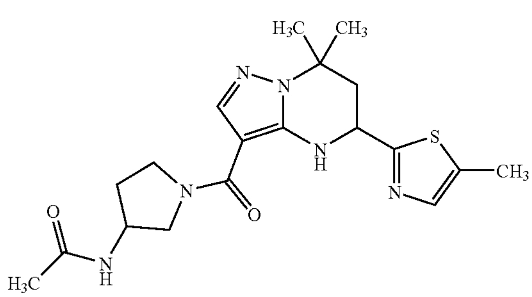 | N-(1-((7,7-dimethyl-5-(5-methyl-1,3-thiazol-2-yl)-4,5,6,7-tetrahydropyrazolo[1,5-a]pyrimidin-3-yl)carbonyl)-3-pyrrolidinyl)acetamide | MS (ESI, m/z) 404 (M + H)+ |

TABLE 4-continued

| Example | Structure | Name | Physiological Data |
|---|---|---|---|
| 568 | 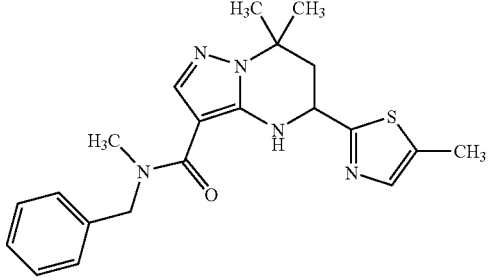 | N-benzyl-N,7,7-trimethyl-5-(5-methyl-1,3-thiazol-2-yl)-4,5,6,7-tetrahydropyrazolo[1,5-a]pyrimidine-3-carboxamade | MS (ESI, m/z) 397 (M + H)+ |
| 569 | 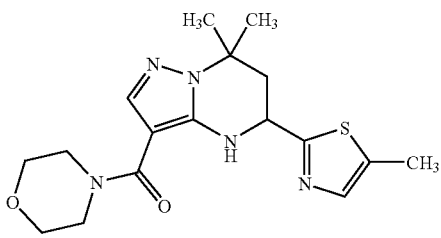 | 7,7-dimethyl-5-(5-methyl-1,3-thiazol-2-yl)-3-(4-morpholinylcarbonyl)-4,5,6,7-tetrahydropyrazolo[1,5-a]pyrimidine | MS (ESI, m/z) 362 (M + H)+ |
| 570 | 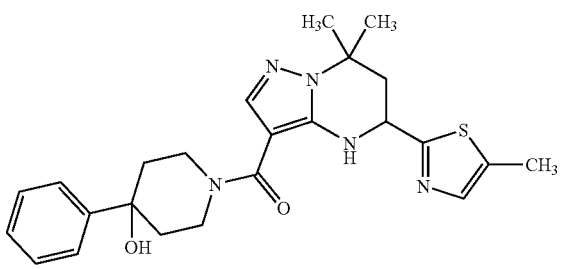 | 1-((7,7-dimethyl-5-(5-methyl-1,3-thiazol-2-yl)-4,5,6,7-tetrahydropyrazolo[1,5-a]pyrimidin-3-yl)carbonyl)-4-phenyl-4-piperidinol | MS (ESI, m/z) 453 (M + H)+ |
| 571 | 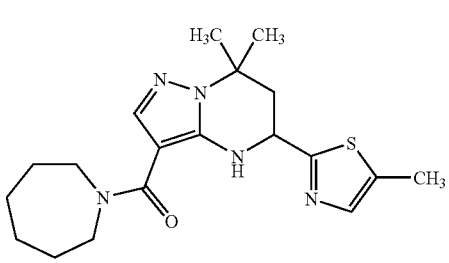 | 3-(1-azepanylcarbonyl)-7,7-dimethyl-5-(5-methyl-1,3-thiazol-2-yl)-4,5,6,7-tetrahydropyrazolo[1,5-a]pyrimidine | MS (ESI, m/z) 375 (M + H)+ |
| 572 | 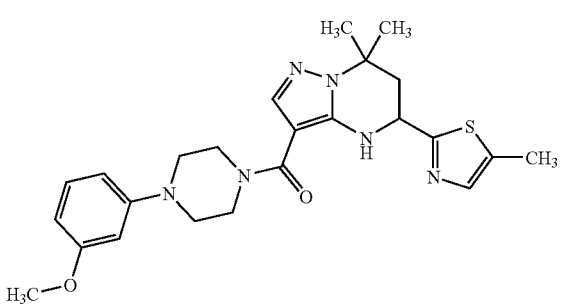 | 3-((4-(3-methoxyphenyl)-1-piperazinyl)carbonyl)-7,7-dimethyl-5-(5-methyl-1,3-thiazol-2-yl)-4,5,6,7-tetrahydropyrazolo[1,5-a]pyrimidine | MS (ESI, m/z) 468 (M + H)+ |

TABLE 4-continued

| Example | Structure | Name | Physiological Data |
|---|---|---|---|
| 573 | 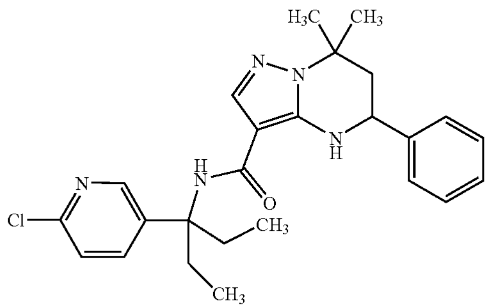 | N-(1-(6-chloro-3-pyridinyl)-1-ethylpropyl)-7,7-dimethyl-5-phenyl-4,5,6,7-tetrahydropyrazolo[1,5-a]pyrimidine-3-carboxamide | mp 223-224° C. |
| 574 | 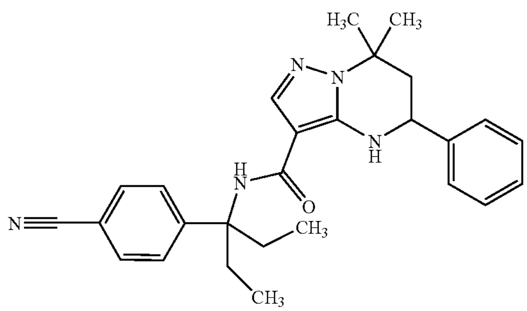 | N-(1-(4-cyanophenyl)-1-ethylpropyl)-7,7-dimethyl-5-phenyl-4,5,6,7-tetrahydropyrazolo[1,5-a]pyrimidine-3-carboxamide | mp 237-238° C. |
| 575 | 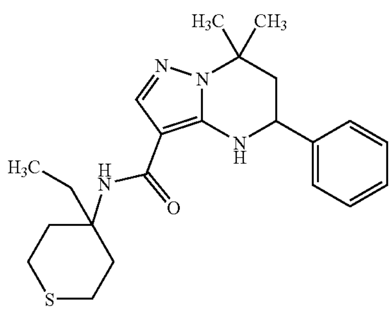 | N-(4-ethyltetrahydro-2H-thiopyran-4-yl)-7,7-dimethyl-5-phenyl-4,5,6,7-tetrahydropyrazolo[1,5-a]pyrimidine-3-carboxamide | mp 97-98° C. |
| 576 | 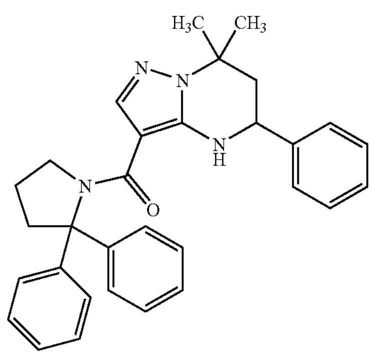 | 3-((2,2-diphenyl-1-pyrrolidinyl)carbonyl)-7,7-dimethyl-5-phenyl-4,5,6,7-tetrahydropyrazolo[1,5-a]pyrimidine | MS (ESI, m/z) 477 (M + H)+ |
| 577 | 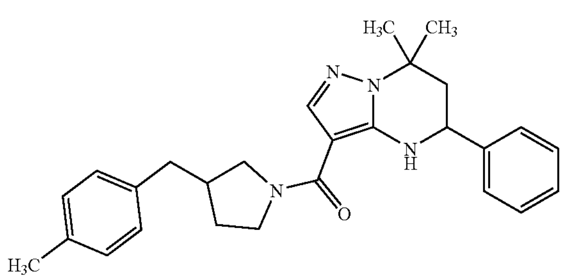 | 7,7-dimethyl-3-((3-(4-methylbenzyl)-1-pyrrolidinyl)carbonyl)-5-phenyl-4,5,6,7-tetrahydropyrazolo[1,5-a]pyrimidine | MS (ESI, m/z) 429 (M + H)+ |

TABLE 4-continued

| Example | Name | Physiological Data |
|---|---|---|
| 578 | 3-((3-(2-chlorobenzyl)-1-pyrrolidinyl)carbonyl)-7,7-dimethyl-5-phenyl-4,5,6,7-tetrahydropyrazolo[1,5-a]pyrimidine | MS (ESI, m/z) 449 (M + H)+ |
| 579 | N-(2,2-bis(4-methoxyphenyl)ethyl)-7,7-dimethyl-5-phenyl-4,5,6,7-tetrahydropyrazolo[1,5-a]pyrimidine-3-carboxamide | MS (ESI, m/z) 511 (M + H)+ |
| 580 | N-(2,2-bis(4-methoxyphenyl)propyl)-7,7-dimethyl-5-phenyl-4,5,6,7-tetrahydropyrazolo[1,5-a]pyrimidine-3-carboxamide | MS (ESI, m/z) 525 (M + H)+ |
| 581 | N-1-adamantyl-5-(2-methoxyphenyl)-7,7-dimethyl-4,5,6,7-tetrahydropyrazolo[1,5-a]pyrimidine-3-carboxamide | mp 280-282° C. |

TABLE 4-continued

| Example | Structure | Name | Physiological Data |
|---------|-----------|------|--------------------|
| 582 | 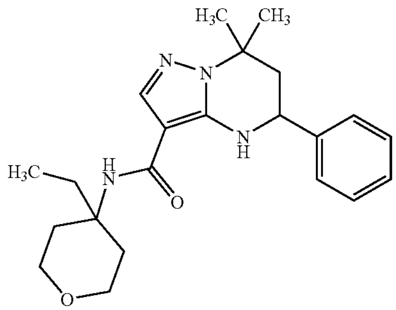 | N-(4-ethyltetrahydro-2H-pyran-4-yl)-7,7-dimethyl-5-phenyl-4,5,6,7-tetrahydropyrazolo[1,5-a]pyrimidine-3-carboxamide | mp 104-105° C. |
| 583 | 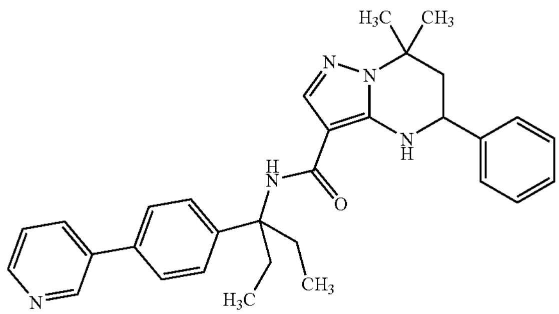 | N-(1-ethyl-1-(4-(3-pyridinyl)phenyl)propyl)-7,7-dimethyl-5-phenyl-4,5,6,7-tetrahydropyrazolo[1,5-a]pyrimidine-3-carboxamide | 2HCl salt mp 168-169° C. |
| 584 | 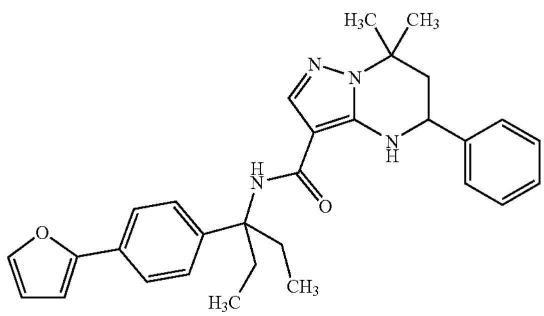 | N-(1-ethyl-1-(4-(2-furyl)phenyl)propyl)-7,7-dimethyl-5-phenyl-4,5,6,7-tetrahydropyrazolo[1,5-a]pyrimidine-3-carboxamide | mp 167-168° C. |
| 585 | 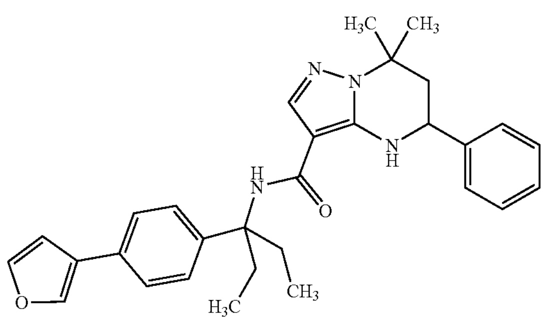 | N-(1-ethyl-1-(4-(3-furyl)phenyl)propyl)-7,7-dimethyl-5-phenyl-4,5,6,7-tetrahydropyrazolo[1,5-a]pyrimidine-3-carboxamide | mp 185-186° C. |
| 586 | 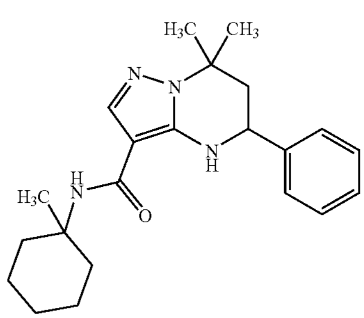 | 7,7-dimethyl-N-(1-methylcyclohexyl)-5-phenyl-4,5,6,7-tetrahydropyrazolo[1,5-a]pyrimidine-3-carboxamide | mp 170-171° C. |

TABLE 4-continued

| Example | Structure | Name | Physiological Data |
|---|---|---|---|
| 587 | 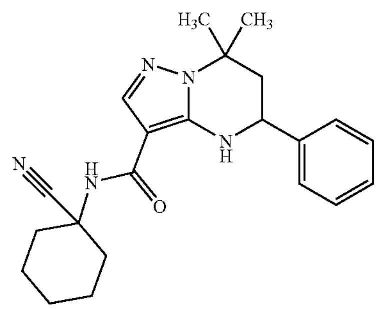 | N-(1-ethynylcyclohexyl)-7,7-dimethyl-5-phenyl-4,5,6,7-tetrahydropyrazolo[1,5-a]pyrimidine-3-carboxamide | mp 201-202° C. |
| 588 | 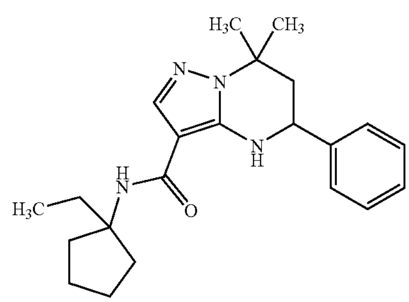 | N-(1-ethylcyclopentyl)-7,7-dimethyl-5-phenyl-4,5,6,7-tetrahydropyrazolo[1,5-a]pyrimidine-3-carboxamide | HCl salt mp 140-142° C. |
| 589 | 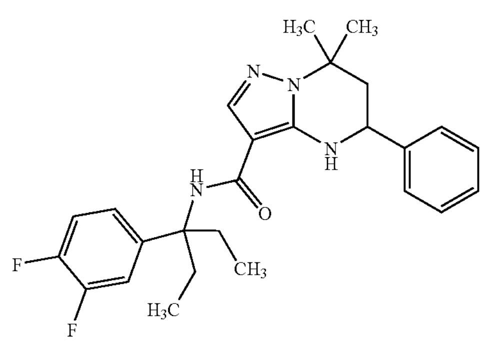 | N-(1-(3,4-difluorophenyl)-1-ethylpropyl)-7,7-dimethyl-5-phenyl-4,5,6,7-tetrahydropyrazolo[1,5-a]pyrimidine-3-carboxamide | mp 171-172° C. |
| 590 | 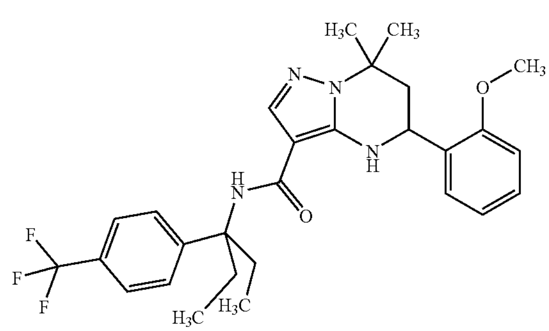 | N-(1-ethyl-1-(4-(trifluoromethyl)phenyl)propyl)-5-(2-methoxyphenyl)-7,7-dimethyl-4,5,6,7-tetrahydropyrazolo[1,5-a]pyrimidine-3-carboxamide | mp 211-213° C. |

TABLE 4-continued

| Example | Structure | Name | Physiological Data |
|---|---|---|---|
| 591 | 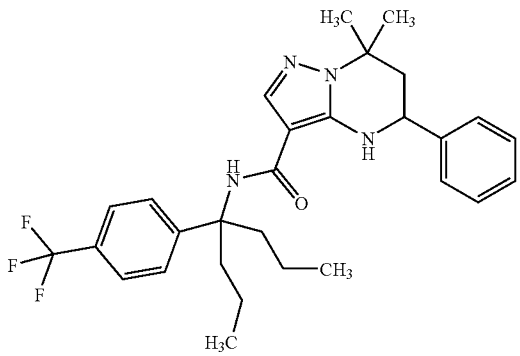 | 1-propyl-1-(4-(trifluoromethyl)phenyl)butyl 7,7-dimethyl-5-phenyl-4,5,6,7-tetrahydropyrazolo[1,5-a]pyrimidine-3-carboxylate | MS (ESI, m/z) 514 (M + H)+ |
| 592 | 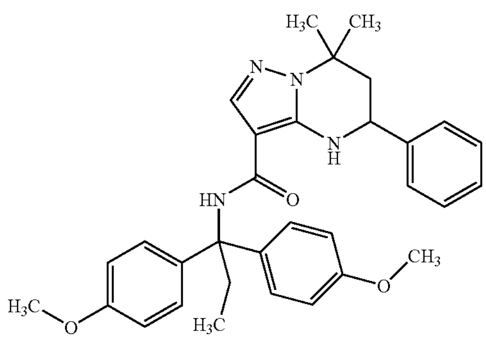 | N-(1,1-bis(4-methoxyphenyl)propyl)-7,7-dimethyl-5-phenyl-4,5,6,7-tetrahydropyrazolo[1,5-a]pyrimidine-3-carboxamide | MS (ESI, m/z) 525 (M + H)+ |
| 593 | 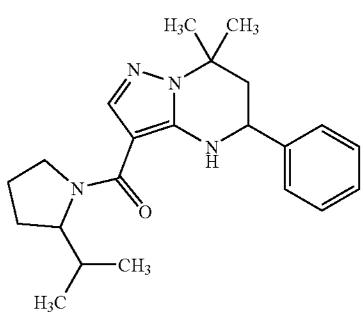 | 3-((2-isopropyl-1-pyrrolidinyl)carbonyl)-7,7-dimethyl-5-phenyl-4,5,6,7-tetrahydropyrazolo[1,5-a]pyrimidine | MS (ESI, m/z) 367 (M + H)+ |
| 594 | 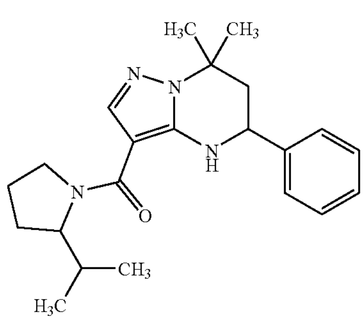 | 3-((2-isopropyl-1-pyrrolidinyl)carbonyl)-7,7-dimethyl-5-phenyl-4,5,6,7-tetrahydropyrazolo[1,5-a]pyrimidine | MS (ESI, m/z) 367 (M + H)+ |

TABLE 4-continued

| Example | Name | Physiological Data |
|---|---|---|
| 595 | 3-((2-isobutyl-1-pyrrolidinyl)carbonyl)-7,7-dimethyl-5-phenyl-4,5,6,7-tetrahydropyrazolo[1,5-a]pyrimidine | MS (ESI, m/z) 381 (M + H)+ |
| 596 | 3-((2-cyclohexyl-1-pyrrolidinyl)carbonyl)-7,7-dimethyl-5-phenyl-4,5,6,7-tetrahydropyrazolo[1,5-a]pyrimidine | MS (ESI, m/z) 407 (M + H)+ |
| 597 | ethyl 4-benzyl-1-((7,7-dimethyl-5-phenyl-4,5,6,7-tetrahydropyrazolo[1,5-a]pyrimidin-3-yl)carbonyl)-4-piperidinecarboxylate | MS (ESI, m/z) 407 (M + H)+ |
| 598 | ethyl 3-benzyl-1-((7,7-dimethyl-5-phenyl-4,5,6,7-tetrahydropyrazolo[1,5-a]pyrimidin-3-yl)carbonyl)-3-piperidinecarboxylate | MS (ESI, m/z) 501 (M + H)+ |
| 599 | 7,7-dimethyl-5-phenyl-3-((3-phenyl-1-pyrrolidinyl)carbonyl)-4,5,6,7-tetrahydropyrazolo[1,5-a]pyrimidine | MS (ESI, m/z) 501 (M + H)+ |

TABLE 4-continued

| Example | Structure | Name | Physiological Data |
|---|---|---|---|
| 600 | 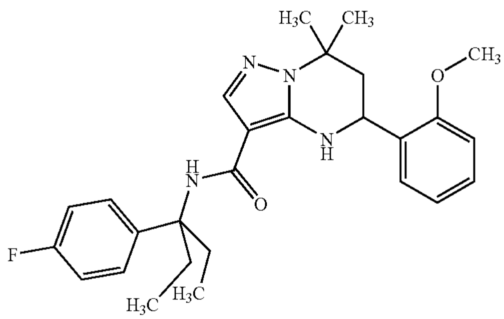 | N-(1-ethyl-1-(4-fluorophenyl)propyl)-5-(2-methoxyphenyl)-7,7-dimethyl-4,5,6,7-tetrahydropyrazolo[1,5-a]pyrimidine-3-carboxamide | mp 206.2-206.3° C. |
| 601 | 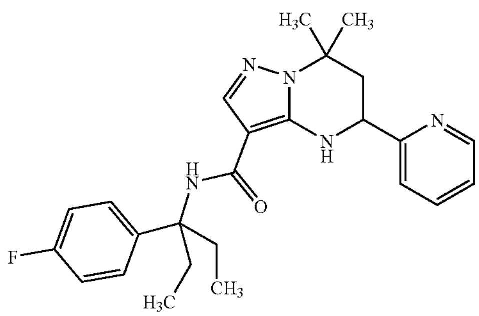 | N-(1-ethyl-1-(4-fluorophenyl)propyl)-7,7-dimethyl-5-(2-pyridinyl)-4,5,6,7-tetrahydropyrazolo[1,5-a]pyrimidine-3-carboxamide | mp 167-169° C. |
| 602 | 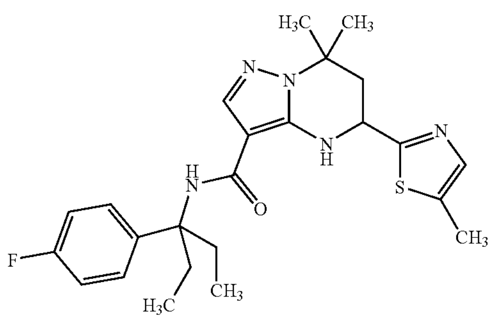 | N-(1-ethyl-1-(4-fluorophenyl)propyl)-7,7-dimethyl-5-(5-methyl-1,3-thiazol-2-yl)-4,5,6,7-tetrahydropyrazolo[1,5-a]pyrimidine-3-carboxamide | mp 163.5-163.6° C. |
| 603 | 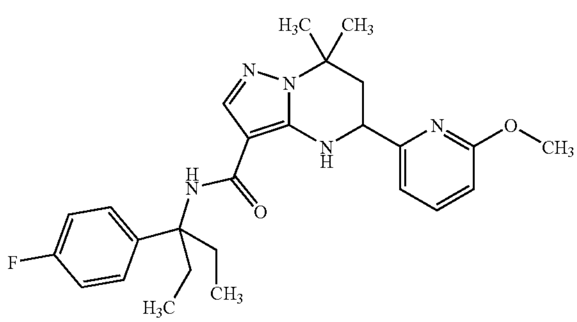 | N-(1-ethyl-1-(4-fluorophenyl)propyl)-5-(6-methoxy-2-pyridinyl)-7,7-tetrahydropyrazolo[1,5-a]pyrimidine-3-carboxamide | mp 156-157° C. |

TABLE 4-continued

| Example | Structure | Name | Physiological Data |
|---|---|---|---|
| 604 | 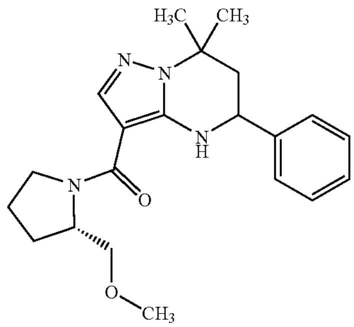 | 3-(((2S)-2-(methoxymethyl)-1-pyrrolidinyl)carbonyl)-7,7-dimethyl-5-phenyl-4,5,6,7-tetrahydropyrazolo[1,5-a]pyrimidine | MS (ESI, m/z) 369 (M + H)+ |
| 605 | 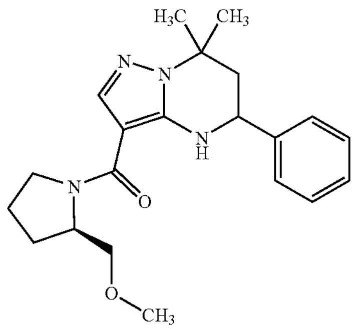 | 3-(((2R)-2-(methoxymethyl)-1-pyrrolidinyl)carbonyl)-7,7-dimethyl-5-phenyl-4,5,6,7-tetrahydropyrazolo[1,5-a]pyrimidine | MS (ESI, m/z) 369 (M + H)+ |
| 606 | 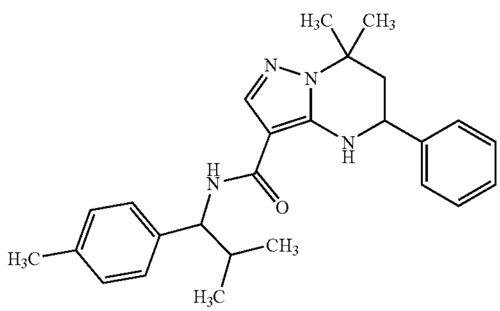 | 7,7-dimethyl-N-(2-methyl-1-(4-methylphenyl)propyl)-5-phenyl-4,5,6,7-tetrahydropyrazolo[1,5-a]pyrimidine-3-carboxamide | MS (ESI, m/z) 417 (M + H)+ |
| 607 | 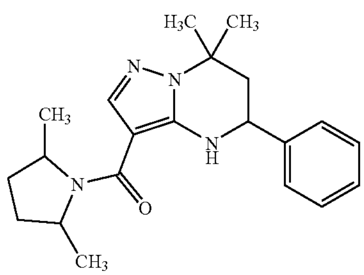 | 3-((2,5-dimethyl-1-pyrrolidinyl)carbonyl)-7,7-dimethyl-5-phenyl-4,5,6,7-tetrahydropyrazolo[1,5-a]pyrimidine | MS (ESI, m/z) 353 (M + H)+ |
| 608 | 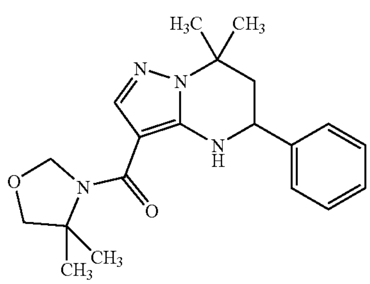 | 3-((4,4-dimethyl-1,3-oxazolidin-3-yl)carbonyl)-7,7-dimethyl-5-phenyl-4,5,6,7-tetrahydropyrazolo[1,5-a]pyrimidine | MS (ESI, m/z) 355 (M + H)+ |

TABLE 4-continued

| Example | Structure | Name | Physiological Data |
|---|---|---|---|
| 609 | 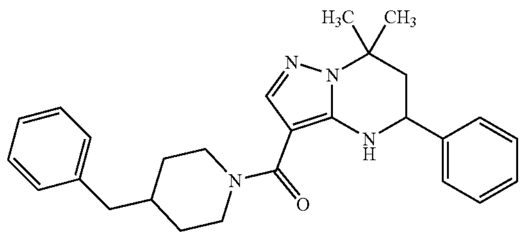 | 3-((4-benzyl-1-piperidinyl)carbonyl)-7,7-dimethyl-5-phenyl-4,5,6,7-tetrahydropyrazolo[1,5-a]pyrimidine | MS (ESI, m/z) 429 (M + H)+ |
| 610 | 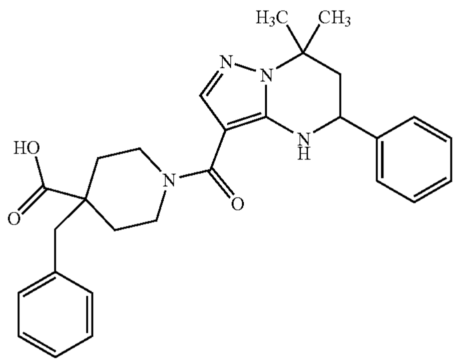 | 4-benzyl-1-((7,7-dimethyl-5-phenyl-4,5,6,7-tetrahydropyrazolo[1,5-a]pyrimidin-3-yl)carbonyl)-4-piperidinecarboxylic acid | MS (ESI, m/z) 473 (M + H)+ |
| 611 | 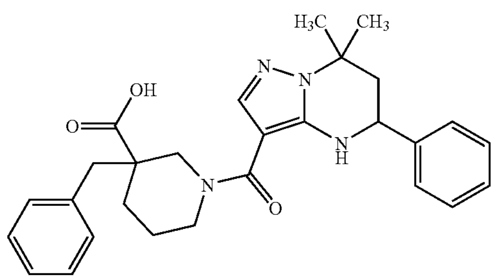 | 3-benzyl-1-((7,7-dimethyl-5-phenyl-4,5,6,7-tetrahydropyrazolo[1,5-a]pyrimidin-3-yl)carbonyl)-3-piperidinecarboxylic acid | MS (ESI, m/z) 473 (M + H)+ |
| 612 | 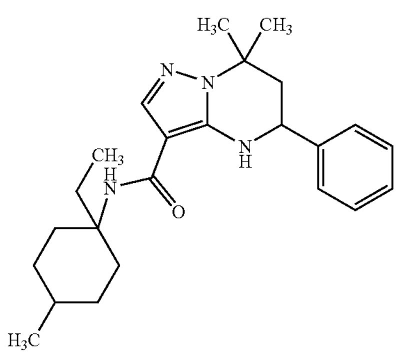 | N-(1-ethyl-4-methylcyclohexyl)-7,7-dimethyl-5-phenyl-4,5,6,7-tetrahydropyrazolo[1,5-a]pyrimidine-3-carboxamide | mp 160-161° C. |
| 613 | 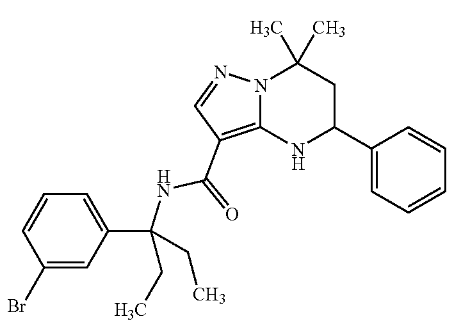 | N-(1-(3-bromophenyl)-1-ethylpropyl)-7,7-dimethyl-5-phenyl-4,5,6,7-tetrahydropyrazolo[1,5-a]pyrimidine-3-carboxamide | mp 195-196° C. |

TABLE 4-continued

| Example | Structure | Name | Physiological Data |
|---|---|---|---|
| 614 | 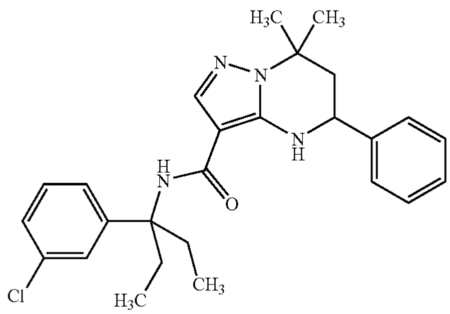 | N-(1-(3-chlorophenyl)-1-ethylpropyl)-7,7-dimethyl-5-phenyl-4,5,6,7-tetrahydropyrazolo[1,5-a]pyrimidine-3-carboxamide | mp 195-196° C. |
| 615 | 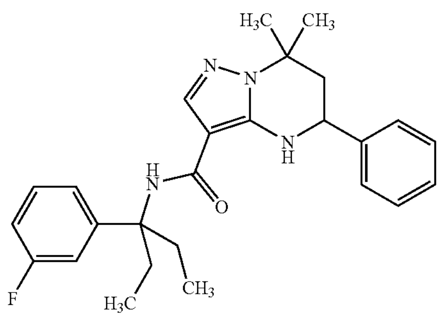 | N-(1-ethyl-1-(3-fluorophenyl)propyl)-7,7-dimethyl-5-phenyl-4,5,6,7-tetrahydropyrazolo[1,5-a]pyrimidine-3-carboxamide | mp 180-181° C. |
| 616 | 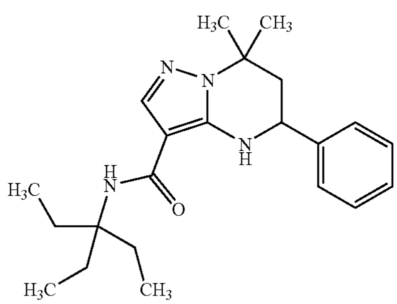 | N-(1,1-diethylpropyl)-7,7-dimethyl-5-phenyl-4,5,6,7-tetrahydropyrazolo[1,5-a]pyrimidine-3-carboxamide | mp 93-94° C. |
| 617 | 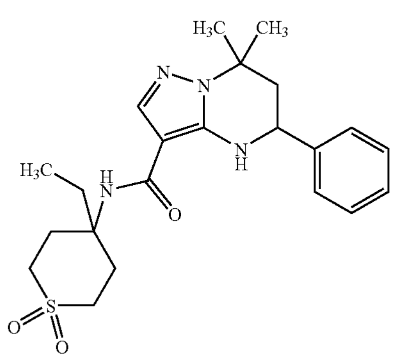 | N-(4-ethyl-1,1-dioxidotetrahydro-2H-thiopyran-4-yl)-7,7-dimethyl-5-phenyl-4,5,6,7-tetrahydropyrazolo[1,5-a]pyrimidine-3-carboxamide | mp 155-156° C. |

TABLE 4-continued

| Example | Structure | Name | Physiological Data |
|---------|-----------|------|--------------------|
| 618 | 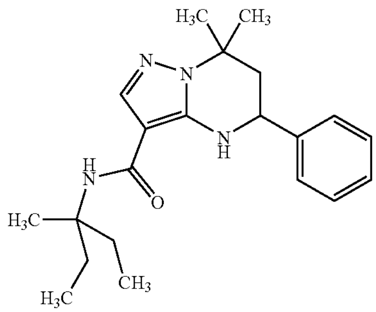 | N-(1-ethyl-1-methylpropyl)-7,7-dimethyl-5-phenyl-4,5,6,7-tetrahydropyrazolo[1,5-a]pyrimidine-3-carboxamide | mp 88-89° C. |
| 619 | 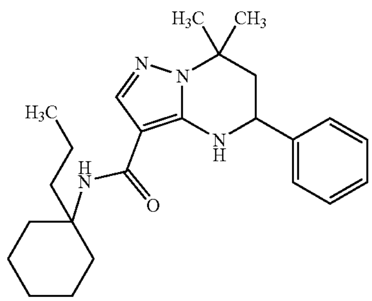 | 7,7-dimethyl-5-phenyl-N-(1-propylcyclohexyl)-4,5,6,7-tetrahydropyrazolo[1,5-a]pyrimidine-3-carboxamide | mp 152-153° C. |
| 620 | 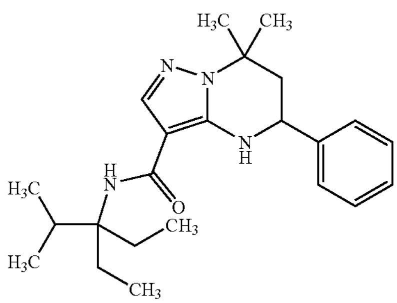 | N-(1,1-diethyl-2-methylpropyl)-7,7-dimethyl-5-phenyl-4,5,6,7-tetrahydropyrazolo[1,5-a]pyrimidine-3-carboxamide | mp 155-156° C. |
| 621 | 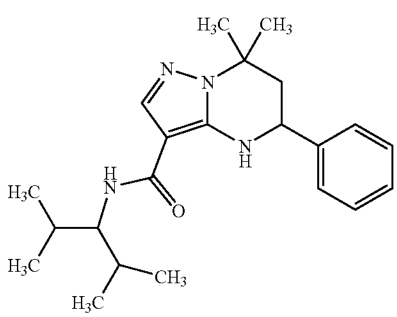 | N-(1-isopropyl-2-methylpropyl)-7,7-dimethyl-5-phenyl-4,5,6,7-tetrahydropyrazolo[1,5-a]pyrimidine-3-carboxamide | mp 168-169° C. |
| 622 | 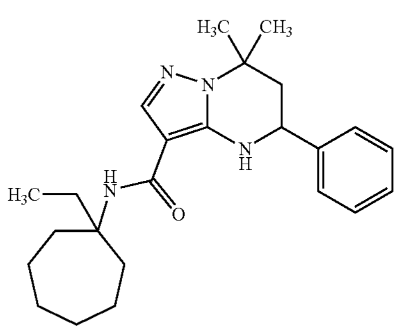 | N-(1-ethylcycloheptyl)-7,7-dimethyl-5-phenyl-4,5,6,7-tetrahydropyrazolo[1,5-a]pyrimidine-3-carboxamide | mp 129-130° C. |

TABLE 4-continued

| Example | Structure | Name | Physiological Data |
|---|---|---|---|
| 623 | 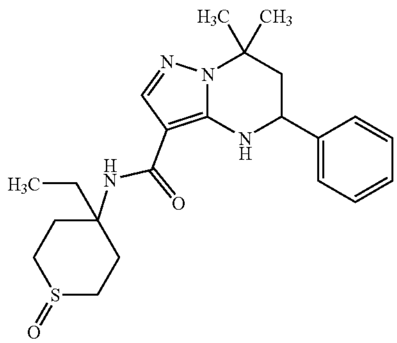 | N-(4-ethyl-1-oxidotetrahydro-2H-thiopyran-4-yl)-7,7-dimethyl-5-phenyl-4,5,6,7-tetrahydropyrazolo[1,5-a]pyrimidine-3-carboxamide | mp 172-173° C. |
| 624 | 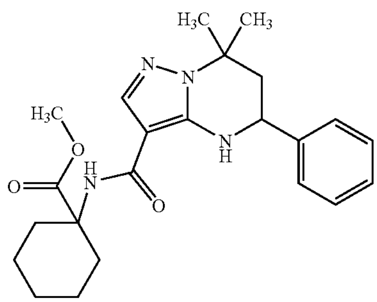 | methyl 1-(((7,7-dimethyl-5-phenyl-4,5,6,7-tetrahydropyrazolo[1,5-a]pyrimidin-3-yl)carbonyl)amino)cyclohexanecarboxylate | mp 184-185° C. |
| 625 | 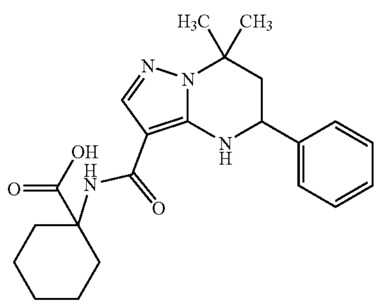 | 1-(((7,7-dimethyl-5-phenyl-4,5,6,7-tetrahydropyrazolo[1,5-a]pyrimidin-3-yl)carbonyl)amino)cyclohexanecarboxylic acid | mp 215-216° C. |
| 626 | 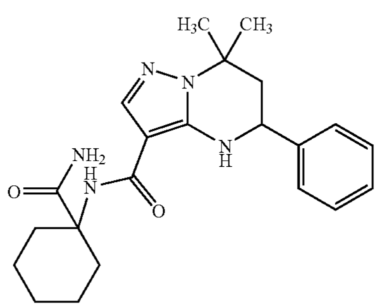 | N-(1-(aminocarbonyl)cyclohexyl)-7,7-dimethyl-5-phenyl-4,5,6,7-tetrahydropyrazolo[1,5-a]pyrimidine-3-carboxamide | mp 140-141° C. |
| 627 | 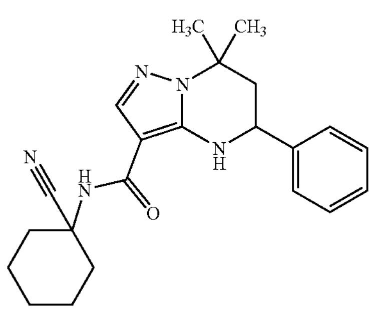 | N-(1-cyanocyclohexyl)-7,7-dimethyl-5-phenyl-4,5,6,7-tetrahydropyrazolo[1,5-a]pyrimidine-3-carboxamide | mp >300° C. |

TABLE 4-continued

| Example | Structure | Name | Physiological Data |
|---|---|---|---|
| 628 | 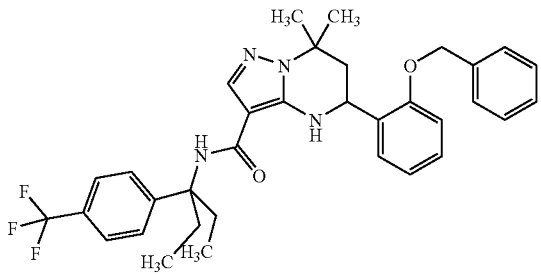 | 5-(2-(benzyloxy)phenyl)-N-(1-ethyl-1-(4-(trifluoromethyl)phenyl)propyl)-7,7-dimethyl-4,5,6,7-tetrahydropyrazolo[1,5-a]pyrimidine-3-carboxamide | MS(ESI, m/z) 591 (M + H)+ |
| 629 | 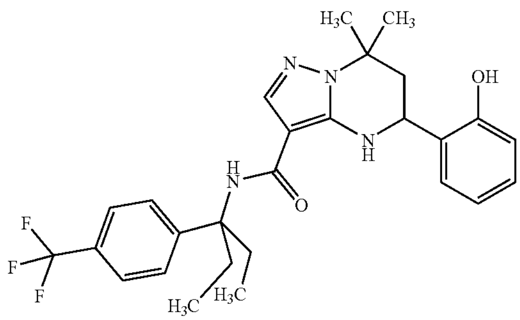 | N-(1-ethyl-1-(4-(trifluoromethyl)phenyl)propyl)-5-(2-hydroxyphenyl)-7,7-dimethyl-4,5,6,7-tetrahydropyrazolo[1,5-a]pyrimidine-3-carboxamide | mp 122-124° C. |
| 630 | 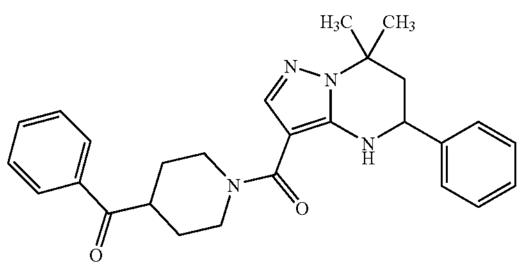 | (1-((7,7-dimethyl-5-phenyl-4,5,6,7-tetrahydropyrazolo[1,5-a]pyrimidin-3-yl)carbonyl)-4-piperidinyl)(phenyl)methanone | MS(ESI, m/z) 443 (M + H)+ |
| 631 | 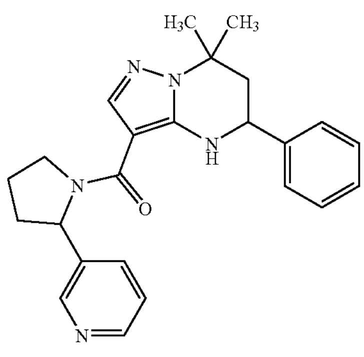 | 7,7-dimethyl-5-phenyl-3-((2-(3-pyridinyl)-1-pyrrolidinyl)carbonyl)-4,5,6,7-tetrahydropyrazolo[1,5-a]pyrimidine | MS(ESI, m/z) 402 (M + H)+ |
| 632 | 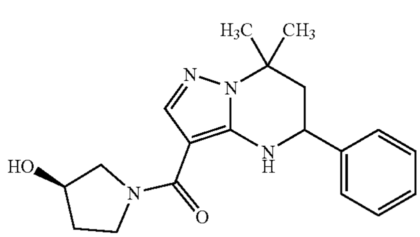 | (3R)-1-((7,7-dimethyl-5-phenyl-4,5,6,7-tetrahydropyrazolo[1,5-a]pyrimidin-3-yl)carbonyl)-3-pyrrolidinol | MS(ESI, m/z) 341 (M + H)+ |

TABLE 4-continued

| Example | Structure | Name | Physiological Data |
|---|---|---|---|
| 633 | 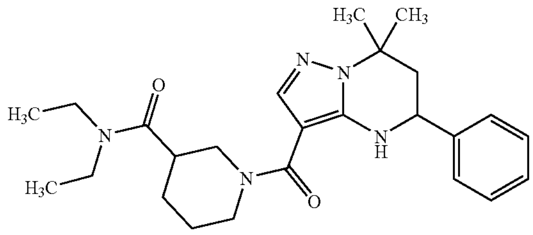 | 1-((7,7-dimethyl-5-phenyl-4,5,6,7-tetrahydropyrazolo[1,5-a]pyrimidin-3-yl)carbonyl)-N,N-diethyl-3-piperidinecarboxamide | MS(ESI, m/z) 438 (M + H)+ |
| 634 | 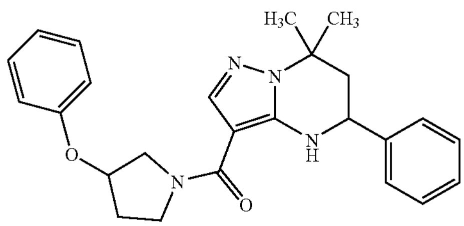 | 7,7-dimethyl-3-((3-phenoxy-1-pyrrolidinyl)carbonyl)-5-phenyl-4,5,6,7-tetrahydropyrazolo[1,5-a]pyrimidine | MS(ESI, m/z) 417 (M + H)+ |
| 635 | 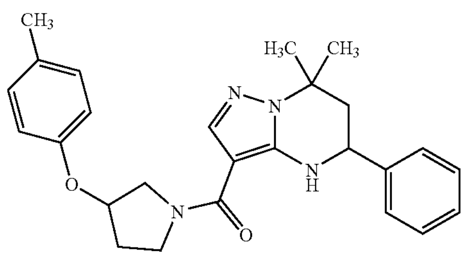 | 7,7-dimethyl-3-((3-(4-methylphenoxy)-1-pyrrolidinyl)carbonyl)-5-phenyl-4,5,6,7-tetrahydropyrazolo[1,5-a]pyrimidine | MS(ESI, m/z) 545 (M + H)+ |
| 636 | 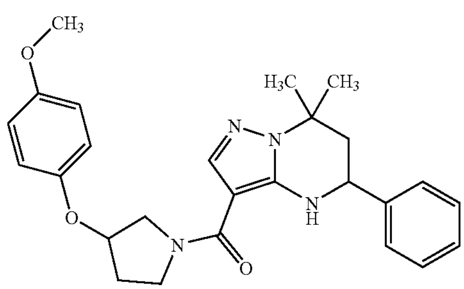 | 3-((3-(4-methoxyphenoxy)-1-pyrrolidinyl)carbonyl)-7,7-dimethyl-5-phenyl-4,5,6,7-tetrahydropyrazolo[1,5-a]pyrimidine | MS(ESI, m/z) 447 (M + H)+ |
| 637 | 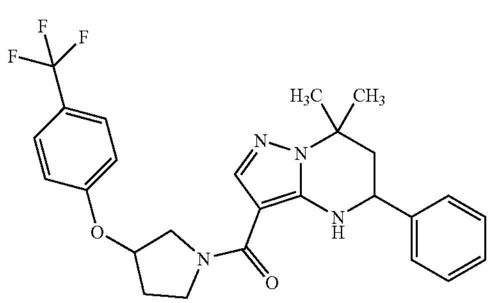 | 7-dimethyl-5-phenyl-3-((3-(4-(trifluoromethyl)phenoxy)-1-pyrrolidinyl)carbonyl)-4,5,6,7-tetrahydropyrazolo[1,5-a]pyrimidine | MS(ESI, m/z) 485 (M + H)+ |
| 638 | 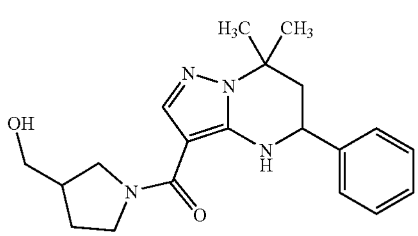 | (1-((7,7-dimethyl-5-phenyl-4,5,6,7-tetrahydropyrazolo[1,5-a]pyrimidin-3-yl)carbonyl)-3-pyrroladinyl)methanol | MS(ESI, m/z) 355 (M + H)+ |

TABLE 4-continued

| Example | Structure | Name | Physiological Data |
|---|---|---|---|
| 639 | 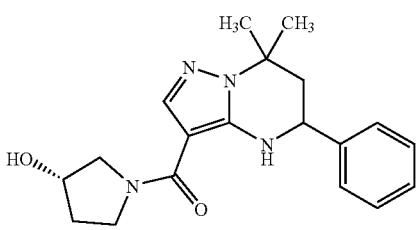 | (3S)-1-((7,7-dimethyl-5-phenyl-4,5,6,7-tetrahydropyrazolo[1,5-a]pyrimidin-3-yl)carbonyl)-3-pyrrolidinol | MS(ESI, m/z) 341 (M + H)+ |
| 640 | 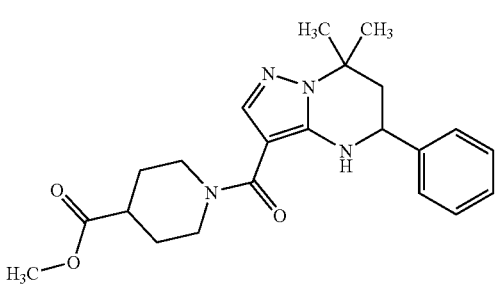 | methyl 1-((7,7-dimethyl-5-phenyl-4,5,6,7-tetrahydropyrazolo[1,5-4-piperidinecarboxylate | MS(ESI, m/z) 397 (M + H)+ |
| 641 | 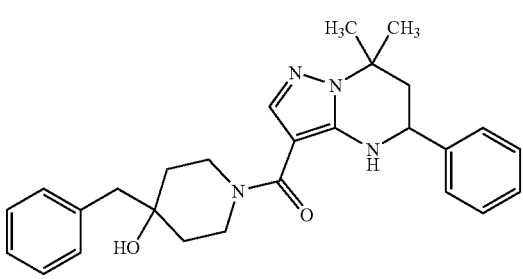 | 4-benzyl-1-((7,7-dimethyl-5-phenyl-4,5,6,7-tetrahydropyrazolo[1,5-a]pyrimidin-3-yl)carbonyl)-4-piperidinol | MS(ESI, m/z) 445 (M + H)+ |
| 642 | 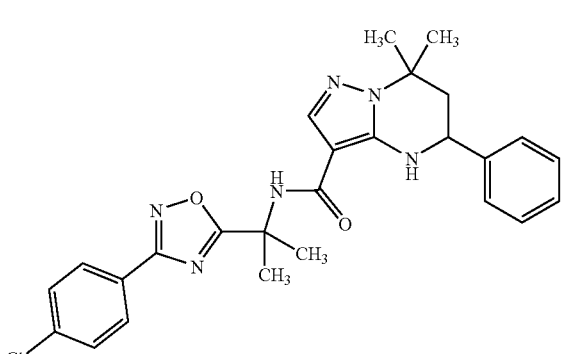 | N-(1-(3-(4-chlorophenyl)-1,2,4-oxadiazol-5-yl)-1-methylethyl)-7,7-dimethyl-5-phenyl-4,5,6,7-tetrahydropyrazolo[1,5-a]pyrimidine-3-carboxamide | MS(ESI, m/z) 491 (M + H)+ |
| 643 | 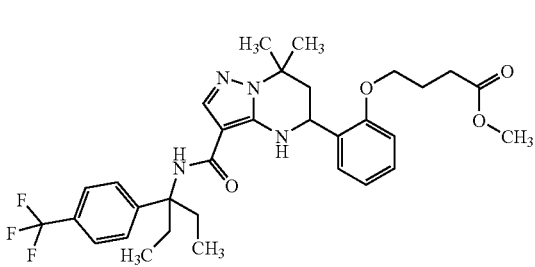 | methyl 4-(2-(3-(((1-ethyl-1-(4-(trifluoromethyl)phenyl)propyl)amino)carbonyl)-7,7-dimethyl-4,5,6,7-tetrahydropyrazolo[1,5-a]pyrimidin-5-yl)phenoxy)butanoate | MS(ESI, m/z) 602 (M + H)+ |

TABLE 4-continued

| Example | Structure | Name | Physiological Data |
|---|---|---|---|
| 644 | 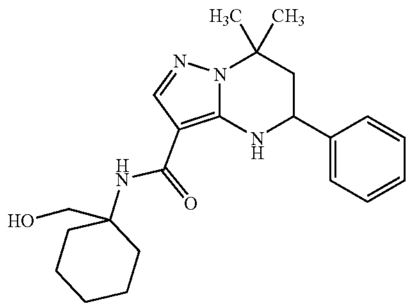 | N-(1-(hydroxymethyl)cyclohexyl)-7,7-dimethyl-5-phenyl-4,5,6,7-tetrahydropyrazolo[1,5-a]pyrimidine-3-carboxamide | mp 175-176° C. |
| 645 | 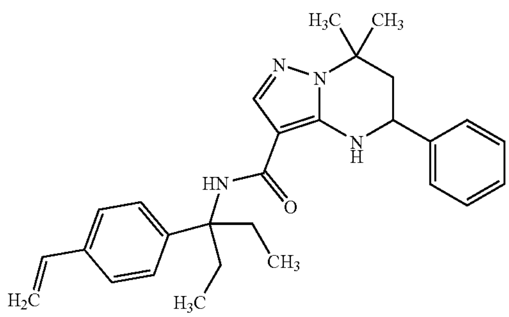 | N-(1-ethyl-1-(4-vinylphenyl)propyl)-7,7-dimethyl-5-phenyl-4,5,6,7-tetrahydropyrazolo[1,5-a]pyrimidine-3-carboxamide | mp 155-156° C. |
| 646 | 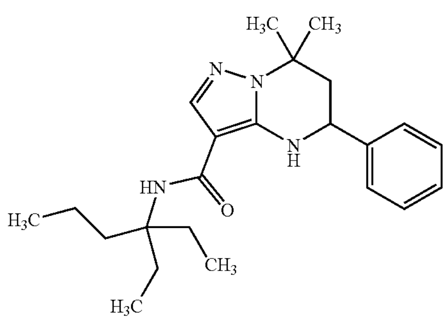 | N-(1,1-diethylbutyl)-7,7-dimethyl-5-phenyl-4,5,6,7-tetrahydropyrazolo[1,5-a]pyrimidine-3-carboxamide | mp 76-77° C. |
| 647 | 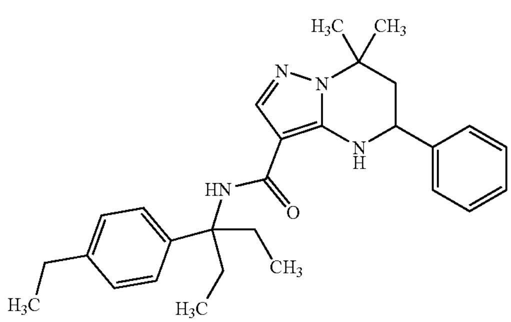 | N-(1-ethyl-1-(4-ethylphenyl)propyl)-7,7-dimethyl-5-phenyl-4,5,6,7-tetrahydropyrazolo[1,5-a]pyrimidine-3-carboxamide | mp 156-157° C. |
| 648 | 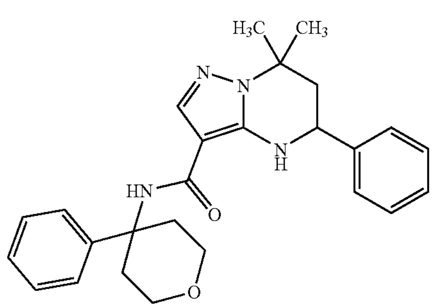 | 7,7-dimethyl-5-phenyl-N-(4-phenyltetrahydro-2H-pyran-4-yl)-4,5,6,7-tetrahydropyrazolo[1,5-a]pyrimidine-3-carboxamide | MS(ESI, m/z) 431 (M + H)+ |

TABLE 4-continued

| Example | Name | Physiological Data |
|---------|------|--------------------|
| 649 | (1-((7,7-dimethyl-5-phenyl-4,5,6,7-tetrahydropyrazolo[1,5-a]pyrimidin-3-yl)carbonyl)-4-piperidinyl)methanol | MS(ESI, m/z) 369 (M + H)+ |
| 650 | (1-((7,7-dimethyl-5-phenyl-4,5,6,7-tetrahydropyrazolo[1,5-a]pyrimidin-3-yl)carbonyl)-4-piperidinyl-4-fluorophenyl)methanol | MS(ESI, m/z) 463 (M + H)+ |
| 651 | (1-((7,7-dimethyl-5-phenyl-4,5,6,7-tetrahydropyrazolo[1,5-a]pyrimidin-3-yl)carbonyl)-2-piperidinyl)methanol | MS(ESI, m/z) 369 (M + H)+ |
| 652 | (1-((7,7-dimethyl-5-phenyl-4,5,6,7-tetrahydropyrazolo[1,5-a]pyrimidin-3-y)carbonyl)-3-piperidiny-methanol | MS(ESI, m/z) 369 (M + H)+ |
| 653 | 1-((7,7-dimethyl-5-phenyl-4,5,6,7-tetrahydropyrazolo[1,5-a]pyrimidin-3-y-carbonyl)-3-piperidinol | MS(ESI, m/z) 355 (M + H)+ |
| 654 | 1-((7,7-dimethyl-5-phenyl-4,5,6,7-tetrahydropyrazolo[1,5-a]pyrimidin-3-yl)carbonyl)-3-piperidinecarboxamide | MS(ESI, m/z) 382 (M + H)+ |

TABLE 4-continued

| Example | Name | Physiological Data |
|---|---|---|
| 655 | 1-((7,7-dimethyl-5-phenyl-4,5,6,7-tetrahydropyrazolo[1,5-a]pyrimidin-3-yl)carbonyl)-4-phenyl-4-pipendinecarbonitrile | MS(ESI, m/z) 440 (M + H)+ |
| 656 | 1-((7,7-dimethyl-5-phenyl-4,5,6,7-tetrahydropyrazolo[1,5-a]pyrimidin-3-yl)carbonyl)-4-(trifluoromethyl)-4-piperidinol | MS(ESI, m/z) 423 (M + H)+ |
| 657 | methyl (2R)-(((7,7-dimethyl-5-phenyl-4,5,6,7-tetrahydropyrazolo[1,5-a]pyrimidin-3-yl)carbonyl)amino)(phenyl)acetate | MS(ESI, m/z) 419 (M + H)+ |
| 658 | methyl (2S)-(((7,7-dimethyl-5-phenyl-4,5,6,7-tetrahydropyrazolo[1,5-a]pyrimidin-3-yl)carbonyl)amino)(phenyl)acetate | MS(ESI, m/z) 419 (M + H)+ |
| 659 | N-((1R)-2-hydroxy-1-phenylethyl)-7,7-dimethyl-phenyl-4,5,6,7-tetrahydropyrazolo[1,5-a]pyrimidine-3-carboxamide | MS(ESI, m/z) 391 (M + H)+ |

TABLE 4-continued

| Example | Structure | Name | Physiological Data |
|---------|-----------|------|--------------------|
| 660 | 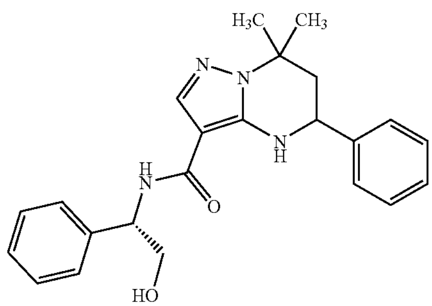 | N-((1S)-2-hydroxy-1-phenylethyl)-7,7-dimethyl-5-phenyl-4,5,6,7-tetrahydropyrazolo[1,5-a]pyrimidine-3-carboxamide | MS(ESI, m/z) 391 (M + H)+ |
| 661 | 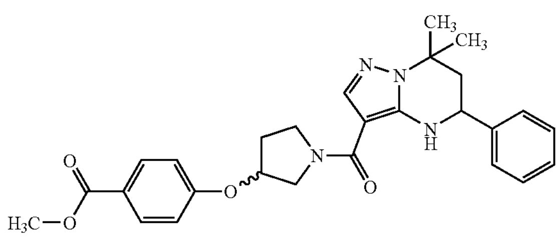 | methyl 4-((1-((7,7-dimethyl-5-phenyl-4,5,6,7-tetrahydropyrazolo[1,5-a]pyrimidin-3-yl)carbonyl)-3-pyrrolidinyl)oxy)benzoate | MS(ESI, m/z) 475 (M + H)+ |
| 662 | 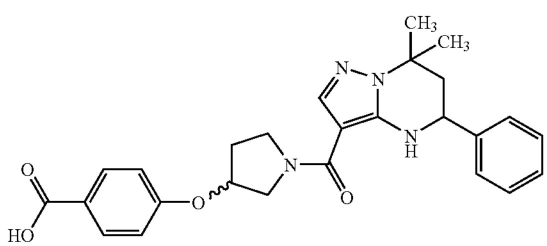 | 4-((1-((7,7-dimethyl-5-phenyl-4,5,6,7-tetrahydropyrazolo[1,5-a]pyrimidin-3-yl)carbonyl)-3-pyrrolidinyl)oxy)benzoic acid | MS(ESI, m/z) 461 (M + H)+ |
| 663 | 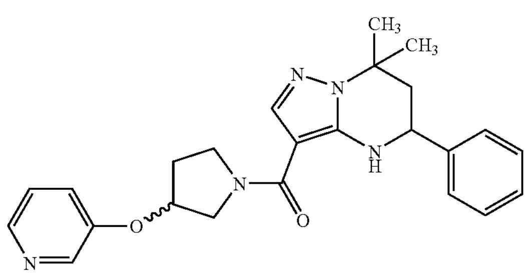 | 7,7-dimethyl-5-phenyl-3-((3-(3-pyridinyloxy)-1-pyrrolidinyl)carbonyl)-4,5,6,7-tetrahydropyrazolo[1,5-a]pyrimidine | MS(ESI, m/z) 418 (M + H)+ |
| 664 | 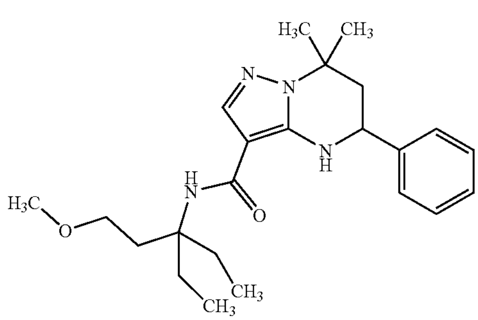 | N-(1,1-diethyl-3-methoxypropyl)-7,7-dimethyl-5-phenyl-4,5,6,7-tetrahydropyrazolo[1,5-a]pyrimidine-3-carboxamide | mp 129-130° C. |

TABLE 4-continued

| Example | Structure | Name | Physiological Data |
|---------|-----------|------|--------------------|
| 665 | 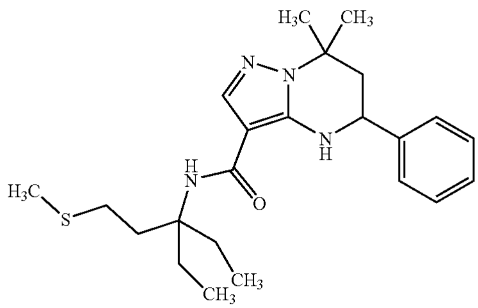 | N-(1,1-diethyl-3-(methylthio)propyl)-7,7-dimethyl-5-phenyl-4,5,6,7-tetrahydropyrazolo[1,5-a]pyrimidine-3-carboxamide | mp 154-155° C. |
| 666 | 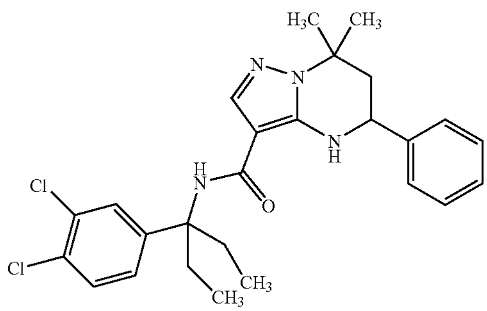 | N-(1-(3,4-dichlorophenyl)-1-ethylpropyl)-7,7-dimethyl-5-phenyl-4,5,6,7-tetrahydropyrazolo[1,5-a]pyrimidine-3-carboxamide | mp 156-157° C. |
| 667 | 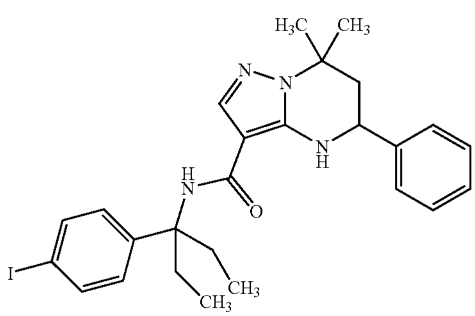 | N-(1-ethyl-1-(4-iodophenyl)propyl)-7,7-dimethyl-5-phenyl-4,5,6,7-tetrahydropyrazolo[1,5-a]pyrimidine-3-carboxamide | mp 182-183° C. |
| 668 | 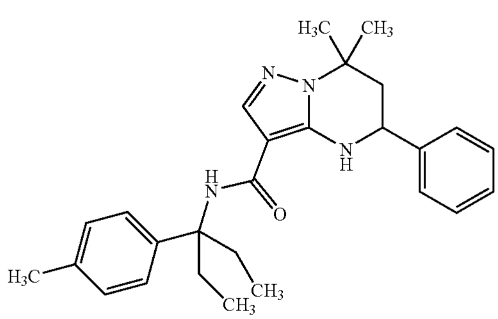 | N-(1-ethyl-1-(4-methylphenyl)propyl)-7,7-dimethyl-5-phenyl-4,5,6,7-tetrahydropyrazolo[1,5-a]pyrimidine-3-carboxamide | HCl salt mp 158-160° C. |

TABLE 4-continued

| Example | Structure | Name | Physiological Data |
|---|---|---|---|
| 669 | 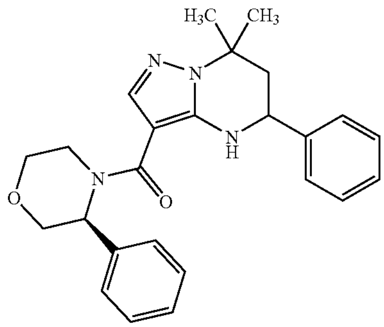 | 7,7-dimethyl-5-phenyl-3-(((3S)-3-phenyl-4-morpholinyl)carbonyl)-4,5,6,7-tetrahydropyrazolo[1,5-a]pyrimidine | MS(ESI, m/z) 417 (M + H)+ |
| 670 | 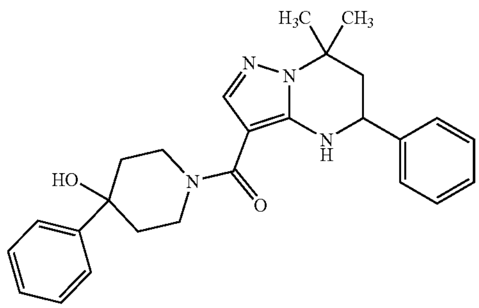 | 1-((7,7-dimethyl-5-phenyl-4,5,6,7-tetrahydropyrazolo[1,5-a]pyrimidin-3-yl)carbonyl)-4-phenyl-4-piperidinol | MS(ESI, m/z) 431 (M + H)+ |
| 671 | 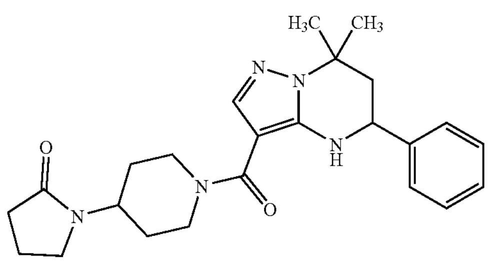 | 1-(1-((7,7-dimethyl-5-phenyl-4,5,6,7-tetrahydropyrazolo[1,5-a]pyrimidin-3-yl)carbonyl)-4-piperidinyl)-2-pyrrolidinone | MS(ESI, m/z) 422 (M + H)+ |
| 672 | 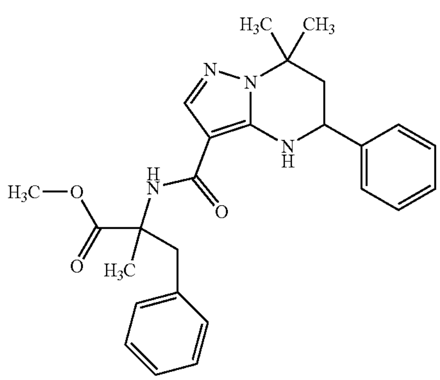 | methyl 2-(((7,7-dimethyl-5-phenyl-4,5,6,7-tetrahydropyrazolo[1,5-a]pyrimidin-3-yl)carbonyl)amino)-2-methyl-3-phenylpropanoate | MS(ESI, m/z) 447 (M + H)+ |
| 673 | 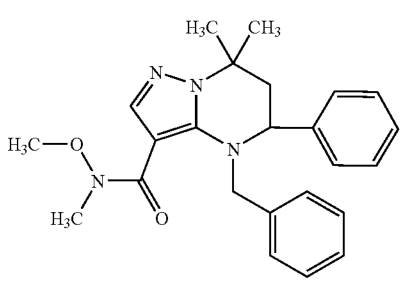 | 4-benzyl-N-methoxy-N,7,7-trimethyl-5-phenyl-4,5,6,7-tetrahydropyrazolo[1,5-a]pyrimidine-3-carboxamide | MS(ESI, m/z) 405 (M + H)+ |

TABLE 4-continued

| Example | Structure | Name | Physiological Data |
|---|---|---|---|
| 674 | 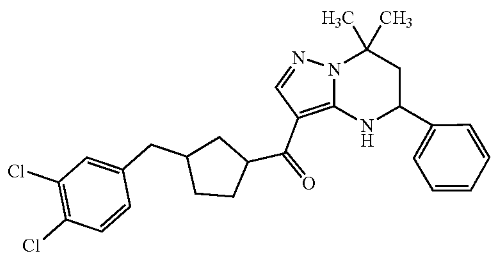 | 3-((3-(3,4-dichlorobenzyl)-1-pyrrolidinyl)carbonyl)-7,7-dimethyl-5-phenyl-4,5,6,7-tetrahydropyrazolo[1,5-a]pyrimidine | MS(ESI, m/z) 484 (M + H)+ |
| 675 | 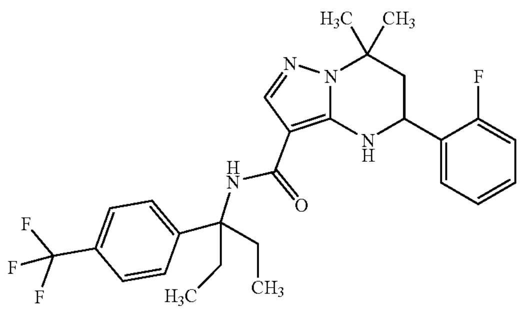 | N-(1-ethyl-1-(4-(trifluoromethyl)phenyl)propyl)-5-(2-fluorophenyl)-7,7-dimethyl-4,5,6,7-tetrahydropyrazolo[1,5-a]pyrimidine-3-carboxamide | mp 200.9-201.0° C. |
| 676 | 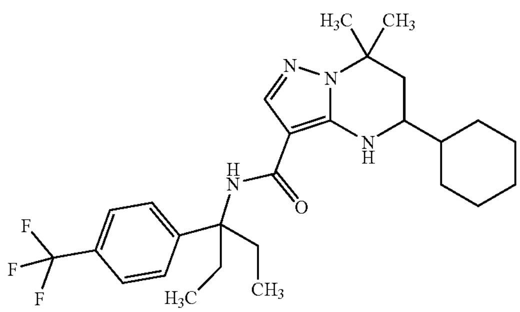 | 5-cyclohexyl-N-(1-ethyl-1-(4-(trifluoromethyl)phenyl)propyl)-7,7-dimethyl-4,5,6,7-tetrahydropyrazolo[1,5-a]pyrimidine-3-carboxamide | mp 178.7-178.9° C. |
| 677 | 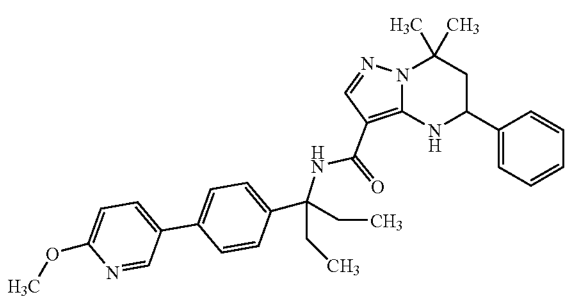 | N-(1-ethyl-1-(4-(6-methoxy-3-pyridinyl)phenyl)propyl)-7,7-dimethyl-5-phenyl-4,5,6,7-tetrahydropyrazolo[1,5-a]pyrimidine-3-carboxamide | mp 172-173° C. |
| 678 | 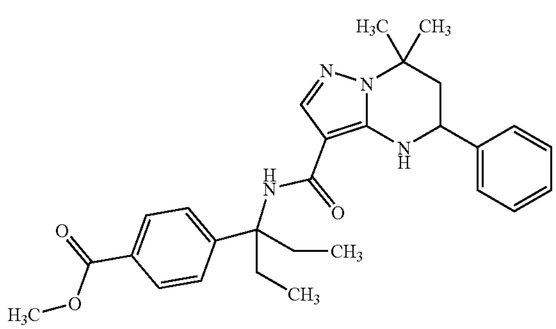 | methyl 4-(1-(((7,7-dimethyl-5-phenyl-4,5,6,7-tetrahydropyrazolo[1,5-a]pyrimidin-3-yl)carbonyl)amino)-1-ethylpropyl)benzoate | mp 180-181° C. |

TABLE 4-continued

| Example | Structure | Name | Physiological Data |
|---|---|---|---|
| 679 | 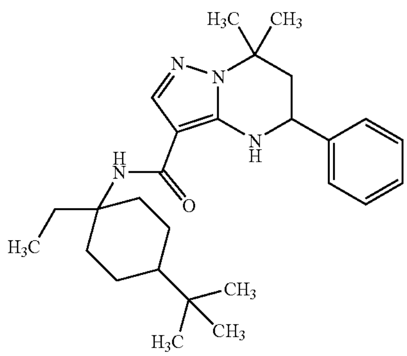 | N-(4-tert-butyl-1-ethylcyclohexyl)-7,7-dimethyl-5-phenyl-4,5,6,7-tetrahydropyrazolo[1,5-a]pyrimidine-3-carboxamide | MS(ESI, m/z) 437 (M + H)+ |
| 680 | 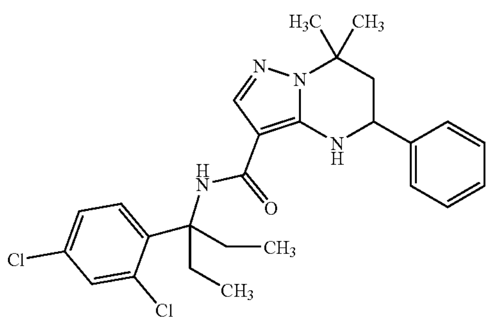 | N-(1-(2,4-dichlorophenyl)-1-ethylpropyl)-7,7-dimethyl-5-phenyl-4,5,6,7-tetrahydropyrazolo[1,5-a]pylimidine-3-carboxamide | mp 220-222° C. |
| 681 | 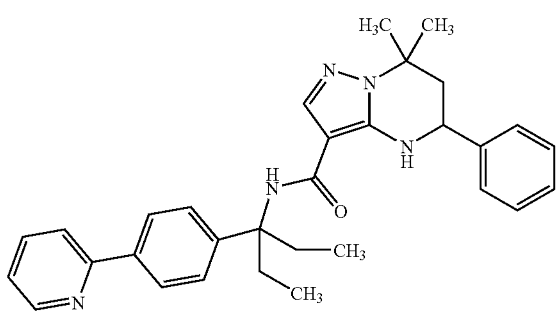 | N-(1-ethyl-1-(4-(2-pyridinyl)phenyl)propyl)-7,7-dimethyl-5-phenyl-4,5,6,7-tetrahydropyrazolo[1,5-a]pyrimidine-3-carboxamide | IR(KBr) 3336, 2975, 1634, 1582, 1532, 1532, 1508, 1456, 1435 cm$^{-1}$ |
| 682 | 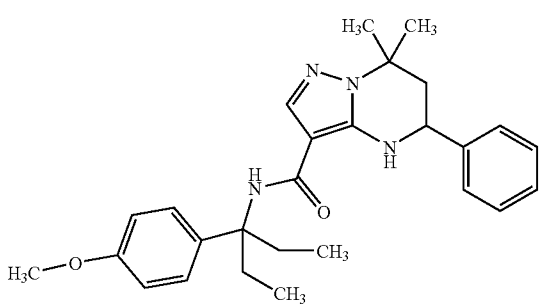 | N-(1-ethyl-1-(4-methoxyphenyl)propyl)-7,7-dimethyl-5-phenyl-4,5,6,7-tetrahydropyrazolo[1,5-a]pyrimidine-3-carboxamide | mp 140-141° C. |

TABLE 4-continued

| Example | Name | Physiological Data |
|---|---|---|
| 683 | N-(1-benzyl-2-hydroxy-1-methylethyl)-7,7-dimethyl-5-phenyl-4,5,6,7-tetrahydropyrazolo[1,5-a]pyrirnidine-3-carboxamide | MS(ESI, m/z) 419 (M + H)+ |
| 684 | 3-((2,2-diallyl-1-pyrrolidinyl)carbonyl)-7,7-dimethyl-5-phenyl-4,5,6,7-tetrahydropyrazolo[1,5-a]pyrimidine | MS(ESI, m/z) 405 (M + H)+ |
| 685 | 3-((2,2-dipropyl-1-pyrrolidinyl)carbonyl)-7,7-dimethyl-5-phenyl-4,5,6,7-tetrahydropyrazolo[1,5-a]pyrimidine | MS(ESI, m/z) 409 (M + H)+ |
| 686 | 2-(1-((7,7-dimethyl-5-phenyl-4,5,6,7-tetrahydropyrazolo[1,5-a]pyrimidin-3-yl)carbonyl)-2-pyrrolidinyl)-2-propanol | MS(ESI, m/z) 383 (M + H)+ |

TABLE 4-continued

| Example | Structure | Name | Physiological Data |
|---|---|---|---|
| 687 | 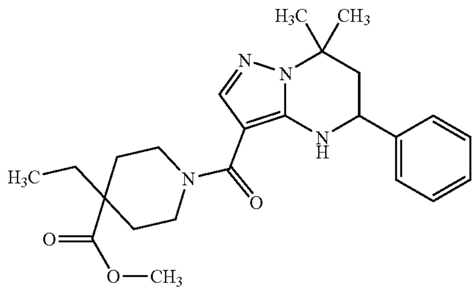 | methyl 1-((7,7-dimethyl-5-phenyl-4,5,6,7-tetrahydropyrazolo[1,5-a]pyrimidin-3-yl)carbonyl)-4-ethyl-4-piperidinecarboxylate | MS(ESI, m/z) 425 (M + H)+ |
| 688 | 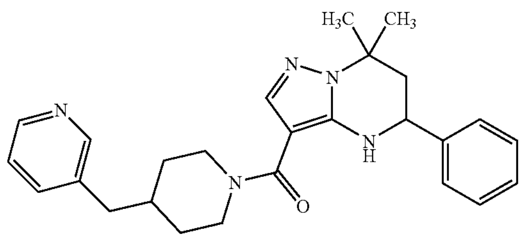 | 7,7-dimethyl-5-phenyl-3-((4-(3-pyridinylmethyl)-1-piperidinyl)carbonyl)-4,5,6,7-tetrahydropyrazolo[1,5-a]pyrimidine | MS(ESI, m/z) 430 (M + H)+ |
| 689 | 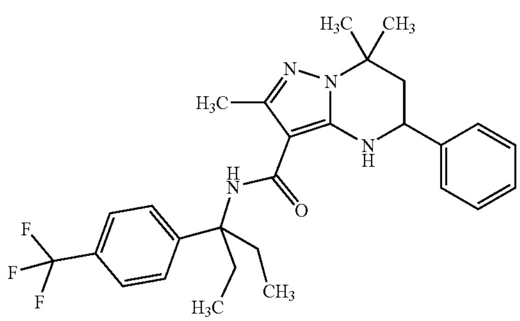 | N-(1-ethyl-1-(4-(trifluoromethyl)phenyl)propyl)-2,7,7-trimethyl-5-phenyl-4,5,6,7-tetrahydropyrazolo[1,5-a]pyrimidine-3-carboxamide | EA Calcd. C; 67.45, H; 6.67, N; 11.24, Found. C; 67.49, H; 6.65, N; 11.08 |
| 690 | 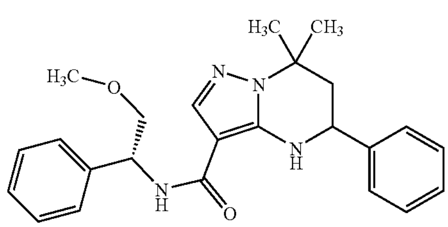 | N-((1R)-2-methoxy-1-phenylethyl)-7,7-dimethyl-5-phenyl-4,5,6,7-tetrahydropyrazolo[1,5-a]pyrimidine-3-carboxamide | MS(ESI, m/z) 405 (M + H)+ |
| 691 | 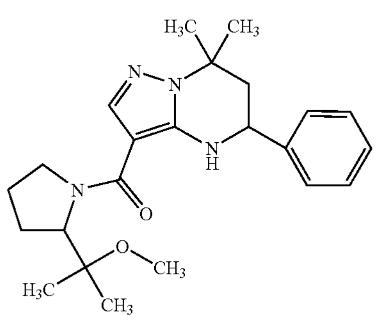 | N-((2-(1-methoxy-1-methylethyl)-1-pyrrolidinyl)carbonyl)-7,7-dimethyl-5-phenyl-4,5,6,7-tetrahydropyrazolo[1,5-a]pyrimidine | MS(ESI, m/z) 397 (M + H)+ |

TABLE 4-continued

| Example | Structure | Name | Physiological Data |
|---|---|---|---|
| 692 | 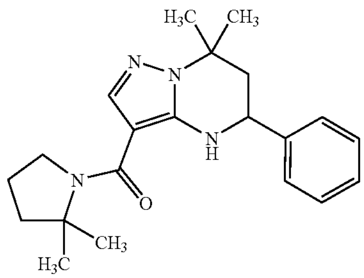 | 3-((2,2-dimethyl-1-pyrrolidinyl)carbonyl)-7,7-dimethyl-5-phenyl-4,5,6,7-tetrahydropyrazolo[1,5-a]pyrimidine | MS(ESI, m/z) 353 (M + H)+ |
| 693 | 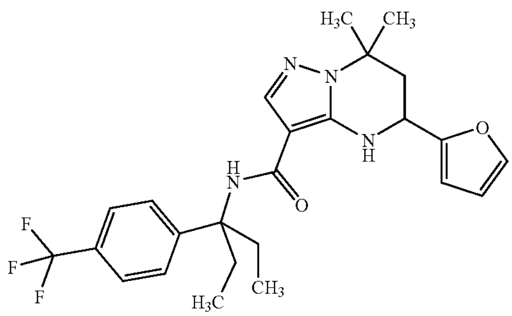 | N-(1-ethyl-1-(4-(trifluoromethyl)phenyl)propyl)-5-(2-furyl)-7,7-dimethyl-4,5,6,7-tetrahydropyrazolo[1,5-a]pyrimidine-3-carboxamide | mp 212-214° C. |
| 694 | 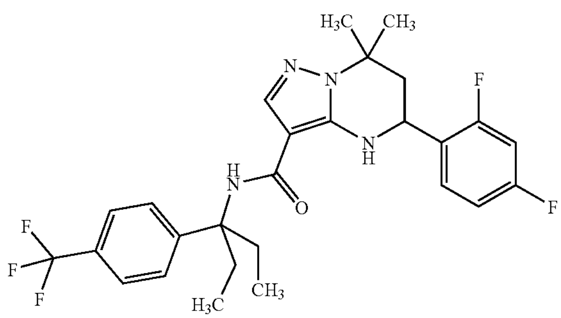 | 5-(2,4-difluorophenyl)-N-(1-ethyl-1-(4-(trifluoromethyl)phenyl)propyl)-7,7-dimethyl-4,5,6,7-tetrahydropyrazolo[1,5-a]pyrimidine-3-carboxamide | mp 198-199° C. |
| 695 | 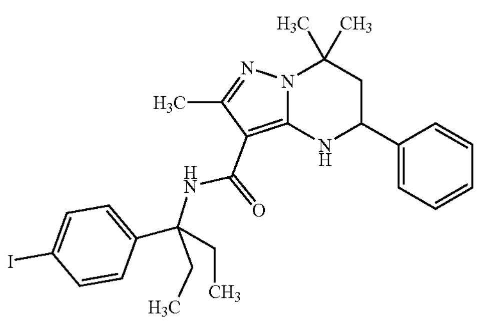 | N-(1-ethyl-1-(4-iodophenyl)propyl)-2,7,7-trimethyl-5-phenyl-4,5,6,7-tetrahydropyrazolo[1,5-a]pyrimidine-3-carboxamide | MS(ESI, m/z) 557 (M + H)+ |
| 696 | 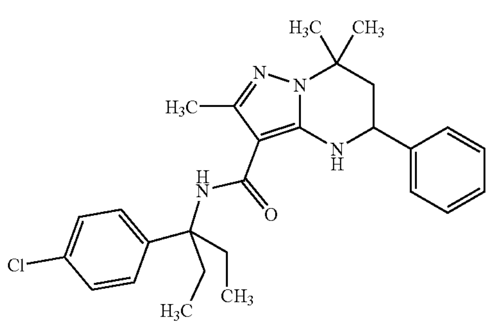 | N-(1-(4-chlorophenyl)-1-ethylpropyl)-2,7,7-trimethyl-5-phenyl-4,5,6,7-tetrahydropyrazolo[1,5-a]pyrimidine-3-carboxamide | mp 146-148° C. |

TABLE 4-continued

| Example | Structure | Name | Physiological Data |
|---|---|---|---|
| 697 | 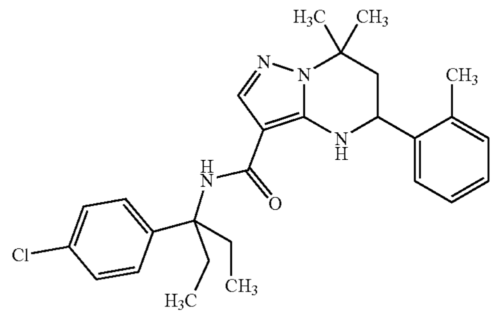 | N-(1-(4-chlorophenyl)-1-ethylpropyl)-7,7-dimethyl-5-(2-methylphenyl)-4,5,6,7-tetrahydropyrazolo[1,5-a]pyrimidine-3-carboxamide | mp 143-145° C. |
| 698 | 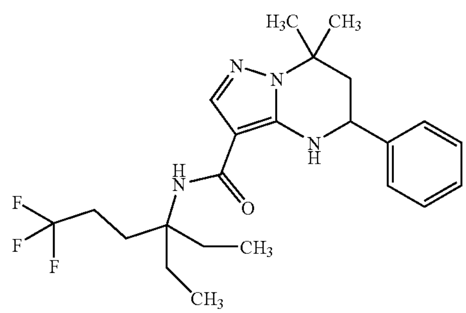 | N-(1,1-diethyl-4,4,4-trifluorobutyl)-7,7-dimethyl-5-phenyl-4,5,6,7-tetrahydropyrazolo[1,5-a]pyrimidine-3-carboxamide | mp 84-85° C. |
| 699 | 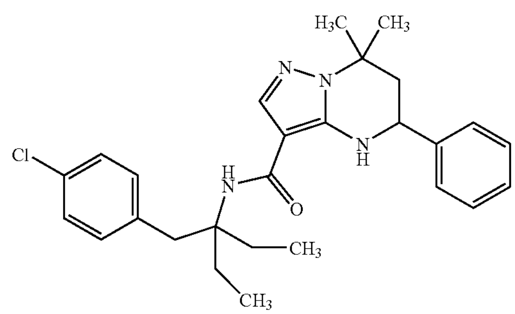 | N-(1-(4-Chlorobenzyl)-1-ethylpropyl)-7,7-dimethyl-5-phenyl-4,5,6,7-tetrahydropyrazolo[1,5-a]pyrimidine-3-carboxamide | mp 156-157° C. |
| 700 | 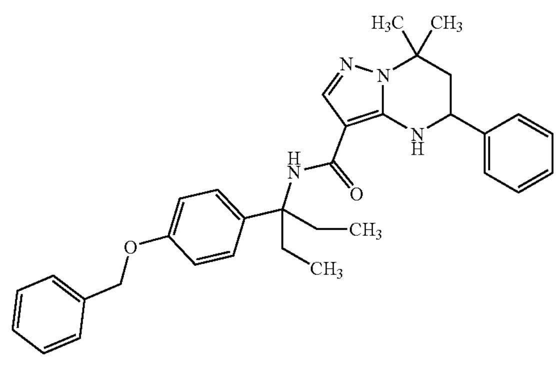 | N-(1-(4-(benzyloxy)phenyl)-1-ethylpropyl)-7,7-dimethyl-5-phenyl-4,5,6,7-tetrahydropyrazolo[1,5-a]pyrimidine-3-carboxamide | MS(ESI, m/z) 523 (M + H)+ |

TABLE 4-continued

| Example | Structure | Name | Physiological Data |
|---|---|---|---|
| 701 | 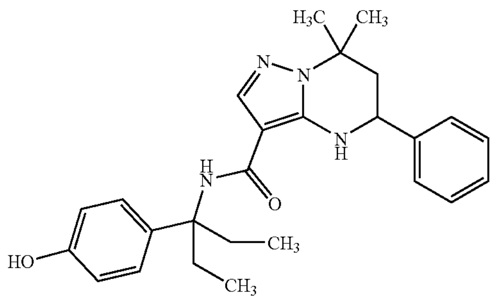 | N-(1-ethyl-1-(4-hydroxyphenyl)propyl)-7,7-dimethyl-5-phenyl-4,5,6,7-tetrahydropyrazolo[1,5-a]pyrimidine-3-carboxamide | mp 152-153° C. |
| 702 | 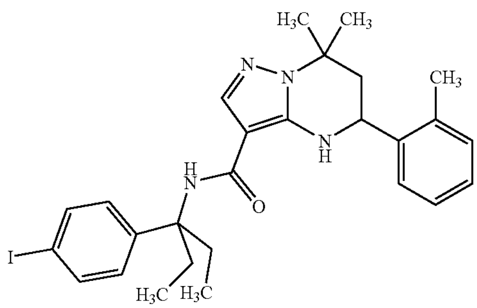 | N-(1-ethyl-1-(4-iodophenyl)propyl)-7,7-dimethyl-5-(2-methylphenyl)-4,5,6,7-tetrahydropyrazolo[1,5-a]pyrimidine-3-carboxamide | EA Calcd. C; 58.27, H; 5.98, N; 10.07. Found. C; 58.47, H; 6.17, N; 9.79 |
| 703 | 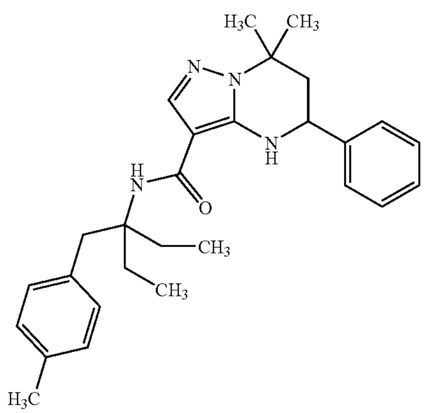 | N-(1-ethyl-1-(4-methylbenzyl)propyl)-7,7-dimethyl-5-phenyl-4,5,6,7-tetrahydropyrazolo[1,5-a]pyrimidine-3-carboxamide | mp 150-151° C. |
| 704 | 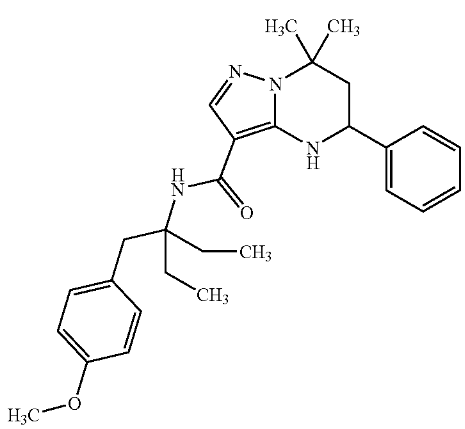 | N-(1-ethyl-1-(4-methoxybenzyl)propyl)-7,7-dimethyl-5-phenyl-4,5,6,7-tetrahydropyrazolo[1,5-a]pyrimidine-3-carboxamide | mp 185-186° C. |

TABLE 4-continued

| Example | Structure | Name | Physiological Data |
|---|---|---|---|
| 705 | 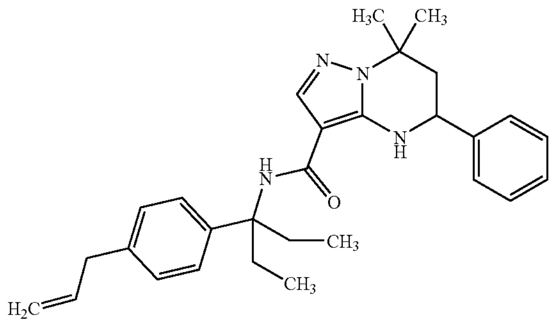 | N-(1-(4-allylphenyl)-1-ethylpropyl)-7,7-dimethyl-5-phenyl-4,5,6,7-tetrahydropyrazolo[1,5-a]pyrimidine-3-carboxamide | mp 147-148° C. |
| 706 | 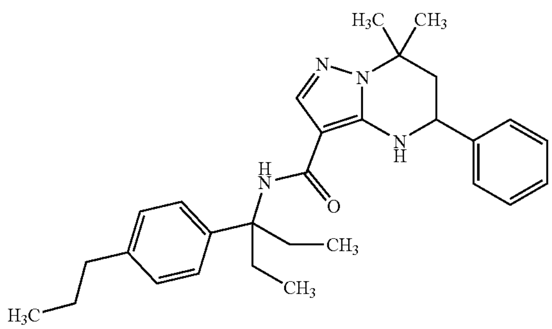 | N-(1-ethyl-1-(4-propylphenyl)propyl)-7,7-dimethyl-5-phenyl-4,5,6,7-tetrahydropyrazolo[1,5-a]pyrimidine-3-carboxamide | mp 177-178° C. |
| 707 | 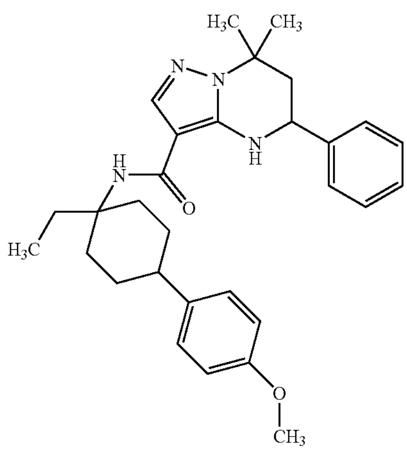 | N-(1-ethyl-4-(4-methoxyphenyl)cyclohexyl)-7,7-dimethyl-5-phenyl-4,5,6,7-tetrahydropyrazolo[1,5-a]pyrimidine-3-carboxamide | MS(ESI, m/z) 487 (M + H)+ |
| 708 | 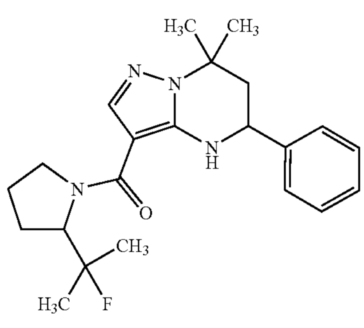 | 3-((2-(1-fluoro-1-methylethyl)-1-pyrrolidinyl)carbonyl)-7,7-dimethyl-5-phenyl-4,5,6,7-tetrahydropyrazolo[1,5-a]pyrimidine | MS(ESI, m/z) 385 (M + H)+ |

TABLE 4-continued

| Example | Structure | Name | Physiological Data |
|---|---|---|---|
| 709 | 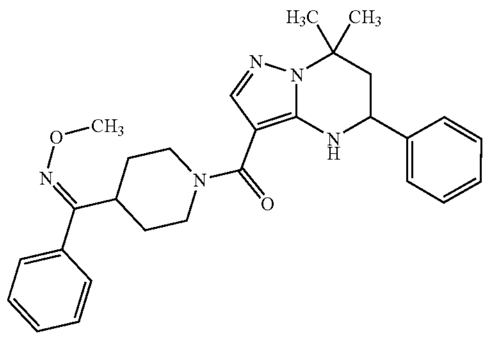 | (E)-(1-((7,7-dimethyl-5-phenyl-4,5,6,7-tetrahydropyrazolo[1,5-a]pyrimidin-3-yl)carbonyl)-4-piperidinyl)(phenyl)methanone O-methyloxime | MS(ESI, m/z) 472 (M + H)+ |
| 710 | 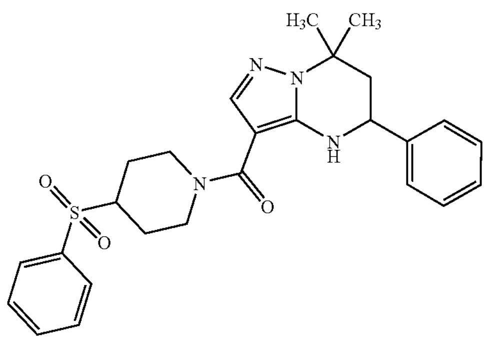 | 7,7-dimethyl-5-phenyl-3-((4-(phenylsulfonyl)-1-piperidinyl)carbonyl)-4,5,6,7-tetrahydropyrazolo[1,5-a]pyrimidine | MS(ESI, m/z) 479 (M + H)+ |
| 711 | 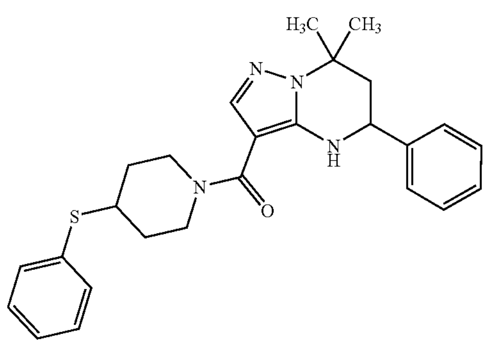 | 7,7-dimethyl-5-phenyl-3-((4-(phenylthio)-1-piperidinyl)carbonyl)-4,5,6,7-tetrahydropyrazolo[1,5-a]pyrimidine | MS(ESI, m/z) 447 (M + H)+ |
| 712 | 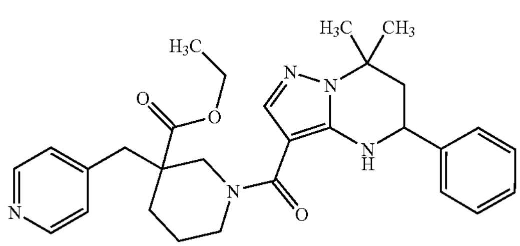 | ethyl 1-((7,7-dimethyl-5-phenyl-4,5,6,7-tetrahydropyrazolo[1,5-a]pyrimidin-3-yl)carbonyl)-3-(4-pyridinylmethyl)-3-piperidinecarboxylate | MS(ESI, m/z) 502 (M + H)+ |

TABLE 4-continued

| Example | Name | Physiological Data |
|---|---|---|
| 713 | 7,7-dimethyl-5-phenyl-3-((4-(4-pyridinyloxy)-1-piperidinyl)carbonyl)-4,5,6,7-tetrahydropyrazolo[1,5-a]pyrimidine | MS(ESI, m/z) 432 (M + H)+ |
| 714 | ethyl 1-((7,7-dimethyl-5-phenyl-4,5,6,7-tetrahydropyrazolo[1,5-a]pyrimidin-3-yl)carbonyl)-3-(2-pyridinylmethyl)-3-piperidinecarboxylate | MS(ESI, m/z) 502 (M + H)+ |
| 715 | ethyl 3-(((7,7-dimethyl-5-phenyl-4,5,6,7-tetrahydropyrazolo[1,5-a]pyrimidin-3-yl)carbonyl)amino)-3-methylbutanoate | MS(ESI, m/z) 399 (M + H)+ |
| 716 | N-(3-(benzylamino)-1,1-dimethyl-3-oxopropyl)-7,7-dimethyl-5-phenyl-4,5,6,7-tetrahydropyrazolo[1,5-a]pyrimidine-3-carboxamide | MS(ESI, m/z) 460 (M + H)+ |
| 717 | N-(1,1-dimethyl-3-(4-methyl-1-piperazinyl)-3-oxopropyl)-7,7-dimethyl-5-phenyl-4,5,6,7-tetrahydropyrazolo[1,5-a]pyrimidine-3-carboxamide | MS(ESI, m/z) 490 (M + H)+ |

TABLE 4-continued

| Example | Structure | Name | Physiological Data |
|---|---|---|---|
| 718 | 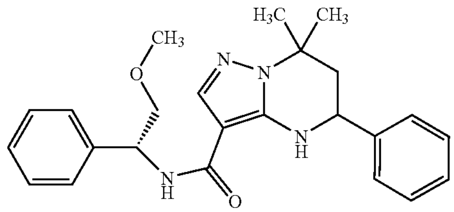 | N-((1R)-2-methoxy-1-phenylethyl)-7,7-dimethyl-5-phenyl-4,5,6,7-tetrahydropyrazolo[1,5-a]pyrimidine-3-carboxamide | MS(ESI, m/z) 405 (M + H)+ |
| 719 | 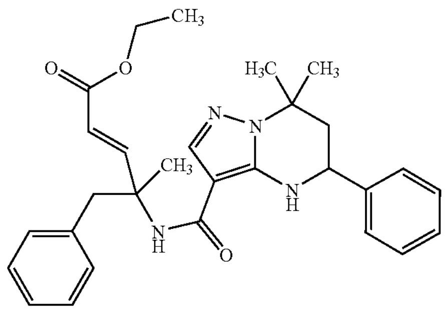 | ethyl (2E)-4-(((7,7-dimethyl-5-phenyl-4,5,6,7-tetrahydropyrazolo[1,5-a]pyrimidin-3-yl)carbonyl)amino)-4-methyl-5-phenyl-2-pentenoate | MS(ESI, m/z) 487 (M + H)+ |
| 720 | 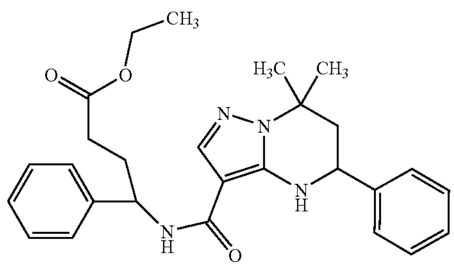 | ethyl 4-(((7,7-dimethyl-5-phenyl-4,5,6,7-tetrahydropyrazolo[1,5-a]pyrimidin-3-yl)carbonyl)amino)-4-phenylbutanoate | MS(ESI, m/z) 461 (M + H)+ |
| 721 | 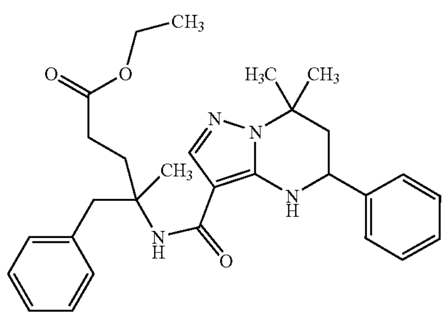 | ethyl 4-(((7,7-dimethyl-5-phenyl-4,5,6,7-tetrahydropyrazolo[1,5-a]pyrimidin-3-yl)carbonyl)amino)-4-methyl-5-phenylpentanoate | MS(ESI, m/z) 489 (M + H)+ |
| 722 | 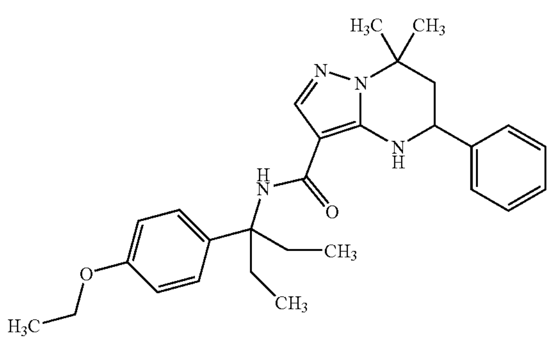 | N-(1-(4-ethoxyphenyl)-1-ethylpropyl)-7,7-dimethyl-5-phenyl-4,5,6,7-tetrahydropyrazolo[1,5-a]pyrimidine-3-carboxamide | mp 141-142° C. |

TABLE 4-continued

| Example | Structure | Name | Physiological Data |
|---|---|---|---|
| 723 | 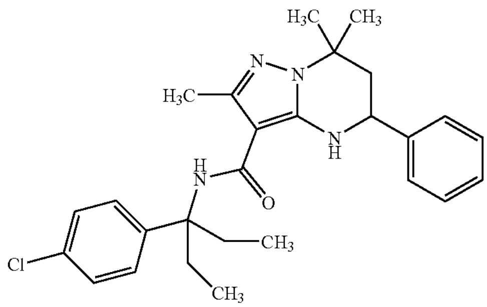 | N-(1-(4-chlorophenyl)-1-ethylpropyl)-2,7,7-trimethyl-5-phenyl-4,5,6,7-tetrahydropyrazolo[1,5-a]pyrimidine-3-carboxamide | HCl salt mp 180-181° C. |
| 724 | 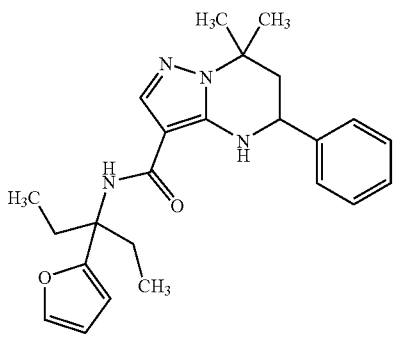 | N-(1-ethyl-1-(2-furyl)propyl)-7,7-dimethyl-5-phenyl-4,5,6,7-tetrahydropyrazolo[1,5-a]pyrimidine-3-carboxamide | MS(ESI, m/z) 407 (M + H)+ |
| 725 | 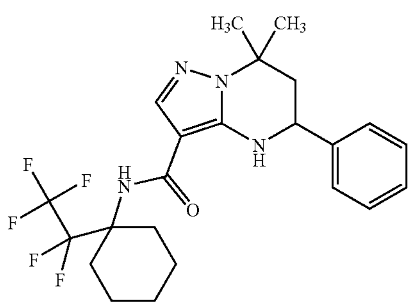 | 7,7-dimethyl-N-(1-(pentafluoroethyl)cyclohexyl)-5-phenyl-4,5,6,7-tetrahydropyrazolo[1,5-a]pyrimidine-3-carboxamide | MS(ESI, m/z) 471 (M + H)+ |
| 726 | 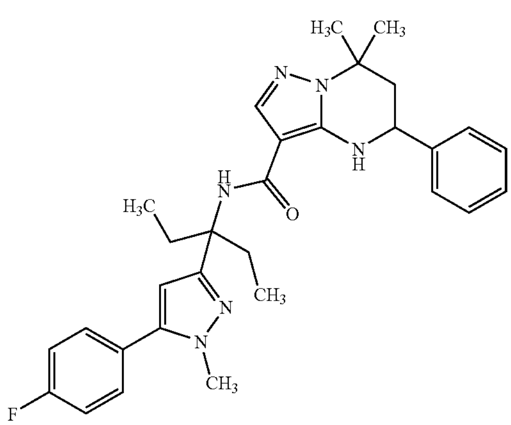 | N-(1-ethyl-1-(5-(4-fluorophenyl)-1-methyl-1H-pyrazol-3-yl)propyl)-7,7-dimethyl-5-phenyl-4,5,6,7-tetrahydropyrazolo[1,5-a]pyrimidine-3-carboxamide | mp 218-219° C. |

TABLE 4-continued

| Example | Structure | Name | Physiological Data |
|---|---|---|---|
| 727 | 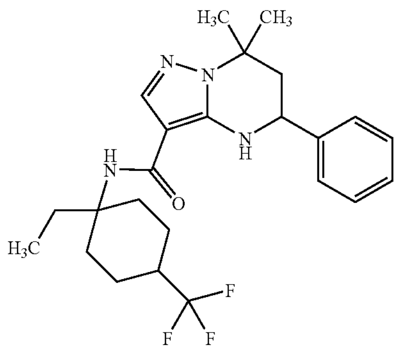 | N-(1-ethyl-4-(trifluoromethyl)cyclohexyl)-7,7-dimethyl-5-phenyl-4,5,6,7-tetrahydropyrazolo[1,5-a]pyrimidine-3-carboxamide | MS(ESI, m/z) 449 (M + H)+ |
| 728 | 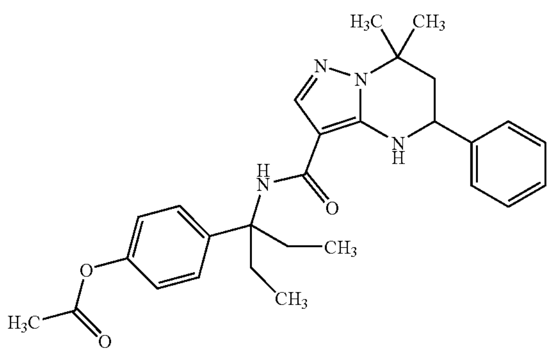 | 4-(1-(((7,7-dimethyl-5-phenyl-4,5,6,7-tetrahydropyrazolo[1,5-a]pyrimidin-3-yl)carbonyl)amino)-1-ethylpropyl)phenyl acetate | mp 171-172° C. |
| 729 | 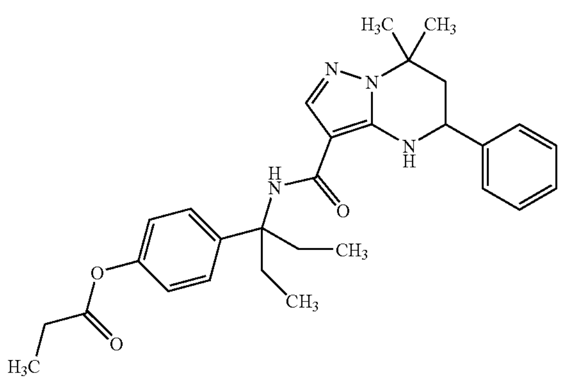 | 4-(1-(((7,7-dimethyl-5-phenyl-4,5,6,7-tetrahydropyrazolo[1,5-a]pyrimidin-3-yl)carbonyl)amino)-1-ethylpropyl)phenyl propionate | mp 172-173° C. |
| 730 | 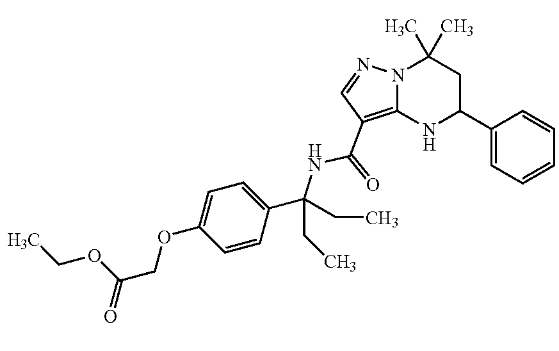 | ethyl (4-(1-(((7,7-dimethyl-5-phenyl-4,5,6,7-tetrahydropyrazolo[1,5-a]pyrimidin-3-yl)carbonyl)amino)-1-ethylpropyl)phenoxy)acetate | mp 178-179° C. |

TABLE 4-continued

| Example | Name | Physiological Data |
|---|---|---|
| 731 | (4-(1-(((7,7-dimethyl-5-phenyl-4,5,6,7-tetrahydropyrazolo[1,5-a]pyrimidin-3-yl)carbonyl)amino)-1-ethylpropyl)phenoxy)acetic acid | mp 213-214° C. |
| 732 | ethyl 4-(1-(((7,7-dimethyl-5-phenyl-4,5,6,7-tetrahydropyrazolo[1,5-a]pyrimidin-3-yl)carbonyl)amino)-1-ethylpropyl)benzoate | mp 181-182° C. |
| 733 | isopropyl 4-(1-(((7,7-dimethyl-5-phenyl-4,5,6,7-tetrahydropyrazolo[1,5-a]pyrimidine-3-yl)carbonyl)amino)-1-ethylpropyl)benzoate | mp 205-206° C. |
| 734 | 4-(1-(((7,7-dimethyl-5-phenyl-4,5,6,7-tetrahydropyrazolo[1,5-a]pyrimidin-3-yl)carbonyl)amino)-1-ethylpropyl)benzoic acid | mp 257-258° C. |
| 735 | 3-((2-(4-chlorophenyl)-1-pyrrolidinyl)carbonyl)-7,7-dimethyl-5-phenyl-4,5,6,7-tetrahydropyrazolo[1,5-a[pyrimidine | MS(ESI, m/z) 436 (M + H)+ |

TABLE 4-continued

| Example | Structure | Name | Physiological Data |
|---|---|---|---|
| 736 | 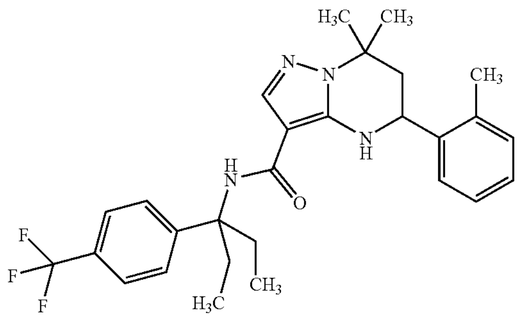 | N-(1-ethyl-1-(4-(trifluoromethyl)phenyl)propyl)-7,7-dimethyl-5-(2-methylphenyl)-4,5,6,7-tetrahydropyrazolo[1,5-a]pyrimidine-3-carboxamide | MS(ESI, m/z) 499 (M + H)+ |
| 737 | 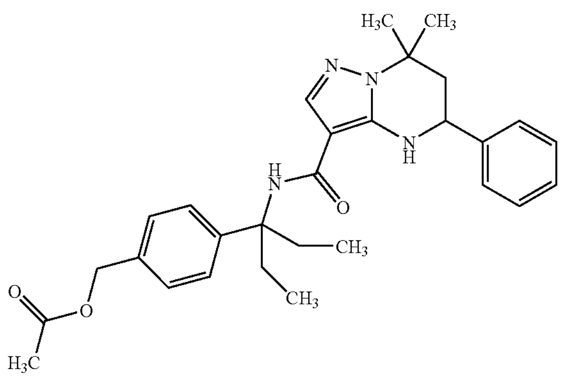 | 4-(1-(((7,7-dimethyl-5-phenyl-4,5,6,7-tetrahydropyrazolo[1,5-a]pyrimidin-3-yl)carbonyl)amino)-1-ethylpropyl)benzyl acetate | mp 185-186° C. |
| 738 | 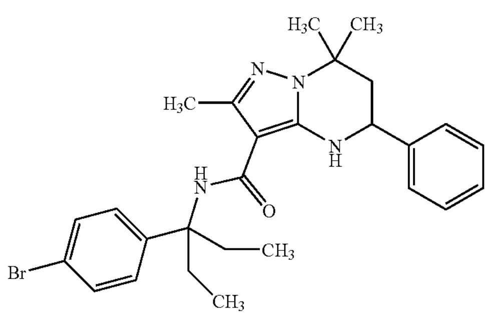 | N-(1-(4-bromophenyl)-1-ethylpropyl)-2,7,7-trimethyl-5-phenyl-4,5,6,7-tetrahydropyrazolo[1,5-a]pyrimidine-3-carboxamide | HCl salt mp 185-187° C. |
| 739 | 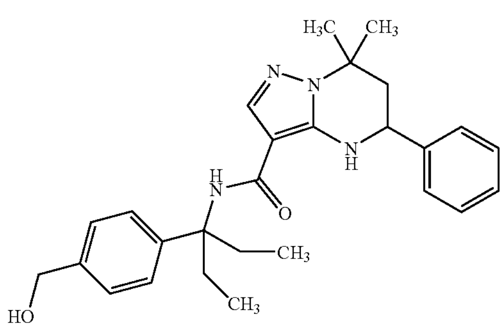 | N-(1-ethyl-1-(4-(hydroxymethyl)phenyl)propyl)-7,7-dimethyl-5-phenyl-4,5,6,7-tetrahydropyrazolo[1,5-a]pyrimidine-3-carboxamide | mp 178-179° C. |

TABLE 4-continued

| Example | Structure | Name | Physiological Data |
|---|---|---|---|
| 740 | 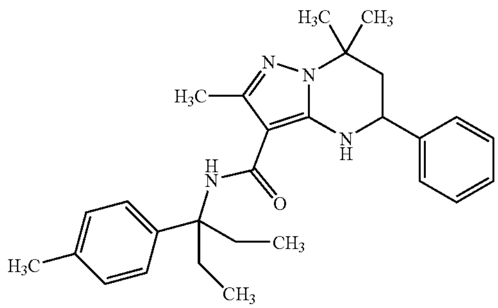 | N-(1-ethyl-1-(4-methylphenyl)propyl)-2,7,7-trimethyl-5-phenyl-4,5,6,7-tetrahydropyrazolo[1,5-a]pyrimidine-3-carboxamide | HCl salt mp 161-162° C. |
| 741 | 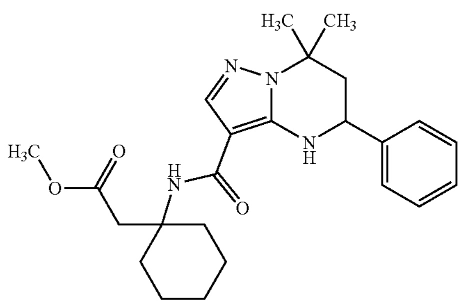 | methyl (1-(((7,7-dimethyl-5-phenyl-4,5,6,7-tetrahydropyrazolo[1,5-a]pyrimidin-3-yl)carbonyl)amino)cyclohexyl)acetate | MS(ESI, m/z) 425 (M + H)+ |
| 742 | 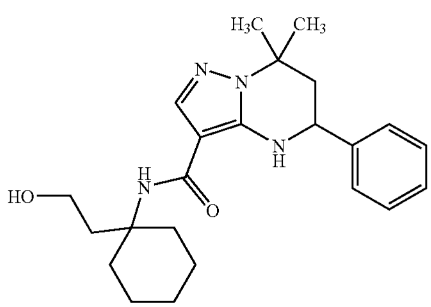 | N-(1-(2-hydroxyethyl)cyclohexyl)-7,7-dimethyl-5-phenyl-4,5,6,7-tetrahydropyrazolo[1,5-a]pyrimidine-3-carboxamide | MS(ESI, m/z) 397 (M + H)+ |
| 743 | 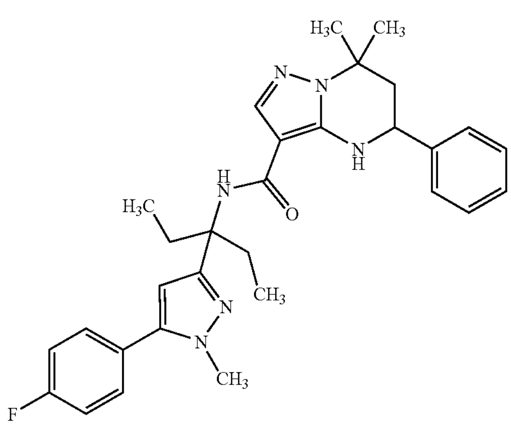 | N-(1-ethyl-1-(5-(4-fluorophenyl)-1-methyl-1H-pyrazol-3-yl)propyl)-7,7-dimethyl-5-phenyl-4,5,6,7-tetrahydropyrazolo[1,5-a]pyrimidine-3-carboxamide | HCl salt MS(ESI, m/z) 515 (M + H)+ |

TABLE 4-continued

| Example | Structure | Name | Physiological Data |
|---|---|---|---|
| 744 | 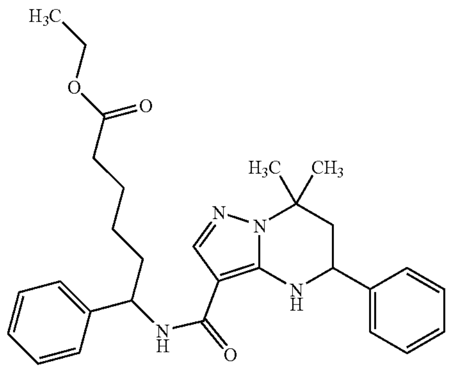 | ethyl 6-(((7,7-dimethyl-5-phenyl-4,5,6,7-tetrahydropyrazolo[1,5-a]pyrimidin-3-yl)carbonyl)amino)-6-phenylhexanoate | MS(ESI, m/z) 489 (M + H)+ |
| 745 | 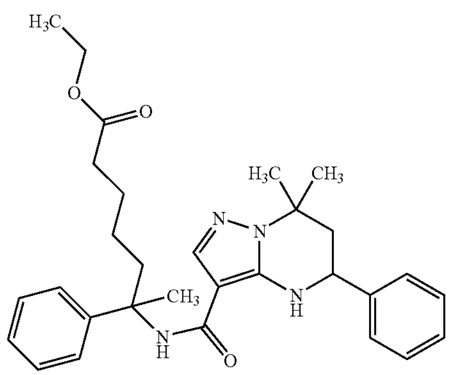 | ethyl 6-(((7,7-dimethyl-5-phenyl-4,5,6,7-tetrahydropyrazolo[1,5-a]pyrimidin-3-yl)carbonyl)amino)-6-phenylheptanoate | MS(ESI, m/z) 503 (M + H)+ |
| 746 | 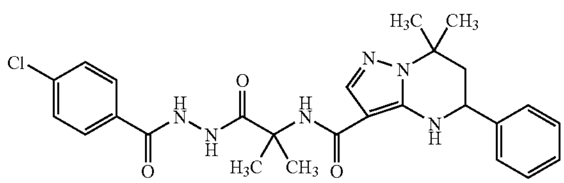 | N-(2-(2-(4-chlorobenzoyl)hydrazino)-1,1-dimethyl-5-phenyl-4,5,6,7-tetrahydropyrazolo[1,5-a]pyrimidine-3-carboxamide | MS(ESI, m/z) 510 (M + H)+ |
| 747 | 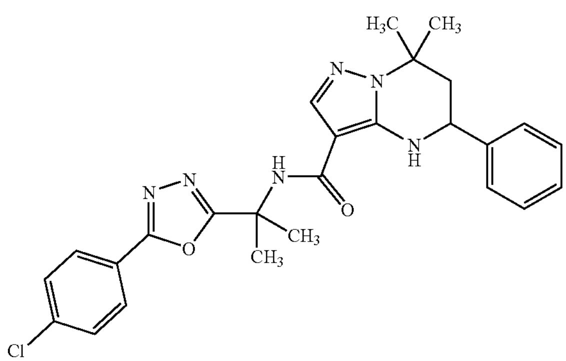 | N-(1-(5-(4-chlorophenyl)-1,3,4-oxadiazol-2-yl)-1-methylethyl)-7,7-dimethyl-5-phenyl-4,5,6,7-tetrahydropyrazolo[1,5-a]pyrimidine-3-carboxamide | MS(ESI, m/z) 491 (M + H)+ |
| 748 | 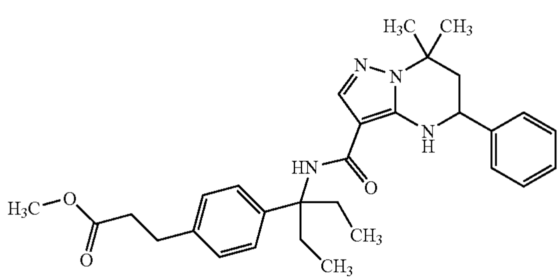 | methyl 3-(4-(1-(((7,7-dimethyl-5-phenyl-4,5,6,7-tetrahydropyrazolo[1,5-a]pyrimidin-3-yl)carbonyl)amino)-1-ethylpropyl)phenyl)propanoate | mp 147-148° C. |

TABLE 4-continued

| Example | Structure | Name | Physiological Data |
|---|---|---|---|
| 749 | 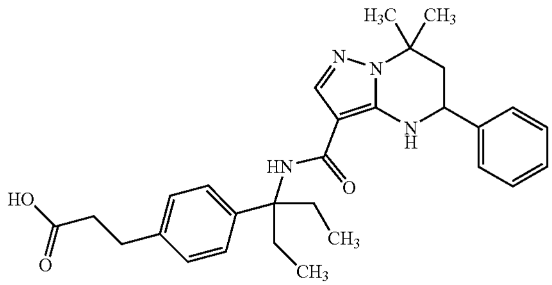 | 3-(4-(1-(((7,7-dimethyl-5-phenyl-4,5,6,7-tetrahydropyrazolo[1,5-a]pyrimidin-3-yl)carbonyl)amino)-1-ethylpropyl)phenyl)propanoic acid | mp 240-241° C. |
| 750 | 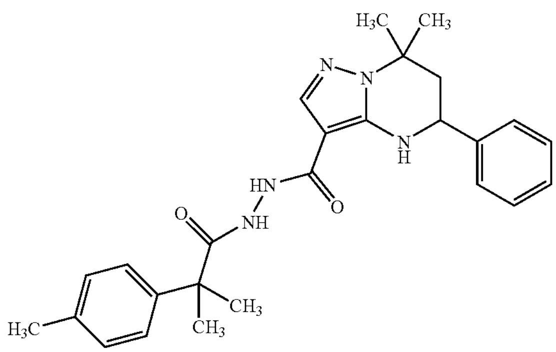 | 7,7-dimethyl-N'-(2-methyl-2-(4-methylphenyl)propanoyl)-5-phenyl-4,5,6,7-tetrahydropyrazolo[1,5-a]pyrimidine-3-carbohydrazide | MS(ESI, m/z) 446 (M + H)+ |
| 751 | 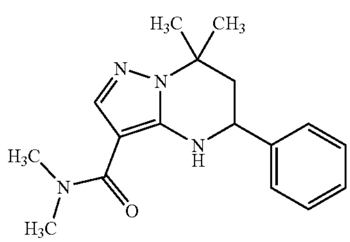 | N,N,7,7-tetramethyl-5-phenyl-4,5,6,7-tetrahydropyrazolo[1,5-a]pyrimidine-3-carboxamide | MS(ESI, m/z) 299 (M + H)+ |
| 752 | 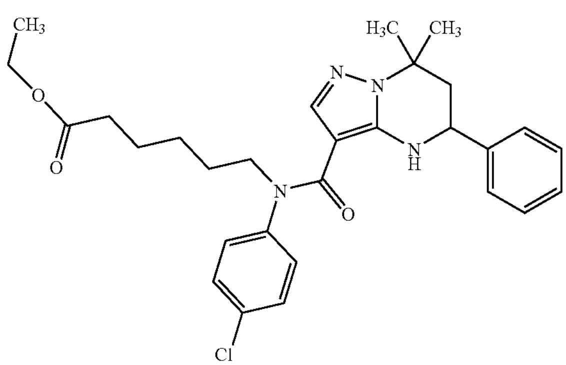 | ethyl 6-((4-chlorophenyl)((7,7-dimethyl-5-phenyl-4,5,6,7-tetrahydropyrazolo[1,5-a]pyrimidin-3-yl)carbonyl)amino)hexanoate | MS(ESI, m/z) 524 (M + H)+ |

TABLE 4-continued

| Example | Structure | Name | Physiological Data |
|---|---|---|---|
| 753 | 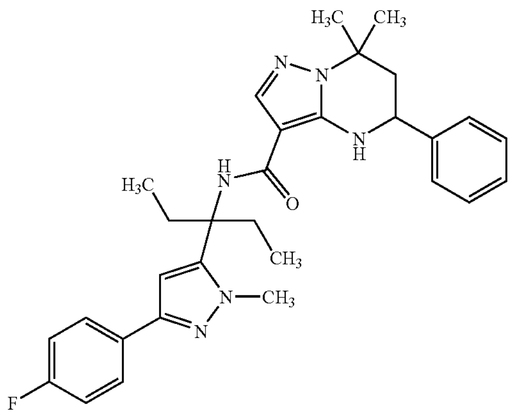 | N-(1-ethyl-1-(3-(4-fluorophenyl)-1-methyl-1H-pyrazol-5-yl)propyl)-7,7-dimethyl-5-phenyl-4,5,6,7-tetrahydropyrazolo[1,5-a]pyrimidine-3-carboxamide | MS(ESI, m/z) 515 (M + H)+ |
| 754 | 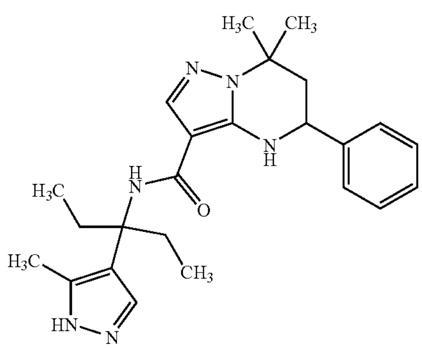 | N-(1-ethyl-1-(5-methyl-1H-pyrazol-4-yl)propyl)-7,7-dimethyl-5-phenyl-4,5,6,7-tetrahydropyrazolo[1,5-a]pyrimidine-3-carboxamide | MS(ESI, m/z) 421 (M + H)+ |
| 755 | 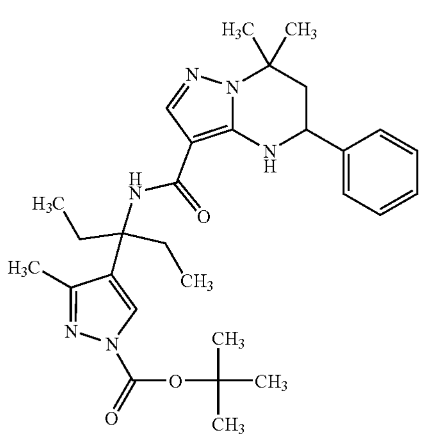 | tert-butyl 4-(1-(((7,7-dimethyl-5-phenyl-4,5,6,7-tetrahydropyrazolo[1,5-a]pyrimidin-3-yl)carbonyl)amino)-1-ethylpropyl)-3-methyl-1H-pyrazole-1-carboxylate | MS(ESI, m/z) 521 (M + H)+ |

TABLE 4-continued

| Example | Structure | Name | Physiological Data |
|---|---|---|---|
| 756 | 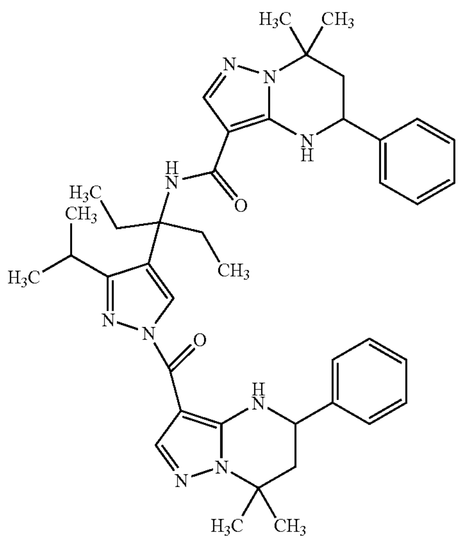 | N-(1-(1-((7,7-dimethyl-5-phenyl-4,5,6,7-tetrahydropyrazolo[1,5-a]pyrimidin-3-yl)carbonyl)-3-isopropyl-1H-pyrazol-4-yl)-1-ethylpropyl)-7,7-dimethyl-5-phenyl-4,5,6,7-tetrahydropyrazolo[1,5-a]pyrimidine-3-carboxamide | MS(ESI, m/z) 702 (M + H)+ |
| 757 | 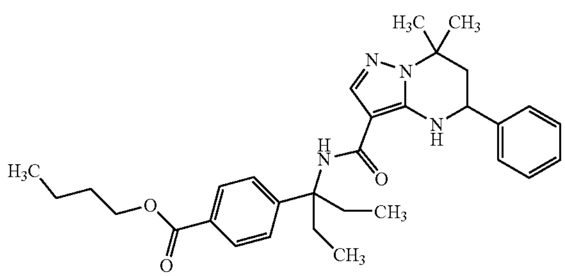 | butyl 4-(1-(((7,7-dimethyl-5-phenyl-4,5,6,7-tetrahydropyrazolo[1,5-a]pyrimidin-3-yl)carbonyl)amino)-1-ethylpropyl)benzoate | mp 139-140° C. |
| 758 | 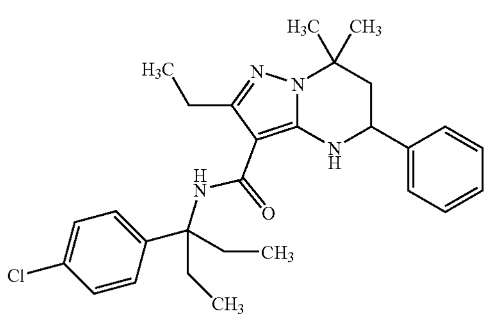 | N-(1-(4-chlorophenyl)-1-ethylpropyl)-2-ethyl-7,7-dimethyl-5-phenyl-4,5,6,7-tetrahydropyrazolo[1,5-a]pyrimidine-3-carboxamide | mp 183-184° C. |
| 759 | 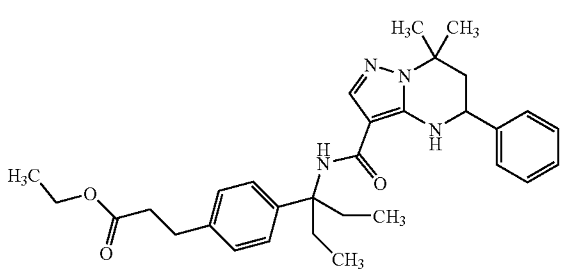 | ethyl 3-(4-(1-(((7,7-dimethyl-5-phenyl-4,5,6,7-tetrahydropyrazolo[1,5-a]pyrimidin-3-yl)carbonyl)amino)-1-ethylpropyl)phenyl)propanoate | mp 135-136° C. |

TABLE 4-continued

| Example | Structure | Name | Physiological Data |
|---|---|---|---|
| 760 | 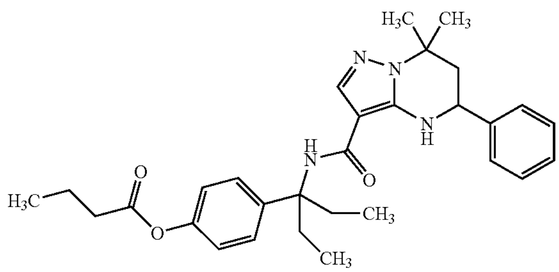 | 4-(1-(((7,7-dimethyl-5-phenyl-4,5,6,7-tetrahydropyrazolo[1,5-a]pyrimidine-3-yl)carbonyl)amino)-1-ethylpropyl)phenyl butyrate | mp 148-149° C. |
| 761 | 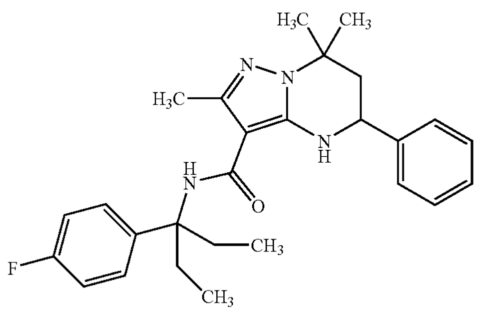 | N-(1-ethyl-1-(4-fluorophenyl)propyl)-2,7,7-trimethyl-5-phenyl-4,5,6,7-tetrahydropyrazolo[1,5-a]pyrimidine-3-carboxamide | mp 182-183° C. |
| 762 | 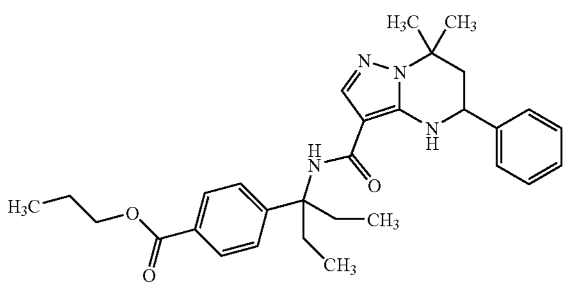 | propyl 4-(1-(((7,7-dimethyl-5-phenyl-4,5,6,7-tetrahydropyrazolo[1,5-a]pyrimidin-3-yl)carbonyl)amino)-1-ethylpropyl)benzoate | mp 162-163° C. |
| 763 | 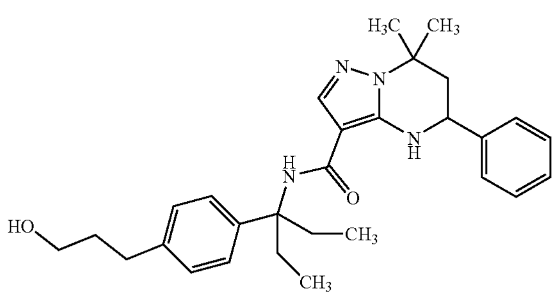 | N-(1-ethyl-1-(4-(3-hydroxypropyl)phenyl)propyl)-7,7-dimethyl-5-phenyl-4,5,6,7-tetrahydropyrazolo[1,5-a]pyrimidine-3-carboxamide | mp 194-195° C. |
| 764 | 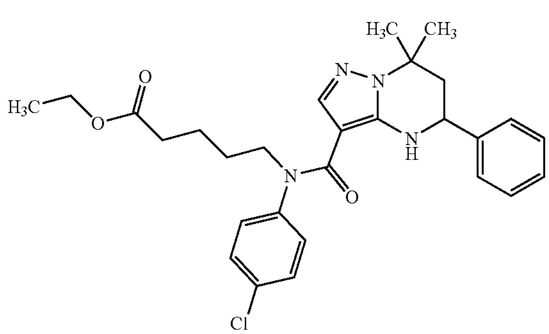 | ethyl 5-((4-chlorophenyl)((7,7-dimethyl-5-phenyl-4,5,6,7-tetrahydropyrazolo[1,5-a]pyrimidin-3-yl)carbonyl)amino)pentanoate | MS(ESI, m/z) 510 (M + H)+ |

TABLE 4-continued

| Example | Structure | Name | Physiological Data |
|---|---|---|---|
| 765 | 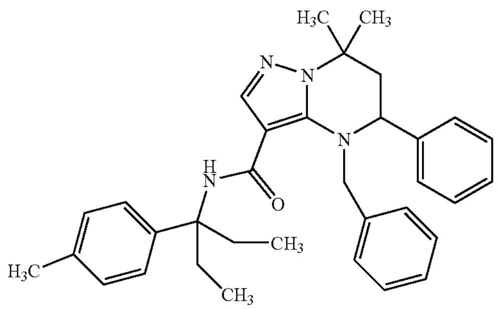 | 4-benzyl-N-(1-ethyl-1-(4-methylphenyl)propyl)-7,7-dimethyl-5-phenyl-4,5,6,7-tetrahydropyrazolo[1,5-a]pyrimidine-3-carboxamide | mp 142-143° C. |
| 766 | 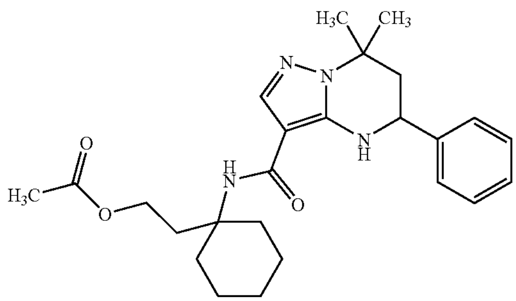 | 2-(1-(((7,7-dimethyl-5-phenyl-4,5,6,7-tetrahydropyrazolo[1,5-a]pyrimidin-3-yl)carbonyl)amino)cyclohexyl)ethyl acetate | MS(ESI, m/z) 439 (M + H)+ |
| 767 | 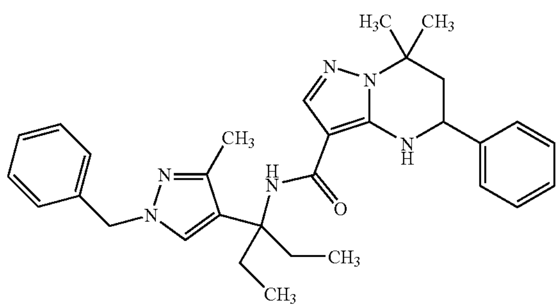 | N-(1-(1-benzyl-3-methyl-1H-pyrazol-4-yl)-1-ethylpropyl)-7,7-dimethyl-5-phenyl-4,5,6,7-tetrahydropyrazolo[1,5-a]pyrimidine-3-carboxamide | MS(ESI, m/z) 511 (M + H)+ |
| 768 | 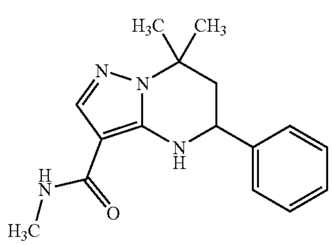 | N,7,7-trimethyl-5-phenyl-4,5,6,7-tetrahydropyrazolo[1,5-a]pyrimidine-3-carboxamide | mp 116-117° C. |
| 769 | 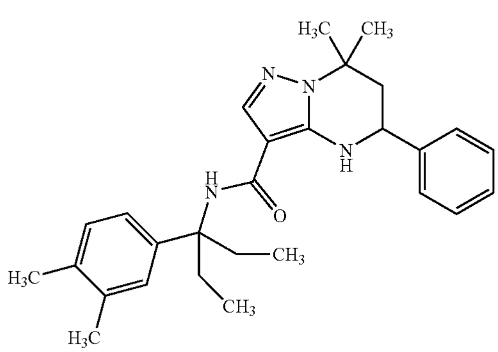 | N-(1-(3,4-dimethylphenyl)-1-ethylpropyl)-7,7-dimethyl-5-phenyl-4,5,6,7-tetrahydropyrazolo[1,5-a]pyrimidine-3-carboxamide | HCl salt mp 137-138° C. |

TABLE 4-continued

| Example | Structure | Name | Physiological Data |
|---|---|---|---|
| 770 | 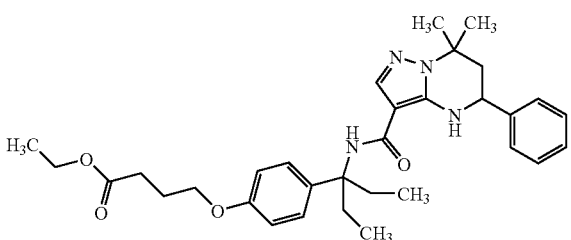 | ethyl 4-(4-(1-(((7,7-dimethyl-5-phenyl-4,5,6,7-tetrahydropyrazolo[1,5-a]pyrimidin-3-yl)carbonyl)amino)-1-ethylpropyl)phenoxy)butanoate | mp 101-102° C. |
| 771 | 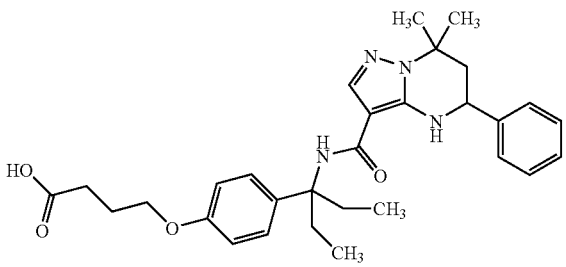 | 4-(4-(1-(((7,7-dimethyl-5-phenyl-4,5,6,7-tetrahydropyrazolo[1,5-a]pyrimidin-3-yl)carbonyl)amino)-1-ethylpropyl)phenoxy)butanoic acid | mp 170-171° C. |
| 772 | 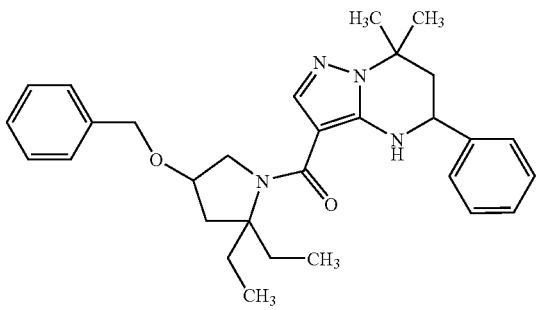 | 3-((4-(benzyloxy)-2,2-diethyl-1-pyrrolidinyl)carbonyl)-7,7-dimethyl-5-phenyl-4,5,6,7-tetrahydropyrazolo[1,5-a]pyrimidine | MS(ESI, m/z) 488 (M + H)+ |
| 773 | 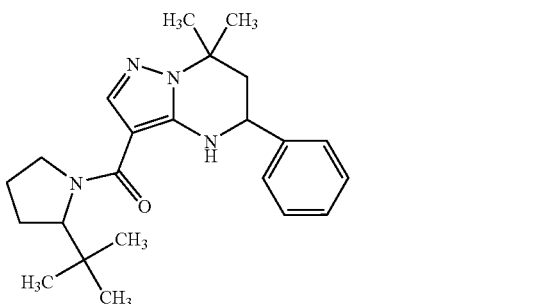 | 3-((2-tert-butyl-1-pyrrolidinyl)carbonyl)-7,7-dimethyl-5-phenyl-4,5,6,7-tetrahydropyrazolo[1,5-a]pyrimidine | MS(ESI, m/z) 382 (M + H)+ |
| 774 | 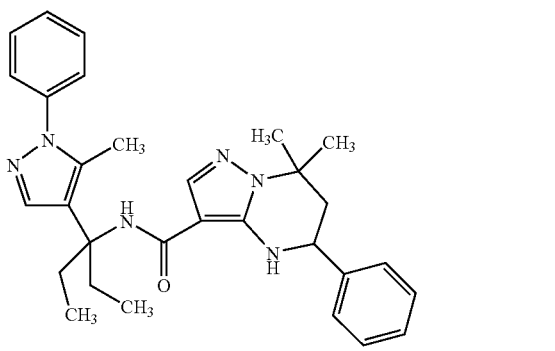 | N-(1-ethyl-1-(5-methyl-1-phenyl-1H-pyrazol-4-yl)propyl)-7,7-dimethyl-5-phenyl-4,5,6,7-tetrahydropyrazolo[1,5-a]pyrimidine-3-carboxamide | MS(ESI, m/z) 497 (M + H)+ |

TABLE 4-continued

| Example | Structure | Name | Physiological Data |
|---|---|---|---|
| 775 | 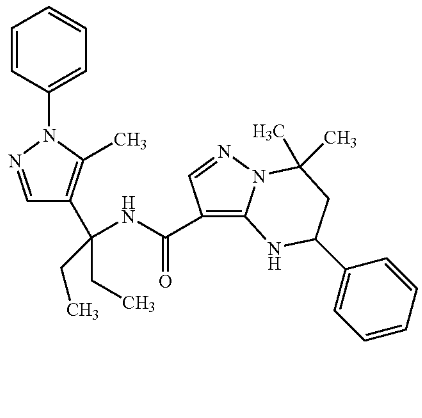 | N-(1-ethyl-1-(5-methyl-1-phenyl-1H-pyrazol-4-yl)propyl)-7,7-dimethyl-5-phenyl-4,5,6,7-tetrahydropyrazolo[1,5-a]pyrimidine-3-carboxamide | HCl salt MS(ESI, m/z) 497 (M + H)+ |
| 776 | 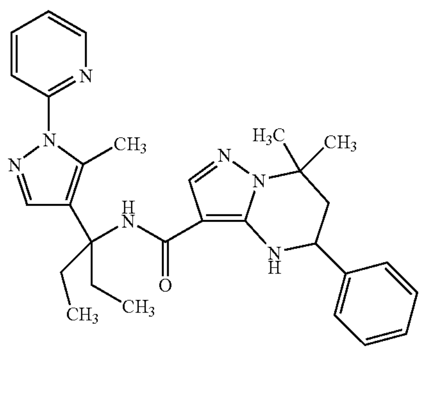 | N-(1-ethyl-1-(5-methyl-1-(2-pyridinyl)-1H-pyrazol-4-yl)propyl)-7,7-dimethyl-5-phenyl-4,5,6,7-tetrahydropyrazolo[1,5-a]pyrimidine-3-carboxamide | MS(ESI, m/z) 498 (M + H)+ |
| 777 | 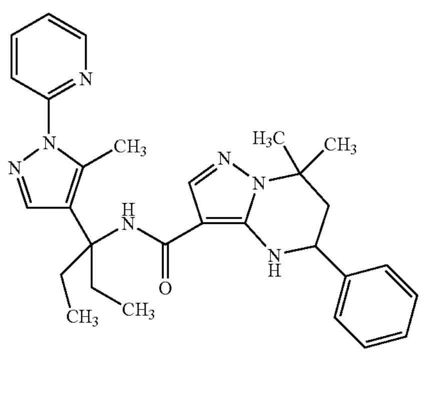 | N-(1-ethyl-1-(5-methyl-1-(2-pyridinyl)-1H-pyrazol-4-yl)propyl)-7,7-dimethyl-5-phenyl-4,5,6,7-tetrahydropyrazolo[1,5-a]pyrimidine-3-carboxamide | HCl salt MS(ESI, m/z) 498 (M + H)+ |
| 778 | 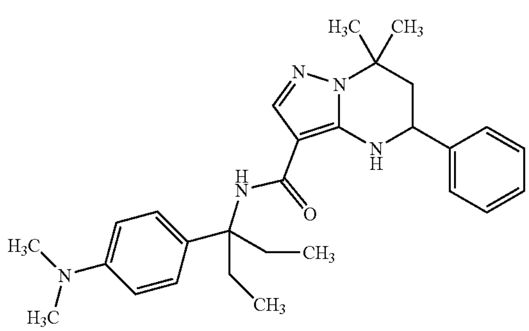 | N-(1-(4-(dimethylamino)phenyl)-1-ethylpropyl)-7,7-dimethyl-5-phenyl-4,5,6,7-tetrahydropyrazolo[1,5-a]pyrimidine-3-carboxamide | mp 128-129° C. |

TABLE 4-continued

| Example | Structure | Name | Physiological Data |
|---|---|---|---|
| 779 | 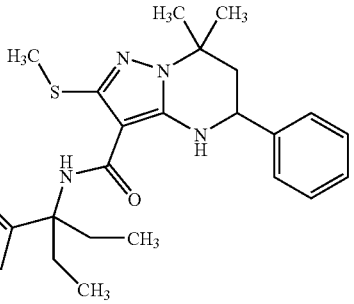 | N-(1-ethyl-1-(4-methylphenyl)propyl)-7,7-dimethyl-2-(methylthio)-5-phenyl-4,5,6,7-tetrahydropyrazolo[1,5-a]pyrimidine-3-carboxamide | HCl salt mp 106-107° C. |
| 780 | 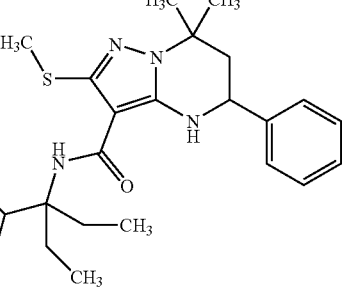 | N-(1-(4-chlorophenyl)-1-ethylpropyl)-7,7-dimethyl-2-(methylthio)-5-phenyl-4,5,6,7-tetrahydropyrazolo[1,5-a]pyrimidine-3-carboxamide | HCl salt mp 115-117° C. |
| 781 | 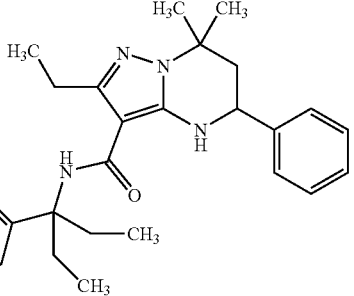 | 2-ethyl-N-(1-ethyl-1-(4-methylphenyl)propyl)-7,7-dimethyl-5-phenyl-4,5,6,7-tetrahydropyrazolo[1,5-a]pyrimidine-3-carboxamide | HCl salt mp 182-183° C. |
| 782 | 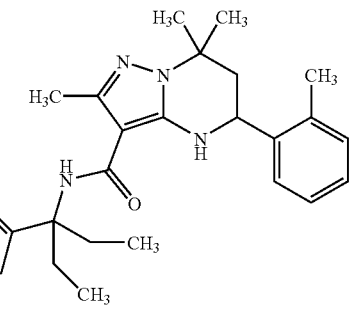 | N-(1-ethyl-1-(4-methylphenyl)propyl)-2,7,7-trimethyl-5-(2-methylphenyl)-4,5,6,7-tetrahydropyrazolo[1,5-a]pyrimidine-3-carboxamide | HCl salt mp 187-188° C. |

TABLE 4-continued

| Example | Structure | Name | Physiological Data |
|---|---|---|---|
| 783 | 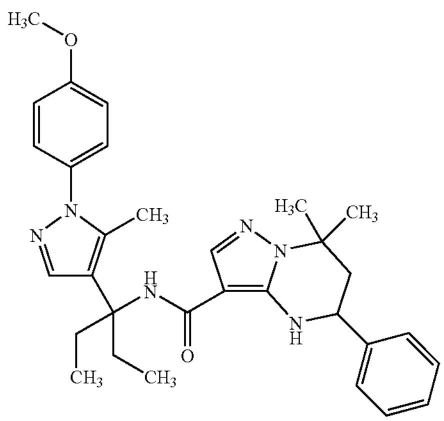 | N-(1-ethyl-1-(1-(4-methoxyphenyl)-5-methyl-1H-pyrazol-4-yl)propyl)-7,7-dimethyl-5-phenyl-4,5,6,7-tetrahydropyrazolo[1,5-a]pyrimidine-3-carboxamide | MS(ESI, m/z) 527 (M + H)+ |
| 784 | 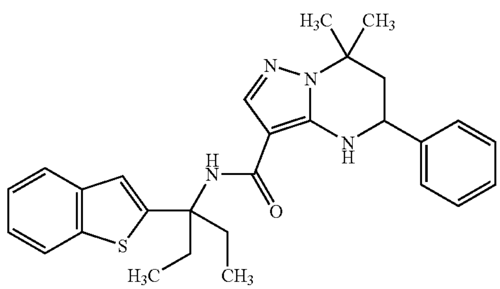 | N-(1-(1-benzothien-2-yl)-1-ethylpropyl)-7,7-dimethyl-5-phenyl-4,5,6,7-tetrahydropyrazolo[1,5-a]pyrimidine-3-carboxamide | MS(ESI, m/z) 473 (M + H)+ |
| 785 | 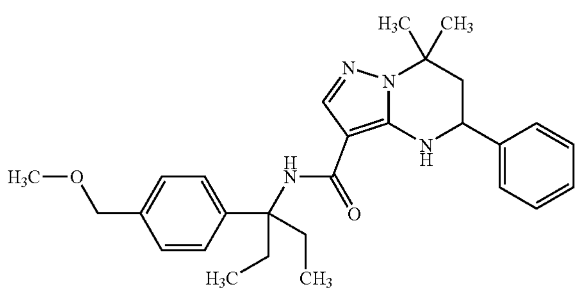 | N-(1-ethyl-1-(4-(methoxymethyl)phenyl)propyl)-7,7-dimethyl-5-phenyl-4,5,6,7-tetrahydropyrazolo[1,5-a]pyrimidine-3-carboxamide | MS(ESI, m/z) 461 (M + H)+ |
| 786 | 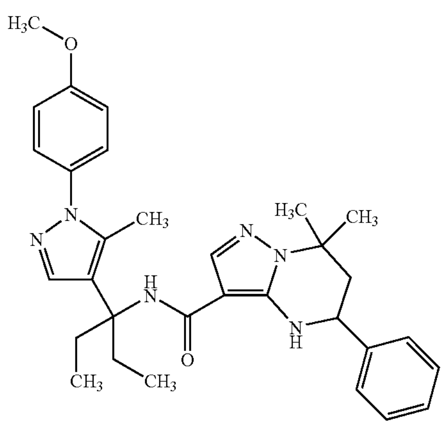 | N-(1-ethyl-1-(1-(4-methoxyphenyl)-5-methyl-1H-pyrazol-4-yl)propyl)-7,7-dimethyl-5-phenyl-4,5,6,7-tetrahydropyrazolo[1,5-a]pyrimidine-3-carboxamide | HCl salt MS(ESI, m/z) 527 (M + H)+ |

TABLE 4-continued

| Example | Structure | Name | Physiological Data |
|---|---|---|---|
| 787 | 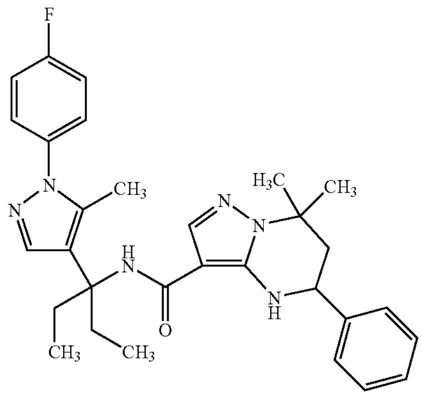 | N-(1-ethyl-1-(1-(4-fluorophenyl)-5-methyl-1H-pyrazol-4-yl)propyl)-7,7-dimethyl-5-phenyl-4,5,6,7-tetrahydropyrazolo[1,5-a]pyrimidine-3-carboxamide | MS(ESI, m/z) 515 (M + H)+ |
| 788 | 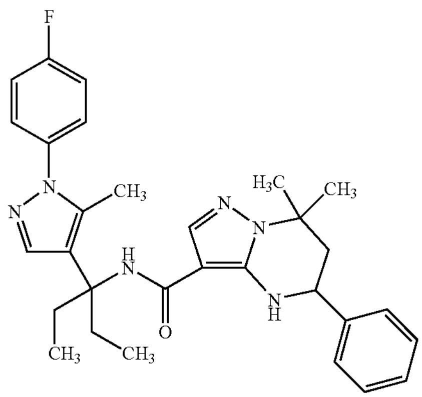 | N-(1-ethyl-1-(1-(4-fluorophenyl)-5-methyl-1H-pyrazol-4-yl)propyl)-7,7-dimethyl-5-phenyl-4,5,6,7-tetrahydropyrazolo[1,5-a]pyrimidine-3-carboxamide | HCl salt MS(ESI, m/z) 515 (M + H)+ |
| 789 | 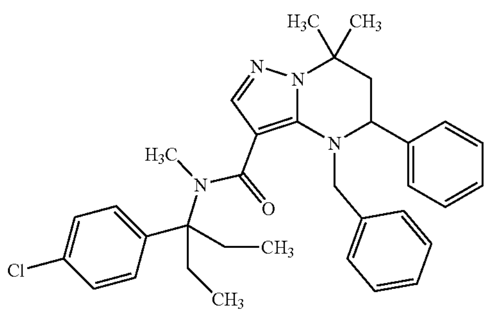 | 4-benzyl-N-(1-(4-chlorophenyl)-1-ethylpropyl)-N,7,7-trimethyl-5-phenyl-4,5,6,7-tetrahydropyrazolo[1,5-a]pyrimidine-3-carboxamide | MS(ESI, m/z) 556 (M + H)+ |
| 790 | 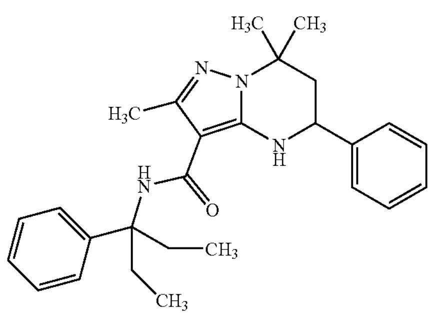 | N-(1-ethyl-1-phenylpropyl)-2,7,7-trimethyl-5-phenyl-4,5,6,7-tetrahydropyrazolo[1,5-a]pyrimidine-3-carboxamide | HCl salt mp 185-186° C. |

TABLE 4-continued

| Example | Structure | Name | Physiological Data |
|---|---|---|---|
| 791 | 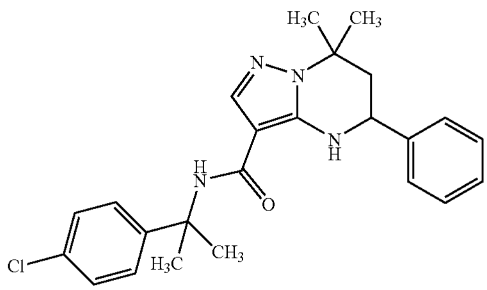 | N-(1-(4-chlorophenyl)-1-methylethyl)-7,7-dimethyl-5-phenyl-4,5,6,7-tetrahydropyrazolo[1,5-a]pyrimidine-3-carboxamide | HCl salt mp 207-208° C. |
| 792 | 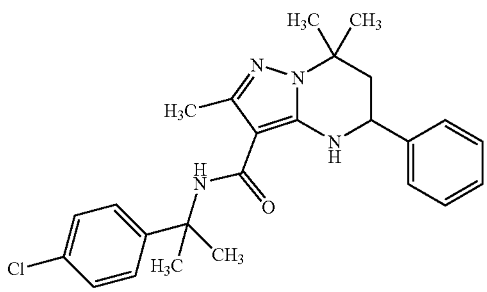 | N-(1-(4-chlorophenyl)-1-methylethyl)-2,7,7-trimethyl-5-phenyl-4,5,6,7-tetrahydropyrazolo[1,5-a]pyrimidine-3-carboxamide | HCl salt mp 204-205° C. |
| 793 | 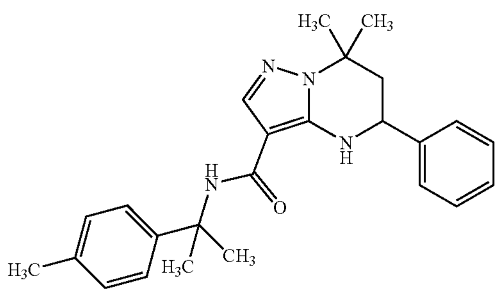 | 7,7-dimethyl-N-(1-methyl-1-(4-methylphenyl)ethyl)-5-phenyl-4,5,6,7-tetrahydropyrazine[1,5-a]pyrimidine-3-carboxamide | HCl salt mp 150-151° C. |
| 794 | 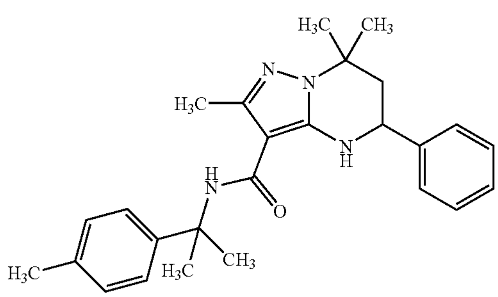 | 2,7,7-trimethyl-N-(1-methyl-1-(4-methylphenyl)ethyl)-5-phenyl-4,5,6,7-tetrahydropyrazolo[1,5-a]pyrimidine-3-carboxamide | HCl salt mp 193-194° C. |
| 795 | 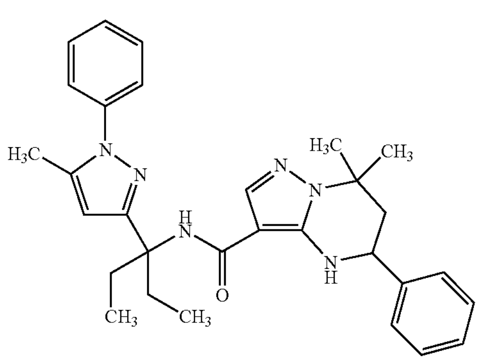 | N-(1-ethyl-1-(5-methyl-1-phenyl-1H-pyrazol-3-yl)propyl)-7,7-dimethyl-5-phenyl-4,5,6,7-tetrahydropyrazolo[1,5-a]pyrimidine-3-carboxamide | MS(ESI, m/z) 497 (M + H)+ |

TABLE 4-continued

| Example | Structure | Name | Physiological Data |
|---|---|---|---|
| 796 | 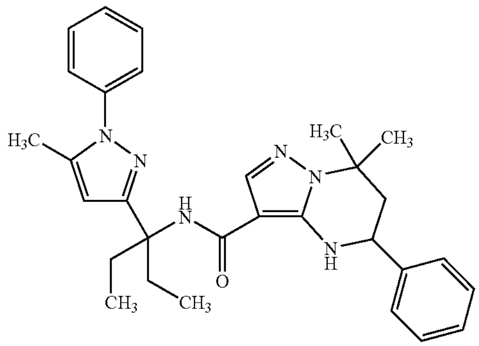 | N-(1-ethyl-1-(5-methyl-1-phenyl-1H-pyrazol-3-yl)propyl)-7,7-dimethyl-5-phenyl-4,5,6,7-tetrahydropyrazolo[1,5-a]pyrimidine-3-carboxamide | HCl salt MS(ESI, m/z) 497 (M + H)+ |
| 797 | 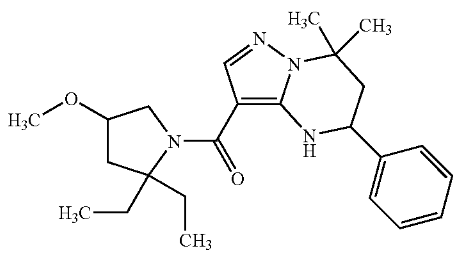 | 3-((2,2-diethyl-4-methoxy-1-pyrrolidinyl)carbonyl)-7,7-dimethyl-5-phenyl-4,5,6,7-tetrahydropyrazolo[1,5-a]pyrimidine | MS(ESI, m/z) 412 (M + H)+ |
| 798 | 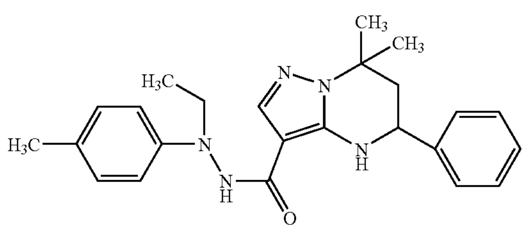 | N'-ethyl-7,7-dimethyl-N'-(4-methylphenyl)-5-phenyl-4,5,6,7-tetrahydropyrazolo[1,5-a]pyrimidine-3-carboxamide | MS(ESI, m/z) 404 (M + H)+ |
| 799 | 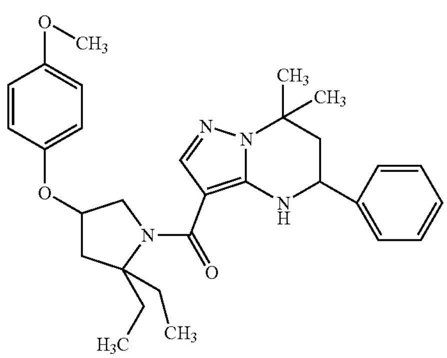 | 3-((2,2-diethyl-4-(4-methoxyphenoxy)-1-pyrrolidinyl)carbonyl)-7,7-dimethyl-5-phenyl-4,5,6,7-tetrahydropyrazolo[1,5-a]pyrimidine | MS(ESI, m/z) 503 (M + H)+ |
| 800 | 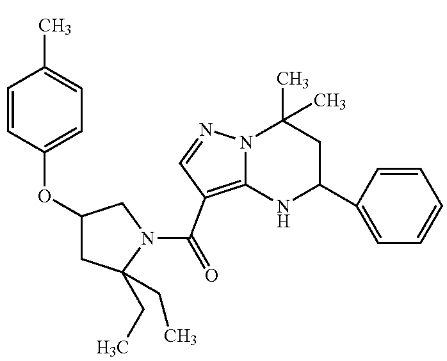 | 3-((2,2-diethyl-4-(4-methylphenoxy)-1-pyrrolidinyl)carbonyl)-7,7-dimethyl-5-phenyl-4,5,6,7-tetrahydropyrazolo[1,5-a]pyrimidine | MS(ESI, m/z) 487 (M + H)+ |

TABLE 4-continued

| Example | Structure | Name | Physiological Data |
|---|---|---|---|
| 801 | 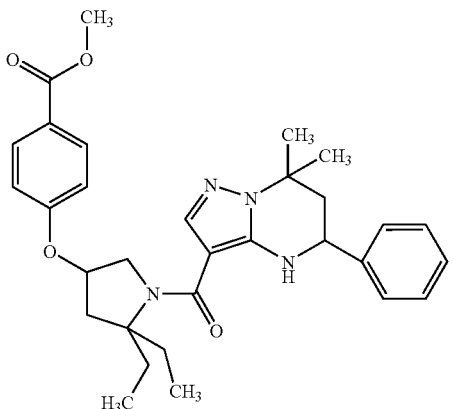 | methyl 4-((1-((7,7-dimethyl-5-phenyl-4,5,6,7-tetrahydropyrazolo[1,5-a]pyrimidin-3-yl)carbonyl)-5,5-diethyl-3-pyrrolidinyl)oxy)benzoate | MS(ESI, m/z) 531 (M + H)+ |
| 802 | 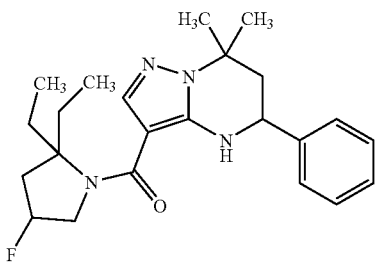 | 3-((2,2-diethyl-4-fluoro-1-pyrrolidinyl)carbonyl)-7,7-dimethyl-5-phenyl-4,5,6,7-tetrahydropyrazolo[1,5-a]pyrimidine | MS(ESI, m/z) 399 (M + H)+ |
| 803 | 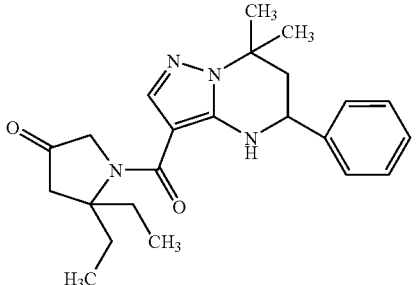 | 1-((7,7-dimethyl-5-phenyl-4,5,6,7-tetrahydropyrazolo[1,5-a]pyrimidin-3-yl)carbonyl)-5,5-diethyl-3-pyrrolidinone | MS(ESI, m/z) 395 (M + H)+ |
| 804 | 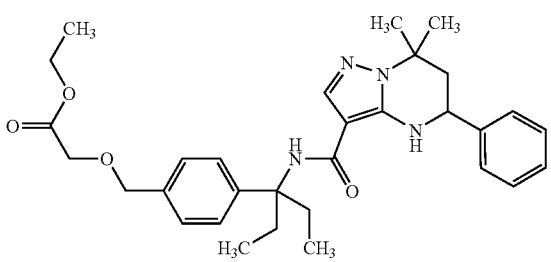 | ethyl ((4-(1-(((7,7-dimethyl-5-phenyl-4,5,6,7-tetrahydropyrazolo[1,5-a]pyrimidin-3-yl)carbonyl)amino)-1-ethylpropyl)benzyl)oxy)acetate | MS(ESI, m/z) 533 (M + H)+ |
| 805 | 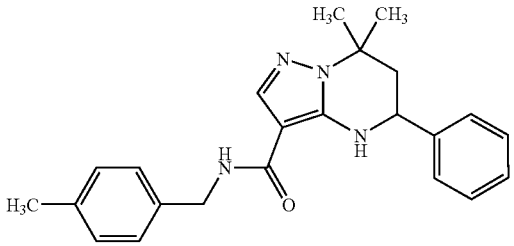 | 7,7-dimethyl-N-(4-methylbenzyl)-5-phenyl-4,5,6,7-tetrahydropyrazolo[1,5-a]pyrimidine-3-carboxamide | MS(ESI, m/z) 375 (M + H)+ |

TABLE 4-continued

| Example | Structure | Name | Physiological Data |
|---------|-----------|------|--------------------|
| 806 | 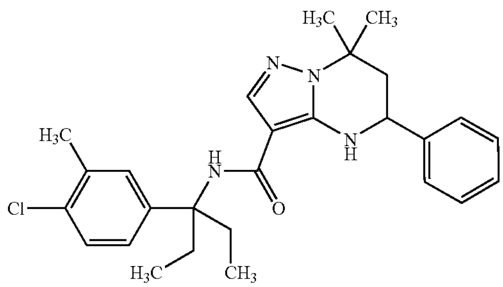 | N-(1-(4-chloro-3-methylphenyl)-1-ethylpropyl)-7,7-dimethyl-5-phenyl-4,5,6,7-tetrahydropyrazolo[1,5-a]pyrimidine-3-carboxamide | MS(ESI, m/z) 465 (M + H)+ |
| 807 | 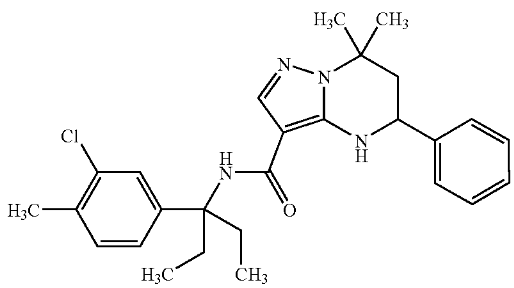 | N-(1-(3-chloro-4-methylphenyl)-1-ethylpropyl)-7,7-dimethyl-5-phenyl-4,5,6,7-tetrahydropyrazolo[1,5-a]pyrimidine-3-carboxamide | MS(ESI, m/z) 465 (M + H)+ |
| 808 | 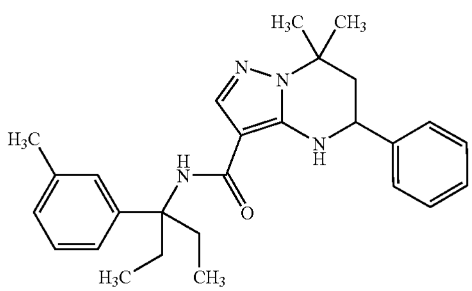 | N-(1-ethyl-1-(3-methylphenyl)propyl)-7,7-dimethyl-5-phenyl-4,5,6,7-tetrahydropyrazolo[1,5-a]pyrimidine-3-carboxamide | MS(ESI, m/z) 431 (M + H)+ |
| 809 | 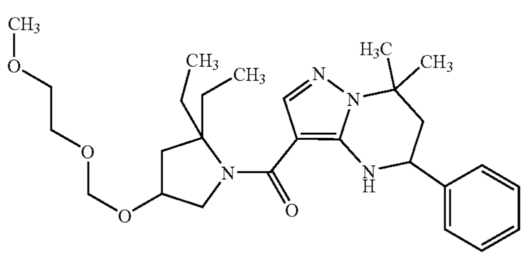 | 3-((2,2-diethyl-4-((2-methoxyethoxy)methoxy)-1-pyrrolidinyl)carbonyl)-7,7-dimethyl-5-phenyl-4,5,6,7-tetrahydropyrazolo[1,5-a]pyrimidine | MS(ESI, m/z) 485 (M + H)+ |
| 810 | 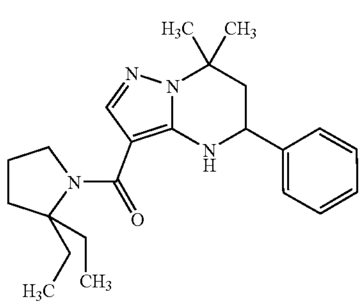 | 3-((2,2-diethyl-1-pyrrolidinyl)carbonyl)-7,7-dimethyl-5-phenyl-4,5,6,7-tetrahydropyrazolo[1,5-a]pyrimidine | MS(ESI, m/z) 381 (M + H)+ |

TABLE 4-continued

| Example | Structure | Name | Physiological Data |
|---|---|---|---|
| 811 | 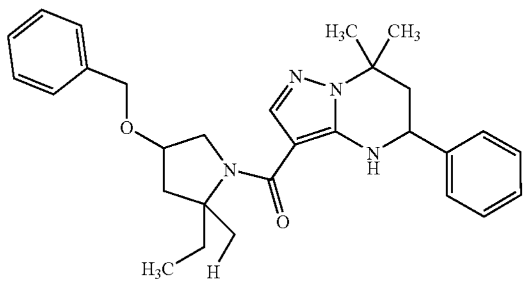 | 3-((4-(benzyloxy)-2,2-diethyl-1-pyrrolidinyl)carbonyl)-7,7-dimethyl-5-phenyl-4,5,6,7-tetrahydropyrazolo[1,5-a]pyrimidine | MS(ESI, m/z) 487 (M + H)+ |
| 812 | 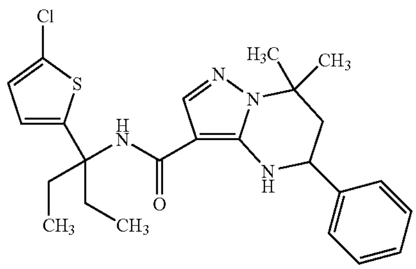 | N-(1-(5-chloro-2-thienyl)-1-ethylpropyl)-7,7-dimethyl-5-phenyl-4,5,6,7-tetrahydropyrazolo[1,5-a]pyrimidine-3-carboxamide | MS(ESI, m/z) 457 (M + H)+ |
| 813 | 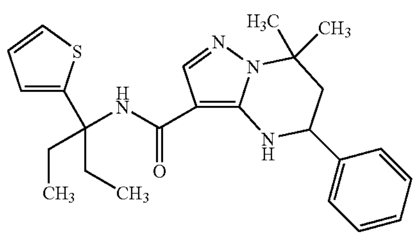 | N-(1-ethyl-1-(2-thienyl)propyl)-7,7-dimethyl-5-phenyl-4,5,6,7-tetrahydropyrazolo[1,5-a]pyrimidine-3-carboxamide | MS(ESI, m/z) 423 (M + H)+ |
| 814 | 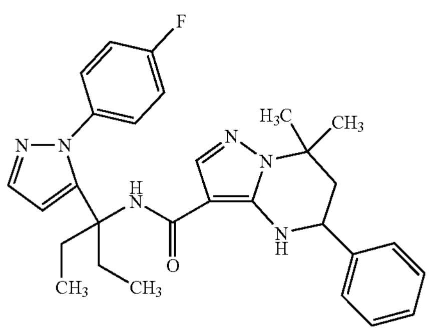 | N-(1-ethyl-1-(1-(4-fluorophenyl)-1H-pyrazol-5-yl)propyl)-7,7-dimethyl-5-phenyl-4,5,6,7-tetrahydropyrazolo[1,5-a]pyrimidine-3-carboxamide | MS(ESI, m/z) 501 (M + H)+ |
| 815 | 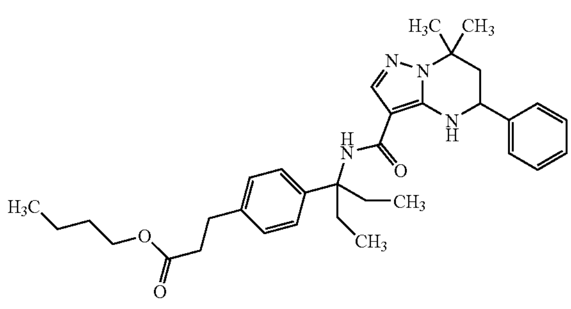 | butyl 3-(4-(1-(((7,7-dimethyl-5-phenyl-4,5,6,7-tetrahydropyrazolo[1,5-a]pyrimidin-3-yl)carbonyl)amino)-1-ethylpropyl)phenyl) propanoate | HCl salt mp 143-144° C. |

TABLE 4-continued

| Example | Structure | Name | Physiological Data |
|---|---|---|---|
| 816 | 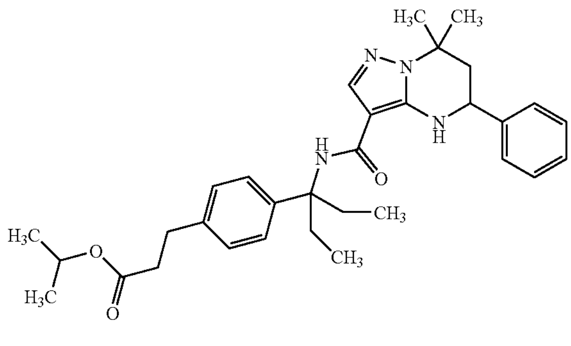 | isopropyl 3-(4-(1-(((7,7-dimethyl-5-phenyl-4,5,6,7-tetrahydropyrazolo[1,5-a]pyrimidin-3-yl)carbonyl)amino)-1-ethylpropyl)phenyl) propanoate | HCl salt mp 150-151° C. |
| 817 | 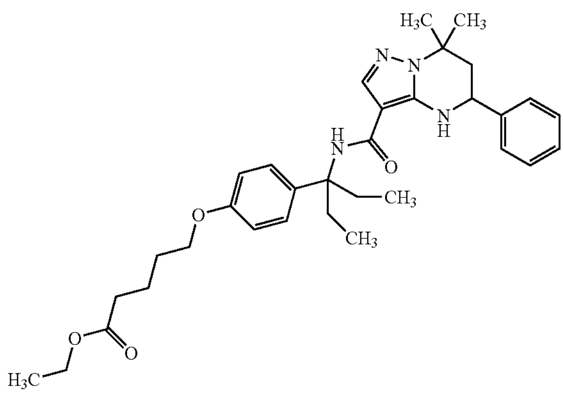 | ethyl 5-(4-(1-(((7,7-dimethyl-5-phenyl-4,5,6,7-tetrahydropyrazolo[1,5-a]pyrimidin-3-yl)carbonyl)amino)-1-ethylpropyl)phenoxy)pentanoate | mp 120-121° C. |
| 818 | 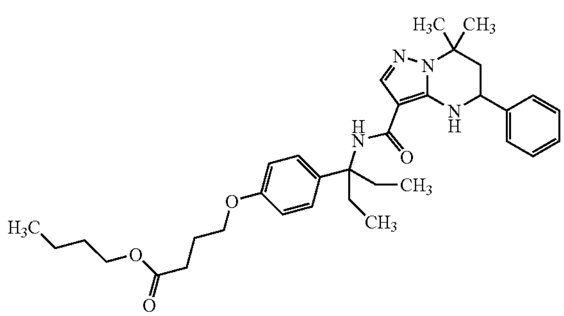 | butyl 4-(4-(1-(((7,7-dimethyl-5-phenyl-4,5,6,7-tetrahydropyrazolo[1,5-a]pyrimidin-3-yl)carbonyl)amino)-1-ethylpropyl)phenoxy)butanoate | mp 133-134° C. |
| 819 | 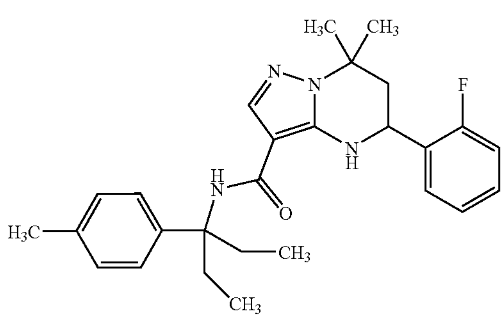 | N-(1-ethyl-1-(4-methylphenyl)propyl)-5-(2-fluorophenyl)-7,7-dimethyl-4,5,6,7-tetrahydropyrazolo[1,5-a]pyrimidine-3-carboxamide | HCl salt mp 144-145° C. |

TABLE 4-continued

| Example | Structure | Name | Physiological Data |
|---------|-----------|------|--------------------|
| 820 | 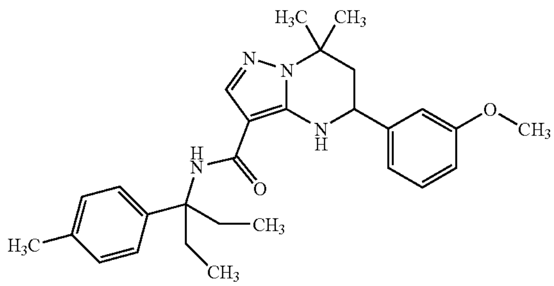 | N-(1-ethyl-1-(4-methylphenyl)propyl)-5-(3-methoxyphenyl)-7,7-dimethyl-4,5,6,7-tetrahydropyrazolo[1,5-a]pyrimidine-3-carboxamide | HCl salt mp 168-169° C. |
| 821 | 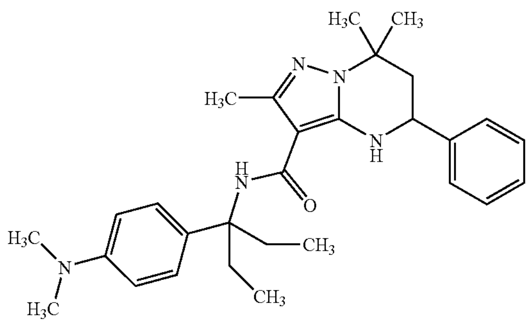 | N-(1-(4-(dimethylamino)phenyl)-1-ethylpropyl)-2,7,7-trimethyl-5-phenyl-4,5,6,7-tetrahydropyrazolo[1,5-a]pyrimidine-3-carboxamide | 2HCl salt mp 140-141° C. |
| 822 | 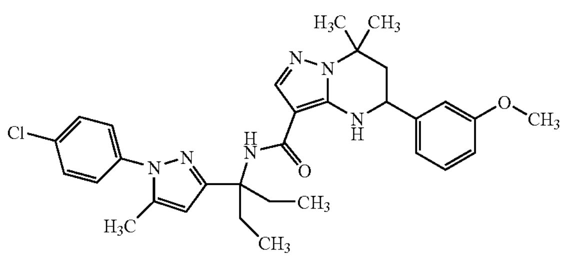 | N-(1-(1-(4-chlorophenyl)-5-methyl-1H-pyrazol-3-yl)-1-ethylpropyl)-7,7-dimethyl-5-phenyl-4,5,6,7-tetrahydropyrazolo[1,5-a]pyrimidine-3-carboxamide | MS(ESI, m/z) 531 (M + H)+ |
| 823 | 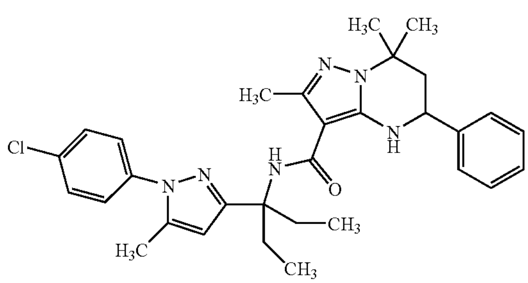 | N-(1-(1-(4-chlorophenyl)-5-methyl-1H-pyrazol-3-yl)-1-ethylpropyl)-2,7,7-trimethyl-5-phenyl-4,5,6,7-tetrahydropyrazolo[1,5-a]pyrimidine-3-carboxamide | HCl salt MS(ESI, m/z) 545 (M + H)+ |
| 824 | 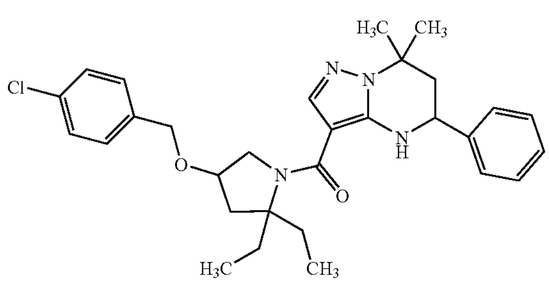 | 3-((4-((4-chlorobenzyl)oxy)-2,2-diethyl-1-pyrrolidinyl)carbonyl)-7,7-dimethyl-5-phenyl-4,5,6,7-tetrahydropyrazolo[1,5-a]pyrimidine | MS(ESI, m/z) 522 (M + H)+ |

TABLE 4-continued

| Example | Structure | Name | Physiological Data |
|---------|-----------|------|--------------------|
| 825 | 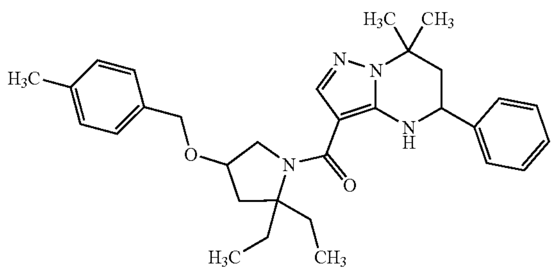 | 3-((2,2-diethyl-4-((4-methylbenzyl)oxy)-1-pyrrolidiny-carbonyl)-7,7-dimethyl-5-phenyl-4,5,6,7-tetrahydropyrazolo[1,5-a]pyrimidine | MS(ESI, m/z) 502 (M + H)+ |
| 826 | 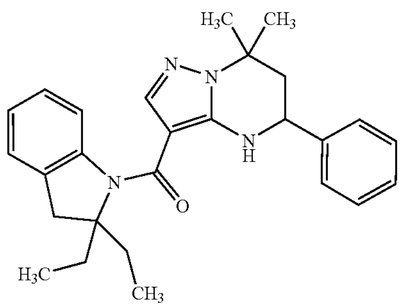 | 3-((2,2-diethyl-2,3-dihydro-1H-indol-1-yl)carbonyl)-7,7-dimethyl-5-phenyl-4,5,6,7-tetrahydropyrazolo[1,5-a]pyrimidine | MS(ESI, m/z) 430 (M + H)+ |
| 827 | 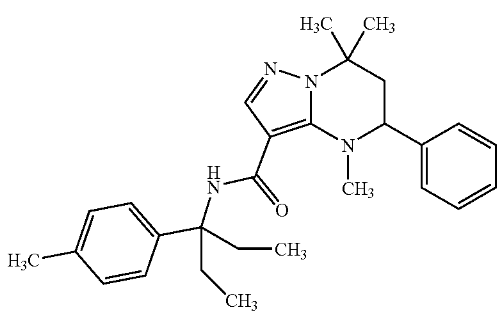 | N-(1-ethyl-1-(4-methylphenyl)propyl)-4,7,7-trimethyl-5-phenyl-4,5,6,7-tetrahydropyrazolo[1,5-a]pyrimidine-3-carboxamide | HCl salt mp 120-121° C. |
| 828 | 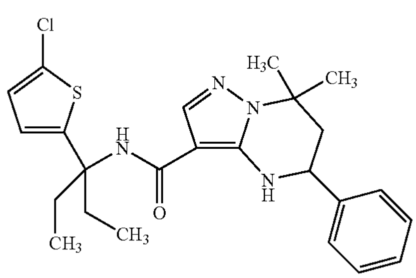 | N-(1-(5-chloro-2-thienyl)-1-ethylpropyl)-7,7-dimethyl-5-phenyl-4,5,6,7-tetrahydropyrazolo[1,5-a]pyrimidine-3-carboxamide | HCl salt MS(ESI, m/z) 457 (M + H)+ |
| 829 | 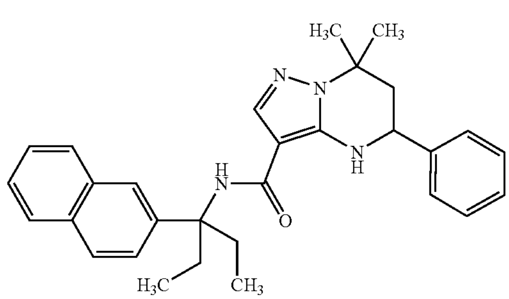 | N-(1-ethyl-1-(2-naphthyl)propyl)-7,7-dimethyl-5-phenyl-4,5,6,7-tetrahydropyrazolo[1,5-a]pyrimidine-3-carboxamide | MS(ESI, m/z) 467 (M + H)+ |

TABLE 4-continued

| Example | Structure | Name | Physiological Data |
|---|---|---|---|
| 830 | 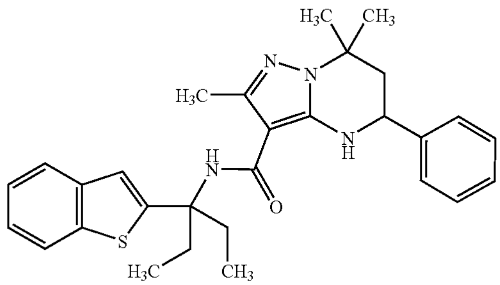 | N-(1-(1-benzothien-2-yl)-1-ethylpropyl)-2,7,7-trimethyl-5-phenyl-4,5,6,7-tetrahydropyrazolo[1,5-a]pyrimidine-3-carboxamide | MS(ESI, m/z) 487 (M + H)+ |
| 831 | 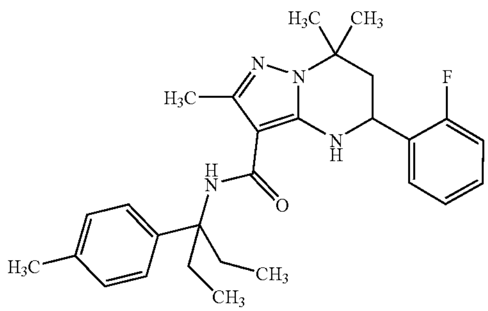 | N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | HCl salt mp 152-153° C. |
| 832 | 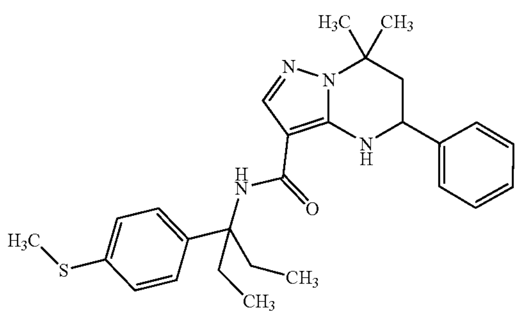 | N-(1-ethyl-1-(4-(methylthio)phenyl)propyl)-7,7-dimethyl-5-phenyl-4,5,6,7-tetrahydropyrazolo[1,5-a]pyrimidine-3-carboxamide | mp 177-178° C. |
| 833 | 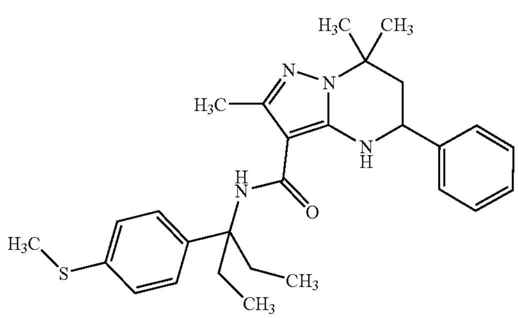 | N-(1-ethyl-1-(4-(methylthio)phenyl)propyl)-2,7,7-trimethyl-5-phenyl-4,5,6,7-tetrahydropyrazolo[1,5-a]pyrimidine-3-carboxamide | mp 149-150° C. |
| 834 | 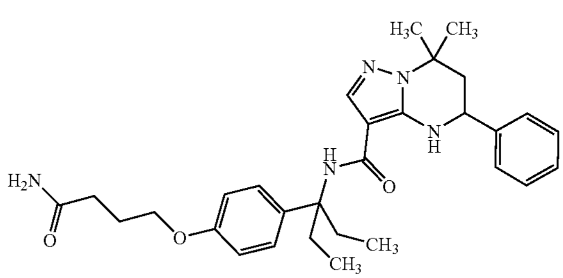 | N-(1-(4-(4-amino-4-oxobutoxy)phenyl)-1-ethylpropyl)-7,7-dimethyl-5-phenyl-4,5,6,7-tetrahydropyrazolo[1,5-a]pyrimidine-3-carboxamide | MS(ESI, m/z) 518 (M + H)+ |

TABLE 4-continued

| Example | Structure | Name | Physiological Data |
|---|---|---|---|
| 835 | 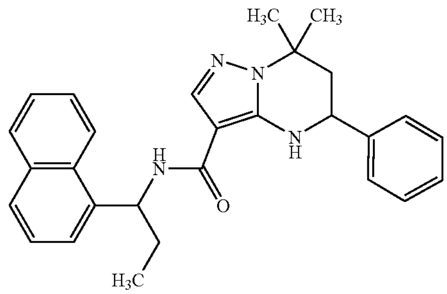 | 7,7-dimethyl-N-(1-(1-naphthyl)propyl)-5-phenyl-4,5,6,7-tetrahydropyrazolo[1,5-a]pyrimidine-3-carboxamide | MS(ESI, m/z) 439 (M + H)+: polar |
| 836 | 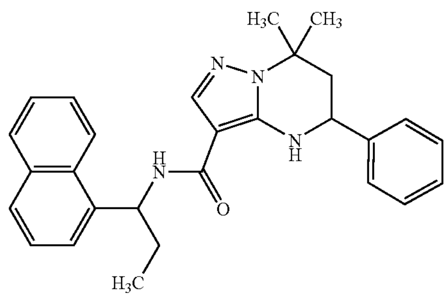 | 7,7-dimethyl-N-(1-(1-naphthyl)propyl)-5-phenyl-4,5,6,7-tetrahydropyrazolo[1,5-a]pyrimidine-3-carboxamide | MS(ESI, m/z) 439 (M + H)+: less polar |
| 837 | 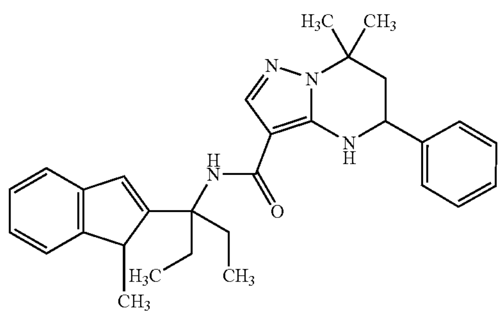 | N-(1-ethyl-1-(1-methyl-1H-indol-2-yl)propy-7,7-dimethyl-5-phenyl-4,5,6,7-tetrahydropyrazolo[1,5-a]pyrimidine-3-carboxamide | MS(ESI, m/z) 470 (M + H)+ |
| 838 | 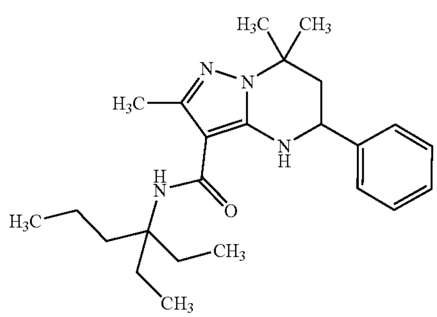 | N-(1,1-diethylbutyl)-2,7,7-trimethyl-5-phenyl-4,5,6,7-tetrahydropyrazolo[1,5-a]pyrimidine-3-carboxamide | HCl salt mp 176-177° C. |
| 839 | 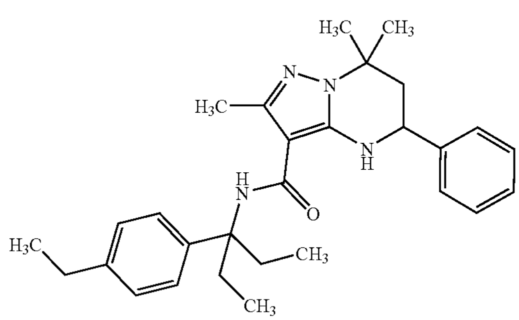 | N-(1-ethyl-1-(4-ethylphenyl)propyl)-2,7,7-trimethyl-5-phenyl-4,5,6,7-tetrahydropyrazolo[1,5-a]pyrimidine-3-carboxamide | HCl salt mp 163-164° C. |

TABLE 4-continued

| Example | Structure | Name | Physiological Data |
|---|---|---|---|
| 840 | 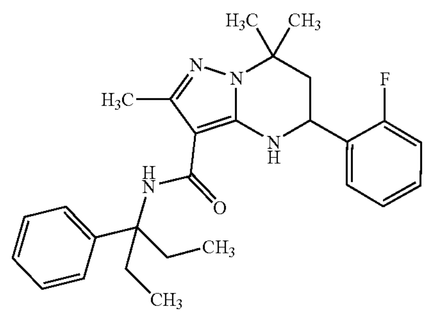 | N-(1-ethyl-1-phenylpropyl)-5-(2-fluorophenyl)-2,7,7-trimethyl-4,5,6,7-tetrahydropyrazolo[1,5-a]pyrimidine-3-carboxamide | HCl salt mp 160-162° C. |
| 841 | 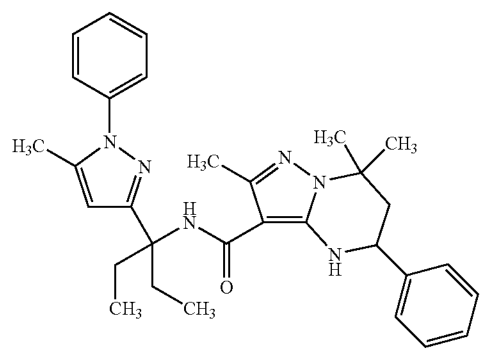 | N-(1-ethyl-1-(5-methyl-1-phenyl-1H-pyrazol-3-yl)propyl)-7,7-dimethyl-5-phenyl-4,5,6,7-tetrahydropyrazolo[1,5-a]pyrimidine-3-carboxamide | MS(ESI, m/z) 511 (M + H)+ |
| 842 | 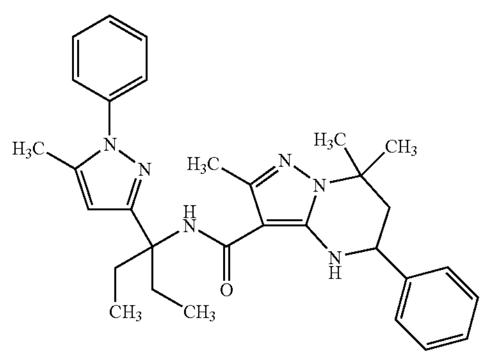 | N-(1-ethyl-1-(5-methyl-1-phenyl-1H-pyrazol-3-yl)propyl)-2,7,7-trimethyl-5-phenyl-4,5,6,7-tetrahydropyrazolo[1,5-a]pyrimidine-3-carboxamide | HCl salt MS(ESI, m/z) 511 (M + H)+ |
| 843 | 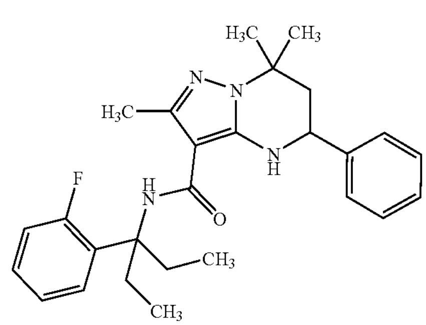 | N-(1-ethyl-1-(2-fluorophenyl)propyl)-2,7,7-trimethyl-5-phenyl-4,5,6,7-tetrahydropyrazolo[1,5-a]pyrimidine-3-carboxamide | HCl salt mp 180-182° C. |

TABLE 4-continued

| Example | Structure | Name | Physiological Data |
|---|---|---|---|
| 844 | 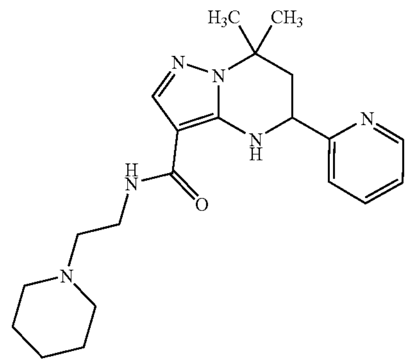 | 7,7-dimethyl-N-(2-(1-piperidinyl)ethyl)-5-(2-pyridinyl)-4,5,6,7-tetrahydropyrazolo[1,5-a]pyrimidine-3-carboxamide | MS(ESI, m/z) 383 (M + H)+ |
| 845 | 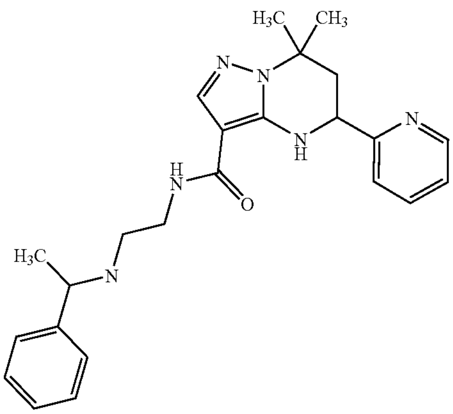 | 7,7-dimethyl-N-(3-(methyl(phenyl)amino)propyl)-5-(2-pyridinyl)-4,5,6,7-tetrahydropyrazolo[1,5-a]pyrimidine-3-carboxamide | MS(ESI, m/z) 419 (M + H)+ |
| 846 | 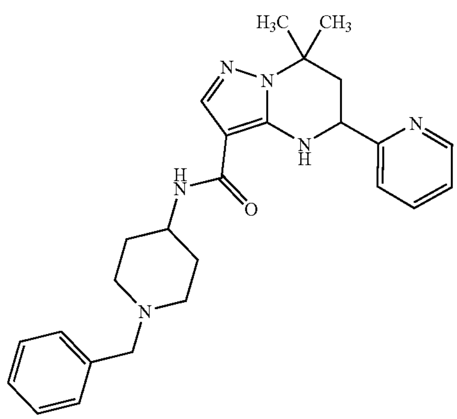 | N-(1-benzyl-4-piperidinyl)-7,7-dimethyl-5-(2-pyridinyl)-4,5,6,7-tetrahydropyrazolo[1,5-a]pyrimidine-3-carboxamide | MS(ESI, m/z) 445 (M + H)+ |
| 847 | 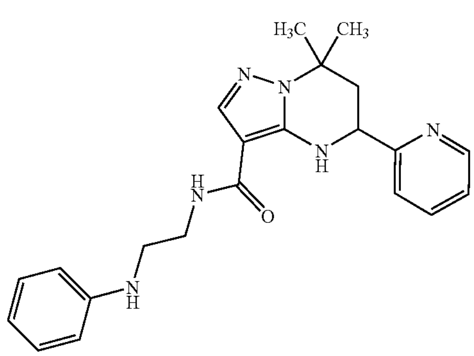 | N-(2-anilinoethyl)-7,7-dimethyl-5-(2-pyridinyl)-4,5,6,7-tetrahydropyrazolo[1,5-a]pyrimidine-3-carboxamide | MS(ESI, m/z) 391 (M + H)+ |

TABLE 4-continued

| Example | Structure | Name | Physiological Data |
|---------|-----------|------|--------------------|
| 848 | 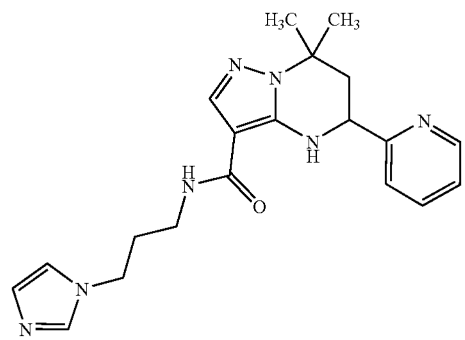 | N-(3-(1H-imidazol-1-yl)propyl)-7,7-dimethyl-5-(2-pyridinyl)-4,5,6,7-tetrahydropyrazolo[1,5-a]pyrimidine-3-carboxamide | MS(ESI, m/z) 380 (M + H)+ |
| 849 | 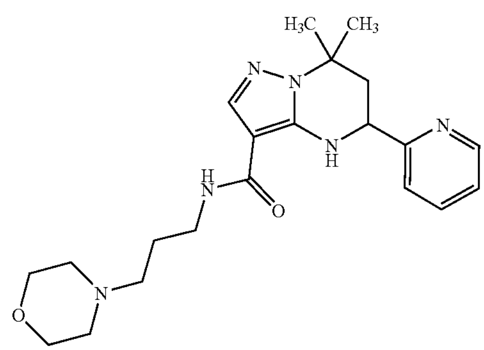 | 7,7-dimethyl-N-(3-4-morpholinyl-propyl)-5-(2-pyridinyl)-4,5,6,7-tetrahydropyrazolo[1,5-a]pyrimidine-3-carboxamide | MS(ESI, m/z) 399 (M + H)+ |
| 850 | 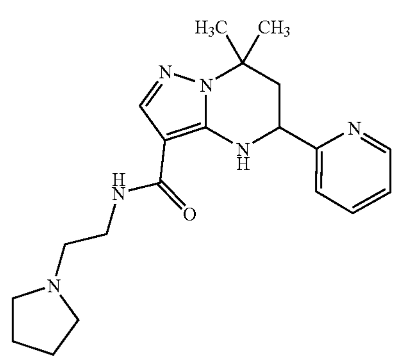 | 7,7-dimethyl-5-(2-pyridinyl)-N-(2-(1-pyrrolidinyl)ethyl)-4,5,6,7-tetrahydropyrazolo[1,5-a]pyrimidine-3-carboxamide | MS(ESI, m/z) 369 (M + H)+ |
| 851 | 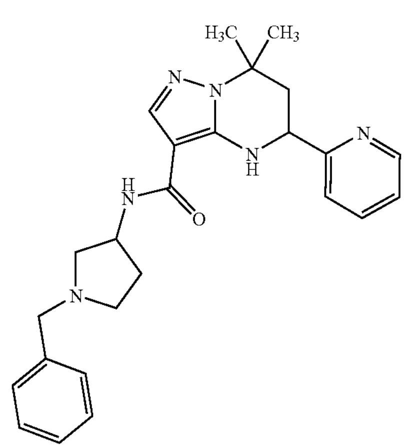 | N-(1-benzyl-3-pyrrolidinyl)-7,7-dimethyl-5-(2-pyridinyl)4,5,6,7-tetrahydropyrazolo[1,5-a]pyrimidine-3-carboxamide | MS(ESI, m/z) 431 (M + H)+ |

TABLE 4-continued

| Example | Structure | Name | Physiological Data |
|---|---|---|---|
| 852 | 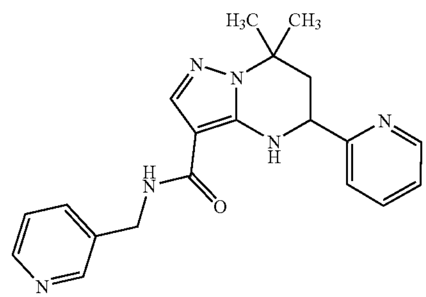 | 7,7-dimethyl-5-(2-pyridinyl)-N-(3-pyridinylmethyl)-4,5,6,7-tetrahydropyrazolo[1,5-a]pyrimidine-3-carboxamide | MS(ESI, m/z) 363 (M + H)+ |
| 853 | 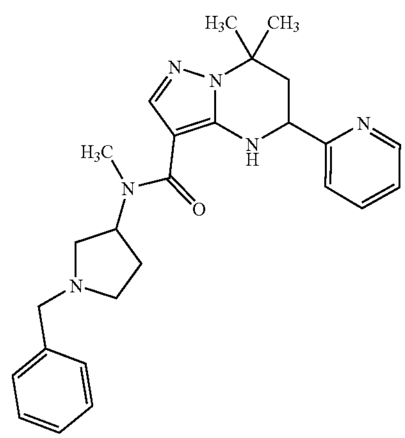 | N-(1-benzyl-3-pyrrolidinyl)-N,7,7-trimethyl-5-(2-pyridinyl)-4,5,6,7-tetrahydropyrazolo[1,5-a]pyrimidine-3-carboxamide | MS(ESI, m/z) 445 (M + H)+ |
| 854 | 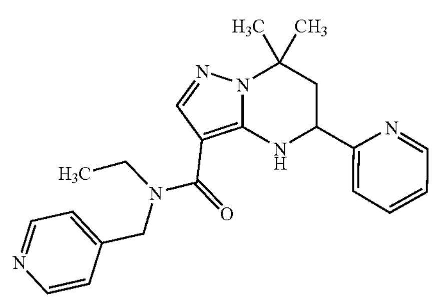 | N-ethyl-7,7-dimethyl-5-(2-pyridinyl)-N-(4-pyridinylmethyl)-4,5,6,7-tetrahydropyrazolo[1,5-a]pyrimidine-3-carboxamide | MS(ESI, m/z) 391 (M + H)+ |
| 855 | 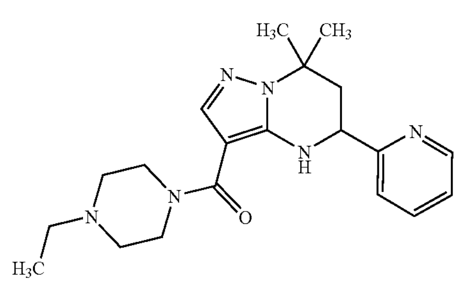 | 3-((4-ethyl-1-piperazinyl)carbonyl)-7,7-dimethyl-5-(2-pylidinyl)-4,5,6,7-tetrahydropyrazolo[1,5-a]pyrimidine | MS(ESI, m/z) 369 (M + H)+ |

TABLE 4-continued

| Example | Structure | Name | Physiological Data |
|---|---|---|---|
| 856 | 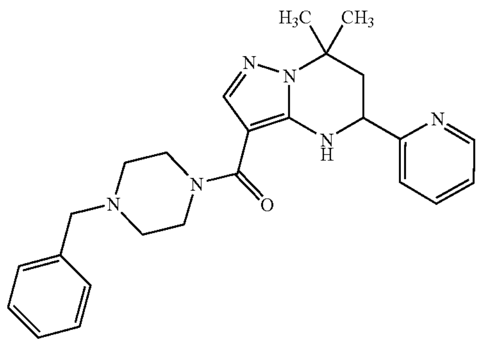 | 3-((4-benzyl-1-piperazinyl)carbonyl)-7,7-dimethyl-5-(2-pyridinyl)-4,5,6,7-tetrahydropyrazolo[1,5-a]pyrimidine | MS(ESI, m/z) 431 (M + H)+ |
| 857 | 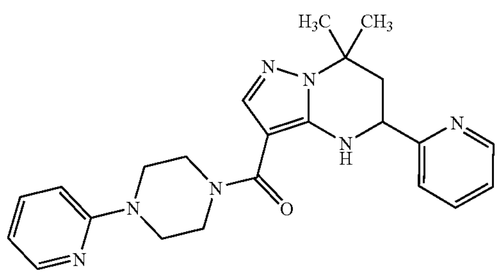 | 7,7-dimethyl-5-(2-pyridinyl)-3-((4-(2-pyridinyl)-1-piperazinyl)carbonyl-4,5,6,7-tetrahydropyrazolo[1,5-a]pyrimidine | MS(ESI, m/z) 417 (M + H)+ |
| 858 | 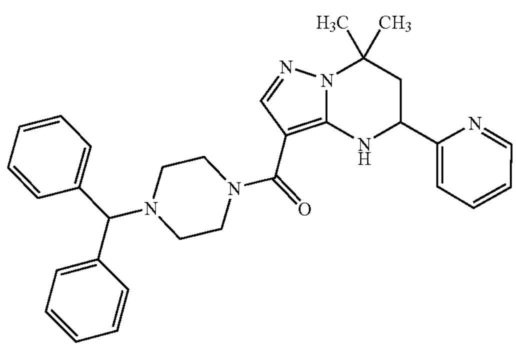 | 3-((4-benzhydryl-1-piperazinyl)carbonyl)-7,7-dimethyl-5-(2-pyridinyl)-4,5,6,7-tetrahydropyrazolo[1,5-a]pyrimidine | MS(ESI, m/z) 507 (M + H)+ |
| 859 | 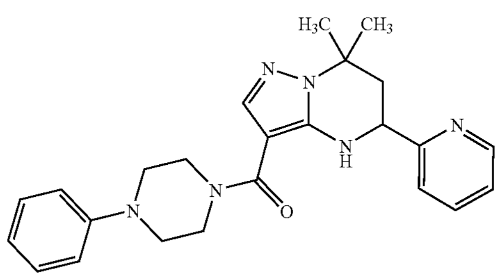 | 7,7-dimethyl-3-((4-phenyl-1-piperazinyl)carbonyl)-5-(2-pyridinyl)-4,5,6,7-tetrahydropyrazolo[1,5-a]pyrimidine | MS(ESI, m/z) 417 (M + H)+ |
| 860 | 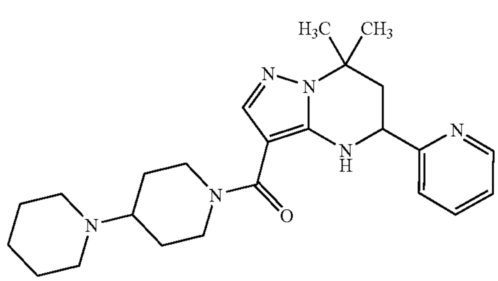 | 1'-((7,7-dimethyl-5-(2-pyridinyl)-4,5,6,7-tetrahydropyrazolo[1,5-a]pyrimidin-3-yl)carbonyl)-1,4'-bipiperidine | MS(ESI, m/z) 423 (M + H)+ |

TABLE 4-continued

| Example | Structure | Name | Physiological Data |
|---|---|---|---|
| 861 | 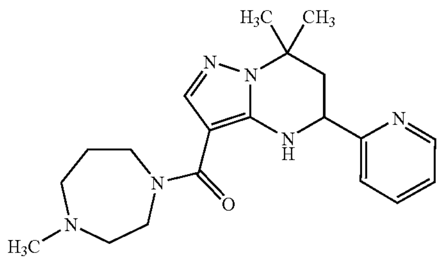 | 7,7-dimethyl-3-((4-methyl-1,4-diazepan-1-yl)carbonyl)-5-(2-pyridinyl)-4,5,6,7-tetrahydropyrazolo[1,5-a]pyrimidine | MS(ESI, m/z) 368 (M + H)+ |
| 862 | 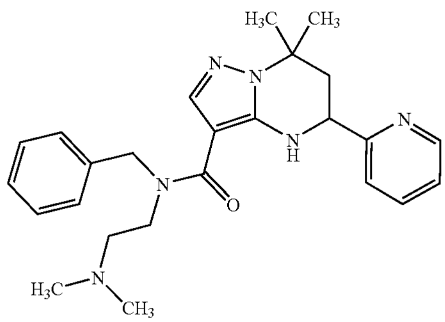 | N-benzyl-N-(2-(dimethylamino)ethyl)-7,7-dimethyl-5-(2-pyridinyl)-4,5,6,7-tetrahydropyrazolo[1,5-a]pyrimidine-3-carboxamide | MS(ESI, m/z) 433 (M + H)+ |
| 863 | 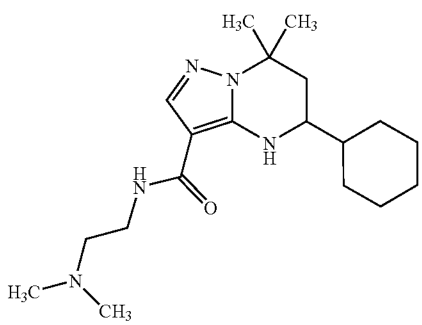 | 5-cyclohexyl-N-(2-(dimethylamino)ethyl)-7,7-dimethyl-4,5,6,7-tetrahydropyrazolo[1,5-a]pyrimidine-3-carboxamide | MS(ESI, m/z) 348 (M + H)+ |
| 864 | 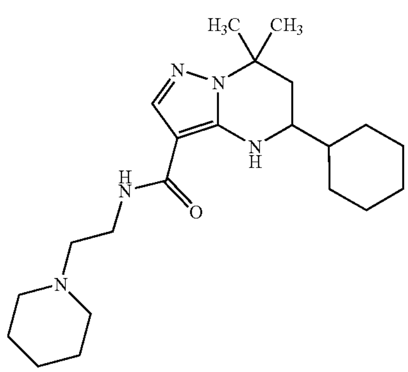 | 5-cyclohexyl-7,7-dimethyl-N-(2-(1-piperidinyl)ethyl)-4,5,6,7-tetrahydropyrazolo[1,5-a]pyrimidine-3-carboxamide | MS(ESI, m/z) 388 (M + H)+ |

TABLE 4-continued

| Example | Structure | Name | Physiological Data |
|---|---|---|---|
| 865 | 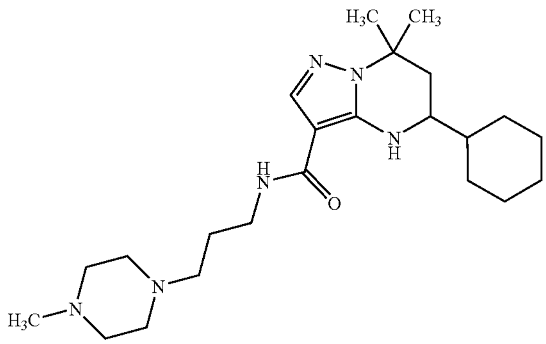 | 5-cyclohexyl-7,7-dimethyl-N-(3-(4-methyl-1-piperazinyl)propyl)-4,5,6,7-tetrahydropyrazolo[1,5-a]pyrimidine-3-carboxamide | MS(ESI, m/z) 417 (M + H)+ |
| 866 | 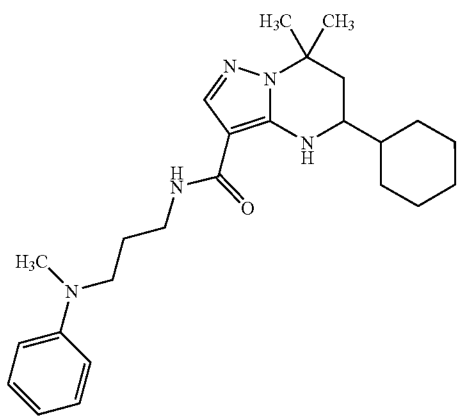 | 5-cyclohexyl-7,7-dimethyl-N-(3-(methyl(phenyl)amino)propyl)-4,5,6,7-tetrahydropyrazolo[1,5-a]pyrimidine-3-carboxamide | MS(ESI, m/z) 424 (M + H)+ |
| 867 | 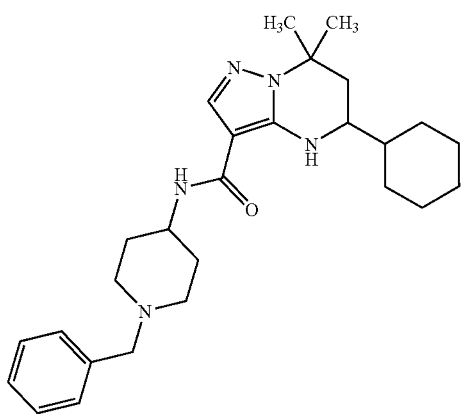 | N-(1-benzyl-4-pipendinyl)-5-cyclohexyl-7,7-dimethyl-4,5,6,7-tetrahydropyrazolo[1,5-a]pyrimidine-3-carboxamide | MS(ESI, m/z) 450 (M + H)+ |
| 954 | 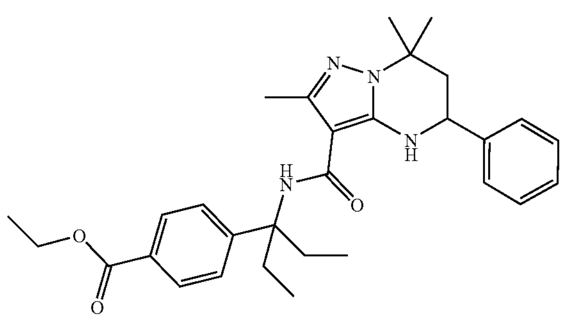 | ethyl 4-(1-ethyl-1-(((2,7,7-trimethyl-5-phenyl-4,5,6,7-tetrahydropyrazolo[1,5-a]pyrimidin-3-yl)carbonyl)amino)propyl)benzoate | mp 152-153° C. |

TABLE 4-continued

| Example | Structure | Name | Physiological Data |
|---|---|---|---|
| 955 | 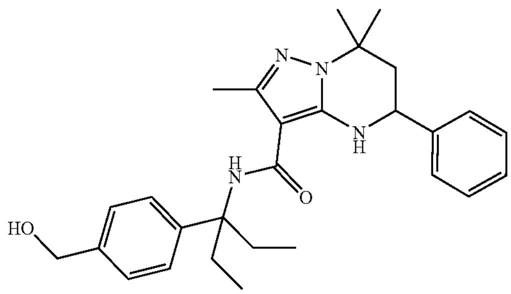 | N-(1-ethyl-1-(4-(hydroxymethyl)phenyl)propyl)-2,7,7-trimethyl-5-phenyl-4,5,6,7-tetrahydropyrazolo[1,5-a]pyrimidine-3-carboxamide | mp 146-147° C. |
| 956 | 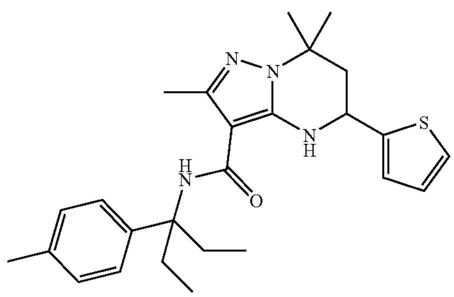 | N-(1-ethyl-1-(4-methylphenyl)propyl)-2,7,7-trimethyl-5-(2-thienyl)-4,5,6,7-tetrahydropyrazolo[1,5-a]pyrimidine-3-carboxamide | mp 149-150° C. HCl salt |
| 957 | 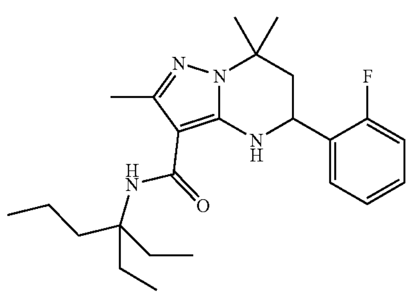 | N-(1,1-diethylbutyl)-5-(2-fluorophenyl)-2,7,7-trimethyl-4,5,6,7-tetrahydropyrazolo[1,5-a]pyrimidine-3-carboxamide | mp 181-182° C. HCl salt |
| 958 | 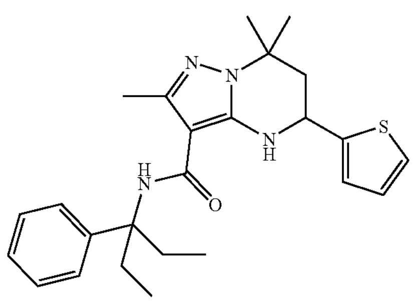 | N-(1-ethyl-1-phenylpropyl)-2,7,7-trimethyl-5-(2-thienyl)-4,5,6,7-tetrahydropyrazolo[1,5-a]pyrimidine-3-carboxamide | mp 171-172° C. HCl salt |
| 959 | 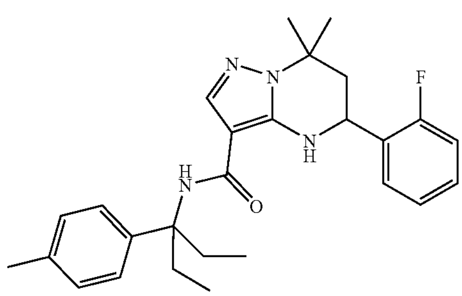 | N-(1-ethyl-1-(4-methylphenyl)propyl)-5-(2-fluorophenyl)-7,7-dimethyl-4,5,6,7-tetrahydropyrazolo[1,5-a]pyrimidine-3-carboxamide | mp 159-160° C. |

TABLE 4-continued

| Example | Name | Physiological Data |
|---|---|---|
| 960 | N-[1-ethyl-1-(4-methylphenyl)propyl]-5-(4-methoxyphenyl)-7,7-dimethyl-4,5,6,7-tetrahydropyrazolo[1,5-a]pyrimidine-3-carboxamide | mp 188-189° C. HCl salt |
| 961 | 5-(2-chlorophenyl)-N-[1-ethyl-1-(4-methylphenyl)propyl]-7,7-dimethyl-4,5,6,7-tetrahydropyrazolo[1,5-a]pyrimidine-3-carboxamide | mp 128-130° C. HCl salt |
| 962 | N-[1-ethyl-1-(4-methylphenyl)propyl]-5-(2-fluorophenyl)-2,7,7-trimethyl-4,5,6,7-tetrahydropyrazolo[1,5-a]pyrimidine-3-carboxamide | mp 139-140° C. |
| 963 | N-(1-ethyl-1-phenylpropyl)-5-(2-fluorophenyl)-2,7,7-trimethyl-4,5,6,7-tetrahydropyrazolo[1,5-a]pyrimidine-3-carboxamide | MS(ESI, m/z) 449 (M + H)+ |
| 964 | N-[1-ethyl-1-(4-methylphenyl)propyl]5-(2-methoxyphenyl)-7,7-dimethy-4,5,6,7-tetrahydropyrazolo[1,5-a]pyrimidine-3-carboxamide | mp 158-159° C. HCl salt |

TABLE 4-continued

| Example | Structure | Name | Physiological Data |
|---|---|---|---|
| 965 | 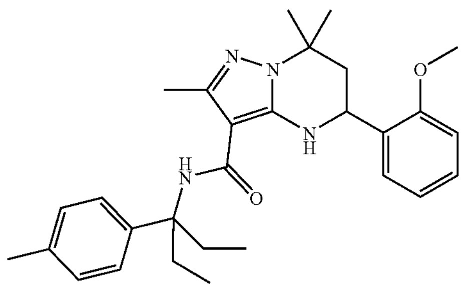 | N-(1-ethyl-1-(4-methylphenyl)propyl)-5-(2-methoxyphenyl)-2,7,7-trimethyl-4,5,6,7-tetrahydropyrazolo[1,5-a]pyrimidtne-3-carboxamide | mp 162-163° C. HCl salt |
| 966 | 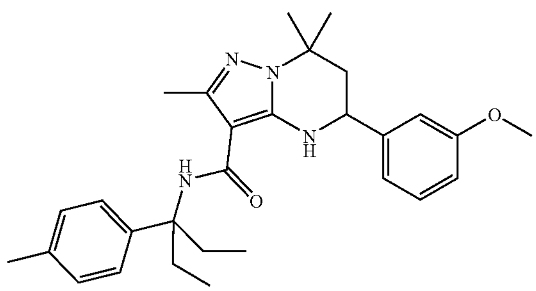 | N-(1-ethyl-1-(4-methylphenyl)propyl)-5-(3-methoxyphenyl)-2,7,7-trimethyl-4,5,6,7-tetrahydropyrazolo[1,5-a]pyrimidine-3-carboxamide | mp 146-146° C. HCl salt |
| 967 | 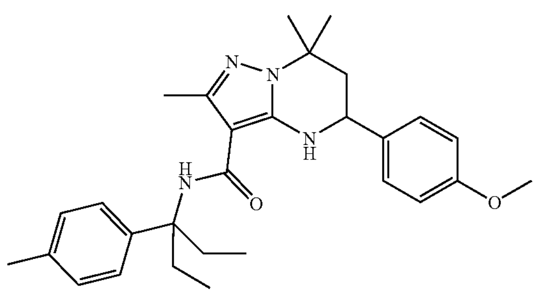 | N-(1-ethyl-1-(4-methylphenyl)propyl)-5-(4-methoxyphenyl)-2,7,7-trimethyl-4,5,6,7-tetrahydropyrazolo[1,5-a]pyrimidine-3-carboxamide | mp 153-154° C. HCl salt |
| 968 | 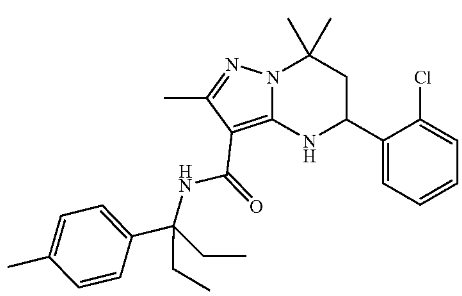 | 5-(2-chlorophenyl)-N-(1-ethyl-1-(4-methylphenyl)propyl)-2,7,7-trimethyl-4,5,6,7-tetrahydropyrazolo[1,5-a]pyrimidine-3-carboxamide | mp 173-174° C. HCl salt |
| 969 | 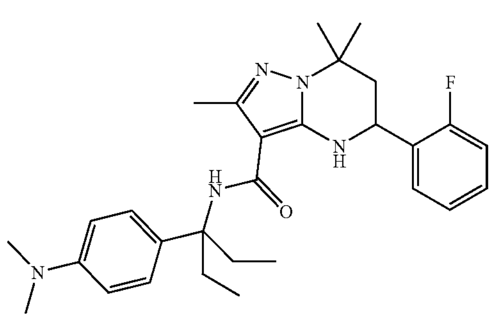 | N-(1-(4-(dimethylamino)phenyl)-1-ethylpropyl)-5-(2-fluorophenyl)-2,7,7-trimethyl-4,5,6,7-tetrahydropyrazolo[1,5-a]pyrimidine-3-carboxamide | mp 152-153° C. 2HCl salt |

TABLE 4-continued

| Example | Structure | Name | Physiological Data |
|---|---|---|---|
| 970 | 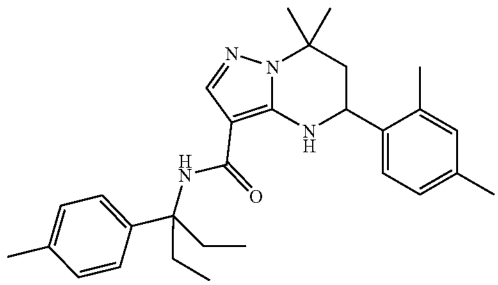 | 5-(2,4-dimethylphenyl)-N-(1-ethyl-1-(4-methylphenyl)propyl)-7,7-dimethyl-4,5,6,7-tetrahydropyrazolo[1,5-a]pyrimidine-3-carboxamide | mp 150-151° C. HCl salt |
| 971 | 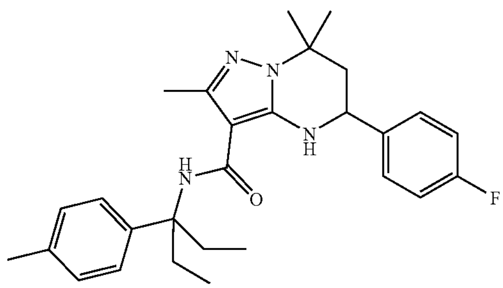 | N-(1-ethyl-1-(4-methylphenyl)propyl)-5-(4-fluorophenyl)-2,7,7-trimethyl-4,5,6,7-tetrahydropyrazolo[1,5-a]pyrimidine-3-carboxamide | mp 166-169° C. HCl salt |
| 972 | 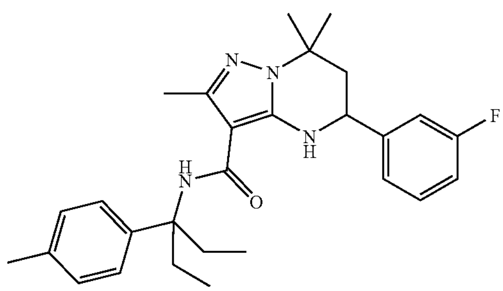 | N-(1-ethyl-1-(4-methylphenyl)propyl)-5-(3-fluorophenyl)-2,7,7-trimethyl-4,5,6,7-tetrahydropyrazolo[1,5-a]pyrimidine-3-carboxamide | mp 152-155° C. HCl salt |
| 973 | 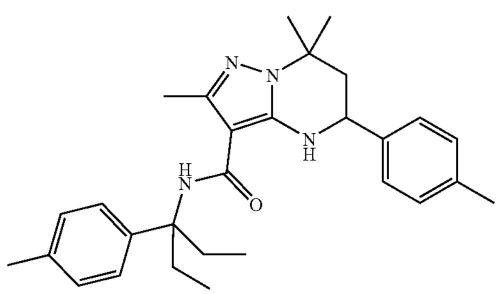 | N-(1-ethyl-1-(4-methylphenyl)propyl)-2,7,7-trimethyl-5-(4-methylphenyl)-4,5,6,7-tetrahydropyrazolo[1,5-a]pyrimidine-3-carboxamide | mp 152-154° C. HCl salt |
| 974 | 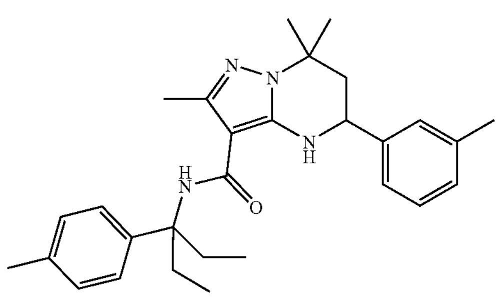 | N-(1-ethyl-1-(4-methylphenyl)propyl)-2,7,7-trimethyl-5-(3-methylphenyl)-4,5,6,7-tetrahydropyrazolo[1,5-a]pyrimidine-3-carboxamide | mp 120-123° C. HCl salt |

TABLE 4-continued

| Example | Structure | Name | Physiological Data |
|---|---|---|---|
| 975 | 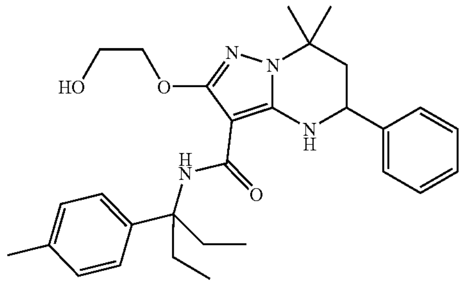 | N-(1-ethyl-1-(4-methylphenyl)propyl)-2-(2-hydroxyethoxy)-7,7-dimethyl-5-phenyl-4,5,6,7-tetrahydropyrazolo[1,5-a]pyrimidine-3-carboxamide | mp 115-117° C. |
| 976 | 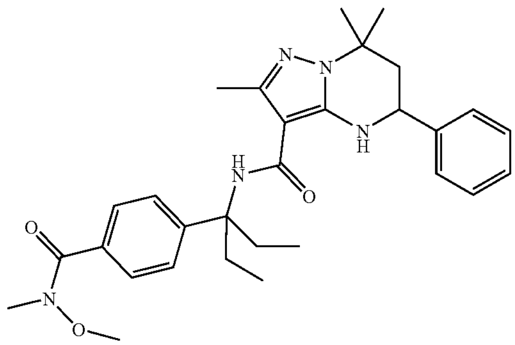 | N-(1-ethyl-1-(4-((methoxy(methyl)amino)carbonyl)phenyl)propyl)-2,7,7-trimethyl-5-phenyl-4,5,6,7-tetrahydropyrazolo[1,5-a]pyrimidine-3-carboxamide | MS(ESI, m/z) 518 (M + H)+ |
| 977 | 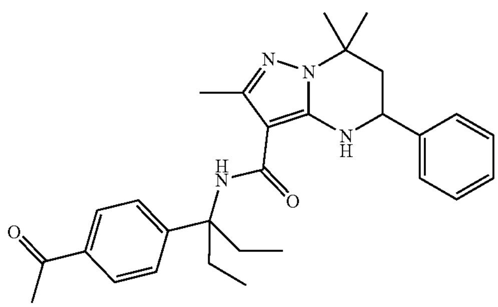 | N-(1-(4-acetylphenyl)-1-ethylpropyl)-2,7,7-trimethyl-5-phenyl-4,5,6,7-tetrahydropyrazolo[1,5-a]pyrimidine-3-carboxamide | mp 200-202° C. |
| 978 | 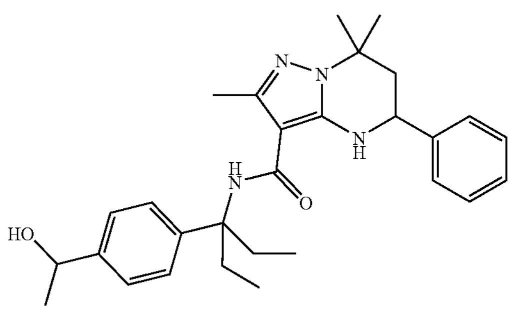 | N-(1-ethyl-1-(4-(1-hydroxyethyl)phenyl)propyl)-2,7,7-trimethyl-5-phenyl-4,5,6,7-tetrahydropyrazolo[1,5-a]pyrimidine-3-carboxamide | mp 165-166° C. |
| 979 | 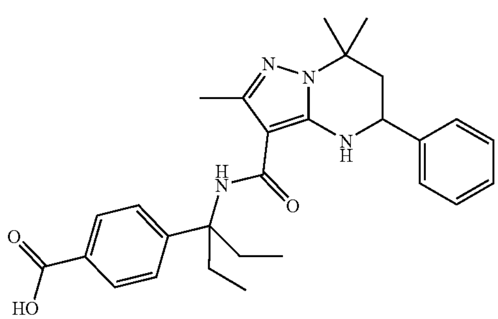 | 4-(1-ethyl-1-(((2,7,7-trimethyl-5-phenyl-4,5,6,7-tetrahydropyrazolo[1,5-a]pyrimidin-3-yl)carbonyl)amino)propyl)benzoic acid | mp 244-246° C. |

TABLE 4-continued

| Example | Structure | Name | Physiological Data |
|---|---|---|---|
| 980 | 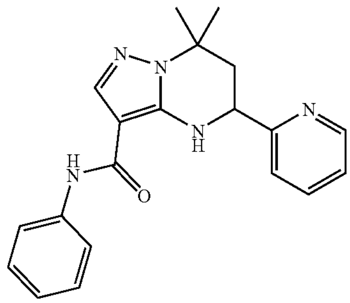 | 7,7-dimethyl-N-phenyl-5-(2-pyridinyl)-4,5,6,7-tetrahydropyrazolo[1,5-a]pyrimidine-3-carboxamide | MS(ESI, m/z) 348 (M + H)+ |
| 981 | 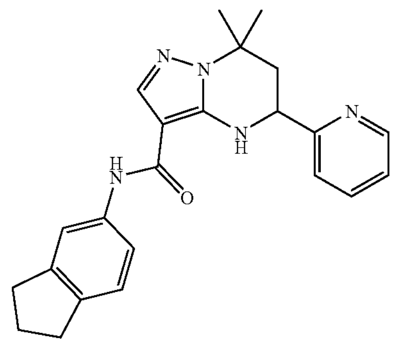 | N-2,3-dihydro-1H-inden-5-yl-7,7-dimethyl-5-(2-pyridinyl)-4,5,6,7-tetrahydropyrazolo[1,5-a]pyrimidine-3-carboxamide | MS(ESI, m/z) 388 (M + H)+ |
| 982 | 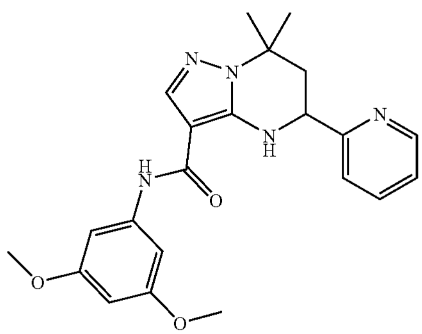 | N-(3,5-dimethoxyphenyl)-7,7-dimethyl-5-(2-pyridinyl)-4,5,6,7-tetrahydropyrazolo[1,5-a]pyrimidine-3-carboxamide | MS(ESI, m/z) 408 (M + H)+ |
| 983 | 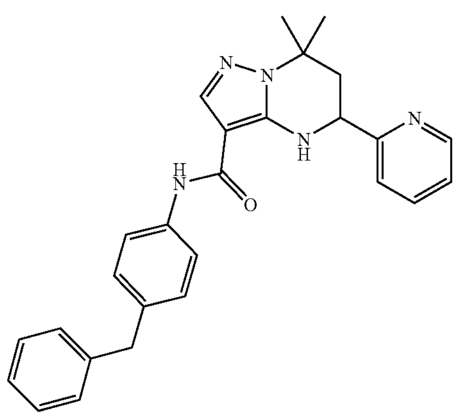 | N-(4-benzylphenyl)-7,7-dimethyl-5-(2-pyridinyl)-4,5,6,7-tetrahydropyrazolo[1,5-a]pyrimidine-3-carboxamide | MS(ESI, m/z) 438 (M + H)+ |

TABLE 4-continued

| Example | Structure | Name | Physiological Data |
|---|---|---|---|
| 984 | 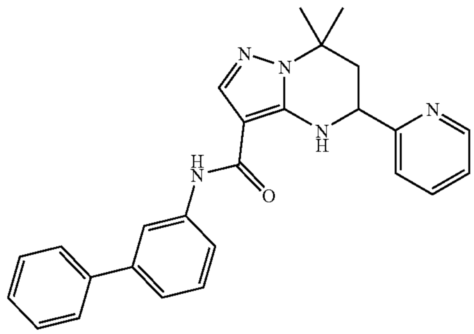 | N-1,1'-biphenyl-3-yl-7,7-dimethyl-5-(2-pyridinyl)-4,5,6,7-tetrahydropyrazolo[1,5-a]pyrimidine-3-carboxamide | MS(ESI, m/z) 424 (M + H)+ |
| 985 | 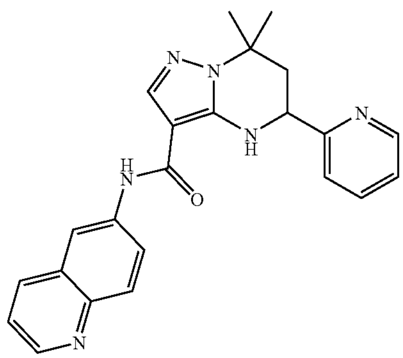 | 7,7-dimethyl-5-(2-pyridinyl)-N-6-quinolinyl-4,5,6,7-tetrahydropyrazolo[1,5-a]pyrimidine-3-carboxamide | MS(ESI, m/z) 399 (M + H)+ |
| 986 | 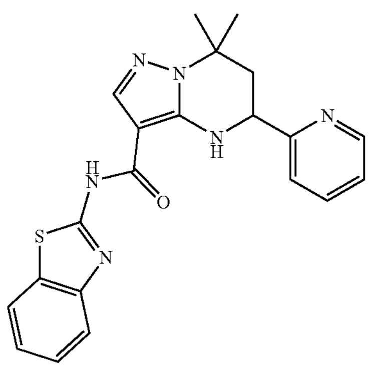 | N-1,3-benzothiazol-2-yl-7,7-dimethyl-5-(2-pyridinyl)-4,5,6,7-tetrahydropyrazolo[1,5-a]pyrimidine-3-carboxamide | MS(ESI, m/z) 405 (M + H)+ |
| 987 | 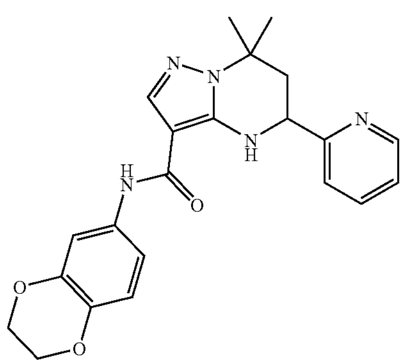 | N-2,3-dihydro-1,4-benzodioxin-6-yl-7,7-dimethyl-5-(2-pyridinyl)-4,5,6,7-tetrahydropyrazolo[1,5-a]pyrimidine-3-carboxamide | MS(ESI, m/z) 406 (M + H)+ |

TABLE 4-continued

| Example | Name | Physiological Data |
|---|---|---|
| 988 | 7,7-dimethyl-5-(2-pyridinyl)-N-3-quinolinyl-4,5,6,7-tetrahydropyrazolo[1,5-a]pyrimidine-3-carboxamide | MS(ESI, m/z) 399 (M + H)+ |
| 989 | 5-cyclohexyl-7,7-dimethyl-N-phenyl-4,5,6,7-tetrahydropyrazolo[1,5-a]pyrimidine-3-carboxamide | MS(ESI, m/z) 353 (M + H)+ |
| 990 | 5-cyclohexyl-N-2,3-dihydro-1H-inden-5-yl-7,7-dimethyl-4,5,6,7-tetrahydropyrazolo[1,5-a]pyrimidine-3-carboxamide | MS(ESI, m/z) 393 (M + H)+ |
| 991 | 5-cyclohexyl-N-(3,5-dimethoxyphenyl)-7,7-dimethyl-4,5,6,7-dimethyl-4,5,6,7-tetrahydropyrazolo[1,5-a]pyrimidine-3-carboxamide | MS(ESI, m/z) 413 (M + H)+ |

TABLE 4-continued

| Example | Structure | Name | Physiological Data |
|---|---|---|---|
| 992 | 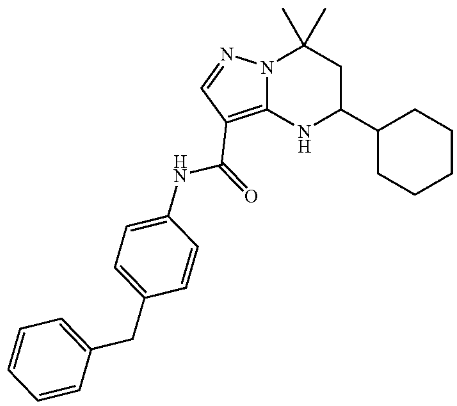 | N-(4-benzylphenyl)-5-cyclohexyl-7,7-dimethyl-4,5,6,7-tetrahydropyrazolo[1,5-a]pyrimidine-3-carboxamide | MS(ESI, m/z) 443 (M + H)+ |
| 993 | 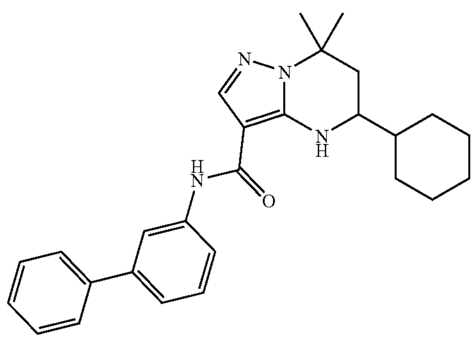 | N-1,1'-biphenyl-3-yl-5-cyclohexyl-7,7-dimethyl-4,5,6,7-tetrahydropyrazolo[1,5-a]pyrimidine-3-carboxamide | MS(ESI, m/z) 429 (M + H)+ |
| 994 | 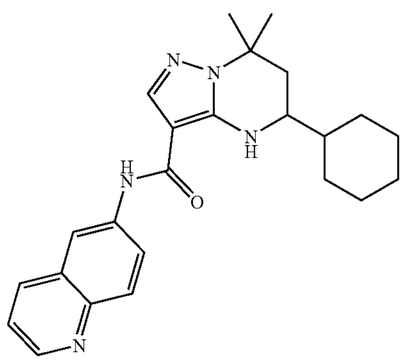 | 5-cyclohexyl-7,7-dimethyl-N-6-quinolinyl-4,5,6,7-tetrahydropyrazolo[1,5-a]pyrimidine-3-carboxamide | MS(ESI, m/z) 404 (M + H)+ |
| 995 | 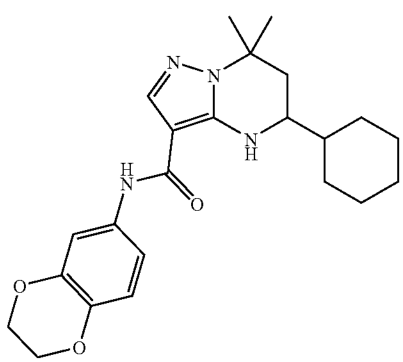 | 5-cyclohexyl-N-2,3-dihydro-1,4-benzodioxin-6-yl-7,7-dimethyl-4,5,6,7-tetrahydropyrazolo[1,5-a]pyrimidine-3-carboxamide | MS(ESI, m/z) 411 (M + H)+ |

TABLE 4-continued

| Example | Structure | Name | Physiological Data |
|---|---|---|---|
| 996 | 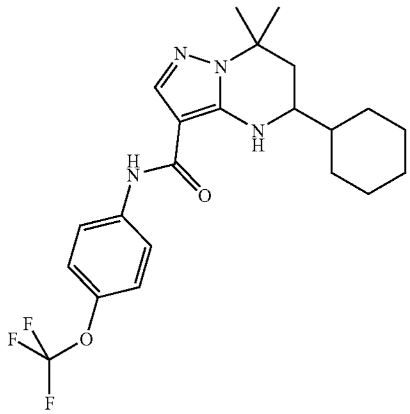 | 5-cyclohexyl-7,7-dimethyl-N-(4-(trifluoromethoxy)phenyl)-4,5,6,7-tetrahydropyrazolo[1,5-a]pyrimidine-3-carboxamide | MS(ESI, m/z) 437 (M + H)+ |
| 997 | 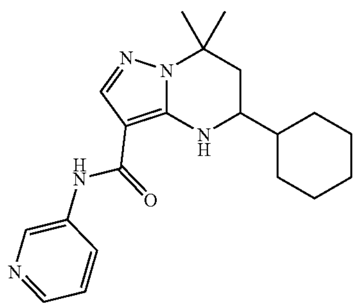 | 5-cyclohexyl-7,7-dimethyl-N-3-pyridinyl-4,5,6,7-tetrahydropyrazolo[1,5-a]pyrimidine-3-carboxamide | MS(ESI, m/z) 354 (M + H)+ |
| 998 | 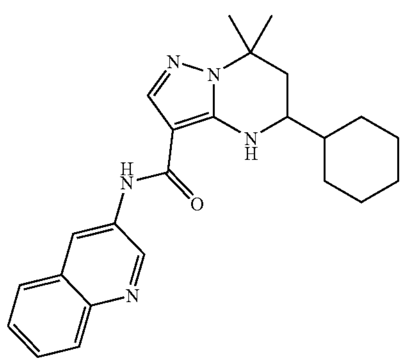 | 5-cyclohexyl-7,7-dimethyl-N-3-quinolinyl-4,5,6,7-tetrahydropyrazolo[1,5-a]pyrimidine-3-carboxamide | MS(ESI, m/z) 404 (M + H)+ |
| 999 | 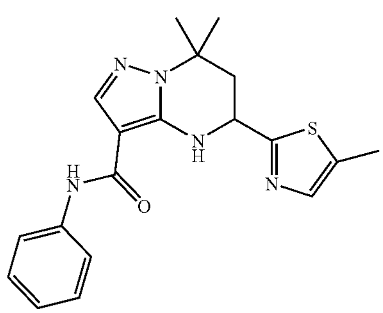 | 7,7-dimethyl-5-(5-methyl-1,3-thiazol-2-yl)-N-phenyl-4,5,6,7-tetrahydropyrazolo[1,5-a]pyrimidine-3-carboxamide | MS(ESI, m/z) 368 (M + H)+ |

TABLE 4-continued

| Example | Structure | Name | Physiological Data |
|---|---|---|---|
| 1000 | 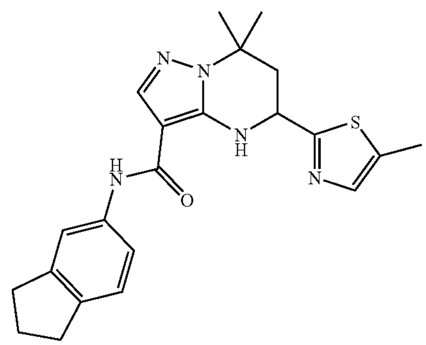 | 2,3-dihydro-1H-inden-5-yl-7,7-dimethyl-5-(5-methyl-1,3-thiazol-2-yl)-4,5,6,7-tetrahydropyrazolo[1,5-a]pyrimidine-3-carboxamide | MS(ESI, m/z) 408 (M + H)+ |
| 1001 | 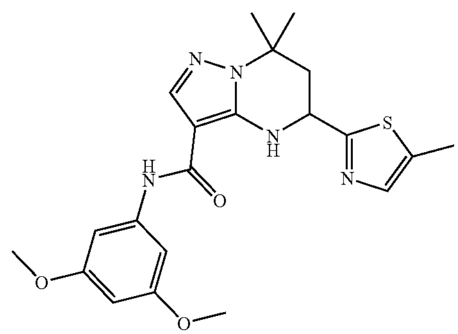 | N-(3,5-dimethoxyphenyl)-7,7-dimethyl-5-(5-methyl-1,3-thiazol-2-yl)-4,5,6,7-tetrahydropyrazolo[1,5-a]pyrimidine-3-carboxamide | MS(ESI, m/z) 428 (M + H)+ |
| 1002 | 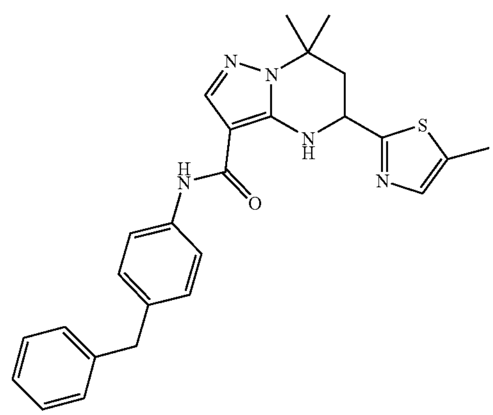 | N-(4-benzylphenyl)-7,7-dimethyl-5-(5-methyl-1,3-thiazol-2-yl)-4,5,6,7-tetrahydropyrazolo[1,5-a]pyrimidine-3-carboxamide | MS(ESI, m/z) 458 (M + H)+ |
| 1003 | 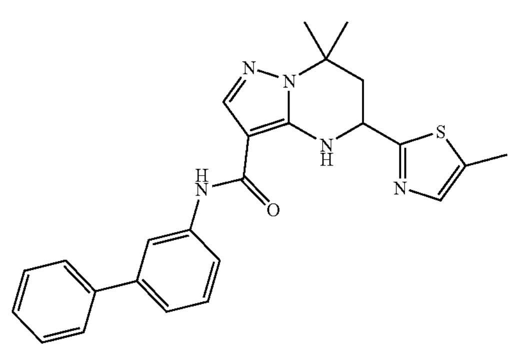 | N-1,1'-biphenyl-3-yl-7,7-dimethyl-5-(5-methyl-1,3-thiazo-2-yl)-4,5,6,7-tetrahydropyrazolo[1,5-a]pyrimidine-3-carboxamide | MS(ESI, m/z) 444 (M + H)+ |

TABLE 4-continued

| Example | Structure | Name | Physiological Data |
|---|---|---|---|
| 1004 | 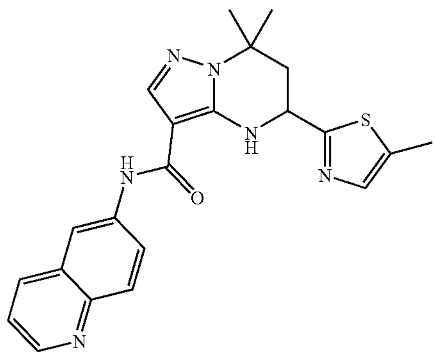 | 7,7-dimethyl-5-(5-methyl-1,3-thiazol-2-yl)-N-6-quinolinyl-4,5,6,7-tetrahydropyrazolo[1,5-a]pyrimidine-3-carboxamide | MS(ESI, m/z) 419 (M + H)+ |
| 1005 | 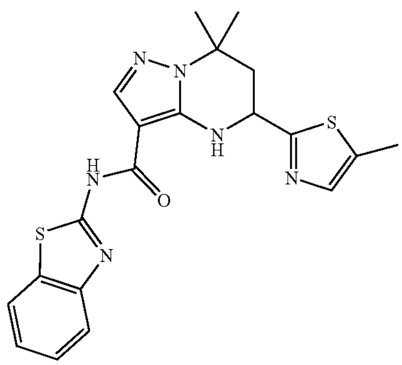 | N-1,3-benzothiazol-2-yl-7,7-dimethyl-5-(5-methyl-1,3-thiazol-2-yl)-4,5,6,7-tetrahydropyrazolo[1,5-a]pyrimidine-3-carboxamide | MS(ESI, m/z) 425 (M + H)+ |
| 1006 | 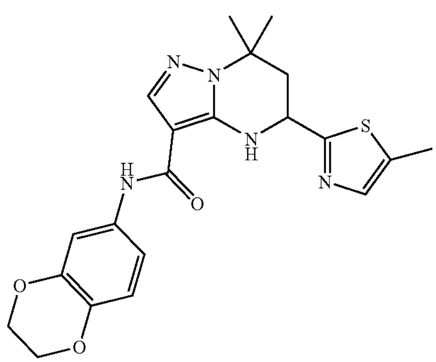 | N-2,3-dihydro-1,4-benzodioxin-6-yl-7,7-dimethyl-5-(5-methyl-1,3-thiazol-2-yl)-4,5,6,7-tetrahydropyrazolo[1,5-a]pyrimidine-3-carboxamide | MS(ESI, m/z) 426 (M + H)+ |
| 1007 | 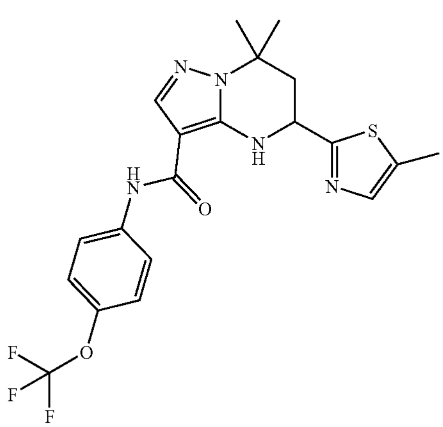 | 7,7-dimethyl-5-(5-methyl-1,3-thiazol-2-yl)-N-(4-(trifluoromethoxy)phenyl)-4,5,6,7-tetrahydropyrazolo[1,5-a]pyrimidine-3-carboxamide | MS(ESI, m/z) 452 (M + H)+ |

TABLE 4-continued

| Example | Structure | Name | Physiological Data |
|---|---|---|---|
| 1008 | 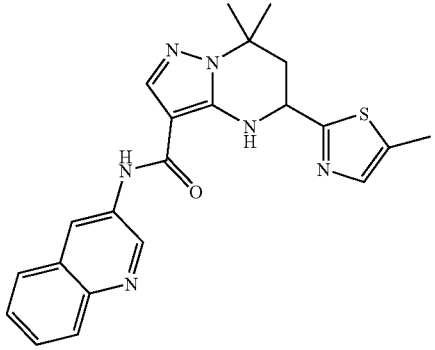 | 7,7-dimethyl-5-(5-methyl-1,3-thiazol-2-yl)-N-3-quinolinyl-4,5,6,7-tetrahydropyrazolo[1,5-a]pyrimidine-3-carboxamide | MS(ESI, m/z) 419 (M + H)+ |

EXAMPLE 1009

Ethyl 7,7-dimethyl-5-phenyl-4,5,6,7-tetrahydropyrazolo[1,5-a]pyrimidine-3-carboxylate Racemic compound obtained in Example 16 (80 g) was subjected to preparative high performance liquid chromatography (HPLC) to afford optically pure materials (38 g, 99.8% ee (shorter retention time) and 39 g, 99.4% ee (longer retention time)). [column: CHIRALCEL OD 50 mmϕ×500 mm (manufactured by Daicel Kagaku Kogyo Kabushiki Kaisha), temperature: 30° C., mobile phase: hexane/Ethanol=95/5, flow rate: 60 ml/minute, detection wavelength: 254 nm, and 1 shot: about 800 mg].

Compounds of Examples 1010-1017 shown in the Table 8~11, were prepared in a manner similar to that described in Example 1009.

TABLE 8

| Example | Structure | Name | Physiological Data |
|---|---|---|---|
| 1010 | 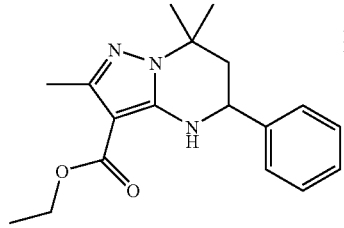 | ethyl 2,7,7-trimethyl-phenyl-4,5,6,7-tetrahydropyrazolo[1,5-a]pyrimidine-3-carboxylate | MS(ESI, m/z) 314 (M + H)+, shorter retention time |
| 1011 | 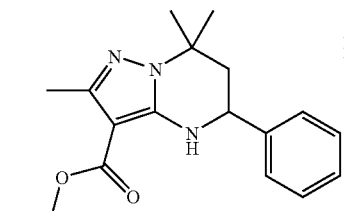 | ethyl 2,7,7-trimethyl-5-phenyl-4,5,6,7-tetrahydropyrazolo[1,5-a]pyrimidine-3-carboxylate | MS(ESI, m/z) 314 (M + H)+, longer retention time |

The determination of the optical purity was carried out by HPLC using a chiral column (column: CHIRALCEL OD 4.6 mmφ×250 mm (manufactured by Daicel Kagaku Kogyo Kabushiki Kaisha), temperature: about 30° C., mobile phase: hexane/ethanol=96/4, flow rate: 0.5 ml/minute, and detection wavelength: 254 nm).

TABLE 9

| 1012 | | ethyl 5-(2-fluorophenyl)-7,7-dimethyl-4,5,6,7-tetrahydropyrazolo[1,5-a]pyrimidine-3-carboxylate | MS(ESI, m/z) 318 (M + H)+, shorter retention time |
|---|---|---|---|
| 1013 | | ethyl 5-(2-fluorophenyl)-7,7-dimethyl-4,5,6,7-tetrahydropyrazolo[1,5-a]pyrimidine-3-carboxylate | MS(ESI, m/z) 318 (M + H)+, longer retention time |

The determination of the optical purity was carried out by HPLC using a chiral column (column: CHIRALPAK AD 4.6 mmφ×250 mm (manufactured by Daicel Kagaku Kogyo Kabushiki Kaisha), temperature: about 30° C., mobile phase: hexane/IPA =95/5, flow rate: 0.5 ml/minute, and detection wavelength: 254 nm).

TABLE 10

| 1014 | | ethyl 5-(2-fluorophenyl)-2,7,7-trimethyl-4,5,6,7-tetrahydropyrazolo[1,5-a]pyrimidine-3-carboxylate | MS(ESI, m/z) 332 (M + H)+, shorter retention time |
|---|---|---|---|
| 1015 | | ethyl 5-(2-fluorophenyl)-2,7,7-trimethyl-4,5,6,7-tetrahydropyrazolo[1,5-a]pyrimidine-3-carboxylate | MS(ESI, m/z) 332 (M + H)+, longer retention time |

The determination of the optical purity was carried out by HPLC using a chiral column (column: CHIRALPAK AD 4.6 mmφ×250 mm (manufactured by Daicel Kagaku Kogyo Kabushiki Kaisha), temperature: about 30° C., mobile phase: hexane/ethanol=995/5, flow rate: 0.5 ml/minute, and detection wavelength: 220 nm).

TABLE 11

| 1016 | ethyl 5-(2-chlorophenyl)-2,7,7-trimethyl-4,5,6,7-tetrahydropyrazolo[1,5-a]pyrimidine-3-carboxylate | MS(ESI, m/z) 348 (M + H)+, shorter retention time |
|---|---|---|
| 1017 | ethyl 5-(2-chlorophenyl)-2,7,7-trimethyl-4,5,6,7-tetrahydropyrazolo[1,5-a]pyrimidine-3-carboxylate | MS(ESI, m/z) 348 (M + H)+, longer retention time |

The determination of the optical purity was carried out by HPLC using a chiral column (column: CHIRALCEL OD 4.6 mmφ×250 mm (manufactured by Daicel Kagaku Kogyo Kabushiki Kaisha), temperature: about 30° C., mobile phase: hexane/ethanol=95/5, flow rate: 0.5 ml/minute, and detection wavelength: 258 nm).

EXAMPLE 1018

(−)-7,7-Dimethyl-5-phenyl-4,5,6,7-tetrahydropyrazolo[1,5-a]pyrimidine-3-carboxylic acid

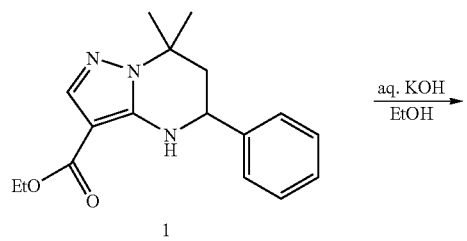

-continued

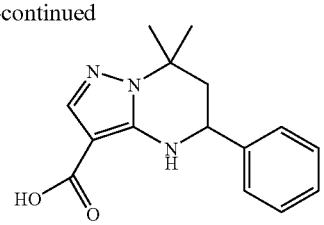

A mixture of 1(0.73 g) obtained in Example 1009, KOH (0.41 g), H$_2$O(20 ml) and EtOH (20 mL) was stirred at 90° C. for 12 h, acidified with 1N HCl, and extracted with AcOEt. The extract was washed with brine, dreid over MgSO$_4$, and concentrated in vacuo to give 0.55 g (83% yield) of the title compound as colorless prisms ([α]$_D^{20°\ C.}$=−85.33, in CHCl$_3$, C=0.46). mp 205-206° C., $^1$H NMR (CDCl$_3$, 300 MHz): 1.59 (3H, s), 1.66 (3H, s), 2.05-2.15 (2H, m), 4.64 (1H, dd, J=9.6, 5.4 Hz), 6.04 (1H, s), 7.30-7.41 (5H, m), 7.73 (1H, s)

Compounds of Examples 1019-1027 shown in the Table 12, were prepared in a manner similar to that described in Example 1018.

TABLE 12

| Example | Structure | Name | Physiological Data |
|---|---|---|---|
| 1019 | 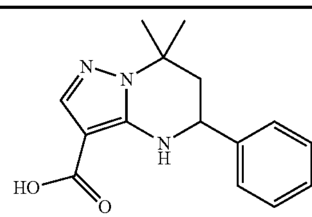 | (+)-7,7-dimethyl-5-phenyl-4,5,6,7-tetrahydropyrazolo[1,5-a]pyrimidine-3-carboxylic acid | mp 205-206° C. [α]$_D^{20°\ C.}$ = 86.01, in CHCl$_3$, C = 0.48. |

TABLE 12-continued

| Example | Structure | Name | Physiological Data |
|---|---|---|---|
| 1020 | 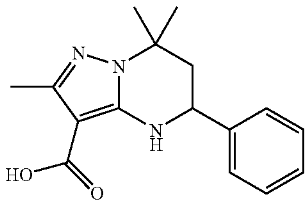 | (+)-2,7,7-trimethyl-5-phenyl-4,5,6,7-tetrahydropyrazolo[1,5-a]pyrimidine-3-carboxylic acid | mp 190-192° C. $[\alpha]_D^{21°\ C.}$ = 103.65, in CHCl$_3$, C = 1.17. |
| 1021 | 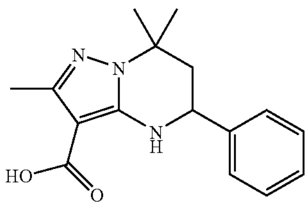 | (−)-2,7,7-trimethyl-5-phenyl-4,5,6,7-tetrahydropyrazolo[1,5-a]pyrimidine-3-carboxylic acid | mp 190–192° C. $[\alpha]_D^{21°\ C.}$ = −109.21, in CHCl$_3$, C = 1.25. |
| 1022 | 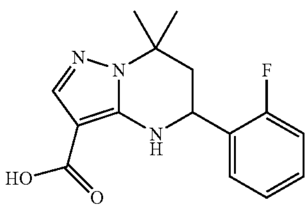 | (+)-5-(2-fluorophenyl)-7,7-dimethyl-4,5,6,7-tetrahydropyrazolo[1,5-a]pyrimidine-3-carboxylic acid | mp 169-170° C. $[\alpha]_D^{20°\ C.}$ = 107.91, in CHCl$_3$, C = 0.48. |
| 1023 | 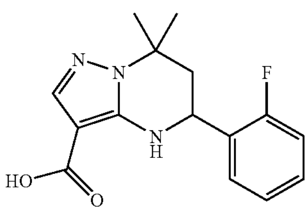 | (−)-5-(2-fluorophenyl)-7,7-dimethyl-4,5,6,7-tetrahydropyrazolo[1,5-a]pyrimidine-3-carboxylic acid | mp 165-166° C. $[\alpha]_D^{20°\ C.}$ = −108.59, in CHCl$_3$, C = 0.47. |
| 1024 | 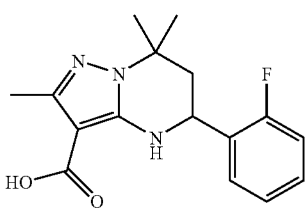 | (+)-5-(2-fluorophenyl)-2,7,7-trimethyl-4,5,6,7-tetrahydropyrazolo[1,5-a]pyrimidine-3-carboxylic acid | mp 150-151° C. $[\alpha]_D^{21°\ C.}$ = 123.34, in CHCl$_3$, C = 0.33. |
| 1025 | 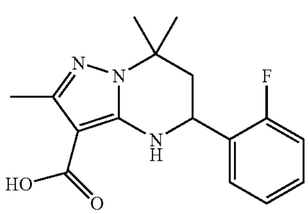 | (−)-5-(2-fluorophenyl)-2,7,7-trimethyl-4,5,6,7-tetrahydropyrazolo[1,5-a]pyrimidine-3-carboxylic acid | mp 150-151° C. $[\alpha]_D^{21°\ C.}$ = −122.39, in CHCl$_3$, C = 0.47. |
| 1026 | 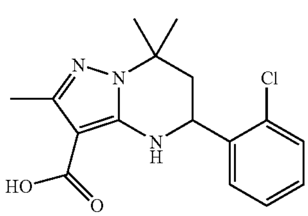 | (+)-5-(2-chlorophenyl)-2,7,7-trimethyl-4,5,6,7-tetrahydropyrazolo[1,5-a]pyrimidine-3-carboxylic acid | mp 163-164° C. $[\alpha]_D^{21°\ C.}$ = 177.21, in CHCl$_3$, C = 0.28. |

TABLE 12-continued

| Example | Structure | Name | Physiological Data |
|---|---|---|---|
| 1027 | 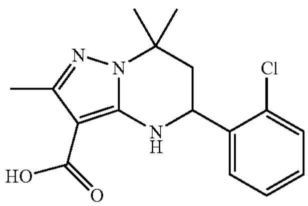 | (−)-5-(2-chlorophenyl)-2,7,7-trimethyl-4,5,6,7-tetrahydropyrazolo[1,5-a]pyrimidine-3-carboxylic acid | mp 163-164° C. $[\alpha]_D^{21° C.}$ = −166.12, in CHCl$_3$, C = 0.25. |

EXAMPLE 1028

(S)-N-(1-(4-Chlorophenyl)-1-ethylpropyl)-7,7-dimethyl-5-phenyl-4,5,6,7-tetrahydropyrazolo[1,5-a]pyrimidine-3-carboxamide hydrochloride

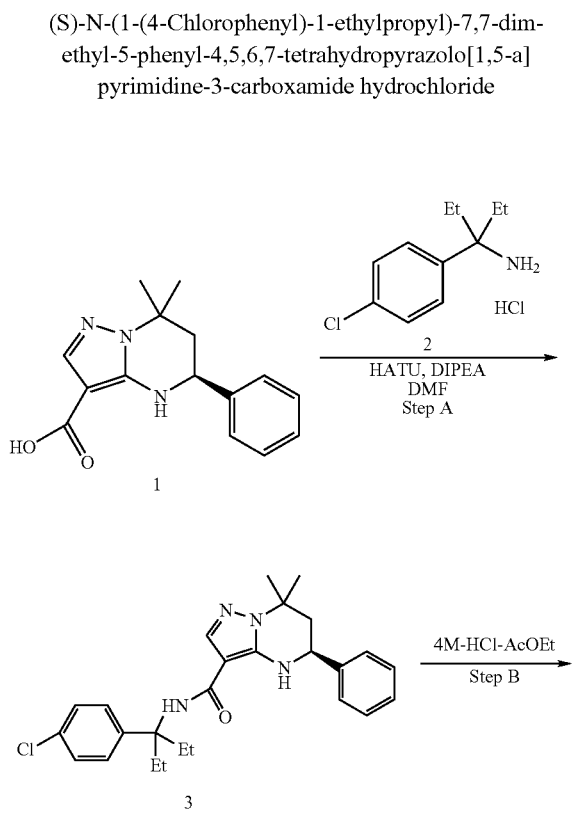

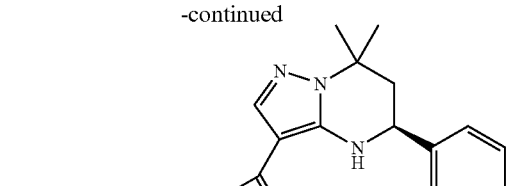

Step A: To a solution of 1 (0.4 g, 1.47 mmol) and HATU (0.67 g, 1.77 mmol) in DMF (5 mL) was added DIPEA (0.57 g, 4.41 mmol) at room temperature. After 1 h, compound 2 (0.41 g, 1.77 mmol) was added thereto. The resulting mixture was stirred at 80° C. for 12 h, and concentrated in vacuo. The residue was diluted with AcOEt, washed with sat.NaHCO$_3$aq and brine, dried over MgSO$_4$, and concentrated in vacuo. The residue was chromatographed on silica gel with AcOEt/hexane (1/1) to give 0.41 g (62% yield) of compound 4 as colorless prisms. mp 105-106° C. $[\alpha]_D^{20° C.}$=−17.68 in CHCl$_3$, C=0.30. Step B: To a stirred solution of compound 3 (90 mg, 0.2 mmol) in Et$_2$O (3 mL) was added 4M HCl-AcOEt (0.1 mL, 0.4 mmol) at room temperature. The precipitate was collected by filtration to give 60 mg (62% yield) of compound 4 as prisms. mp 130-132° C. $[\alpha]_D^{20° C.}$=24.3 in CHCl$_3$ C=0.48.

Compounds of Examples 1029-1122 shown in the Table 13, were prepared in a manner similar to that described in Example 1028.

TABLE 13

| Example | Structure | Name | Physiological Data |
|---|---|---|---|
| 1029 | 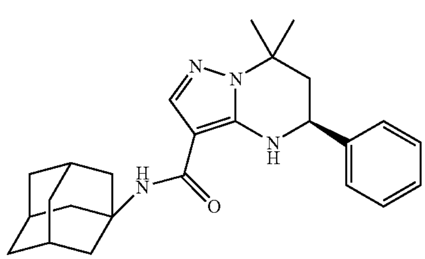 | (5S)-N-1-adamantyl-7,7-dimethyl-5-phenyl-4,5,6,7-tetrahydropyrazolo[1,5-a]pyrimidine-3-carboxamide | mp 226-227° C. $[\alpha]_D^{20° C.}$ = −37.40 in CHCl$_3$, C = 0.24. |

TABLE 13-continued

| Example | Structure | Name | Physiological Data |
|---|---|---|---|
| 1030 | 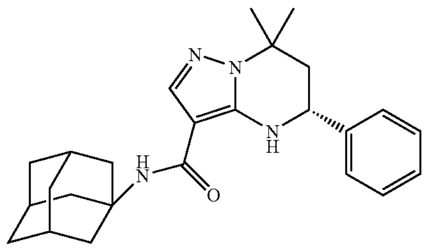 | (5R)-N-1-adamantyl-7,7-dimethyl-5-phenyl-4,5,6,7-tetrahydropyrazolo[1,5-a]pyrimidine-3-carboxamide | mp 226-227° C. [α]$_D^{20° C.}$ = 37.0 in CHCl$_3$, C = 0.24. |
| 1031 | 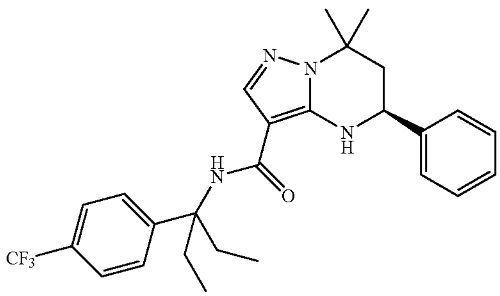 | (5S)-N-(1-ethyl-1-(4-(trifluoromethyl)phenyl)propyl)-7,7-dimethyl-5-phenyl-4,5,6,7-tetrahydro-pyrazolo]1,5-a]pyrimidine-3-carboxamide | mp 165-166° C. [α]$_D^{20° C.}$ = −15.10 in CHCl$_3$, C = 0.25. |
| 1032 | 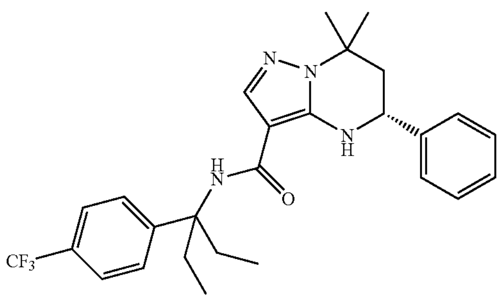 | (5R)-N-(1-ethyl-1-(4-(trifluoromethyl)phenyl)propyl)-7,7-dimethyl-5-phenyl-4,5,6,7-tetrahydro-pyrazolo[1,5-a]pyrimidine-3-carboxamide | mp 165-166° C. [α]$_D^{20° C.}$ = 14.4 in CHCl$_3$, C = 0.25. |
| 1033 | 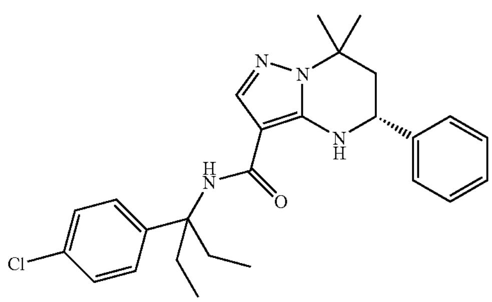 | (5R)-N-(1-(4-chlorophenyl)-1-ethylpropyl)-7,7-dimethyl-5-phenyl-4,5,6,7-tetrahydropyrazolo[1,5-a]pyrimidine-3-carboxamide | mp 105-106° C. [α]$_D^{20° C.}$ = 17.92 in CHCl$_3$, C = 0.28. |
| 1034 | 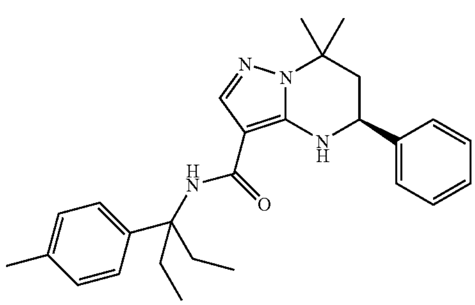 | (5S)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 139-140° C. [α]$_D^{20° C.}$ = −19.67 in CHCl$_3$, C = 0.34 |

| Example | Structure | Name | Physiological Data |
|---|---|---|---|
| 1035 | 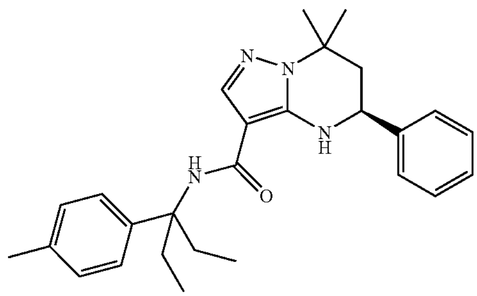 | (5S)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 142-143° C., $[\alpha]_D^{21°\ C.} = 31.05$ in $CHCl_3$, C = 0.65. HCl salt |
| 1036 | 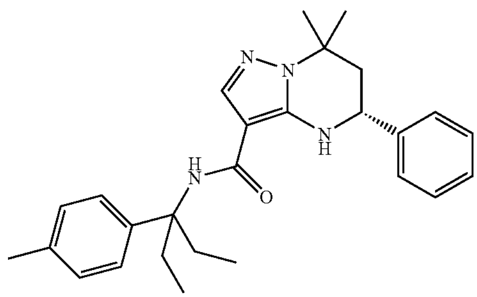 | (5R)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 139-140° C. $[\alpha]_D^{22°\ C.} = 16.33$ in $CHCl_3$, C = 0.60. |
| 1037 | 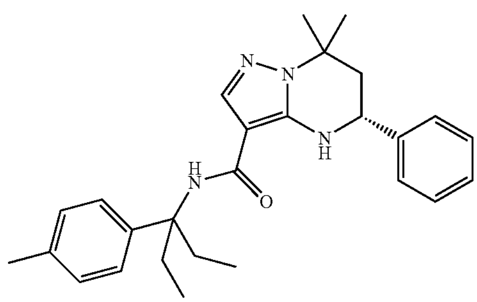 | (5R)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 150-151° C., $[\alpha]_D^{21°\ C.} = -27.99$ in $CHCl_3$, C = 0.80. HCl salt |
| 1038 | 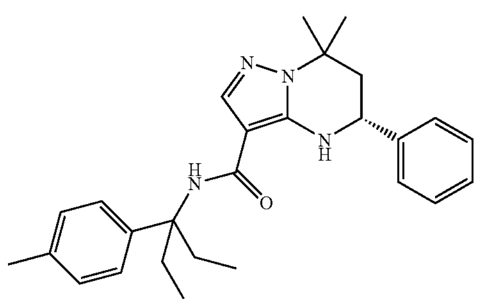 | (5R)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 140-141° C. $[\alpha]_D^{22°\ C.} = -14.02$ in $CHCl_3$, C = 0.30. $PhSO_3H$ salt |
| 1039 | 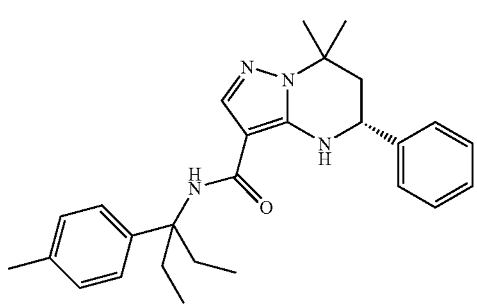 | (5R)-N-(1-ethyl-1-(4-methylphenyl)propyl)-7,7-dimethyl-5-phenyl-4,5,6,7-tetrahydropyrazolo[1,5-a]pyrimidine-3-carboxamide | mp 151-152° C. $[\alpha]_D^{21°\ C.} = -14.42$ in $CHCl_3$, C = 0.33. p-TsOH salt |

TABLE 13-continued

| Example | Structure | Name | Physiological Data |
|---|---|---|---|
| 1040 | 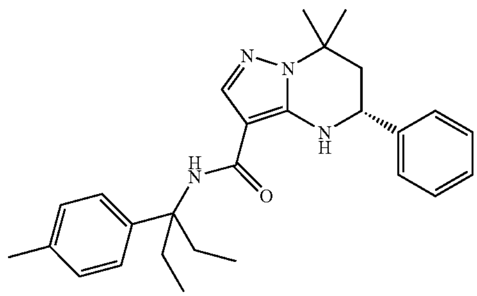 | (5R)-N-(1-ethyl-1-(4-methylphenyl)propyl)-7,7-dimethyl-5-phenyl-4,5,8,7-tetrahydropyrazolo[1,5-a]pyrimidine-3-carboxamide | mp 140-141° C. $[\alpha]_D^{21°\,C.} = -9.10$ in CHCl$_3$, C = 0.40. 0.5 H$_2$SO$_4$ salt |
| 1041 | 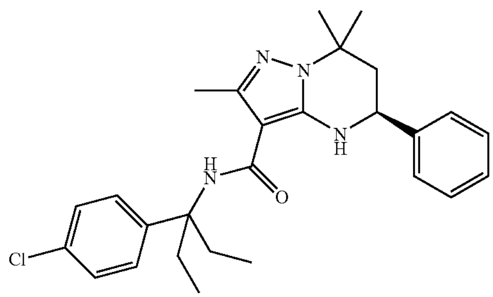 | (5S)-N-(1-(4-chlorophenyl)-1-ethylpropyl)-2,7,7-trimethyl-5-phenyl-4,5,6,7-tetrahydropyrazolo[1,5-a]pyrimidine-3-carboxamide | mp 131-132° C. $[\alpha]_D^{20°\,C.} = -22.83$ in CHCl$_3$, C = 0.22. |
| 1042 | 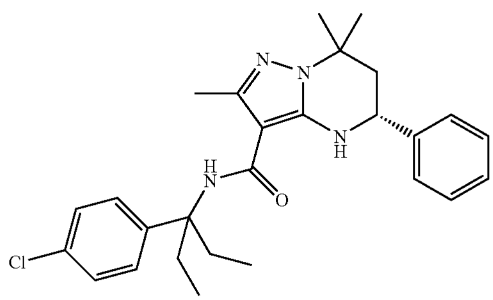 | (5R)-N-(1-(4-chlorophenyl)-1-ethylpropyl)-2,7,7-trimethyl-5-phenyl-4,5,6,7-tetrahydropyrazolo[1,5-a]pyrimidine-3-carboxamide | mp 128-129° C. $[\alpha]_D^{20°\,C.} = 22.44$ in CHCl$_3$, C = 0.23. |
| 1043 | 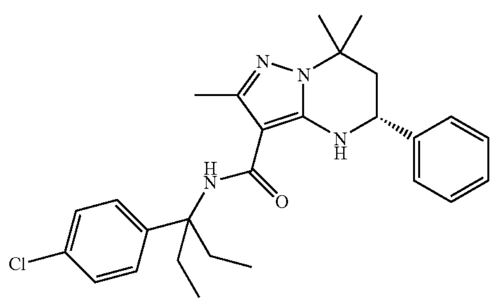 | (5R)-N-(1-(4-chlorophenyl)-1-ethylpropyl)-2,7,7-trimethyl-5-phenyl-4,5,6,7-tetrahydropyrazolo[1,5-a]pyrimidine-3-carboxamide | mp 193-194° C. $[\alpha]_D^{21°\,C.} = -7.85$ in CHCl$_3$, C = 0.30. HCl salt |
| 1044 | 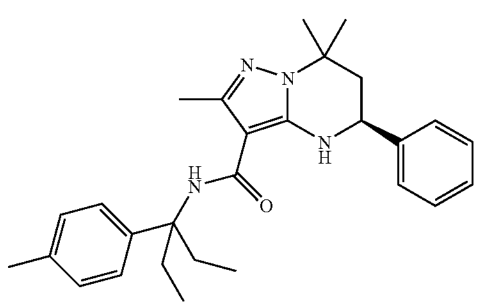 | (5S)-N-(1-ethyl-1-(4-methylphenyl)propyl)-2,7,7-trimethyl-5-phenyl-4,5,6,7-tetrahydropyrazolo[1,5-pyrimidine-3-carboxamide | mp 78-80° C. $[\alpha]_D^{20°\,C.} = -23.5$ in CHCl$_3$, C = 0.51. |

TABLE 13-continued

| Example | Structure | Name | Physiological Data |
| --- | --- | --- | --- |
| 1045 | 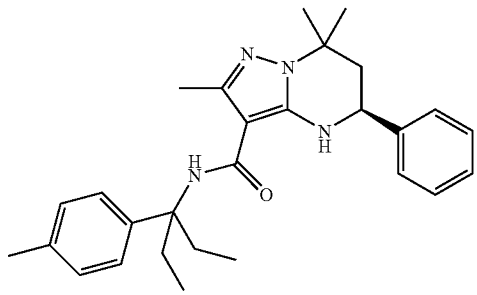 | (5S)-N-(1-ethyl-1-(4-methylphenyl)propyl)-2,7,7-trimethyl-5-phenyl-4,5,6,7-tetrahydropyrazolo[1,5-a]pyrimidine-3-carboxamide | mp 194-195° C. $[\alpha]_D^{20°\,C.} = 9.3$ in CHCl$_3$, C = 0.48. HCl salt |
| 1046 | 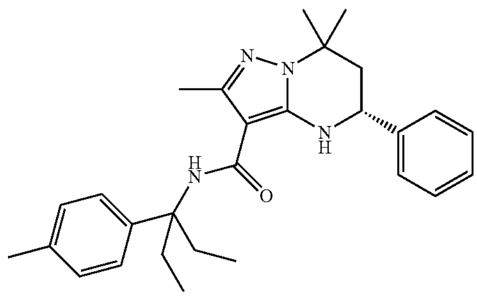 | (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide | mp 78-80° C. $[\alpha]_D^{20°\,C.} = 25.3$ CHCl$_3$, C = 0.50. |
| 1047 | 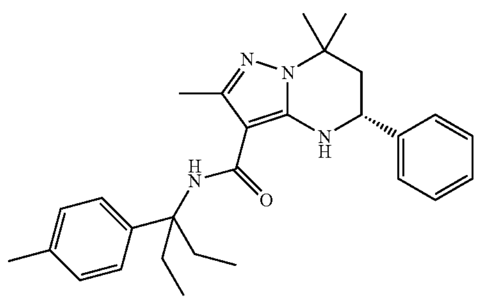 | (5R)-N-(1-ethyl-1-(4-methylphenyl)propyl)-2,7,7-trimethyl-5-phenyl-4,5,8,7-tetrahydropyrazolo[1,5-a]pyrimidine-3-carboxamide | mp 206-207° C. $[\alpha]_D^{25°\,C.} = -8.1$ in CHCl$_3$, C = 0.52. HCl salt |
| 1048 | 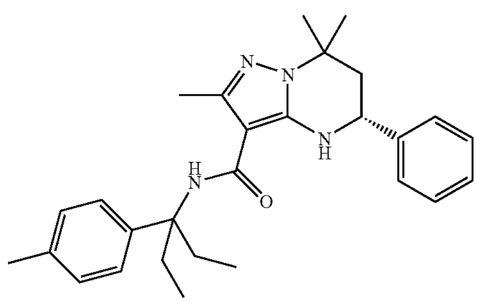 | (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide | mp 188-189° C. $[\alpha]_D^{20°\,C.} = -4.4$ in CHCl$_3$, C = 0.44. CH$_3$SO$_3$H salt |
| 1049 | 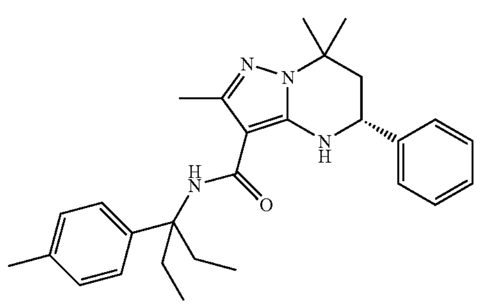 | (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide | mp 161-162° C. $[\alpha]_D^{20°\,C.} = -9.5$ in CHCl$_3$, C = 0.50. PhSO$_3$H salt |

TABLE 13-continued

| Example | Structure | Name | Physiological Data |
|---|---|---|---|
| 1050 | 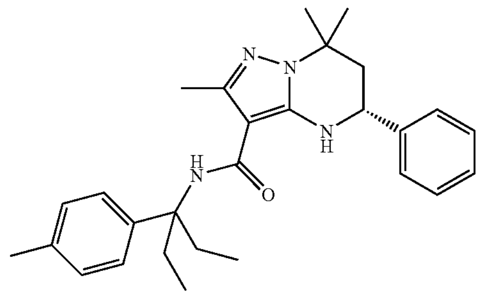 | (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide | mp 120-122° C. $[\alpha]_D^{20°\ C.} = -8.8$ in CHCl$_3$, C = 0.51. p-TsOH salt |
| 1051 | 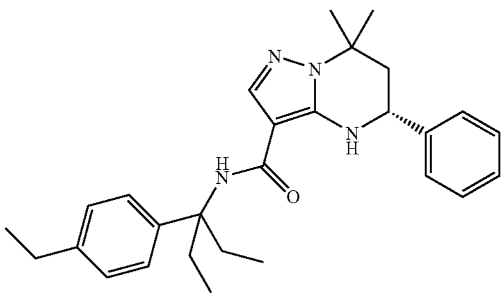 | (5R)-N-(1-ethyl-1-(4-ethylphenyl)propyl)-7,7-dimethyl-5-phenyl-4,5,6,7-tetrahydropyrazolo[1,5-a]pyrimidine-3-carboxamide | mp 149-150° C., $[\alpha]_D^{21°\ C.} = -16.76$ in CHCl$_3$, C = 0.39. HCl salt |
| 1052 | 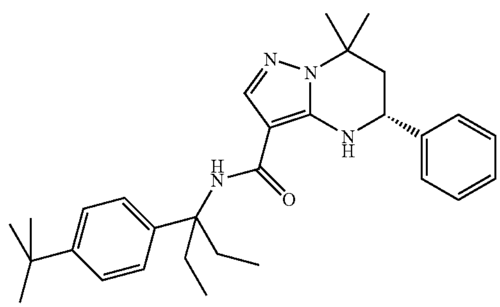 | (5R)-N-(1-(4-tert-butylphenyl)-1-ethylpropyl)-7,7-dimethyl-5-phenyl-4,5,6,7-tetrahydropyrazolo[1,5-a]pyrimidine-3-carboxamide | mp 139-140° C., $[\alpha]_D^{21°\ C.} = -13.94$ in CHCl$_3$, C = 0.36. HCl salt |
| 1053 | 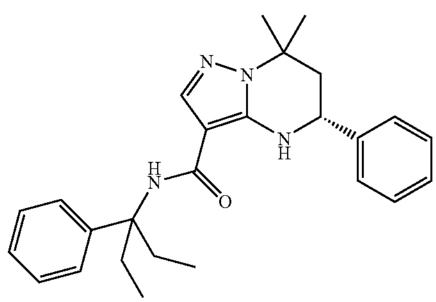 | (5R)-N-(1-ethyl-1-phenylpropyl)-7,7-dimethyl-5-phenyl-4,5,6,7-tetrahydropyrazolo[1,5-a]pyrimidine-3-carboxamide | mp 129-130° C., $[\alpha]_D^{20°\ C.} = -24.66$ in CHCl$_3$, C = 0.38. HCl salt |
| 1054 | 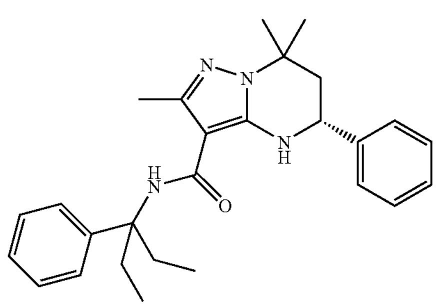 | (5R)-N-(1-ethyl-1-phenylpropyl)-2,7,7-trimethyl-5-phenyl-4,5,6,7-tetrahydropyrazolo[1,5-a]pyrimidine-3-carboxamide | mp 185-186° C., $[\alpha]_D^{20°\ C.} = -10.56$ in CHCl$_3$, C = 0.39 HCl salt |

TABLE 13-continued

| Example | Structure | Name | Physiological Data |
|---|---|---|---|
| 1055 | 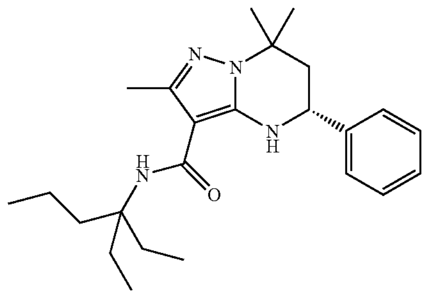 | (5R)-N-(1,1-diethylbutyl)-2,7,7-trimethyl-5-phenyl-4,5,6,7-tetrahydro-pyrazolo[1,5-a]pyrimidine-3-carboxamide | mp 176-177° C. $[\alpha]_D^{21° C.} = -1.98$ in CHCl$_3$, C = 0.35. HCl salt |
| 1056 | 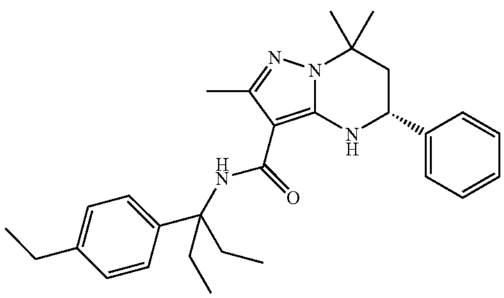 | (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide | MS(ESI, m/z) 459 (M + H)+, $[\alpha]_D^{20° C.} = 25.0$ in CHCl$_3$, C = 0.53. |
| 1057 | 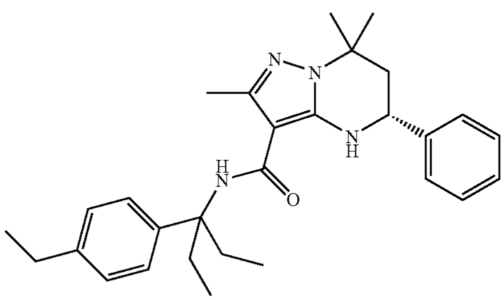 | (5R)-N-(1-ethyl-1-(4-ethylphenyl)propyl)-2,7,7-trimethyl-5-phenyl-4,5,6,7-tetrahydropyrazolo]1,5-a]pyrimidine-3-carboxamide | mp 163-164° C., $[\alpha]_D^{21° C.} = -7.96$ CHCl$_3$, C = 0.46. HCl salt |
| 1058 | 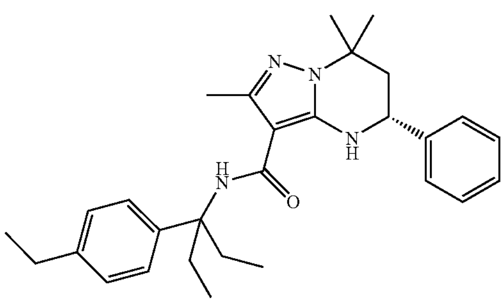 | (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide | mp 160-161° C., $[\alpha]_D^{20° C.} = -2.9$ in CHCl$_3$, C = 0.56. CH$_3$SO$_3$H salt |
| 1059 | 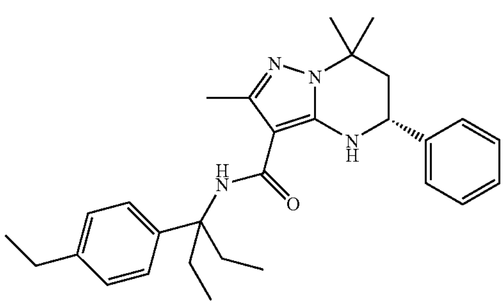 | (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide | mp 165-166° C., $[\alpha]_D^{21° C.} = -7.4$ in CHCl$_3$, C = 0.49. PhSO$_3$H salt |

TABLE 13-continued

| Example | Structure | Name | Physiological Data |
| --- | --- | --- | --- |
| 1060 | 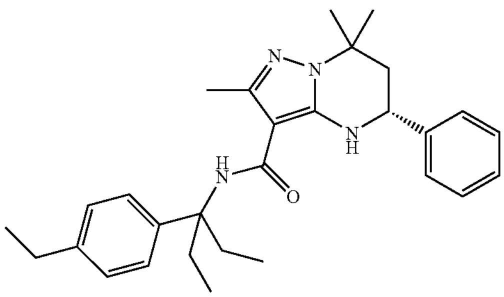 | (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide | mp 160-161° C., [α]$_D^{21° C.}$ = −8.1 in CHCl$_3$, C = 0.49. P-TsOH salt |
| 1061 | 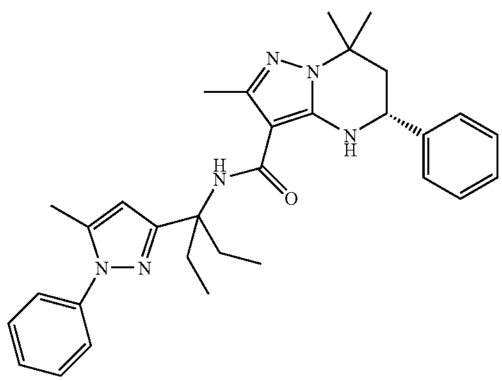 | (5R)-N-(1-ethyl-1-(5-methyl-1-phenyl-1H-pyrazol-3-yl)propyl)-2,7,7-trimethyl-5-phenyl-4,5,6,7-tetrahydropyrazolo[1,5-a]pyrimidine-3-carboxamide | MS(ESI, m/z) 511 (M + H)+ |
| 1062 | 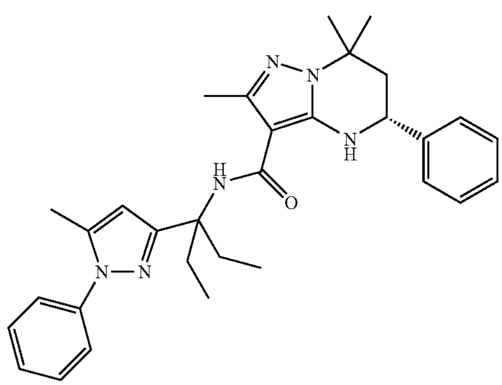 | (5R)-N-(1-ethyl-1-(5-methyl-1-phenyl-1H-pyrazol-3-yl)propyl)-2,7,7-trimethyl-5-phenyl-4,5,6,7-tetrahydropyrazolo[1,5-a]pyrimidine-3-carboxamide | mp 194-195° C. 2HCl salt |
| 1063 | 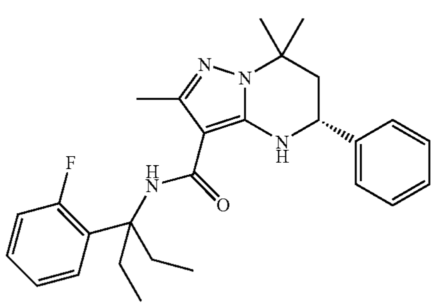 | (5R)-N-(1-ethyl-1-(2-fluorophenyl)propyl)-2,7,7-trimethyl-5-phenyl-4,5,6,7-tetrahydropyrazolo[1,5-a]pyrimidine-3-carboxamide | mp 180-182° C., [α]$_D^{21° C.}$ = −8.60 in CHCl$_3$, C = 0.62. HCl salt |

TABLE 13-continued

| Example | Structure | Name | Physiological Data |
|---|---|---|---|
| 1064 | 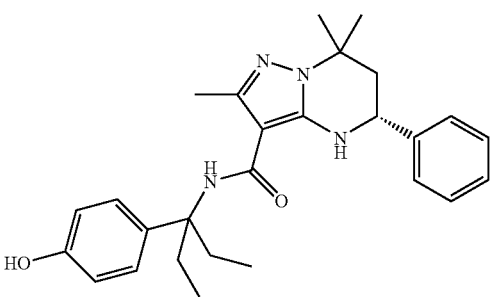 | (5R)-N-(1-ethyl-1-(4-hydroxyphenyl)propyl)-2,7,7-trimethyl-5-phenyl-4,5,6,7-tetrahydro-pyrazolo[1,5-a]pyrimidine-3-carboxamide | mp 160-161° C., $[\alpha]_D^{21°\ C.} = 15.41$ in CHCl$_3$, C = 0.36. |
| 1065 | 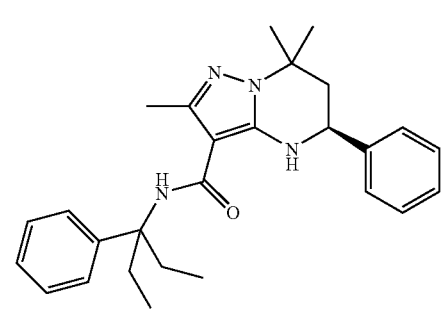 | (5S)-N-(1-ethyl-1-phenylpropyl)-2,7,7-trimethyl-5-phenyl-4,5,6,7-tetrahydropyrazolo[1,5-a]pyrimidine-3-carboxamide | mp 182-183° C., $[\alpha]_D^{21°\ C.} = 11.36$ in CHCl$_3$, C = 0.36. HCl salt |
| 1066 | 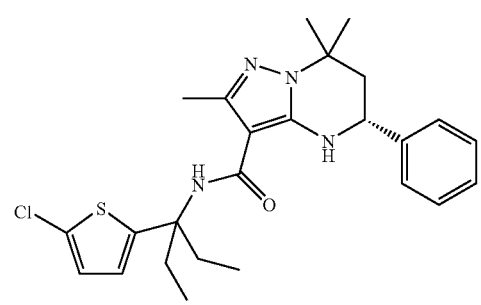 | (5R)-N-(1-(5-chloro-2-thienyl)-1-ethylpropyl)-2,7,7-trimethyl-5-phenyl-4,5,6,7-tetrahydropyrazolo]1,5-a]pyrimidine-3-carboxamide | MS(ESI, m/z) 471 (M + H)+ |
| 1067 | 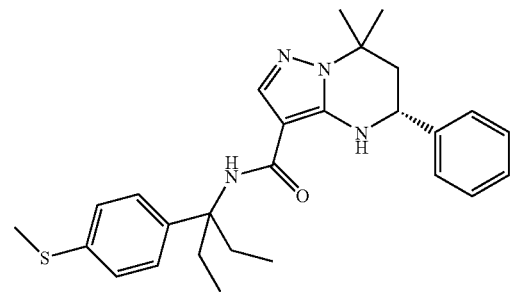 | (5R)-N-(1-ethyl-1-(4-(methylthio)phenyl)propyl)-7,7-dimethyl-5-phenyl-4,5,6,7-tetrahydro-pyrazolo]1,5-a]pyrimidine-3-carboxamide | mp 151-152° C., |
| 1068 | 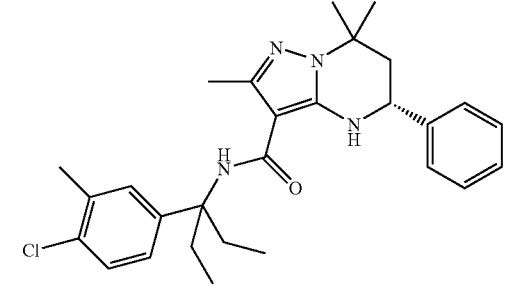 | (5R)-N-(1-(4-chloro-3-methylphenyl)-1-ethylpropyl)-2,7,7-trimethyl-5-phenyl-4,5,6,7-tetrahydropyrazolo[1,5-a]pyrimidine-3-carboxamide | mp 150-151° C. HCl salt |

TABLE 13-continued

| Example | Structure | Name | Physiological Data |
|---------|-----------|------|--------------------|
| 1069 | 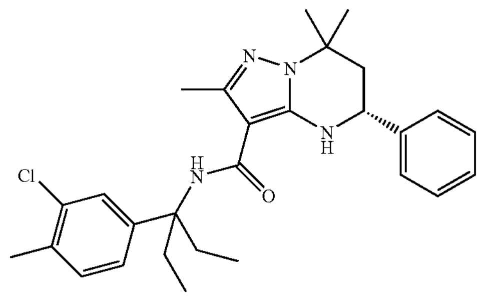 | (5R)-N-(1-(3-chloro-4-methylphenyl)-1-ethylpropyl)-2,7,7-trimethyl-5-phenyl-4,5,6,7-tetrahydropyrazolo[1,5-a]pyrimidine-3-carboxamide | mp 129-130° C. HCl salt |
| 1070 | 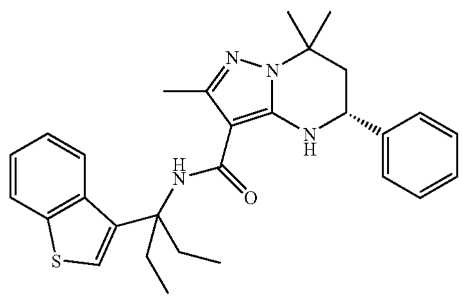 | (5R)-N-(1-(1-benzothien-2-yl)-1-ethylpropyl)-2,7,7-trimethyl-5-phenyl-4,5,8,7-tetrahydropyrazolo[1,5-a]pyrimidine-3-carboxamide | mp 127-128° C. HCl salt |
| 1071 | 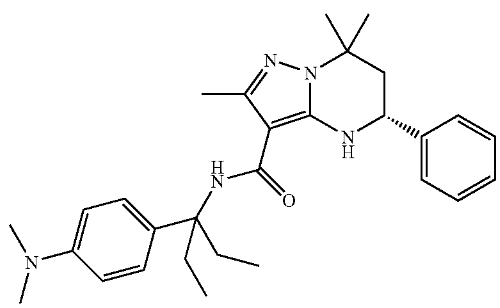 | (5R)-N-(1-(4-(dimethylamino)phenyl)-1-ethylpropyl)-2,7,7-trimethyl-5-phenyl-4,5,6,7-tetrahydropyrazolo[1,5-a]pyrimidine-3-carboxamide | mp 141-142° C. HCl salt |
| 1072 | 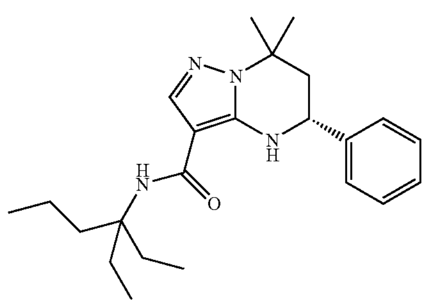 | (5R)-N-(1,1-diethylbutyl)-7,7-dimethyl-5-phenyl-4,5,6,7-tetrahydro-pyrazolo]1,5-a]pyrimidine-3-carboxamide | mp 185-186° C., HCl salt |
| 1073 | 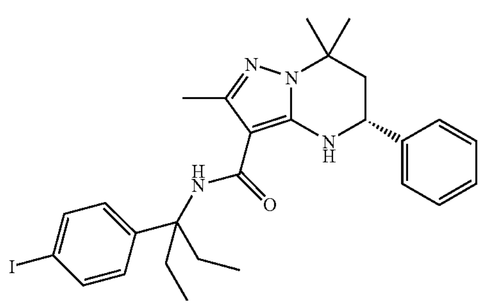 | (5R)-N-(1-ethyl-1-(4-iodophenyl)propyl)-2,7,7-trimethyl-5-phenyl-4,5,6,7-tetrahydropyrazolo[1,5-a]pyrimidine-3-carboxamide | mp 179-180° C., HCl salt |

TABLE 13-continued

| Example | Structure | Name | Physiological Data |
|---|---|---|---|
| 1074 | 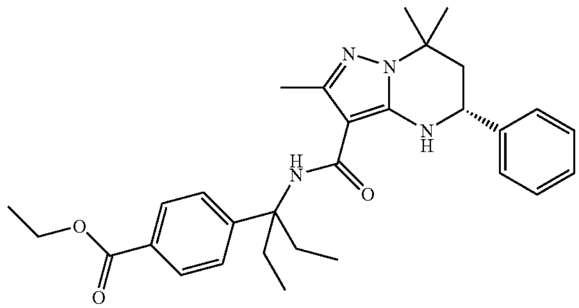 | (5R)-ethyl 4-(1-ethyl-1-(((2,7,7-trimethyl-5-phenyl-4,5,6,7-tetrahydropyrazolo[1,5-a]pyrimidin-3-yl)carbonyl)-amino)propyl)benzoate | mp 125-126° C., HCl salt |
| 1075 | 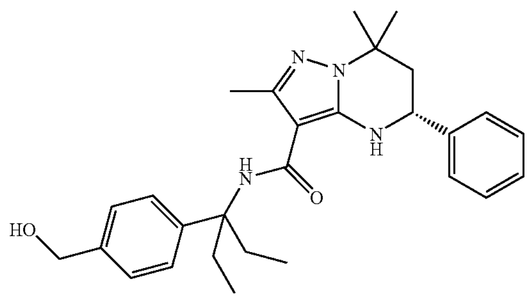 | (5R)-N-(1-ethyl-1-(4-(hydroxymethyl)phenyl)-propyl)-2,7,7-trimethyl-5-phenyl-4,5,6,7-tetrahydropyrazolo[1,5-a]pyrimidine-3-carboxamide | mp 168-169° C. HCl salt |
| 1076 | 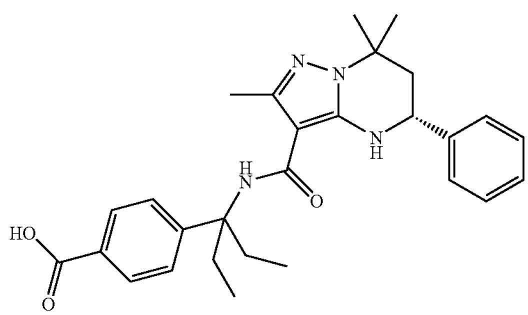 | (5R)-4-(1-ethyl-1-((((-2,7,7-trimethyl-5-phenyl-4,5,6,7-tetrahydropyrazolo[1,5-a]pyrimidin-3-yl)carbonyl)-amino)propyl)benzoic acid | mp 234-236° C. |
| 1077 | 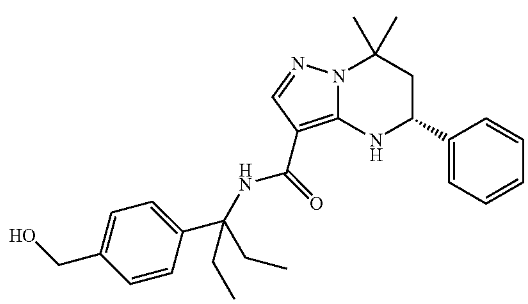 | (5R)-N-(1-ethyl-1-(4-(hydroxymethyl)phenyl)-propyl)-7,7-dimethyl-5-phenyl-4,5,6,7-tetrahydropyrazolo[1,5-a]pyrimidine-3-carboxamide | mp 159-160° C., HCl salt |
| 1078 | 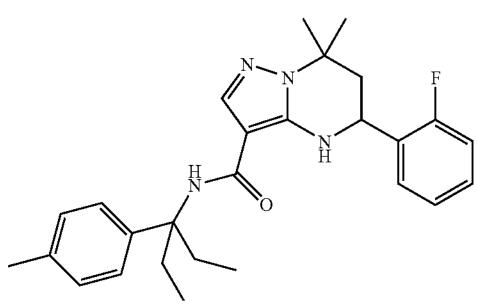 | (+)-N-[1-ethyl-1-(4-methylphenyl)propyl]-5-(2-fluorophenyl)-7,7-dimethyl-4,5,6,7-tetrahydropyrazolo[1,5-a]pyrimidine-3-carboxamide | mp 139-140° C., $[\alpha]_D^{20° C.}$ = +9.66 in CHCl$_3$, C = 0.47. HCl salt |

TABLE 13-continued

| Example | Structure | Name | Physiological Data |
|---|---|---|---|
| 1079 | 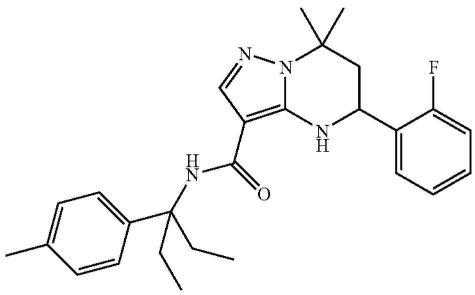 | (+)-N-[1-ethyl-1-(4-methylphenyl)propyl]-5-(2-fluorophenyl)-7,7-dimethyl-4,5,6,7-tetrahydropyrazolo[1,5-a]pyrimidine-3-carboxamide | mp 161-163° C.<br>$[\alpha]_D^{20°\,C.} = 39.5$<br>in $CHCl_3$, C = 0.50. |
| 1080 | 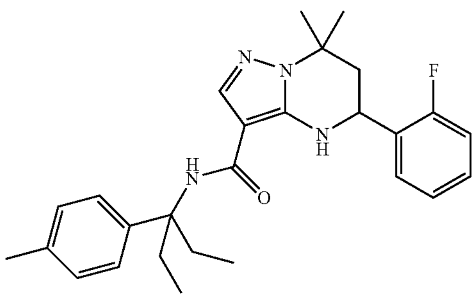 | | mp 135-136° C.,<br>$[\alpha]_D^{20°\,C.} = -11.19$<br>in $CHCl_3$, C = 0.49.<br>HCl salt of Example 1079 |
| 1081 | 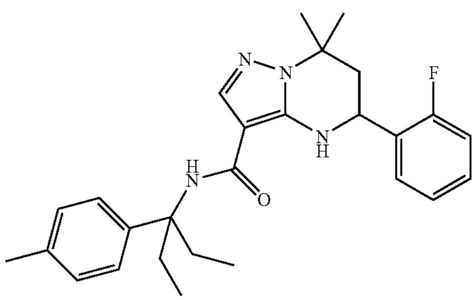 | | mp 144-146° C.<br>$[\alpha]_D^{20°\,C.} = 5.1$<br>in $CHCl_3$, C = 0.50.<br>p-TsOH salt of Example 1079 |
| 1082 | 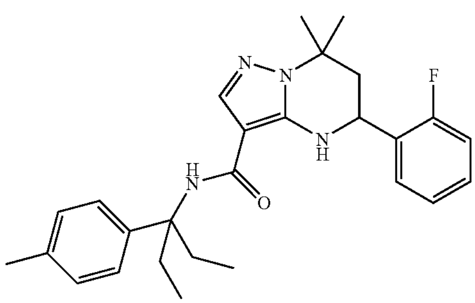 | | mp 147-149° C.<br>$[\alpha]_D^{20°\,C.} = -4.1$<br>in $CHCl_3$, C = 0.49.<br>$PhSO_3H$ salt of Example 1079 |
| 1083 | 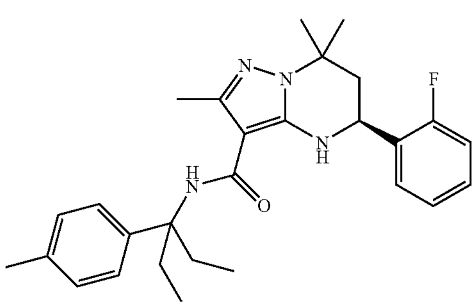 | (5S)-N-(1-ethyl-1-(4-methylphenyl)propyl)-5-(2-fluorophenyl)-2,7,7-trimethyl-4,5,6,7-tetrahydropyrazolo]1,5-a]pyrimidine-3-carboxamide | mp 203-204° C.<br>$[\alpha]_D^{20°\,C.} = -1.29$<br>in $CHCl_3$, C = 0.54.<br>HCl salt |

TABLE 13-continued

| Example | Structure | Name | Physiological Data |
| --- | --- | --- | --- |
| 1084 | 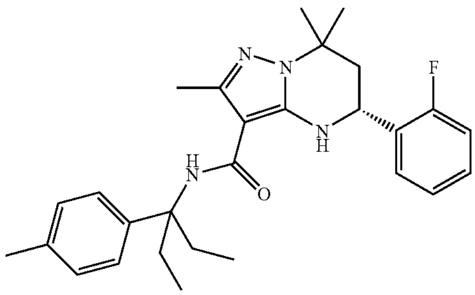 | (5R)-N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | MS(ESI, m/z) 463 (M + H)+ |
| 1085 | 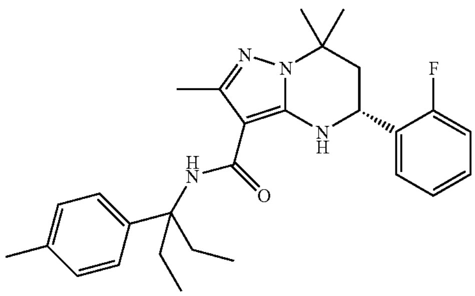 | (5R)-N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | mp 156-158° C.<br>$[\alpha]_D^{20°\ C.} = 1.29$<br>in $CHCl_3$, C = 0.52.<br>HCl salt |
| 1086 | 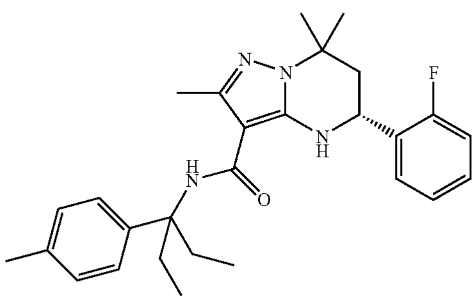 | (5R)-N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | mp 180-181° C.<br>$[\alpha]_D^{20°\ C.} = 4.9$<br>in $CHCl_3$, C = 0.52.<br>$CH_3SO_3H$ salt |
| 1087 | 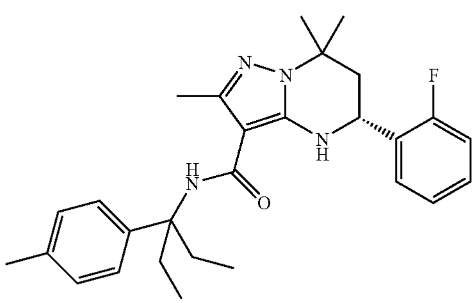 | (5R)-N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | mp 172-174° C.<br>$[\alpha]_D^{20°\ C.} = 0.4$<br>in $CHCl_3$, C = 0.48.<br>p-TsOH salt |
| 1088 | | (5R)-N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide | mp 170-171° C.<br>$[\alpha]_D^{20°\ C.} = -0.1$<br>in $CHCl_3$, C = 0.49.<br>$PhSO_3H$ salt | ns
TABLE 13-continued

| Example | Structure | Name | Physiological Data |
|---|---|---|---|
| 1089 | 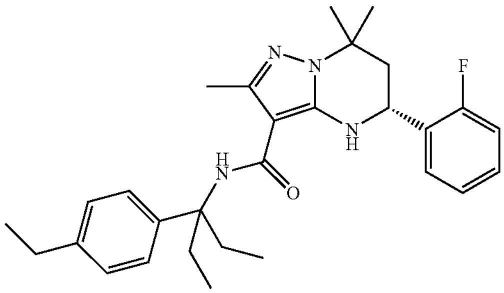 | (5R)-N-(1-ethyl-1-(4-ethylphenyl)propyl)-5-(2-fluorophenyl)-2,7,7-trimethyl-4,5,6,7-tetrahydropyrazolo[1,5-a]pyrimidine-3-carboxamide | mp 138-139° C.<br>$[\alpha]_D^{20°\,C.} = 2.6$<br>in CHCl$_3$, C = 0.57.<br>HCl salt |
| 1090 | 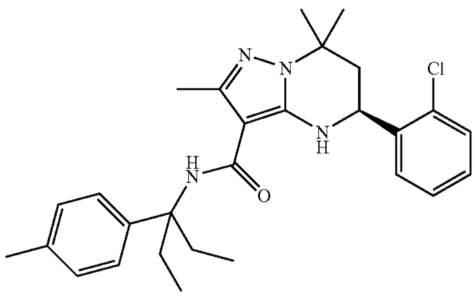 | (5S)-5-(2-chlorophenyl)-N-(1-ethyl-1-(4-methyl-phenyl)propyl)-2,7,7-trimethyl-4,5,6,7-tetrahydropyrazolo[1,5-a]pyrimidine-3-carboxamide | mp 173-174° C.<br>$[\alpha]_D^{20°\,C.} = -48.2$<br>in CHCl$_3$, C = 0.50.<br>HCl salt |
| 1091 | 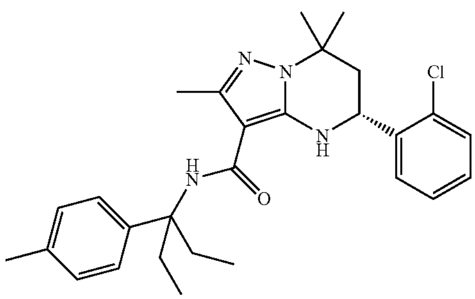 | (5R)-5-(2-chlorophenyl)-N-(1-ethyl-1-(4-methyl-phenyl)propyl)-2,7,7-trimethyl-4,5,6,7-tetrahydropyrazolo[1,5-a]pyrimidine-3-carboxamide | mp 136-137° C.<br>$[\alpha]_D^{20°\,C.} = 66.9$<br>in CHCl$_3$, C = 0.50. |
| 1092 | 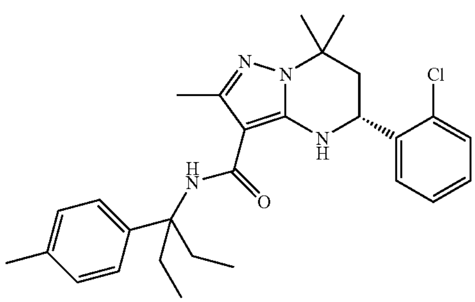 | (5R)-5-(2-chlorophenyl)-N-(1-ethyl-1-(4-methyl-phenyl)propyl)-2,7,7-trimethyl-4,5,6,7-tetrahydropyrazolo[1,5-a]pyrimidine-3-carboxamide | mp 176-177° C.<br>$[\alpha]_D^{20°\,C.} = 48.0$<br>in CHCl$_3$, C = 0.57.<br>HCl salt |
| 1093 | 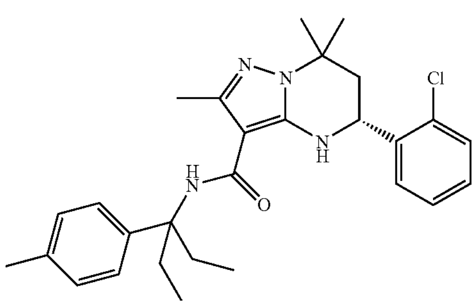 | (5R)-5-(2-chlorophenyl)-N-(1-ethyl-1-(4-methyl-phenyl)propyl)-2,7,7-trimethyl-4,5,6,7-tetrahydropyrazolo[1,5-a]pyrimidine-3-carboxamide | mp 171-172° C.<br>$[\alpha]_D^{20°\,C.} = 42.4$<br>in CHCl$_3$, C = 0.62.<br>CH$_3$SO$_3$H salt |

TABLE 13-continued

| Example | Structure | Name | Physiological Data |
|---------|-----------|------|---------------------|
| 1094 | 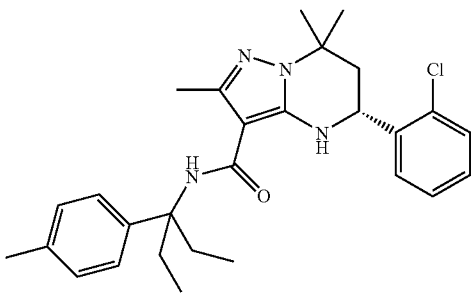 | (5R)-5-(2-chlorophenyl)-N-(1-ethyl-methylphenyl)-propyl)-2,7,7-trimethyl-4,5,6,7-tetrahydropyrazolo]1,5-a]pyrimidine-3-carboxamide | mp 150-151° C. $[\alpha]_D^{20°\ C.} = 37.8$ in CHCl$_3$, C = 0.51. P-TsOH salt |
| 1095 | 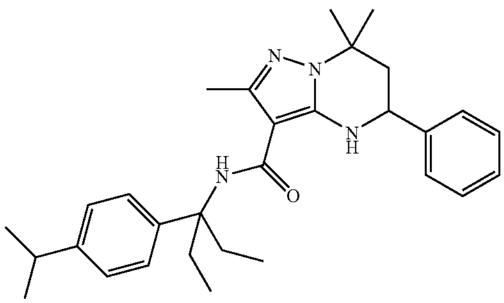 | N-(1-ethyl-1-(4-isopropyl-phenyl)propyl)-2,7,7-trimethyl-5-phenyl-4,5,6,7-tetrahydropyrazolo[1,5-a]pyrimidine-3-carboxamide | mp 134-136° C. HCl salt |
| 1096 | 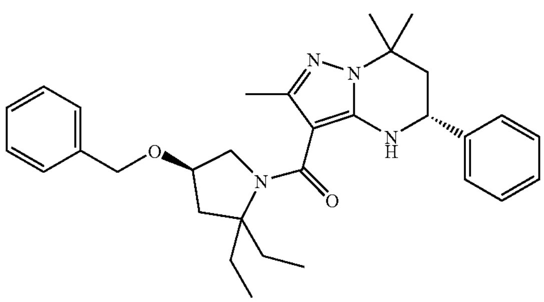 | (5R)-3-(((4R)-4-(benzyloxy)-2,2-diethyl-1-pyrrolidinyl)-carbonyl)-2,7,7-trimethyl-5-phenyl-4,5,6,7-tetrahydropyrazolo[1,5-a]pyrimidine | MS(ESI, m/z) 501 (M + H)+ HCl salt |
| 1097 | 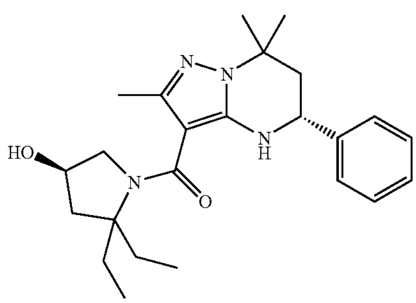 | (3R)-5,5-diethyl-1-(((5R)-2,7,7-trimethyl-5-phenyl-4,5,6,7-tetrahydropyrazolo[1,5-a]pyrimidin-3-yl)carbonyl)-3-pyrrolidinol | mp 162-164° C. |
| 1098 | 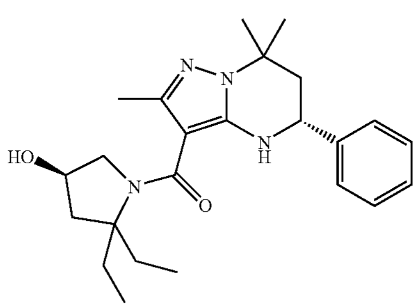 | (3R)-5,5-diethyl-1-(((5R)-2,7,7-trimethyl-5-phenyl-4,5,6,7-tetrahydropyrazolo[1,5-a]pyrimidin-3-yl)carbonyl)-3-pyrrolidinol | mp 140-142° C. HCl salt |

TABLE 13-continued

| Example | Structure | Name | Physiological Data |
|---|---|---|---|
| 1099 | 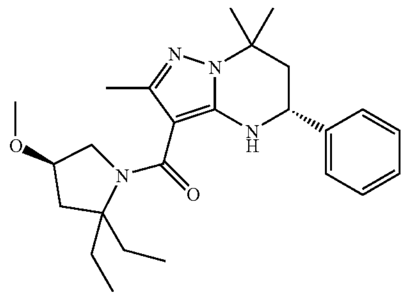 | (5R)-3-(((4R)-2,2-diethyl-4-methoxy-1-pyrrolidinyl)-carbonyl)-2,7,7-trimethyl-5-phenyl-4,5,6,7-tetrahydro-pyrazolo]1,5-a]pyrimidine | mp 132-134° C. |
| 1100 | 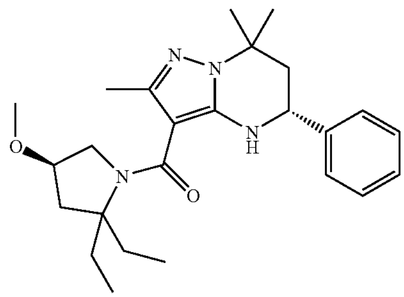 | (5R)-3-(((4R)-2,2-diethyl-4-methoxy-1-pyrrolidinyl)-carbonyl)-2,7,7-trimethyl-5-phenyl-4,5,6,7-tetrahydro-pyrazolo[1,5-a]pyrimidine | HCl salt EA Calcd. For $C_{25}H_{37}N_4O_2Cl \bullet H_2O$: C. 62.68; H. 8.21; N. 11.70. Found. C. 62.89; H. 8.43; N. 11.50. |
| 1101 | 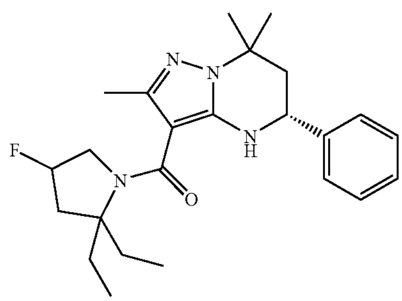 | (5R)-3-((2,2-diethyl-4-fluoro-1-pyrrolidinyl)carbonyl)-2,7,7-trimethyl-5-phenyl-4,5,6,7-tetrahydropyrazolo[1,5-a]pyrimidine | MS(ESI, m/z) 413 (M + H)+ |
| 1102 | 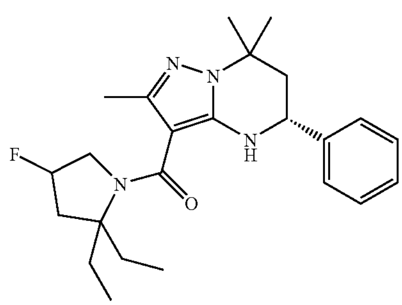 | (5R)-3-((2,2-diethyl-4-fluoro-1-pyrrolidinyl)carbonyl)-2,7,7-trimethyl-5-phenyl-4,5,6,7-tetrahydropyrazolo[1,5-tetrahydropyrazolo[1,5-a]pyrimidine | HCl salt EA Calcd. For $C_{24}H_{34}N_4OClF \bullet 0.9H_2O$: C. 61.96; H. 7.76; N. 12.04. Found. C. 62.26; H. 8.01; N. 11.83 |
| 1103 | 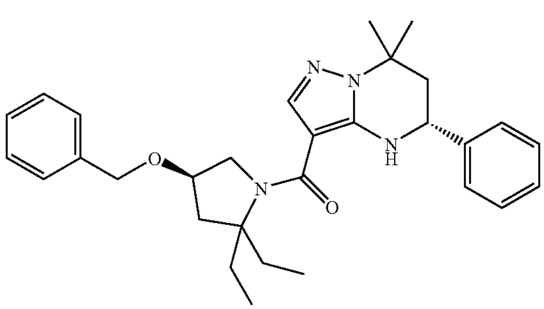 | (5R)-3-(((4R)-4-(benzyloxy)-2-diethyl-1-pyrrolidinyl)-carbonyl)-7,7-dimethyl-5-phenyl-4,5,6,7-tetrahydropyrazolo[1,5-a]pyrimidine | mp 118-120° C. |

TABLE 13-continued

| Example | Structure | Name | Physiological Data |
|---|---|---|---|
| 1104 | 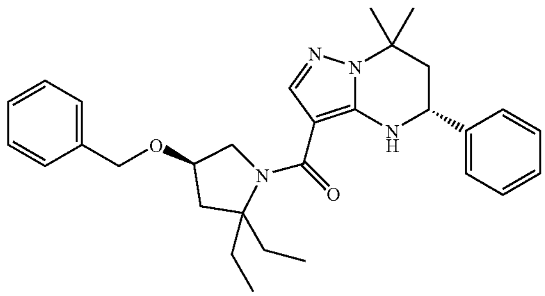 | (5R)-3-(((4R)-4-(benzyloxy)-2,2-diethyl-1-pyrrolidinyl)-carbonyl)-7,7-dimethyl-5-phenyl-4,5,6,7-tetrahydropyrazolo[1,5-a]pyrimidine | HCl salt EA Calcd. For $C_{30}H_{39}N_4O_2Cl \cdot H_2O$: C. 66.59; H. 7.64; N. 10.35. Found. C. 66.83; H. 7.73; N. 10.05 |
| 1105 | 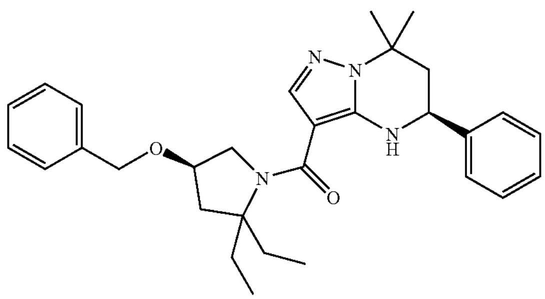 | (5S)-3-(((4R)-4-(benzyloxy)-2,2-diethyl-1-pyrrolidinyl)-carbonyl)-7,7-dimethyl-5-phenyl-4,5,6,7-tetrahydropyrazolo]1,5-a]pyrimidine | mp 172-174° C. |
| 1106 | 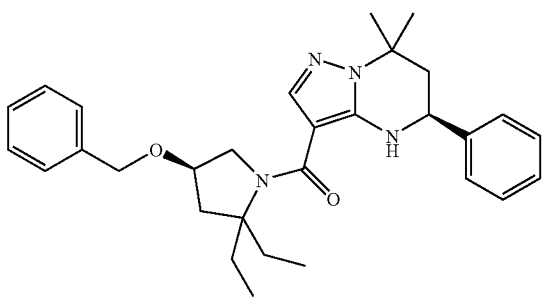 | (5S)-3-(((4R)-4-(benzyloxy)-2,2-diethyl-1-pyrrolidinyl)-carbonyl)-7,7-dimethyl-5-phenyl-4,5,6,7-tetrahydropyrazolo[1,5-a]pyrimidine | HCl salt $^1$H-NMR (CDCl$_3$) δ: 0.82 (6H, dt, J=36.3, 7.2 Hz), 1.58-1.72 (1H, m), 1.93 (6H, d, J=54.3 Hz), 2.00-2.26 (7H, m), 3.67 (1H, dd, J=12.3, 2.7 Hz), 3.79 (1H, dd, J=9.9, 5.4 Hz), 4.15-4.24 (1H, m), 4.56 (2H, dd, J=39.3, 12.0 Hz), 4.64 (1H, dd, J=10.2, 4.8 Hz), 7.30-7.46 (10H, m), 7.88 (1H, bs). |
| 1107 | 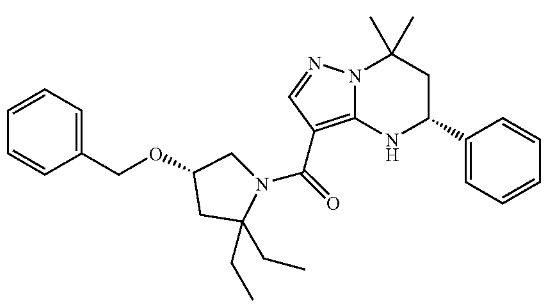 | (5R)-3-(((4S)-4-(benzyloxy)-2,2-diethyl-1-pyrrolidinyl)-carbonyl)-7,7-dimethyl-5-phenyl-4,5,6,7-tetrahydropyrazolo[1,5-a]pyrimidine | mp 173-175° C. |
| 1108 | 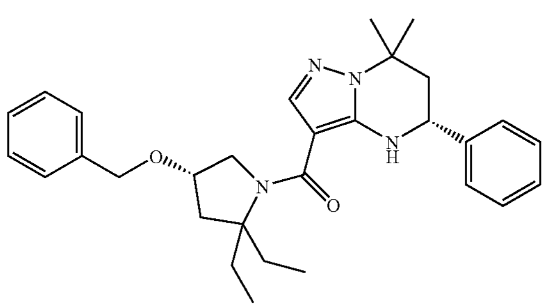 | (5R)-3-(((4S)-4-(benzyloxy)-2,2-diethyl-1-pyrrolidinyl)-carbonyl)-7,7-dimethyl-5-phenyl-4,5,6,7-tetrahydropyrazolo[1,5-a]pyrimidine | HCl salt $^1$H-NMR (CDCl$_3$) δ: 0.83 (6H, dt, J=30.9, 7.5 Hz), 1.60-1.78 (1H, m), 1.68 (6H, d, J=24.3 Hz), 1.96-2.24 (7H, m), 3.70-3.78 (1H, m), 3.88-4.00 (1H, m), 4.14-4.24 (1H, m), 4.54 (2H, dd, J=25.2, 11.7 Hz), 4.61 (1H, dd, J=9.6, 3.9 Hz), 7.28-7.44 (10H, m), 7.59 (1H, bs). |

TABLE 13-continued

| Example | Structure | Name | Physiological Data |
|---|---|---|---|
| 1109 | 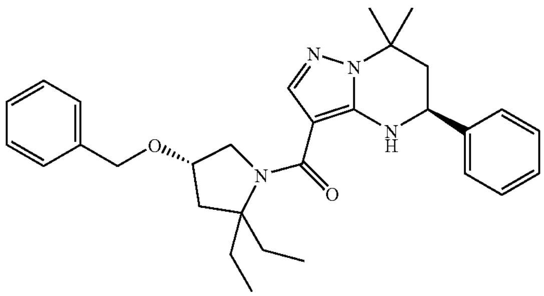 | (5S)-3-(((4S)-4-(benzyloxy)-2,2-diethyl-1-pyrrolidinyl)-carbonyl)-7,7-dimethyl-5-phenyl-4,5,6,7-tetrahydropyrazolo[1,5-a]pyrimidine | mp 116-118° C. |
| 1110 | 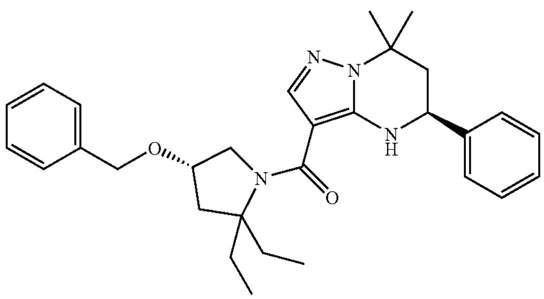 | (5S)-3-(((4S)-4-(benzyloxy)-2,2-diethyl-1-pyrrolidinyl)-7,7-dimethyl-5-phenyl-4,5,6,7-tetrahydro-pyrazolo[1,5-a]pyrimidine | HCl salt<br>$^1$H-NMR (CDCl$_3$) δ: 0.84 (6H, dt, J=14.4, 9.2 Hz), 1.68-2.24 (8H, m), 1.86 (6H, d, J=43.5 Hz), 3.50-3.60 (1H, m), 3.76-3.92 (1H, m), 4.14-4.27 (1H, m), 4.57 (2H, dd, J=33.9, 12.0 Hz), 4.58-4.68 (1H, m), 7.30-7.46 (10H, m), 7.79 (1H, bs). |
| 1111 | 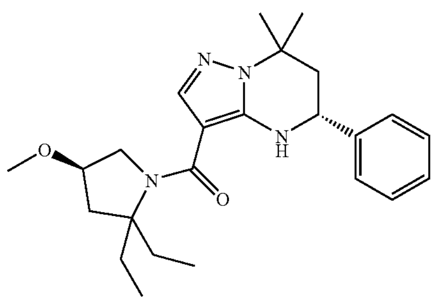 | (5R)-3-(((4R)-2,2-diethyl-4-methoxy-1-pyrrolidinyl)-carbonyl)-7,7-dimethyl-5-phenyl-4,5,6,7-tetrahydropyrazolo[1,5-a]pyrimidine | mp 148-150° C. |
| 1112 | 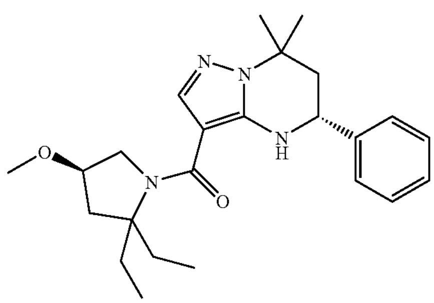 | (5R)-3-(((4R)-2,2-diethyl-4-methoxy-1-pyrrolidinyl)-carbonyl)-7,7-dimethyl-5-phenyl-4,5,6,7-tetrahydropyrazolo[1,5-a]pyrimidine | mp 148-150° C.<br>HCl salt |
| 1113 | 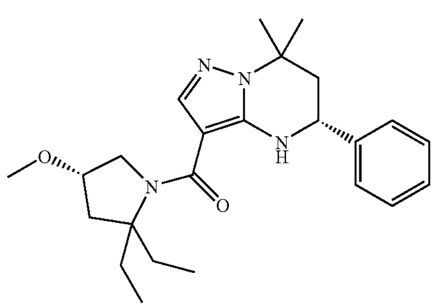 | (5R)-3-(((4S)-2,2-diethyl-4-methoxy-1-pyrrolidinyl)-carbonyl)-7,7-dimethyl-5-phenyl-4,5,6,7-tetrahydropyrazolo[1,5-a]pyrimidine | mp 122-124° C. |

TABLE 13-continued

| Example | Structure | Name | Physiological Data |
|---|---|---|---|
| 1114 | 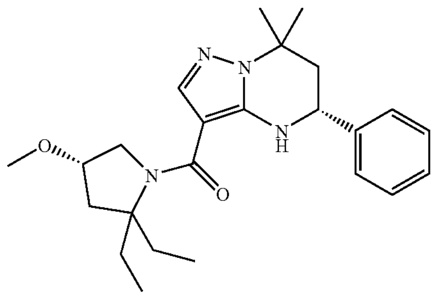 | (5R)-3-(((4S)-2,2-diethyl-4-methoxy-1-pyrrolidinyl)-carbonyl)-7,7-dimethyl-5-phenyl-4,5,6,7-tetrahydropyrazolo[1,5-a]pyrimidine | mp 122-124° C. HCl salt |
| 1115 | 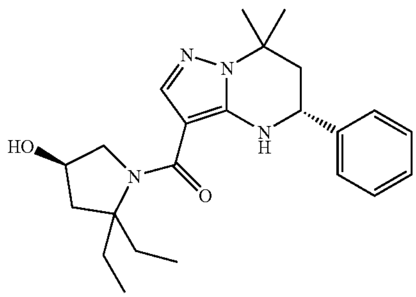 | (3R)-1-(((5R)-7,7-dimethyl-5-phenyl-4,5,6,7-tetrahydropyrazolo]1,5-a]pyrimidin-3-yl)carbonyl)-5,5-diethyl-3-pyrrolidinol | mp 250-252° C. |
| 1116 | 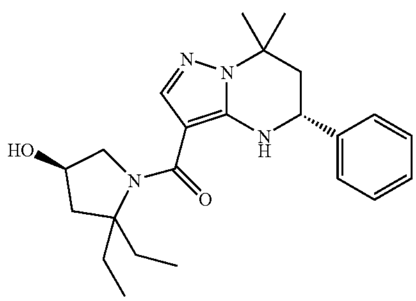 | (3R)-1-(((5R)-7,7-dimethyl-5-phenyl-4,5,6,7-tetrahydropyrazolo[1,5-a]pyrimidin-3-yl)carbonyl)-5,5-diethyl-3-pyrrolidinol | mp 250-252° C. HCl salt |
| 1117 | 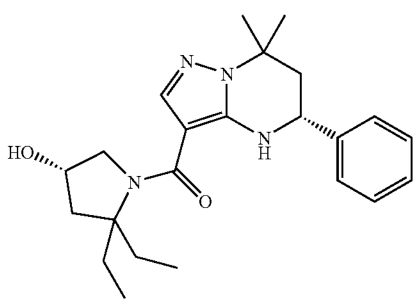 | (3S)-1-(((5R)-7,7-dimethyl-5-phenyl-4,5,6,7-tetrahydropyrazolo[1,5-a]pyrimidin-3-yl)carbonyl)-5,5-diethyl-3-pyrrolidinol | mp 249-251° C. |
| 1118 | 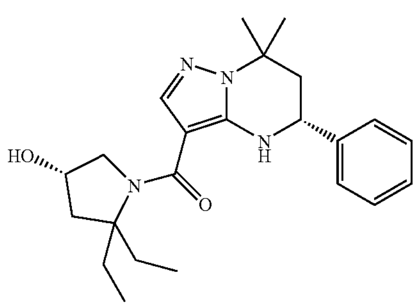 | (3S)-1-(((5R)-7,7-dimethyl-5-phenyl-4,5,6,7-tetrahydropyrazolo[1,5-a]pyrimidin-3-yl)carbonyl)-5,5-diethyl-3-pyrrolidinol | mp 247-249° C. HCl salt |

TABLE 13-continued

| Example | Structure | Name | Physiological Data |
|---|---|---|---|
| 1119 | 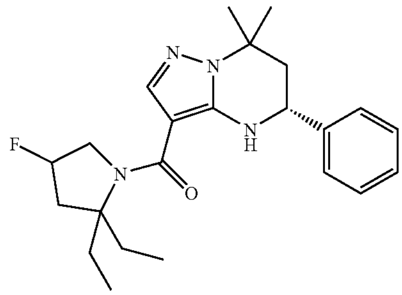 | (5R)-3-((2,2-diethyl-4-fluoro-1-pyrrolidinyl)carbonyl)-7,7-dimethyl-5-phenyl-4,5,6,7-tetrahydropyrazolo[1,5-a]pyrimidine | mp 210-212° C. more polar |
| 1120 | 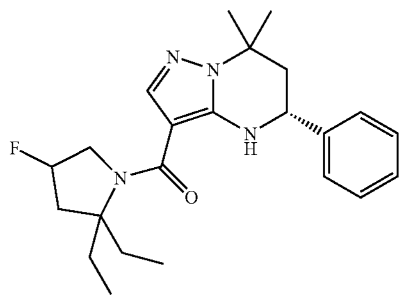 | | mp 209-211° C. HCl salt of Example 1119 |
| 1121 | 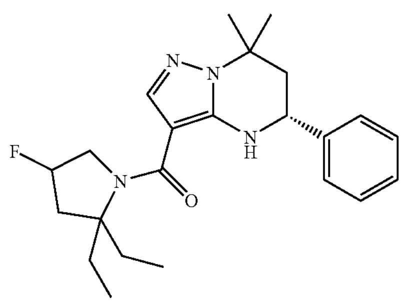 | (5R)-3-((2,2-diethyl-4-fluoro-1-pyrrolidinyl)carbonyl)-7,7-dimethyl-5-phenyl-4,5,6,7-tetrahydropyrazolo[1,5-a]pyrimidine | mp 216-218° C. less polar |
| 1122 | 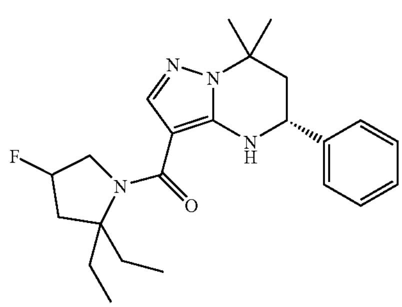 | | mp 216-218° C. HCl salt of Example 1121 |

EXAMPLE 435

N-(1-adamantyl)-7-ethyl-5-phenyl-7-(trifluoromethyl)-4,5,6,7-tetrahydropyrazolo[1,5-a]pyrimidine-3-carboxamide

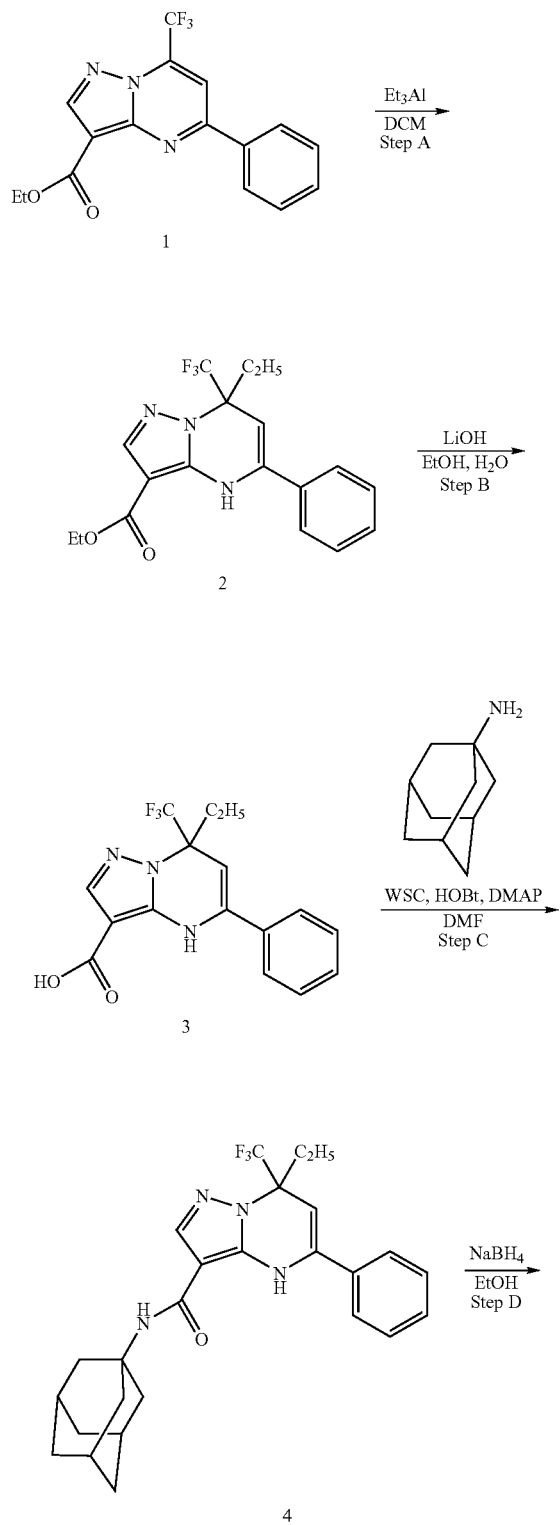

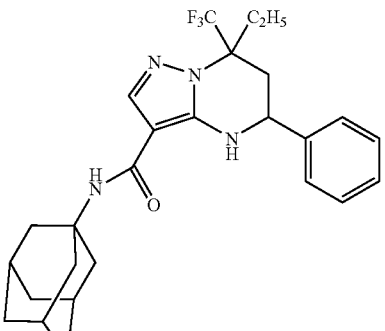

Step A: To a stirred solution of compound 1 (2.00 g, 6.00 mmol) in DCM (50 mL) was added triethylaluminium (2.0 M hexane solution, 18 mL, 36 mmol) at room temperature. After the mixture was stirred for 2 h, it was quenched with water, and extracted with AcOEt. The extract was successively washed with water and brine, dried over $MgSO_4$ and then concentrated in vacuo to give compound 2 (2.20 g, 100% yield) as yellow syrup. MS(ESI,m/z) 366 $(M+H)^+$.

Step B: A mixture of compound 2 (2.20 g, 6.00 mmol), LiOH (0.51 g, 12.15 mmol), EtOH (50 mL) and $H_2O$ (30 mL) was stirred at 70° C. for 12 h, concentrated in vacuo, diluted with aq.citric acid solution and extracted with AcOEt. The extract was successively washed with water, saturated $NaHCO_3$ solution and brine, dried over $MgSO_4$ and then concentrated to give compound 3 (2.00 g, 100%) as colorless crystals. MS(ESI,m/z) 352 $(M+H)^+$.

Step C: 1-Adamantylamine (0.72 g, 4.76 mmol) was added to a suspension of compound 3 (1.60 g, 4.74 mmol), WSC (0.91 g, 4.74 mmol), HOBt (0.64 g, 4.74 mmol) and DMAP (0.58 g, 4.75 mmol) in DMF (20 mL). The reaction mixture was stirred at 70° C. for 13 h and then concentrated in vacuo. The residue was chromatographed on silica gel with AcOEt/hexane (1/6) as an eluent to give compound 4 (0.71 g, 32%) as colorless crystals. MS(ESI,m/z) 472 $(M+H)^+$.

Step D: To a solution of 4 (0.58 g, 1.23 mmol) in EtOH was added $NaBH_4$ (0.2 g, 5.29 mmol) at room temperature. The whole was stirred at 60° C. for 3 h, concentrated in vacuo, diluted with water and extracted with AcOEt. The extract was successively washed with aq. $NaHCO_3$, water and brine, dried over $MgSO_4$ and then concentrated to give 0.43 g (74%) of compound 5 as colorless crystals. MS(ESI,m/z) 474 $(M+H)^+$.

Compounds of Examples 436, shown in the Table 5, were prepared in a manner similar to that described in Example 435.

TABLE 5

| Example | Structure | Name | Physical Data |
|---|---|---|---|
| 436 | 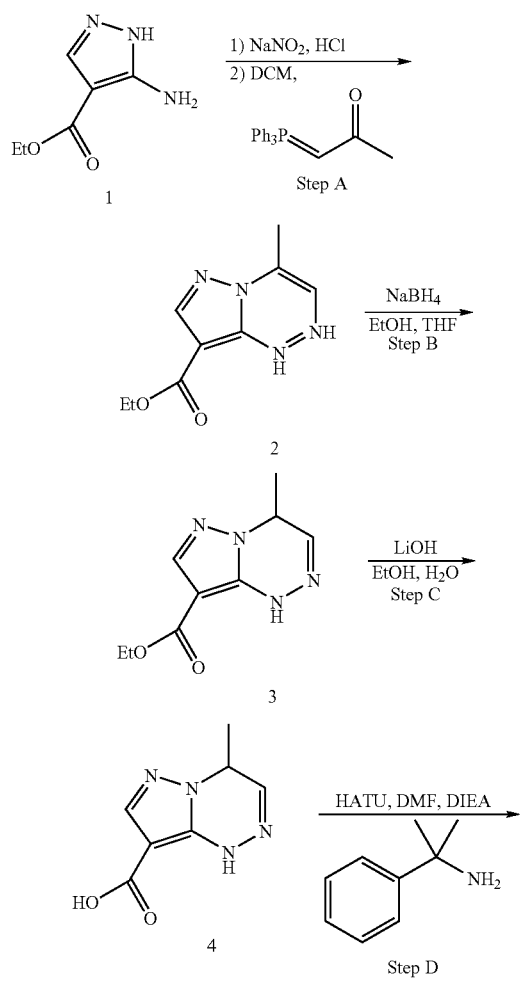 | N-(1-adamantyl)-7-methyl-5-phenyl-7-(trifluoromethyl)-4,5,6,7-tetrahydropyrazolo[1,5-a]pyrimidine-3-carboxamide | MS(ESI, m/z) 462 (M + H)+ |

EXAMPLE 437

2-cyclohexyl-4-methyl-N-(1-methyl-1-phenylethyl)-1,2,3,4-tetrahydropyrazolo[5,1-c][1,2,4]triazine-8-carboxamide

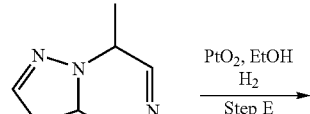

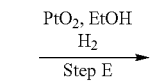

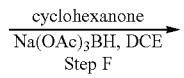

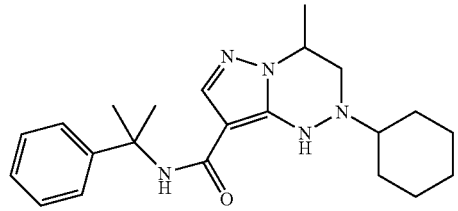

Step A: To a 250 mL round bottom flask equipped with magnetic stir bar and 2 addition funnels was added 1.0 g (6.44 mmol) of compound 1 by 3.5 ml of conc. hydrochloric acid and 7.0 ml of water. The solution was cooled to 0° C. and a solution containing 0.50 g (7.25 mmol) of sodium nitrite in 2 ml of water dropwise. After complete addition, the reaction was allowed to stir for 30 min. at 0° C., followed by the addition of 65 ml of dichloromethane and 35 ml of a saturated sodium bicarbonate solution while maintaining the reaction temperature below 10° C. A solution containing 2.05 g (6.44 mmol) of 1-triphenylphosphoroanylidene-2-propanone in 30 ml of dichloromethane was then added dropwise. After complete addition, the reaction was allowed to stir for 5 min., diluted with 50 ml of dichloromethane and washed with water. The organic phase was separate and the solvent removed under reduced pressure to afford 3.50 g (100%) of crude compound 2 which is taken on without further purification. MS Calcd.: 206. Found 207 (M+H).

Step B: To a solution containing the crude product from above in 30 ml of ethanol and 30 ml of THF under a nitrogen atmosphere was added 1.20 g (3.72 mmol) of sodium borohydride. The reaction was allowed to stir at room temperature for 30 min. The reaction was diluted with ethyl acetate and washed with water. The organic phase was dried over MgSO$_4$. Filtration, removal of solvent and purification of the residue via Biotage chromatography eluting with 70% AcOEt/hexanes gave 0.79 g (58.9%) of compound 3 as a pale yellow solid. MS Calcd.: 208. Found 209 (M+H).

Step C: A solution containing 0.54 g (2.59 mmol) of compound 3 and 0.18 g of LiOH (7.52 mmol) in 15 ml of ethanol and 10 ml of water was heated to 70° C. After 1.5 h, HPLC of reaction mixture indicated no starting material remaining. The ethanol was removed under reduced pressure and the residue acidified with 1N hydrochloric acid and extracted with ethyl acetate. The organic phase was dried over magnesium sulfate. Filtration and removal of solvent gave 0.48 g (92.2%) of compound 4. MS Calcd.: 180. Found 181 (M+H).

Step D: To a solution containing 2.80 g (15.54 mmol) of compound 4 in 150 ml of DMF under a nitrogen atmosphere was added 6.50 g (17.10 mmol) of HATU, 2.31 g (17.10 mmol) of cumyl amine and 2.98 ml (17.10 mmol) of diisopropylethylamine. The reaction was heated to 50° C. overnight, diluted with ethyl acetate and washed with water. The organic phase was dried over magnesium sulfate. Filtration, removal of solvent and purification of the residue via Biotage chromatography eluting with 60% AcOEt/hexanes gave 3.09 g (66.9%) of compound 5. MS Calcd.: 297; Found 298 (M+H).

Step E: To a Parr flask was added 1.11 g (3.90 mmol) of compound 5 and 75 ml of EtOH. The flask was purged with nitrogen and 0.30 g of platinum oxide added. The flask was evacuated and pressurized to 20 psig hydrogen (3×) then pressurized to 50 psig hydrogen and shaken for 1 h. After completion as determined by HPLC, the reaction was filtered through GF/F filter paper and the filtrate concentrated under reduced pressure to afford 1.1 g (100%) of compound 6. MS Calcd.: 299. Found 300 (M+H).

Step F: To a solution containing 0.43 g (1.44 mmol) of compound 6 in 40 ml of DCE under a nitrogen atmosphere was added 0.30 ml (2.89 mmol) of cyclohexanone followed by 0.90 g (4.25 mmol) of sodium triacetoxy borohydride. The reaction was allowed to stir at room temperature overnight. The reaction was diluted with dichloromethane and washed with saturated sodium bicarbonate solution. The organic phase was dried over MgSO$_4$. Filtration, removal of solvent and purification of the residue via Biotage chromatography eluting with 75% AcOEt/hexanes gave 0.35 g (63.7%) of compound 7. MS Calcd.: 381. Found 382 (M+H).

EXAMPLE 438

4-Methyl-N-(1-methyl-1-phenylethyl)-2-phenyl-1,2,3,4-tetrahydropyrazolo[5,1-c][1,2,4]triazine-8-carboxamide

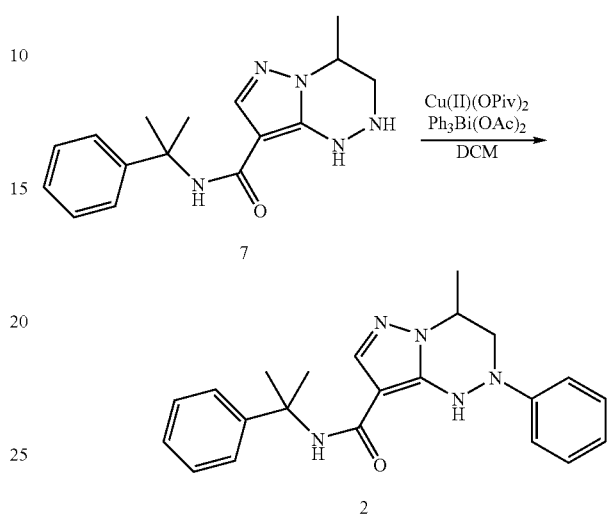

To a solution containing 0.20 g (0.71 mmol) of compound 1 in 25 ml of DCM under a nitrogen atmosphere at −78° C. was added 0.36 g (0.64 mmol) of triphenylbismuth diacetate followed by 0.02 g (0.075 mmole) of copper (II) dipivalate. The reaction was allowed to warm to 0° C. over 1.5 h. The reaction was diluted with dichloromethane and washed with saturate sodium bicarbonate. The organic phase was dried over magnesium sulfate. Filtration, removal of solvent and purification of the residue via Biotage chromatography eluting with 70% AcOEt/hexanes gave 0.025 g (9.4%) of compound 2. MS Calcd.: 375. Found 376 (M+H).

EXAMPLE 1123

1-(7,7-Dimethyl-5-phenyl-4,5,6,7-tetrahydropyrazolo[1,5-a]pyrimidin-3-yl)-2-methyl-2-(4-methylphenyl)-1-propanone

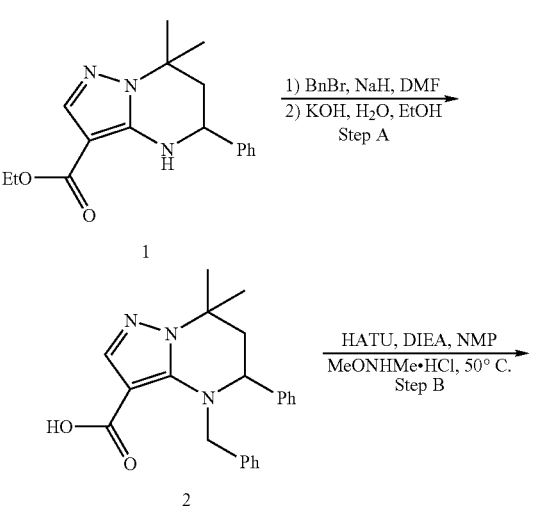

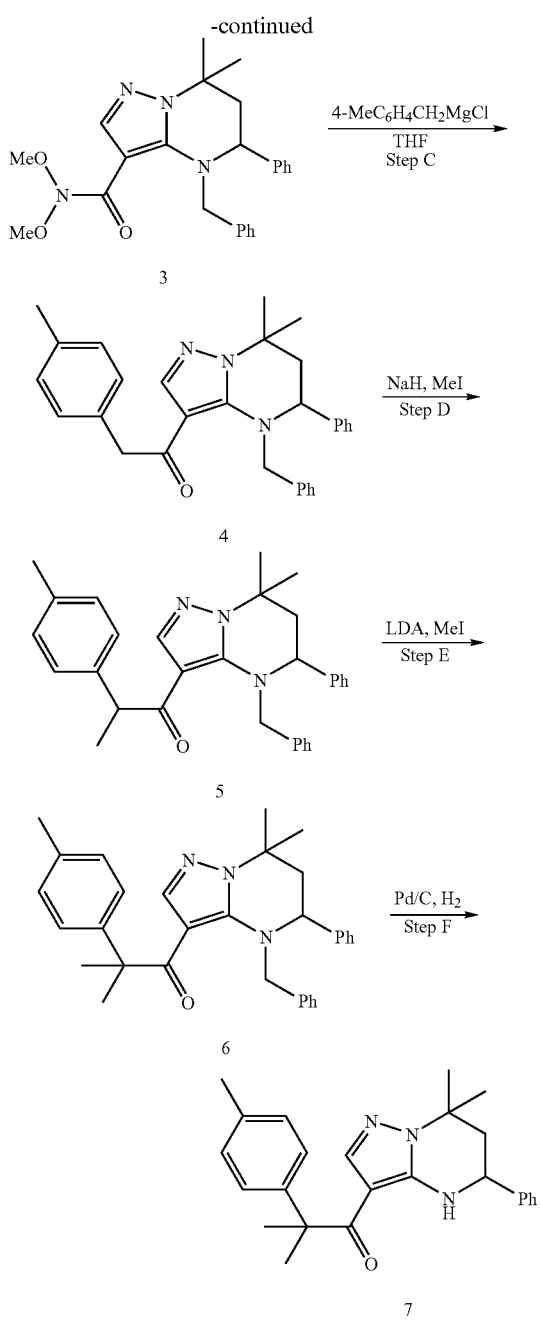

Step A 4-Benzyl-7,7-dimethyl-5-phenyl-4,5,6,7-tetrahydro-pyrazolo[1,5-a]pyrimidine-3-carboxylic acid (2): To a 100 mL round bottom flask equipped with a magnetic stir bar was added 1.80 g (6.01 mmol) of 7,7-dimethyl-5-phenyl-4,5,6,7-tetrahydro-pyrazolo[1,5-a]pyrimidine-3-carboxylic acid ethyl ester, 30 mL of DMF and 0.786 mL (6.61 mmol) of benzyl bromide, followed by 0.265 g (6.6 mmol) of sodium hydride (60% dispersion in mineral oil) which was added in several portions. After 2 h, the reaction was quenched with water and the product was extracted with AcOEt. The combined organic layers were washed with brine, dried over sodium sulfate, filtered and concentrated to give the crude N-benzylated ester as a golden colored oil. The crude ester was dissolved in 15 mL of ethanol and 2.5 mL of 6 N potassium hydroxide was added. The solution was then heated to 70° C. for 18 h at which time no starting material could be detected by HPLC analysis. The crude reaction mixture was concentrated in vacuo and diluted with water. The aqueous solution was acidified with 6 N HCl and the resulting cream-colored precipitate was collected by filtration. The crude acid thus isolated was dissolved in AcOEt, dried over sodium sulfate, filtered and concentrated to a cream colored powder. The resulting acid was washed with several portions of hexanes and dried in vacuo to give 1.95 g (90%) of the title compound as an off white powder. $^1$H NMR (DMSO-$d_6$) δ 1.10 (s, 3H), 1.40 (s, 3H), 1.98-2.16 (m, 2H), 3.71 (d, J=15.4 Hz, 1H), 4.36 (dd, J=4.5, 11.5 Hz, 1H), 5.81 (d, J=15.6 Hz), 6.97 (dd, J=1.4, 7.2 Hz, 2H), 7.26-7.45 (m, 7H), 7.67 (s, 1H), 11.81 (s, 1H). MS Calcd.: 361. Found: 344 (M-OH).

Step B

4-Benzyl-7,7-dimethyl-5-phenyl-4,5,6,7-tetrahydropyrazolo[1,5-a]pyrimidine-3-carboxylic acid methoxy-methyl-amide (3): To a 5 mL NMP solution containing 0.72 g (1.99 mmol) of 2 was added 0.91 g (2.39 mmol) of O-7-azabenzotriazolo-1-yl)-N,N,N',N'-tetramethyluroniumhexafluorophosphate (HATU) and 0.416 mL (2.39 mmol) of diisopropylethylamine. After stirring for 30 min, 0.233 g (2.39 mmol) of O,N-dimethyl-hydroxylamine hydrochloride was added and the reaction heated to 50° C. After 1 h, the reaction mixture was poured into water and extracted with AcOEt. The combined organic layers were washed with brine, dried over sodium sulfate, filtered and concentrated in vacuo to give a crude oil. Purification of this oil by flash chromatography eluting with a 60 to 50% hexanes/AcOEt gradient gave 0.65 g (81%) of the title compound as a light golden colored solid. $^1$H NMR (CDCl$_3$) δ 1.37 (s, 3H), 1.56 (s, 3H), 2.06-2.16 (m, 2H), 3.25 (s, 3H), 3.49 (s, 3H), 3.90 (d, J=16.0 Hz, 1H), 4.45 (dd, J=5.1, 11.3 Hz, 1H), 5.06 (d, J=16.2 Hz, 1H), 6.98 (dd, J=1.8, 6.1 Hz, 2H), 7.20-7.24 (m, 3H), 7.30-7.34 (m, 1H), 7.37-7.41 (m, 4H), 7.74 (s, 1H). MS Calcd.: 404. Found: 405 (M+H).

Step C 1-(4-Benzyl-7,7-dimethyl-5-phenyl-4,5,6,7-tetrahydro-pyrazolo[1,5-a]pyrimidin-3-yl)-2-(4-methylphenyl)ethanone (4): To 0.65 g (1.61 mmol) of 3 dissolved in 20 mL of THF was added 6.4 mL (3.2 mmol) of a 0.5 M solution of 4-methylbenzylmagnesium chloride in THF via syringe over 10 min. After stirring at room temperature for 1 h, the reaction was quenched by addition of approximately 2 mL of saturated aqueous ammonium chloride. The reaction was then diluted with AcOEt and dried over sodium sulfate. Filtering the solution through a short plug of silica gel and concentrating in vacuo provided the crude product as an oil. Purification of this oil by flash chromatography eluting with 75% hexanes/AcOEt gave 0.64 g (89%) of the title compound as a white foam. MS Calcd.: 449. Found: 450 (M+H).

Step D 1-(4-Benzyl-7,7-dimethyl-5-phenyl-4,5,6,7-tetrahydro-pyrazolo[1,5-a]pyrimidin-3-yl)-2-(4-methylphenyl)-1-propanone (5): To 0.64 g (1.42 mmol) of 4 dissolved in 10 mL of THF was added 0.177 mL (2.85 mmol) of iodomethane followed by 0.11 g (2.8 mmol) of sodium hydride (60% dispersion in mineral oil). After stirring at room temperature for 2 h, the reaction was quenched by addition of approximately 2 mL of saturated aqueous ammonium chloride. The reaction was then diluted with AcOEt and dried over sodium sulfate. Filtering the solution through a short plug of silica gel and concentrating in vacuo provided the crude product. Purification by flash chromatography eluting with 90% hexanes/ethyl acetate gave 0.42 g (64%) of the title compound as a cream colored powder. MS Calcd.: 463. Found: 464 (M+H).

Step E 1-(4-Benzyl-7,7-dimethyl-5-phenyl-4,5,6,7-tetrahydro-pyrazolo[1,5-a]pyrimidin-3-yl)-2-methyl-2-(4-methylphenyl)-1-propanone (6): To 0.110 mL (0.785 mmol) of diisopropyl amine dissolved in 5 mL of THF at −78° C. was added 0.314 mL (0.785 mmol) of a 2.5 M solution of n-butyllithium in hexanes. After stirring for 30 min, 0.28 g (0.604 mmol) of 5 was added as a solution in 1 mL of THF. The reaction was stirred at room temperature for 1 h before 0.049 mL (0.79 mmol) of iodomethane was added as a solution in 1 mL of THF. After 1 h the reaction was quenched by addition of approximately 0.5 mL of saturated aqueous ammonium chloride, diluted with AcOEt and dried over sodium sulfate. Filtering the solution through a short plug of silica gel and concentrating in vacuo provided the crude product. Purification by flash chromatography eluting with 90% hexanes/AcOEt gave 0.067 g (23%) of the title compound as an off white solid. MS Calcd.: 477. Found: 478 (M+H).

Step F 1-(7,7-Dimethyl-5-phenyl-4,5,6,7-tetrahydropyrazolo[1,5-a]pyrimidin-3-yl)-2-methyl-2-(4-methylphenyl)-1-propanone (7): To 0.060 g (0.126 mmol) of 6 dissolved in 4 mL of 1:1 THF:ethanol was added 0.080 g of 10% palladium on carbon. The reaction vessel was capped with a rubber septum and charged with hydrogen via a balloon. After 1 h, the catalyst was removed via filtration and the filtrate concentrated to a cream colored solid. Purification by flash chromatography eluting with 90% hexanes/ethyl acetate gave 0.041 g (84%) of the title compound as a white solid. $^1$H NMR (CDCl$_3$) δ 1.49 (s, 3H), 1.54 (s, 9H), 2.04-2.11 (m, 2H), 2.32 (s, 3H), 4.63 (dd, J=4.1, 10.7 Hz, 1H), 6.66 (s, 1H), 7.12-7.26 (m, 5H), 7.31-7.44 (m, 5H). MS Calcd.: 387; Found: 388 (M+H).

Compounds of Examples 1124-1131 shown in the Table 14, were prepared in a manner similar to that described in Example 1123.

TABLE 14

| | | | |
|---|---|---|---|
| 1124 | | 2-(1,1'-biphenyl-4-yl)-1-(7,7-dimethyl-5-phenyl-4,5,6,7-tetrahydropyrazolo[1,5-a]pyrimidin-3-yl)ethanone | MS(ESI, m/z) 422 (M + H)+ |
| 1125 | | 1-(4-benzyl-7,7-dimethy-5-phenyl-4,5,6,7-tetrahydropyrazolo[1,5-a]pyrimidin-3-yl)-2-phenylethanone | MS(ESI, m/z) 436 (M + H)+ |
| 1126 | | 1-(4-benzyl-7,7-dimethyl-5-phenyl-4,5,6,7-tetrahydropyrazolo[1,5-a]pyrimidin-3-yl)-2-phenyl-1-propanone | MS(ESI, m/z) 450 (M + H)+ |

TABLE 14-continued

| | | | |
|---|---|---|---|
| 1127 | 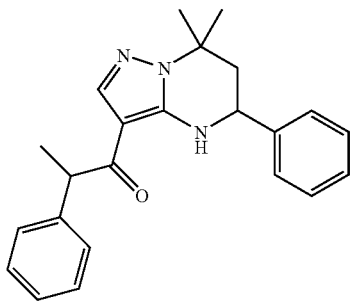 | 1-(7,7-dimethyl-5-phenyl-4,5,6,7-tetrahydropyrazolo[1,5-a]pyrimidin-3-yl)-2-phenyl-1-propanone | MS(ESI, m/z) 360 (M + H)+ |
| 1128 | 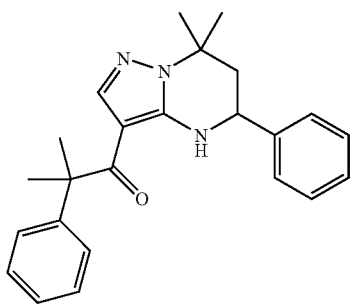 | (1-(7,7-dimethyl-5-phenyl-4,5,6,7-tetrahydropyrazolo[1,5-a]pyrimidin-3-yl)-2-methyl-2-phenyl-1-propanone | MS(ESI, m/z) 374 (M + H)+ |
| 1129 | 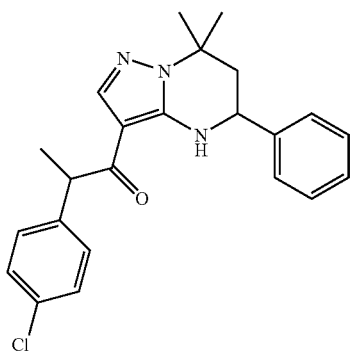 | 2-(4-chlorophenyl)-1-(7,7-dimethyl-5-phenyl-4,5,6,7-tetrahydropyrazolo[1,5-a]pyrimidin-3-yl)-1-propanone | MS(ESI, m/z) 395 (M + H)+ |
| 1130 | 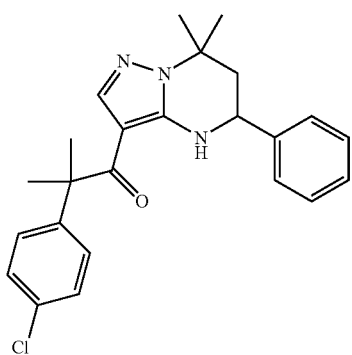 | 2-(4-chlorophenyl)-1-(7,7-dimethyl-5-phenyl-4,5,6,7-tetrahydropyrazolo[1,5-a]pyrimidin-3-yl)-2-methyl-1-propanone | MS(ESI, m/z) 409 (M + H)+ |

TABLE 14-continued

| 1131 | 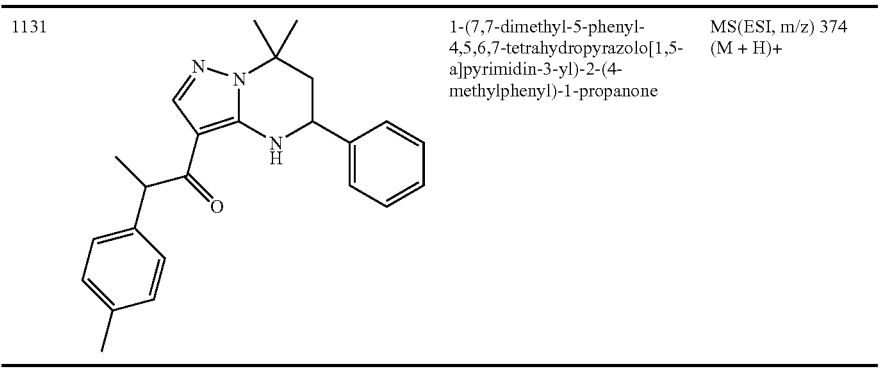 | 1-(7,7-dimethyl-5-phenyl-4,5,6,7-tetrahydropyrazolo[1,5-a]pyrimidin-3-yl)-2-(4-methylphenyl)-1-propanone | MS(ESI, m/z) 374 (M + H)+ |

EXAMPLE 1132

7,7-Dimethyl-3-((1-methyl-1-(4-methylphenyl)ethyl)sulfonyl)-5-phenyl-4,5,6,7-tetrahydropyrazolo[1,5-a]pyrimidine

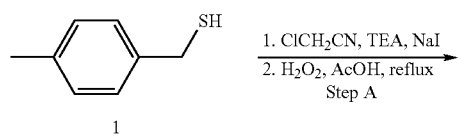
1
1. ClCH₂CN, TEA, NaI
2. H₂O₂, AcOH, reflux
Step A

2
TEOF, Ac₂O, reflux
Step B

3
1. N₂H₄·H₂O, EtOH
2. PhCOCH=CMe₂, TFA MeOCH₂CH₂OH, 130° C.
Step C

4
NaH, BnBr
Step E

5

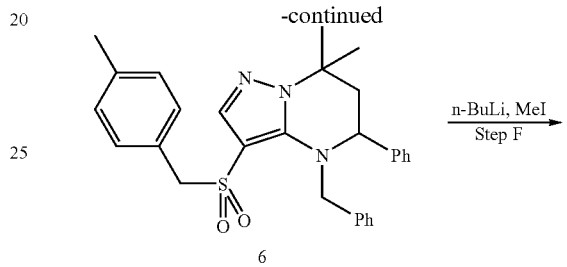
6
n-BuLi, MeI
Step F

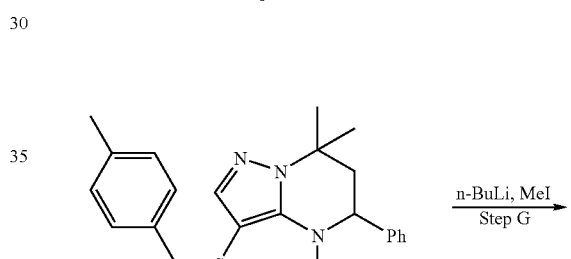
7
n-BuLi, MeI
Step G

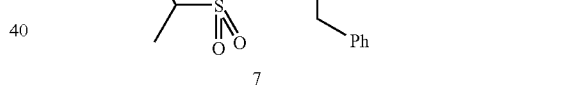
Pd/C, H₂
Step D

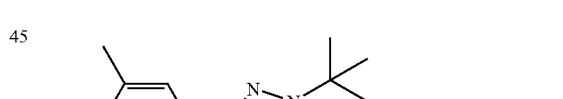
Pd/C, H₂
Step H

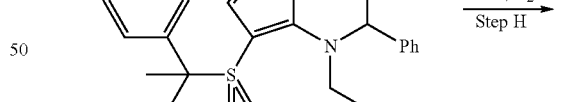
8

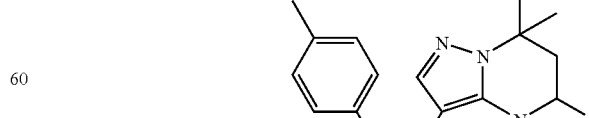

9

Step A p-Tolylmethanesulfonylacetonitrile (2): To a 10 mL ethanol solution containing 4.1 g (30 mmol) of p-tolylmethanethiol at 0° C. was added 4.1 mL (30 mmol) of triethylamine and 4.4 g (30 mmol) of sodium iodide. After allowing the reaction to stir at room temperature for approximately 30 min, the reaction cooled to 0° C. and 1.9 mL (30 mmol) of chloroacetonitrile was added dropwise as a solution in 10 mL of ethanol. The reaction was allowed to reach room temperature overnight and was subsequently filtered and concentrated. The concentrate was partitioned between water and ether and separated. The ether layer was washed successively with 2 N sodium carbonate and brine and was then concentrated to an oil that solidified. The crude solid was then dissolved in 90 mL of glacial acetic acid, treated with 12.1 mL (107 mmol) of 30% hydrogen peroxide and heated to 100° C. The reaction was cooled to room temperature after 3 h at which time a white solid precipitated. The precipitate was collected via filtration, washed with glacial acetic acid and dried in vacuo to give 6.4 g (69%) of the title compound as a white solid. $^1$H NMR (CDCl$_3$) δ 2.39 (s, 3H), 3.70 (s, 2H), 4.48 (s, 2H), 7.32 (dd, J=7.3, 40.2 Hz, 4H).

Step B

3-Ethoxy-2-p-tolylmethanesulfonylacrylonitrile (3): To a solution of 4.4 g (21 mmol) of 2 in 17.5 mL (105 mmol) of triethylorthoformate was added 9.9 mL (105 mmol) of acetic anhydride. The resulting solution was heated to reflux for 18 h before being concentrated to a solid. Recrystallization from AcOEt-hexanes gave 5.0 g (90%) of the title compound as a white solid.

$^1$H NMR (CDCl$_3$) δ 1.29 (t, J=7.0 Hz, 3H), 2.36 (s, 3H), 4.19 (q, J=7.0 Hz, 2H), 4.35 (s, 2H), 7.23 (dd, J=8.0, 19.9 Hz) 7.37 (s, 1H).

Step C 7,7-Dimethyl-3-(4-methylbenzyl)sulfonyl)-5-phenyl-4,7-dihydropyrazolo[1,5-a]pyrimidine (4): A slurry of 1.9 g (7.2 mmol) of 3 in 25 mL of ethanol was treated with 0.38 mL (7.9 mmol) of hydrazine monohydrate and heated to reflux for 3 h. The reaction was concentrated in vacuo to give crude 4-p-tolylmethanesulfonyl-2H-pyrazol-3-ylamine as a tan solid. The crude pyrazole, 1.3 g (7.9 mmol) of 3-methyl-1-phenyl-but-2-en-1-one and 2.8 mL (36 mmol) of trifluoroacetic acid was dissolved in 25 mL of 2-methoxyethanol and heated to reflux for 3 days. The reaction was then cooled to room temperature, concentrated in vacuo and dissolved in AcOEt. This solution was washed successively with saturated sodium bicarbonate, water and brine before being dried over sodium sulfate. The solution was filtered, concentrated in vacuo and the resulting crude material was purified by flash chromatography eluting with a 75 to 33% hexanes/AcOEt gradient to give 1.25 g (44%) of the title compound as a powder. $^1$H NMR (CDCl$_3$) δ 1.67 (s, 6H), 2.13 (s, 3H), 4.26 (s, 2H), 4.81 (d, J=2.0 Hz, 1H), 6.39 (s, 1H), 7.05 (dd, J=8.0, 18.5 Hz, 4H), 7.20 (dd, J=3.7, 7.4 Hz, 2H), 7.36-7.39 (m, 3H), 7.52 (s, 1H). MS Calcd.: 393. Found: 394 (M+H).

Step D 7,7-Dimethyl-3-((4-methylbenzyl)sulfonyl)-5-phenyl-4,5,6,7-tetrahydropyrazolo[1,5-a]pyrimidine (5): To 0.500 g (1.27 mmol) of 4 dissolved in 8 mL of 1:1 THF:ethanol was added 0.50 g of 10% palladium on carbon. The reaction vessel was capped with a rubber septum and charged with hydrogen via a balloon. After 2 days at room temperature, the catalyst was removed via filtration and the filtrate concentrated to a solid. Purification by flash chromatography eluting with a 75 to 33% hexanes/AcOEt gradient gave 0.385 g (77%) of the title compound as a white solid. $^1$H NMR (CDCl$_3$) δ 1.49 (s, 3H), 1.59 (s, 3H), 1.83-1.97 (m, 2H), 2.37 (s, 3H), 4.09-4.24 (m, 3H), 5.03 (s, 1H), 7.06-7.13 (m, 6H), 7.30-7.39 (m, 3H), 7.45 (s, 1H). MS Calcd.: 395. Found: 396 (M+H).

Step E

4-Benzyl-7,7-dimethyl-3-((4-methylbenzyl)sulfonyl)-5-phenyl-4,5,6,7-tetrahydropyrazolo[1,5-a]pyrimidine (6): To a solution of 0.34 g (0.86 mmol) of 5 in 10 mL of THF at 0° C. was added 0.128 mL (1.07 mmol) of benzyl bromide followed by 0.034 g (0.86 mmol) of sodium hydride (60% dispersion in mineral oil). The reaction was allowed to warm to room temperature after 30 min and stirred for an additional 30 min before being quenched with water. The quenched reaction was diluted with five volumes of water and extracted with AcOEt. The combined organic layers were washed with brine, dried over sodium sulfate, filtered and concentrated in vacuo. The crude product was purified by flash chromatography eluting with 70% hexanes/AcOEt to give 0.39 g (93%) of the title compound as a white solid. $^1$H NMR (CDCl$_3$) δ 1.27 (s, 3H), 1.52 (s, 3H), 1.93-2.05 (m, 2H), 2.27 (s, 3H), 3.83 (d, J=15.8 Hz, 1H), 4.18-4.30 (m, 3H), 5.51 (d, J=15.8 Hz, 1H), 6.98-7.00 (m, 2H), 7.09 (dd, J=8.2, 12.1 Hz, 4H), 7.17 (d, J=6.8 Hz, 2H), 7.26-7.30 (m, 3H), 7.32-7.40 (m, 3H), 7.47 (s, 1H)

Step F

4-Benzyl-7,7-dimethyl-3-((1-(4-methylphenyl)ethyl)sulfonyl)-5-phenyl-4,5,6,7-tetrahydropyrazolo[1,5-a]pyrimidine (7): A solution of 0.23 g (0.47 mmol) of 6 in 4 mL of THF was cooled to 0° C. and treated with 0.24 mL (0.59 mmol) of n-butyllithium (2.5 M solution in hexanes) and allowed to reach room temperature for 20 min. After cooling the reaction to 0° C., 0.103 mL (1.66 mmol) of iodomethane was added as a solution in 2 mL of THF. The reaction was allowed to warm to room temperature for 30 min at which time the reaction was quenched with a few drops of saturated ammonium chloride. The reaction was dried over sodium sulfate, filtered and concentrated in vacuo. The residue was purified by flash chromatography eluting with 80% hexanes/AcOEt to give 0.14 g (60%) of the title compound as a white solid. MS Calcd.: 499. Found: 500 (M+H).

Step G

4-Benzyl-7,7-dimethyl-3-((1-methyl-1-(4-methylphenyl)ethyl)sulfonyl)-5-phenyl-4,5,6,7-tetrahydropyrazolo[1,5-a]pyrimidine (8): Using the method described for the synthesis of 7, the title compound was prepared in 51% isolated yield. MS Calcd.: 513. Found: 514 (M+H).

Step H 7,7-Dimethyl-3-((1-methyl-1-(4-methylphenyl)ethyl)sulfonyl)-5-phenyl-4,5,6,7-tetrahydropyrazolo[1,5-a]pyrimidine (9): To 0.075 g (0.146 mmol) of 8 dissolved in 6 mL of 1:1 THF:ethanol was added 0.10 g of 10% palladium on carbon. The reaction vessel was capped with a rubber septum and charged with hydrogen via a balloon. After 2 h at room temperature, the catalyst was removed via filtration and the filtrate concentrated to give 0.056 g (91%) of the title compound as a white solid. MS Calcd.: 423. Found: 424 (M+H).

Compounds of Examples 1133-1134, shown in the Table 15, were prepared in a manner similar to that described in Example 1132.

TABLE 15

| | | | |
|---|---|---|---|
| 1133 | 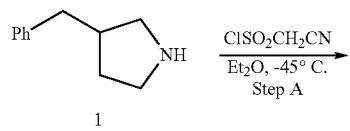 | 3-((1-(4-chlorophenyl)ethyl)sulfonyl)-7,7-dimethyl-5-phenyl-4,5,6,7-tetrahydropyrazolo[1,5-a]pyrimidine | MS(ESI, m/z) 431 (M + H)+ |
| 1134 | | 3-((1-(4-chlorophenyl)-1-methylethyl)sulfonyl)-7,7-dimethyl-5-phenyl-4,5,6,7-tetrahydropyrazolo[1,5-a]pyrimidine | MS(ESI, m/z) 445 (M + H)+ |

EXAMPLE 1135

3-(3-Benzylpyrrolidine-1-sulfonyl)-7,7-dimethyl-5-phenyl-4,5,6,7-tetrahydropyrazolo[1,5-a]pyrimidine

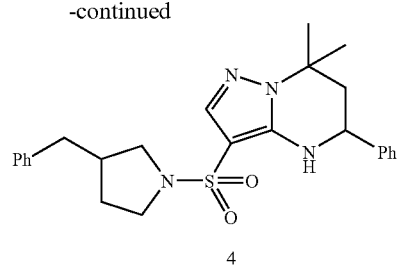

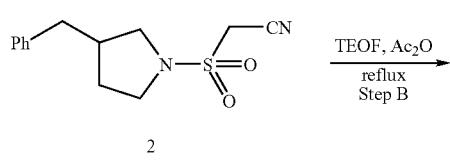

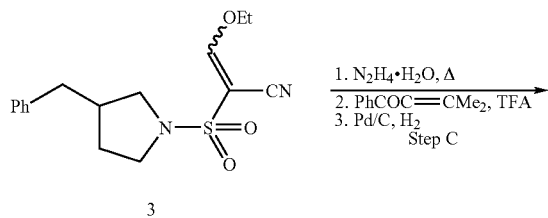

Step A (3-Benzylpyrrolidine-1-sulfonyl)acetonitrile (2): To a 20 mL ether solution containing 1.34 g (8.31 mmol) of 3-benzylpyrrolidine cooled to −45° C. was added 0.61 g (4.4 mmol) of 2-cyanoethanesulfonyl chloride as a solution in 10 mL of ether. The reaction was allowed to warm to room temperature and was stirred for 24 h over which time an oil formed on the flask wall. The ether solution was poured away from the oil and filtered through a short plug of silica gel. The filtrate thus obtained was concentrated in vacuo to give a solid that was purified by flash chromatography eluting with 75% hexanes/AcOEt to give 1.25 g (44%) of the title compound as a wax.

$^1$H NMR (CDCl$_3$) δ 1.73-1.83 (m, 1H), 2.08-2.15 (m, 1H), 2.57-2.67 (m, 1H), 2.71-2.79 (m, 2H), 3.21 (dd, J=8.2, 9.7, Hz, 1H), 3.49-3.55 (m, 1H), 3.63 (dd, J=7.0, 9.4 Hz, 1H), 3.69-3.74 (m, 1H), 3.95 (s, 2H), 7.16 (d, J=7.4 Hz, 2H), 7.21-7.33 (m, 3H).

Step B 2-(3-Benzylpyrrolidine-1-sulfonyl)-3-ethoxyacrylonitrile (3): To a solution of 0.14 g (0.53 mmol) of 2 in 0.43 mL (2.6 mmol) of triethylorthoformate was added 0.25 mL (2.6 mmol) of acetic anhydride. The resulting solution was heated to reflux for 4 h before being concentrated to an oil. The crude oil thus obtained was purified by flash chromatography eluting with 75% hexanes/AcOEt to give 0.079 g (46%) of the title compound as a yellow oil. $^1$H NMR (CDCl$_3$) δ 1.42 (t, J=7.2 Hz, 3H), 1.67-1.77 (m, 1H), 2.01-2.09 (m, 1H), 2.53-2.62 (m, 1H), 2.71 (d, J=7.4 Hz, 2H), 3.05 (dd, J=8.4, 9.8 Hz, 1H), 3.35-3.41 (m, 1H), 3.48 (dd, J=7.0, 9.5 Hz, 1H), 3.53-3.59 (m, 1H), 4.31 (q, J=7.2 Hz, 2H), 7.15-7.17 (m, 2H), 7.19-7.23 (m, 1H), 7.26-7.31 (m, 2H), 7.76 (s, 1H).

Step C 3-(3-Benzylpyrrolidine-1-sulfonyl)-7,7-dimethyl-5-phenyl-4,5,6,7-tetrahydropyrazolo[1,5-a]pyrimidine (4): A 2 mL ethanol solution containing 0.079 g (0.247 mmol) of 3 was treated with 0.013 mL (0.27 mmol) of hydrazine monohydrate and heated to reflux for 5 h. The reaction was concentrated in vacuo to give crude 4-(3-benzylpyrrolidine-1-sulfonyl)-2H-pyrazol-3-ylamine. The crude pyrazole thus obtained was dissolved in 2 mL of 2-methoxyethanol containing 0.044 g (0.27 mmol) of 3-methyl-1-phenyl-but-2-en-1-one and 0.038 mL (0.49 mmol) of trifluoroacetic acid was added. The mixture was refluxed for three days then concentrated and purified by flash chromatography eluting with 60% hexanes/AcOEt to give 3-(3-benzylpyrrolidine-1-sulfonyl)-7,7-dimethyl-5-phenyl-4,7-dihydropyrazolo[1,5-a]pyrimidine that was found to be only 90% pure by HPLC analysis. This material was then dissolved in 1 mL of 1:1 THF:ethanol and 0.010 g of 10% palladium on carbon. The reaction vessel was capped with a rubber septum and charged with hydrogen via a balloon. After 90 min at room temperature, the catalyst was removed via filtration and the filtrate concentrated to an oil. Purification by flash chromatography eluting with 75% hexanes/AcOEt gave 0.024 g (20% from 3) of the title compound as a light yellow oil. $^1$H NMR (CDCl$_3$) δ 1.55-1.66 (m, 7H), 1.94-2.03 (m, 1H), 2.08-2.16 (m, 2H), 2.37-2.50 (m, 1H), 2.58-2.70 (m, 2H), 2.90-2.97 (m, 1H), 3.18-3.27 (m, 1H), 3.31-3.42 (m, 2H), 4.53-4.60 (m, 1H), 5.71 (s, 1H), 7.11-7.14 (m, 2H), 7.19-7.23 (m, 1H), 7.26-7.40 (m, 7H), 7.53 (s, 1H). MS Calcd.: 450. Found: 451 (M+H).

EXAMPLE 1136

4,4-Dimethyl-8-[5-(1-methyl-1-phenyl-ethyl)-[1,3,4] oxadiazol-2-yl]-2-phenyl-1,2,3,4-tetrahydropyrrolo [1,2-a]pyrimidine

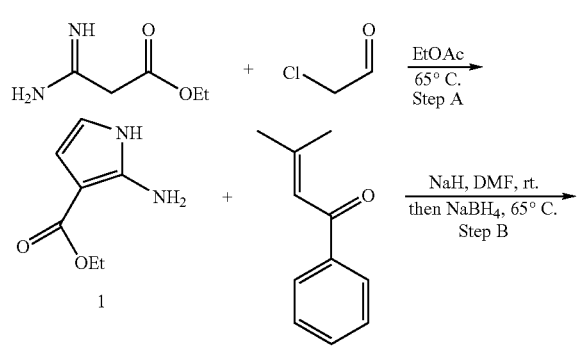

Step A

2-Amino-1H-pyrrole-3-carboxylic acid ethyl ester (1): Carbamimidoyl-acetic acid ethyl ester (3.357 g, 25.8 mmol) was dissolved in AcOEt (20 mL). Chloroacetaldehyde (50% solution in water, 1.8 mL, 28.7 mmol) was added rapidly at room temperature. The solution stirred for 2 minutes until a precipitant formed. The solution was then brought to 65° C. for 0.5 h. The reaction mixture was then cooled and flash chromatographed with AcOEt. Product containing fractions were concentrated to give the desired material as a green solid. 0.68 g obtained, 31% yield. $^1$H NMR (400 MHz, CDCl$_3$) δ 1.32 (t, J=7.2 Hz, 3H), 4.24 (q, J=7.0 Hz, 2H), 5.08 (brs, 2H), 6.10-6.13 (m, 1H), 6.25 (t, J=3.12, 1 Hz), 8.60 (brs, 1H); MS Calcd.: 154. Found 155 (M+H).

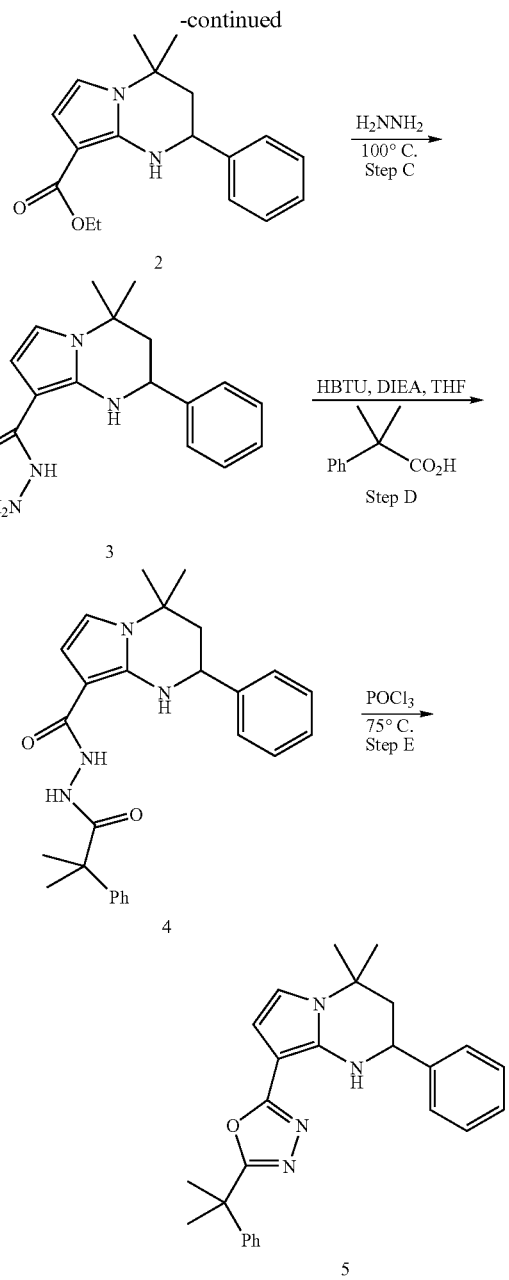

Step B 4,4-Dimethyl-2-phenyl-1,2,3,4-tetrahydro-pyrrolo[1,2-a]pyrimidine-8-carboxylic acid ethyl ester (2): Compound 1 (0.68 g, 4.41 mmol) was dissolved in DMF (5 mL). NaH (60% in mineral oil, 0.19 g, 4.7 mmol) was added at room temperature affording rapid gas evolution. The reaction stirred for 0.5 h upon which 3-methyl-1-phenyl-but-2-en-1-one (0.50 g, 3.15 mmol) was added. The reaction stirred for 0.5 h upon which EtOH (5 mL) and NaBH$_4$ (1.19 g) were added. The solution was brought to 60° C. for 0.5 h. and then cooled to room temperature. The solution was quenched with water, extracted with Et$_2$O (3 times), dried (Na$_2$SO$_4$) and concentrated. Flash chromatography (10% AcOEt) to give the desired product as a tan solid (0.60 g, 63% yield). MS Calcd.: 298. Found 299 (M+H).

Step C 4,4-Dimethyl-2-phenyl-1,2,3,4-tetrahydro-pyrrolo[1,2,-a]pyrimidine-8-carboxylic acid hydrazide (3): Compound 2 (0.210 g, was diluted with anhydrous hydrazine (5 mL) and heated to 100° C. for 3 days. The reaction was then cooled and diluted with water. The solution was extracted with AcOEt (3 times), dried (Na$_2$SO$_4$) and concentrated. The residue was flash chromatographed (10% MeOH/AcOEt) to give the desired material. 0.12 g, 60% yield). $^1$H NMR (400 MHz, CDCl$_3$) δ 1.54 (s, 6H), 1.99-2.13 (m, 2H), 3.89 (brs, 2H), 4.64 (dd, J=3.5, 11.7 Hz, 1H), 6.02 (d, J=3.9 Hz), 6.22 (d, J=3.9 Hz, 1H), 6.55 (brs, 1H), 6.74 (brs, 1H), 7.31-7.46 (m, 5H). MS Calcd.: 284. Found 285 (M+H).

Step D 4,4-Dimethyl-2-phenyl-1,2,3,4-tetrahydro-pyrrolo[1,2,-a]pyrimidine-8-carboxylic acid N-(2-methyl-2-phenyl-propionyl)-hydrazide (4):

Compound 3 (0.085 g, 0.30 mmol) was dissolved in THF (2 mL). HBTU (0.136 g, 0.36 mmol), α,α-dimethyl-phenylacetic acid (0.059 g, 0.36 mmol), and DIEA (0.10 mL, 0.60 mmol) were added. The reaction stirred for 2 h. and was concentrated. Flash chromatography (50% AcOEt/hexanes) gave the desired product. 0.123 g obtained (96% yield). $^1$H NMR (400 MHz, CDCl$_3$) δ 1.49 (s, 3H), 1.50 (s, 3H), 1.60 (s, 3H), 1.61 (s, 3H), 1.95-2.10 (m, 2H), 4.56 (dd, J=3.1, 11.3 Hz, 1H), 6.13 (d, J=3.5 Hz, 1H), 6.17 (d, 3.5 Hz, 1H), 6.65 (brs, 1H), 7.22-7.43 (m, 1H), 7.81 (brs, 1H), 7.92 (brs, 1H). MS Calcd.: 430. Found 431 (M+H).

Step E 4,4-Dimethyl-8-[5-(1-methyl-1-phenyl-ethyl)-[1,3,4]oxadiazol-2-yl]-2-phenyl-1,2,3,4-tetrahydropyrrolo[1,2-a]pyrimidine (5): Compound 4 (0.060 g, 0.14 mmol) was diluted in POCl$_3$ (3 mL). The solution was heated to 75° C. for 3 h. The solution was cooled and carefully quenched with water. The solution was diluted with AcOEt and the mixture carefully neutralized with sat. NaHCO$_3$. The organic layer was separated and the aqueous layer was extracted twice more with AcOEt portions. The combined organic layers were dried (Na$_2$SO$_4$), concentrated, and flash chromatographed to give the desired product as a white solid. 0.016 g obtained (28% yield). $^1$H NMR (400 MHz, CDCl$_3$) δ 1.55 (s, 6H), 1.80 (s, 6H), 2.02-2.16 (m, 2H), 4.68 (dd, J=3.2, 11.6 Hz, 1H), 6.23 (d, J=3.2 Hz, 1H), 6.30 (d, J=3.2 Hz, 1H), 7.20-7.46 (m, 10H). MS Calcd.; 412. Found 413 (M+H).

EXAMPLE 1137

3-Methyl-2-phenyl-2,3-dihydro-1H-imidazo[1,2-b]pyrazole-7-carboxylic acid[1-ethyl-1-(4-trifluoromethyl-phenyl)-propyl]-amide

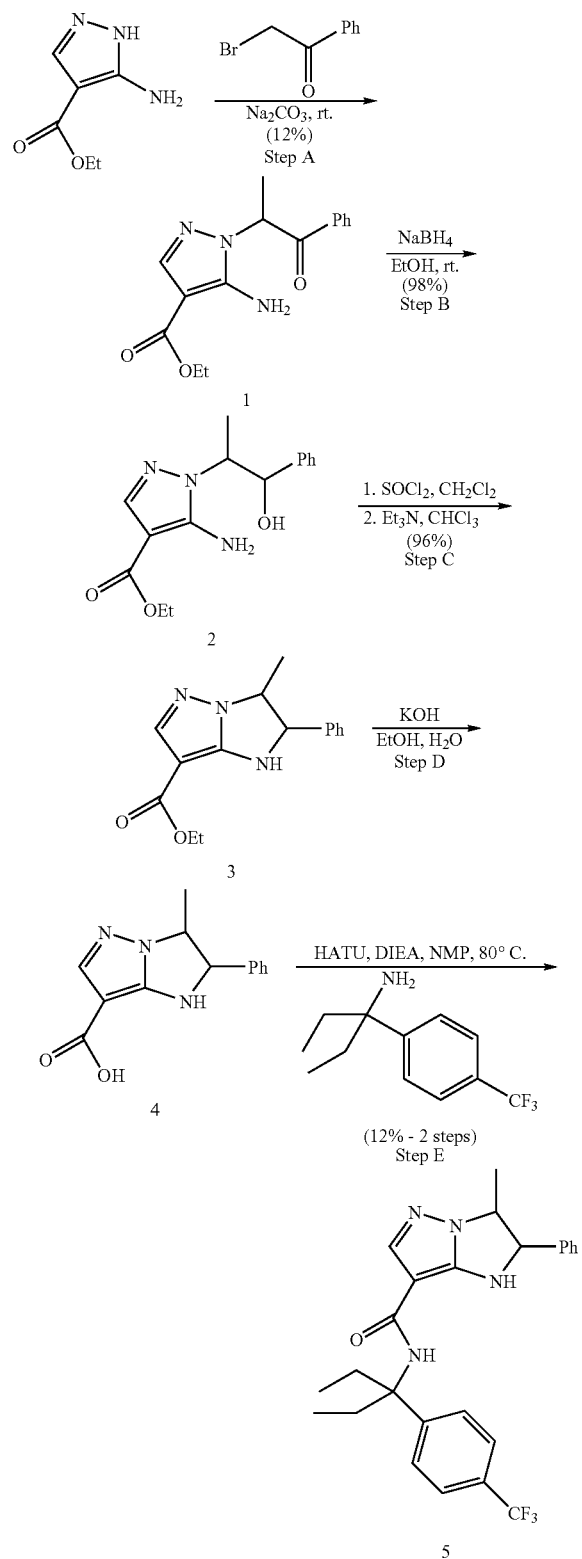

Step A

5-Amino-1-(1-methyl-2-oxo-2-phenyl-ethyl)-1H-pyrazole-4-carboxylic acid ethyl ester (1): 5-Amino-1H-pyrazole-4-carboxylic acid ethyl ester (7.35 g, 47.3 mmol) was dissolved in 160 mL of DMF. $Na_2CO_3$ (5.02 g, 47.3 mmol) was added followed by 2-bromopropiophenone (7.2 mL, 47.3 mmol). The reaction stirred at room temperature for 2 days. The solution was diluted with AcOEt and the organic layer was washed with sat. $NaHCO_3$, brine, dried ($MgSO_4$), and concentrated. Flash chromatography (20-45% AcOEt/hexane) gave the desired product (1.58 g, 12% yield). $^1$H NMR (400 MHz, $CDCl_3$) δ 1.3 (t, J=7.0 Hz, 3H), 1.7 (d, J=7.4 Hz, 3H), 4.2 (q, J=7.0 Hz, 2H), 5.4 (bs, 2H), 5.9 (q, J=7.0 Hz, 1H), 7.41-7.59 (m, 3H), 7.60 (s, 1H), 8.0 (d, J=8.0 Hz, 2H).

Step B

5-Amino-1-(2-hydroxy-1-methyl-2-phenyl-ethyl)-1H-pyrazole-4-carboxylic acid ethyl ester (2): Compound 1 (0.7 g, 2.43 mmol) was dissolved in 34 mL EtOH. $NaBH_4$ (0.18 g, 4.87 mmol) was added in one shot. The reaction stirred at room temperature for 0.5 h. The solution was quenched with sat. $NH_4Cl$ and extracted with $CH_2Cl_2$ (3 times). The organic layer was washed with brine, dried ($MgSO_4$), concentrated to give a fluffy white solid 2 (0.69 g, 98% yield). MS: Calcd.: 289. Found: 290 (M+H).

Step C

3-Methyl-2-phenyl-2,3-dihydro-1H-imidazo[1,2-b]pyrazole-7-carboxylic acid ethyl ester (3): Compound 2 (0.80 g, 2.8 mmol) was dissolved in $CH_2Cl_2$. $SOCl_2$ (0.61 mL, 8.3 mmol) was added dropwise. After 90 minutes, the solution was concentrated to give a yellow solid. After pumping on high vacuum for 5 minutes, the solid was dissolved in $CHCl_3$. $Et_3N$ (2.7 mL, 19.5 mmol) was added dropwise and the reaction mixture stirred for 1 hour. The reaction was quenched with water and diluted with AcOEt. The solution was washed with sat. $NH_4Cl$, sat. $NaHCO_3$, brine, and then dried ($MgSO_4$). Flash chromatography (20% AcOEt/hexane) gave both the syn (0.10 g, 14%) and anti (0.62 g, 82%) isomers 3. Anti isomer $^1$H NMR (400 MHz, $CDCl_3$) δ 1.23 (t, J=7.0 Hz, 3H), 1.80 (d, J=6.6 Hz, 3H), 4.10-4.20 (m, 2H), 4.25-4.35 (m, 1H), 4.38 (brs, 1H), 5.10 (d, J=9.8 Hz, 1H), 7.17-7.25 (m, 5H), 7.59 (s, 1H). Syn isomer $^1$H NMR (400 MHz, $CDCl_3$) δ 1.28 (d, J=7.0 Hz, 3H), 7.38 (t, J=7.4 Hz, 3H), 4.25-4.35 (m, 2H), 7.43-7.52 (m, 1H), 5.17 (brs, 1H), 5.23 (d, J=9.8 Hz, 1H), 7.37-7.45 (m, 5H).

Step D and E

3-Methyl-2-phenyl-2,3-dihydro-1H-imidazo[1,2-b]pyrazole-7-carboxylic acid[1-ethyl-1-(4-trifluoromethyl-phenyl)-propyl]-amide (5)

Compound 3 (0.085 g, 0.3 mmol) was dissolved in EtOH (3 mL). KOH (6M in water, 0.9 mL, 1.78 mmol) was added. The reaction stirred at 60° C. for 3 h. The solution was cooled, diluted with AcOEt (10 mL) and water (10 mL) and shaken vigorously. The Aqueous layer was separated and acidified to pH=3. This acidic layer was then extracted with AcOEt (3 times). The combined AcOEt layers were washed with brine, dried ($Na_2SO_4$) and concentrated. The residue was then dissolved in NMP (1 mL) and 1-ethyl-1-(4-trifluoromethyl-phenyl)-propylamine (0.087 g, 0.37 mmol), HATU (0.14 g, 0.37 mmol), and DIEA (0.14 mL, 0.78 mmol) were added. The reaction was heated to 80° C. for 2 days. The solution was then cooled, washed with water, dried ($MgSO_4$), and concentrated. Flash chromatography (20% AcOEt/hexanes) gave 0.017 g (12% yield) of amide 5.

$^1$H NMR (400 MHz, $CDCl_3$) δ 0.79-0.83 (m, 6H), 1.26 (d, J=7.0 Hz, 3H), 1.99-2.05 (m, 2H), 2.23-2.31 (m, 2H), 4.44-4.48 (m, 1H), 5.19 (brs, 1H), 5.24 (d, J=10 Hz, 1H), 5.66 (brs, 1H), 7.37-7.63 (m, 9H). MS Calcd.: 456; Found: 457 (M+H).

EXAMPLE 1138

8-Methyl-5-phenyl-5,6,7,8-tetrahydro-4H-pyrazolo[1,5,a][1,3]diazepine-3-carboxylic acid (1-methyl-1-phenyl-ethyl)-amide

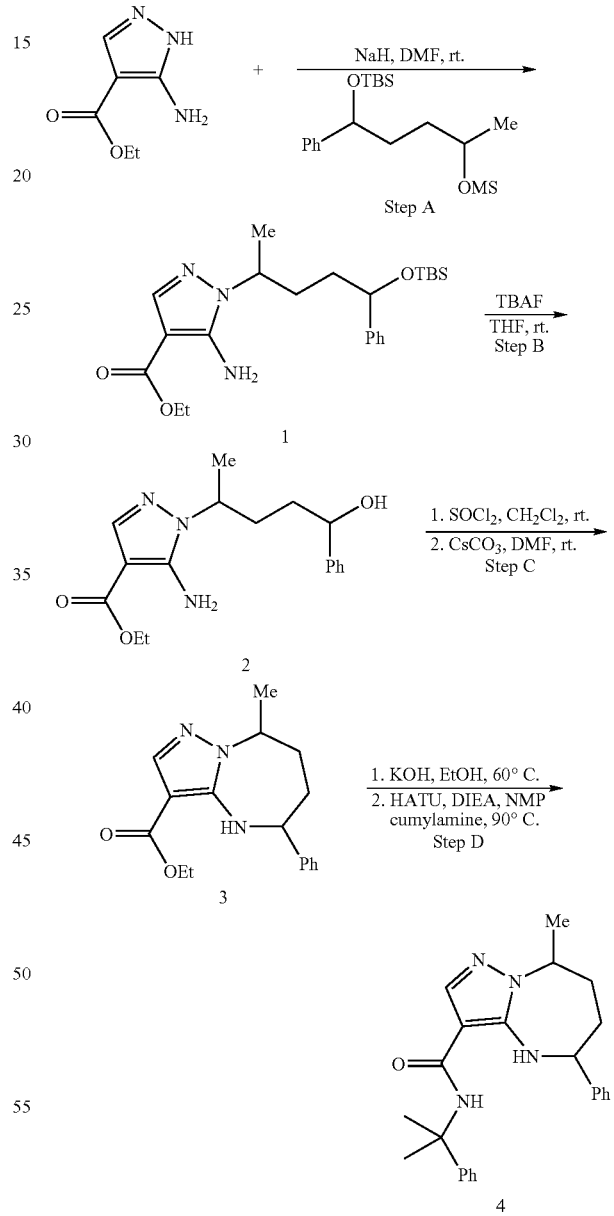

Step A

5-Amino-1-[4-tert-butyl-dimethyl-silanyloxy]-1-methyl-4-phenyl-butyl]-1H-pyrazole-4-carboxylic acid ethyl ester (1): 5-Amino-1H-pyrazole-4-carboxylic acid ethyl ester (1.60 g, 10.3 mmol) was dissolved in 10 mL of DMF. The solution was cooled to 0° C. and NaH (60% in mineral oil, 0.82 g, 20.6 mmol) was added in one portion. The reaction warmed to room temperature after $H_2$ evolution ceased. The reaction stirred for 0.5 h till a bright orange color persisted. The reaction was again brought to 0° C. and methanesulfonic acid 4-(tert-butyl-dimethyl-silanyloxy)-1-methyl-4-phenyl-butyl ester (3.49 g, 9.38 mmol) was then added as a solution in 6 mL DMF. The reaction warmed to room temperature and stirred for 2.5 days. The solution was quenched with water and diluted with AcOEt. The organic layer was separated and the aqueous layer was extracted twice more with AcOEt. The combined organic layers were dried ($MgSO_4$), concentrated and flash chromatographed (15% AcOEt/hexanes) to give 0.530 g (13% yield) of the desired product as an oil. $^1H$ NMR (400 MHz, $CDCl_3$) δ 0.16 (s, 3H), 0.17 (s, 3H), 1.04 (d, J=10 Hz, 9H), 1.48-1.52 (m, 3H), 1.55 (d, J=6.4 Hz, 3H), 1.60 (d, J=6.8 Hz, 3H—other diastereomer), 1.62-1.75 (m, 2H), 1.97-2.07 (m, 2H), 2.10-2.20 (m, 2H—other diastereomer), 4.02-4.07 (m, 1H), 4.21-4.29 (m, 1H—other diastereomer), 4.40-4.43 (m, 2H), 4.79-4.86 (m, 1H), 5.04 (brs, 1H), 5.25 (brs, 1H—other diastereomer), 7.36-7.47 (m, 5H), 7.79 (s, 1H); MS Calcd.: 431. Found 432 (M+H).

Step B and C

8-Methyl-5-phenyl-5,6,7,8-tetrahydro-4H-pyrazolo[1,5,a][1,3]diazepine-3-carboxylic acid ethyl ester (3): Compound 1 (2.0 g, 4.6 mmol) was dissolved in 9 mL THF. TBAF (1M in THF, 13.9 mL, 13.9 mmol) was added at room temperature. The reaction stirred for 0.5 h. The reaction was diluted with ether and washed with brine and water. The ether layer was dried ($MgSO_4$) and concentrated to give the crude alcohol product 2. MS Cald.: 317. Found 318 (M+H).

Alcohol 2 was taken up in $CH_2Cl_2$ (80 mL). $SOCl_2$ (1.7 mL, 23.4 mmol) was added. After 1 h, the solution was concentrated and re-dissolved in 80 mL DMF. $CsCO_3$ (12.6 g, 39 mmol) was added. After 3 h, additional $CsCO_3$ (12.6 g, 39 mmol) was added. The reaction ran 1.5 days. The reaction was quenched with water and diluted with AcOEt. After separation of the organic layer, the aqueous layer was washed twice with AcOEt. The combined organic layers were dried ($MgSO_4$), concentrated, and flash chromatographed to give 0.35 g (26% yield) of a mixture of cis and trans isomers which were readily separated.

Anti isomer—$^1H$ NMR (400 MHz, $CDCl_3$) δ 1.24 (t, J=7.0 Hz, 3H), 1.40 (d, J=7.0 Hz, 3H), 1.93-2.34 (m, 4H), 4.05 (d, 1H), 4.09-4.23 (m, 2H), 4.79-4.85 (m, 1H), 6.40 (bs, 1H), 7.27-7.44 (m, 5H), 7.64 (s, 1H). MS Calcd.: 299; Found 300 (M+H). Syn isomer—$^1H$ NMR (400 MHz, $CDCl_3$) δ 1.24 (t, J=7.0 Hz, 3H), 1.68 (d, J=7.0 Hz, 3H), 1.70-1.80 (m, 1H), 2.00-2.23 (m, 3H), 4.17-4.30 (m, 4H), 6.43 (brs, 1H), 7.22-7.40 (m, 5H), 7.63 (s, 1H). MS Calcd.: 299. Found 300 (M+H).

Step D

8-Methyl-5-phenyl-5,6,7,8-tetrahydro-4H-pyrazolo[1,5,a][1,3]diazepine-3-carboxylic acid (1-methyl-1-phenyl-ethyl)-amide (4): Compound 3 (0.074 g, 0.25 mmol) was diluted with EtOH (0.8 mL). KOH (6M in water, 0.23 mL) was added and the reaction stirred at 60° C. for 3.5 h. The solution was cooled and diluted with AcOEt and water. After vigorous shaking, the aqueous layer was removed and acidified to pH=3. The aqueous layer was then extracted with AcOEt(3 times). The organic layers were combined, dried ($MgSO_4$), and concentrated to give 0.070 g of desired carboxylic acid. MS Calcd.: 271. Found 272 (M+H).

This acid residue (0.070 g, 0.26 mmol) was dissolved in NMP (2 mL). HATU (0.12 g, 0.31 mmol) and cumylamine (0.042 g, 0.31 mmol) were added followed by DIEA (0.090 mL, 0.52 mmol). The reaction stirred at 90° C. for 2 h. The solution was cooled to room temperature and diluted with water. The solution was extracted from AcOEt (3 times), dried ($MgSO_4$), and concentrated. Flash chromatography (30% AcOEt/hexanes) gave the desired product. 0.065 g obtained (65% yield). $^1H$ NMR (400 MHz, $CDCl_3$) δ 1.65 (d, J=6.6 Hz, 3H), 1.71 (s, 3H), 1.75 (s, 3H), 2.00-2.21 (m, 4H), 4.21-4.29 (m, 2H), 5.80 (brs, 1H), 7.02 (brs, 1H), 7.18-7.47 (m, 10H), 7.49 (s, 1H); MS Calcd.: 388. Found 389 (M+H).

EXAMPLE 1142

(1R,4S)-1,3,3-trimethylbicyclo[2.2.1]hept-2-yl-5-(2-fluorophenyl)-2,7,7-trimethyl-4,5,6,7-tetrahydropyrazolo[1,5-a]pyrimidine-3-carboxylate

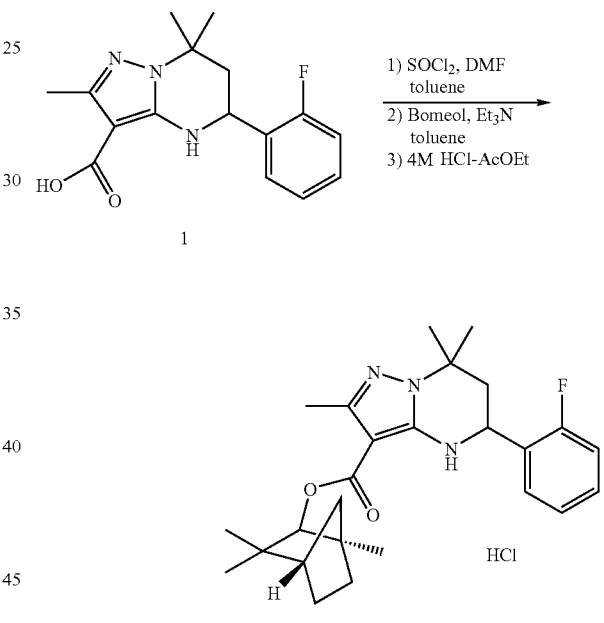

1) To a solution of 1 (0.4 g, 1.32 mmol) and DMF (1 drop) in toluene (4 mL) was added $SOCl_2$ (0.31, 2.64 mmol) at room temperature. After stirring at 60° C. 1 h, the solvent was concentrated in vacuo. The residue was diluted with toluene, and borneol (0.3 g, 1.98 mmol) and $Et_3N$ (0.3 g, 2.90 mmol) was added there to. After stirring at 60° C. 1 h, the reaction mixture was washed with 1N HCl and brine, dried over $MgSO_4$, and concentrated in vacuo. Flash chromatography to give the desired product as oil. To a stirred solution of the oil obtained (90 mg, 0.2 mmol) in AcOEt (2 mL) was added 4M HCl-AcOEt (0.5 mL, 2.0 mmol) at room temperature. The precipitate was collected by filtration to give 2 as HCl salt. MS Calcd.: 440. Found 441 (M+H).

Compounds of Examples 1139-1141 shown in the Table 16, were prepared in a manner similar to that described in Example 1142.

TABLE 16

| | | | |
|---|---|---|---|
| 1139 | 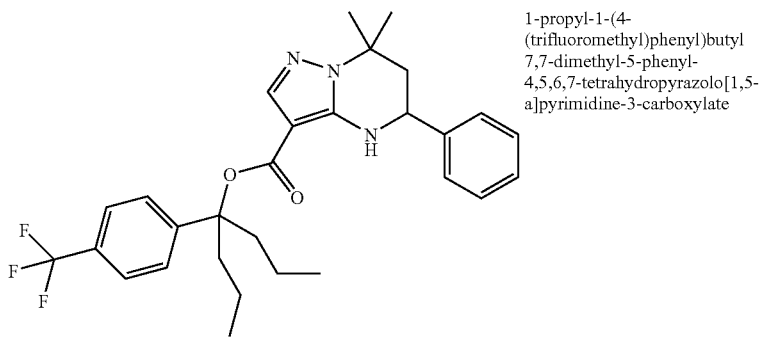 | 1-propyl-1-(4-(trifluoromethyl)phenyl)butyl 7,7-dimethyl-5-phenyl-4,5,6,7-tetrahydropyrazolo[1,5-a]pyrimidine-3-carboxylate | MS(ESI, m/z) 514 (M + H)+ |
| 1140 | 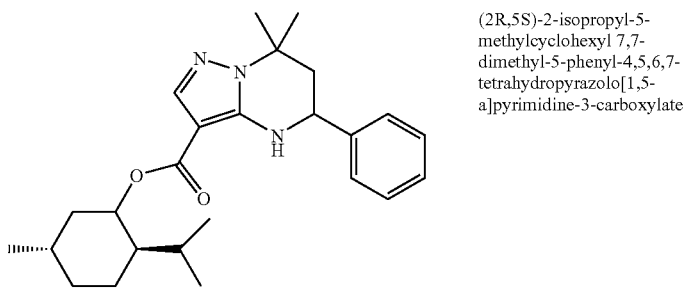 | (2R,5S)-2-isopropyl-5-methylcyclohexyl 7,7-dimethyl-5-phenyl-4,5,6,7-tetrahydropyrazolo[1,5-a]pyrimidine-3-carboxylate | mp 123-124° C. |
| 1141 | 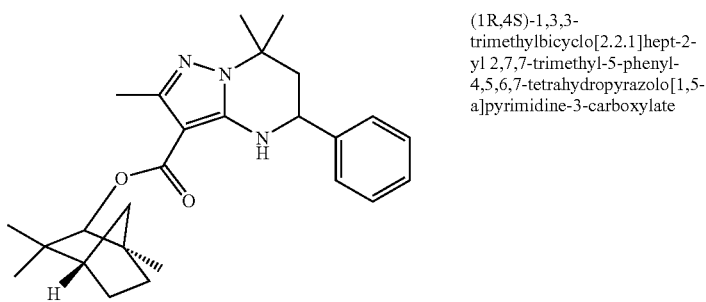 | (1R,4S)-1,3,3-trimethylbicyclo[2.2.1]hept-2-yl 2,7,7-trimethyl-5-phenyl-4,5,6,7-tetrahydropyrazolo[1,5-a]pyrimidine-3-carboxylate | mp 149-150° C. HCl salt |

Compounds of Examples 868-923 and 1143-1146 shown in the table 6, were prepared from compound of Examples 35 in a manner similar to that described in followed reference 1~6.

1) Poulan R F., Tartar A L., Deprez B p., *Tetrahedron Lett.* 2001, 42, 1495.
2) Rigo B., Cauliesz P., Fasseur D., Couturier D., *Synthetic Communications* 1986, 16, 1665.
3) Carlsen H J., Jorgensen K B., *J. Heterocyclic Chem.,* 1994, 31, 805.
4) Kiryanov A A., Sampson P., Seed J., *J. Org. Chem.,* 2001, 66, 7925.
5) Kelly T R., Lang F R., *Tetrahedron Lett.,* 1995, 36, 5319.
6) Walia J S., Walia A S., Lankin D C., Petterson R C., Singh J., *J. Heterocyclic Chem.,* 1985, 22, 1117.

TABLE 6

| Example | Structure | Name | Physiological Data |
|---|---|---|---|
| 868 | 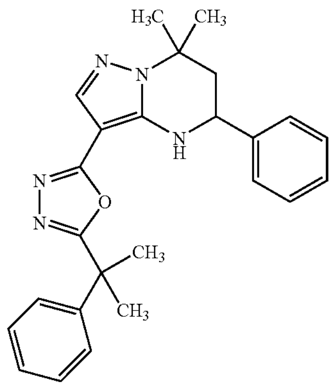 | 7,7-dimethyl-3-(5-(1-methyl-1-phenylethyl)-1,3,4-oxadiazol-2-yl)-5-phenyl-4,5,6,7-tetrahydropyrazolo[1,5-a]pyrimidine | MS(ESI, m/z) 414 (M + H)+ |
| 869 | 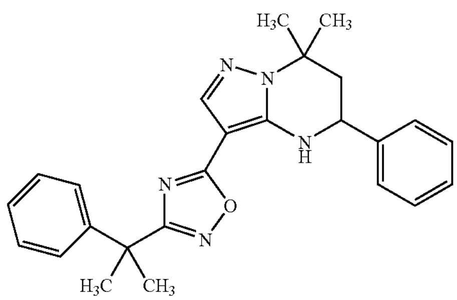 | 7,7-dimethyl-3-(3-(1-methyl-1-phenylethyl)-1,2,4-oxadiazol-5-yl)-5-phenyl-4,5,6,7-tetrahydropyrazolo[1,5-a]pyrimidine | MS(ESI, m/z) 414 (M + H)+ |
| 870 | 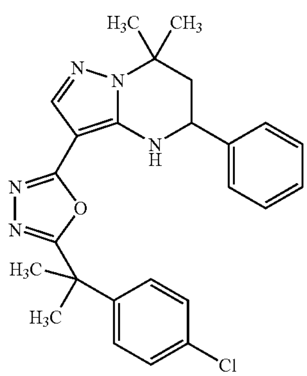 | 3-(5-(1-(4-chlorophenyl)-1-methylethyl)-1,3,4-oxadiazol-2-yl)-7,7-dimethyl-5-phenyl-4,5,6,7-tetrahydropyrazolo[1,5-a]pyrimidine | MS(ESI, m/z) 449 (M + H)+ |
| 871 | 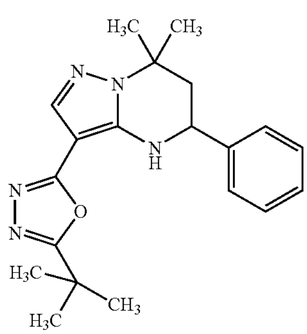 | 3-(5-tert-butyl-1,3,4-oxadiazol-2-yl)-7,7-dimethyl-5-phenyl-4,5,6,7-tetrahydropyrazolo[1,5-a]pyrimidine | MS(ESI, m/z) 352 (M + H)+ |

TABLE 6-continued

| Example | Structure | Name | Physiological Data |
|---|---|---|---|
| 872 | 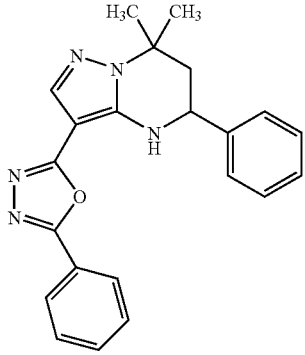 | 7,7-dimethyl-5-phenyl-3-(5-phenyl-1,3,4-oxadiazol-2-yl)-4,5,6,7-tetrahydropyrazolo[1,5-a]pyrimidine | MS(ESI, m/z) 372 (M + H)+ |
| 873 | 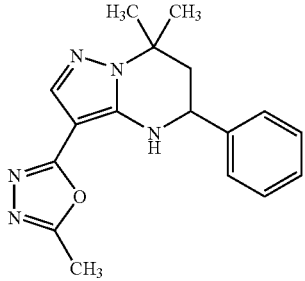 | 7,7-dimethyl-3-(5-methyl-1,3,4-oxadiazol-2-yl)-5-phenyl-4,5,6,7-tetrahydropyrazolo[1,5-a]pyrimidine | MS(ESI, m/z) 310 (M + H)+ |
| 874 | 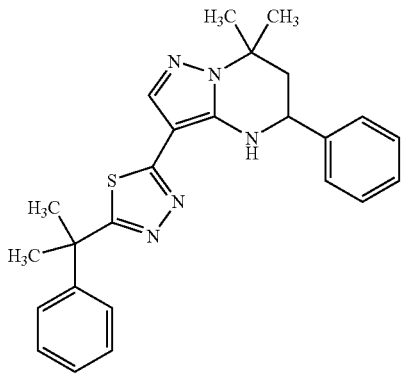 | 7,7-dimethyl-3-(5-(1-methyl-1-phenylethyl)-1,3,4-thiadiazol-2-yl)-5-phenyl-4,5,6,7-tetrahydropyrazolo[1,5-a]pyrimidine | MS(ESI, m/z) 430 (M + H)+ |
| 875 | 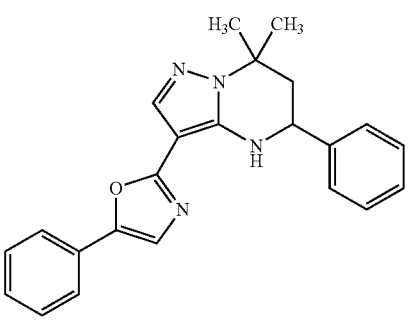 | 7,7-dimethyl-5-phenyl-3-(5-phenyl-1,3-oxazol-2-yl)-4,5,6,7-tetrahydropyrazolo[1,5-a]pyrimidine | MS(ESI, m/z) 371 (M + H)+ |

TABLE 6-continued

| Example | Structure | Name | Physiological Data |
|---|---|---|---|
| 876 | 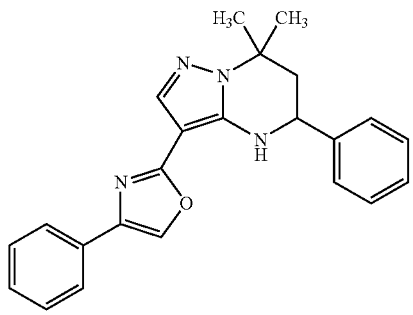 | 7,7-dimethyl-5-phenyl-3-(4-phenyl-1,3-oxazol-2-yl)-4,5,6,7-tetrahydropyrazolo[1,5-a]pyrimidine | MS(ESI, m/z) 371 (M + H)+ |
| 877 | 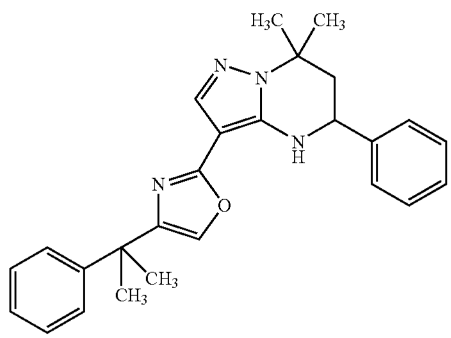 | 7,7-dimethyl-3-(4-(1-methyl-1-phenylethyl)-1,3-oxazol-2-yl)-5-phenyl-4,5,6,7-tetrahydropyrazolo[1,5-a]pyrimidine | MS(ESI, m/z) 413 (M + H)+ |
| 888 | 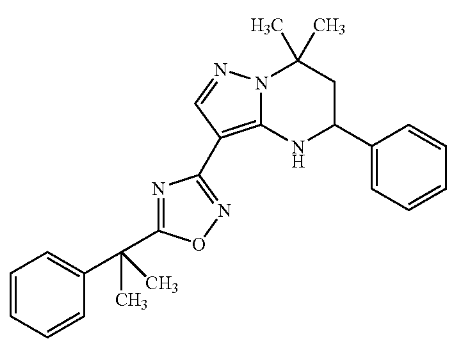 | 7,7-dimethyl-3-(5-(1-methyl-1-phenylethyl)-1,2,4-oxadiazol-3-yl)-5-phenyl-4,5,6,7-tetrahydropyrazolo[1,5-a]pyrimidine | MS(ESI, m/z) 414 (M + H)+ |
| 889 | 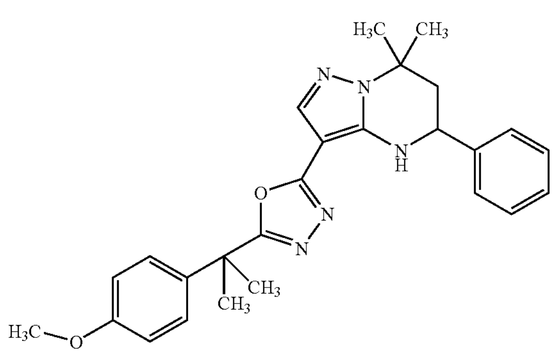 | 3-(5-(1-(4-methoxyphenyl)-1-methylethyl)-1,3,4-oxadiazol-2-yl)-7,7-dimethyl-5-phenyl-4,5,6,7-tetrahydropyrazolo[1,5-a]pyrimidine | MS(ESI, m/z) 444 (M + H)+ |

TABLE 6-continued

| Example | Structure | Name | Physiological Data |
|---|---|---|---|
| 890 | 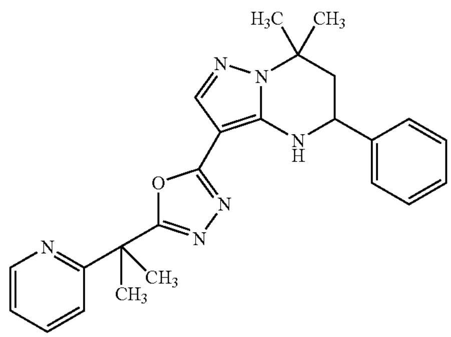 | 7,7-dimethyl-3-(5-(1-methyl-1-(2-pyridinyl)ethyl)-1,3,4-oxadiazol-2-yl)-5-phenyl-4,5,6,7-tetrahydropyrazolo[1,5-a]pyrimidine | MS(ESI, m/z) 415 (M + H)+ |
| 891 | 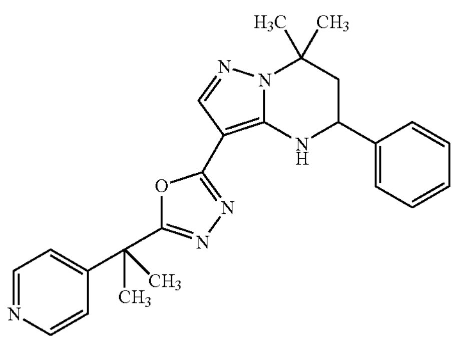 | 7,7-dimethyl-3-(5-(1-methyl-1-(4-pyridinyl)ethyl)-1,3,4-oxadiazol-2-yl)-5-phenyl-4,5,6,7-tetrahydropyrazolo[1,5-a]pyrimidine | MS(ESI, m/z) 415 (M + H)+ |
| 892 | 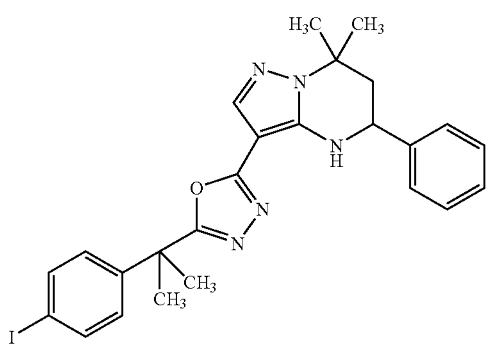 | 3-(5-(1-(4-iodophenyl)-1-methylethyl)-1,3,4-oxadiazol-2-yl)-7,7-dimethyl-5-phenyl-4,5,6,7-tetrahydropyrazolo[1,5-a]pyrimidine | MS(ESI, m/z) 540 (M + H)+ |
| 893 | 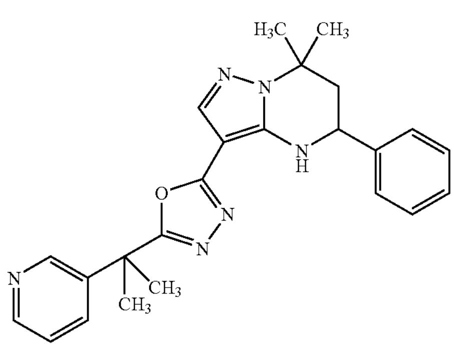 | 7,7-dimethyl-3-(5-(1-methyl-1-(3-pyridinyl)ethyl)-1,3,4-oxadiazol-2-yl)-5-phenyl-4,5,6,7-tetrahydropyrazolo[1,5-a]pyrimidine | MS(ESI, m/z) 415 (M + H)+ |

TABLE 6-continued

| Example | Structure | Name | Physiological Data |
|---|---|---|---|
| 894 | 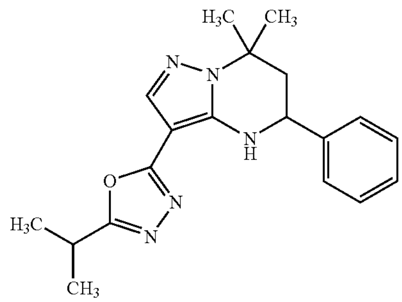 | 3-(5-isopropyl-1,3,4-oxadiazol-2-yl)-7,7-dimethyl-5-phenyl-4,5,6,7-tetrahydropyrazolo[1,5-a]pyrimidine | MS(ESI, m/z) 338 (M + H)+ |
| 895 | 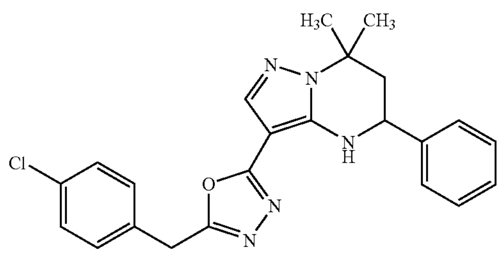 | 3-(5-(4-chlorobenzyl)-1,3,4-oxadiazol-2-yl)-7,7-dimethyl-5-phenyl-4,5,6,7-tetrahydropyrazolo(1,5-a]pyrimidine | MS(ESI, m/z) 421 (M + H)+ |
| 896 | 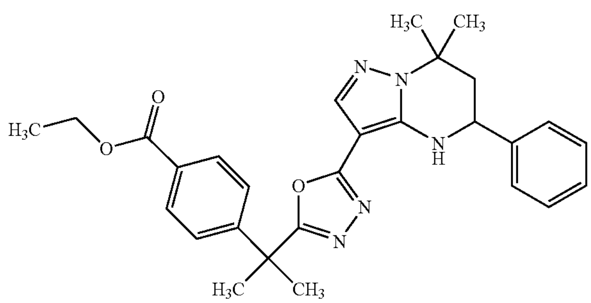 | ethyl 4-(1-(5-(7,7-dimethyl-5-phenyl-4,5,6,7-tetrahydropyrazolo[1,5-a]pyrimidin-3-yl)-1,3,4-oxadiazol-2-yl)-1-methylethyl)benzoate | MS(ESI, m/z) 486 (M + H)+ |
| 897 | 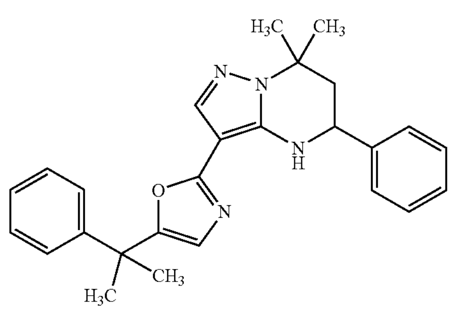 | 7,7-dimethyl-3-(5-(1-methyl-1-phenylethyl)-1,3-oxazol-2-yl)-5-phenyl-4,5,6,7-tetrahydropyrazolo[1,5-a]pyrimidine | MS(ESI, m/z) 413 (M + H)+ |
| 898 | 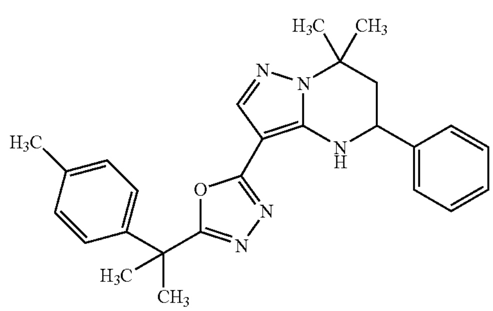 | 7,7-dimethyl-3-(5-(1-methyl-1-(4-methylphenyl)ethyl)-1,3,4-oxadiazol-2-yl)-5-phenyl-4,5,6,7-tetrahydropyrazolo[1,5-a]pyrimidine | MS(ESI, m/z) 414 (M + H)+ |

TABLE 6-continued

| Example | Structure | Name | Physiological Data |
|---|---|---|---|
| 899 | 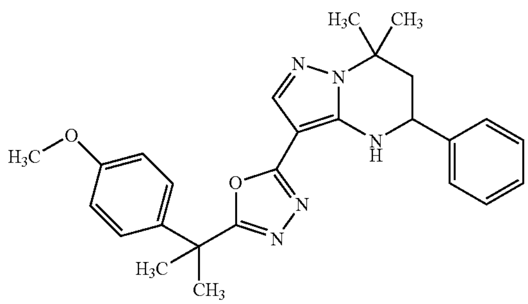 | 3-(5-(1-(4-methoxyphenyl)-1-methylethyl)-1,3,4-oxadiazol-2-yl)-7,7-dimethyl-5-phenyl-4,5,6,7-tetrahydropyrazolo[1,5-a]pyrimidine | MS(ESI, m/z) 444 (M + H)+ |
| 900 | 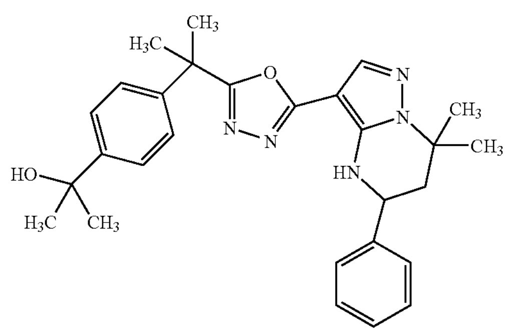 | 2-(4-(1-(5-(7,7-dimethyl-5-phenyl-4,5,6,7-tetrahydropyrazolo[1,5-a]pyrimidin-3-yl)-1,3,4-oxadiazol-2-yl)-1-methylethyl)phenyl)-2-propanol | MS(ESI, m/z) 472 (M + H)+ |
| 901 | 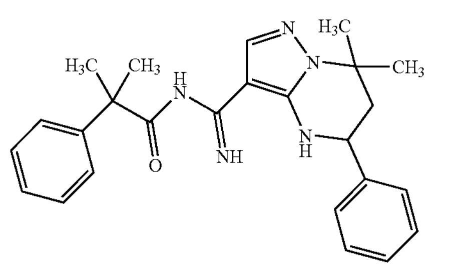 | N-((7,7-dimethyl-5-phenyl-4,5,6,7-tetrahydropyrazolo[1,5-a]pyrimidin-3-yl)(imino)methyl)-2-methyl-2-phenylpropanamide | MS(ESI, m/z) 416 (M + H)+ |
| 902 | 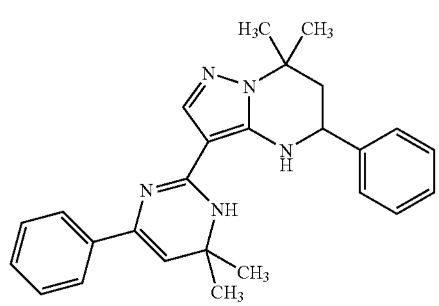 | 3-(4,4-dimethyl-6-phenyl-1,4-dihydro-2-pyrimidinyl)-7,7-dimethyl-5-phenyl-4,5,6,7-tetrahydropyrazolo[1,5-a]pyrimidine | MS(ESI, m/z) 412 (M + H)+ |
| 903 | 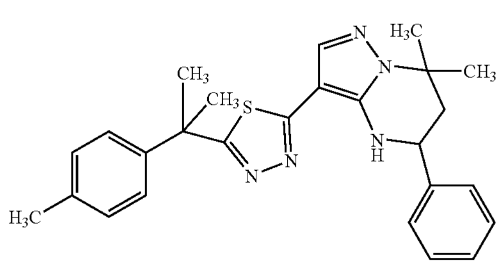 | 7,7-dimethyl-3-(5-(1-methyl-1-(4-methylphenyl)ethyl)-1,3,4-thiadiazol-2-yl)-5-phenyl-4,5,6,7-tetrahydropyrazolo[1,5-a]pyrimidine | MS(ESI, m/z) 444 (M + H)+ |

TABLE 6-continued

| Example | Structure | Name | Physiological Data |
|---|---|---|---|
| 904 | 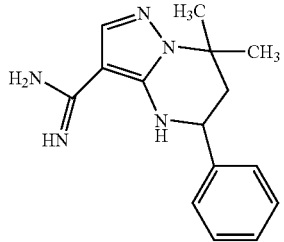 | 7,7-dimethyl-5-phenyl-4,5,6,7-tetrahydropyrazolo[1,5-a]pyrimidine-3-carboximidamide | MS(ESI, m/z) 270 (M + H)+ |
| 905 | 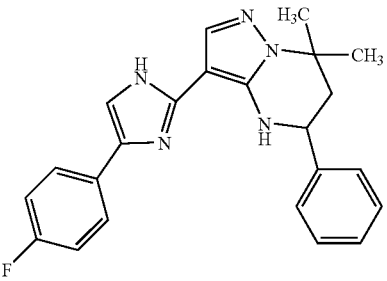 | 3-(4-(4-fluorophenyl)-1H-imidazol-2-yl)-7,7-dimethyl-5-phenyl-4,5,6,7-tetrahydropyrazolo[1,5-a]pyrimidine | MS(ESI, m/z) 388 (M + H)+ |
| 906 | 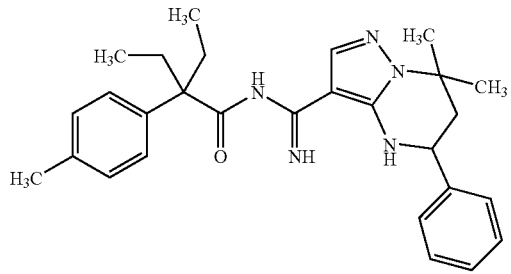 | N-((7,7-dimethyl-5-phenyl-4,5,6,7-tetrahydropyrazolo[1,5-a]pyrimidin-3-yl)(imino)methyl)-2-ethyl-2-(4-methylphenyl)butanamide | MS(ESI, m/z) 458 (M + H)+ |
| 907 | 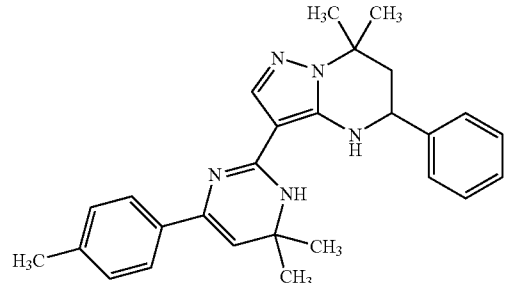 | 3-(4,4-dimethyl-6-(4-methylphenyl)-1,4-dihydro-2-pyrimidinyl)-7,7-dimethyl-5-phenyl-4,5,6,7-tetrahydropyrazolo[1,5-a]pyrimidine | MS(ESI, m/z) 426 (M + H)+ |
| 908 | 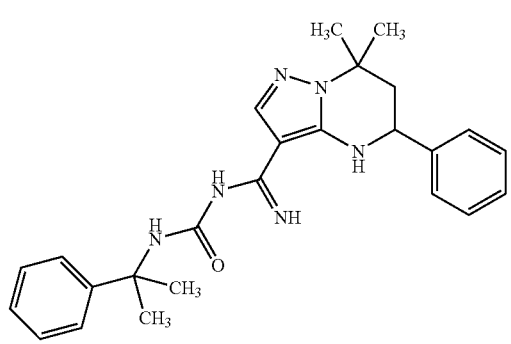 | 7,7-dimethyl-N-(((1-methyl-1-phenylethyl)amino)carbonyl)-5-phenyl-4,5,6,7-tetrahydropyrazolo[1,5-a]pyrimidine-3-carboximidamide | MS(ESI, m/z) 431 (M + H)+ |

TABLE 6-continued

| Example | Name | Physiological Data |
|---------|------|--------------------|
| 909 | 7,7-dimethyl-5-phenyl-N-((((1S)-1-phenylethyl)-amino)carbonyl)-4,5,6,7-tetrahydropyrazolo[1,5-a]pyrimidine-3-carboximidamide | MS(ESI, m/z) 417 (M + H)+ |
| 910 | 7,7-dimethyl-3-(1-methyl-5-(1-methyl-1-phenylethyl)-1H-imidazol-2-yl)-5-phenyl-4,5,6,7-tetrahydropyrazolo[1,5-a]pyrimidine | MS(ESI, m/z) 427 (M + H)+ |
| 911 | 3-(5-(1-ethyl-1-(4-methylphenyl)propyl)-1,3,4-oxadiazol-2-yl)-7,7-dimethyl-5-phenyl-4,5,6,7-tetrahydropyrazolo[1,5-a]pyrimidine | MS(ESI, m/z) 457 (M + H)+ |
| 912 | 7,7-dimethyl-3-(3-(1-methyl-1-phenylethyl)-1H-1,2,4-triazol-5-yl)-5-phenyl-4,5,6,7-tetrahydropyrazolo[1,5-a]pyrimidine | MS(ESI, m/z) 414 (M + H)+ |
| 913 | 3-(4,4-dimethyl-6-(4-methylphenyl)-1,4,5,6-tetrahydro-2-pyrimidinyl)-7,7-dimethyl-5-phenyl-4,5,6,7-tetrahydropyrazolo[1,5-a]pyrimidine | MS(ESI, m/z) 428 (M + H)+ |

TABLE 6-continued

| Example | Structure | Name | Physiological Data |
|---|---|---|---|
| 914 | 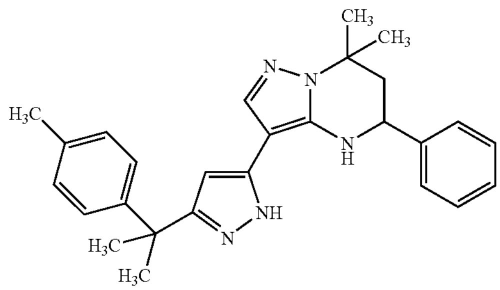 | 7,7-dimethyl-3-(3-(1-methyl-1-(4-methylphenyl)ethyl)-1H-pyrazol-5-yl)-5-phenyl-4,5,6,7-tetrahydropyrazolo[1,5-a]pyrimidine | MS(ESI, m/z) 426 (M + H)+ |
| 915 | 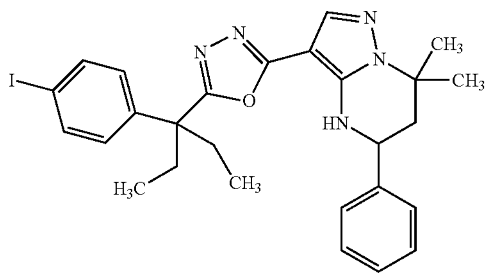 | 3-(5-(1-ethyl-1-(4-iodophenyl)propyl)-1,3,4-oxadiazol-2-yl)-7,7-dimethyl-5-phenyl-4,5,6,7-tetrahydropyrazolo[1,5-a]pyrimidine | MS(ESI, m/z) 568 (M + H)+ |
| 916 | 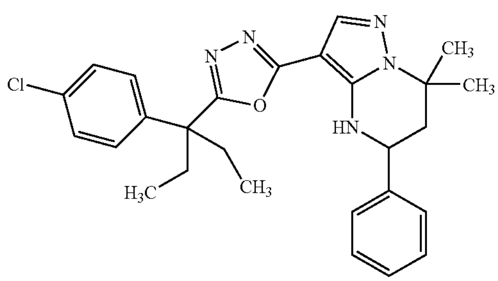 | 3-(5-(1-(4-chlorophenyl)-1-ethylpropyl)-1,3,4-oxadiazol-2-yl)-7,7-dimethyl-5-phenyl-4,5,6,7-tetrahydropyrazolo[1,5-a]pyrimidine | MS(ESI, m/z) 476 (M + H)+ |
| 917 | 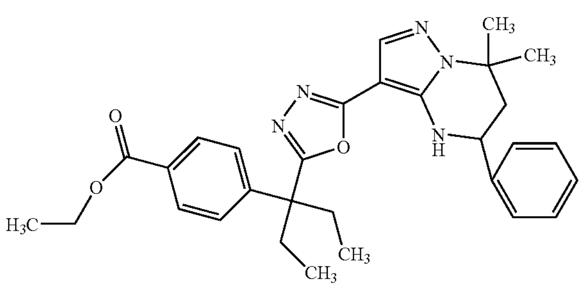 | ethyl 4-(1-(5-(7,7-dimethyl-5-phenyl-4,5,6,7-tetrahydropyrazolo[1,5-a]pyrimidin-3-yl)-1,3,4-oxadiazol-2-yl)-1-ethylpropyl)benzoate | MS(ESI, m/z) 514 (M + H)+ |
| 918 | 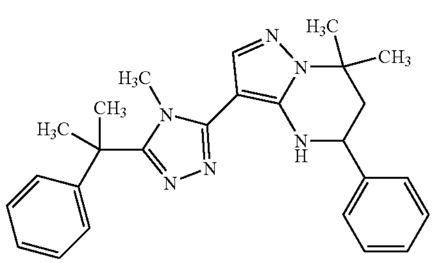 | 7,7-dimethyl-3-(4-methyl-5-(1-methyl-1-phenylethyl)-4H-1,2,4-triazol-3-yl)-5-phenyl-4,5,6,7-tetrahydropyrazolo]1,5-a]pyrimidine | MS(ESI, m/z) 427 (M + H)+ |

TABLE 6-continued

| Example | Structure | Name | Physiological Data |
| --- | --- | --- | --- |
| 919 | 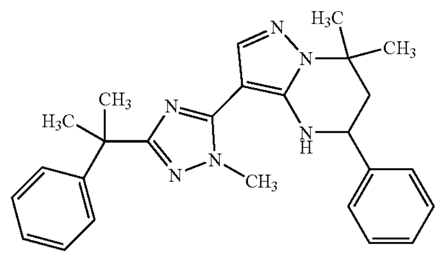 | 7,7-dimethyl-3-(1-methyl-3-(1-methyl-1-phenylethyl)-1H-1,2,4-triazol-5-yl)-5-phenyl-4,5,6,7-tetrahydropyrazolo[1,5-a]pyrimidine | MS(ESI, m/z) 427 (M + H)+ |
| 920 | 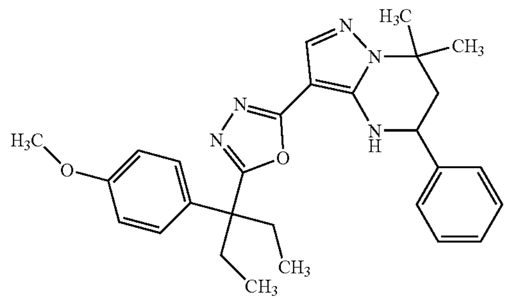 | 3-(5-(1-ethyl-1-(4-methoxyphenyl)propyl)-1,3,4-oxadiazol-2-yl)-7,7-dimethyl-5-phenyl-4,5,6,7-tetrahydropyrazolo[1,5-a]pyrimidine | MS(ESI, m/z) 472 (M + H)+ |
| 921 | 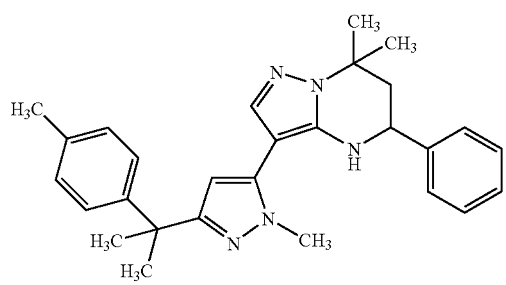 | 7,7-dimethyl-3-(1-methyl-3-(1-methyl-1-(4-methylphenyl)-ethyl)-1H-pyrazol-5-yl)-5-phenyl-4,5,6,7-tetrahydropyrazolo[1,5-a]pyrimidine | MS(ESI, m/z) 440 (M + H)+ |
| 922 | 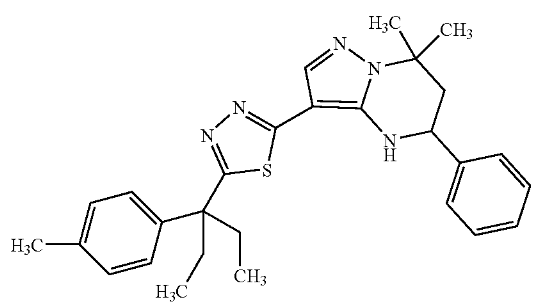 | 3-(5-(1-ethyl-1-(4-methylphenyl)propyl)-1,3,4-thiadiazol-2-yl)-7,7-dimethyl-5-phenyl-4,5,6,7-tetrahydropyrazolo[1,5-a]pyrimidine | MS(ESI, m/z) 472 (M + H)+ |
| 923 | 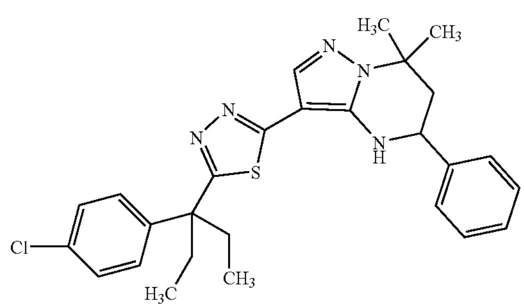 | 3-(5-(1-(4-chlorophenyl)-1-ethylpropyl)-1,3,4-thiadiazol-2-yl)-7,7-dimethyl-5-phenyl-4,5,6,7-tetrahydropyrazolo[1,5-a]pyrimidine | MS(ESI, m/z) 492 (M + H)+ |

TABLE 6-continued

| Example | Structure | Name | Physiological Data |
|---|---|---|---|
| 1143 | 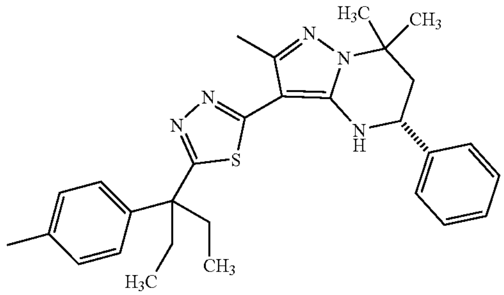 | (5R)-3-(5-(1-ethyl-1-(4-methylphenyl)propyl)-1,3,4-thiadiazol-2-yl)-2,7,7-trimethyl-5-phenyl-4,5,6,7-tetrahydropyrazolo[1,5-a]pyrimidine | mp 132-134° C. |
| 1144 | 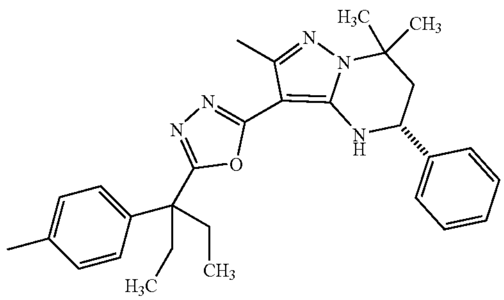 | (5R)-3-(5-(1-ethyl-1-(4-methylphenyl)propyl)-1,3,4-oxadiazol-2-yl)-2,7,7-trimethyl-5-phenyl-4,5,6,7-tetrahydropyrazolo[1,5-a]pyrimidine | MS(ESI, m/z) 470 (M + H)+ |
| 1145 | 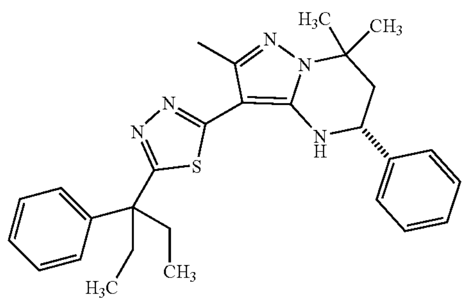 | (5R)-3-(5-(1-ethyl-1-phenylpropyl)-1,3,4-thiadiazol-4,5,6,7-tetrahydropyrazolo[1,5-a]pyrimidine | mp 174-175° C. |
| 1146 | 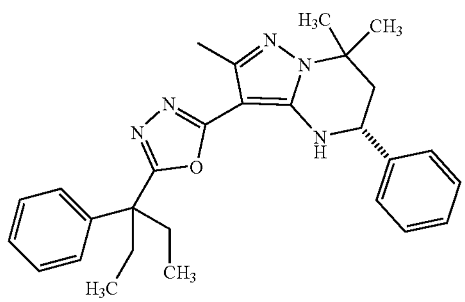 | (5R)-3-(5-(1-ethyl-1-phenylpropyl)-1,3,4-oxadiazol-2-yl)-2,7,7-trimethyl-5-phenyl-4,5,6,7-tetrahydropyrazolo[1,5-a]pyrimidine | MS(ESI, m/z) (M + H)+ |

Experiment 1

Strategy for cloning of the cDNAs encoding the human CaR

Strategy for cloning of the cDNAs encoding the human CaR is shown below. To amplify the cDNA encoding the N-terminal moiety of the human CaR, the synthetic DNA primers, Cal-U: 5'-AGAGTCGACGCCACCATGGCATTT-TATAGCTGCTGCTGG-3' and Cal-L: 5'-AAAT-GAGCTCTCGGTTGGTGGCCTTGAC-3', were constructed. In this case, SalI site was added at the 5' end of amplified cDNA. To amplify the cDNA encoding the C-terminal moiety of the human CaR, the synthetic DNA primers, Ca2-U: 5'-AAACGAGCTCTCCTACCTCCTCCTCTTC-3' and Ca2-L: 5'-TCTGCGGCCGCTCCCTAGCCCAGTCT-TCTCCTTCC-3', were constructed. In this case, NotI site was added at the 3' end of amplified cDNA. PCR was carried out by Hot Start method. The reaction solution of the upper phase was added of 1 pg of the human kidney-derived cDNA (TOYOBO), 0.3 mM dNTPs and 2.5 unit LA Taq DNA polymerase (Takara shuzo co.) and filled up to 30 µl with water and buffer attached to the enzyme. To the reaction solution of the lower phase was added 12.5 µM each of the synthetic primers and 0.5 mM dNTPs and filled up to 20 µl with water and buffer attached to the enzyme. The reaction solution of the upper phase was added on the lower phase covered with an AmpliWax PCR Gem100 (Takara Shuzo Co.). The samples were subject to PCR amplification using a Thermal Cycler (Perkin-Elmer Co.). The amplified cDNAs were confirmed by agarose gel electrophoresis.

Experiment 2

Preparation of CaR-Expression CHO Cells

The PCR products obtained in Experiment 1 were separated by agarose gel electrophoresis. The PCR products were excised and purified from the gel and subcloned into pT7Blue-T vector (Takara Shuzo Co.). The cDNA fragment encoding the N-terminal moiety of the human CaR was released from the subcloned pT7Blue-T vector treated with SalI and SacI. The cDNA fragment encoding the C-terminal moiety of the human CaR was released from the subcloned pT7Blue-T vector treated with SacI and NotI. Using DNA Ligation kit (Takara Shuzo Co.), these fragments were inserted between the site of SalI- and NotI- in the digested pMSRαneo vector. Thus, the pMSRαneo-CaR for animal cell expression was constructed.

Ten μg of the pMSRαneo-CaR was added to the solution containing $8\times10^6$ CHO-K1 cells, and transfection was carried out using Gene Pulser (0.4 cm cuvette, 0.25 kV, 960 mF) (Bio-Rad Laboratories). The cells were cultured in HamF12 containing 10% fetal calf serum for one day. After passage, the cells were cultured in HamF12 containing 10% fetal and 500 μg/ml Genetisine. The cells were seeded on 96-well plate in $1\times10^3$ cells/well and transformants, CaR-expressing CHO cells, were selected in the selection medium.

Experiment 3

Selection of the CaR-Expressing CHO Cell Line by Calcium Mobilization Assay

A method for calcium mobilization assay is shown below. The CaR-expressing CHO cells were seeded on a 96-well white plate in $2\times10^4$ cells/well, followed by cultivation for 48 hours. After washing the cells with Phosphate-Buffered Saline, 100 μl of buffer solution (120 mM NaCl, 22 mM NaHCO$_3$, 6 mM KCl, 0.2 mM CaCl$_2$, 1 mM MgCl$_2$, 5 mM glucose, 5 mM HEPES (pH 7.4)) containing 5 μM FuraPE3AM (Texas Fluorescence Laboratories) was added to the wells and kept at 37° C. for 1 hour. The cells were washed twice with Phosphate-Buffered Saline. After adding 180 μl of the reaction buffer solution (130 mM NaCl, 5.4 mM KCl, 0.2 mM CaCl$_2$, 0.9 mM MgCl$_2$, 10 mM glucose, 20 mM HEPES (pH 7.4)) to the wells, 20 μl of 60 mM CaCl$_2$ was added and intracellular calcium concentration were measured with a fluorometric imaging plate reader (FDSS 2000, Hamamatsu photonics). One clone increasing intracellular calcium concentration was selected and used for the following experiment.

Experiment 4

GTPγS Binding Assay

Preparation of membrane fraction is described bellow. The human CaR-expressing CHO cells were inoculated to a F500 flask in $1.8\times10^5$ cells/flask followed by cultivation for 2 days. The cells were scraped with 10 ml of Phosphate-Buffered Saline containing 0.02% EDTA. After centrifugation (2000 rpm, 10 min) of the cells, the cell pellet was resuspended into 12 ml of homogenate buffer solution (10 mM NaHCO$_3$, 1 mM EDTA, 1× Protease inhibitor cocktail (pH 7.4)) and homogenized by Polytron™ (20000 rpm, 1 min). The cell debris was removed by centrifugation (2000 rpm, 10 min), and then the CaR-expressing cell membrane fraction was collected by ultracentrifugation (Beckman 70 Ti type rotor, 30000 rpm, 1 hour).

The GTPγS binding activity was measured as follows. Twenty μg of the CaR-expressing cell membrane was incubated with test compounds for 10 min. The assays were carried out at room temperature for an hour in a reaction solution mixture containing 20 mM HEPES (pH.7.4), 100 mM NaCl, 1 mM MgCl$_2$, 167 μg/ml DTT, 5 μM guanosine 5'-diphosphate, 0.4 nM [$^{35}$S]-guanosine 5'-(γ-thio) triphosphate ([$^{35}$S]-GTPγS) and 6 mM CaCl$_2$. The mixture was filtered through a GF/C filter. After washing fourth with 300 μl of Phosphate-Buffered Saline, the amount of [$^{35}$S]-GTPγS bound to the filter was measured using a Top-count scintillation counter.

Effects of test compounds on [$^{35}$S]-GTPγS binding were expressed in percentage terms. This was calculated from the equation $[100\times(t'-b)]/(t-b)$ where t', t and b are values of [$^{35}$S]-GTPγS binding (dpm), t' in the presence of 6 mM calcium and the test compound, t in the presence of 6 mM calcium only and b in the absence of both 6 mM calcium and the test compound.

The antagonist dose-dependently decreased [$^{35}$S]-GTPγS binding in membrane preparation. The agonist dose-dependently increased [$^{35}$S]-GTPγS binding in membrane preparation.

The results are shown in Table 7.

TABLE 7

| Ex. No. | [$^{35}$S]-GTP γ S binding (%) |
| --- | --- |
| 318* | 34 (1 μM) |
| 335* | 0 (1 μM) |
| 310* | 0 (1 μM) |
| 312* | 10 (1 μM) |
| 436* | 12 (1 μM) |
| 423* | 0 (1 μM) |
| 111** | 256 (10 μM) |

*antagonist
**agonist

INDUSTRIAL APPLICABILITY

Compound (I), (II), (III) or (IIIa) of the present invention has an excellent Ca receptor modulating activity and enhances the secretion of PTH, and therefore useful as drugs for treating bone diseases, kidney-acting drugs, central nervous system and endocrine-acting drugs, digestive system-acting drugs, and the like.

The invention claimed is:
1. A compound selected from the group consisting of
N-(1-ethyl-1-(4-methylphenyl)propyl)-7,7-dimethyl-5-phenyl-4,5,6,7-tetrahydropyrazolo[1,5-a]pyrimidine-3-carboxamide or a salt thereof,
N-(1-ethyl-1-(4-methylphenyl)propyl)-5-(2-fluorophenyl)-7,7-dimethyl-4,5,6,7-tetrahydropyrazolo[1,5-a]pyrimidine-3-carboxamide or a salt thereof,
N-(1-ethyl-1-(4-methylphenyl)propyl)-2,7,7-trimethyl-5-phenyl-4,5,6,7-tetrahydropyrazolo[1,5-a]pyrimidine-3-carboxamide or a salt thereof,
N-(1-ethyl-1-(4-ethylphenyl)propyl)-2,7,7-trimethyl-5-phenyl-4,5,6,7-tetrahydropyrazolo[1,5-a]pyrimidine-3-carboxamide or a salt thereof,
N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide or a salt thereof,

N-(1-ethyl-1-(4-ethylphenyl)propyl)-5-(2-fluorophenyl)-2,7,7-trimethyl-4,5,6,7-tetrahydropyrazolo[1,5-a]pyrimidine-3-carboxamide or a salt thereof, 5-(2-chlorophenyl)-N-(1-ethyl-1-(4-methylphenyl)propyl)-2,7,7-trimethyl-4,5,6,7-tetrahydropyrazolo[1,5-a]pyrimidine-3-carboxamide or a salt thereof, N-(1-(4-(dimethylamino)phenyl)-1-ethylpropyl)-5-(2-fluorophenyl)-2,7,7-trimethyl-4,5,6,7-tetrahydropyrazolo[1,5-a]pyrimidine-3-carboxamide or a salt thereof, N-(1,1-diethylbutyl)-5-(2-fluorophenyl)-2,7,7-trimethyl-4,5,6,7-tetrahydropyrazolo[1,5-a]pyrimidine-3-carboxamide or a salt thereof, N-(1-ethyl-1-phenylpropyl)-5-(2-fluorophenyl)-2,7,7-trimethyl-4,5,6,7-tetrahydropyrazolo[1,5-a]pyrimidine-3-carboxamide or a salt thereof, 3-(5-(1-ethyl-1-(4-methylphenyl)propyl)-1,3,4-oxadiazol-2-yl)-2,7,7-trimethyl-5-phenyl-4,5,6,7-tetrahydropyrazolo[1,5-a]pyrimidine or a salt thereof, 3-(5-(1-ethyl-1-(4-methylphenyl)propyl)-1,3,4-thiadiazol-2-yl)-2,7,7-trimethyl-5-phenyl-4,5,6,7-tetrahydropyrazolo[1,5-a]pyrimidine or a salt thereof, 3-((4-(benzyloxy)-2,2-diethyl-1-pyrrolidinyl)carbonyl)-7,7-dimethyl-5-phenyl-4,5,6,7-tetrahydropyrazolo[1,5-a]pyrimidine or a salt thereof, 3-((2,2-diethyl-4-methoxy-1-pyrrolidinyl)carbonyl)-7,7-dimethyl-5-phenyl-4,5,6,7-tetrahydropyrazolo[1,5-a]pyrimidine or a salt thereof, and 3-((2,2-diethyl-4-fluoro-1-pyrrolidinyl)carbonyl)-7,7-dimethyl-5-phenyl-4,5,6,7-tetrahydropyrazolo[1,5-a]pyrimidine or a salt thereof.

2. The compound according to claim 1, which is an optically active compound.

3. N-(1-ethyl-1-(4-methylphenyl)propyl)-2,7,7-trimethyl-5-phenyl-4,5,6,7-tetrahydropyrazolo[1,5-a]pyrimidine-3-carboxamide hydrochloride.

4. (5S)-N-(1-ethyl-1-(4-methylphenyl)propyl)-2,7,7-trimethyl-5-phenyl-4,5,6,7-tetrahydropyrazolo[1,5-a]pyrimidine-3-carboxamide or a salt thereof.

5. (5S)-N-(1-ethyl-1-(4-methylphenyl)propyl)-2,7,7-trimethyl-5-phenyl-4,5,6,7-tetrahydropyrazolo[1,5-a]pyrimidine-3-carboxamide hydrochloride.

6. (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide or a salt thereof.

7. (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide hydrochloride.

8. (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide methanesulfonate.

9. (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide benzenesulfonate.

10. (5R)-N-(1-ethyl-1-(4-methylphenyl)propyl)-2,7,7-trimethyl-5-phenyl-4,5,6,7-tetrahydropyrazolo[1,5-a]pyrimidine-3-carboxamide p-toluenesulfonate.

11. N-(1-ethyl-1-(4-ethylphenyl)propyl)-2,7,7-trimethyl-5-phenyl-4,5,6,7-tetrahydropyrazolo[1,5-a]pyrimidine-3-carboxamide hydrochloride.

12. (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide or a salt thereof.

13. (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide hydrochloride.

14. (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide methanesulfonate.

15. (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide benzenesulfonate.

16. (5R)-N-(1-ethyl-1-(4-ethylphenyl)propyl)-2,7,7-trimethyl-5-phenyl-4,5,6,7-tetrahydropyrazolo[1,5-a]pyrimidine-3-carboxamide p-toluenesulfonate.

17. N-(1-ethyl-1-(4-methylphenyl)propyl)-7,7-dimethyl-5-phenyl-4,5,6,7-tetrahydropyrazolo[1,5-a]pyrimidine-3-carboxamide or a salt thereof.

18. N-(1-ethyl-1-(4-methylphenyl)propyl)-5-(2-fluorophenyl)-7,7-dimethyl-4,5,6,7-tetrahydropyrazolo[1,5-a]pyrimidine-3-carboxamide or a salt thereof.

19. N-(1-ethyl-1-(4-methylphenyl)propyl)-2,7,7-trimethyl-5-phenyl-4,5,6,7-tetrahydropyrazolo[1,5-a]pyrimidine-3-carboxamide or a salt thereof.

20. N-(1-ethyl-1-(4-ethylphenyl)propyl)-2,7,7-trimethyl-5-phenyl-4,5,6,7-tetrahydropyrazolo[1,5-a]pyrimidine-3-carboxamide or a salt thereof.

21. N-(1-ethyl-1-(4-methylphenyl)propyl)-5-(2-fluorophenyl)-2,7,7-trimethyl-4,5,6,7-tetrahydropyrazolo[1,5-a]pyrimidine-3-carboxamide or a salt thereof.

22. N-(1-ethyl-1-(4-ethylphenyl)propyl)-5-(2-fluorophenyl)-2,7,7-trimethyl-4,5,6,7-tetrahydropyrazolo[1,5-a]pyrimidine-3-carboxamide or a salt thereof.

23. 5-(2-chlorophenyl)-N-(1-ethyl-1-(4-methylphenyl)propyl)-2,7,7-trimethyl-4,5,6,7-tetrahydropyrazolo[1,5-a]pyrimidine-3-carboxamide or a salt thereof.

24. N-(1-(4-(dimethylamino)phenyl)-1-ethylpropyl)-5-(2-fluorophenyl)-2,7,7-trimethyl-4,5,6,7-tetrahydropyrazolo[1,5-a]pyrimidine-3-carboxamide or a salt thereof.

25. N-(1,1-diethylbutyl)-5-(2-fluorophenyl)-2,7,7-trimethyl-4,5,6,7-tetrahydropyrazolo[1,5-a]pyrimidine-3-carboxamide or a salt thereof.

26. N-(1-ethyl-1-phenylpropyl)-5-(2-fluorophenyl)-2,7,7-trimethyl-4,5,6,7-tetrahydropyrazolo[1,5-a]pyrimidine-3-carboxamide or a salt thereof.

27. 3-(5-(1-ethyl-1-(4-methylphenyl)propyl)-1,3,4-oxadiazol-2-yl)-2,7,7-trimethyl-5-phenyl-4,5,6,7-tetrahydropyrazolo[1,5-a]pyrimidine or a salt thereof.

28. 3-(5-(1-ethyl-1-(4-methylphenyl)propyl)-1,3,4-thiadiazol-2-yl)-2,7,7-trimethyl-5-phenyl-4,5,6,7-tetrahydropyrazolo[1,5-a]pyrimidine or a salt thereof.

29. 3-((4-(benzyloxy)-2,2-diethyl-1-pyrrolidinyl)carbonyl)-7,7-dimethyl-5-phenyl-4,5,6,7-tetrahydropyrazolo[1,5-a]pyrimidine or a salt thereof.

30. 3-((2,2-diethyl-4-methoxy-1-pyrrolidinyl)carbonyl)-7,7-dimethyl-5-phenyl-4,5,6,7-tetrahydropyrazolo[1,5-a]pyrimidine or a salt thereof.

31. 3-((2,2-diethyl-4-fluoro-1-pyrrolidinyl)carbonyl)-7,7-dimethyl-5-phenyl-4,5,6,7-tetrahydropyrazolo[1,5-a]pyrimidine or a salt thereof.

* * * * *